(12) United States Patent
Lind et al.

(10) Patent No.: US 9,873,693 B2
(45) Date of Patent: Jan. 23, 2018

(54) METHODS OF TREATMENT USING PYRIDINONYL PDK1 INHIBITORS

(71) Applicants: Sunesis Pharmaceuticals, Inc., South San Franciso, CA (US); Millennium Pharmaceuticals, Inc., Cambridge, MA (US)

(72) Inventors: Kenneth Egnard Lind, Arlington, MA (US); Kathy Cao, Sunnyvale, CA (US); Edward Yin-shiang Lin, Chestnut Hill, MA (US); Thinh Ba Nguyen, Santa Clara, CA (US); Bradley T. Tangonan, San Francisco, CA (US); Daniel A. Erlanson, San Francisco, CA (US); Kevin Guckian, Marlborough, MA (US); Robert Lowell Simmons, San Francisco, CA (US); Wen-cherng Lee, Lexington, MA (US); Lihong Sun, Lexington, MA (US); Stig Hansen, Kensington, CA (US); Nuzhat Pathan, San Diego, CA (US); Lei Zhang, Cheshire, CT (US)

(73) Assignees: Sunesis Pharmaceuticals, Inc., South San Francisco, CA (US); Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/328,256

(22) Filed: Jul. 10, 2014

(65) Prior Publication Data

US 2015/0018351 A1    Jan. 15, 2015

Related U.S. Application Data

(62) Division of application No. 12/307,104, filed as application No. PCT/US2007/015397 on Jul. 2, 2007, now Pat. No. 8,778,977.

(60) Provisional application No. 60/919,057, filed on Mar. 19, 2007, provisional application No. 60/806,414, filed on Jun. 30, 2006.

(51) Int. Cl.

| | |
|---|---|
| A61K 31/5377 | (2006.01) |
| A61K 31/506 | (2006.01) |
| A61K 31/519 | (2006.01) |
| A61K 31/4985 | (2006.01) |
| A61K 31/444 | (2006.01) |
| A61K 31/4439 | (2006.01) |
| A61K 31/4436 | (2006.01) |
| A61K 31/443 | (2006.01) |
| A61K 31/4412 | (2006.01) |
| C07D 487/04 | (2006.01) |
| C07D 471/04 | (2006.01) |
| C07D 417/14 | (2006.01) |
| C07D 417/12 | (2006.01) |
| C07D 413/14 | (2006.01) |
| C07D 413/12 | (2006.01) |
| C07D 409/14 | (2006.01) |
| C07D 409/12 | (2006.01) |
| C07D 405/14 | (2006.01) |
| C07D 405/12 | (2006.01) |
| C07D 401/14 | (2006.01) |
| C07D 401/12 | (2006.01) |
| C07D 211/86 | (2006.01) |
| C07D 213/64 | (2006.01) |
| C07D 407/14 | (2006.01) |

(52) U.S. Cl.
CPC .......... *C07D 471/04* (2013.01); *A61K 31/443* (2013.01); *A61K 31/444* (2013.01); *A61K 31/4412* (2013.01); *A61K 31/4436* (2013.01); *A61K 31/4439* (2013.01); *A61K 31/4985* (2013.01); *A61K 31/506* (2013.01); *A61K 31/519* (2013.01); *A61K 31/5377* (2013.01); *C07D 211/86* (2013.01); *C07D 213/64* (2013.01); *C07D 401/12* (2013.01); *C07D 401/14* (2013.01); *C07D 405/12* (2013.01); *C07D 405/14* (2013.01); *C07D 407/14* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C07D 487/04* (2013.01)

(58) Field of Classification Search
CPC .............. A61K 31/5377; A61K 31/506; A61K 31/519; A61K 31/4985; A61K 31/444; A61K 31/4439; A61K 31/4436; A61K 31/443; A61K 31/4412; C07D 487/04; C07D 471/04; C07D 417/14; C07D 417/12; C07D 413/14; C07D 413/12; C07D 409/12; C07D 409/14; C07D 405/12; C07D 405/14; C07D 401/12; C07D 401/14; C07D 211/86
See application file for complete search history.

(56) References Cited

U.S. PATENT DOCUMENTS

| | | | |
|---|---|---|---|
| 4,132,795 A | 1/1979 | Hitzel et al. | |
| 4,181,658 A | 1/1980 | Hitzel et al. | |

(Continued)

FOREIGN PATENT DOCUMENTS

| | | | |
|---|---|---|---|
| DE | 2621958 A1 | 12/1977 | |
| DE | 2706977 A1 | 8/1978 | |

(Continued)

OTHER PUBLICATIONS

Peifer et al. ChemMedChem 2008, 3, 1810-1838.*

(Continued)

*Primary Examiner* — Matthew Coughlin
(74) *Attorney, Agent, or Firm* — Choate, Hall & Stewart LLP

(57) ABSTRACT

The present invention provides pyridinonyl PDK1 inhibitors and methods of treating cancer using the same.

15 Claims, 2 Drawing Sheets

(56) References Cited

U.S. PATENT DOCUMENTS

| | | | |
|---|---|---|---|
| 5,023,265 | A | 6/1991 | Scherlock et al. |
| 6,337,336 | B1 | 1/2002 | Mewshaw et al. |
| 7,544,690 | B2 | 6/2009 | Sekiguchi et al. |
| 8,778,977 | B2 | 7/2014 | Lind et al. |
| 2005/0182061 | A1 | 8/2005 | Green et al. |
| 2005/0288290 | A1 | 12/2005 | Borzilleri et al. |
| 2008/0103139 | A1 | 5/2008 | Ishizuka et al. |
| 2010/0144730 | A1 | 6/2010 | Lind et al. |

FOREIGN PATENT DOCUMENTS

| | | | |
|---|---|---|---|
| EP | 0500297 | A1 | 8/1992 |
| EP | 1477186 | A1 | 11/2004 |
| EP | 1806342 | A1 | 7/2007 |
| JP | S52-142075 | | 11/1977 |
| JP | S53-103477 | A | 9/1978 |
| JP | 2001-519345 | A | 10/2001 |
| JP | 2004315511 | A | 11/2004 |
| JP | 2005-506330 | A | 3/2005 |
| JP | 2005-523237 | A | 8/2005 |
| JP | 2008-539275 | A | 11/2008 |
| WO | WO-1999018096 | A1 | 4/1999 |
| WO | WO-2002028820 | A1 | 4/2002 |
| WO | WO-03/024962 | A1 | 3/2003 |
| WO | WO-2003059871 | A1 | 7/2003 |
| WO | WO-03/070277 | A1 | 8/2003 |
| WO | WO-2004046122 | A2 | 6/2004 |
| WO | WO-2005048948 | A2 | 6/2005 |
| WO | WO-2005/117867 | A2 | 12/2005 |
| WO | WO-2006004833 | A2 | 1/2006 |
| WO | WO-2006046778 | A1 | 5/2006 |
| WO | WO-2006062224 | A1 | 6/2006 |
| WO | WO-2006116713 | A1 | 11/2006 |
| WO | WO-2007108750 | A1 | 9/2007 |
| WO | WO-2007146824 | A2 | 12/2007 |
| WO | WO-2008/005457 | A2 | 1/2008 |
| WO | WO-2008/063202 | A2 | 5/2008 |
| WO | WO-2008063232 | A2 | 5/2008 |

OTHER PUBLICATIONS

Flynn et al. Curr. Biol. 2000; 10: 1439-42.*
Mora et al. Seminars in Cell & Developmental Biology, 2004, 15, 161-170.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) pp. 427-431.*
Kamb, Nature Reviews Drug Discovery 4, 161-165 (Feb. 2005).*
Luo et al. Cell 2009, 136, 823-837.*
Roberts, Jr et al., JAMA 292(17): 2130-2140 (2004).*
Kola, Nature Reviews Drug Discovery 3, 711-715 (2004).*
CAS Registry entry for Registry No. 320419-91-8, which entered STN on Feb. 6, 2001.
Hyuma Masu et al., "Creation of Concave-Shape Conformation in Crystal Structures Using an Iminodicarbonyl Linker. An Application to Solid-State Intramolecular [4+4] Photocycloaddition Reactions of 2-Pyridone Derivatives" Bulletin of the Chemical Society of Japan, Tokyo, JP, vol. 78, No. 6, Jun. 1, 2005.
Sergey V. Ryabukhin et al., "3-Formylchromones in Guareschi synthesis of 5-(20hydroxybenzoyl)-2-pyridone," SYNLETT, No. 13, May 6, 2004.
Supplementary European Search Report, EP07810166, dated Dec. 6, 2010.
Zh A. Krasnaya et al., "Synthesis of esters of delta-aminopentadiene-carboxylic acids," Bulletin of the Academy of Sciences of the USSR, Division of Chemical Science, No. 9, 1973.
International Search Report for PCT/US2007/015397, 3 pages (dated Apr. 11, 2008).
Written Opinion for PCT/US2007/015397, 4 pages (dated Apr. 11, 2008).

* cited by examiner

METHODS OF TREATMENT USING PYRIDINONYL PDK1 INHIBITORS

CROSS-REFERENCES TO RELATED APPLICATIONS

This application is a divisional of U.S. application Ser. No. 12/307,104 filed on Feb. 8, 2010, now granted as U.S. Pat. No. 8,778,977, which is a National Stage entry of International Application No. PCT/IB07/15397 filed on Jul. 2, 2007, which claims priority to U.S. Provisional Patent Application Ser. No. 60/806,414 filed on Jun. 30, 2006 and U.S. Provisional Patent Application Ser. No. 60/919,057 filed on Mar. 19, 2007, the entire contents of each of which are hereby incorporated by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

The 3-phosphoinositide-dependent protein kinase-1 (PDK1) includes a 556 amino acid protein, an N-terminal catalytic domain, and a C-terminal pleckstrin homology (PH) domain that activates substrate kinases via activation loop phosphorylation (Belham, C. et al., Curr. Biol., 9, pp. R93-R96, 1999). PDK1 is involved in regulating the activity of AGC subfamily of protein kinases (Alessi, D. et al., Biochem. Soc. Trans, 29: 1 (2001)) such as isoforms of protein kinase B (PKB, also known as AKT), p70 ribosomal S6 kinase (S6K) (Avruch, J. et al., Prog. Mol. Subcell. Biol., 26: 115, (2001)), p90 ribosomal S6 kinase (Frodin, M. et al., EMBO J., 19: 2924-2934, (2000)), and protein kinase C(PKC) (an 80 kDa enzyme that is recruited to the plasma membrane by diacylglycerol and, in many cases, by calcium) (Le Good et al., Science 281: 2042-2045 (1998). PDK1 mediated signaling increases in response to insulin, growth factors, and extracellular matrix cell binding (integrin signaling) resulting in diverse cellular events such as cell survival, growth, proliferation and glucose regulation [(Lawlor, M. A. et al., J. Cell Sci., 114, pp. 2903-2910, 2001), (Lawlor, M. A. et al., EMBO J., 21, pp. 3728-3738, 2002)]. Elevated PDK1 signaling has been detected in several cancers resulting from distinct genetic events such as PTEN mutations or over-expression of certain key regulatory proteins [(Graff, J. R., Expert Opin. Ther. Targets, 6, pp. 103-113, 2002), (Brognard, J., et al., Cancer Res., 61, pp. 3986-3997, 2001)].

The tumor-suppressor phosphatase with tensin homology (PTEN) is an important negative regulator of the cell-survival signaling pathway initiated by phosphatidylinositol 3-kinase (PI3K). The PDK1/Akt pathway is activated in many cancer via mutations in Receptor Tyrosine Kinases (RTKs), Ras, PI-3 kinase or PTEN (Cully et al., Nature Reviews Cancer 6:184-192 (2006)). The potential of PDK1 inhibitors as anti-cancer compounds was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., Curr. Biol., 10: 1439-1442 (2000)).

Moreover, currently known inhibitors of PDK1 typically affect both PDK1 mediated Akt phosphorylation and PDK1 mediated PKC phosphorylation thereby raising concerns regarding clinical side effects. Feldman et al., J. Biol. Chem. 280: 19867-19874 (2005).

Consequently, there is a great need in the art for effective inhibitors of PDK1. The present invention fulfills these and other needs.

BRIEF SUMMARY OF THE INVENTION

In one aspect, the present invention provides a pyridinonyl PDK1 inhibitor.

In another aspect, the present invention provides a method of decreasing PDK1 catalytic activity. The method includes contacting a PDK1 with an effective amount of a pyridinonyl PDK1 inhibitor.

In another aspect, the present invention provides a method of treating cancer in a subject in need thereof. The method includes administering to the subject a therapeutically effective amount of a pyridinonyl PDK1 inhibitor.

In another aspect, the present invention provides methods for selectively reducing PDK1 mediated phosphorylation of Akt relative to phosphorylation of PKC. The method includes contacting PDK1 with a compound of the present invention in the presence of Akt and PKC.

DETAILED DESCRIPTION OF THE INVENTION

Abbreviations and Definitions

Figure 1:
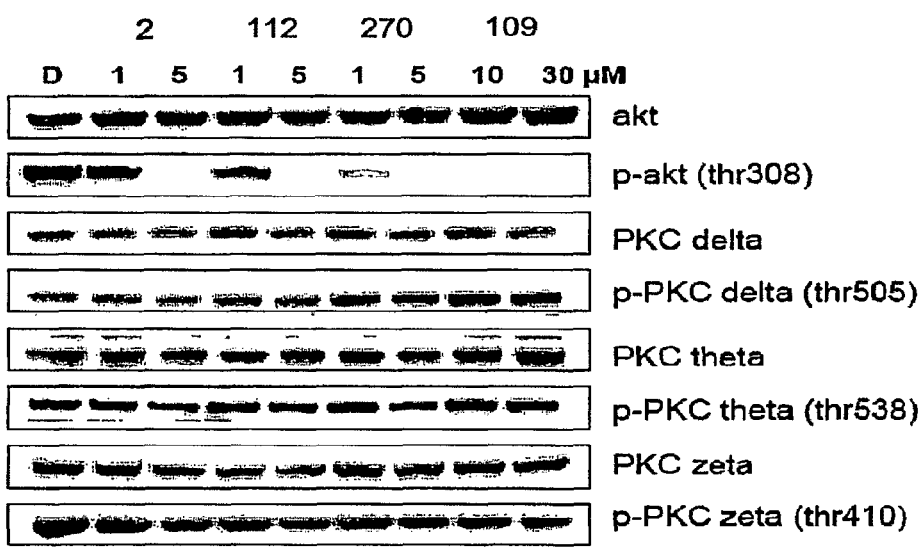
FIG. 1 illustrates selective inhibition of PDK1 mediated phosphorylation of Akt relative to PDK1 mediated phosphorylation of PKC isoforms using different concentrations of compounds of the present invention.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene" by itself or as part of another substituent means a divalent radical derived from an alkyl, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—O$CH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "aryl" means, unless otherwise stated, a polyunsaturated, aromatic, hydrocarbon substituent which can be a single ring or multiple rings (preferably from 1 to 3 rings) which are fused together (i.e. a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e. multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent means a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S($O_2$)—R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —$NO_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl; substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The symbol "$\sim\!\!\sim$" denotes the point of attachment of a chemical moiety to the remainder of a molecule or chemical formula.

I. PYRIDINONYL PDK1 INHIBITORS

In one aspect, the present invention provides a pyridinonyl PDK1 inhibitor. The pyridinonyl PDK1 inhibitors of the present invention include a pyridinonyl core, typically a 2-pyridinonyl core, and an amide substituent, typically at the 3-position of the pyridinonyl core. The pyridinonyl PDK1 inhibitor may additionally include a substituted or unsubstituted benzyl substituent at the 1-position of the pyridinonyl core thereby forming a benzyl-pyridinonylamide PDK1 inhibitor. The pyridinonyl PDK1 inhibitors, benzyl-pyridinonyl PDK1 inhibitors, and benzyl-pyridinonylamide PDK1 inhibitors include the compounds described below in Formulae (I)-(XV), and are also referred to herein as the compounds of the present invention.

The pyridinonyl PDK1 inhibitors of the present invention decrease PDK1 catalytic activity upon contact with a PDK1 protein. In some embodiments, the pyridinonyl PDK1 inhibitor includes a hydrogen bond donor and a hydrogen bond acceptor. Without being bound by theory, the hydrogen bond acceptor may interact with the amide backbone nitrogen of A162 of PDK1 and the hydrogen bond donor may interact with the amide backbone oxygen of S160 of PDK1.

In some embodiments, the pyridinonyl PDK1 inhibitor of the present invention has the formula:

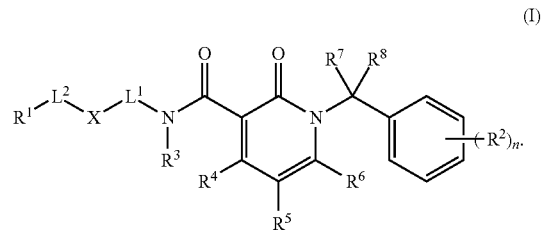

(I)

In Formula (I), n is an integer from 0 to 5 (e.g. 1 to 5 such as 1 or 2). In one embodiment, n is 1 to 3. In another embodiment, n is 1. In another embodiment, n is 2. In another embodiment, n is 3.

$L^1$ and $L^2$ may independently be absent, —O—, —NR$^A$— (e.g. —NH), —S—, —S(O)—, S(O)$_2$—, substituted or unsubstituted alkylene, or substituted or unsubstituted heteroalkylene. R$^A$ is hydrogen, substituted or unsubstituted alkyl (e.g. unsubstituted C$_1$ to C$_{10}$ alkyl), substituted or unsubstituted heteroalkyl, substituted or unsubstituted cycloalkyl, substituted or unsubstituted heterocycloalkyl, substituted or unsubstituted aryl, or substituted or unsubstituted heteroaryl, $L^1$ and $L^2$ may also be substituted or unsubstituted C$_1$-C$_{10}$ alkylene or substituted or unsubstituted 2 to 20 membered heteroalkylene. Appropriate substituents for $L^1$ and $L^2$ include, for example, hydroxyl, cyano, halogen, oxo, amino, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl (e,g, furanyl, thiophenyl, imidazolyl, pyrrolyl, oxazolyl, pyridinyl, isothiazolyl, isooxazolyl, and pyrazolyl).

In some embodiments, $L^1$ has the formula:

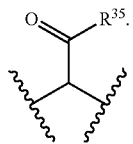

R$^{35}$ is —OR$^{36}$ or —NHR$^{36}$. R$^{36}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, R$^{36}$ is hydrogen, unsubstituted alkyl, unsubstituted heteroalkyl, unsubstituted cycloalkyl, unsubstituted heterocycloalkyl, unsubstituted aryl, or unsubstituted heteroaryl.

In one embodiment, $L^1$ is absent, —O—, —NR$^A$—, or —S—. R$^A$ may be hydrogen or a substituted or unsubstituted alkyl (e.g. C$_1$-C$_3$ alkyl). $L^2$ may be a substituted or unsubstituted C$_1$-C$_5$ alkylene, a substituted or unsubstituted C$_2$-C$_5$ alkenylene, or a substituted or unsubstituted C$_2$-C$_5$ alkynylene. In another embodiment, $L^1$ is absent, a substituted or unsubstituted C$_1$-C$_5$ alkylene, a substituted or unsubstituted C$_2$-C$_5$ alkenylene, or a substituted or unsubstituted C$_2$-C$_5$ alkynylene, and $L^2$ is absent, —O—, —NR$^A$—, or —S—.

In some embodiments, $L^1$ and $L^2$ are independently —O—, —NR$^A$—, —S—, —S(O)—, S(O)$_2$—, substituted or unsubstituted C$_2$-C$_{20}$ alkylene, or substituted or unsubstituted heteroalkylene. $L^1$ and $L^2$ may also independently be —O—, —NR$^A$—, —S—, —S(O)—, S(O)$_2$—, substituted or unsubstituted C$_3$-C$_{20}$ alkylene, or substituted or unsubstituted heteroalkylene. $L^1$ and $L^2$ may also independently be —O—, —NR$^A$—, —S—, —S(O)—, S(O)$_2$—, substituted or unsubstituted C$_3$-C$_{10}$ alkylene, or substituted or unsubstituted heteroalkylene.

In another embodiment, $L^1$ is —O—, —NR$^A$—, or —S— where R$^A$ is hydrogen or C$_1$-C$_3$ alkyl, and $L^2$ is a C$_1$-C$_5$ alkylene, C$_2$-C$_5$ alkenylene, or C$_2$-C$_5$ alkynylene. In another embodiment, $L^1$ is a C$_1$-C$_5$ alkylene, C$_2$-C$_5$ alkenylene, or C$_2$-C$_5$ alkynylene, and $L^2$ is —O—, —NR$^A$—, —S— where R$^A$ is hydrogen or C$_1$-C$_3$ alkyl.

In another embodiment, $L^1$ and $L^2$ are independently —O—, —S—, —NR$^A$— or a substituted or unsubstituted C$_1$-C$_6$ alkyldiene or C$_2$-C$_6$ alkenyldiene chain wherein up to two non-adjacent methylene units are independently optionally replaced by —C(=O)—, —CO$_2$—, —C(=O)C (=O)—, —C(=O)NR$^{A1}$—, —OC(=O)—, —OC(=O) NR$^{A1}$—, —R$^{A1}$NR$^{B1}$—, —NR$^{A1}$NR$^B$C(=O)—, —NR$^{A1}$C (=O)—, —NR$^{A1}$CO$_2$—, —NR$^{A1}$C(=O)NR$^{B1}$—, —S(=O)—, —SO$_2$—, —NR$^{A1}$SO$_2$—, —SO$_2$NR$^{A1}$—, NR$^{A1}$SO$_2$NR$^{B1}$—; wherein each occurrence of R$^{A1}$ and R$^{B1}$ is independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl or substituted or unsubstituted acyl. In some embodiments, $L^1$ is —CH$_2$—CH=CH—.

In another embodiment, $L^1$ and $L^2$ are independently absent, —(CH$_2$)$_o$—O—(CH$_2$)$_p$—, —(CH$_2$)$_o$S(CH$_2$)$_p$—, —(CH$_2$)$_o$NR$^{A2}$(CH$_2$)$_p$—, —(CH$_2$)$_o$C(=O)(CH$_2$)$_p$—, —(CH$_2$)$_o$CO$_2$(CH$_2$)$_p$—, —(CH$_2$)$_o$C(=O)C(=O)(CH$_2$)$_p$—, —(CH$_2$)$_o$C(=O)NR$^{A2}$(CH$_2$)$_p$—, —(CH$_2$)$_o$OC(=O) (CH$_2$)$_p$—, —(CH$_2$)$_o$OC(=O)NR$^{A2}$(CH$_2$)$_p$—, —(CH$_2$)$_o$NR$^{A2}$NR$^{B2}$(CH$_2$)$_p$, —(CH$_2$)$_o$NR$^{A2}$NR$^{B2}$C(=O)(CH$_2$)$_p$—, —(CH$_2$)$_o$NR$^{A2}$C(=O)(CH$_2$)$_p$—, —(CH$_2$)$_o$NR$^{A2}$CO$_2$ (CH$_2$)$_p$—, —(CH$_2$)$_o$NR$^{A2}$C(=O)NR$^{B2}$(CH$_2$)$_p$—, —(CH$_2$)$_o$S(=O)(CH$_2$)$_p$—, —(CH$_2$)$_o$SO$_2$(CH$_2$)$_p$—, —(CH$_2$)$_o$NR$^{A2}$SO$_2$(CH$_2$)$_p$—, —(CH$_2$)$_o$SO$_2$NR$^{A2}$(CH$_2$)$_p$—, —(CH$_2$)$_o$NR$^{A2}$SO$_2$NR$^{B2}$(CH$_2$)$_p$—, wherein each occurrence of R$^{A2}$ and R$^{B2}$ is independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl or acyl, and o and p are each independently an integer from 0 to 5.

In one embodiment, $L^1$ and $L^2$ are independently absent, —(CH$_2$)$_o$O(CH$_2$)$_p$—, —(CH$_2$)$_o$S(CH$_2$)$_p$—, —(CH$_2$)$_o$NR$^{A3}$ (CH$_2$)$_p$—, —(CH$_2$)$_o$C(=O)(CH$_2$)$_p$—, —(CH$_2$)$_o$CO$_2$ (CH$_2$)$_p$—, —(CH$_2$)$_o$C(=O)C(=O)(CH$_2$)$_p$—, —(CH$_2$)$_o$C (=O)NR$^{A3}$(CH$_2$)$_p$—, —(CH$_2$)$_o$OC(=O)(CH$_2$)$_p$—, —(CH$_2$)$_o$OC(=O)NR$^{A3}$(CH$_2$)P—, —(CH$_2$)$_o$NR$^{A3}$NR$^{B3}$ (CH$_2$)$_p$—, —(CH$_2$)$_o$NR$^{A3}$NR$^{B3}$C(=O)(CH$_2$)$_p$—, —(CH$_2$)$_o$NR$^{A3}$C(=O)(CH$_2$)$_p$—, —(CH$_2$)$_o$NR$^{A3}$CO$_2$(CH$_2$)$_p$—, —(CH$_2$)$_o$NR$^{A3}$C(=O)NR$^{B3}$(CH$_2$)$_p$—, —(CH$_2$)$_o$S(=O) (CH$_2$)$_p$—, —(CH$_2$)$_o$SO$_2$(CH$_2$)$_p$—, —(CH$_2$)$_o$NR$^{A3}$SO$_2$ (CH$_2$)$_p$—, —(CH$_2$)$_o$SO$_2$NR$^{A3}$(CH$_2$)$_p$—, —(CH$_2$)$_o$NR$^{A3}$SO$_2$NR$^{B3}$(CH$_2$)$_p$—, wherein each occurrence of R$^{A3}$ and R$^{B3}$ is independently hydrogen, C$_1$-C$_3$ alkyl, phenyl, C$_3$-C$_6$ cycloalkyl, or C$_{1-C6}$ acyl, and o and p are each independently an integer from 0 to 2.

In another embodiment, both $L^1$ and $L^2$ are absent. In other embodiments, $L^1$ is substituted or unsubstituted alkylene and $L^2$ is absent.

X is absent, substituted or unsubstituted cycloalkylene, substituted or unsubstituted heterocycloalkylene, substituted or unsubstituted arylene, or substituted or unsubstituted heteroarylene. In certain embodiments, X is optionally substituted with one or more oxo, —OR$^{10}$, —S(O)$_n$R$^{11}$, —C(O) R$^{12}$, —NR$^{13}$R$^{14}$, or unsubstituted alkyl. R$^{10}$, R$^{11}$, R$^{12}$, R$^{13}$, and R$^{14}$ are, independently, as defined below. In another embodiment, X is optionally substituted with one or more oxo, —OH, —NH$_2$, —CN, —CF$_3$, —NO$_2$, halogen, or C$_{1-3}$ alkyl. In some embodiments, where X is substituted or unsubstituted phenylene, then L, is —O—, —NH—, —S—, —S(O)—, S(O)$_2$—, substituted or unsubstituted alkylene, or substituted or unsubstituted heteroalkylene. In certain embodiments, if X is phenylene and $L^1$ is absent, then R$^2$ is halogen (e.g. fluorine). In other embodiments, if X is absent, then $L^1$, $L^2$, or the combination of $L^1$ and $L^2$, is a substituted or unsubstituted alkylene including a linear chain of at least four atoms or a substituted or unsubstituted heteroalkylene including a linear chain of at least four atoms.

In some embodiments, X is absent. In other embodiments, X is a substituted or unsubstituted arylene. X may also be phenylene optionally substituted with one or more oxo, —OH, —NH$_2$, —CN, —CF$_3$, —NO$_2$, halogen, or C$_1$-C$_3$ alkyl. In another embodiment, X is phenylene optionally substituted with Cl, F, OH, —NH$_2$, —CN, —CF$_3$, or CH$_3$. In some embodiments, X is substituted or unsubstituted phenylene and L$^2$ is absent. X may also be substituted or unsubstituted tetrahydronaphthalenylene, substituted or unsubstituted adamantanylene, or substituted or unsubstituted naphthylenylene.

In certain embodiments, X is a substituted or unsubstituted cyclopentylene, or a substituted or unsubstituted cyclohexylene. In other embodiments, X is an unsubstituted cyclopentylene or a cyclohexylene. X may also be cyclopentylene or cyclohexylene optionally substituted with one or more oxo, —OH, —NH$_2$, —CN, —CF$_3$, —NO$_2$, halogen, or C$_{1-3}$ alkyl. In another embodiment, X is a cyclopentylene or a cyclohexylene optionally substituted with —Cl, —F, —OH, —NH$_2$, —CN, —CF$_3$, or —CH$_3$.

In other embodiments, X is a substituted or unsubstituted pyrrolidinylene, substituted or unsubstituted imidazolidinylene, or substituted or unsubstituted piperidinylene. X may also be a unsubstituted pyrrolidinylene, imidazolidinylene, or piperidinylene. In certain embodiments, X is a pyrrolidinylene, imidazolidinylene, or piperidinylene optionally substituted with one or more oxo, —OH, —NH$_2$, —CN, —CF$_3$, —NO$_2$, halogen, or C$_{1-3}$ alkyl. In another embodiment, X is a pyrrolidinylene, imidazolidinylene, or piperidinylene optionally substituted with Cl, F, OH, —NH$_2$, —CN, —CF$_3$, or CH$_3$.

In other embodiments, X is a substituted or unsubstituted heteroarylene. In another embodiment, X is a substituted or unsubstituted triazinylene, substituted or unsubstituted pyridinylene 1-oxide, substituted or unsubstituted furanylene, substituted or unsubstituted pyrrolylene, substituted or unsubstituted oxazolylene, substituted or unsubstituted imidazolylene, substituted or unsubstituted pyrazolylene, substituted or unsubstituted isoxazolylene, substituted or unsubstituted isothiazolylene, substituted or unsubstituted thiazolylene, substituted or unsubstituted pyridinylene, substituted or unsubstituted pyrimidinylene, or substituted or unsubstituted pyridazinylene. X may also be substituted or unsubstituted pyrrolopyridylene, substituted or unsubstituted pyrrolopyrimidinylene, substituted or unsubstituted pyrrolopyrazinylene, substituted or unsubstituted pyrazolopyridylene, substituted or unsubstituted pyrazolopyrimidinylene, substituted or unsubstituted pyrazolopyrazinylene, substituted or unsubstituted amino-benzimidazolylene, substituted or unsubstituted 2-indolinonylene, substituted or unsubstituted 2-benzimidazolinonylene, substituted or unsubstituted 2-pyrrolidinonylene, substituted or unsubstituted benzimidazolylene, substituted or unsubstituted indazolylene, substituted or unsubstituted tetrazolylene, substituted or unsubstituted pyridinonylene (e.g. pyridin-2-one-ylene), substituted or unsubstituted 5,8-dihydro-6H-pyrido-pyrimidin-7-one-ylene, substituted or unsubstituted imidazopyridinon-2-ylene (e.g. 1,3-Dihydro-imidazo[4,5-c]pyridin-2-onylene), substituted or unsubstituted indolylene, substituted or unsubstituted benzothiadiazolylene, substituted or unsubstituted benzo-oxodiazolylene, substituted or unsubstituted imidazopyridinylene, substituted or unsubstituted triazolopyridinonylene, substituted or unsubstituted dihydro-pyrazolonylene, substituted or unsubstituted triazolopyridinylene (e.g. [1,2,4]triazolo[1,5-a]pyridinylene). In some embodiments, the substituted or unsubstituted pyrrolopyridylene is substituted or unsubstituted 7-azaindolylene (i.e. 1H-pyrrolo[2,3-b]pyridinylene). The 7-azaindolylene may be substituted at the 4, 5, or 6 position. The 7-azaindolylene may be attached to the remainder of the molecule at the 2 position. In some embodiments, X is indazolylene.

In another embodiment, X is substituted or unsubstituted furanylene, substituted or unsubstituted pyrrolylene, substituted or unsubstituted oxazolylene, substituted or unsubstituted imidazolylene, substituted or unsubstituted pyrazolylene, substituted or unsubstituted isoxazolylene, substituted or unsubstituted isothiazolylene, substituted or unsubstituted thiazolylene, substituted or unsubstituted pyridinylene, substituted or unsubstituted pyrimidinylene, or substituted or unsubstituted pyridazinylene.

In another embodiment, X is furanylene, pyrrolylene, oxazolylene, imidazolylene, pyrazolylene, isoxazolylene, isothiazolylene, thiazolylene, pyridinylene, pyrimidinylene, or pyridazinylene optionally substituted with one or more oxo, —OH, —NH$_2$, —CN, —CF$_3$, —NO$_2$, halogen, or C$_{1-3}$ alkyl. In another embodiment, X is furanylene, pyrrolylene, oxazolylene, imidazolylene, pyrazolylene, isoxazolylene, isothiazolylene, thiazolylene, pyridinylene, pyrimidinylene, or pyridazinylene optionally substituted with Cl, F, OH, —NH$_2$, —CN, —CF$_3$, or CH$_3$. In another embodiment, X is thiophenylene, imidazolylene, or thiazolylene optionally substituted with one or more oxo, —OH, —NH$_2$, —CN, —CF$_3$, —NO$_2$, halogen, or C$_{1-3}$ alkyl. In another embodiment X is thiophenenylene, imidazolylene, or thiazolylene optionally substituted Cl, F, OH, —NH$_2$, —CN, —CF$_3$, or CH$_3$.

In certain embodiments, X is a fused ring heteroarylene, such as a 5,6-fused ring heteroarylene, a 6,5-fused ring heteroarylene, or a 6,6-fused ring heteroarylene. In some embodiments, X is absent.

R$^1$ is substituted or unsubstituted cycloalkyl, substituted or unsubstituted heterocycloalkyl, substituted or unsubstituted aryl, or substituted or unsubstituted heteroaryl. R$^1$ may be substituted or unsubstituted pyrrolopyridyl, substituted or unsubstituted pyrrolopyrimidinyl, substituted or unsubstituted pyrrolopyrazinyl, substituted or unsubstituted pyridinyl 1-oxide, substituted or unsubstituted pyrazolopyridyl, substituted or unsubstituted pyrazolopyrimidinyl, substituted or unsubstituted pyrazolopyrazinyl, substituted or unsubstituted amino-benzimidazolyl, substituted or unsubstituted 2-indolinonyl, substituted or unsubstituted quinolinyl, substituted or unsubstituted 2-benzimidazolinonyl, substituted or unsubstituted 2-pyrrolidinonyl, substituted or unsubstituted benzimidazolyl, substituted or unsubstituted tetrazolyl, substituted or unsubstituted pyridinonyl (e.g. pyridin-2-one-yl), substituted or unsubstituted pyrazolyl, substituted or unsubstituted 5,8-dihydro-6H-pyrido-pyrimidin-7-one-yl, substituted or unsubstituted indazolyl, substituted or unsubstituted dihydro-imidazopyridinon-2-yl (e.g. 1,3-Dihydro-imidazo[4,5-c]pyridin-2-onyl), substituted or unsubstituted indolyl, substituted or unsubstituted benzothiadiazolyl, substituted or unsubstituted benzo-oxodiazolyl, substituted or unsubstituted imidazopyridinyl, substituted or unsubstituted triazolopyridinonyl, substituted or unsubstituted dihydro-pyrazolonyl, substituted or unsubstituted triazolopyridinyl (e.g. [1,2,4]triazolo[1,5-a]pyridinyl), substituted or unsubstituted tetrahydronaphthalenyl, substituted or unsubstituted adamantanyl, or substituted or unsubstituted naphthylenyl, or substituted or unsubstituted pyrimidinyl. In some embodiments, the substituted or unsubstituted pyrrolopyridyl is substituted or unsubstituted 7-azaindolyl (i.e. 1H-pyrrolo[2,3-b]pyridinyl). The 7-azaindole may be substituted at the 4, 5, or 6 positions. The 7-azaindole may be attached to the remainder of the molecule at the 2 position.

$R^1$ may also be substituted or unsubstituted thiophenyl, substituted or unsubstituted thiazolyl, substituted or unsubstituted thiophenyl, substituted or unsubstituted furanyl, substituted or unsubstituted imidazolyl, substituted or unsubstituted triazinyl, substituted or unsubstituted pyrrolyl, substituted or unsubstituted oxazolyl, substituted or unsubstituted pyrazolyl, substituted or unsubstituted isoxazolyl, substituted or unsubstituted isothiazolyl, substituted or unsubstituted pyridinyl, or substituted or unsubstituted pyridazinyl. In some embodiments, $R^1$ is not substituted or unsubstituted aryl or substituted or unsubstituted cycloalkyl. In other embodiments, $R^1$ is not phenyl or substituted or unsubstituted cyclohexyl.

In some embodiments, if X is substituted or unsubstituted phenylene and $L^1$ is absent, then $R^1$ is not substituted or unsubstituted pyridinyl, substituted or unsubstituted benzoxazolyl, substituted or unsubstituted quinazolinyl, or substituted or unsubstituted phenyl. In certain embodiments, if X is substituted or unsubstituted phenylene, then $R^1$ is not cyclohexyl. In other embodiments, if X is substituted or unsubstituted phenylene, then $R^1$ is substituted or unsubstituted heterocycloalkyl, substituted or unsubstituted aryl, or substituted or unsubstituted heteroaryl.

In certain embodiments, if X is substituted or unsubstituted phenylene and $L^1$ is absent, then $R^1$ is substituted or unsubstituted pyrrolopyridyl, substituted or unsubstituted quinolinylene, substituted or unsubstituted pyrrolopyrimidinyl, substituted or unsubstituted pyrrolopyrazinyl, substituted or unsubstituted pyrazolopyridyl, substituted or unsubstituted pyrazolopyrimidinyl, substituted or unsubstituted pyridinyl 1-oxide, substituted or unsubstituted pyrazolopyrazinyl, substituted or unsubstituted amino-benzimidazolyl, substituted or unsubstituted 2-indolinonyl, substituted or unsubstituted 2-benzimidazolinonyl, substituted or unsubstituted 2-pyrrolidinonyl, substituted or unsubstituted benzimidazolyl, substituted or unsubstituted tetrazolyl, substituted or unsubstituted pyridinonyl (e.g. pyridin-2-one-yl), substituted or unsubstituted pyrazolyl, substituted or unsubstituted 5,8-dihydro-6H-pyrido-pyrimidin-7-one-yl, substituted or unsubstituted indazolyl, substituted or unsubstituted dihydro-imidazopyridinon-2-yl (e.g. 1,3-Dihydro-imidazo[4,5-c]pyridin-2-onyl), substituted or unsubstituted indolyl, substituted or unsubstituted benzothiadiazolyl, substituted or unsubstituted benzo-oxodiazolyl, substituted or unsubstituted imidazopyridinyl, substituted or unsubstituted triazolopyridinonyl, substituted or unsubstituted dihydro-pyrazolonyl, substituted or unsubstituted triazolopyridinyl (e.g. [1,2,4]triazolo[1,5-a]pyridinyl), substituted or unsubstituted tetrahydronaphthalenyl, substituted or unsubstituted adamantanyl, or substituted or unsubstituted naphthylenyl, or substituted or unsubstituted pyrimidinyl. In some embodiments, the substituted or unsubstituted pyrrolopyridyl is substituted or unsubstituted 7-azaindolyl (i.e. 1H-pyrrolo[2,3-b]pyridinyl), substituted or unsubstituted thiophenyl, substituted or unsubstituted thiazolyl, substituted or unsubstituted thiophenyl, substituted or unsubstituted furanyl, substituted or unsubstituted imidazolyl, substituted or unsubstituted triazinyl, substituted or unsubstituted pyrrolyl, substituted or unsubstituted oxazolyl, substituted or unsubstituted pyrazolyl, substituted or unsubstituted isoxazolyl, substituted or unsubstituted isothiazolyl, or substituted or unsubstituted pyridazinyl. In other embodiments, if X is substituted or unsubstituted phenylene, then $R^1$ is not cyclohexyl.

In some embodiments, where $R^1$ is substituted or unsubstituted phenyl and X is absent, the $L^1$ is not absent. For example, $L^1$ may be —O—, —NH—, —S—, —S(O)—, $S(O)_2$—, substituted or unsubstituted alkylene, or substituted or unsubstituted heteroalkylene. In certain embodiments, where $R^1$ is substituted or unsubstituted phenyl, then X is not substituted or unsubstituted pyridinonyl or substituted or unsubstituted imidazolylene. For example, where $R^1$ is substituted or unsubstituted phenyl, then X is a substituted or unsubstituted triazinylene, substituted or unsubstituted furanylene, substituted or unsubstituted pyrrolylene, substituted or unsubstituted oxazolylene, substituted or unsubstituted pyrazolylene, substituted or unsubstituted isoxazolylene, substituted or unsubstituted isothiazolylene, substituted or unsubstituted thiazolylene, substituted or unsubstituted pyridinylene, substituted or unsubstituted pyrimidinylene, or substituted or unsubstituted pyridazinylene, substituted or unsubstituted pyrrolopyridylene, substituted or unsubstituted pyrrolopyrimidinylene, substituted or unsubstituted pyrrolopyrazinylene, substituted or unsubstituted pyrazolopyridylene, substituted or unsubstituted pyrazolopyrimidinylene, substituted or unsubstituted pyrazolopyrazinylene, substituted or unsubstituted amino-benzimidazolylene, substituted or unsubstituted 2-indolinonylene, substituted or unsubstituted 2-benzimidazolinonylene, substituted or unsubstituted benzimidazolylene, substituted or unsubstituted indazolylene, substituted or unsubstituted tetrazolylene, substituted or unsubstituted pyridinonylene (e.g. pyridin-2-one-ylene), substituted or unsubstituted 5,8-dihydro-6H-pyrido-pyrimidin-7-one-ylene, substituted or unsubstituted imidazopyridinon-2-ylene (e.g. 1,3-Dihydro-imidazo[4,5-c]pyridin-2-onylene), substituted or unsubstituted indolylene, substituted or unsubstituted benzothiadiazolylene, substituted or unsubstituted benzo-oxodiazolylene, substituted or unsubstituted imidazopyridinylene, substituted or unsubstituted triazolopyridinonylene, substituted or unsubstituted dihydro-pyrazolonylene, substituted or unsubstituted triazolopyridinylene (e.g. [1,2,4]triazolo[1,5-a]pyridinylene).

$R^1$ may also be substituted or unsubstituted pyrimidinyl when $L^1$ is —NH-$L^{1A}$- thereby forming a substituent with the formula $R^1$—NH-$L^{1A}$, wherein $L^{1A}$ is absent, substituted or unsubstituted alkylene, or substituted or unsubstituted heteroalkylene. In some embodiments, the substituted or unsubstituted pyrimidinyl is a substituted or unsubstituted pyrimidin-2-yl.

$R^2$, $R^4$, $R^5$, $R^6$, $R^7$, and $R^8$ are independently hydrogen, halogen, —OH, —$CF_3$, —$NO_2$, —$OR^{10}$, —$S(O)_nR^{11}$, —$C(O)R^{12}$, —$NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$, $R^4$, $R^5$, $R^6$, $R^7$, and $R^8$ may be, independently, hydrogen, halogen, —OH, —$CF_3$, —$NO_2$, —$OR^{10}$, —$S(O)_nR^{11}$, —$C(O)R^{12}$, —$NR^{13}R^{14}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^3$ may be hydrogen, —OH, —$CF_3$, —$OR^{10}$, —$S(O)_nR^{11}$, —$C(O)R^{12}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^6$ may be hydrogen, halogen, —$CF_3$, —$NO_2$, —$OR^{10}$, —$S(O)_nR^{11}$, —$C(O)R^{12}$, —$NR^{13}R^{14}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^{10}$ may be, independently, —C(O)$R^{15}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^{11}$ may be, independently, hydrogen, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^{12}$ and $R^{15}$ may be, independently, hydrogen, —$NR^{19}R^{20}$, —$OR^{21}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^{13}$ may be, independently, hydrogen, —C(O)$R^{15}$, —S(O)$_2R^{16}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^{14}$, $R^{17}$, $R^{18}$, $R^{19}$, $R^{20}$ and $R^{21}$ may be, independently, hydrogen, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl.

In some embodiments, $R^2$, $R^3$, $R^4$, $R^5$, $R^6$, $R^7$, and $R^8$ are independently hydrogen, Cl, F, —$CF_3$, —$NO_2$, —$NH_2$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl. $R^2$, $R^3$, $R^4$, $R^5$, $R^6$, $R^7$, and $R^8$ may also be, independently, hydrogen, Cl, F, —$CF_3$, —$NO_2$, —$NH_2$, or substituted or unsubstituted $C_1$-$C_{10}$ alkyl, or substituted or unsubstituted 2 to 10 membered heteroalkyl. In other embodiments, $R^2$, $R^3$, $R^4$, $R^5$, $R^6$, $R^7$, and $R^8$ are independently hydrogen, Cl, F, —$CF_3$, —$NO_2$, —$NH_2$, unsubstituted $C_1$-$C_5$ alkyl, or unsubstituted 2 to 5 membered heteroalkyl. $R^2$, $R^3$, $R^4$, $R^5$, $R^6$, $R^7$, and $R^8$ may also be independently hydrogen, Cl, F, —$CF_3$, or unsubstituted $C_1$-$C_5$ alkyl. In certain embodiments, $R^3$, $R^4$, $R^5$, $R^6$, $R^7$, and $R^8$ are independently hydrogen, Cl, F, —$CF_3$, or unsubstituted $C_1$-$C_5$ alkyl. In certain embodiments, $R^2$ is a halogen (e.g. fluorine) and n is 2 or 3. In some embodiments, $R^2$ is substituted at the meta and para positions only.

In some embodiments, $R^6$ is hydrogen, halogen, —$CF_3$, —$NO_2$, —$OR^{10}$, —S(O)$_nR^{11}$, —C(O)$R^{12}$, —$NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In certain embodiments, $R^4$, $R^5$, and $R^6$ are hydrogen. In some embodiments, $R^7$ and $R^8$ are hydrogen.

$R^3$ is hydrogen, —OH, —$CF_3$, —$OR^{10}$, —S(O)$_nR^{11}$, —C(O)$R^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, where $R^3$ is an aryl of heteroaryl, the aryl or heteroaryl is a fused ring aryl or heteroaryl, respectively, such as tetrahydronaphthalenyl, indazolyl, or napthalenyl. In some embodiments, $R^3$ is a heteroaryl selected from pyrazolyl oxadiazolyl, pyridinyl, pyrazinyl, pyrimidinyl, 1,1 cyclopropylenyl, and pyrazolyl. In some embodiment, $R^3$ is hydrogen.

$R^3$ is optionally attached to X thereby forming a substituted or unsubstituted cycloalkyl, substituted or unsubstituted heterocycloalkyl, substituted or unsubstituted aryl, or substituted or unsubstituted heteroaryl. Thus, where $R^3$ is attached to X, the $R^3$, the amide nitrogen, $L^1$, and X combine to form a substituted or unsubstituted cycloalkyl, substituted or unsubstituted heterocycloalkyl, substituted or unsubstituted aryl, or substituted or unsubstituted heteroaryl. In some embodiments, the aryl or heteroaryl is a fused ring aryl or heteroaryl, respectively. Certain compounds where $R^3$ is attached to X to form a substituted tetrahydro-quinolinyl and a piperazinyl is shown below:

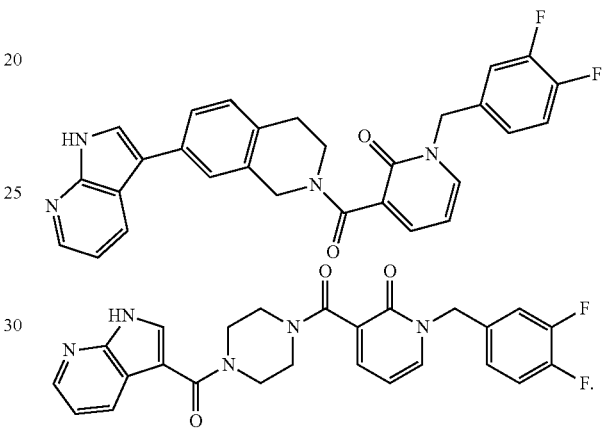

$R^{10}$ is independently —C(O)$R^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{11}$ is optionally —$NR^{17}R^{18}$, and wherein if n is 1 or 2, then $R^{11}$ is not hydrogen. $R^{12}$ and $R^{15}$ are independently hydrogen, —$NR^{19}R^{20}$, —$OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ is independently hydrogen, —C(O)$R^{15}$, —S(O)$_2R^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{14}$, $R^{17}$, $R^{18}$, $R^{19}$, $R^{20}$ and $R^{21}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is independently hydrogen, —$NR^{19}R^{20}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

One skilled in the art will understand that the compound of Formula (I) may include more than one of a specific R group. Where more than one of a specific R group is present, each R group is optionally different. For example, the compound of Formula (I) may include more than one of $R^{10}$, $R^{11}$, $R^{12}$, $R^{13}$, $R^{14}$, $R^{15}$, $R^{16}$, $R^{17}$, $R^{18}$, $R^{19}$, $R^{20}$ and/or $R^{21}$. Where more than one of $R^{10}$ is present, for example, each $R^{10}$ is optionally different. The same would hold true for more than one $R^{11}$, $R^{12}$, $R^{13}$, $R^{14}$, $R^{15}$, $R^{16}$, $R^{17}$, $R^{18}$, $R^{19}$, $R^{20}$ or $R^{21}$.

In some embodiments, $R^1$ includes a hydrogen bond donor and a hydrogen bond acceptor, or $L^2$-$R^1$ includes a hydrogen bond donor and a hydrogen bond acceptor. The distance between the hydrogen bond donor and the pyridinone amide nitrogen may be about 7-8 Å when said compound is bound to PDK1. An exemplary set of coordinates for PDK1 that may be used is 1z5m.pdb deposited with the RSCB protein data bank. The distance between the hydrogen bond acceptor and the pyridinone amide nitrogen may be about 8.5-9.5 Å when said compound is bound to PDK1. The determination of the distance between the pyridinone amide nitrogen and the hydrogen bond acceptor and donor is determined using computer modeling techniques known in the art. For example, suitable modeling programs include Macromodel (version 9.1, Schrodinger LLC, New York, N.Y. 2005) and ICM (version 3.406, Molsoft LLC, San Diego Calif. 2006).

In certain embodiments of the compound of Formula (I), the distance between the hydrogen bond donor and the pyridinone amide nitrogen is about 7-8 Å. In other embodiments, the compound of Formula (I) is such that the distance between the hydrogen bond acceptor and the pyridinone amide nitrogen is about 8.5-9.5 Å. In certain other embodiments, the compound of Formula (I) includes 6 atoms (i.e. at least 6 atoms) between the hydrogen bond donor and the pyridinone amide nitrogen. The compound of Formula (I) may also include 8 atoms between the hydrogen bond acceptor and the pyridinone amide nitrogen. The number of atoms between the hydrogen bond donor or acceptor and the pyridinone amide nitrogen does not include the amide nitrogen atom or the hydrogen bond donor or acceptor. The number of atoms is counted along the shortest path without regard to cyclic structures. For illustrative purposes, the below compound includes 4 atoms between the hydrogen bond donor and the pyridinone amide nitrogen, and 6 atoms between the hydrogen bond acceptor and the pyridinone amide nitrogen:

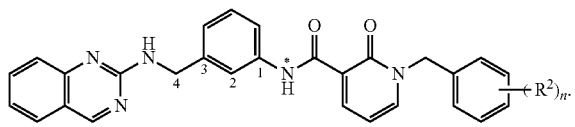

For clarity, the pyridinone amide nitrogen is labeled with an asterisk. By contrast, the following compound includes 6 atoms between the hydrogen bond donor and the pyridinone amide nitrogen and 8 atoms between the hydrogen bond acceptor and the pyridinone amide nitrogen:

In some embodiments, if X is phenylene and $R^1$ is quinazoline or phenyl, then the compound includes 6 atoms between the hydrogen bond donor and the pyridinone amide nitrogen.

$R^1$ or -$L^2$-$R^1$ may include one atom between the hydrogen bond donor and the hydrogen bond acceptor. The hydrogen bond acceptor may form part of $R^1$ and the hydrogen bond donor may form part of $L^2$ or $R^1$.

The hydrogen bond donor is the combination of a strongly electronegative heteroatom relative to carbon (e.g. such as oxygen, or nitrogen) covalently bound to a hydrogen atom that forms part of the hydrogen bond. In some embodiments, the hydrogen bond donor is —N(H)— or —NH$_2$. The hydrogen bond acceptor is a heteroatom having a lone pair of electrons that from part of the hydrogen bond. In some embodiments, the hydrogen bond acceptor is =O or —N=.

In some embodiments, the hydrogen bond acceptor and donor that form part of the $R^1$ or -$L^2$-$R^1$ substituents are capable of hydrogen bonding to the amide backbone nitrogen of A162 of PDK1 and the amide backbone oxygen of S160 of PDK1, respectively.

In some embodiments, $R^1$ is a purine mimetic. A "purine mimetic," as used herein, is a substituted or unsubstituted six-membered ring fused with a five membered ring having at least two nitrogens. Thus, the purine mimetics of the present invention include substituted or unsubstituted aryl fused rings, substituted or unsubstituted heteroaryl fused rings such as substituted or unsubstituted benzothiadiazolyl, substituted or unsubstituted benzo-oxodiazolyl, substituted or unsubstituted imidazopyridinyl, substituted or unsubstituted pyrrolopyridinyl (e.g. 7-azaindole), and substituted or unsubstituted triazolopyridinyl.

In certain embodiments, where X is phenylene, $R^1$ is a substituted or unsubstituted fused ring heteroaryl comprising at least one heteroatom in each ring. In other embodiments, where $R^1$ is phenyl and X is absent, then the phenyl $R^1$ is substituted with —NH—C(O)—$R^9$, wherein $R^9$ is unsubstituted $C_1$-$C_{10}$ alkyl or —NH$_2$. In other embodiments, where $R^1$ is imidazolyl and X is absent, then the $R^1$-imidazolyl is not substituted with a phenyl-containing substituent. In other embodiments, where $R^1$ is imidazolyl and X is absent, then the compound includes 6 atoms between the hydrogen bond donor and the pyridinone amide nitrogen.

In certain embodiments, X is absent, substituted or unsubstituted $C_3$-$C_6$ cycloalkyl, substituted or unsubstituted 3 to 6 membered heterocycloalkyl, or substituted or unsubstituted heteroaryl. X may also be absent or substituted or unsubstituted heteroaryl. In some embodiments, X is substituted or unsubstituted thiazolyl. $L^2$ may unsubstituted $C_1$-$C_5$ alkylene or absent. $R^1$ may be substituted or unsubstituted pyrrolopyridyl.

In some embodiments, X is absent. $L^2$ may be absent or —O—. $L^1$ may be unsubstituted $C_1$-$C_5$ alkylene. $R^1$ may be substituted or unsubstituted 2-benzimidazolinonyl.

In other embodiments, the compound of Formula (I) has the formula:

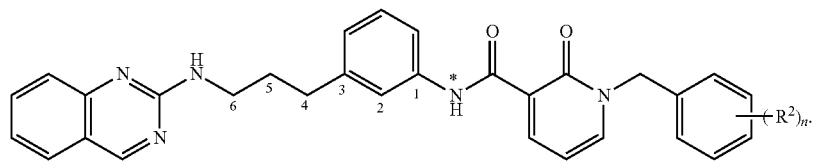

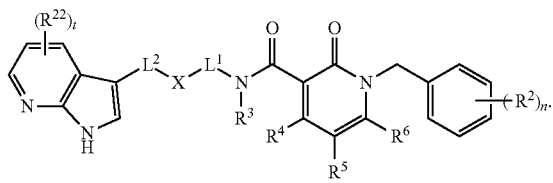
(II)

In Formula (II), the variables are as defined in Formula (I) above. $R^{22}$ is hydrogen, halogen, —OH, —CF$_3$, —NO$_2$, —OR$^{10}$, —S(O)$_n$R$^{11}$, —C(O)R$^{12}$, —NR$_{13}$R$_{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol t represents and integer form 1 to 4. In some embodiment, t is 1. In some embodiments, X is a substituted or unsubstituted 5-membered heteroaryl. One skilled in the art will recognize that $R^{22}$ may be at any position on the 1H-Pyrrolo[2,3-b]pyridinyl group (e.g. on the pyrrolo or pyridinyl portion).

In other embodiments of Formula (I) or (II), X has the formula:

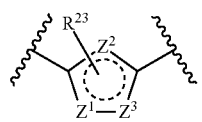
(III)

In Formula (III), $Z^1$, $Z^2$, and $Z^3$ are independently —N═, —NH—, —O—, —S—, or —CH═. $R^{23}$ is hydrogen, halogen, OH, —CF$_3$, —NO$_2$, —OR$^{10}$, —S(O)$_n$R$^{11}$, —C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. One skilled in the art will recognize that $R^{23}$ may be attached at $Z^1$, $Z^2$, or $Z^3$ as the normal rules of chemical valency allow. For example, where $Z^1$ is —NH—, $R^{23}$ may be attached to nitrogen to form —N(R$^{23}$)—.

In other embodiments of Formula (I) or (I), $L^1$ is —C(R$^{24}$)(R$^{25}$)—, wherein $R^{24}$ and $R^{25}$ are independently is hydrogen, halogen, —OH, —CF$_3$, NO$_2$, —OR$^{10}$, S(O)$_n$R$^{11}$, C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In other embodiments, $L^2$ is absent. $R^{10}$, $R^{11}$, $R^{12}$, $R^{13}$, and $R^{14}$ are, independently, as defined above in the description of Formula (I).

In other embodiments of Formula (I) or (II), X is substituted or unsubstituted phenylene and $L^2$ is absent.

In other embodiments, the compound of Formula (I) has the formula:

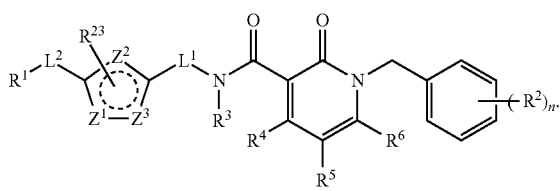
(IV)

In Formula (IV), the variables are as defined in Formula (I) above and $R^{23}$, $Z^1$, $Z^2$, and $Z^3$ are as defined above in the description of Formula (III). In some embodiments of Formula (IV), $L^1$ is —C(R$^{24}$)(R$^{25}$)—, wherein $R^{24}$ and $R^{25}$ are as defined above in the description of Formula (II). In other embodiments, $L^2$ is absent. In some embodiments, $R^3$ is hydrogen. $R^4$, $R^5$, and $R^6$ may also be hydrogen. One skilled in the art will recognize that $R^{23}$ may be attached at $Z^1$, $Z^2$, or $Z^3$ as the normal rules of chemical valency allow. For example, where $Z^1$ is —NH—, $R^{23}$ may be attached to nitrogen to form —N(R$^{23}$)—.

In other embodiments, the compound of Formula (I) has the formula:

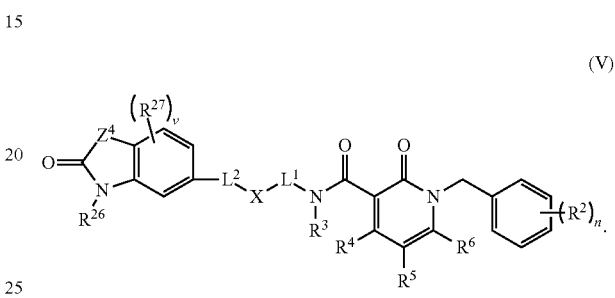
(V)

In Formula (V), the variables are as defined in Formula (I) above. $Z^4$ is —N(R$^{28}$)—, —C(R$^{29}$)(R$^{30}$)—, or

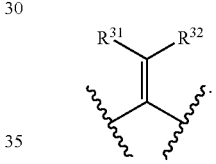

The symbol v is an integer from 1 to 3. $R^{26}$, $R^{27}$, $R^{28}$, $R^{29}$, $R^{30}$, $R^{31}$, and $R^{32}$ are independently selected from hydrogen, halogen, —OH, —CF$_3$, —NO$_2$, —OR$^{10}$, —S(O)$_n$R$^{11}$, —C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{26}$, $R^{27}$, $R^{28}$, $R^{29}$, $R^{30}$, $R^{31}$, and $R^{32}$ may also independently be hydrogen, halogen, —OH, —CF$_3$, —NO$_2$, —OR$^{10}$, —S(O)R$^{11}$, —C(O)R$^{12}$, —NR$^{13}$R$^{14}$, unsubstituted C$_1$-C$_{10}$ alkyl, or unsubstituted 2 to 20 membered heteroalkyl. In some embodiments, $R^{27}$ is not hydrogen. In certain embodiments, $R^{26}$ and $R^{28}$ are hydrogen, and $R^{27}$ is hydrogen or halogen. In other embodiments, $R^{26}$ is methyl and $R^{28}$ is hydrogen. $R^{10}$, $R^{11}$, $R^{12}$, $R^{13}$, and $R^{14}$ are, independently, as defined above in the description of Formula (I). In some embodiments of Formula (V), $R^4$, $R^5$, and $R^6$ are hydrogen. $R^3$ may also be hydrogen. $R^5$ may be halogen (e.g. Cl).

In some embodiments, $R^{29}$ and $R^{30}$ are independently hydrogen or unsubstituted C$_1$-C$_{10}$ alkyl (e.g. a C$_1$-C$_5$ alkyl such as methyl). In other embodiments, $R^{31}$ is a substituted or unsubstituted heteroaryl (e.g. a five-membered heteroaryl) or substituted or unsubstituted C$_1$-C$_{10}$ alkyl. $R^{32}$ may be hydrogen.

In some embodiments of Formula (V), X is absent. $L^2$ may be —O—. $L^1$ may be substituted or unsubstituted alkylene and $L^2$ may be absent. $L^1$ may also be —C(R$^{24}$)(R$^{25}$)—, wherein $R^{24}$ and $R^{25}$ are independently is hydrogen, halogen, —OH, —CF$_3$, —NO$_2$, —OR$^{10}$, —S(O)$_n$R$^{11}$, —C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In other embodiments, the compound of Formula (I) has the formula

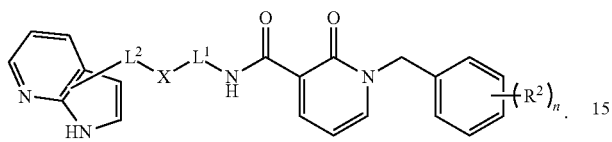

(VI)

In Formula (VI), the variables are as defined in Formula (I) above.

In other embodiments, the compound of Formula (I) has the formula

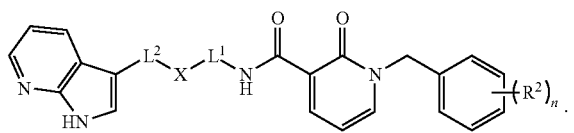

(VII)

In Formula (VII), the variables are as defined in Formula (I) above. In some embodiments, X is substituted or unsubstituted heteroarylene, such as substituted or unsubstituted pyridinylene.

In other embodiments, the compound of Formula (I) has the formula:

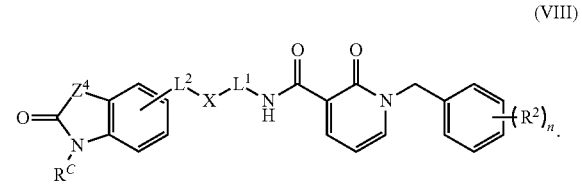

(VIII)

In Formula (VIII), R$^C$ is hydrogen, or C$_{1-3}$ alkyl and the remaining the variables are as defined in Formula (I) above.

In other embodiments, the compound of Formula (I) has the formula:

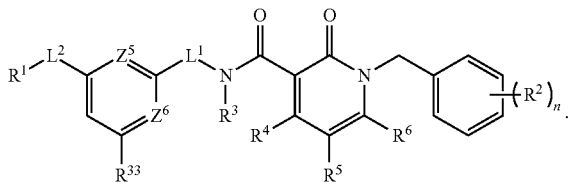

(IX)

The variables of Formula (IX) are as defined above in the description of Formula (I). Z$^5$ and Z$^6$ are independently =N— and =C(R$^{23}$)—. R$^{23}$ is as defined in the description of Formula (III). R$^{33}$ is hydrogen, halogen, —OH, —CF$_3$, —NO$_2$, —OR$^{10}$, —S(O)$_n$R$^{11}$, —C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, one of Z$^5$ and Z$^6$ is =N— and one of Z$^5$ and Z$^6$ is =C(R$^{23}$)—. In other embodiments Z$^6$ is =N— and Z$^5$ is =CH—. R$^{33}$ may be halogen, —OH, —CF$_3$, —NO$_2$, —OR$^{10}$ (e.g. methoxy), —C(O)R$^{12}$ (e.g. —C(O)OCH$_3$, C(O)NHCH$_3$, or —C(O)N(CH$_3$)$_2$), or unsubstituted C$_1$-C$_{10}$ alkyl.

In other embodiments, the compound of Formula (I) has the formula:

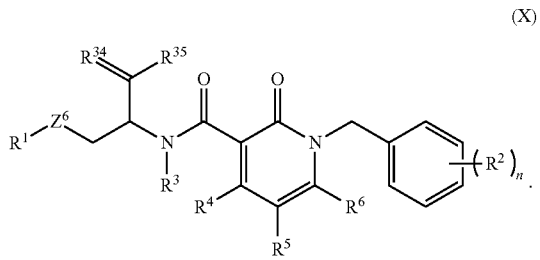

(X)

The variables of Formula (X) are as defined above in the description of Formula (I). R$^{34}$ and R$^{35}$ are independently selected from hydrogen, halogen, —OH, —CF$_3$, —NO$_2$, —OR$^{10}$, —S(O)R$^{11}$, —C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Z$^6$ is =N(R$^{36}$)—, —O—, —S—, or —C(R$^{37}$R$^{38}$)—. R$^{36}$, R$^{37}$, and R$^{38}$ are independently hydrogen, halogen, —OH, —CF$_3$, —NO$_2$, —OR$^{10}$, S(O)$_n$R$^{11}$, —C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, Z$^6$ is —O—.

In another embodiment, the compound of Formula (X) has the formula:

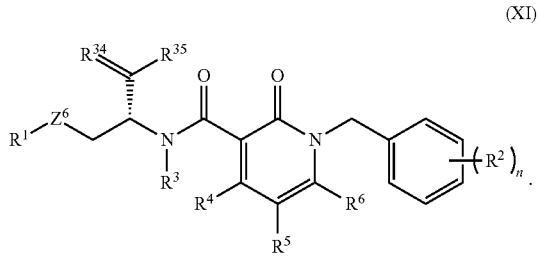

(XI)

In another embodiment, the compound of Formula (I) has the formula:

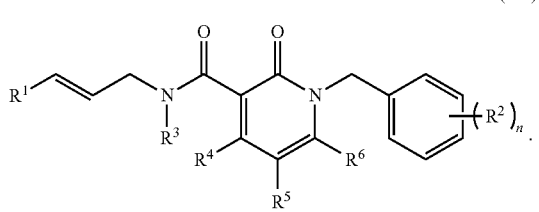

(XII)

The variables of Formula (XII) are as defined above in the description of Formula (I).

In another embodiment, the compound of Formula (I) has the formula:

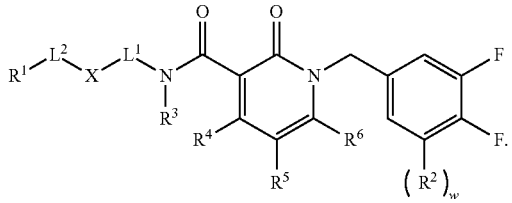

(XIII)

The variables of Formula (XIII) are as defined above in the description of Formula (I). The symbol w represents 0 or 1. In some embodiments, $R^2$ is a halogen, such as fluorine.

In another embodiment, the compound of Formula (I) has the formula:

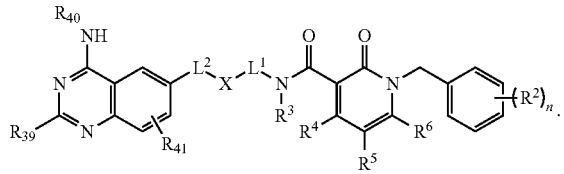

(XIV)

The variables of Formula (XIV) are as defined above in the description of Formula (I). $R^{39}$, $R^{40}$, and $R^{41}$ are independently hydrogen, halogen, —OH, —$CF_3$, —$NO_2$, —$OR^{10}$, —$S(O)_nR^{11}$, —$C(O)R^{12}$, —$NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{39}$ is hydrogen, —OH, —$NHR^{13}$. $R^{39}$ may also simply be hydrogen. In some embodiments, $R^{40}$ is hydrogen, —OH, —$CF_3$, —$OR^{10}$, —$S(O)R^{11}$, —$C(O)R^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{40}$ may also be hydrogen or an unsubstituted $C_1$-$C_{10}$ alkyl. In certain embodiments, $R^{40}$ is hydrogen. $R^{41}$ may be hydrogen or an unsubstituted $C_1$-$C_{10}$ alkyl. $R^{41}$ may also be hydrogen. In some embodiment, X is thiophenylene. $L^1$ may be a bond.

In other embodiments, the compound of Formula (I) has the formula:

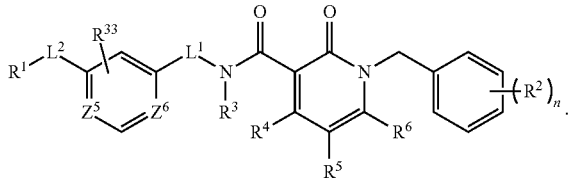

(XV)

The variables of Formula (XV) are as defined above in the description of Formula (I) and Formula (IX). In some embodiments, $Z^5$ and $Z^6$ are =N—.

In some embodiments, each substituted group described above in the compound of Formulae (I)-(XV) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted or unsubstituted cycloalkylene, substituted or unsubstituted heterocycloalkylene, substituted or unsubstituted arylene, or substituted or unsubstituted heteroarylene described above in the compounds of Formulae (I)-(XV) is substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I)-(XV), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene substituted or unsubstituted $C_4$-$C_8$ cycloalkylene, and each substituted or unsubstituted heterocycloalkylene is a substituted or unsubstituted 4 to 8 membered heterocycloalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene substituted or unsubstituted $C_5$-$C_6$ cycloalkylene, and each substituted or unsubstituted heterocycloalkylene is a substituted or unsubstituted 5 to 7 membered heterocycloalkylene.

II. EXEMPLARY SYNTHESES

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Scheme 1

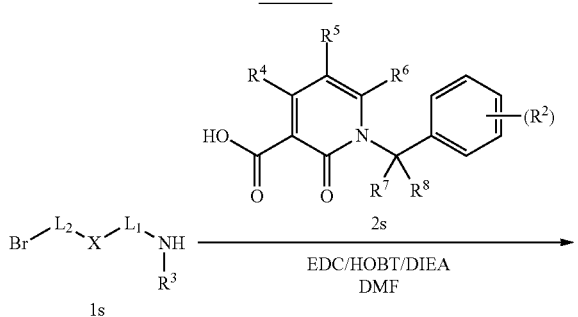

-continued

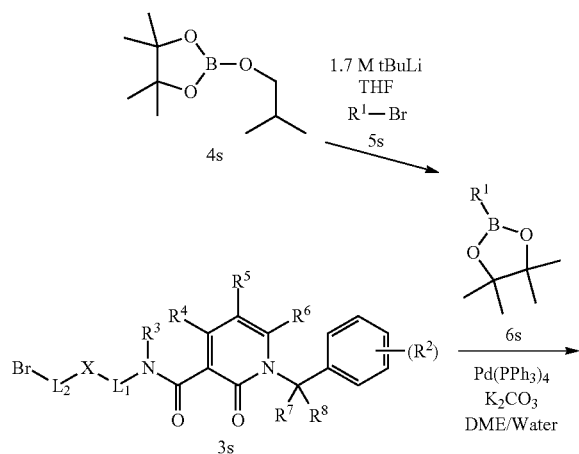

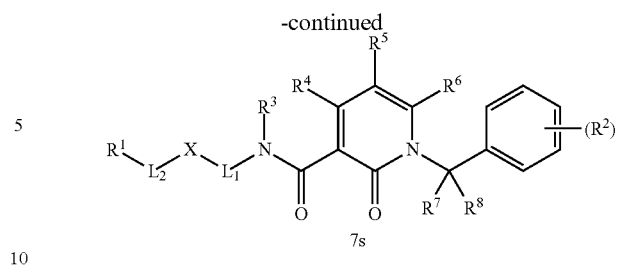

Compounds having the formula of 7s may be synthesized as shown above in Scheme 1. X, $R^1$, $R^2$, $R^3$, $R^4$, $R^5$, $R^6$, $R^7$, and $R^8$ are as defined above. Compound 3s is synthesized using standard amide bond formation chemistry to couple the amine of 1s and the free carboxylic acid of 2s. The activated boronic acid ester 6s is provided by substitution of the bromine of 5s with the precursor boronic acid ester 4s. Coupling of 3s and 5s is performed under standard Suzuki conditions to yield the desired 7s. Alternatively, [1,1'-bis (diphenylphosphino)ferrocene]dichloropalladium(II), complex with dichloromethane (1:1); $Na_2CO_3$; and dioxane/water may be used instead of $Pd(PPh_3)_4$; $K_2CO_3$; and DME/water.

Scheme 2

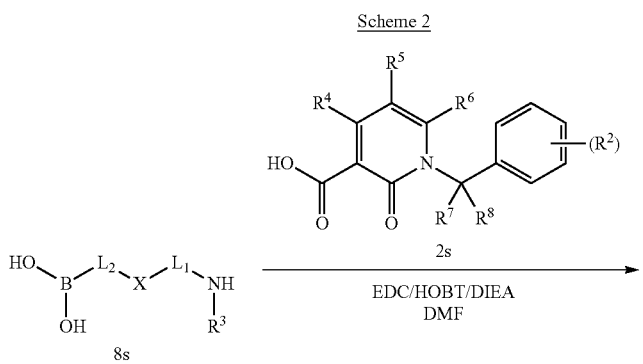

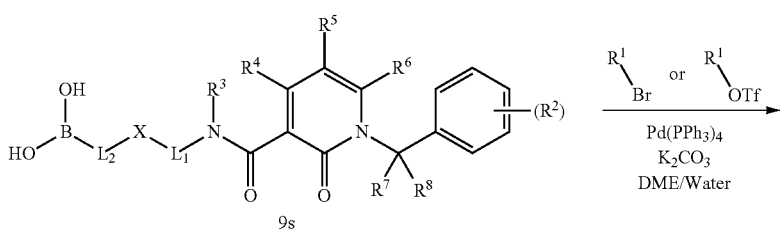

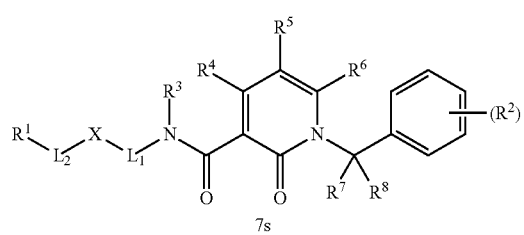

Alternatively, R¹ substituents may be coupled according to Scheme 2 above. Here, 9s is prepared using standard amide bond formation chemistry, then reacted with an activated R¹ substituent using standard Suzuki conditions to provide the desired 7s.

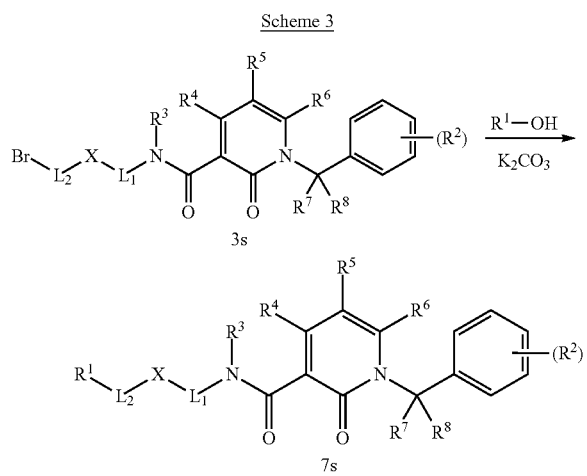

Scheme 3

In other embodiments, 7s is synthesized according to Scheme 3. Substitution of brominated 3s using R¹—OH in the presence of potassium carbonate yields the desired 7s.

III. METHODS

In another aspect, the present invention provides a method of decreasing PDK1 catalytic activity. The method includes contacting a PDK1 with an effective amount of a pyridinonyl PDK1 inhibitor. Therefore, the present invention further provides a method of inhibiting PDK1 catalytic activity by contacting a PDK1 with a pyridinonyl PDK1 inhibitor of the present invention.

PDK1 catalytic activity, as used herein, refers to PDK1 kinase catalytic activity. Thus, where PDK1 catalytic activity is decreased, the phosphorylation of a PDK1 substrate (e.g. Akt) is decreased relative to the phosphorylation rate in the absence of the pyridinonyl PDK1 inhibitor. In some embodiments, the $IC_{50}$ of the pyridinonyl PDK1 inhibitor against PDK1 is less than 1 µM. In other embodiments, the $IC_{50}$ of the pyridinonyl PDK1 inhibitor against PDK1 is less than 500 nM. In other embodiments, the $IC_{50}$ of the pyridinonyl PDK1 inhibitor against PDK1 is less than 100 nM. In other embodiments, the $IC_{50}$ of the pyridinonyl PDK1 inhibitor against PDK1 is less than 10 nM. In other embodiments, the $IC_{50}$ of the pyridinonyl PDK1 inhibitor against PDK1 is less than 1 nM. In other embodiments, the $IC_{50}$ of the pyridinonyl PDK1 inhibitor against PDK1 is from 0.1 nM to 10 µM. In other embodiments, the $IC_{50}$ of the pyridinonyl PDK1 inhibitor against PDK1 is from 0.1 nM to 1 µM. In other embodiments, the $IC_{50}$ of the pyridinonyl PDK1 inhibitor against PDK1 is from 0.1 nM to 100 nM. In other embodiments, the $IC_{50}$ of the pyridinonyl PDK1 inhibitor against PDK1 is from 0.1 nM to 10 nM.

In another aspect, are useful for the treatment of diseases and disorders that may be alleviated by inhibiting (i.e. decreasing) PDK1 catalytic activity (e.g. cancer). By "diseases" is meant diseases, or disease symptoms. Thus, the present invention provides a method of treating cancer in a subject in need thereof. The method includes administering to the subject a therapeutically effective amount of a pyridinonyl PDK1 inhibitor. The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, anaplastic large-cell lymphoma, leukemia (e.g. acute myeloid leukemia, T-cell leukemia, chronic lymphocytic leukemia), multiple myeloma, malignant mesothelioma, malignant melanoma, colon cancer (e.g. microsatellite instability-high colorectal cancer).

In another aspect, the present invention provides methods for selectively reducing PDK1 mediated phosphorylation of Akt relative to phosphorylation of PKC. The method includes contacting PDK1 with a compound of the present invention in the presence of Akt and PKC. PDK1 mediated phosphorylation of Akt is reduced relative to PDK1 mediated phosphorylation of PKC (e.g. PKC isoforms zeta delta and/or theta). In some embodiments, the PDK1 mediated phosphorylation of Akt is inhibited at least 5, 10, 50, 100, or 1000 fold relative to the PDK1 mediated phosphorylation of PKC. Assays for determining the inhibition of PDK1 mediated phosphorylation of Akt and PKC are provided in the Examples below.

In some embodiments, the PDK1 mediated phosphorylation of Akt is reduced relative to phosphorylation of PKC in a cell. Thus, the present invention provides methods for selectively reducing PDK1 mediated phosphorylation of Akt relative to phosphorylation of PKC in a cell. The method includes contacting the cell with a compound of the present invention. PDK1 mediated phosphorylation of Akt is reduced relative to PDK1 mediated phosphorylation of PKC (e.g. PKC isoforms zeta delta and/or theta). In some embodiments, the PDK1 mediated phosphorylation of Akt is inhibited at least 5, 10, 50, 100, or 1000 fold relative to the PDK1 mediated phosphorylation of PKC. Assays for determining the inhibition of PDK1 mediated phosphorylation of Akt and PKC are provided in the Examples below. The cell in which PDK1 mediated phosphorylation of Akt is reduced is typically a mammalian cell, such as a domestic animal (e.g. cat, dog, hose, cow, etc.) of human.

IV. ASSAYS

To develop useful PDK1 inhibitors, candidate inhibitors capable of decreasing PDK1 catalytic activity may be identified in vitro. The activity of the inhibitor compounds can be assayed utilizing methods known in the art and/or those methods presented herein.

Compounds that decrease PDK1 catalytic activity may be identified and tested using biologically active PDK1, either recombinant or naturally occurring. PDK1 can be found in native cells, isolated in vitro, or co-expressed or expressed in a cell. Measuring the reduction in the PDK1 catalytic activity in the presence of an inhibitor relative to the activity in the absence of the inhibitor may be performed using a variety of methods known in the art, such as the assay described in Example 44. Other methods for assaying the activity of PDK1 are known in the art. The selection of appropriate assay methods is well within the capabilities of those of skill in the art.

Once compounds are identified that are capable of reducing PDK1 catalytic activity, the compounds may be further tested for their ability to selectively inhibit PDK1 relative to other enzymes. Inhibition by a compound of the invention is measured using standard in vitro or in vivo assays such as those well known in the art or as otherwise described herein.

Compounds may be further tested in cell models or animal models for their ability to cause a detectable changes in phenotype related to PDK1 activity. In addition to cell cultures, animal models may be used to test inhibitors of PDK1 for their ability to treat cancer in an animal model.

V. PHARMACEUTICAL COMPOSITIONS

In another aspect, the present invention provides pharmaceutical compositions comprising a PDK1 inhibitor compound of the invention or a PDK1 inhibitor compound in combination with a pharmaceutically acceptable excipient (e.g. carrier).

The pharmaceutical compositions include optical isomers, diastereomers, or pharmaceutically acceptable salts of the inhibitors disclosed herein. For example, in some embodiments, the pharmaceutical compositions include a compound of the present invention and citrate as a pharmaceutically acceptable salt. The PDK1 inhibitor included in the pharmaceutical composition may be covalently attached to a carrier moiety, as described above. Alternatively, the PDK1 inhibitor included in the pharmaceutical composition is not covalently linked to a carrier moiety.

A "pharmaceutically suitable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

A. Formulations

The PDK1 inhibitors of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of administered to a mammal can vary depending upon a variety of factors, including a disease that results in increased activity of PDK1, whether the mammal suffers from another disease, and its route of administration; size, age, sex, health, body weight, body mass index, and diet of the recipient; nature and extent of symptoms of the disease being treated (e.g., cancer), kind of concurrent treatment, complications from the disease being treated or other health-related problems. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of reducing the activity of PDK1 catalytic activity, as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring PDK1 inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side-effects. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

IV. EXAMPLES

The examples below are meant to illustrate certain embodiments of the invention, and not to limit the scope of the invention. Abbreviations: AcCN=acetonitrile; BuOH=butanol; DCM=dichloromethane; DIEA, DIPEA=N,N-diisopropylethylamine; DMA=N,N-dimethylacetamide; DMAP=N,N-dimethylaminopyridine; DMF=N, N-dimethylformamide; DMSO=dimethylsulfoxide; EDC=N-(3-dimethylaminopropyl)-N'-ethylcarbodiimide hydrochloride; EtOAc=Ethyl Acetate; HOBt=1-hydroxybenzotriazole; HPLC=high pressure liquid chromatography; MS=mass-spectrometry; MsCl=methanesulfonylchloride; NMR=nuclear magnetic resonance; TFA=trifluoroacetic acid; THF=tetrahydrofuran.

Example 1

1.1 To a 2-dram vial were added (5-amino-pentyl)-carbamic acid tert-butyl ester (0.04 g, 0.2 mmol) and 1-(3-chloro-benzyl)-2-oxo-1,2-dihydro-pyridine-3-carboxylic acid (0.047 g, 0.2 mmol) in 2 ml of $CH_3CN$. To this mixture were added 2-chloro-1,3-dimethylimidazolinium chloride (0.037 g, 0.22 mmol) and di-isopropyl-ethylamine (0.031 g, 0.24 mmol). The vial was capped and shaken at room temperature overnight. The solvent was removed using solvent evaporator GeneVac HT-12. To this vial were added 3 ml of $CH_2Cl_2$ and 1.5 ml of water. The vial was shaken vigorously and the water was removed. The organic solvent was removed using the GeneVac HT-12 to give the oily liquid Compound 1.1. ES (+) MS m/e=448 (M+1).

1.2 To the dry liquid of Compound 1.1 in a 2-dram vial was added 2 ml of $CH_2Cl_2$ and 1 ml of HCl (4.0 M in dioxane). The vial was capped and shaken at room temperature for 3 hours. The mix solvent was removed using the GeneVac HT-12. To the dry compound in 2-dram vial were added s-BuOH (2 ml), N(-6-chloro-pyrimidin-4-yl)-acetamide (0.034 g, 0.2 mmol), and 3 equivalents of $K_2CO_3$. The vial was capped and shaken at 110° C. for 16 hours. The solvent was filtered and concentrated using GeneVac HT-12. The crude product was dissolved in DMSO (3 ml) and purified by using HPLC (reverse phase) to give Compound

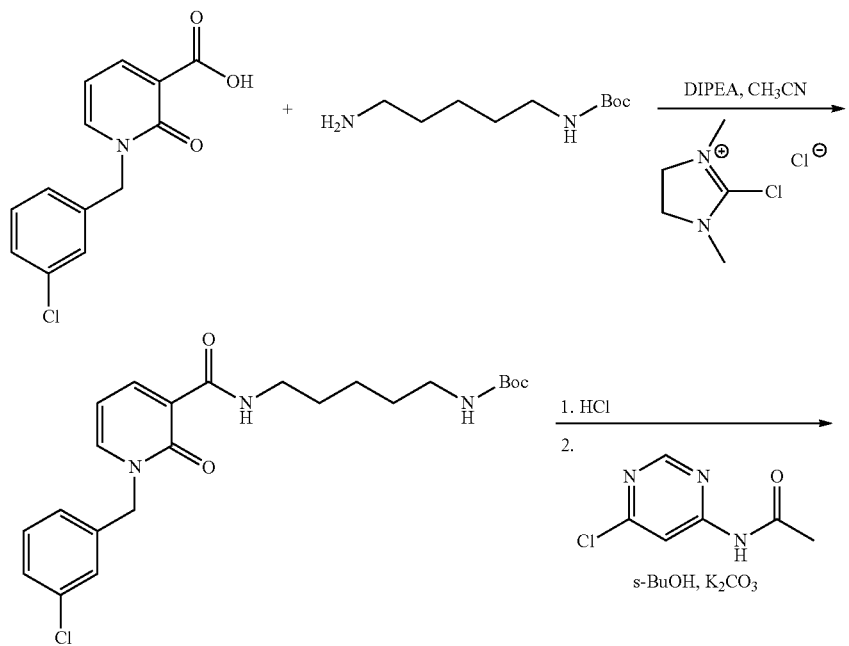

Compound 1.1

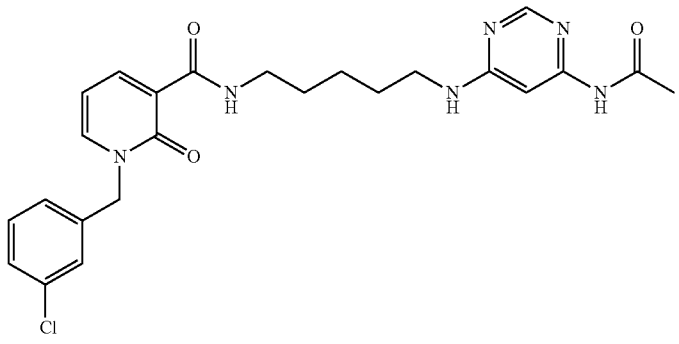

Compound 1.2

1.2. ES (+) MS m/e=483.19 (M+1). 1H NMR (400 MHz, 400 MHz, CD₃OD)™ ppm 1.50 (m, 2H), 1.70 (m, 4H), 2.20 (s, 3H), 3.45 (m, 5H), 5.25 (s, 2H), 6.55 (m, 1H), 7.2-7.4 (m, 6H), 8.00 (s, 1H), 8.30 (s, 1H), 8.50 (s, 1H), 10.0 (s, 1H).

Example 2

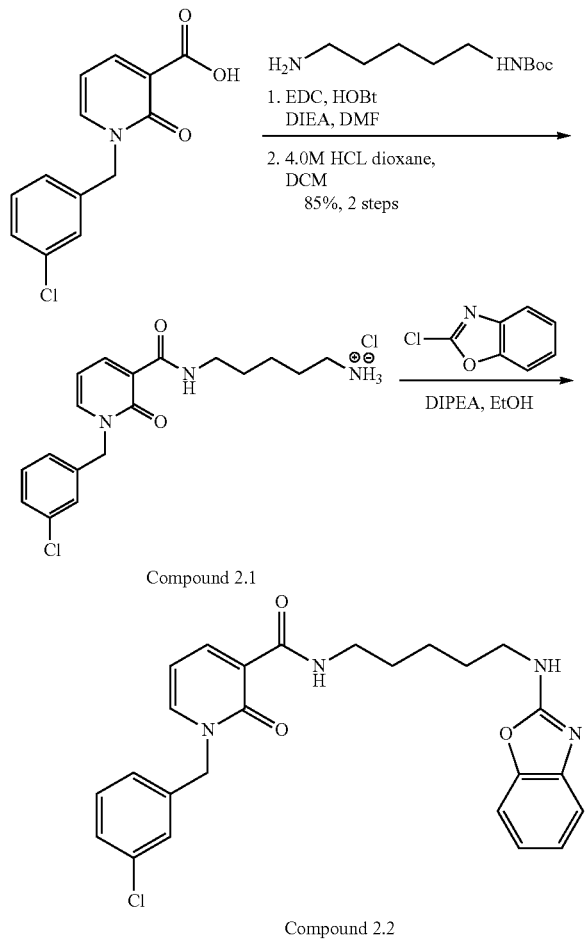

Compound 2.1

Compound 2.2

2.1 1-(3-Chloro-benzyl)-2-oxo-1,2-dihydro-pyridine-3-carboxylic acid (2.59 grams, 9.82 mmol) was combined with N-(3-dimethylaminopropyl)-N'-ethylcarbodiimide hydrochloride (2.07 grams, 10.80 mmol) and 1-hydroxybenzotriazole monohydrate (1.65 grams, 10.80 mmol) in DMF (25 ml). (5-Amino-pentyl)-carbamic acid tert-butyl ester (1.99 grams, 9.82 mmol) dissolved in DMF (25 ml) was added followed by diisopropylethylamine (6.0 ml, 34.37 mmol). The reaction was stirred at ambient temperature for 17 hours, concentrated, and EtOAc was added. The reaction mixture was washed with 1M sodium hydrogen sulfate monohydrate, saturated sodium bicarbonate, brine, dried over sodium sulfate, filtered and concentrated to give 3.76 grams of Boc protected intermediate which was used without further purification. This was dissolved in DCM (20 ml) and 4.0 M HCL p-dioxane (21 ml) was added. After stirring at ambient temperature for 1 hour, the solvents were removed to give Compound 2.1 (3.20 grams, 8.33 mmol, 85%). 1H NMR (400 MHz, DMSO-d6) δ ppm 1.31 (m, 2H) 1.52 (m, 4H) 2.73 (m, 2H) 3.26 (m, 2H) 5.24 (m, 2H) 6.57 (m, 1H) 7.25 (m, 1H) 7.37 (m, 3H) 8.09 (br. s., 3H) 8.27 (m, 1H) 8.34 (m, 1H) 9.63 (m, 1H).

2.2 Compound 2.1 (0.096 grams, 0.25 mmol) and 2-chloro-benzooxazole (0.038 grams, 0.25 mmol) were dissolved in ethanol (1 ml) and diisopropylethylamine (0.152 ml, 0.875 mmol) was added. The reaction was heated in a sealed tube with stirring at 70° C. for 16 hours, cooled, EtOAc was added and the mixture washed with saturated sodium bicarbonate, dried over sodium sulfate, filtered, and evaporated. The crude residue was dissolved in acetonitrile and purified by preparative HPLC to give Compound 2.2 ES (+) MS m/e=467 (M+3). 1H NMR (400 MHz, MeOH-d4) δ ppm 1.40 (m, 2H) 1.61 (m, 4H) 3.30 (m, 2H) 3.38 (m, 2H) 5.10 (m, 2H) 6.43 (m, 1H) 7.18 (m, 5H) 7.36 (m, 1H) 7.88 (m, 1H) 8.26 (m, 1H).

Example 3

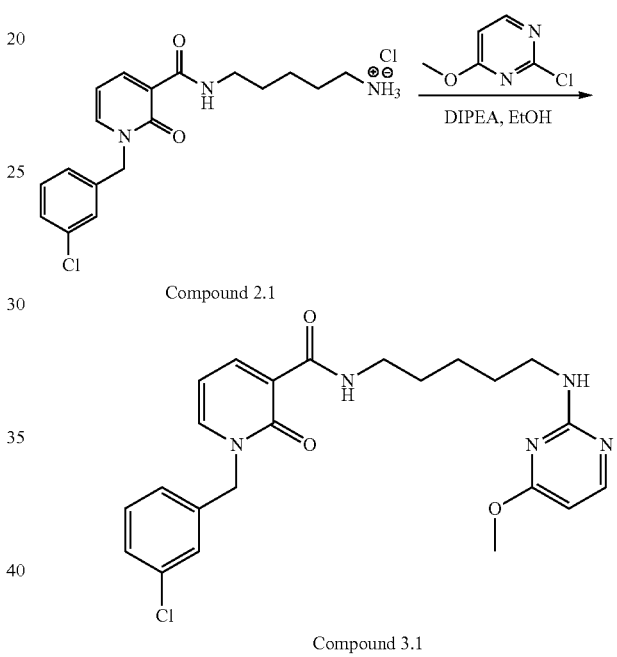

Compound 2.1

Compound 3.1

3.1 This was made as in Example 2.2 except reacting Compound 2.1 with 2-Chloro-4-methoxy-pyrimidine. ES (+) MS m/e=458 (M+3). 1H NMR (400 MHz, MeOH-d4) δ ppm 1.36 (m, 2H) 1.58 (m, 4H) 3.19 (m, 1H) 3.29 (m, 2H) 3.42 (m, 1H) 3.91 (m, 3H) 5.11 (m, 2H) 6.23 (m, 1H) 6.44 (m, 1H) 7.17 (m, 4H) 7.80 (m, 1H) 7.89 (m, 1H) 8.30 (m, 1H).

Example 4

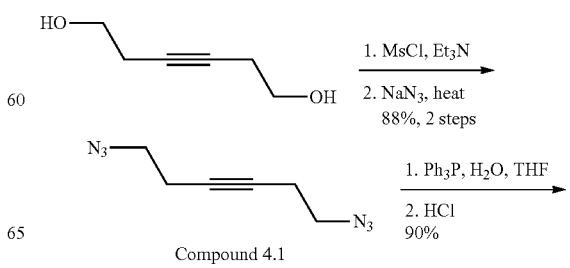

Compound 4.1

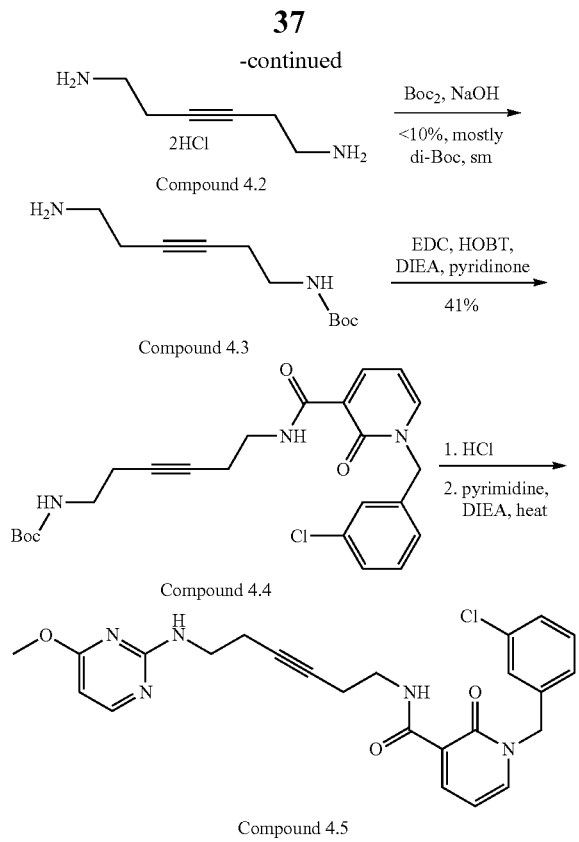

Compound 4.2

Compound 4.3

Compound 4.4

Compound 4.5

4.1 3-hexyne-1,6-diol (10.0 grams, 88.0 mmol) was dissolved in 100 ml dry DCM and chilled in an ice-water bath. To this was slowly added triethylamine (24.5 ml, 176 mmol) and methanesulfonylchloride (13.8 ml, 178 mmol). After ~15 minutes the reaction was removed from the ice bath, allowed to warm to room temperature, and stirred for 3 hours. This was then filtered through a medium glass flit and the precipitate was rinsed with 50 ml DCM. The filtrate was evaporated to dryness to yield 30.9 grams of orange gel which was used without further purification. ES (+) MS m/e=293 (M+23) This was suspended in 100 ml dry DMF and sodium azide was added (32.3 g, 495 mmol). The reaction was heated at 70° C. for 17 hours, after which 150 ml water was added and the reaction was extracted with 4×75 ml diethyl ether. The combine ether fractions were washed with 100 ml water and 100 ml brine, dried over sodium sulfate, filtered, and evaporated to yield Compound 4.1 (12.74 g, 77.7 mmol, 88%) as a yellow liquid which was stored at −20° C. ES (+) MS m/e=329 (2M+1).

4.2 Compound 4.1 (4.52 g, 27.6 mmol) was dissolved in 100 ml THF and triphenylphosphine (14.5 g, 55.2 mmol) was added along with water (1.1 ml, 61 mmol). The reaction was allowed to stir at room temperature under nitrogen for 24 hours, at which point 100 ml of diethyl ether and 15 ml of 4 M HCl in dioxane were added to produce an intense white precipitate. This was filtered through a medium glass flit, the precipitate was rinsed 2× with diethyl ether, and the precipitate was then dried to give Compound 4.2 (4.577 g, 24.7 mmol, 90%) as an off-white solid. 1H NMR (400 MHz, Methanol-d4)™ ppm 2.61 (m, 4H) 3.09 (m, 4H).

4.3 Compound 4.2 (4.551 g, 24.6 mmol) was dissolved in 1 N aqueous sodium hydroxide (50 ml) and then di-tert-butyl-dicarbonate (5.306 g, 24.3 mmol) pre-dissolved in 40 ml para-dioxane was added. After two hours 50 ml water was added, the reaction was extracted with 4×30 ml ethyl acetate, the combined organics were rinsed with 50 ml brine, dried over sodium sulfate, filtered, and evaporated to dryness. This was then purified using flash chromatography on a 13×6.5 cm column, eluting initially with 95:5 DCM to methanol with 2 M ammonia, then switching to 4:1 DCM to methanol with 2 M ammonia. Fractions containing Compound 4.3 were combined and evaporated to give 0.33 grams (1.56 mmol, 6.3%) as a yellow oil. ES (+) MS m/e=213 (M+1).

4.4 1-(3-chlorobenzyl)-2-oxo-1,2-dihydro-3-pyridin-carboxylic acid (0.456 g, 1.73 mmol), 1-hydroxybenzotriazole (0.237 g, 1.76 mmol), and N-(3-dimethylaminopropyl)-N'-ethylcarbodiimide hydrochloride (0.328 g, 1.71 mmol) were suspended in 5 ml dry DMF and added to Compound 4.3 (0.33 g, 1.56 mmol) along with another 5 ml DMF. Diisopropylethylamine (0.55 ml, 3.1 mmol) was added and the reaction was stirred for 22 hours at room temperature. The reaction was then flooded with 80 ml ethyl acetate, rinsed with 2×40 ml 1 M aqueous sodium hydrogen sulfate, 2×40 ml saturated sodium bicarbonate, and 40 ml brine, dried over sodium sulfate, filtered, and evaporated to a yellow oil which was purified by flash chromatography on a 14×4.5 cm column, first with 60:40 ethyl acetate to hexane, then 75:25 ethyl acetate to hexane. Pure fractions were combined and evaporated to yield Compound 4.4 as a colorless resin (0.292 g, 41%). ES (+) MS m/e=458 (M+1). 1H NMR (400 MHz, CHLOROFORM-D) ™ ppm 1.43 (m, 9H) 2.36 (m, 2H) 2.46 (m, 2H) 3.22 (m, 2H) 3.58 (m, 2H) 5.20 (m, 2H) 5.70 (m, 1H) 7.17 (m, 1H) 7.32 (m, 2H) 7.54 (m, 1H) 8.58 (m, 1H) 10.00 (m, 1H).

4.5 This was made as in Example 3.1, but starting with Compound 4.4. ES (+) MS m/e=466.9 (M+1). 1H NMR (400 MHz, CHLOROFORM-D) ™ ppm 2.45 (m, 2H) 2.53 (m, 2H) 3.55 (m, 2H) 3.64 (m, 2H) 4.07 (s, 3H) 5.20 (s, 2H) 6.16 (m, 1H) 6.46 (m, 1H) 7.15 (m, 1 H) 7.24 (s, 1H) 7.29 (m, 2H) 7.55 (m, 1H) 7.77 (m, 1H) 8.55 (m, 1H) 10.03 (m, 1H) 10.28 (m, 1H).

Example 5

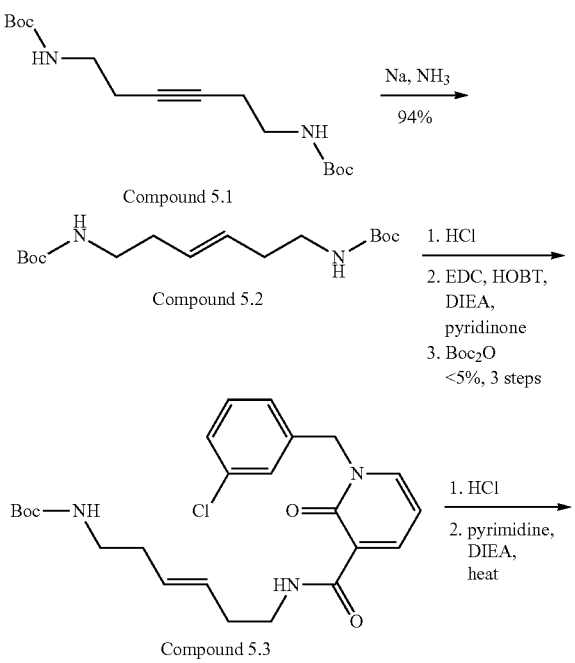

Compound 5.1

Compound 5.2

Compound 5.3

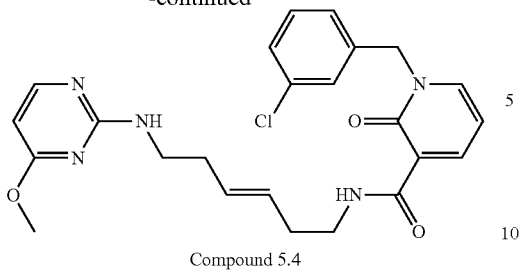

Compound 5.4

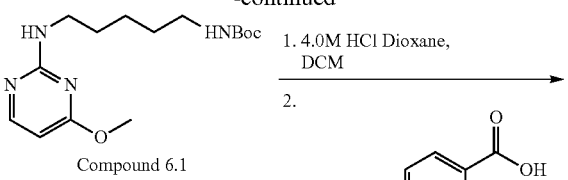

Compound 6.1

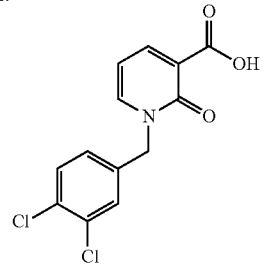

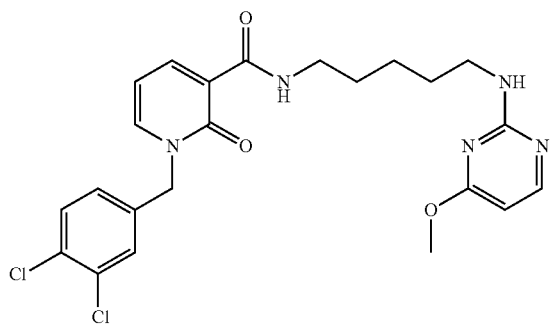

Compound 6.2

5.1 Compound 5.1 was isolated during the synthesis of Compound 4.3 as a white solid in 38% yield. ES (+) MS m/e=335 (M+23).

5.2 Compound 5.1 (0.757 g, 2.43 mmol) was dissolved in 15 ml of dry THF and added to 50-100 ml of liquid ammonia cooled in a dry-ice acetone bath. A cube of sodium metal (0.8 g, 34 mmol) was cut into pieces and added to the reaction, which became dark blue. After two hours the reaction was quenched with ammonium chloride (2.02 g) and allowed to warm to room temperature. The reaction was then diluted with 80 ml ethyl acetate and washed with 50 ml water, 40 ml saturated sodium bicarbonate, and 40 ml brine, dried over sodium sulfate, filtered, and evaporated to dryness to yield Compound 5.2 as an off-white solid (0.719 g, 2.29 mmol, 94%). ES (+) MS m/e=337 (M+23).

5.3 Compound 5.2 (0.716 g, 2.28 mmol) was deprotected with 20 ml of 4 M HCl in dioxane for 75 minutes and then evaporated to dryness. This was then suspended in 15 ml dry DMF to which was added to a suspension containing 1-(3-chlorobenzyl)-2-oxo-1,2-dihydro-3-pyridin-carboxylic acid (0.603 g, 2.29 mmol), 1-hydroxybenzotriazole (0.319 g, 2.36 mmol), and N-(3-dimethylaminopropyl)-N'-ethylcarbodiimide hydrochloride (0.445 g, 2.32 mmol) in 10 ml dry DMF. Diisopropylethylamine (1.6 ml, 9.19 mmol) was added and the reaction was stirred for 17 hours at room temperature at which time di-tert-butyl-dicarbonate (0.513 g, 2.35 mmol) was added and the reaction allowed to proceed for three days. The reaction was then diluted with 50 ml of 1 M aqueous sodium hydrogen sulfate, extracted with 4×30 ml ethyl acetate, and the combined organics were rinsed with 50 ml of 1 M aqueous sodium hydrogen sulfate, 2×50 ml of saturated aqueous sodium bicarbonate, 50 ml brine, dried over sodium sulfate, filtered, evaporated to dryness, and purified three times using flash chromatography, first with 80:20 ethyl acetate to hexane, then 97:3 DCM to methanol, and finally 80:20 ethyl acetate to hexane. Compound 5.3 was isolated as a yellow oil (39 mg, 0.085 mmol, 3.7%). ES (+) MS m/e=460 (M+1).

5.4 This was made as in Example 3.x, but starting with Compound 5.3. ES (+) MS m/e=468 (M+1).

Example 6

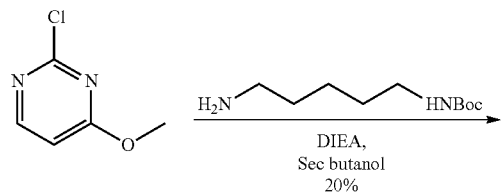

6.1 2-Chloro-4-methoxy-pyrimidine (1.09 grams, 7.51 mmol) and (5-amino-pentyl)-carbamic acid tert-butyl ester (1.52 grams, 7.51 mmol) and diisopropylethylamine (6.54 ml, 37.6 mmol) were combined in sec-butanol (10 ml) and heated to 160° C. by microwave irradiation for 20 minutes. The reaction mixture was diluted with EtOAc and washed with saturated sodium bicarbonate, brine, dried over sodium sulfate, filtered and concentrated. The crude residue was purified by column chromatography on silica (5% MeOH/DCM) to yield Compound 6.1 (0.459 grams, 1.48 mmol, 20%). 1H NMR (400 MHz, MeOH-d4) δ ppm 1.26 (m, 2H) 1.31 (m, 9H) 1.39 (m, 2H) 1.50 (m, 2H) 2.92 (m, 2H) 3.22 (m, 2H) 3.76 (m, 3H) 5.87 (m, 1H) 7.78 (m, 1H).

6.2 Compound 6.1 (0.459 grams, 1.48 mmol) was dissolved in DCM (5 ml) and 4.0 M HCl in p-dioxane (3 ml) was added. After 30 minutes, the reaction was concentrated and the residue made into a 0.3 M solution in dimethylacetamide. 1.0 ml (0.185 mmol) of this solution was combined with 1-(3,4-Dichloro-benzyl)-2-oxo-1,2-dihydro-pyridine-3-carboxylic acid (0.055 grams, 0.185 mmol), N-(3-dimethylaminopropyl)-N'-ethylcarbodiimide hydrochloride (0.043 grams, 0.22 mmol), 1-hydroxybenzotriazole monohydrate (0.034 grams, 0.22 mmol), and diisopropylethylamine (0.161 ml, 0.925 mmol). After stirring 16 hours at ambient temperature EtOAc was added and the reaction washed with saturated sodium bicarbonate, brine, dried over sodium sulfate, filtered and concentrated. The residue was dissolved in DMSO and purified by prep HPLC to give Compound 6.2. ES (+) MS m/e=492 (M+2). 1H NMR (400 MHz, MeOH-d4) δ ppm 1.37 (m, 2H) 1.57 (m, 4H) 3.29 (m, 2H) 3.41 (m, 2H) 3.91 (m, 3H) 5.11 (m, 2H) 6.23 (m, 1H) 6.45 (m, 1H) 7.13 (m, 1H) 7.38 (m, 2H) 7.81 (m, 1H) 7.92 (m, 1H) 8.29 (m, 1H).

Example 7

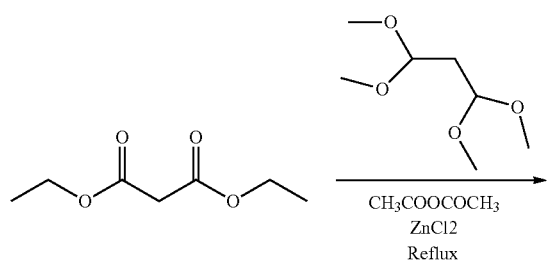

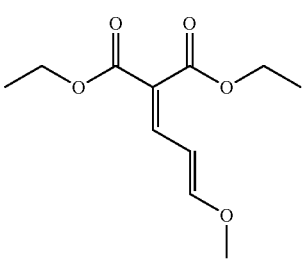

Compound 7.1

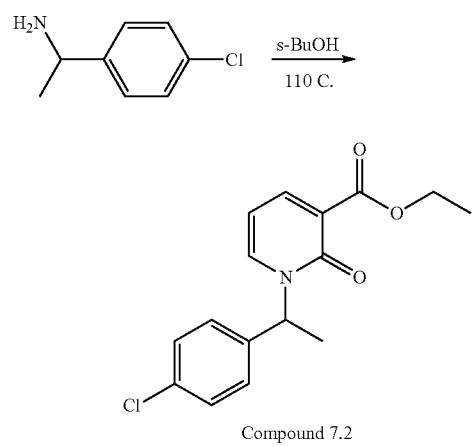

Compound 7.2

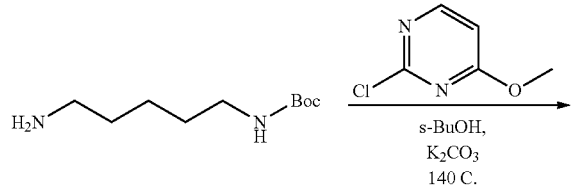

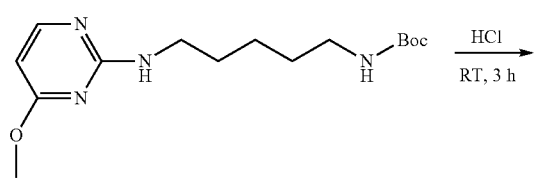

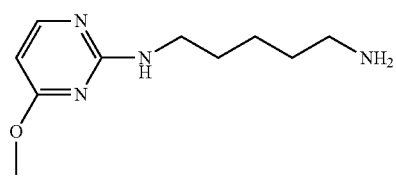

Compound 7.3

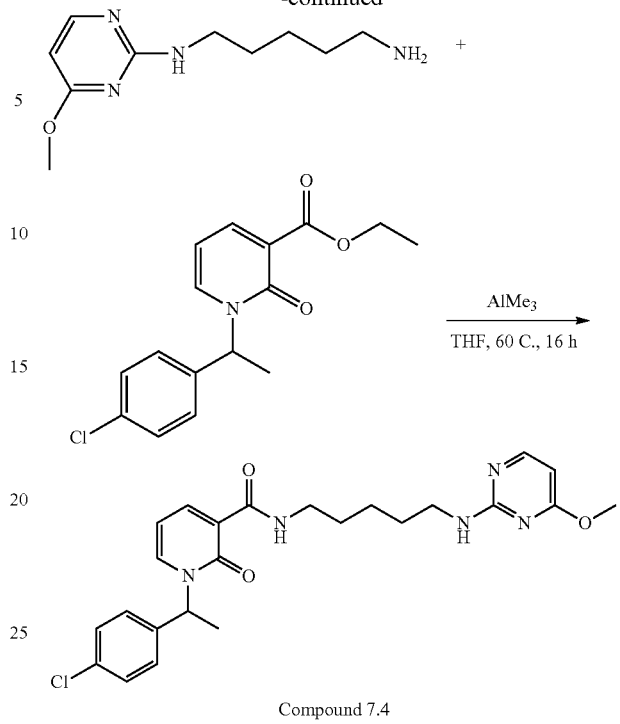

Compound 7.4

7.1 Diethyl malonate (160 g, 1.0 mole) was added slowly to a stirred, refluxing solution of maloaldehyde bis(dimethyl acetal) (246.3 g, 1.5 mole), acetic anhydride (306 g, 2.0 moles) and zinc chloride (10 g, 0.073 mole) over a period of 30 minutes. The mixture was heated for 1 hour, and after that a Dean-Stark apparatus was connected and the lower boiling point components were distilled off. Additional acetic anhydride (150 ml) was added and refluxing was continued for 1 hour. The reaction mixture was distilled to give the Compound 7.1 as a yellow oil (100 g, 45%), b.p. 139-143 C at 0.8 mm Hg. ES (+) MS m/e=229 (M+1).

7.2 The diethyl [3-methoxypro-2enylidene]malonate (1.0 g, 4.4 mmol), Compound 7.1, was added to a 2-dram vial in 2 ml of s-BuOH. To the mixture was added 1-(4-chlorophenyl)-ethylamine (0.71 g, 4.6 mmole). The reaction mixture was heated to 110° C. for 16 hours. When the reaction was completed, the solvent was removed using GeneVac HT-12 to give Compound 7.2. ES (+) MS m/e=306 (M+1).

7.3 To a 2-dram vial were added (5-amino-pentyl)-carbamic acid tert-butyl ester (0.04 g, 0.2 mmol) and 2-chloro-4-methoxy-pyrimidine (0.029 g, 0.2 mmol) in 2 ml of s-BuOH and 0.2 ml of di-isopropylethylamine. The vial was capped and shaken at 140° C. for 16 hours. The solvent was filtered and removed using the GeneVac HT-12 to give Compound 7.3. ES (+) MS m/e=111 (M+1).

7.4 To the vial of Compound 7.3 was added 2 ml of MeOH and 1 ml of HCl (4.0 M in dioxane). The vial was capped and shaken at room temperature for 3 hours. The mix solvent was removed using the GeneVac HT-12. To the dry compound in 2-dram vial were added 1-[1-(4-Chloro-phenyl)-ethyl]-2-oxo-1,2-dihydro-pyridine-3-carboxylic acid ethyl ester, (Compound 7.2, 0.061 g, 0.2 mmol) and 2 ml of dry THF. The mixture was shaken vigorously to provide a homogenous solution. To this mixture was added AlMe$_3$ (0.2 ml, 2.0 M in toluene). The vial was capped and shaken at 65° C. for 16 hours. The reaction mixture was quenched with 1 ml of HCl (4.0 M in water). The solvent was concentrated using GeneVac HT-12. The crude product was dissolved in DMSO (3 ml) and purified by using HPLC (reverse phase) to give Compound 7.4. ES (+) MS m/e=470.2 (M+1). 1H NMR (400 MHz, CD₃OD) ™ ppm 1.13 (m, 2H), 1.50 (m, 2H), 1.6-1.8 (m, 5H), 3.45 (m, 3H), 3.55 (1H), 4.05 (m, 4H), 6.34 (m, 2H), 6.55 (m, 1H), 7.37 (m, 5H), 7.85 (m, 1H), 7.95 (m, 1H), 8.40 (m, 1H).

Example 8

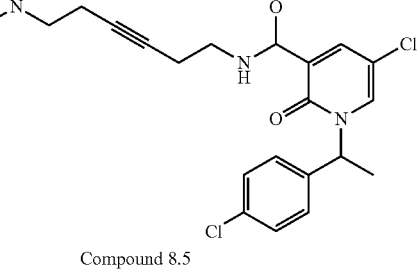

Compound 8.5

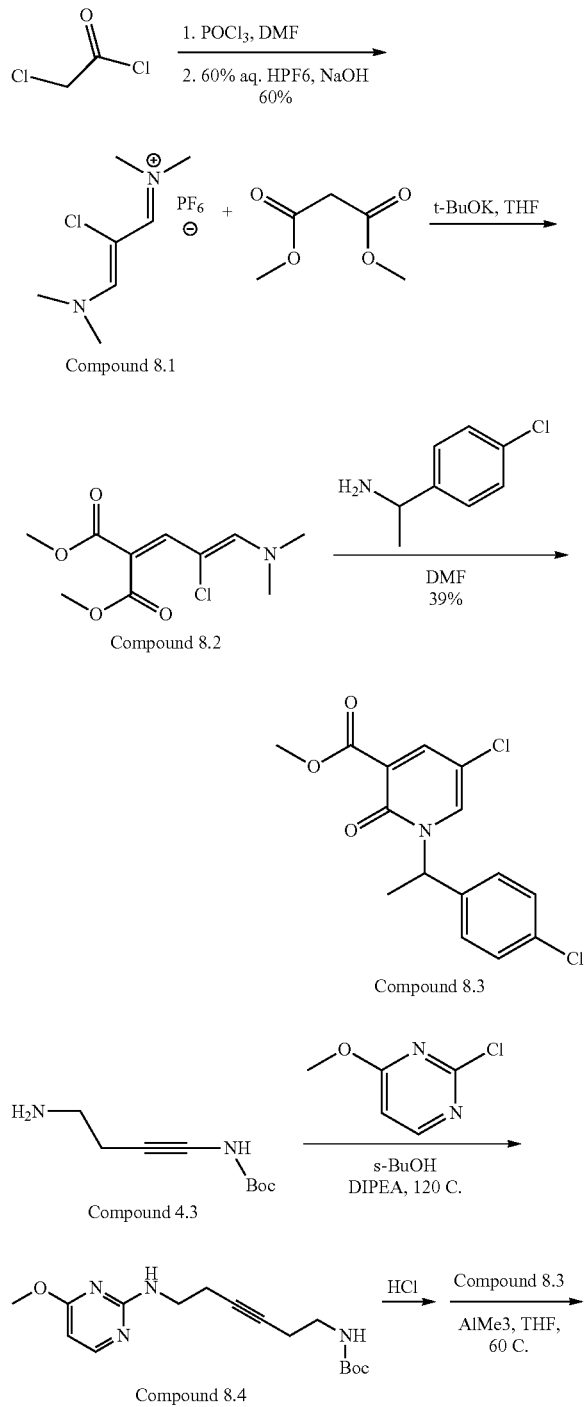

8.1 To anhydrous DMF (60 ml) at 50° C. with stirring was added chloroacetylchloride (9.95 ml, 125 mmol). The mixture was heated to 70° C. and phosphorus oxychloride (11.44 ml, 125 mmol) was added via syringe pump at 5 ml/hour. After addition was complete, the reaction was stirred at this temperature for an additional 3 hours at which point it was cooled to ambient temperature and transferred to an addition funnel. In a second addition funnel was placed 5N NaOH (70 ml). These were added concurrently over 1 hour to a solution at 0° C. containing 5N NaOH (37 ml), water (150 ml), and 60% aq. hexafluorophosphoric acid (19 ml). The mixture was aged 1 additional hour and filtered through a course frit glass funnel. The precipitate was dried to yield Compound 8:1 (23.15 grams, 75 mmol, 60%); 1H NMR (400 MHz,) δ ppm 3.28 (s, 6H) 3.46 (s, 6H) 7.78 (s, 2H).

8.2 Malonic acid dimethyl ester (2.88 ml, 25.13 mmol) was dissolved in dry THF (50 ml) under a nitrogen atmosphere, chilled to 0° C. on an ice bath and potassium tert butoxide (1.0M in THF, 26.39 ml, 26.39 mmol) was added drop wise via addition funnel. After addition was complete the ice bath was removed and the reaction stirred for 45 minutes. Compound 8.1 (11.56 grams, 37.70 mmol) was added in one portion and the reaction heated at 45° C. for 6 hours, then concentrated to yield Compound 8.2 which was used without further purification.

8.3 Compound 8.2 (1.24 grams, 5 mmol) was dissolved in DMF (17 ml), cooled on an ice bath, 1-(4-Chloro-phenyl)-ethylamine (0.778 ml, 5 mmol) was added and the reaction heated to 85° C. with stirring for 24 hours. The reaction was cooled to room temperature, diluted with EtOAc, washed with 1M HCl, water, saturated sodium bicarbonate, brine, dried over sodium sulfate, filtered, and concentrated. This residue was purified by column chromatography on silica (30% EtOAc/Hexanes) to yield Compound 8.3 (0.642 grams, 1.97 mmol, 39%).

8.4 To a 2-dram vial were added (6-amino-hex-3-ynyl)-carbamic acid tert-butyl ester (0.04 g, 0.2 mmol, Compound 4.3), 2-chloro-4-methoxy-pyrimidine (0.029 g, 0.2 mmol), 2 ml of s-BuOH, and 0.2 ml of di-isopropylethylamine. The vial was capped and shaken at 130 C for 16 hours. The solvent was filtered and removed using the GeneVac HT-12 to give Compound 8.4. ES (+) MS m/e=321 (M+1).

8.5 To the vial of Compound 8.4 were added 2 ml of MeOH and 1 ml of HCl (4.0 M in dioxane). The vial was capped and shaken at room temperature for 3 hours. The mixed solvent was removed using the GeneVac HT-12. To the dry compound in 2-dram vial were added 5-chloro-1-[1-(4-chloro-phenyl)-ethyl]-2-oxo-1,2-dihydro-pyridine-3-carboxylic acid methyl ester (0.065 g, 0.2 mmol) and 2 ml of dry THF. The mixture was shaken vigorously to provide a homogenous solution. To this mixture was added AlMe₃ (0.3 ml, 2.0 M in toluene). The vial was capped and shaken at 65° C. for 16 hours. The reaction mixture was quenched with 1 ml of HCl (4.0 M in water). The solvent was concentrated using GeneVac HT-12. The crude product was dissolved in DMSO (3 ml) and purified by using HPLC (reverse phase) to give Compound 8.5. ES (+) MS m/e=514.1 (M+1). 1H NMR (400 MHz, CD$_3$OD)$^{TM}$ ppm 1.75 (d, J=7 Hz, 3H), 2.4-2.6 (m, 4H), 3.5-3.7 (m, 4H), 4.15 (m, 4H), 6.50 (s, 1H), 7.2-7.5 (m, 6H), 8.00 (s, 2H), 8.40 (s, 1H).

to which was added 1 ml of 4.0 M HCl in para-dioxane. The reaction was stirred for 2 hours at room temperature and the solvent was evaporated to dryness. ES (+) MS m/e=211 (M+1).

9.2 Diethyl(3-methoxypro-2enylidene)malonate (0.5 g, 2.19 mmol) was dissolved in 2 ml 2-butanol and 3,4-difluorobenzylamine (0.31 g, 2.19 mmol) was added. This was stirred at room temperature for 2 hours and heated to 90 degrees overnight. Target mass was identified as the major product and the solvent was removed by GeneVac. ES (+) MS m/e=295 (M+1).

9.3 Compound 9.2 (86 mg, 0.3 mmol) and Compound 9.1 (63 mg, 0.3 mmol) were dissolved in 1 ml N,N-dimethyl- Example 9

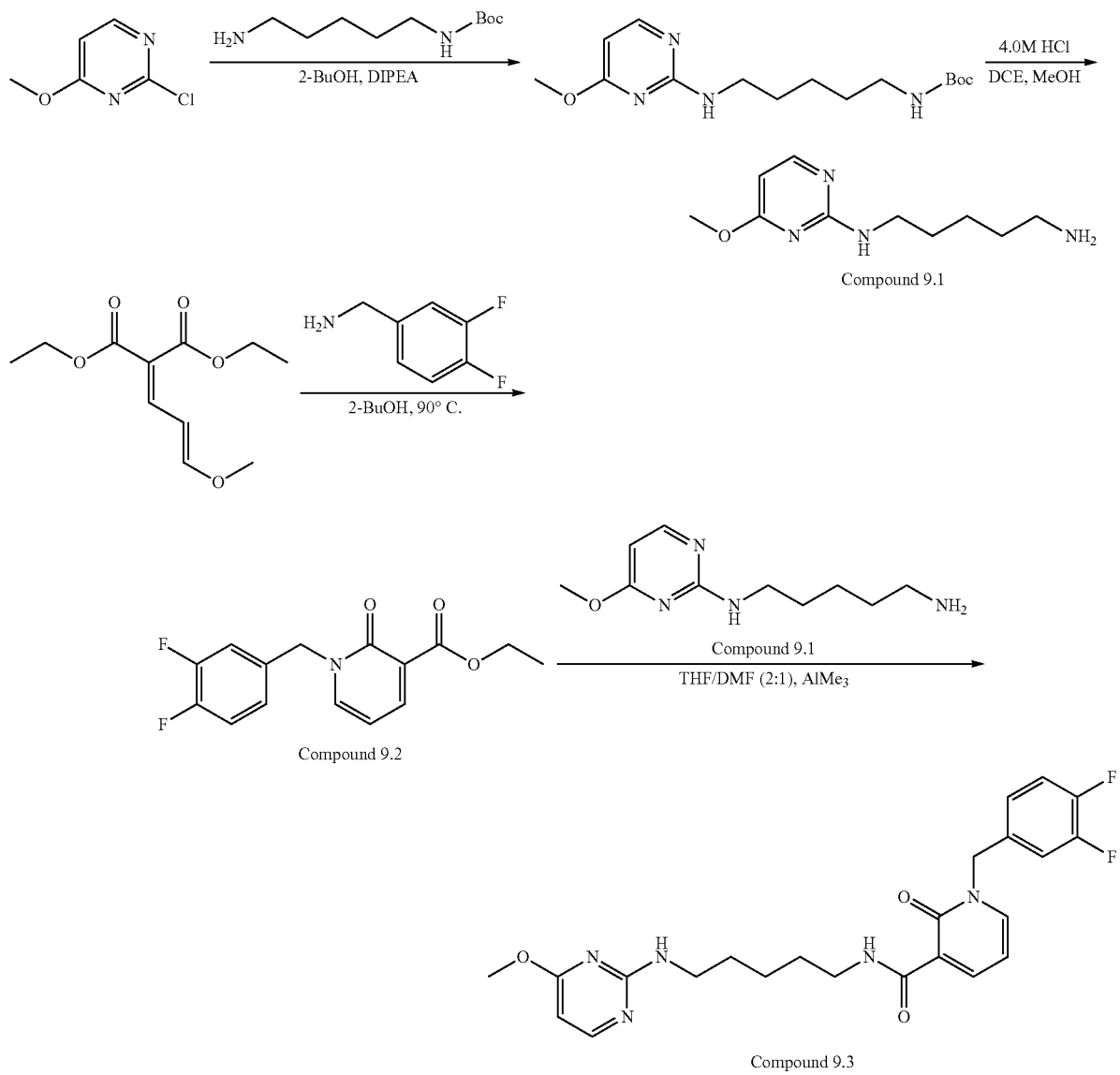

9.1 2-Chloro-4-methoxypyrimidine (Aldrich, 0.144 g, 1 mmol) and N-(5-aminoamyl)carbamic acid tert-butylester (TCI, 0.202 g, 1 mmol) were mixed in 2-butanol and N,N-diisopropylethylamine (0.7 ml, 4 mmol) were added. The reaction was heated at 135° C. for 16 hours and the solvent was removed in vacuo to yield clear gel. This gel was dissolved in 2 ml of dichloroethane and 1 ml methanol, formamide and 2 ml tetrahydrofuran, and then trimethylaluminum (2.0 M in toluene, 0.4 ml) was added. The reaction was heated at 70° C. for 14 hours. Then 0.5 ml of 3 N HCl was added along with 1 ml of acetonitrile, which formed two layers. The top layer contained the desired product and the solvent was removed. The product was purified by reverse phase high-performance-liquid-chromatography and lyophilized to yield white powder. ES (+) MS m/e=459 (M+1). ¹H NMR (400 MHz, DMSO-D6) ™ ppm 9.62 (d, 1H, J=5 Hz), 8.60 (br s, 1H), 8.32 (d, 1H, J=6 Hz), 8.21 (d, 1H, J=6.4 Hz), 8.10 (br s, 1H), 7.45-7.38 (m, 2H), 7.16 (br s, 1H), 6.57 (t, 1H, J=7 Hz), 6.33 (d, 1H, J=5 Hz), 5.19 (s, 2H), 3.93 (s, 3H), 3.54 (br s, 2H), 3.27 (t, 2H, J=7 Hz), 1.58 (t, 2H, J=7 Hz), 1.52 (t, 2H, J=7 Hz), 1.33 (t, 2H, J=7 Hz).

Example 10

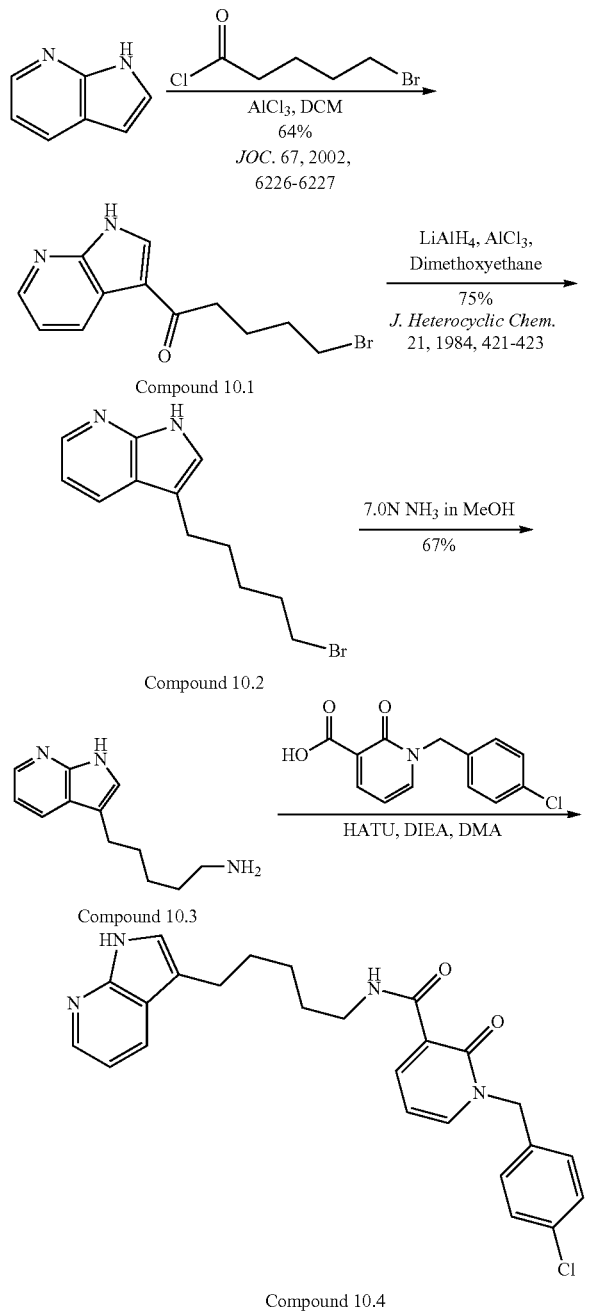

10.1 Aluminum chloride (2.8 grams, 21.0 mmol) was suspended in dry DCM under a nitrogen atmosphere in a flame-dried 3-neck round bottom flask. 1H-Pyrrolo[2,3-b]pyridine (0.5 grams, 4.2 mmol) was added and the mixture stirred at ambient temperature for 1 hour at which point 5-bromo-pentanoyl chloride (2.81 ml, 21 mmol) was added drop wise. After 1 hour of stirring at ambient temperature, the mixture was cooled to at 0° C. and MeOH (20 ml) was added cautiously to quench. After warming to room temp over 30 minutes, the reaction was concentrated and purified by column chromatography on silica (2% MeOH/DCM) to yield Compound 10.1 (0.750 grams, 2.67 mmol, 64%). 1H NMR (400 MHz, DMSO-d6) δ ppm 1.74 (m, 2H) 1.87 (m, 2H) 2.91 (m, 2H) 3.57 (m, 2H) 7.23 (m, 1H) 8.30 (m, 1H) 8.48 (m, 2H) 12.46 (m, 1H).

10.2 To an ice cooled suspension of lithium aluminum hydride (1.0 M in THF, 3.66 ml) in anhydrous dimethoxyethane (5 ml) under a nitrogen atmosphere in a flame-dried round bottom flask was added aluminum chloride (0.949 grams, 7.11 mmol) portion-wise. Compound 10.1 (0.5 grams, 1.78 mmol) dissolved in dimethoxyethane (36 ml) was added dropwise. The ice bath was removed, the reaction stirred for 40 minutes, and water (10 ml) was added cautiously to quench. The mixture was extracted with DCM, the organic layer dried over sodium sulfate, filtered, and concentrated. The residue was purified by column chromatography on silica (30% EtOAc/hexanes) to yield Compound 10.2 (0.357 grams, 1.34 mmol, 75%). ES (+) MS m/e=269 (M+2).

10.3 Compound 10.2 (0.341 grams, 1.28 mmol) was dissolved in 7 N ammonia in MeOH (10 ml) and placed in a glass bomb. The reaction was sealed and heated at 80° C. for 16 hours, cooled to room temperature, concentrated and used without further purification. ES (+) MS m/e=204 (M+1).

10.4 Compound 10.3 (0.041 grams, 0.2 mmol) was mixed with O-(7-Azabenzotriazole-1-yl)-N,N,N'N'-tetramethyluronium hexafluorophosphate (0.091 grams, 0.239 mmol) and diisopropylethylamine (0.200 ml, 0.351 mmol) in dimethylacetamide (2 ml) and stirred at ambient temperature for 16 hours. The mixture was concentrated, dissolved in DMSO and purified by prep HPLC to yield Compound 10.4. 1H NMR (400 MHz, DMSO-d6) δ ppm 1.35 (m, 2H) 1.52 (m, 2H) 1.66 (m, 2H) 2.69 (m, 2H) 3.26 (m, 2H) 5.22 (m, 2H) 6.57 (m, 1H) 7.23 (m, 2H) 7.37 (m, 4H) 8.27 (m, 4H) 9.63 (m, 1H) 11.94 (m, 1H).

Example 11

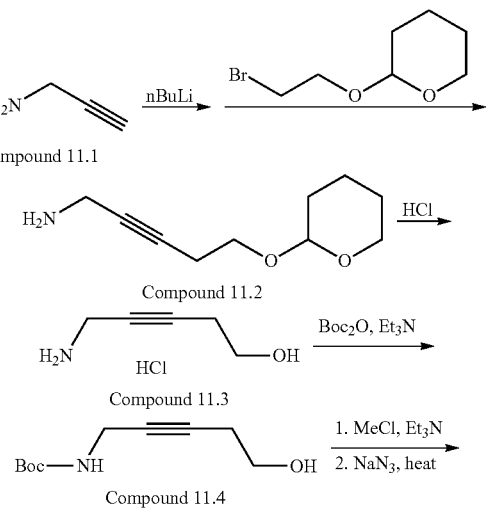

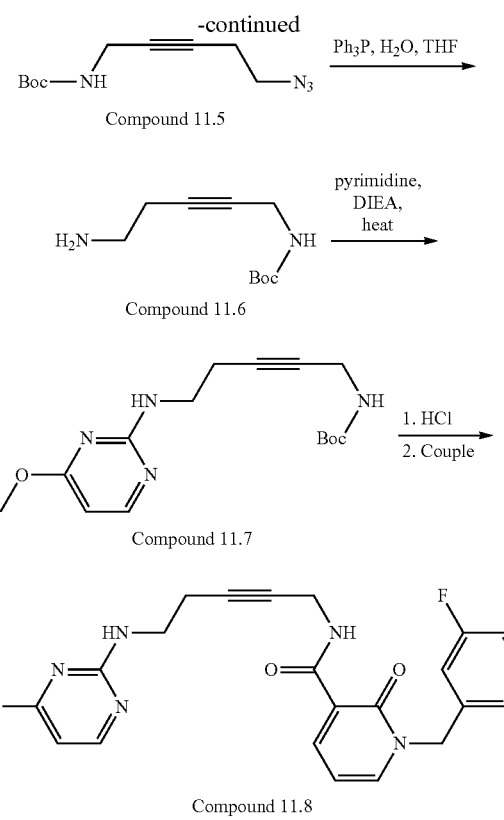

11.5 Compound 11.5 was prepared as Compound 4.1, starting with Compound 11.4 instead of 3-hexyne-1,6-diol. ES (+) MS m/e=247 (M+23). 1H NMR (400 MHz, CHLOROFORM-D) $^{TM}$ ppm 1.45 (s, 9H) 2.47 (m, 2H) 3.37 (m, 2H) 3.91 (m, 2H) 4.66 (m, 1H).

11.6 Compound 11.5 (1.158 g, 5.17 mmol) was dissolved in 5 ml dry THF and then triphenylphosphine (1.489 g, 5.68 mmol) and water (0.2 ml, 11.1 mmol) was added along with another 5 ml THF. The reaction was heated to 60° C. for 23 hours under nitrogen, at which point solvent was evaporated and the product was purified on silica gel chromatography using a 17×4.25 cm column, eluting first with 95:5 DCM:2 M ammonia in methanol, then switching to 90:10 DCM:2 M ammonia in methanol. The product was evaporated to yield Compound 11.6 as a yellow oil (0.772 g, 3.90 mmol, 75%). ES (+) MS m/e=199 (M+1). 1H NMR (400 MHz, CHLOROFORM-D) $^{TM}$ ppm 1.45 (s, 9H) 2.32 (m, 2H) 2.82 (m, 2H) 3.48 (m, 2H) 3.91 (m, 2H) 4.77 (m, 1H).

11.7 Compound 11.7 was prepared as in Example 3.x, but starting with Compound 11.6.

11.8 Compound 11.8 was prepared analogously to Example 21.4, but starting with Compound 11.7 instead of Compound 21.3. ES (+) MS m/e=453.9 (M+1).

Example 12

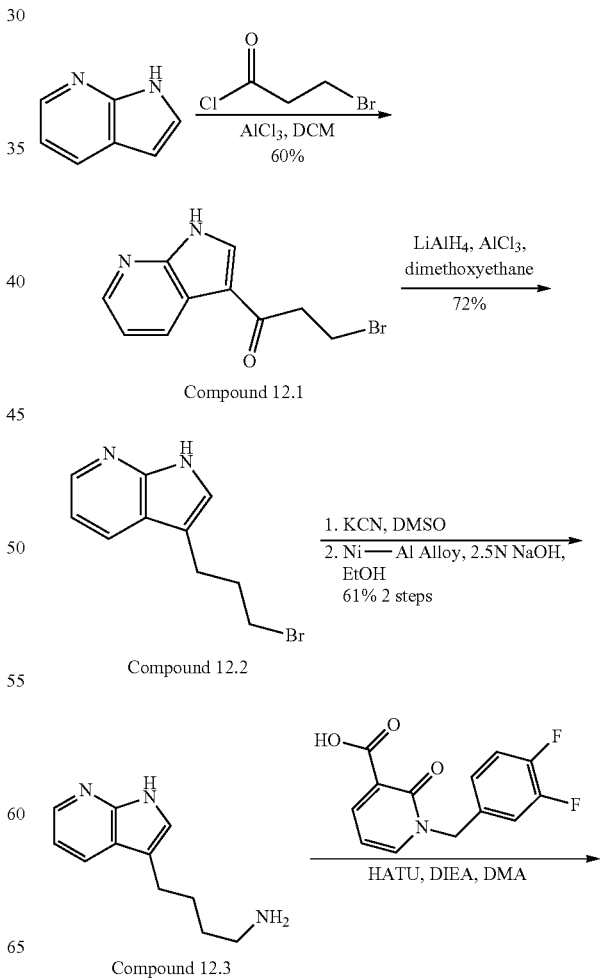

11.1 Compound 11.1 was prepared as described in Wipf et al. Org. Lett. 2004 6(20) 3593-3595.

11.2 Compound 11.1 (3.664 g, 18.37 mmol) was dissolved in 35 ml dry THF and 8 ml of 2.5 M n-butyllithium in THF was added (20 mmol) under nitrogen. The reaction was stirred for 30 minutes, at which point 2.8 ml 2-(2-bromoethoxy)tetrahydro-2H-pyran was added (18.5 mmol). The reaction was heated to 60° C. for 23 hours, the diluted with 100 ml ethyl acetate and rinsed with 40 ml brine, dried over sodium sulfate, filtered, and evaporated to dryness to yield 5.707 g of Compound 11.2 as a brown oil which was used without further purification. ES (+) MS m/e=184 (M+1).

11.3 Compound 11.2 was deprotected in 20 ml acetonitrile with 100 ml of aqueous 1 M HCl for 90 minutes, and then extracted with 2×30 ml diethyl ether. The aqueous layer was filtered and evaporated to a black oil which was redissolved in minimal methanol and triturated with 100 ml of cold DCM. This was filtered through a medium glass frit and the precipitate was collected and used without further purification (1.18 g, 8.74 mmol, 48% from 11.1). ES (+) MS m/e=100 (M+1). 1H NMR (400 MHz, methanol-d4) $^{TM}$ ppm 2.44 (m, 2H) 3.65 (m, 2H) 3.74 (m, 2H).

11.4 Compound 11.3 (1.179 g, 8.73 mmol) was suspended in 10 ml dry acetonitrile, and then triethylamine (2.5 ml, 17.9 mmol), di-tert-butyl-dicarbonate 1.925 g, 8.82 mmol), and 10 ml more acetonitrile were added. After 30 minutes add 10 ml dry THF. After four days the reaction was flooded with 50 ml 1 M aqueous sodium hydrogen sulfate and extracted with 3×30 ml ethyl acetate. The combined organics were rinsed with 50 ml brine, dried over sodium sulfate, filtered, and evaporated to a black oil which was purified by column chromatography on a 16×4.25 cm column, eluting with 95:5 DCM to methanol. Compound 11.4 was recovered as a yellow oil (1.057 g, 5.31 mmol, 61%). ES (+) MS m/e=222 (M+23).

-continued

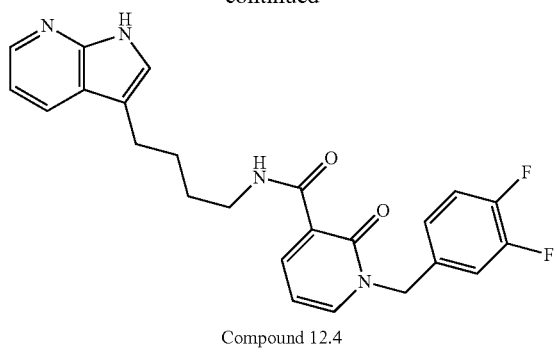

Compound 12.4

12.1 This was made as in Example 10.1 except reacting 1H-Pyrrolo[2,3-b]pyridine with 3-Bromo-propionyl chloride. (60%) ES (+) MS m/e=255 (M+2).

12.2 This was made as in Example 10.2 except starting with Compound 12.1. (72%) ES (+) MS m/e=241 (M+2).

12.3 Compound 12.2 (0.635 grams, 2.66 mmol) was mixed with potassium cyanide (0.264 grams, 3.98 mmol). DMSO (9 ml) was added and the reaction heated at 50° C. for 16 hours, diluted with EtOAc, washed with water, brine, dried over sodium sulfate, filtered, and concentrated. The residue was dissolved in EtOH (7.5 ml) and 2.5N NaOH (7.5 ml) was added and the mixture cooled to 0° C. on an ice bath. Nickel-aluminum alloy (Fluka No. 72240, 3.70 grams) was added via powder addition funnel over 30 minutes, the ice bath was removed and the reaction stirred for an additional 2 hours. The reaction mixture was filtered through celite, water (20 ml) was added and the mixture extracted with DCM, dried over sodium sulfate, filtered, and concentrated to yield Compound 12.3 (0.305 grams, 1.91 mmol, 1.61 mmol, 84%). ES (+) MS m/e=190 (M+1).

12.4 This was made as in Example 10.4 except using Compound 12.3 and 1-(3,4-Difluoro-benzyl)-2-oxo-1,2-dihydro-pyridine-3-carboxylic acid. 1H NMR (400 MHz, DMSO-d6) δ ppm 1.54 (m, 2H) 1.67 (m, 2H) 2.73 (m, 2H) 3.32 (m, 2H) 5.18 (m, 2H) 6.55 (m, 1H) 7.16 (m, 2H) 7.40 (m, 3H) 8.25 (m, 4H) 9.64 (m, 1H) 11.81 (m, 1H).

Example 13

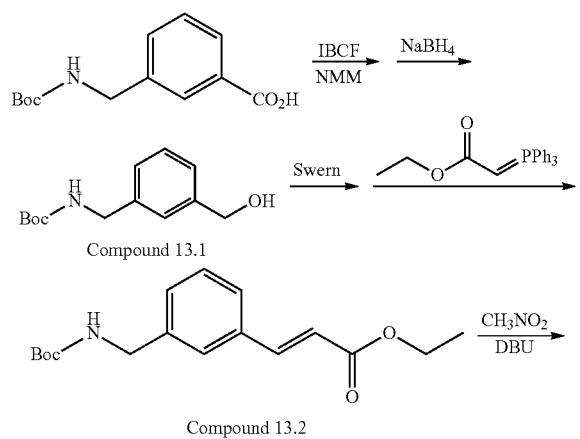

Compound 13.2

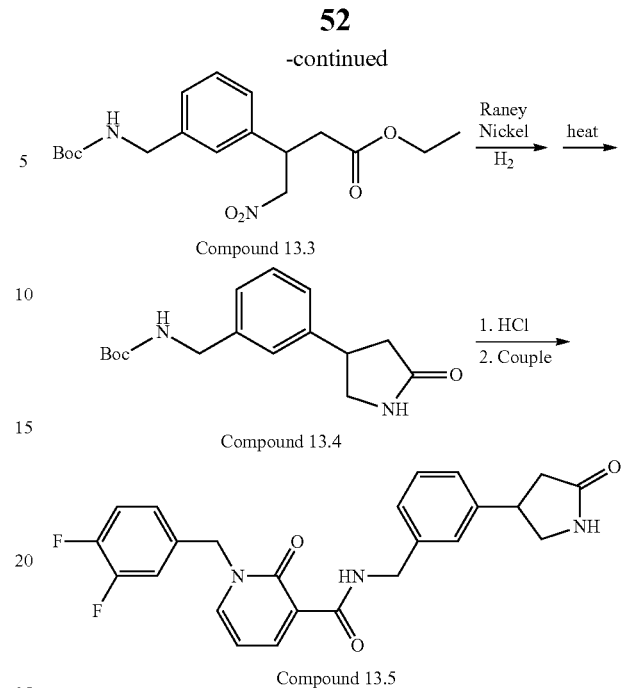

Compound 13.5

13.1 Boc-Mamb-OH (Chem-Impex, 1.765, 7.02 mmol) was dissolved in 20 ml dry THF, chilled in an ice-water bath, and N-methyl-morpholine (0.77 ml, 7.0 mmol) was added, followed by isobutyl chloroformate (0.91 ml, 7.0 mmol). The reaction was stirred on ice for 10 minutes at which point it was filtered through a medium glass frit, the precipitate was rinsed with 2×10 ml dry THF, and the filtrate was chilled again in the ice-water bath. Sodium borohydride was added (0.815 g, 21.5 mmol), followed by 10 ml methanol, and the reaction was allowed to proceed for 30 minutes, at which point it was evaporate to dryness, resuspended in 80 ml ethyl acetate, rinsed with 2×40 ml 1 M aqueous sodium hydrogen sulfate, 2×40 ml saturated aqueous sodium bicarbonate, 40 ml brine, dried over sodium sulfate, filtered, and evaporated to dryness to yield Compound 13.1 (1.542 g, 6.51 mmol, 93%). ES (+) MS m/e=260 (M+23).

13.2 10 ml of dry THF was chilled under nitrogen in a dry-ice acetone bath. Oxalyl chloride (0.57 ml, 6.54 mmol) was added, followed by DMSO (0.46 ml, 6.48 mmol). The reaction was stirred at −78° C. for 15 minutes, at which point Compound 13.1 (1.542 g, 6.51 mmol) was added as a solution in 10 ml dry THF. The reaction was stirred at −78° C. for 15 minutes, and then triethylamine (4.5 ml, 32.3 mmol) was added and the reaction was removed from the dry-ice acetone bath. The reaction was stirred for 30 minutes, and then carboethoxymethylene triphenylphosphine (2.281 g, 6.54 mmol) was added along with 20 ml dry DCM. The reaction was allowed to stir overnight, at which point solvent was removed by rotary evaporation and the residue was redissolved in 100 ml ethyl acetate, rinsed with 2×50 ml 1 M aqueous sodium hydrogen sulfate, 2×50 ml saturated aqueous sodium bicarbonate, 50 ml brine, dried over sodium sulfate, filtered, evaporated, and purified by flash chromatography with 80:20 hexane to ethyl acetate (Rf=0.23) to yield Compound 13.2 as a colorless oil (0.913 g, 2.99 mmol, 46%). ES (+) MS m/e=328 (M+23). 1H NMR (400 MHz, CHLOROFORM-D) $^{TM}$ ppm 1.34 (m, 3H) 1.47 (s, H) 9 4.26 (m, 2H) 4.34 (m, 2H) 4.91 (m, 1H) 6.44 (m, 1H) 7.33 (m, 2H) 7.43 (m, 2H) 7.67 (m, 1H).

13.3 Compound 13.2 (0.913 g, 2.99 mmol) was dissolved in nitromethane (0.82 ml, 15.1 mmol) and 1,8-diazabicyclo[5.4.0]-undec-7-ene (DBU, 0.45 ml, 3.01 mmol) was added. The reaction was allowed to proceed for 80 minutes, at which point it was flooded with 80 ml ethyl acetate, rinsed with 2×40 ml 1 M aqueous sodium hydrogen sulfate, 2×40 ml water, 40 ml brine, dried over sodium sulfate, filtered, and evaporated to yield Compound 13.3 as a yellow oil (1.082 g, 2.95 mmol, 94%) which was used without further purification. ES (+) MS m/e=389 (M+23).

DCM to methanol to yield Compound 13.3 (0.205 g, 0.707 mmol, 52%). ES (+) MS m/e=313 (M+23). 1H NMR (400 MHz, CHLOROFORM-D) $^{TM}$ ppm 1.47 (s, 9H) 2.49 (m, 1H) 2.73 (m, 1H) 3.42 (m, 1H) 3.73 (m, 2H) 4.31 (m, 2H) 4.87 (m, 1H) 5.74 (m, 1H) 7.18 (m, 3H) 7.32 (m, 1H).

13.5 Compound 13.5 was prepared analogously to Example 21.4, but starting with Compound 13.4 instead of Compound 21.3. ES (+) MS m/e=437.9 (M+1).

Example 14

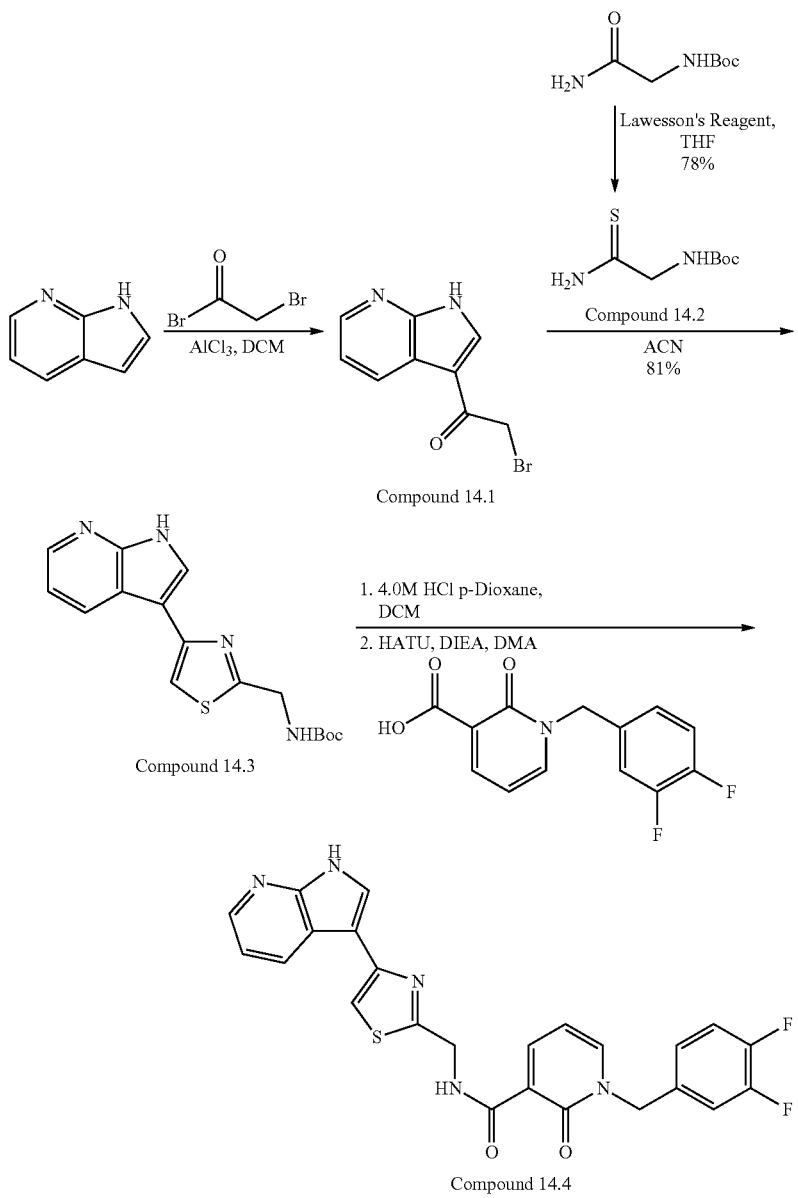

13.4 Compound 13.3 (0.5 g, 1.36 mmol) in 10 ml ethanol was hydrogenated on a Parr shaker for 1 hour at 22 psi with 0.7 ml of 50% Raney-nickel slurry in water. The reaction was filtered through celite and evaporated to dryness. The residue was redissolved in dry toluene and heated to 115° C. for 5 days under nitrogen. The reaction was then evaporated to dryness and purified by flash chromatography with 95:5

14.1 This was made as in example 10.1 except using bromoacetyl bromide. Product was recrystallized from MeOH. ES (+) MS m/e=241 (M+2).

14.2 Carbamoylmethyl-carbamic acid tert-butyl ester (10.88 grams, 62.46 mmol) and Lawesson's Reagent (15.66 grams, 38.72 mmol) were dissolved in THF (200 ml) and stirred under a nitrogen atmosphere at ambient temperature for 24 hours. The solvent was removed and the residue purified by column chromatography on silica (20% EtOAc/hexanes) to yield Compound 14.2 (9.21 grams, 48.41 mmol, 78%). 1H NMR (400 MHz, DMSO-d6) δ ppm 1.36 (s, 9H) 3.80 (m, 2H) 7.03 (m, 1H) 8.99 (m, 1H) 9.66 (m, 1H).

14.3 Compound 14.1 (0.308 grams, 1.28 mmol) was mixed with Compound 14.2 (0.245 grams, 1.28 mmol) and AcCN (6 ml) was added. The reaction was stirred at ambient temperature for 20 hours followed by 80° C. for 2 hours. The mixture was cooled to room temperature, diluted with EtOAc, washed with saturated sodium bicarbonate, brine, dried over sodium sulfate, filtered, and concentrated to yield Compound 14.3 (0.344 grams, 1.04 mmol, 81%). ES (+) MS m/e=331 (M+1).

14.4 This was deprotected as in Example 6.2 except using Compound 14.3 and then coupled as in Example 12.4. 1H NMR (400 MHz, DMSO-d6) δ ppm 2.49 (m, 1H) 4.88 (m, 2H) 5.25 (m, 2H) 6.62 (m, 1H) 7.19 (m, 2H) 7.44 (m, 2H) 7.76 (m, 1H) 8.00 (m, 1H) 8.28 (m, 1H) 8.41 (m, 1H) 8.59 (m, 1H) 10.38 (m, 1H) 12.01 (m, 1H).

Example 15 the residue was partitioned between 50 ml DCM and 50 ml water twice. The combined organic layer was washed with saturated NaHCO$_3$ solution, brine, and dried over Na$_2$SO$_4$, then filtered and concentrated in vacuo. The residue was loaded onto a flash column of 5 cm×20 cm, then eluted with ethyl acetate in hexane (20% to 50%). The fractions with the desired mass were combined and rotovapped to dryness and yielded 0.309 g of dark yellow oil (15%). ES (+) MS m/e=360 (M+23).

15.2 Compound 15.1 (0.309 g, 0.95 mmol) was dissolved in 5 ml of ethanol, and palladium (10% (weight) on activated carbon, 100 mg, 0.95 mmol) was added, then a hydrogen balloon was attached. After 3 hours the reaction was complete by LC-MS, the palladium was filtered off through celite and the solvent was evaporated in vacuo to yield 0.24 g of dark brown solid (95%). ES (+) MS m/e=268 (M+1).

15.3 Compound 15.2 (0.24 g, 0.9 mmol) was dissolved in 3 ml N,N-dimethylformamide and 1,1'-carbonyl-diimidazole (162 mg, 1.0 mmol) was added. The reaction vessel was placed on the shaker with the temperature set at 60° C. for 4 hours. The solvent was removed using GeneVac and the residue was used for the next step without further purification. ES (+) MS m/e=193 (M-Boc).

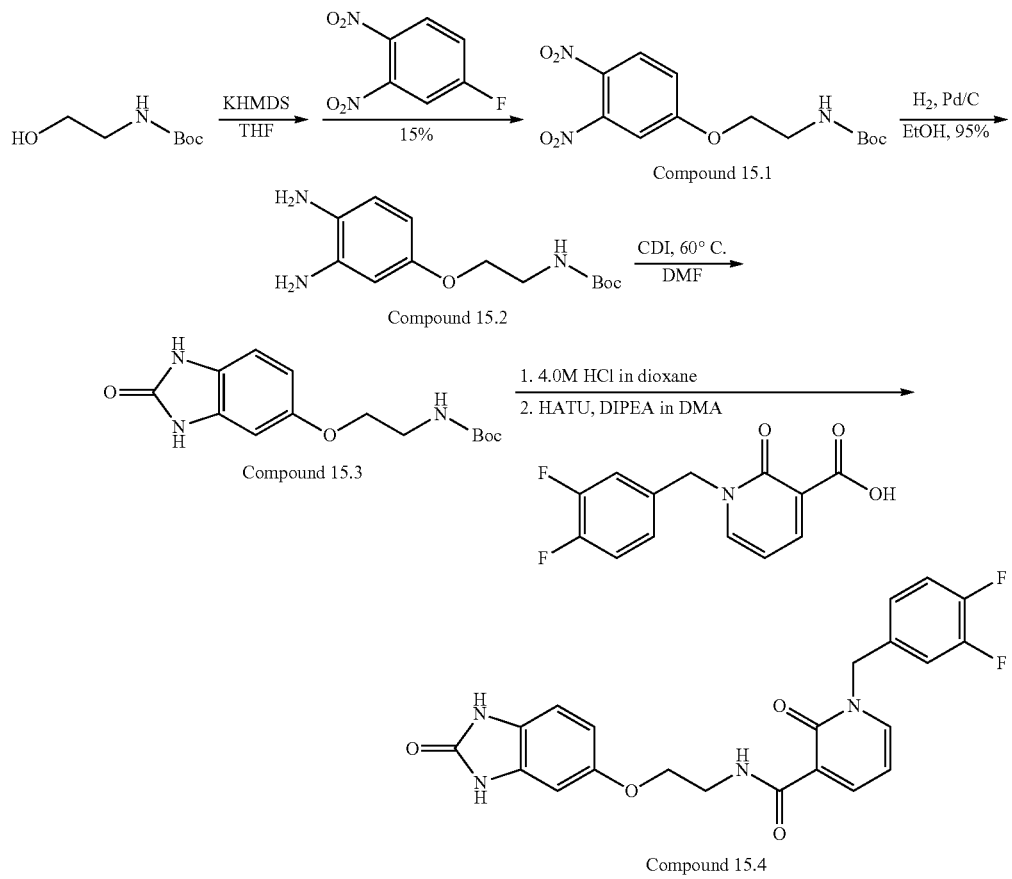

15.1 Tert-butyl N-(2-hydroxy)carbamate (Chem-Impex, 1.02 grams, 6.3 mmol) was dissolved in 10 ml dry tetrahydrofuran, and added to potassium bis(trimethylsilyl)-amide (0.5 M in toluene, 13.8 ml, 6.9 mmol) under nitrogen and stirred at room temperature. After 30 minutes, 3,4-dinitrofluorobenzene (1.15 g, 6.3 mmol) was added and heated at 60° C. for 3 hours. The solvent was evaporated in vacuo and 15.4 Compound 15.3 (0.205 g, 0.7 mmol) was dissolved in 1 ml dichloroethane and 0.5 ml methanol, then 1.0 ml of 4.0 M HCL in para-dioxane was added. After 2.5 hours, the solvent was removed by blowing air on hot plate to dryness. The residue was coupled with 1-(3,4-difluoro-benzyl)-2-oxo-1,2-dihydro-pyridine-3-carboxylic acid (0.186 g, 0.7 mmol, Compound 20.2), using 2-(7-Aza-1H-benzotriazole- 1-yl)-1,1,3,3,-tetramethyluroniumhexafluorophosphate (0.304 g, 0.8 mmol) as the coupling agent, and N,N-diiropropylethylamine (0.4 ml, 2.3 mmol) as base in 4 ml of N,N-dimethylacetamide for 2 hours. After removing the solvent by GeneVac, the residue was purified using reverse-phase HPLC and lyophilized to give white powder (30 mg, 0.07 mmol). ES (+) MS m/e=441 (M+1). ¹H NMR (400 MHz, DMSO-D6)™ ppm 10.51 (s, 1H) 10.38 (s, 1H), 9.88 (t, 1H, J=5.4 Hz), 8.36 (dd, 1H, J=7 Hz, J=2 Hz), 8.22 (d, 1H, J=2 Hz), 7.47-7.37 (m, 2H), 7.16 (d, 1H, J=8 Hz), 6.78 (d, 1H, J=8.8 Hz), 6.59-6.52 (m, 3H), 5.20 (s, 2H), 4.01 (t, 2H, J=5.4 Hz), 3.63 (dt, 2H, J=5.8 Hz, J=5.4 Hz).

Example 16

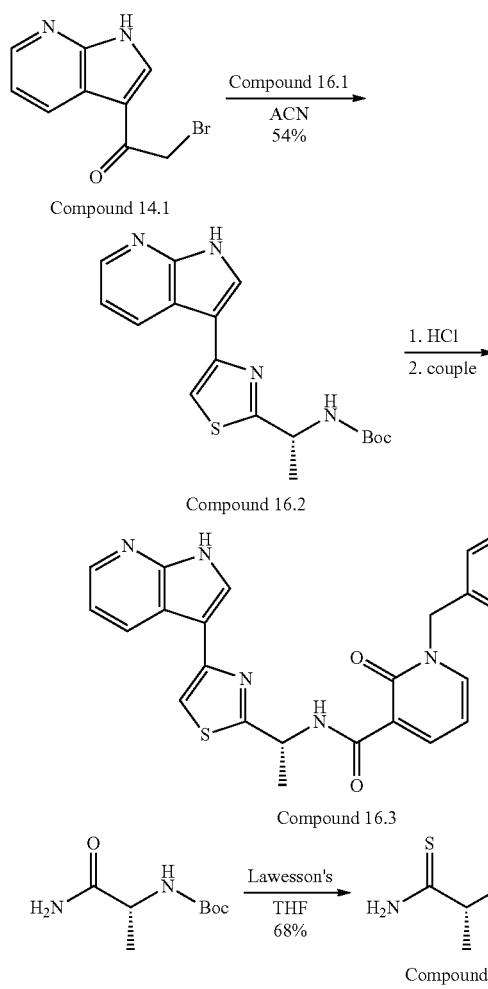

16.1 Boc-D-ala-NH₂ (5 g, 26.56 mmol) and Lawesson's reagent (6.66 g, 16.47 mmol) were suspended in 90 ml THF and stirred at room temperature under nitrogen. After three days, the mixture was concentrated under vacuum and the crude was purified by chromatography to give Compound 16.1 (3.68 g, 68%) as a white solid. ES (+) MS m/e=205 (M+1).

16.2 Compound 1.6.1 (1.23 g, 6 mmol) and Compound 14.1 (1.43 g, 6 mmol) were suspended in 30 ml acetonitrile. The mixture was heated at 50° C. for 1 hour, stirred at room temperature overnight and then heated at 80° C. for 30 minutes. The reaction was cooled, filtered, Compound 16.2 (1.12 g, 54%) was collected as a yellow solid which was used without further purification. ES (+) MS m/e=345 (M+1).

16.3 This was made as in Example 15.4 except starting with Compound 16.2. ES (+) MS m/e=492 (M+1). ¹H NMR (400 MHz, DMSO-d6)™ ppm 1.66 (d, J=6.85 Hz, 3H) 5.25 (m, 2H) 5.47 (m, 1H) 6.62 (t, J=6.85 Hz, 1H) 7.19 (m, 2H) 7.44 (m, 2H) 7.78 (m, 1H) 8.03 (d, J=2.45 Hz, 1H) 8.28 (m, 2H) 8.41 (dd, J=7.34, 2.45 Hz, 1H) 8.66 (m, 1H) 10.46 (d, J=7.34 Hz, 1H) 12.06 (m, 1H).

Example 17

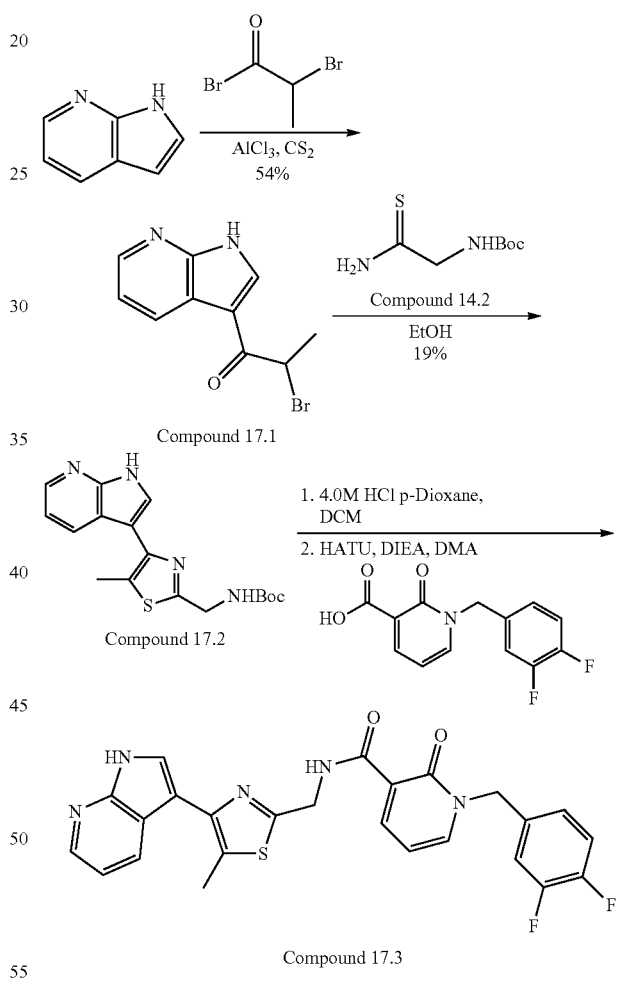

17.1 1H-Pyrrolo[2,3-b]pyridine (7.54 grams, 64 mmol) was dissolved in carbon disulfide (200 ml) under a nitrogen atmosphere in a flame-dried 3-neck round bottom flask fitted with a reflux condenser and an addition funnel. Trichloroaluminum (30 grams, 225 mmol) was added portion-wise with vigorous stirring at ambient temperature and then the mixture was heated to 50° C. 2-Bromo-propionyl bromide (6.77 ml, 64 mmol) in carbon disulfide (50 ml) was added dropwise via addition funnel at 50° C. The reaction was then stirred for an additional 40 minutes at this temperature, allowed to cool to ambient temperature and water (250 ml) was slowly added to quench. The layers were separated, the organics concentrated and recrystallized from MeOH to yield Compound 17.1 (8.74 grams, 34.53 mmol, 54%). ES (+) MS m/e=255 (M+2).

17.2 Compound 17.1 (1.0 gram, 3.95 mmol) and Compound 14.2 (0.752 grams, 3.95 mmol) were dissolved in EtOH (20 ml) and heated at reflux for 16 hours. The mixture was cooled to ambient temperature, diluted with DCM, washed with saturated sodium bicarbonate, dried over sodium sulfate, filtered, and concentrated to yield Compound 17.2 (0.254 grams, 0.737 mmol, 19%). ES (+) MS m/e=345 (M+1).

17.3 This was deprotected as in Example 6.2 except using Compound 17.2 and then coupled as in example 12.4 1H NMR (400 MHz, DMSO-d6) δ ppm 2.51 (m, 3H) 4.81 (m, 2H) 5.25 (m, 2H) 6.61 (m, 1H) 7.10 (m, 1H) 7.19 (m, 1H) 7.43 (m, 2H) 7.75 (m, 1H) 8.28 (m, 2H) 8.41 (m, 1H) 8.56 (m, 1H) 10.35 (m, 1H) 12.05 (m, 1H).

Example 18

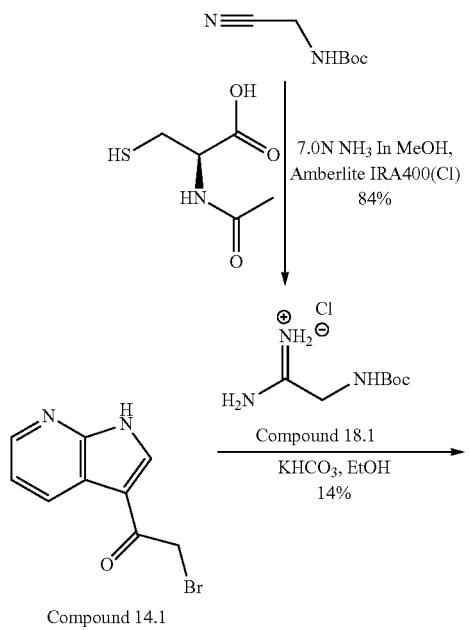

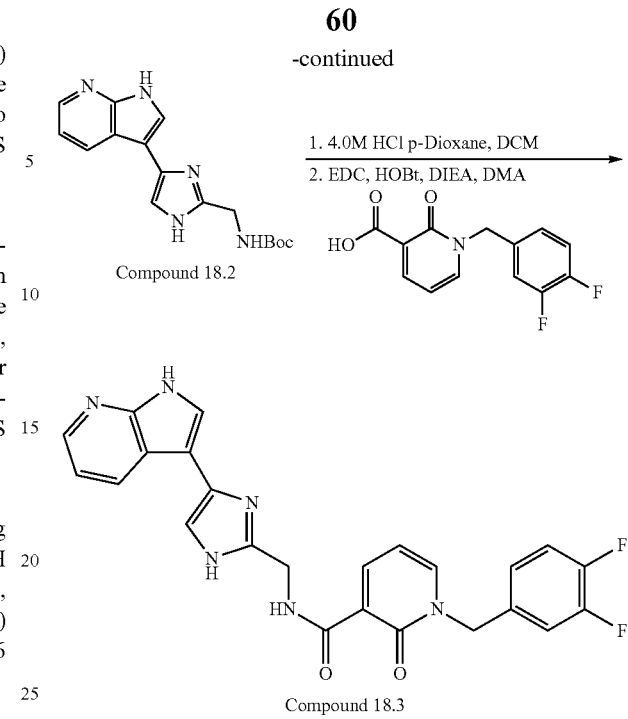

18.1 Cyanomethyl-carbamic acid tert-butyl ester (10 grams, 64.02 mmol) and 2-acetylamino-3-mercapto-propionic acid (10.45 grams, 64.02 mmol) were dissolved in 7N ammonia in methanol (140 ml) and heated at 60° C. in a sealed glass bomb for 5 hours. The reaction was cooled to ambient temperature, the solvent removed and the residue dissolved in water (250 ml). The aqueous layer was washed with ether and then loaded onto an ion exchange column (Amberlite IRA-400Cl) charged with saturated ammonium chloride, eluting with water. The pure fractions were combined and lyophilized to yield Compound 18.1 (11.30 grams, 53.89 mmol, 84%). ES (+) MS m/e=174 (M+1).

18.2 Compound 14.1 (1.49 grams, 6.22 mmol) and potassium bicarbonate (1.04 grams, 10.37 mmol) were dissolved in EtOH (35 ml) and stirred at room temperature for 2 hours. Compound 18.1 (1.45 grams, 6.91 mmol) was added and the reaction heated to 50° C. for 16 hours followed by 60° C. for 4 hours. The mixture was cooled to room temperature and filtered through a medium frit glass funnel, the cake washed with hot ethanol, the filtrate concentrated, and the residue purified by column chromatography on silica (1-10% MeOH/DCM) to yield Compound 18.2 (0.272 grams, 0.868 mmol, 16%). ES (+) MS m/e=314 (M+1).

18.3 This was made as in example 6.2 except using with Compound 18.2 and 1-(3,4-Difluoro-benzyl)-2-oxo-1,2-dihydro-pyridine-3-carboxylic acid. 1H NMR (400 MHz, MeOH-d4) δ ppm 3.23 (m, 1H) 4.59 (m, 2H) 5.09 (m, 2H) 6.43 (m, 1H) 7.12 (m, 4H) 7.57 (m, 1H) 7.90 (m, 1H) 8.12 (m, 2H) 8.34 (m, 1H).

Example 19

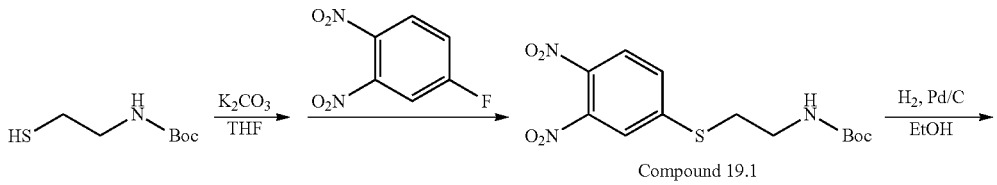

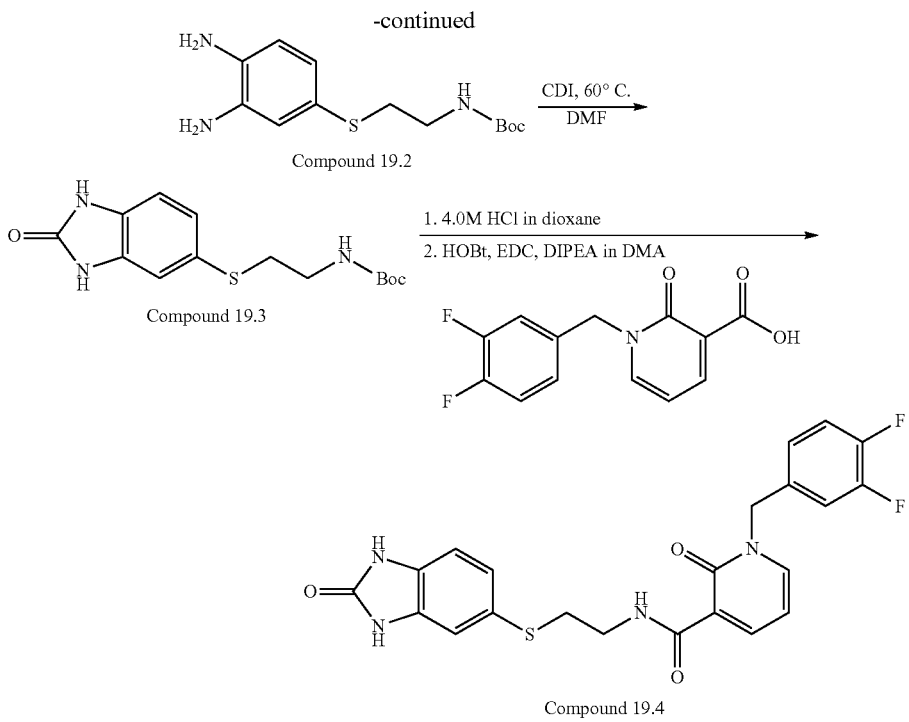

Compound 19.4 was prepared in the same way as Compound 15.4 (unless noted below) using the thiol (tert-butyl N-(2-mercaptoethyl)carbamate, Aldrich) instead of the alcohol tert-butyl N-(2-hydroxy)carbamate.

19.1 Potassium carbonate was used as base and the yield after column chromatography was 22%. ES (+) MS m/e=366 (M+23).

19.2 The yield after the reduction was 89%. ES (+) MS m/e=306 (M+23).

19.3 The crude mixture was purified by preparatory thin-layer-chromatography with 7% methanol in dichloromethane as the eluent to give brown solid (41% yield). ES (+) MS m/e=210 (M-Boc).

19.4 The procedure is the same as in 15.4 except that 1.2 equivalent of 1-hydroxybenzotriazole hydrate (HOBt) and 1-ethyl-(3-dimethylaminopropyl)carbodiimide hydrochloride (EDC) were used as the coupling agents instead of 2-(7-Aza-1H-benzotriazole-1-yl)-1,1,3,3,-tetramethyluroniumhexafluorophosphate (HATU). ES (+) MS m/e=458 (M+1). $^1$H NMR (400 MHz, DMSO-D6)$^{TM}$ ppm 10.66 (s, 1H), 10.64 (s, 1H), 9.79 (t, 1H, J=6 Hz), 8.31 (dd, 1H, J=6 Hz, J=2 Hz), 8.21 (dd, 1H, J=6 Hz, J=2 Hz), 7.47-7.38 (m, 2H), 7.18 (br s, 1H), 7.03-6.97 (m, 2H), 6.84 (d, 1H, J=6 Hz), 6.55 (t, 1H, J=7 Hz), 5.20 (s, 2H), 3.41 (t, 2H, J=6.4 Hz), 2.99 (t, 2H, J=6.8 Hz).

Example 20

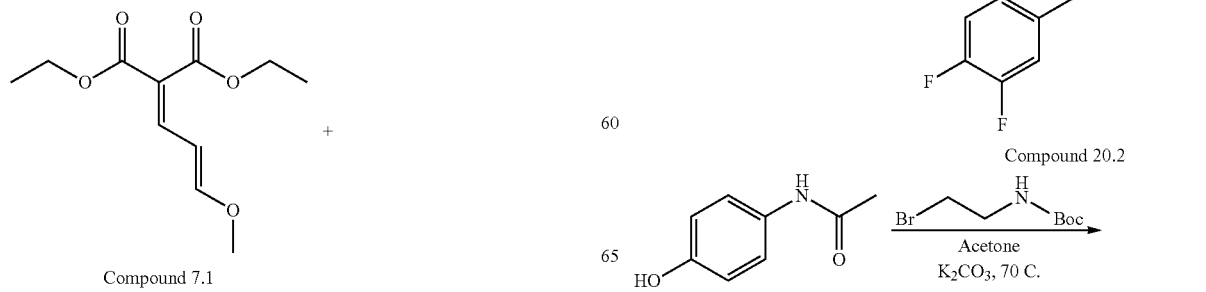

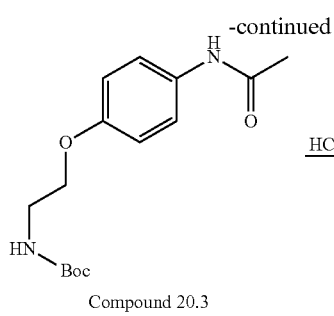

Compound 20.3

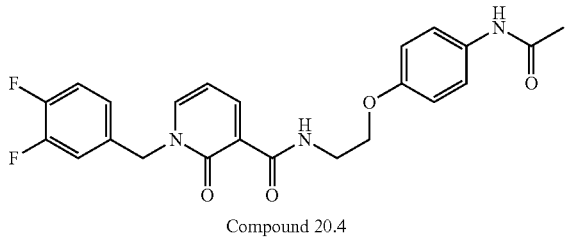

Compound 20.4

20.1 The diethyl [3-methoxypro-2enylidene]malonate (0.288 g, 1 mmole, Compound 7.1) was added to a 2-dram vial in 2 ml of s-BuOH. To the mixture was added 3,4-difluorobenzylamine (0.143 g, 1 mmole). The reaction mixture was heated to 100° C. for 3 hours. The solvent was removed to give Compound 20.1. ES (+) MS m/e=294 (M+1).

20.2 To a vial containing Compound 20.1 (0.293 g, 1 mmol) was added 1.1 equivalent of 6.0 M NaOH. The mixture was heated to 60° C. overnight. When the hydrolysis was completed, 1.2 equivalents of 4.0 M HCl was added to give a precipitate. The solid was filtered and washed three times with water. The yellow solid is more than 90% pure as determined by HPLC-ELSD. The yield is 80%. ES (+) MS m/e=266 (M+1). 1H NMR (400 MHz, DMSO-D6)$^{TM}$ ppm 5.3 (s, 2H), 6.80 (m, 1H), 7.20 (m, 1H), 7.4-7.5 (m, 2H), 8.40 (m, 2H), 14.30 (br, 1H).

20.3 To a 2-dram vial were added N-(4-hydroxy-phenyl)-acetamide (0.151 g, 1.0 mmol), (2-bromo-ethyl)-carbamic acid tert-butyl ester (0.224 g, 1.0 mmol), and K$_2$CO$_3$ (0.414 g, 3.0 mmol) in 2 ml of acetone. The vial was capped and shaken at 70° C. for 16 h. The solvent was filtered and concentrated using the GeneVac HT-12 to give Compound 20.3. ES (+) MS m/e=295 (M+1).

20.4 To the crude Compound 20.3 in a 2-dram vial were added 2 ml of MeOH and 1 ml of HCl (4.0 M in dioxane). The mixture was capped and shaken at room temperature for 3 hours. The solvent was removed using the GeneVac HT-12. To this residue were added 2 ml of DMF, 1-(3,4-difluoro-benzyl)-2-oxo-1,2-dihydro-pyridine-3-carboxylic acid (0.265 g, 1.0 mmol), 1-hydroxybenzotriazole (0.169 g, 1.1 mmol), 1-ethyl-(3-dimethylaminopropyl)carbodiimide hydrochloride (0.210 g, 1.1 mmol), and di-isopropylethyl-amine (0.15 g, 1.1 mmol). The vial was capped and shaken at room temperature for 16 hours. The solvent was concentrated using GeneVac HT-12. The crude product was dissolved in DMSO (3 ml) and purified by using HPLC (reverse phase) to give Compound 20.4. ES (+) MS m/e=441.9 (M+1). 1H NMR (400 MHz, CD$_3$OD)$^{TM}$ ppm 2.10 (s, 3H), 3.75 (t, J=7 Hz, 2H), 4.15 (t, J=7 Hz, 2H), 5.25 (s, 2H), 6.50 (m, 1H), 6.65 (m, 1H), 7.15 (m, 1H), 7.2-7.4 (m, 7H), 8.05 (s, 1H), 8.55 (s, 1H).

Example 21

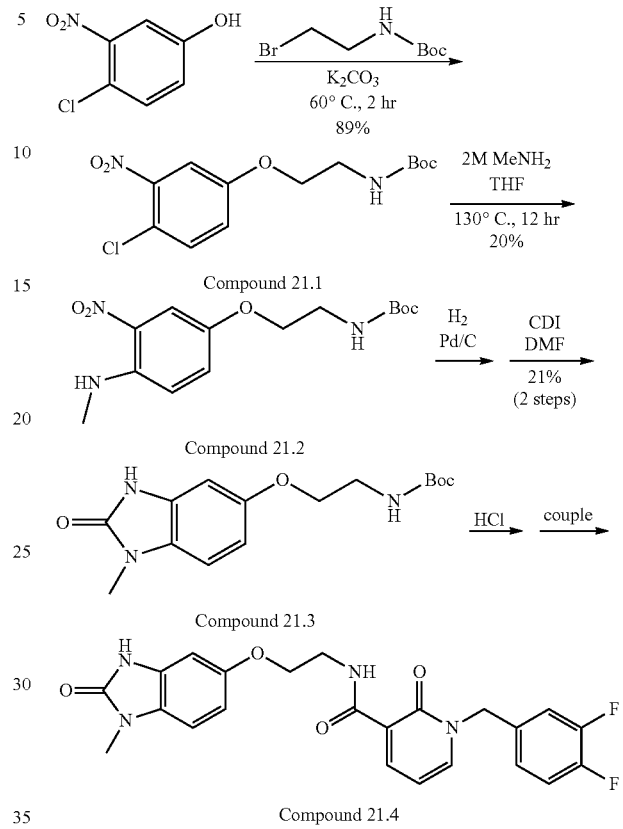

21.1 4-chloro-3-nitrophenol (2.96 g, 17.0 mmol) and 2-(Boc-amino)ethyl bromide (3.79 g, 16.9 mmol) were dissolved in 10 ml dry DMF, potassium carbonate (2.37 g, 17.1 mmol) was added, along with another 10 ml dry DMF, and the reaction was heated for 2.5 hours at 60° C. The reaction was then flooded with 100 ml ethyl acetate, rinsed with 2×50 ml water, 50 ml saturated aqueous sodium bicarbonate, 50 ml brine, dried over sodium sulfate, filtered, and evaporated to a yellow solid (4.764 g, 15.0 mmol, 89%) which was used without further purification. ES (+) MS m/e=339 (M+23).

21.2 Compound 21.1 (2.059 g, 6.50 mmol) was heated with 20 ml of 2 M methylamine in THF in a bomb at 130° C. overnight, although at some point the seal ruptured and most of the reaction evaporated. The remaining residue was redissolved in 50 ml ethyl acetate, rinsed with 50 ml water, 50 ml brine, dried over sodium sulfate, filtered, evaporated to a dark red oil, and purified by flash chromatography on a 15.5×4.25 cm column with 70:30 hexane to ethyl acetate to yield partially pure Compound 21.2 (contaminated with ~50% of Compound 21.1) as a dark red solid (0.4 g, 1.29 mmol). ES (+) MS m/e=334 (M+23).

21.3 Impure Compound 21.2 (0.4 g, 1.29 mmol) was hydrogenated at atmospheric pressure with Pd/C (0.281 g of 10% wet Pd on C) in 40 ml methanol for 2.5 hours, filtered through celite with additional methanol, and evaporated to a red oil. This was dissolved in 5 ml dry DMF and 1,1'-carbonyldiimidazole (0.219 g, 1.35 mmol) was added along with another 5 ml dry DMF and triethylamine (0.53 ml, 3.81 mmol). The reaction was heated under nitrogen to 80° C. for 40 minutes and then allowed to cool to room temperature and stir overnight. The reaction was then flooded with ethyl acetate and rinsed with 2×40 ml 1 M aqueous sodium hydrogen sulfate, 40 ml brine, dried over sodium sulfate, filtered, and evaporated to an orange oil which was purified by silica gel chromatography on a 14.5×2.5 cm column eluted with 97:3 DCM to methanol to provide Compound 21.3 as an off-white solid (0.08 g, 0.261 mmol, 21%). ES (+) MS m/e=308 (M+1). 1H NMR (400 MHz, Solvent)$^{TM}$ ppm 1.44 (s, 9H) 3.34 (m, 3H) 3.40 (m, 2H) 3.97 (m, 2H) 6.72 (m, 2H) 6.98 (m, 1H).

21.4 Compound 21.3 (80 mg, 0.261 mmol) was deprotected in 5 ml of 4 M HCl in dioxane for 1 hour at room temperature, evaporated to dryness, co-evaporated twice from DCM, and vacuumed to a purple solid. Meanwhile, 1-(3,4-Difluoro-benzyl)-2-oxo-1,2-dihydro-pyridine-3-carboxylic acid (72 mg, 0.272 mmol), 1-hydroxybenzotriazole (40 mg, 0.296 mmol), and N-(3-dimethylaminopropyl)-N'-ethylcarbodiimide hydrochloride (53 mg, 0.276 mmol) were dissolved in 1 ml dry DMF and added to the amine with another 2 ml dry DMF, followed by triethylamine (0.11 ml, 0.791 mmol). The reaction was allowed to proceed for 16.5 hours, at which point it was flooded with 40 ml ethyl acetate, rinsed with 2×20 ml 1 M aqueous sodium hydrogen sulfate, 2×20 ml saturated aqueous sodium bicarbonate, 20 ml brine, dried over sodium sulfate, filtered, evaporated, purified by reverse-phase preparative HPLC, and lyophilized to yield Compound 21.4 as an off-white solid. ES (+) MS m/e=455 (M+1). 1H NMR (400 MHz, Solvent)$^{TM}$ ppm 3.34 (s, 3H) 3.77 (m, 2H) 4.12 (m, 2H) 5.23 (s, 2H) 6.56 (m, 1H) 6.75 (m, 2H) 6.97 (m, 1H) 7.20 (m, 2H) 7.32 (m, 1H) 8.02 (m, 1H) 8.45 (m, 1H).

Example 22

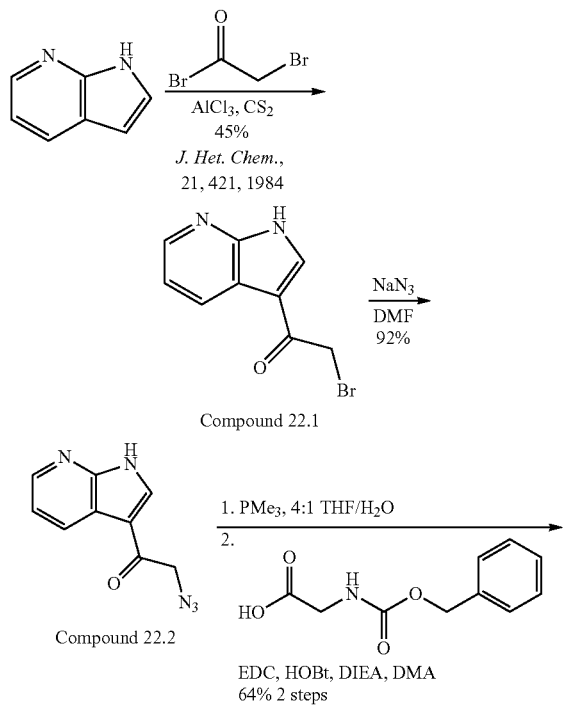

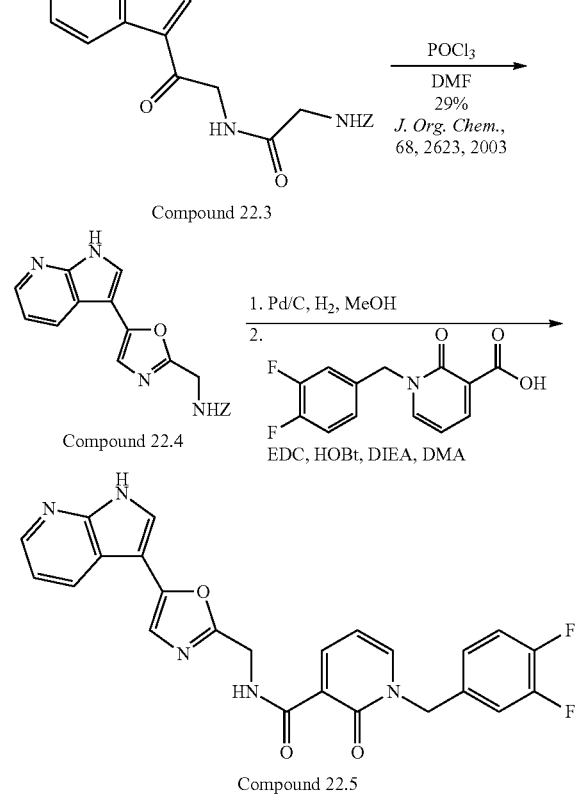

22.1 In a flame-dried three neck round bottom flask, 1H-Pyrrolo[2,3-b]pyridine (7.54 grams, 64 mmol) was dissolved in carbon disulfide (200 ml) under a nitrogen atmosphere with mechanical stirring. Trichloroaluminum (30 grams, 225 mmol) was added portion-wise. The mixture was heated to 50° C. and bromoacetyl bromide (5.59 ml, 64 mmol) in carbon disulfide (50 ml) was added drop wise via addition funnel. The reaction was stirred at 50° C. for 2 hours and then cooled to room temperature, then chilled on an ice bath to 0° C. and carefully quenched with water (500 ml). The mixture was filtered through a medium frit glass funnel and the cake recrystallized from MeOH to yield Compound 22.1 (6.95 grams, 28.86 mmol, 45%). ES (+) MS m/e=241 (M+2).

22.2 Compound 22.1 (2.0 grams, 8.37 mmol) and sodium azide (1.63 grams, 25.10 mmol) were dissolved in DMF (40 ml) and heated at 50° C. for 2 hours. The DMF was evaporated, the residue suspended in water, and extracted with EtOAc. The organic layer was dried over sodium sulfate, filtered, and concentrated to yield Compound 22.2 (1.55 grams, 7.70 mmol, 92%) ES (+) MS m/e=202 (M+1).

22.3 Compound 22.2 (0.760 grams, 3.85 mmol) was dissolved in THF (16 ml) and water (4 ml). Trimethylphosphine (1.0 M in THF, 13.2 ml, 13.22 mmol) was added and the reaction was stirred at room temperature for 2 hours and then concentrated. ES (+) MS m/e=176 (M+1). This residue was dissolved in dimethylacetamide (19 ml) and combined with N-(3-dimethylaminopropyl)-N'-ethylcarbodiimide hydrochloride (0.870 grams, 4.54 mmol), 1-hydroxybenzotriazole monohydrate (0.695 grams, 4.54 mmol), benzyloxycarbonylamino-acetic acid (0.791 grams, 3.78 mmol) and diisopropylethylamine (3.29 ml, 18.9 mmol). The reaction was stirred at ambient temperature for 16 hours, concentrated, dissolved in EtOAc, washed with saturated sodium bicarbonate, brine, dried over sodium sulfate, filtered, and concentrated to yield Compound 22.3 (0.889 grams, 2.43 mmol, 64% 2-steps). ES (+) MS m/e=367 (M+1).

22.4 Compound 22.3 (0.684 grams, 1.87 mmol) was dissolved in DMF (10 ml) and phosphorus oxychloride (0.513 ml, 5.60 mmol) was added. The reaction was heated to 50° C. for 10 minutes, cooled to room temperature and quenched with water (10 ml). The mixture was basified with 4 N NaOH to pH 11 and extracted with EtOAc. The combined organics were washed with brine, dried over sodium sulfate, filtered, and concentrated. The residue was purified by column chromatography on silica (5% MeOH/DCM) to yield Compound 22.4 (0.244 grams, 0.7 mmol, 29%). ES (+) MS m/e=349 (M+1).

22.5 Compound 22.4 was dissolved in MeOH (3 ml) and a small spatula scoop of palladium on carbon (wet Degussa type E101 NE/W) was added. The mixture was placed under a hydrogen balloon for 1 hour and the mixture filtered through celite and concentrated. ES (+) MS m/e=215 (M+1). This residue was taken forward as in example 18.3 to yield Compound 22.5. ES (+) MS m/e=462 (M+1). 1H NMR (400 MHz, DMSO-d6) δ ppm 4.70 (m, 2H) 5.24 (m, 2H) 6.61 (m, 1H) 7.18 (m, 2H) 7.43 (m, 3H) 7.87 (m, 1H) 8.29 (m, 3H) 8.39 (m, 1H) 10.21 (m, 1H) 12.16 (m, 1H).

Example 23

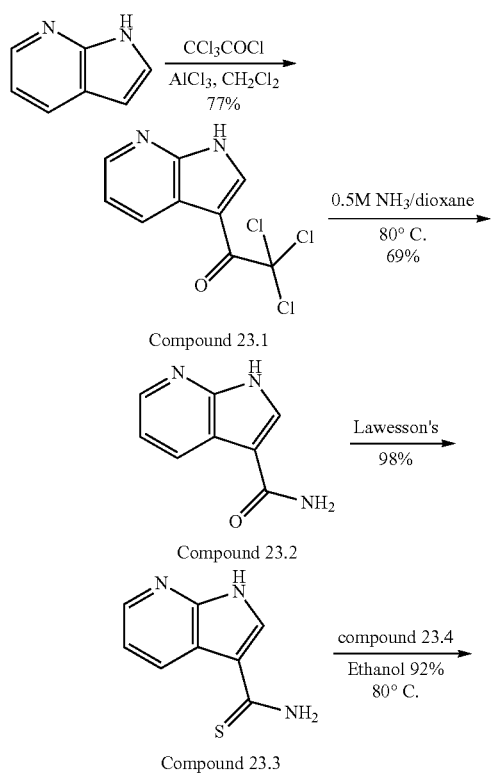

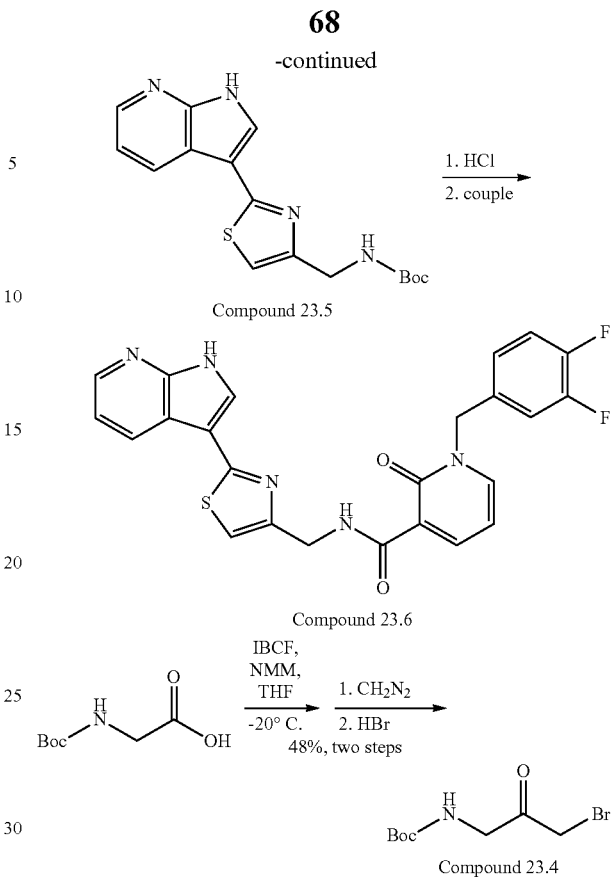

23.1 7-azaindole (5.0 grams, 42.3 mmol) was dissolved in 100 ml anhydrous DCM. To this was added aluminum chloride (19.7 grams, 148 mmol) potionwise while stirring under nitrogen. Then a solution of trichloroacetyl chloride (4.75 ml, 42.3 mmol) in 25 ml dry DCM was added slowly. The mixture was stirred at room temperature for six hours. The mixture was then chilled in an ice-water bath and 60 ml water was added very slowly to produce large amount of white precipitate. This was filtered, the precipitate was re-suspended in DCM and washed with copious 2% HCl. This was filtered again and dried to give Compound 23.1 (8.63 g, 77%) as a white solid, which was used without further purification: 1H NMR (400 MHz, DMSO-d6) ™ ppm 7.36 (dd, J=7.83, 4.40 Hz, 1H) 8.41 (dd, J=4.89, 1.47 Hz, 1H) 8.50 (dd, J=8.31, 1.96 Hz, 1H) 8.68 (m, 1H) 13.16 (m, 1H).

23.2 Compound 23.1 (1.71 g, 6.49 mmol) was suspended in 120 ml of 0.5 M ammonia in dioxane in a sealed bottle and heated at 80° C. for three days. The mixture was then filtered and Compound 23.2 (0.72 g, 69%) was collected as a brown solid which was used without further purification. ES (+) MS m/e=162 (M+1). $^1$H NMR (400 MHz, DMSO-d6) $^{TM}$ ppm 6.93 (m, 1H) 7.14 (dd, J=7.83, 4.40 Hz, 1H) 7.52 (m, 1H) 8.14 (m, 1H) 8.24 (d, J=4.40 Hz, 1H) 8.43 (d, J=7.83 Hz, 1H) 12.06 (m, 1H).

23.3 Compound 23.2 (0.5 g, 3.10 mmol) and Lawesson's reagent (0.78 g, 1.92 mmol) were suspended in 15 ml THF and stirred overnight at room temperature under nitrogen. The reaction was then heated at 50° C. for three hours under nitrogen, at which point solvent was evaporated under vacuum and the crude was purified by chromatography to yield Compound 23.3 (0.539 g, 98%) as a brown solid. ES (+) MS m/e=178 (M+1). $^1$H NMR (400 MHz, DMSO-d6)<sup>TM</sup> ppm 7.19 (dd, J=8.31, 4.89 Hz, 1H) 8.21 (d, J=2.45 Hz, 1H) 8.26 (dd, J=4.40, 0.98 Hz, 1H) 8.97 (m, 2H) 9.10 (m, 1H) 12.29 (m, 1H).

23.4 A solution of Boc-protected glycine (2.92 g, 16.67 mmol) in 85 ml dry THF under nitrogen was chilled to −20° C. Isobutyl chloroformate (2.16 ml, 16.67 mmol) was added followed by N-methylmorpholine (1.83 ml, 16.67 mmol) dropwise. After 20 minutes, the reaction mixture was quickly filtered and added to a precooled (0° C.) ether solution of diazomethane (50 mmol). The reaction was allowed to warm to room temperature overnight. The reaction was then flooded with ether and water. The aqueous layer was extracted with ethyl acetate. The combined organic layers were rinsed with saturated sodium bicarbonate, brine, evaporated to get a brown oil. This oil was dissolved in 20 ml THF, chilled in ice-water bath, and a solution of 33% HBr in acetic acid (3.02 ml, 16.67 mmol) was added. The mixture was stirred for 20 minutes, evaporated, then co-evaporated with toluene a couple times to get a yellow oil. This was purified by chromatography to give Compound 23.4 (2.12 g, 46%) as pale yellow oil. ES (+) MS m/e=274 (M+Na).

23.5 Compound 23.3 (0.2 g, 1.13 mmol) was dissolved in 6 ml absolute ethanol and Compound 23.4 (0.285 g, 1.13 mmol) was added. The reaction was heated at 80° C. for 2 hours and then flooded with ethyl acetate, rinsed with saturated sodium bicarbonate, brine, dried over sodium sulfate, filtered, and evaporated to yield Compound 23.5 (0.34 g, 92%) as a brown oil which was used without further purification. ES (+) MS m/e=331 (M+1).

23.6 This was made as in Example 15.4, but using Compound 23.5. ES (+) MS m/e=478 (M+1). <sup>1</sup>H NMR (400 MHz, DMSO-d6) <sup>TM</sup> ppm 4.64 (d, J=5.38 Hz, 2H) 5.23 (m, 2H) 6.60 (t, J=6.85 Hz, 1H) 7.19 (m, 2H) 7.30 (m, 1H) 7.42 (m, 2H) 8.21 (d, J=2.93 Hz, 1H) 8.24 (dd, J=6.85, 2.45 Hz, 1H) 8.32 (d, J=3.42 Hz, 1H) 8.40 (dd, J=7.34, 2.45 Hz, 1H) 8.65 (dd, J=7.83, 0.98 Hz, 1H) 10.26 (t, J=5.38 Hz, 1H) 12.28 (m, 1H).

Example 24

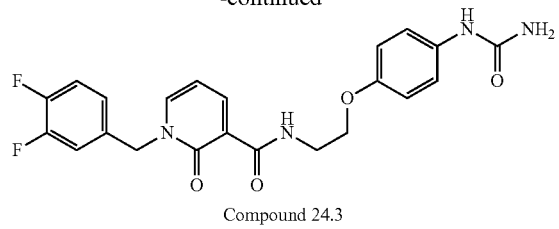

Compound 24.3

24.1 To a 2-dram vial were added (4-hydroxy-phenyl)-carbamic acid tert-butyl ester (0.209 g, 1.0 mmol), (2-bromo-ethyl)-carbamic acid tert-butyl ester (0.224 g, 1.0 mmol), and K<sub>2</sub>CO<sub>3</sub> (0.414 g, 3.0 mmol) in 2 ml of acetone. The vial was capped and shaken at 70° C. for 16 h. The solvent was filtered and concentrated using the GeneVac HT-12 to give a crude Compound 24.1. ES (+) MS m/e=353 (M+1).

24.2 To the crude intermediate of Compound 24.1 were added 2 ml of MeOH and 2 ml of HCl (4.0 M in dioxane). The mixture was capped and shaken at room temperature for 3 hours. The solvent was removed using the GeneVac HT-12. To the residue were added 2 ml of CH<sub>3</sub>CN, 1-(3,4-difluoro-benzyl)-2-oxo-1,2-dihydro-pyridine-3-carboxylic acid (0.133 g, 0.5 mmol, Compound 20.2), 2-chloro-1,3-dimethylimidazolinium chloride (0.101 g, 0.6 mmol), and di-isopropylethylamine (0.29 g, 2.3 mmol). The vial was capped and shaken at room temperature for 16 hours. The solvent was concentrated using GeneVac HT-12 to give a crude product of Compound 24.2. ES (+) MS m/e=400 (M+1).

24.3 To the vial containing the crude Compound 24.2 were added 1 ml of acetic acid, 1 ml of water, and KNCO (0.162 g, 2 mmol). The vial was capped and shaken at room temperature for 16 hours. The solvent was concentrated using GeneVac HT-12. The crude product was dissolved in DMSO (3 ml) and purified by using HPLC (reverse phase) to give Compound 24.3. ES (+) MS m/e=442.9 (M+1). 1H NMR (400 MHz, CD<sub>3</sub>OD) <sup>TM</sup> ppm 2.60 (s, 2H), 3.65 (t, J=7 Hz, 2H), 4.0 (t, J=7 Hz, 2H), 5.15 (s, 2H), 6.45 (m, 1H), 6.75 (m, 2H), 7.1-7.5 (m, 7H), 7.90 (s, 1H), 8.40 (s, 1H).

Example 25

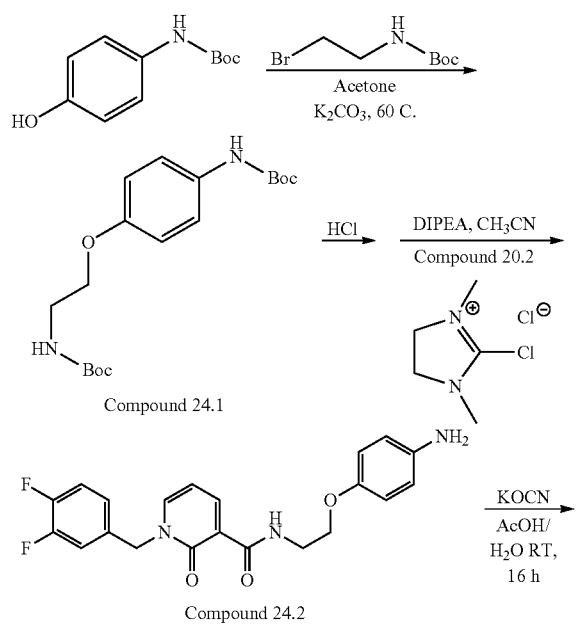

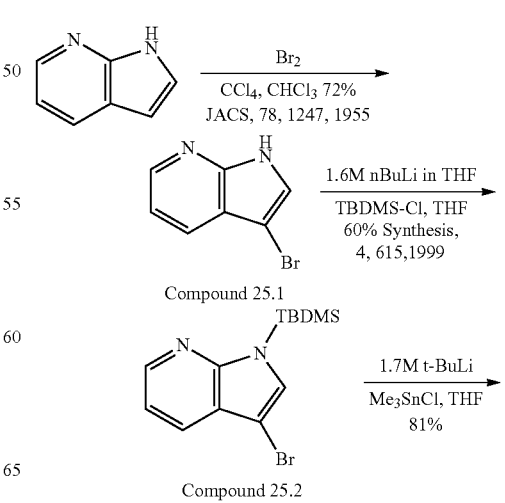

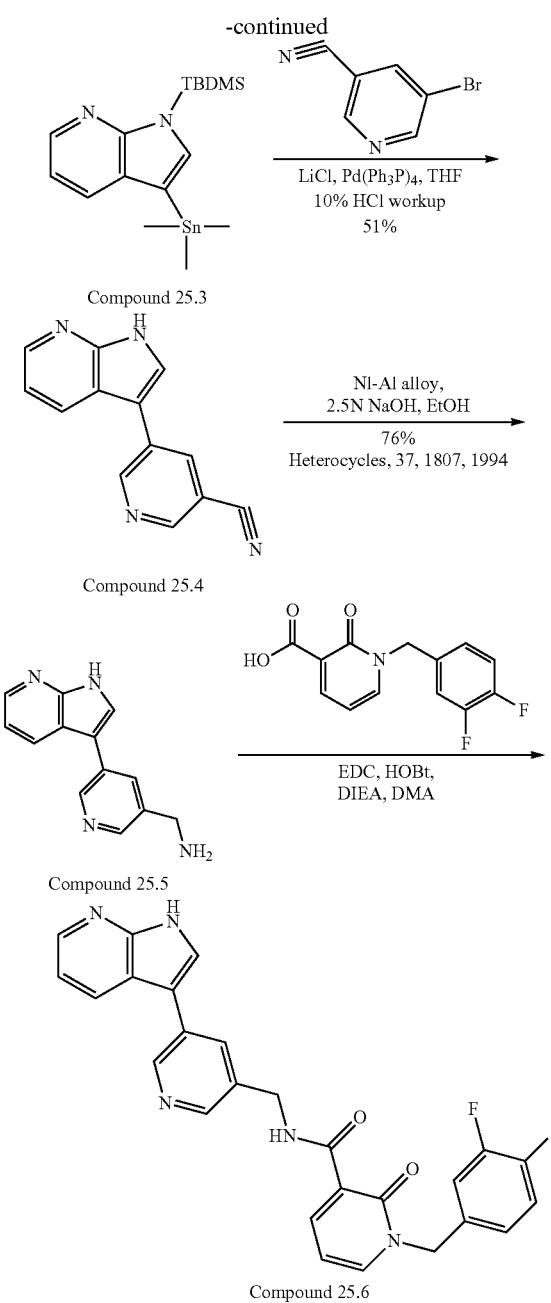

Compound 25.3

Compound 25.4

Compound 25.5

Compound 25.6

25.1 1H-Pyrrolo[2,3-b]pyridine (5.0 grams, 42.29 mmol) was dissolved in chloroform (67 ml) under a nitrogen atmosphere and chilled to 0° C. Bromine (2.17 ml, 42.29 mmol) diluted in carbon tetrachloride (85 ml) was added dropwise via addition funnel. The reaction was stirred for an additional 30 minutes at 0° C. and water (100 ml) was added, the aqueous layer was separated, filtered, basified with 5N NaOH to pH 11, and the precipitate collected by filtration to yield Compound 25.1 (6.02 grams, 35.12 mmol). ES (+) MS m/e=199 (M+2).

25.2 Compound 25.1 (5.4 grams, 27.11 mmol) was dissolved in dry THF (87 ml) under a nitrogen atmosphere and cooled to −78° C. n-Butyl lithium (1.6M in Hexanes, 18.9 ml, 30.15 mmol) was added slowly and after an additional 30 minutes of stirring at −78° C. tert-butyldimethylsilyl-chloride (4.55 grams, 30.15 mmol) in THF (30 ml) was added via addition funnel. The cooling bath was removed and the reaction stirred for 3 hours, flooded with ether (200 ml), washed with brine, dried over sodium sulfate, filtered and concentrated. The residue was purified by column chromatography on silica (5-50% DCM/hexanes) to yield Compound 25.2 (4.79 grams, 15.39 mmol, 56%). 1H NMR (400 MHz, CDCl$_3$) δ ppm 0.63 (m, 6H) 0.94 (m, 9H) 7.10 (m, 1H) 7.24 (m, 1H) 7.81 (m, 1H) 8.30 (m, 1H).

25.3 Compound 25.2 (1.0 gram, 3.21 mmol) was dissolved in dry THF (16 ml) under a nitrogen atmosphere in a flame-dried round bottom flask and chilled to −90° C. and tert-butyl lithium (1.7 M in pentane, 3.78 ml, 6.42 mmol) was added. The reaction was stirred for 5 minutes at −90° C. and then trimethyltinchloride (1.0 M in diethyl ether, 4.82 ml, 4.82 mmol) was added and the reaction stirred 1 hour at −90° C. The cooling bath was removed and the reaction stirred for 1 hour and then quenched with water (2 ml). The reaction was diluted with ether, washed with brine, dried over sodium sulfate, filtered, and concentrated to give Compound 25.3 which was taken on crude (1.25 grams, 3.16 mmol, 99%).

25.4 Compound 25.3 (0.814 grams, 2.06 mmol), 5-bromo-nicotinonitrile (0.754 grams, 4.12 mmol), tetrakis (triphenylphosphine) palladium (0) (0.476 grams, 0.412 mmol), and lithium chloride (0.262 grams, 6.18 mmol) were dissolved in dry THF (11 ml) under a nitrogen atmosphere and heated to reflux for 24 hours. Diethyl ether (10 ml) and 10% HCL (20 ml) were added and the layers separated. The aqueous layer was basified with 40% NaOH to pH 11 and extracted with DCM. The combined organic layers were dried over sodium sulfate, filtered, and concentrated. The residue was purified by column chromatography on silica (3% MeOH/DCM) to yield Compound 25.4 (0.231 grams, 1.05 mmol, 51%). ES (+) MS m/e=221 (M+1).

25.5 Compound 25.4 (0.218 grams, 0.992 mmol) was dissolved in EtOH (3.9 ml), 2.5N NaOH (3.9 ml) was added and the mixture cooled to 0° C. on an ice bath. Nickel-aluminum alloy (Fluka No. 72240, 1.92 grams) was added via powder addition funnel over 30 minutes, the ice bath was removed and the reaction stirred for an additional 30 minutes. The reaction mixture was filtered through celite, water (10 ml) was added and the mixture extracted with DCM, dried over sodium sulfate, filtered, and concentrated to yield Compound 25.5 (0.168 grams, 0.749 mmol, 76%). ES (+) MS m/e=225 (M+1).

25.6 Compound 25.5 (0.168 grams, 0.749), 1-(3,4-difluoro-benzyl)-2-oxo-1,2-dihydro-pyridine-3-carboxylic acid (0.200 grams, 0.749 mmol), N-(3-dimethylaminopropyl)-N'-ethylcarbodiimide hydrochloride (0.172 grams, 0.899 mmol) and 1-hydroxybenzotriazole monohydrate (0.138 grams, 0.899 mmol), and diisopropylethylamine (0.652 ml, 3.75 mmol) were dissolved in dimethylacetamide (4 ml) and stirred at ambient temperature for 17 hours. The reaction was diluted with EtOAc, washed with saturated sodium bicarbonate, brine, dried over sodium sulfate, filtered, and concentrated. The residue was purified by column chromatography on silica (3% MeOH/DCM) to yield Compound 25.6 (0.066 grams, 0.140 mmol, 19%). ES (+) MS m/e=472 (M+1). 1H NMR (400 MHz, DMSO-d6) δ ppm 4.59 (m, 2H) 5.20 (m, 2H) 6.58 (m, 1H) 7.14 (m, 2H) 7.40 (m, 2H) 8.00 (m, 1H) 8.08 (m, 1H) 8.22 (m, 1H) 8.29 (m, 2H) 8.39 (m, 2H) 8.84 (m, 1H) 10.11 (m, 1H) 12.06 (m, 1H).

Example 26

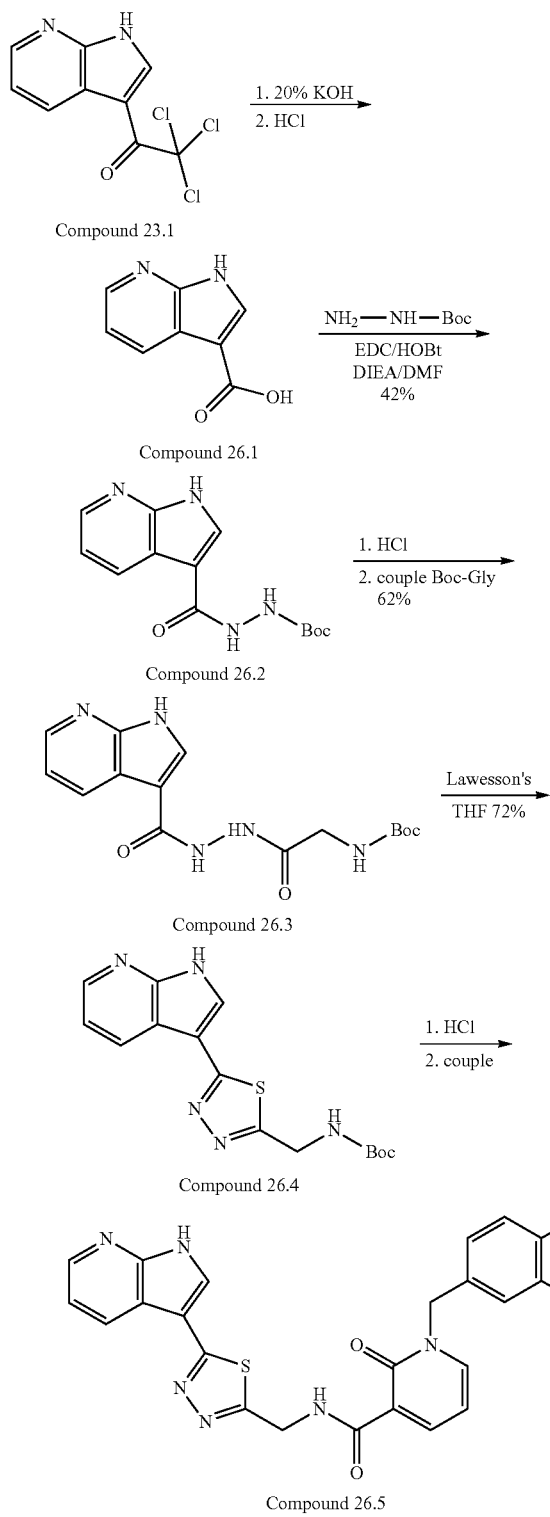

separated by centrifugation, washed with copious water and dried to give Compound 26.1 (1.63 g) as a white solid. ES (+) MS m/e=163 (M+1).

26.2 Compound 26.1 (5.72 g, 35.3 mmol), 1-(3-Dimethylaminopropyl)-3-ethylcarbodiimide hydride (6.77 g, 35.3 mmol) and 1-hydroxybenzotriazole hydrate (5.4 g, 35.3 mmol) were suspended in 90 ml DMF. Then tert-butyl carbazate (4.67 g, 35.3 mmol) was added followed by diisopropylethylamine (12.3 ml, 70.6 mmol). The reaction was stirred overnight at room temperature. Then the solvent was removed under vacuum and the residue was flooded with ethyl acetate, rinsed with saturated sodium bicarbonate, brine, dried over sodium sulfate, filtered, and evaporated to dryness. This was purified using flash chromatography to give Compound 26.2 (4.06 g, 42%) as a white solid. ES (+) MS m/e=277 (M+1).

26.3 Compound 26.2 (2.57 g, 9.3 mmol) was deprotected with 20 ml of 4 M HCl in dioxane for 30 minutes and then evaporated to dryness. One-third of this (3 mmol) was coupled with Boc-glycine (526 mg, 3 mmol) following the procedure described in Example 26.2. Compound 26.3 was isolated as a brown oil (0.62 g, 62%). ES (+) MS m/e=334 (M+1).

26.4 Compound 26.3 (540 mg, 1.62 mmol) and Lawesson's reagent (680 mg, 1.68 mmol) were suspended in 6 ml dry THF and heated at 60° C. for two hours. The solvent was then removed by evaporation and the crude product was purified by chromatography to give Compound 26.4 (388 mg, 72%). ES (+) MS m/e=332 (M+1). $^1$H NMR (400 MHz, DMSO-d6) $^{TM}$ ppm 1.41 (m, 9H) 4.51 (d, J=6.36 Hz, 2H) 7.27 (dd, J=7.83, 4.40 Hz, 1H) 7.84 (t, J=5.87 Hz, 1H) 8.34 (m, 2H) 8.51 (dd, J=8.31, 1.47 Hz, 1H) 12.44 (m, 1H).

26.5 Compound 26.4 (388 mg, 1.17 mmol) was deprotected with 20 ml of 4 M HCl in dioxane for 30 minutes and then evaporated to dryness. Part of it (180 mg, 0.3 mmol) was taken on to final product as described in Example 15.4. ES (+) MS m/e=479 (M+1). $^1$H NMR (400 MHz, DMSO-d6) $^{TM}$ ppm 4.92 (d, J=5.87 Hz, 2H) 5.22 (m, 2H) 6.61 (t, J=6.85 Hz, 1H) 7.19 (m, 1H) 7.26 (dd, J=7.83, 4.89 Hz, 1H) 7.44 (m, 2H) 8.29 (m, 2H) 8.34 (dd, J=4.40, 1.47 Hz, 1H) 8.40 (dd, J=7.34, 1.96 Hz, 1H) 8.51 (dd, J=7.83, 0.98 Hz, 1H) 10.32 (t, J=6.36 Hz, 1H) 12.42 (m, 1H).

Example 27

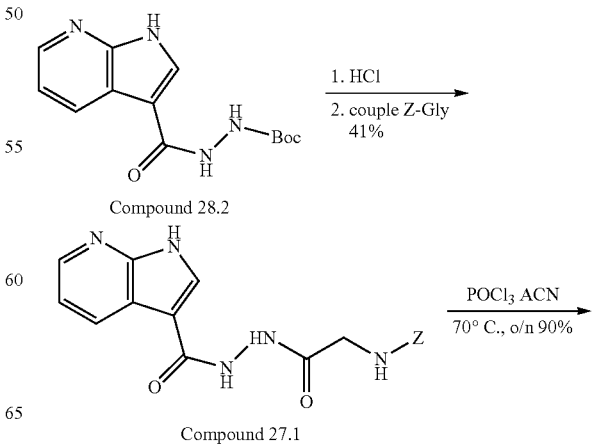

26.1 Compound 23.1 (2.5 g, 9.51 mmol) was dissolved in 25 ml 20% aqueous KOH solution while stirring. After two hours, the solution was adjusted to pH 2 with concentrated HCl. A white precipitate formed at this stage. The solid was -continued

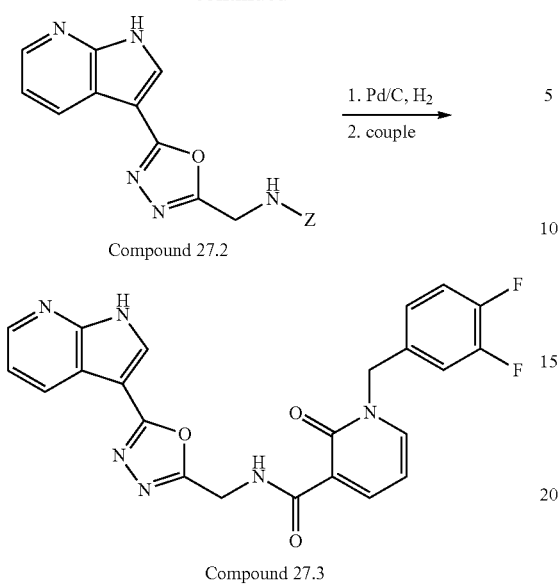

27.1 This was made as in Example 26.3 except using N-Cbz-glycine. The product was isolated as a white solid (447 mg, 41%). ES (+) MS m/e=368 (M+1).

27.2 Compound 27.1 (287 mg, 0.78 mmol) was suspended in 8 ml anhydrous acetonitrile and phosphoryl chloride (80 μl, 0.86 mmol) was added. The reaction was heated at 70° C. for six hours, at which point more phosphoryl chloride (80 μl, 0.86 mmol) was added and the reaction allowed to proceed overnight. The reaction was then cooled, flooded with ethyl acetate, washed with saturated sodium bicarbonate, brine, dried over sodium sulfate, filtered, and evaporated to yield Compound 27.2 (250 mg, 90%) as a yellow solid. ES (+) MS m/e=350 (M+1).

27.3 Compound 27.2 (195 mg, 0.56 mmol) was deprotected by hydrogenation overnight with 10% Pd/C in MeOH on a Parr shaker. The mixture was then filtered through Celite. The filtrate was evaporated to get a yellow solid, which was reacted according to Example 15.4 to give Compound 27.3 as an off-white solid. ES (+) MS m/e=463 (M+1). $^1$H NMR (400 MHz, DMSO-d6) $^{TM}$ ppm 4.83 (d, J=5.87 Hz, 2H) 5.23 (m, 2H) 6.60 (t, J=6.85 Hz, 1H) 7.20 (m, 1H) 7.26 (dd, J=7.34, 4.89 Hz, 1H) 7.44 (m, 2H) 8.28 (m, 2H) 8.38 (m, 3H) 10.22 (t, J=5.87 Hz, 1H) 12.56 (m, 1H).

Example 28

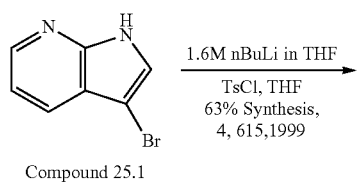

-continued

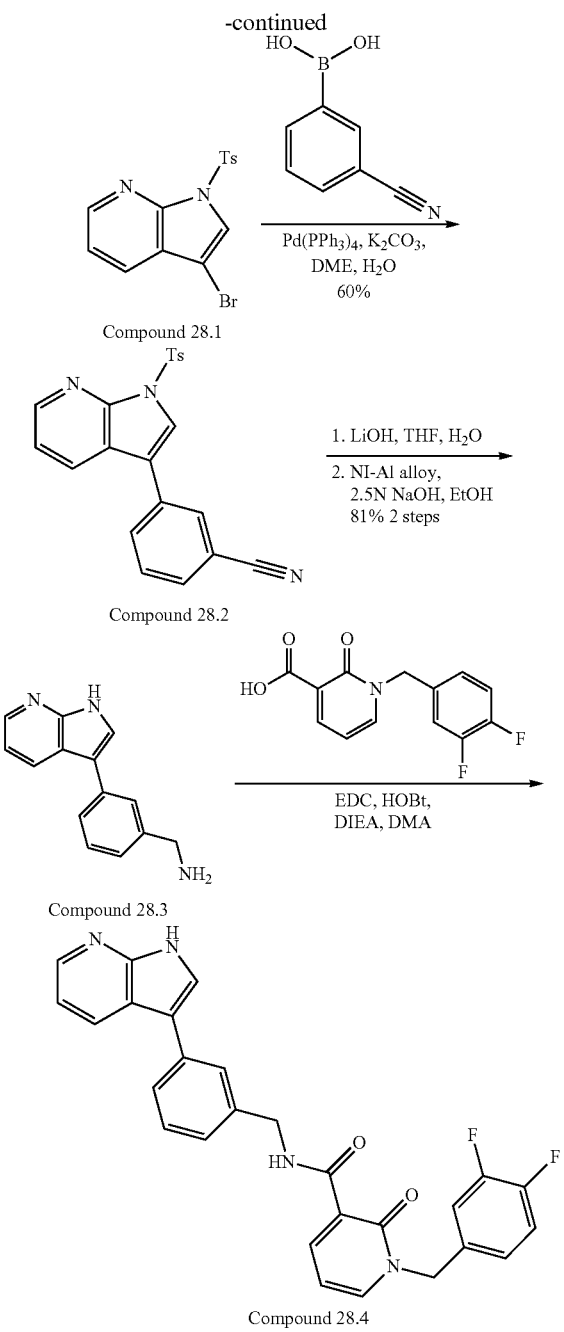

28.1 This was made as in example 25.2 except using 4-methyl-benzenesulfonyl chloride. Product was purified by column chromatography on silica (DCM) (63%). ES (+) MS m/e=351 (M).

28.2 Compound 28.1 (0.600 grams, 1.71 mmol), 3-benzonitrileboronicacid (0.170 grams, 1.16 mmol), tetrakis(triphenylphosphine) palladium (0) (0.198 grams, 0.171 mmol), potassium carbonate (0.827 grams, 5.98 mmol) were combined with dimethoxyethane 97.5 ml), water (1.8 ml) and heated by microwave irradiation at 130° C. for 10 minutes. The reaction was diluted with EtOAc, washed with saturated sodium bicarbonate, dried over sodium sulfate, filtered through celite and concentrated. The residue was purified by column chromatography on silica (20% EtOAc/hexanes) to yield Compound 28.2 (0.386 grams, 1.03 mmol, 60%). ES (+) MS m/e=374 (M+1).

28.3 Compound 28.2 (0.386 grams, 1.04 mmol) was dissolved in THF (10 ml) and 2N LiOH (6 ml) was added. The reaction was stirred at ambient temperature for 1 hour and then 70° C. for 16 hours. The reaction was diluted with EtOAc, washed with 1M sodium carbonate, brine, dried over sodium sulfate, filtered and concentrated. ES (+) MS m/e=220 (M+1). This nitrile was converted to a benzyl amine by the procedure in Example 25.5 to yield Compound 28.3 (0.141 grams, 0.632 mmol, 81%). ES (+) MS m/e=224 (M+1).

28.4 This was made as in example 25.6 except using Compound 28.3. ES (+) MS m/e=471 (M+1). 1H NMR (400 MHz, DMSO-d6) δ ppm 4.56 (m, 2H) 5.10 (m, 2H) 6.45 (m, 1H) 7.10 (m, 5H) 7.29 (m, 1H) 7.46 (m, 1H) 7.56 (m, 2H) 7.89 (m, 1H) 8.10 (m, 1H) 8.19 (m, 1H) 8.38 (m, 1H).

Example 29

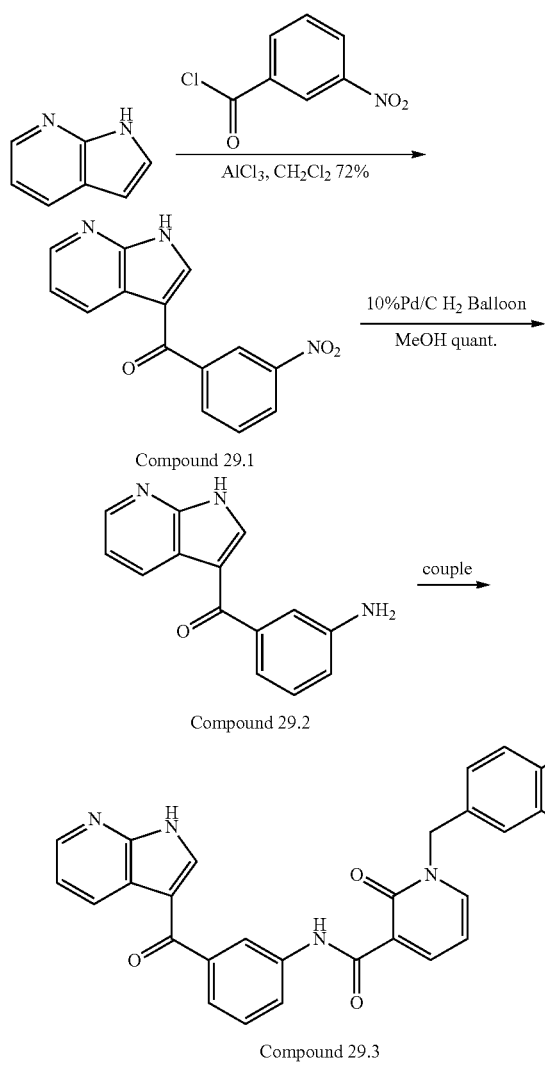

Compound 29.1

Compound 29.2

Compound 29.3

29.1 Aluminum chloride (17.5 grams, 131 mmol) was suspended in 200 ml anhydrous DCM under nitrogen and 7-azaindole (5.16 g, 43.6 mmol) was added. After one hour, 3-nitrobenzoyl chloride (24.3 g, 131 mmol) was added potionwise. The reaction was stirred at room temperature for two hours, and then more aluminum chloride (17.5 grams, 131 mmol) was added. After two days, the reaction was chilled in an ice-water bath and 200 ml MeOH was added slowly to produce an intense white precipitate. This was filtered and the precipitate was re-suspended in 500 ml DCM and washed with copious 2% HCl. The suspension was then filtered, and Compound 29.1 was isolated as a white solid (8.09 g, 72%). ES (+) MS m/e=268 (M+1). $^1$H NMR (400 MHz, DMSO-d6) $^{TM}$ ppm 7.33 (dd, J=7.83, 4.89 Hz, 1H) 7.83 (t, J=7.83 Hz, 1H) 8.25 (m, 2H) 8.40 (dd, J=4.89, 1.47 Hz, 1H) 8.44 (m, 1H) 8.49 (m, 1H) 8.56 (dd, J=7.83, 1.47 Hz, 1H) 12.84 (m, 1H).

29.2 Compound 29.1 (500 mg, 1.87 mmol) was suspended in 20 ml MeOH and 200 mg of 10% Pd/C was added. This was hydrogenated (H$_2$ balloon) overnight. The mixture was filtered through Celite, the filtrate was evaporated to give Compound 29.2 as a light yellow solid (520 mg, quant.). ES (+) MS m/e=238 (M+1).

29.3 This was made as in Example 15.4. ES (+) MS m/e=485 (M+1). $^1$H NMR (400 MHz, DMSO-d6) $^{TM}$ ppm 5.29 (m, 2H) 6.69 (dd, J=7.34, 6.36 Hz, 1H) 7.22 (m, 1H) 7.30 (dd, J=7.83, 4.89 Hz, 1H) 7.48 (m, 4H) 7.82 (d, J=7.34 Hz, 1H) 8.15 (d, J=2.93 Hz, 1H) 8.22 (m, 1H) 8.32 (dd, J=6.85, 1.96 Hz, 1H) 8.38 (d, J=4.40 Hz, 1H) 8.49 (dd, J=6.85, 2.45 Hz, 1H) 8.54 (d, J=7.83 Hz, 1H) 12.14 (m, 1H) 12.66 (m, 1H).

Example 30

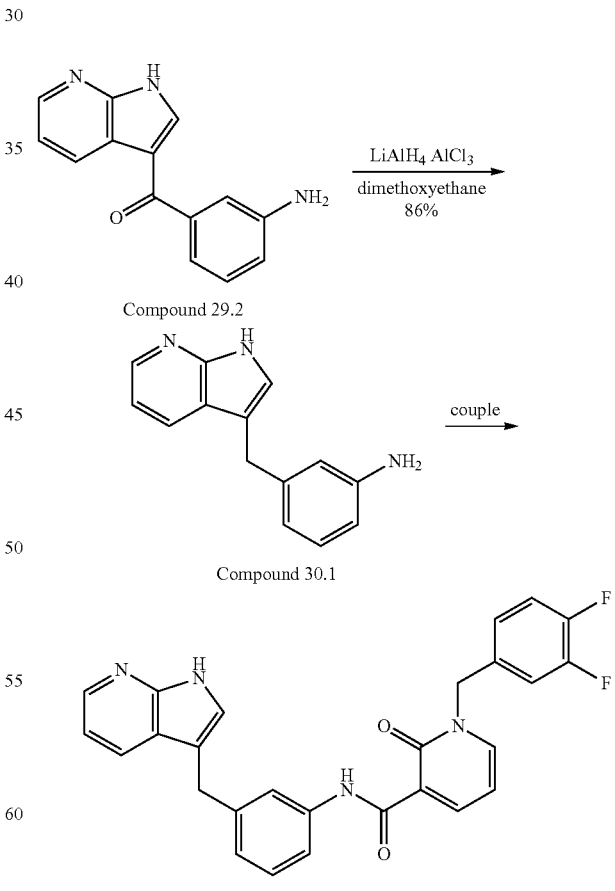

Compound 30.1

Compound 30.2

30.1 A suspension of 1.0 M lithium aluminum hydride (1.74 ml, 1.74 mmol) in 8 ml anhydrous dimethoxyethane was chilled in an ice-water bath under nitrogen and aluminum chloride (0.45 g, 3.38 mmol) was added slowly. Then a solution of Compound 29.2 (200 mg, 0.84 mmol) in 30 ml anhydrous dimethoxyethane was added slowly. After ~10 minutes the reaction was removed from the ice-water bath, allowed to warm to room temperature, and stirred for 2 hours. The reaction was quenched with 10 ml water and extracted with DCM twice. The combined DCM layers were dried over sodium sulfate and concentrated to give Compound 30.1 (162 mg, 86%) as a brown oil. ES (+) MS m/e=224 (M+1).

30.2 This was made as in Example 15.4. ES (+) MS m/e=471 (M+1). $^1$H NMR (400 MHz, DMSO-d6) $^{TM}$ ppm 4.05 (m, 2H) 5.26 (m, 2H) 7.04 (d, J=7.83 Hz, 1H) 7.09 (m, 1H) 7.10 (m, 1H) 7.18 (m, 1H) 7.24 (t, J=7.34 Hz, 1H) 7.48 (m, 5H) 7.98 (d, J=7.83 Hz, 1H) 8.23 (d, J=4.89 Hz, 1H) 8.28 (dd, J=6.85, 1.47 Hz, 1H) 8.45 (dd, J=6.85, 1.96 Hz, 1H) 11.70 (m, 1H) 11.92 (m, 1H).

Example 31

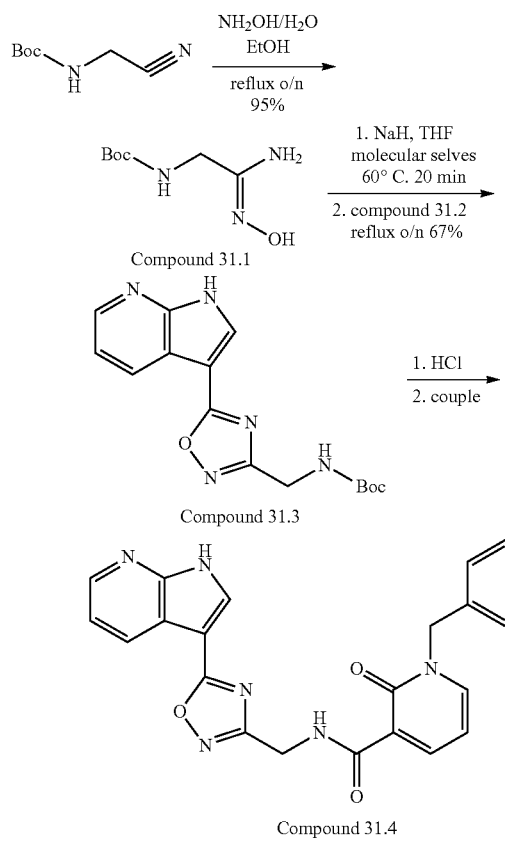

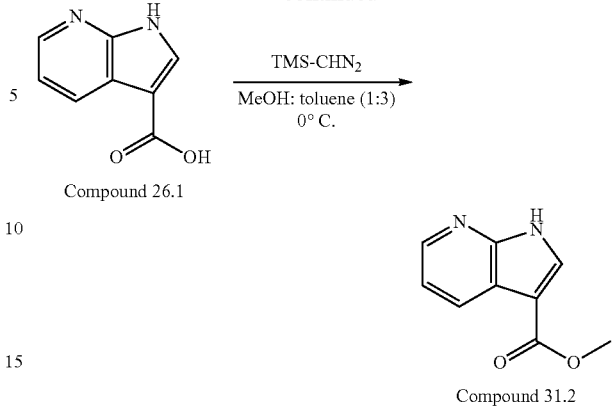

31.1 N-(tert-butoxycarbonyl)-2-aminoacetonitrile (4 g, 25.6 mmol) was dissolved in 10 ml ethanol and an aqueous solution of 50% hydroxylamine (2.36 ml, 38.4 mmol) was added. The reaction was heated at 80° C. overnight. The solvent was removed under vacuum and the residue was extracted with DCM. The combined DCM layers were dried over sodium sulfate and evaporated to yield Compound 31.1 (4.62 g, 95%) as an off-white solid. $^1$H NMR (400 MHz, DMSO-d6) $^{TM}$ ppm 1.37 (m, 9H) 3.48 (d, J=6.36 Hz, 2H) 5.22 (m, 2H) 6.94 (t, J=5.87 Hz, 1H) 8.97 (m, 1H).

31.2 Compound 26.1 (0.81 g, 5 mmol) was suspended in a mixture of MeOH and toluene (10 ml, 1:3) and chilled in ice-water bath. A solution of 2 M (trimethylsilyl) diazomethane in hexanes (3 ml, 6 mmol) was added dropwise. The reaction was then removed from the ice-water bath, allowed to warm to room temperature, and stirred for 1 hour. The reaction was evaporated and co-evaporated with DCM a couple times to give Compound 31.2 (785 mg). ES (+) MS m/e=177 (M+1).

31.3 Compound 31.1 (380 mg, 2 mmol) was dissolved in 15 ml dry THF containing 4-Å powdered molecular sieves (0.8 g). This mixture was stirred for 30 minutes. Sodium hydride (84 mg of 60% dispersion in oil, 2.1 mmol) was added and the mixture was heated at 60° C. for 20 minutes. The reaction was cooled to room temperature, and a solution of Compound 31.2 (0:9 g, 5 mmol) in dry THF was added. The resulting mixture was heated at reflux for 22 hours, cooled, filtered, and the filtrate concentrated under vacuum. The residue was purified by chromatography to afford Compound 31.3 (214 mg, 67%) as a white solid. ES (+) MS m/e=316 (M+1).

31.4 This was made as in Example 15.4, but starting with Compound 31.3. ES (+) MS m/e=463 (M+1). $^1$H NMR (400 MHz, DMSO-d6) $^{TM}$ ppm 4.71 (d, J=5.87 Hz, 2H) 5.23 (m, 2H) 6.60 (t, J=6.85 Hz, 1H) 7.20 (m, 1H) 7.31 (m, 1H) 7.44 (m, 2H) 8.27 (dd, J=6.36, 1.96 Hz, 1H) 8.40 (m, 3H) 8.52 (d, J=1.96 Hz, 1H) 10.22 (t, J=5.87 Hz, 1H) 12.83 (m, 1H)

Example 32

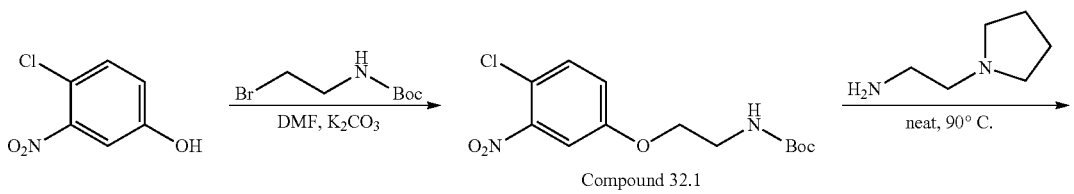

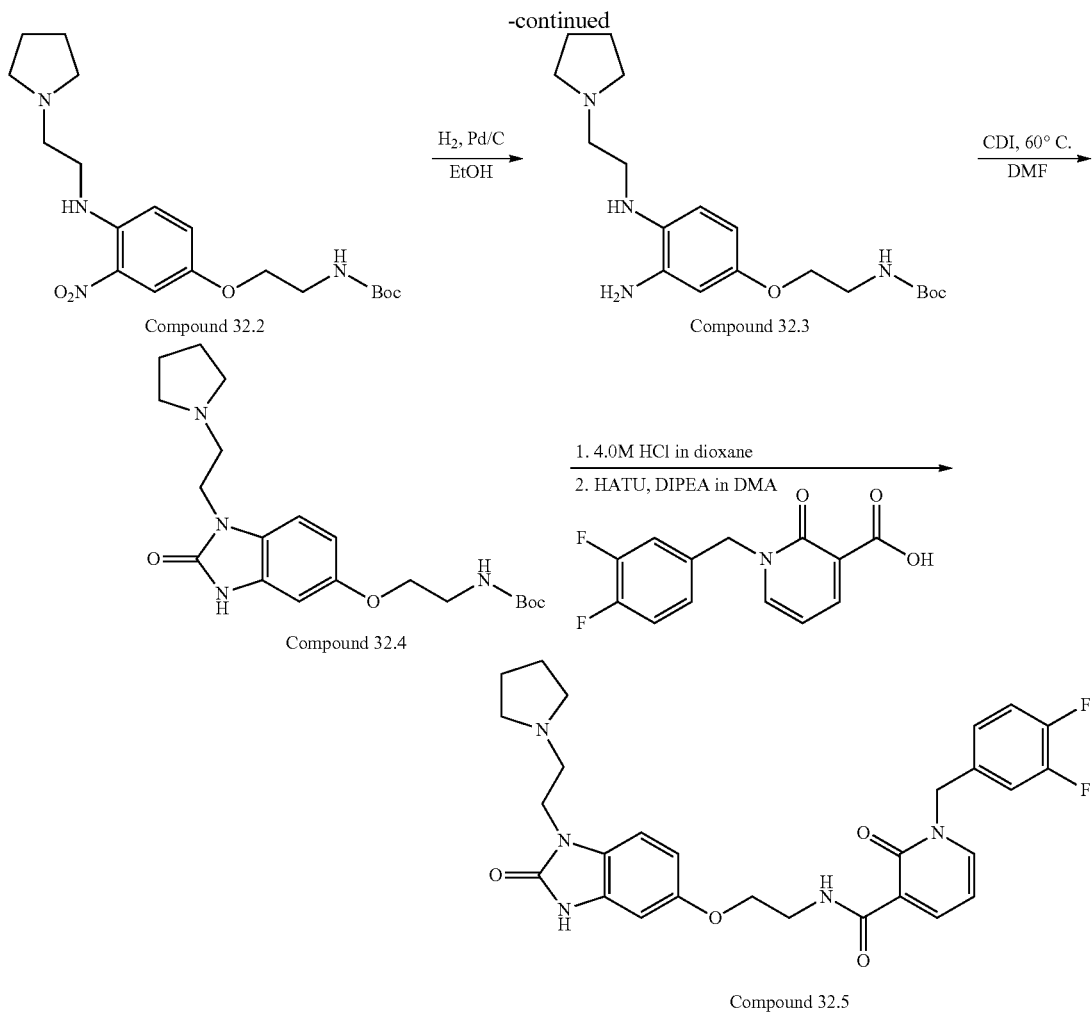

32.1 4-Chloro-3-nitrophenol (Aldrich, 3.08 grams, 17.8 mmol) was dissolved in 20 ml dry N,N-dimethylformamide and Boc-2-aminoethylbromide (Chem-Impex, 3.94 g, 17.6 mmol) and potassium carbonate (2.45 g, 17.8 mmol) were added. The reaction was heated at 60° C. for 4 hours and then flooded with 100 ml ethyl acetate, washed with 50 ml water twice, with 50 ml of 3 N sodium hydroxide solution twice, treated with brine and dried over $Na_2SO_4$. The organic solvent was removed in vacuo to yield yellow oil (2.2 g, 40%). ES (+) MS m/e=339 (M+23).

32.2 Compound 32.1 (0.7 g, 2.2 mmol) was dissolved in N-(2-aminoethyl)pyrrolidine (5.0 g, 44 mmol) and heated at 90° C. in a pressure vessel. After 60 hours, it was diluted with 30 ml of dichloromethane and washed with 25 ml of 0.5 M HCl twice, treated with brine and dried over $Na_2SO_4$. The solvent was evaporated in vacuo to yield 0.33 g of crude mixture, which was purified using preparatory thin-layer-chromatography with 7% methanol in dichloromethane as the eluent. The dried material weighed 56 mg (6% yield). ES (+) MS m/e=396 (M+1).

32.3 Compound 32.2 (56 mg, 0.14 mmol) was dissolved in 3 ml ethanol and palladium (10 wt. % on activated carbon, 15 mg, 0.14 mmol) was added. The reaction was stirred vigorously under a $H_2$ balloon for 2 hours until the reduction was complete. The reaction was then filtered through celite and the solvent was removed in vacuo to yield brown solid (50 mg, 98%). ES (+) MS m/e=366 (M+1).

32.4 Compound 32.4 was prepared from Compound 32.3 using the same method described in example 15 (15.3). ES (+) MS m/e=392 (M+1).

32.5 Compound 32.4 was coupled with 1-(3,4-difluoro-benzyl)-2-oxo-1,2-dihydro-pyridine-3-carboxylic acid with the same method described in example 15 (15.4).

$^1$H NMR (400 MHz, methanol-D4) $^{TM}$ ppm 10.35 (br s, 1H), 8.45 (dd, 1H, J=7 Hz, J=2 Hz), 8.02 (dd, 1H, J=7 Hz, J=2 Hz), 7.34-7.17 (m, 3H), 7.09 (d, 1H, J=8 Hz), 6.78 (d, 2H, J=8 Hz), 6.56 (t, 1H, J=7 Hz), 5.23 (s, 2H), 4.24 (t, 2H, J=6 Hz), 4.12 (t, 2H, J=5.4 Hz), 3.80-3.76 (m, 4H), 3.60 (t, 2H, J=5.6 Hz), 3.15 (br d, 2H, J=8 Hz), 2.16 (br s, 2H), 2.00 (br d, 2H, J=5 Hz).

Example 33

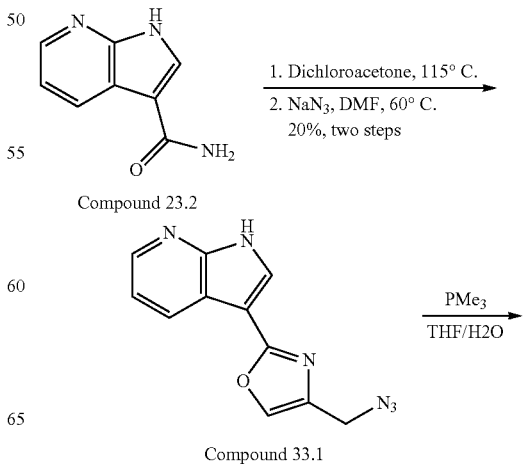

-continued

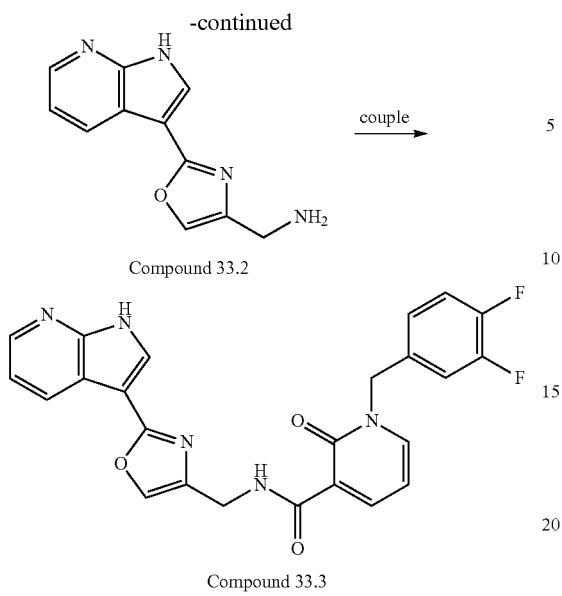

Compound 33.2

Compound 33.3

33.1 Compound 23.2 (1.61 g, 10 mmol) and 1,3-dichloroacetone (3.81 g, 30 mmol) were fused at 115° C. under nitrogen. After fusion the mixture was stirred for 1 hour. Then water was added and the mixture was extracted with DCM. The organic layers were dried and evaporated. The resulting residue and sodium azide (1.95 g, 30 mmol) were dissolved in 30 ml DMF and the reaction was heated at 60° C. for 90 minutes. The reaction was then flooded with ethyl acetate, washed with water, dried over sodium sulfate, filtered and evaporated to dryness. This was purified by chromatography to give Compound 33.1 (470 mg, 20%) as an off-white solid. ES (+) MS m/e=241 (M+1). $^1$H NMR (400 MHz, DMSO-d6) $^{TM}$ ppm 4.41 (m, 2H) 7.26 (dd, J=7.83, 4.40 Hz, 1H) 8.12 (m, 1H) 8.19 (d, J=2.45 Hz, 1H) 8.35 (dd, J=4.89, 1.47 Hz, 1H) 8.45 (dd, J=7.83, 0.98 Hz, 1H) 12.39 (m, 1H).

33.2 Compound 33.1 (464 mg, 1.93 mmol) was dissolved in a mixture of THF and water (10 ml, 4:1) and a solution of 1.0 M trimethylphosphine in THF (6.76 ml, 6.76 mmol) was added via syringe. The reaction was stirred for 40 minutes at room temperature. This was then evaporated, co-evaporated with toluene a couple times to give Compound 33.2 (765 mg, 1.93 mmol) as a brown oil which was used without further purification. ES (+) MS m/e=215 (M+1).

33.3 This was made as in Example 15.4. ES (+) MS m/e=462 (M+1). $^1$H NMR (400 MHz, DMSO-d6) $^{TM}$ ppm 4.46 (d, J=5.38 Hz, 2H) 5.21 (m, 2H) 6.59 (t, J=6.85 Hz, 1H) 7.17 (m, 1H) 7.24 (m, 1H) 7.41 (m, 2H) 7.95 (m, 1H) 8.16 (d, J=2.45 Hz, 1H) 8.23 (dd, J=6.85, 2.45 Hz, 1H) 8.34 (m, 1H) 8.39 (t, J=1.96 Hz, 1H) 8.48 (d, J=7.83 Hz, 1H) 10.05 (dd, J=10.27, 4.89 Hz, 1H) 12.37 (m, 1H).

Examples 34-36

Compound 34

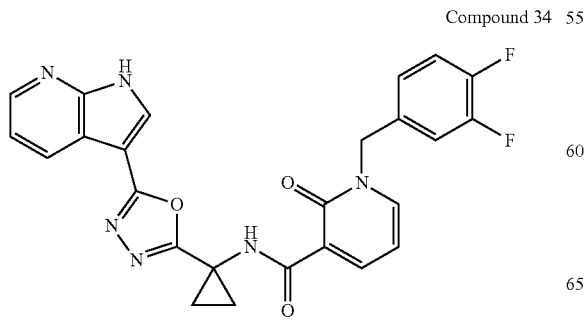

-continued

Compound 35

Compound 36

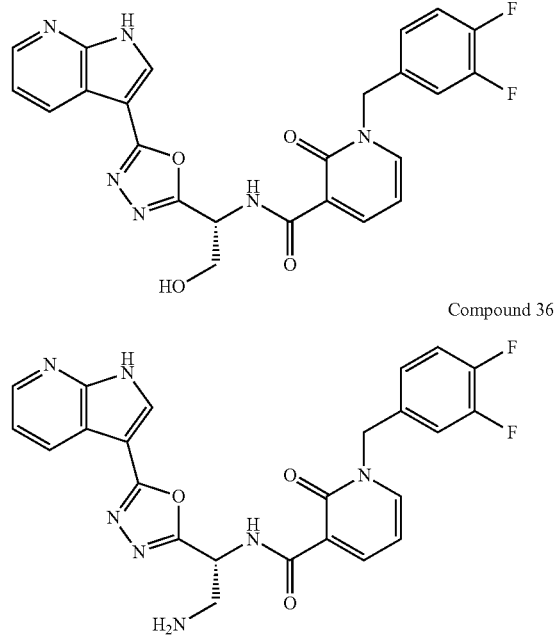

34 This is made as Compound 27.3 but starting with N-Cbz-1-Amino-cyclopropanecarboxylic acid instead of N-Cbz-glycine.

35 This is made as Compound 27.3 but starting with N-Cbz-serine instead of N-Cbz-glycine.

36 This is made as Compound 27.3 but starting with 2-Benzyloxycarbonylamino-3-tert-butoxycarbonylamino-propionic acid of N-Cbz-glycine, followed by a final deprotection (HCl).

Examples 37-39

Compound 37

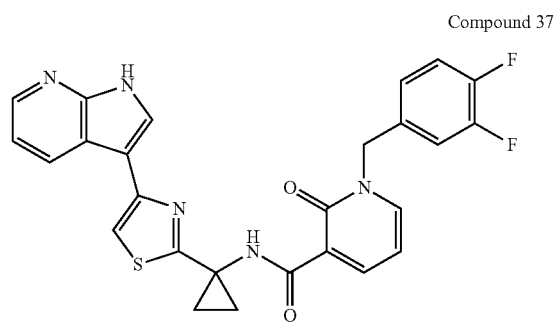

Compound 38

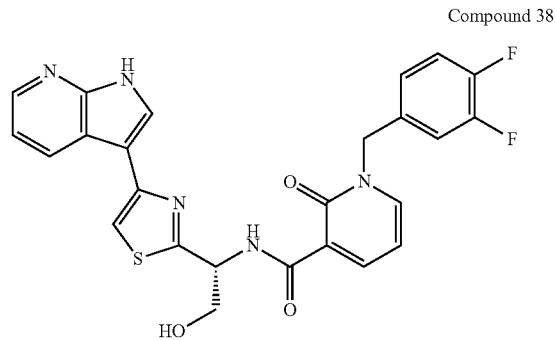

-continued

Compound 39

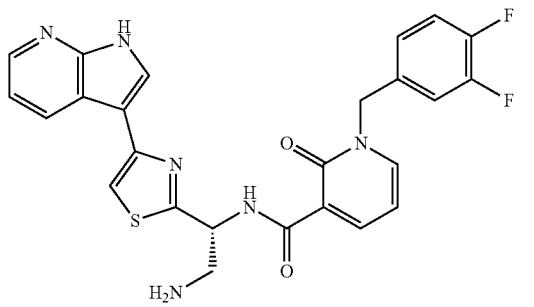

37 This is made as Compound 14.4 but starting with (1-Carbamoyl-cyclopropyl)-carbamic acid tert-butyl ester instead of Carbamoylmethyl-carbamic acid tert-butyl ester.

38 This is made as Compound 14.4 but starting with (1-Carbamoyl-2-hydroxy-ethyl)-carbamic acid tert-butyl ester instead of Carbamoylmethyl-carbamic acid tert-butyl ester.

39 This is made as Compound 14.4 but starting with (2-tert-Butoxycarbonylamino-2-carbamoyl-ethyl)-carbamic acid benzyl ester instead of Carbamoylmethyl-carbamic acid tert-butyl ester, followed by a final hydrogenolysis.

Example 40

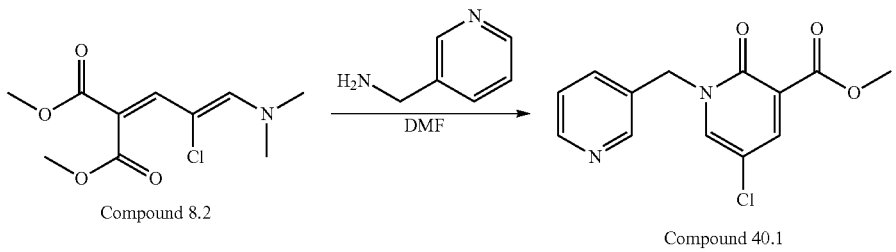

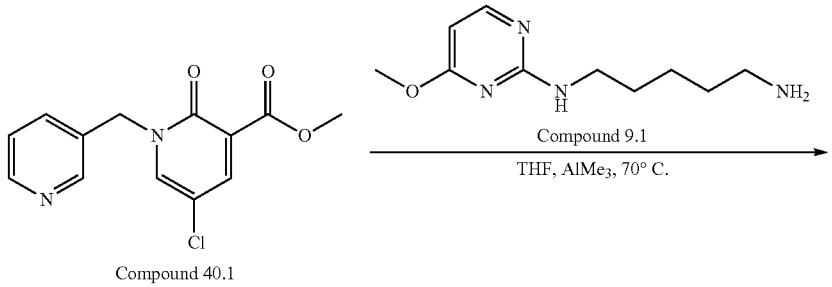

Compound 40.2

40.1 Compound 40.1 was made using the same procedure as in Compound 8.3; Pyridin-3-yl-methylamine was used in place of 1-(4-chloro-phenyl)-ethylamine to give Compound 40.1. ES (+) MS m/e=279 (M+1).

40.2 To the 2-dram vial of Compound 40.1 was added Compound 9.1, (42 mg, 0.2 mmol) and 2 ml of dry THF. The mixture was shaken vigorously to provide a homogenous solution. To this mixture was added $AlMe_3$ (0.2 ml, 2.0 M in toluene). The vial was capped and shaken at 65° C. for 16 hours. The reaction mixture was quenched with 1 ml of HCl (4.0 M in water). The solvent was concentrated using GeneVac HT-12. The crude product was dissolved in DMSO (3 ml) and purified by using HPLC (reverse phase) to give Compound 40.2. ES (+) MS m/e=456.9 (M+1). 1H NMR (400 MHz, $CD_3OD$)$^{TM}$ ppm 1.1-1.5 (m, 2H), 1.6-18 (m, 4H), 3.40 (m, 2H), 3.50 (m, 2H), 4.10 (s, 3H), 5.30 (s, 2H), 6.3-6.4 (m, 1H), 7.3 (m, 1H), 7.4 (m, 1H), 7.8-8.0 (m, 4H), 8.25 (s, 1H), 8.35 (s, 1H), 8.50 (m, 1H).

Example 41

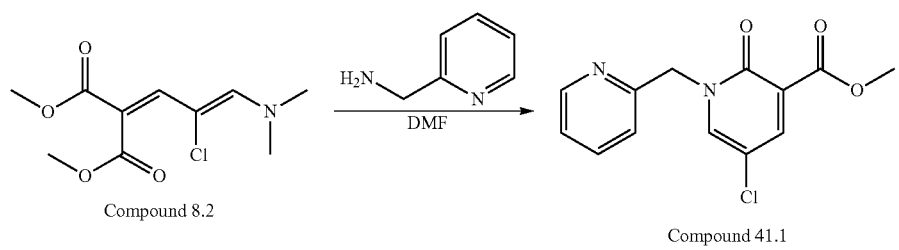

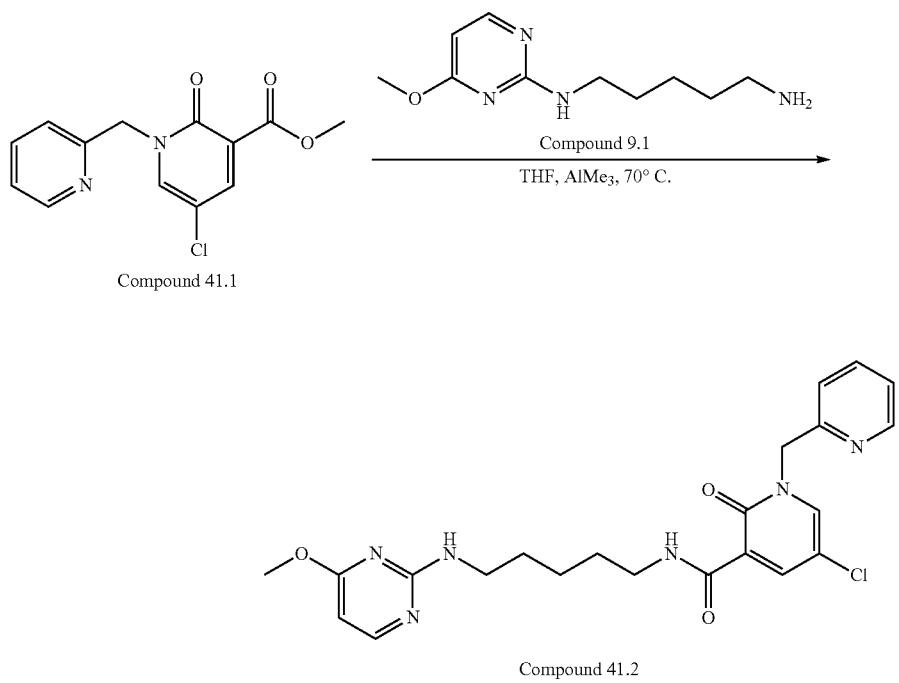

41.1 Compound 41.1 was made using the same procedure as in Compound 8.3; Pyridin-2-yl-methylamine was used in place of 1-(4-chloro-phenyl)-ethylamine to give Compound 41.1. ES (+) MS m/e=279 (M+1).

41.2 Compound 41.2 was made using the same procedure as in Compound 40.2; 5-Chloro-2-oxo-1-pyridin-2-ylmethyl-1,2-dihydro-pyridine-3-carboxylic acid methyl ester was used in place of 5-chloro-2-oxo-1-pyridin-3-ylmethyl-1,2-dihydro-pyridine-3-carboxylic acid methyl ester to give Compound 41.2 after purification by using HPLC (reverse phase). ES (+) MS m/e=456.9 (M+1).

Example 42

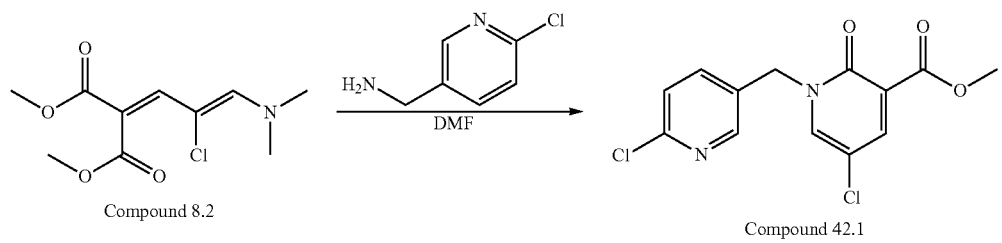

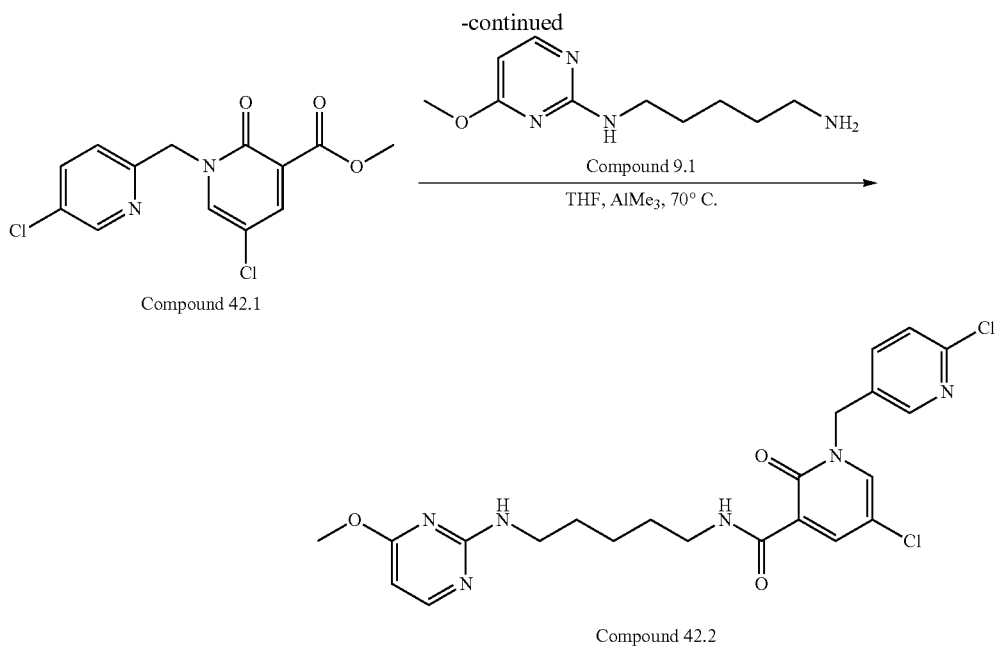

Compound 42.1

Compound 42.2

42.1 Compound 42.1 was made using the same procedure as in Compound 8.3; (6-Chloro-pyridin-3-yl)-methylamine was used in place of 1-(4-chloro-phenyl)-ethylamine to give Compound 42.1. ES (+) MS m/e=313 (M+1).

42.2 Compound 42.2 was made using the same procedure as in Compound 40.2; 5-Chloro-1-(6-chloro-pyridin-3-ylmethyl)-2-oxo-1,2-dihydro-pyridine-3-carboxylic acid methyl ester was used in place of 5-chloro-2-oxo-1-pyridin-3-ylmethyl-1,2-dihydro-pyridine-3-carboxylic acid methyl ester to give Compound 42.2 after purification by using HPLC (reverse-phase). ES (+) MS m/e=492 (M+1).

Example 43

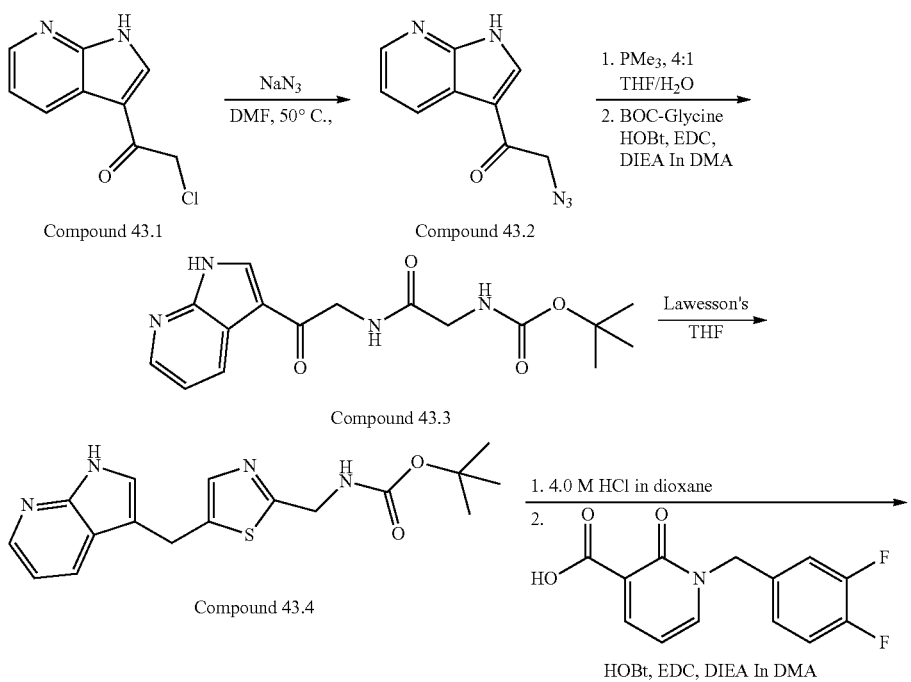

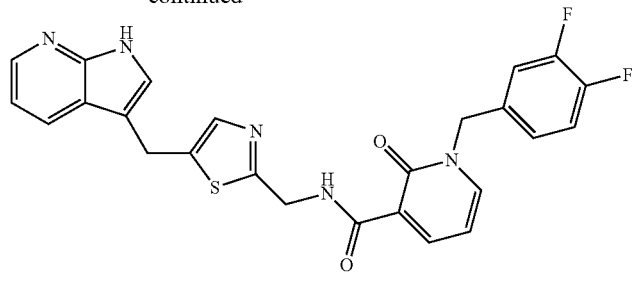

Compound 43.5

43.1 This compound was prepared as in Example 10.1 except using chloroacetylbromide instead of 5-bromo-pentanoyl chloride. ES (+) MS m/e=196 (M+1).

43.2 Compound 43.1 (1.5 g, 7.69 mmol) and sodium azide (1.5 g, 23 mmol) were dissolved in N,N-dimethylformamide (38 ml) and heated at 50° C. After 30 minutes, the reaction was complete and the heat was turned off. The reaction mixture was diluted with 100 ml of water and extracted with ethyl acetate. The organic layer was treated with brine, dried over sodium sulfate, filtered, and concentrated in vacuo to yield compound 43.2 (1.5 g, 97%). ES (+) MS m/e=202 (M+1).

43.3 Compound 43.2 (1.5 g, 7.46 mmol) and 26 ml of 1.0 M of trimethylphosphine were added to the solvent mixture of 30 ml THF and 7.4 ml water. Bubbles formed and the solution became clear afterwards. After stirring at room temperature for an hour, the solvent was evaporated by vacuum and the residue was used to couple with Boc-glycine using the same procedure described in Example 19 (Compound 19.4). The solvent was removed in vacuo and the residue was purified by silica column using 5 to 7% methanol in dichloromethane to yield 0.6 g of solid (25%). ES (+) MS m/e=333 (M+1).

43.4 Compound 43.3 (0.5 g, 1.5 mmol) and Lawesson's reagent (0.38 g, 0.93 mmol) were dissolved in 10 ml of THF and stirred overnight at room temperature under nitrogen. Additional Lawesson's reagent (0.16 g, 0.4 mmol) was added and the reaction was heated at 40° C. for 30 minutes under nitrogen, at which point the solvent was removed by vacuum and the crude product was purified by silica column using 5% methanol in dichloromethane to yield 0.18 g of white solid (36%). ES (+) MS m/e=331 (M+1).

43.5 The deprotection of BOC and the coupling were done as in Example 19 (Compound 19.4) starting with Compound 43.4 instead of 19.3. The solvent was removed in vacuo and the residue was purified by reverse-phase HPLC. ES (+) MS m/e=479 (M+1). $^1$H NMR (400 MHz, DMSO-D6)$^{TM}$ ppm 4.82 (d, J=5.8 Hz, 2H) 5.24 (s, 2H) 6.62 (m, 1H) 7.20 (m, 2H) 7.45 (m, 2H) 7.91 (s, 1H) 8.02 (s, 1H), 8.26 (m, 1H), 8.30 (m, 2H), 8.43 (m, 1H), 10.32 (t, J=6.0 Hz, 1H), 12.13 (s, 1H).

Example 44

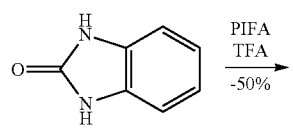

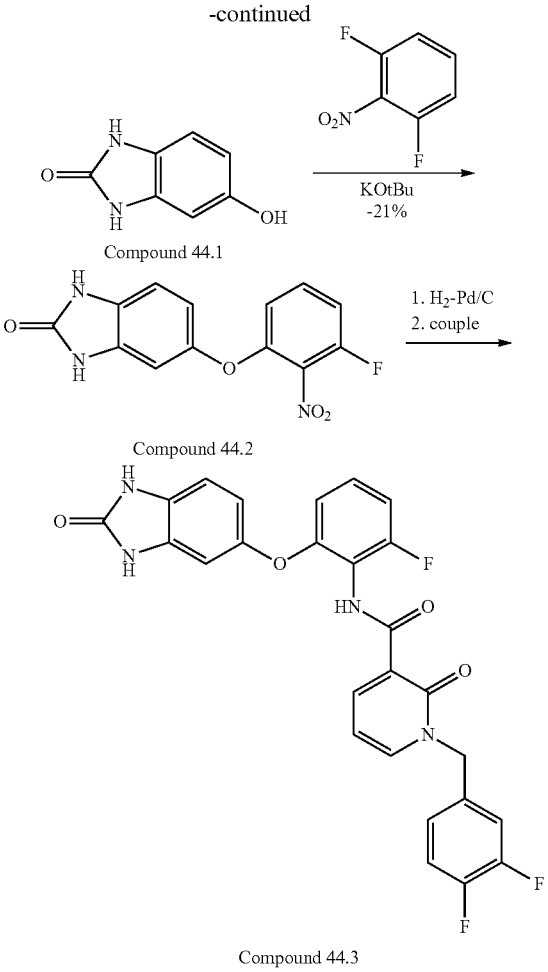

44.1 This compound was made according to the procedure described in J. Org. Chem. 2002, 67, 7424-7428. The product was crystallized from water to yield a dark gray solid in 47% yield. ES (+) MS m/e=173 (M+23).

44.2 Compound 44.1 (230 mg, 1.53 mmol) and 2,6-difluoronitrobenzene (252 mg, 1.58 mmol) were dissolved in 8 ml dry DMF and 1.6 ml of 1 M potassium t-butoxide in THF was added. The reaction was stirred at room temperature overnight, then flooded with 50 ml EtOAC, rinsed with 2×25 ml saturated sodium bicarbonate, 25 ml brine, dried over sodium sulfate, filtered, and evaporated partially to dryness. The solid was resuspended in 5 ml dry THF and filtered to yield 58 mg of yellow solid. The remaining solution was purified by column chromatography using a 15.5×2.5 cm column and eluting with 95:5 DCM:methanol to yield an additional 43 mg of off-white solid. Both of these were combined to yield a total of 92 mg (0.318 mmol, 21%). ES (+) MS m/e=290 (M+1).

44.3 Compound 44.2 (92 mg, 0.318 mmol) was dissolved in 10 ml methanol and 5 ml EtOAc. To this was added wet 10% Pd/C (76 mg), and the compound was placed under a hydrogen-containing balloon for two hours before being filtered and evaporated to yield a pale beige solid (79 mg, 0.305 mmol, 96%). ES (+) MS m/e=260 (M+1). This was then coupled to the pyridinone as described in Example 21.4. HPLC purification of the final product yielded Compound 44.3 as a pale yellow solid (14 mg, 0.0276 mmol, 9%). ES (+) MS m/e=507 (M+1).

Example 45

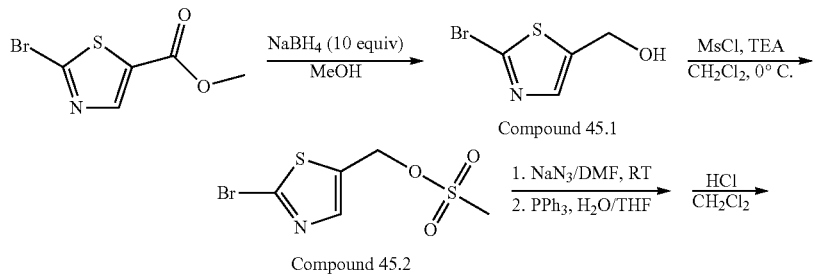

Compound 45.1

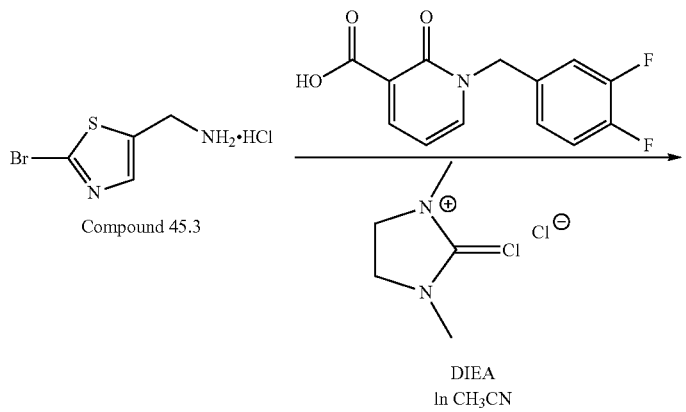

Compound 45.2

Compound 45.3

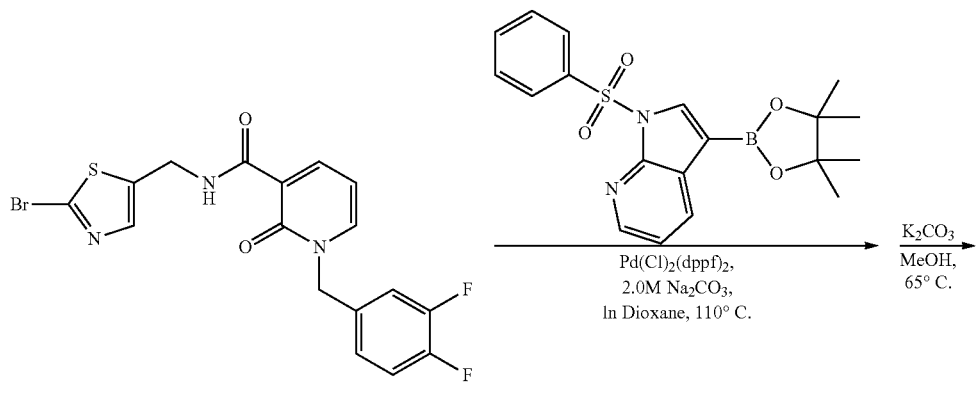

Compound 45.4

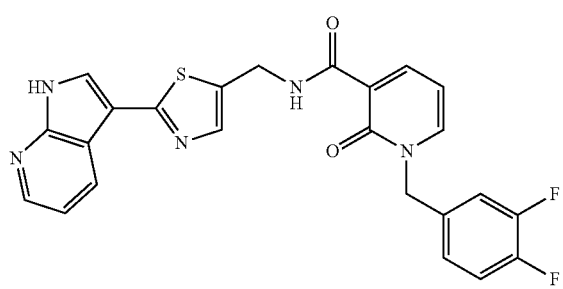

Compound 45.5

45.1 Methyl 2-bromothiazole-5-carboxylate (Combi-blocks, 4.94 g, 0.023 mole) was dissolved in 45 ml of methanol and sodium borohydride (8.5 g, 0.23 mole) was added slowly over 30 minutes. The reaction was complete after 1 hour, at which point the solvent was removed in vacuo and the residue was partitioned between ethyl acetate and water. The organic layer was treated with brine, dried over sodium sulfate, filtered, and dried to give yellow solid (3.67 g, 86%). ES (+) MS m/e=193 (M+1).

45.2 Compound 45.1 (3.67 g, 19 mmol) and triethylamine (3.0 ml, 22 mmol) were suspended in 30 ml of dichloromethane, to which methanesulfonylchloride (1.7 ml, 22 mmol) was slowly added in an ice bath. The reaction mixture was stirred at room temperature for an hour and the solvent was removed in vacuo. The crude was partitioned between ethyl acetate and water and the organic layer was treated with brine, dried over sodium sulfate, filtered and dried to give 4.5 g of solid (87% yield).

ES (+) MS m/e=272 (M+1).

45.3 Compound 45.2 (4.5 g, 16.6 mmol) and sodium azide (1.18 g, 18.1 mmol) were dissolved in 20 ml of N,N-dimethylformamide and stirred at room temperature overnight. The reaction mixture was diluted with 100 ml of water and extracted with ethyl acetate and diethyl ether. The combined organic layer was treated with brine, dried over MgSO$_4$, filtered, and dried in vacuo to yield yellow oil (3.5 g, 96%). ES (+) MS m/e=220 (M+1). To this yellow oil (3.5 g, 16.0 mmol) was added 30 ml of THF, triphenylphosphine (4.2 g, 16.0 mmol) and water (0.6 ml, 33.3 mmol). The reaction was stirred at room temperature overnight and the solvent was removed in vacuo. The crude was dissolved in dichloromethane and then 4.0 M HCl in p-dioxane (4 ml, 16 mmol) was added, and the reaction was stirred for half an hour. The precipitates were filtered through a glass flit and thoroughly washed with dichloromethane and diethylether. The solid was dried in a vacuum oven for an hour to yield light yellow solid. ES (+) MS m/e=195 (M+1).

45.4 Compound 45.3 (1.0 g, 4.35 mmol) and 1-(3,4-difluoro-benzyl)-2-oxo-1,2-dihydro-pyridine-3-carboxylic acid were coupled as in Example 1 (Compound 1.1) except using excess di-isopropyl-ethylamine (3.78 ml, 16.0 mmol). The reaction was complete in 10 minutes and the solvent was removed in vacuo. The crude residue was partitioned between 0.5 N NaOH and ethyl acetate, and the organic layer was treated with brine, dried over MgSO$_4$, filtered and dried in vacuo to yield 1.1 g of solid (63%). ES (+) MS m/e=441 (M+1).

45.5 Compound 45.4 (0.1 g, 0.23 mmol), Compound 57.3 (0.096 g, 0.25 mmol), 2.0 M aqueous sodium carbonate (0.5 ml, 1.0 mmol) and [1,1'-bis(diphenylphosphino)ferrocene]palladium(II)dichloride dichloromethane complex (1:1) (0.022 g, 0.027 mmol) were dissolved in 2 ml of p-dioxane and the reaction mixture was heated at 110° C. for 2 hours. The solvent was removed in vacuo and the crude product was purified by preparatory thin-layer-chromatography using 2, to 4% methanol in dichloromethane to yield white solid (45 mg, 32%). ES (+) MS m/e=619 (M+1). The pure solid (45 mg, 0.07 mmol) was deprotected using potassium carbonate (40 mg, 0.29 mmol) in 2 ml methanol at refluxing temperature for one hour. The solvent was evaporated in vacuo and the crude was purified by preparatory thin-layer-chromatography using 4% methanol in dichloromethane to obtain white solid (17 mg, 50%). ES (+) MS m/e=478 (M+1). $^1$H NMR (400 MHz, DMSO-D6)$^{TM}$ ppm 4.71 (d, J=5.87 Hz, 2H) 5.19 (m, 2H) 6.60 (m, 1H) 7.18 (m, 2H) 7.42 (m, 2H) 7.68 (m, 1H) 8.14 (m, 1H) 8.24 (m, 1H) 8.30 (m, 1H) 8.40 (m, 1H) 8.47 (m, 1H) 10.08 (m, 1H) 12.21 (m, 1H).

Example 46

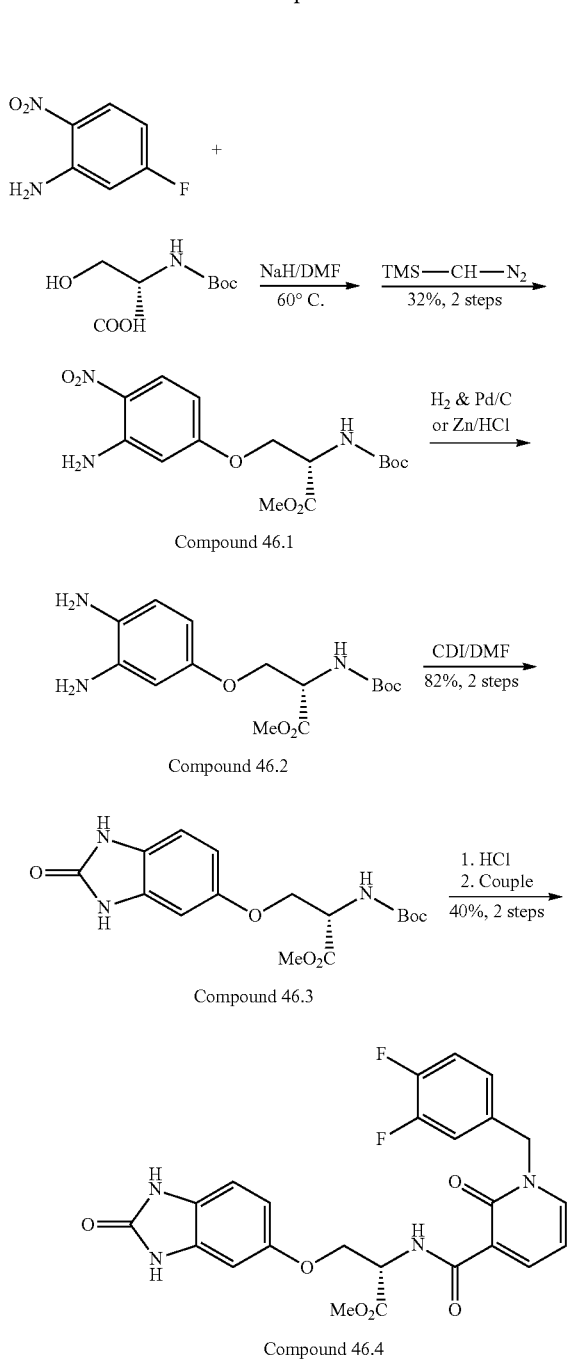

Compound 46.1

Compound 46.2

Compound 46.3

Compound 46.4

46.1 N-Boc-protected serine (1.337 g, 6.51 mmol) and 5-fluoro-2-nitroaniline (1.010 g, 6.47 mmol) were dissolved in 20 ml dry DMF, to which was added 60% sodium hydride in mineral oil (0.573 g, 14.3 mmol). The dark red solution was stirred overnight at ambient temperature and then heated to 60° C. for one day. The reaction was then evaporated to dryness, suspended in 50 ml water, and extracted with 2×50 ml EtOAc. The aqueous (product-containing) layer was acidified with 1 M NaHSO$_4$ and then extracted with 3×30 ml EtOAc. These combined extracts were rinsed with 50 ml brine and then dried over sodium sulfate and evaporated to dryness to yield a yellow solid (1.539 g, 70%) which was used without further purification. This was dissolved in 20 ml toluene and 3 ml methanol to which was then added 2 M TMS-diazomethane in hexane (3 ml, 6 mmol). The reaction was then evaporated to dryness and purified by silica gel chromatography to yield Compound 46.1 (0.516 g, 1.45 mmol) in 32% yield. MS m/e=378 (M+23).

46.2 Compound 46.1 (0.514 g, 1.45 mmol) was dissolved in a mixture of 15 ml methanol and 15 ml EtOAc, 10% wet Pd/C was added (0.317 g), and the reaction was hydrogenated under a balloon for 72 hours. The reaction was filtered through Celite and evaporated to dryness to yield Compound 46.2 as a dark blackish foam (0.451 g, 1.39 mmol) which was used without further purification. MS m/e=348 (M+23).

46.3 Compound 46.2 (0.451 g, 1.39 mmol) was dissolved in 10 ml dry DMF, and 1,1'-carbonyldiimidazole (0.24 g, 1.48 mmol) was added. After two hours the reaction was flooded with 50 ml EtOAc, rinsed with 2×25 ml water, 2×25 ml saturated sodium bicarbonate, 25 ml brine, dried over sodium sulfate, filtered, and evaporated to dryness to yield Compound 46.3 as a brown solid (0.397 g, 1.13 mmol) in 82% yield. MS m/e=374 (M+23).

46.4 Compound 46.4 was prepared analogously to Example 21.4, but starting with Compound 46.3 instead of Compound 21.3. ES (+) MS m/e=499 (M+1).

Example 47

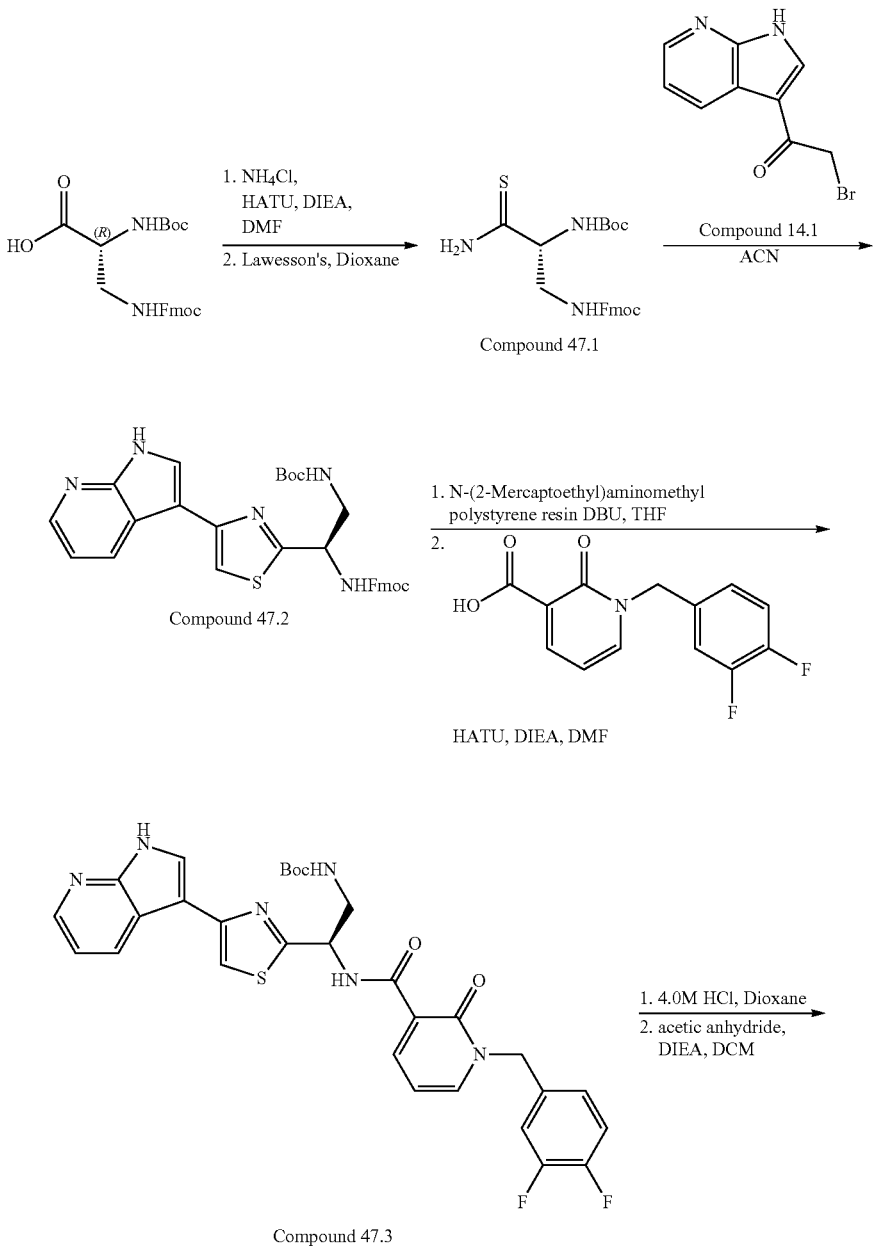

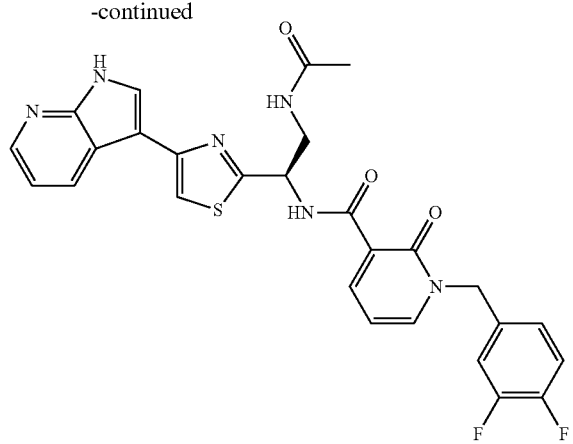

Compound 47.4

47.1 (D)-2-tert-Butoxycarbonylamino-3-(9H-fluoren-9-ylmethoxycarbonylamino)-propionic acid (3.50 grams, 8.21 mmol) was dissolved in DMF (41 ml), chilled to 0° C., O-(7-Azabenzotriazole-1-yl)-N,N,N'N'-tetramethyluronium hexafluorophosphate (4.06 grams, 10.67 mmol) was added followed by diisopropylethylamine (4.3 ml, 24.64 mmol) and then ammonium chloride (0.878 grams, 16.41 mmol). The reaction was stirred for 16 hours at ambient temperature, flooded with EtOAc, washed with water, saturated sodium bicarbonate, brine, dried over sodium sulfate, filtered, and concentrated. Lawesson's Reagent, p-dioxane (41 ml) and tetrahydrofuran (10 ml) were added and the reaction heated to 50° C. for 3 hours. The mixture was concentrated and purified by silica gel chromatography (3% MeOH in dichloromethane) to yield Compound 47.1 (2.04 grams, 4.62 mmol). ES (+) MS m/e=464 (M+Na).

47.2 Compound 47.1 (0.5 grams 1.13 mmol) and Compound 14.1 (0.271 grams, 1.13 mmol) were dissolved in acetonitrile (6 ml) and heated at 80° C. for 1.5 hours. The solvent was evaporated, the residue dissolved in ethyl acetate, washed with saturated sodium bicarbonate, dried over sodium sulfate, filtered, and evaporated to yield Compound 47.2 (0.465 grams, 0.799 mmol). ES (+) MS nm/e=481 (M-Boc).

47.3 Compound 47.2 (0.465 grams, 0.799 mmol) was dissolved in tetrahydrofuran and placed in a screw-cap resin reactor containing N-(2-mercaptoethyl)amino methyl polystyrene resin (6.24 grams), then DBU (60 µL, 0.399 mmol) was added. The reactor was purged with nitrogen and shaken at room temperature for 1.5 hours. The resin solution was collected and the resin washed with tetrahydrofuran and methanol. The combined organics were concentrated and mixed with Compound 20.2 (0.212 grams, 0.799 mmol) and O-(7-Azabenzotriazole-1-yl)-N,N,N'N'-tetramethyluronium hexafluorophosphate (0.334 grams, 0.879 mmol). N,N-dimethylformamide (4 ml) was added followed by diisopropylethylamine (0.487 mL, 2.79 mmol). The reaction was stirred at ambient temperature for 30 minutes and then was flooded with ethyl acetate, washed with 0.1M HCl, saturated sodium bicarbonate, brine, dried over sodium sulfate, filtered and concentrated to yield Compound 47.3 (0.440 grams, 0.725 mmol). ES (+) MS m/e=607 (M+H).

47.4 Compound 47.3 (0.340 grams, 0.5 mmol) was dissolved in dichloromethane (3 ml) and 4.0 M HCl in p-Dioxane (5 ml) was added. The solution was stirred for 30 minutes at ambient temperature and then concentrated. A small amount of this solid (~50 mg) was dissolved in dichloromethane (0.5 mL), diisopropylethylamine (86 µl, 0.5 mmol) followed by acetic anhydride (9 µl, 0.1 mmol) were added, the solution stirred at ambient temperature for 10 minutes and then concentrated. The residue was dissolved in methanol and purified by prep HPLC to yield Compound 47.4 (0.008 grams, 0.015 mmol). ES (+) MS m/e=549 (M+H). 1H NMR (400 MHz, DMSO-d6) δ ppm 1.77 (s, 3H) 3.54 (m, 1H) 3.78 (m, 1H) 5.26 (d, J=4.89 Hz, 2H) 5.52 (m, 1H) 6.61 (dd, J=13.69, 6.85 Hz, 1H) 7.15 (m, 1H) 7.23 (m, 1H) 7.44 (m, 2H) 7.78 (m, 1H) 8.02 (m, 1H) 8.14 (m, 1H) 8.27 (m, 2H) 8.39 (m, 1H) 8.64 (d, J=7.83 Hz, 1H) 10.49 (d, J=8.31 Hz, 1H) 11.99 (s, 1H).

Example 48

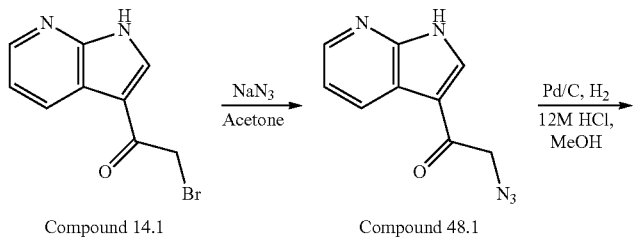

Compound 14.1     Compound 48.1

-continued
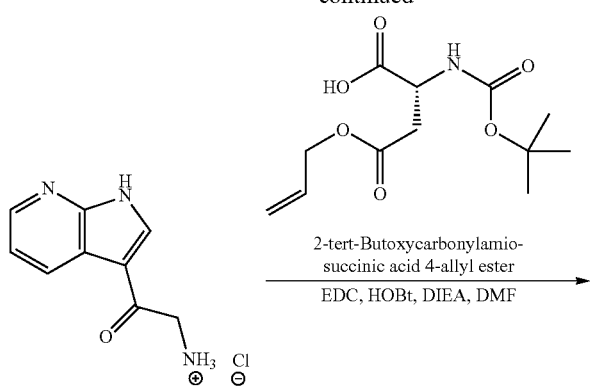
Compound 48.2
2-tert-Butoxycarbonylamio-
succinic acid 4-allyl ester
———————————————→
EDC, HOBt, DIEA, DMF
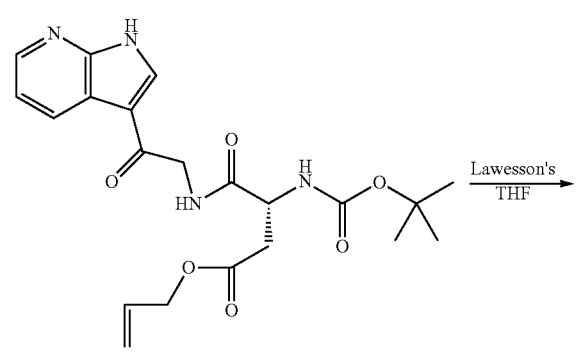
Compound 48.3
Lawesson's
————→
THF
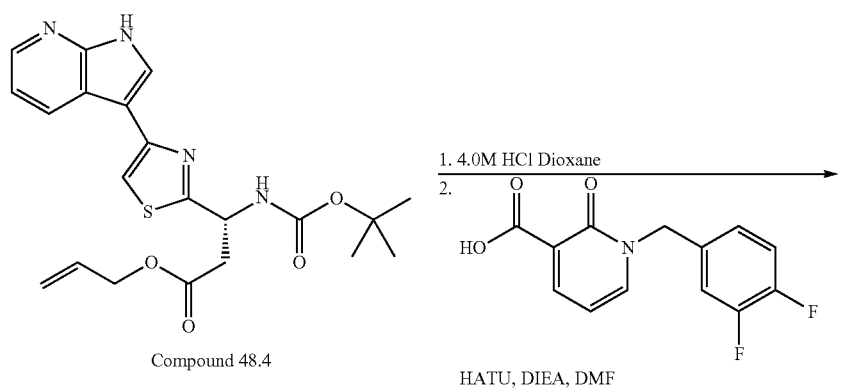
Compound 48.4
1. 4.0M HCl Dioxane
2. [pyridinone-benzyl-difluoro carboxylic acid]
————————————————→
HATU, DIEA, DMF
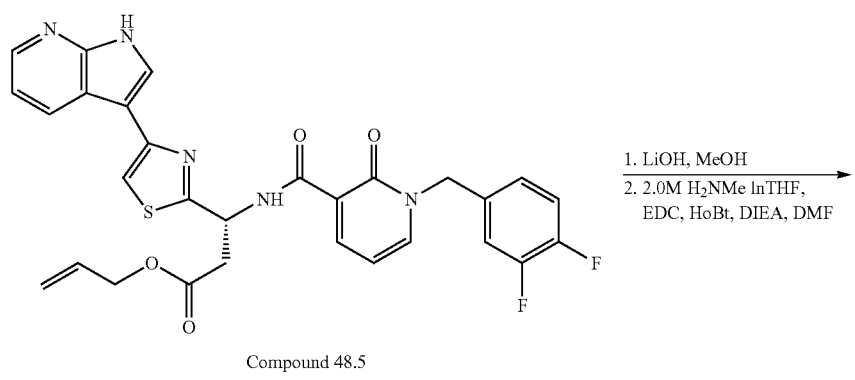
Compound 48.5
1. LiOH, MeOH
2. 2.0M H$_2$NMe InTHF,
   EDC, HoBt, DIEA, DMF
————————————————→

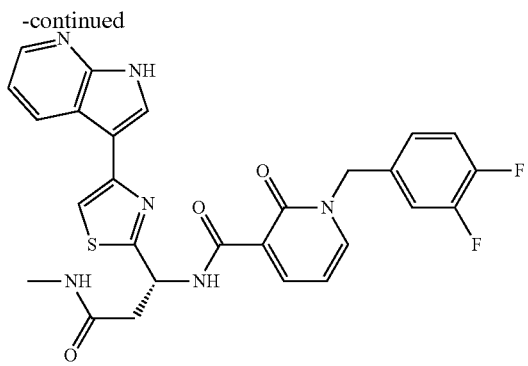

Compound 48.6

48.1 Compound 14.1 (4.18 grams, 17.50 mmol) was mixed with sodium azide (1.71 grams, 26.25 mmol), suspended in acetone (90 ml) and stirred at ambient temperature for 16 hours. The mixture was filtered through a medium frit glass funnel and the solvent removed to yield Compound 48.1 (3.50 grams, 17.39 mmol). ES (+) MS m/e=202 (M+H).

48.2 Compound 48.1 (0.386 grams, 1.92 mmol) and palladium on carbon (50 milligrams Degussa Type E101 NE/W wet) were suspended in methanol (10 ml), 12 N HCl (0.243 mL) was added, and the mixture was placed on a Parr shaker at 20 psi for 2 hours. The mixture was filtered though Celite, co-evaporated with IPA, slurried with diethyl ether and filtered to yield Compound 48.2 as a white cake (2.22 grams, 0.895 mmol). ES (+) MS m/e=176 (M+H).

48.3 Compound 48.2 (2.22 grams, 8.95 mmol), 2-tert-butoxycarbonylamino-succinic acid 4-allyl ester (2.44 grams, 8.95 mmol), N-(3-dimethylaminopropyl)-N'-ethyl-carbodiimide hydrochloride (2.23 grams, 11.64 mmol) and 1-hydroxybenzotriazole monohydrate (1.78 grams, 11.64 mmol) were dissolved in N,N-dimethylformamide (45 ml) and diisopropylethylamine (8 ml, 44.75 mmol) was added. The reaction was stirred at ambient temperature for 17 hours, flooded with ethyl acetate, washed with 0.1M HCl, saturated sodium bicarbonate, brine, dried over sodium sulfate, filtered and evaporated to yield Compound 48.3 (2.98 grams, 6.92 mmol). ES (+) MS m/e=330 (M-Boc).

48.4 Compound 48.3 (2.98 grams, 6.92 mmol) and Lawesson's reagent (2.80 grams, 6.92 mmol) were dissolved in tetrahydrofuran (35 ml) and heated at 60° C. for 2 hours. The reaction was cooled to ambient temperature and concentrated. The residue was purified by silica gel chromatography (5% methanol in dichloromethane) to yield Compound 48.4 (2.75 grams, 6.42 mmol). ES (+) MS m/e=429 (M+H).

48.5 Compound 48.4 (2.65 grams, 6.18 mmol) was dissolved in dichloromethane (31 ml) and 4.0M HCl p-Dioxane (20 ml) was added. The solution was stirred at ambient temperature for 30 minutes and concentrated. To this residue was added Compound 20.2 (1.64 grams, 6.18 mmol), O-(7-Azabenzotriazole-1-yl)-N,N,N'N'-tetramethyluronium hexafluorophosphate (2.82 grams, 7.42 mmol) and N,N-dimethylformamide (31 ml) followed by diisopropylethylamine (5.24 ml, 30 mmol). The reaction was stirred for 30 minutes at ambient temperature, flooded with ethyl acetate, washed with 0.1 M HCl, saturated sodium bicarbonate, brine, dried over sodium sulfate, filtered, and evaporated to yield Compound 48.5 (1.21 grams, 2.1 mmol). ES (+) MS m/e=576 (M+H).

48.6 Compound 48.5 (1.16 grams, 2.02 mmol) was dissolved in methanol (10 ml) and 2.0 N LiOH (2.12 ml, 4.24 mmol) was added. The reaction was stirred at ambient temperature for 2 hours at which point 10% HCl (10 ml) was added and the mixture concentrated, coevaporated with isopropyl alcohol, dissolved (in 10% methanol in dichloromethane), filtered through a medium glass frit funnel, and concentrated. This residue (0.16 grams, 0.3 mmol) was combined with N-(3-dimethylaminopropyl)-N'-ethylcarbodiimide hydrochloride (69 milligrams, 0.36 mmol), 1-hydroxybenzotriazole monohydrate (55 milligrams, 0.36 mmol) and dissolved in N,N-dimethylformamide (2 ml). Methylamine 2.0 M in tetrahydrofuran (0.375 ml, 0.75 mmol) was added followed by diisopropylethylamine (0.261 ml, 1.5 mmol). The reaction was stirred at ambient temperature for 16 hours and then flooded with ethyl acetate, washed with 0.1 M HCl, saturated sodium bicarbonate, brine, dried over sodium sulfate, filtered, and evaporated. This residue was purified by prep. HPLC to yield Compound 48.6 (33 milligrams, 0.05 mmol). ES (+) MS m/e=549 (M+H). 1H NMR (400 MHz, DMSO-d6) δ ppm 2.53 (d, J=4.40 Hz, 3H) 2.88 (s, 2H) 5.22 (d, J=5.87 Hz, 2H) 5.69 (m, 1H) 6.59 (m, 1H) 7.18 (m, 2H) 7.43 (m, 2H) 7.89 (m, 1H) 7.98 (m, 2H) 8.24 (m, 2H) 8.30 (m, 1H) 8.39 (m, 1H) 10.51 (d, J=8.31 Hz, 1H) 12.12 (s, 1H).

Example 49

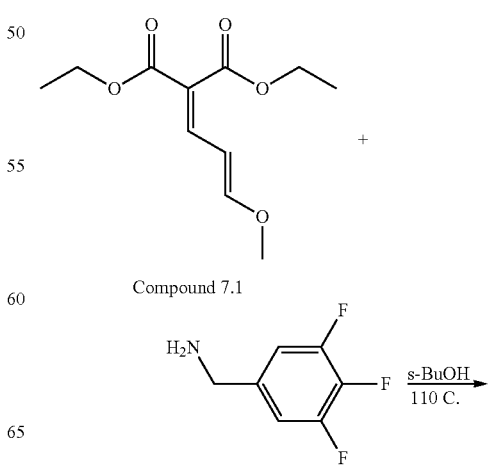

Compound 7.1

-continued

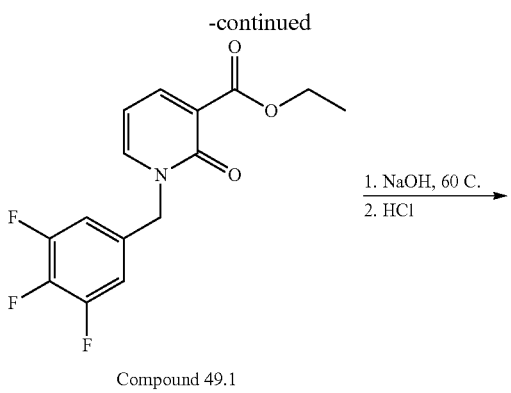

Compound 49.1

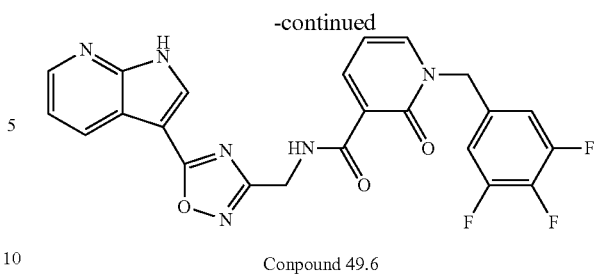

Conpound 49.6

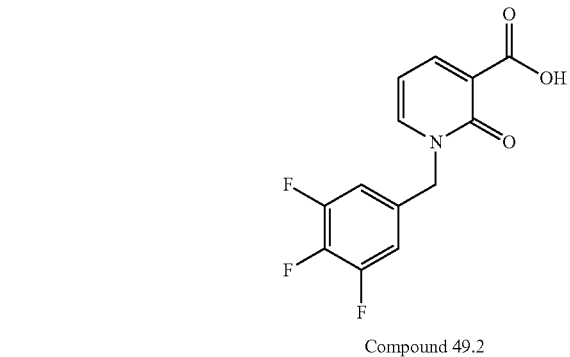

Compound 49.2

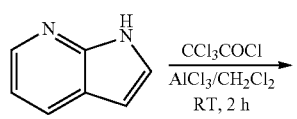

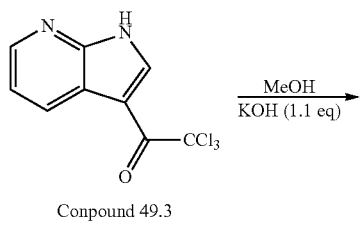

Conpound 49.3

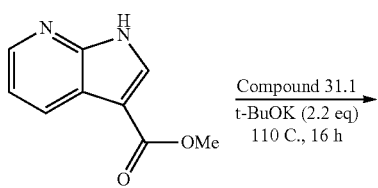

Conpound 49.4

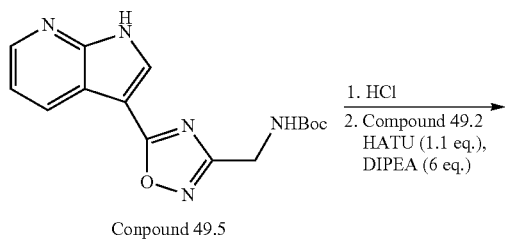

Conpound 49.5

49.1 The diethyl [3-methoxypro-2enylidene]malonate (1.0 g, 4.4 mmol), Compound 7.1, was added to a 2-dram vial in 2 ml of s-BuOH. To the mixture was added 3,4,5-trifluorobenzylamine (0.74 g, 4.6 mmole). The reaction mixture was heated to 110° C. for 16 hours. When the reaction was completed, the solvent was removed using GeneVac HT-12 to give Compound 49.1. ES (+) MS m/e=312 (M+1).

49.2 To the 2-dram vial containing crude Compound 49.1 was added 1.1 equivalent of NaOH (3.0 M solution). The vial was capped and shaken at RT for 3 h. The reaction was quenched with 1.1 equivalent of HCl (3.0 M solution). The solid was filtered and washed with water three times. ES (+) MS m/e=284 (M+1).

49.3 To a 100 ml round bottom flask was added 7-azaindole (15 g, 127 mmol) in 50 ml of $CH_2Cl_2$. To this, $AlCl_3$ (35 g, 2 eq.) was added and stirred at RT for 30 minutes followed by addition of trichloro-acetyl chloride (23.45 g, 128 mmol) slowly at RT. After 2 h, the reaction was quenched with water. The solid was filtered and washed with water three times. ES (+) MS m/e=264 (M+1).

49.4 To the 250 ml round bottom flask containing Compound 49.3 was added MeOH (100 ml) and the reaction was stirred to dissolve the solid. After 30 minutes, KOH (20% solution, 1.1 equivalent) was added and the reaction was stirred for 3 h. The reaction was quenched with HCl (1.1 eq.) and ethyl acetate was used to do the workup. Removal of ethyl acetate provided a solid. ES (+) MS m/e=177 (M+1).

49.5 To a round bottom flask (500 ml) was added Compound 49.4 in dioxane (200 ml) and s-BuOH (200 ml). To this, Compound 31.1 was added (1 equivalent) and t-BuOK (2.2 equivalents) was added. The reaction was refluxed at 110° C. for 16 h. The reaction was cooled down and water was added until the appearance of precipitation. The solid was filtered and checked by HPLC. ES (+) MS m/e=316 (M+1).

49.6 To a 10 dram-vial containing Compound 49.5 (0.4 mmol), 2 ml of $CH_2Cl_2$, and 1 ml of MeOH was added 6 equivalents of HCl (4.0 M in dioxane). The reaction mixture was shaken at room temperature for 3 h. The solvent was removed under vacuum and the residue was dissolved in 2 ml of DMA (dimethylacetamide). To this, Compound 49.2 and DIPEA (6 eq.) were added followed by HATU (1.1 eq.): 2-(7-aza-1H-benzotriazole-1-yl)-1,1-3,3-tetramethyluronium hexafluorophosphate. The reaction was shaken at RT for 2 h. The solvent was concentrated using GeneVac HT-12. The crude product was dissolved in DMSO (3 ml) and purified by using HPLC (reverse phase) to give Compound 49.6. ES (+) MS m/e=481 (M+1). 1H NMR (400 MHz, DMSO-d-6)$^{TM}$ 4.72 (s, 2H), 5.24 (s, 2H), 6.63 (t, J=8 Hz, 1H), 7.3-7.4 (m, 3H), 8.28 (d, J=3 Hz, 1H), 8.41 (m, 3H), 8.54 (d, J=3 Hz, 1H), 10.20 (s, 1H), 12.84 (s, 1H).

Example 50

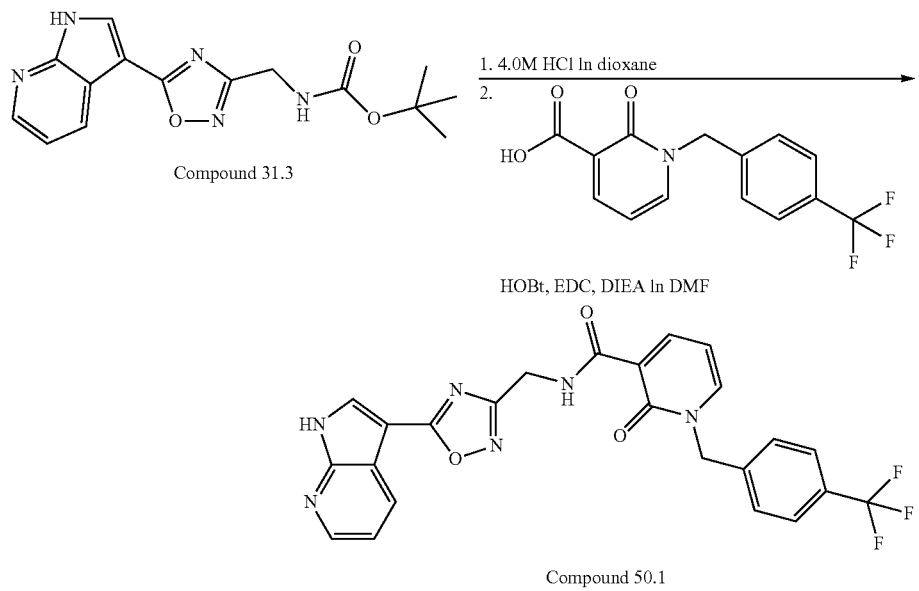

50.1 Compound 31.3 (0.063 g, 0.2 mmol) was deprotected and coupled with 1-(4-trifluoromethyl-benzyl)-2-oxo-1,2-dihydro-pyridine-3-carboxylic acid (ASDI-Inter, 0.066 g, 0.2 mmol) in 2 ml of N,N-dimethylformamide as described in Example 19.4. $^1$H NMR (400 MHz, DMSO-D6) $^{TM}$ ppm 4.70 (d, J=5.9 Hz, 2H) 5.33 (m, 2H) 7.30 (m, 1H) 7.56 (m, 2H), 7.73 (m, 2H), 8.32 (m, 1H), 8.40 (m, 1H), 8.52 (m, 1H), 8.66 (m, 1H), 8.76 (m, 1H) 10.09 (m, 1H) 12.82 (s, 1H).

Example 51

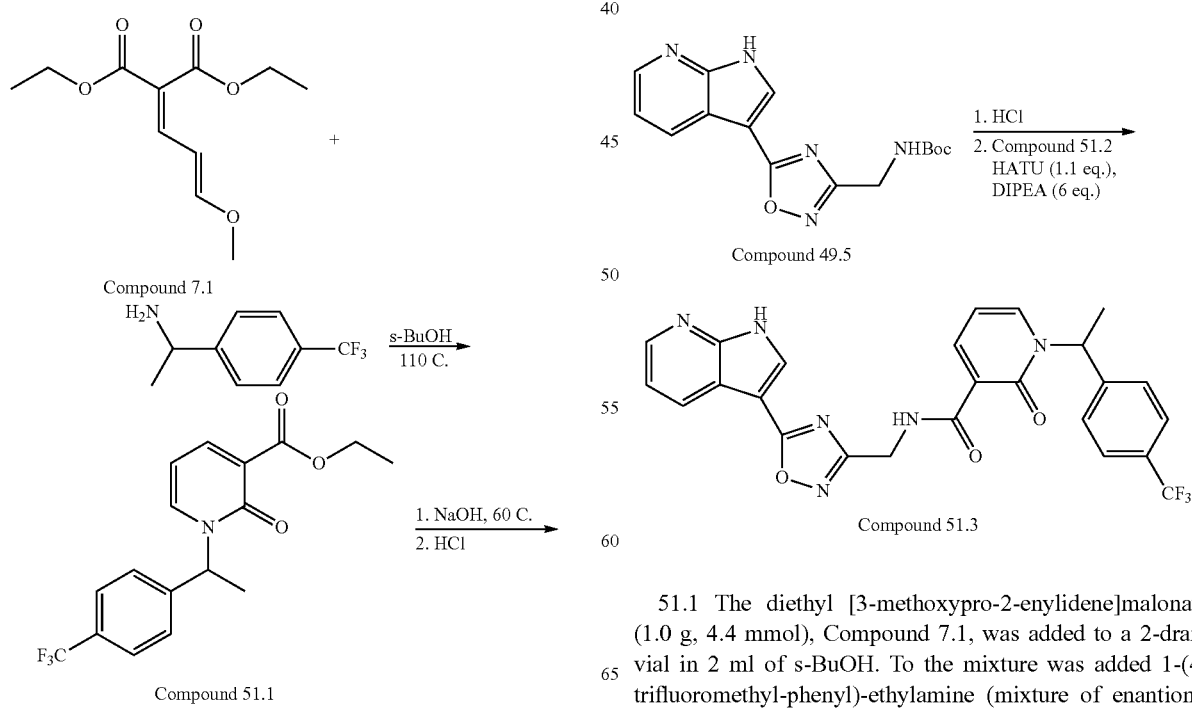

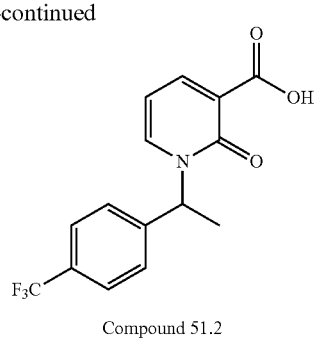

51.1 The diethyl [3-methoxypro-2-enylidene]malonate (1.0 g, 4.4 mmol), Compound 7.1, was added to a 2-dram vial in 2 ml of s-BuOH. To the mixture was added 1-(4-trifluoromethyl-phenyl)-ethylamine (mixture of enantiomers) (0.74 g, 4.6 mmole). The reaction mixture was heated to 110° C. for 16 hours. When the reaction was completed, the solvent was removed using GeneVac HT-12 to give Compound 51.1. ES (+) MS m/e=340 (M+1).

51.2 To the 2-dram vial containing crude Compound 51.1 was added 1.1 equivalent of NaOH (3.0 M solution). The vial was capped and shaken at RT for 3 h. The reaction was quenched with 1.1 equivalent of HCl (3.0 M solution). The precipitate was filtered and washed with water three times. ES (+) MS m/e=312 (M+1).

51.3 To 10 dram-vial containing Compound 49.5 (0.17 mmol) and 2 ml of CH$_2$Cl$_2$ and 1 ml of MeOH was added 6 equivalents of HCl (4.0 M in dioxane). The reaction mixture was shaken at RT for 3 h. The solvent was removed under vacuum and the residue was dissolved in 2 ml of DMA. To this, Compound 51.2 (0.1 mmol) and DIPEA (6 eq.) were added followed by HATU (1.1 eq.): 2-(7-aza-1H-benzotriazole-1-yl)-1,1,3,3-tetramethyluronium hexafluorophosphate. The reaction was shaken at RT for 2 h. The solvent was concentrated using GeneVac HT-12. The crude product was dissolved in DMSO (3 ml) and purified by using HPLC (reverse phase) to give Compound 51.3. ES (+) MS m/e=509 (M+1). 1H NMR (400 MHz, DMSO-d-6) $^{TM}$ 1.47 (d, J=5 Hz, 3H), 2.43 (s, 2H), 4.65 (s, 2H), 6.23 (q, J=8 Hz, 1H), 6.57 (t, J=8 Hz, 1H), 7.2-7.3 (m, 1H), 7.47 (d, J=9 Hz, 2H), 7.68 (d, J=9 Hz, 2H), 8.11 (d, J=6 Hz, 1H), 8.34 (t, J=7 Hz, 2H), 8.47 (s, 1H), 10.18 (t, J=6 Hz, 1H), 12.76 (s, 1H).

Example 52

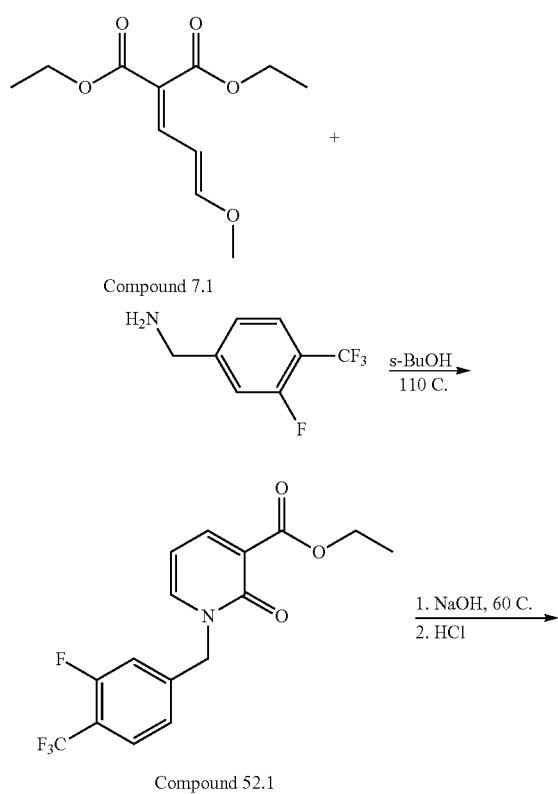

Compound 7.1

Compound 52.1

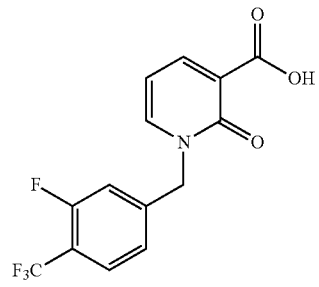

Compound 52.2

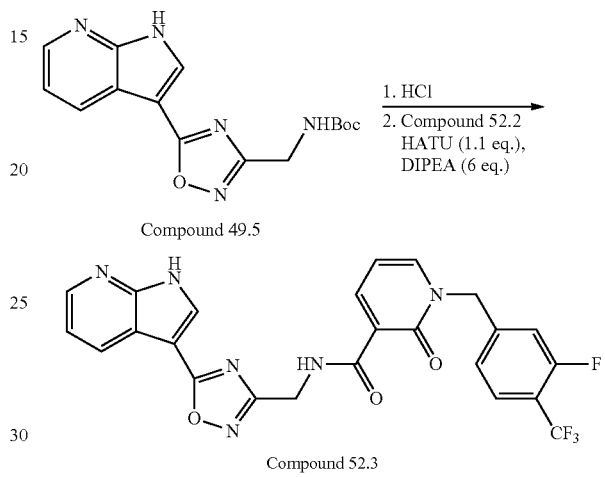

Compound 49.5

1. HCl
2. Compound 52.2
HATU (1.1 eq.),
DIPEA (6 eq.)

Compound 52.3

52.1 The diethyl [3-methoxypro-2-enylidene]malonate (1.0 g, 4.4 mmol), Compound 7.1, was added to a 2-dram vial in 2 ml of s-BuOH. To the mixture was added 3-fluoro-4-trifluoromethylbenzylamine (0.74 g, 4.6 mmole). The reaction mixture was heated to 110° C. for 16 hours. When the reaction was completed, the solvent was removed using GeneVac HT-12 to give Compound 52.1. ES (+) MS m/e=344 (M+1).

52.2 To the 2-dram vial containing crude Compound 52.1 was added 1.1 equivalent of NaOH (3.0 M solution). The vial was capped and shaken at RT for 3 h. The reaction was quenched with 1.1 equivalent of HCl (3.0 M solution). The precipitate was filtered and washed with water three times. ES (+) MS m/e=316 (M+1).

52.3 To a 10 dram-vial containing Compound 49.5 (0.17 mmol) and 2 ml of CH$_2$Cl$_2$ and 1 ml of MeOH was added 6 equivalents of HCl (4.0 M in dioxane). The reaction mixture was shaken at RT for 3 h. The solvent was removed under vacuum and the residue was dissolved in 2 ml of DMA. To this, Compound 52.2 (0.1 mmol) and DIPEA (6 eq.) were added followed by HATU (1.1 eq.): 2-(7-aza-1H-benzotriazole-1-yl)-1,1-3,3-tetramethyluronium hexafluorophosphate. The reaction was shaken at RT for 2 h. The solvent was concentrated using GeneVac HT-12. The crude product was dissolved in DMSO (3 ml) and purified by using HPLC (reverse phase) to give Compound 52.3. ES (+) MS m/e=513 (M+1). 1H NMR (400 MHz, DMSO-d-6) $^{TM}$ 4.64 (s, 2H), 5.30 (s, 2H), 6.58 (t, J=8 Hz, 1H), 7.25 (t, J=7 Hz, 2H), 7.43 (d, J=12 Hz, 1H), 7.72 (t, J=7 Hz, 1H), 8.23 (d, J=7 Hz, 1H), 8.3-8.4 (m, 3H), 8.47 (s, 1H), 10.12 (t, J=6 Hz, 1H), 12.76 (s, 1H).

Example 53

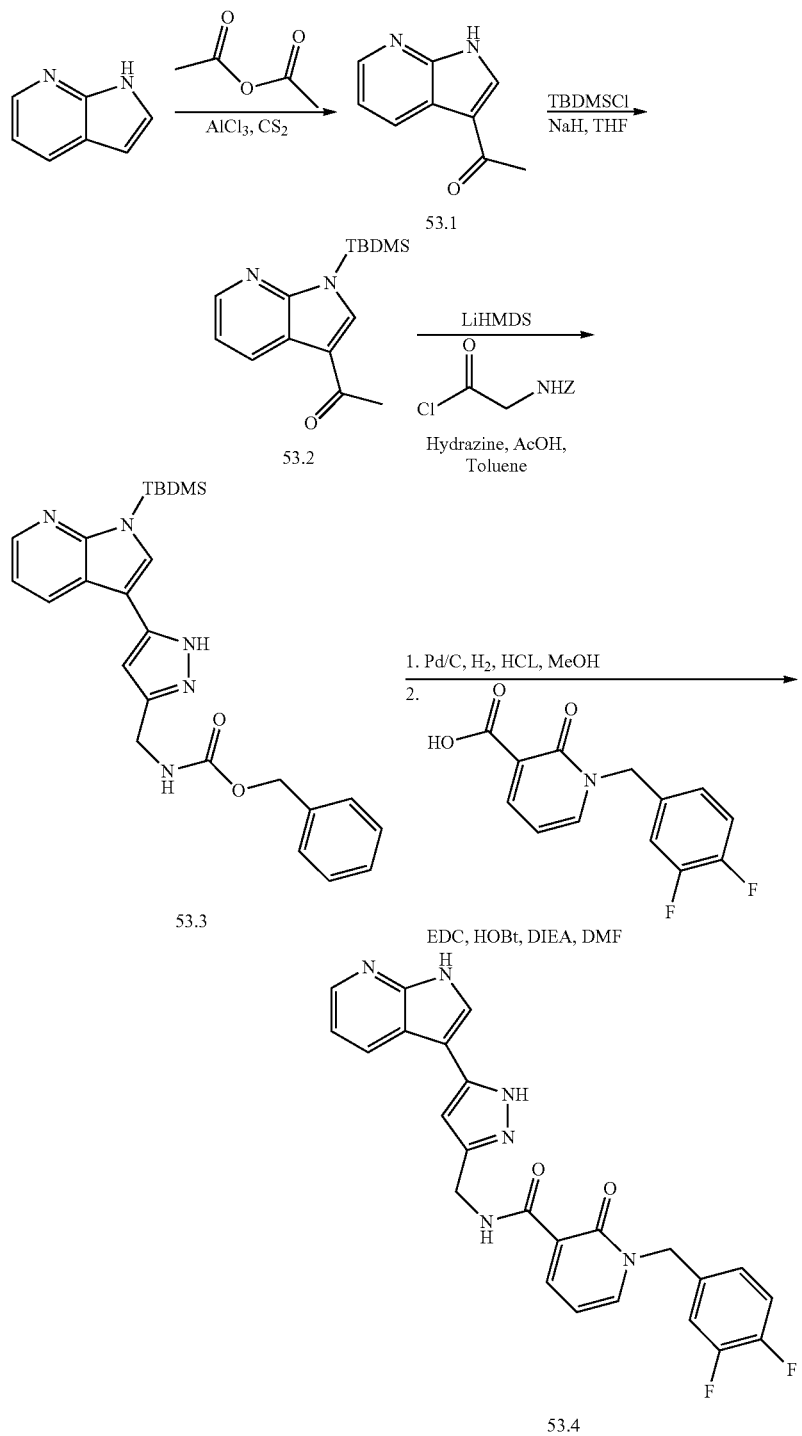

53.1 7-azaindole (1.18 grams, 10 mmol) was dissolved in carbon disulfide (500 mL) under a nitrogen atmosphere and aluminum chloride (10 grams, 75 mmol) was added portion-wise at room temperature. The mixture was heated to 50° C. and acetic anhydride (2.9 ml, 21.16 mmol) was added dropwise. The reaction was stirred at 50° C. for 2 hours, cooled to room temperature and quenched with water (50 ml). The layers were separated, the aqueous concentrated, dissolved in 1N HCl (25 mL) and washed with hexanes. The solution was basified with 4N NaOH to pH 9 and then extracted with ethyl acetate, dried over magnesium sulfate, filtered, and concentrated to yield Compound 53.1 (1.06 grams, 6.62 mmol). ES (+) MS m/e=161 (M+H).

53.2 Compound 53.1 (1.0 gram, 6.24 mmol) was dissolved in tetrahydrofuran (31 ml) and sodium hydride (0.302 grams, 7.55 mmol) was added portion-wise at room temperature. The mixture was stirred for 1 hour at room temperature and then chilled to 0° C. on an ice bath. Tert-butyldimethylsilylchloride (0.941 grams, 6.24 mmol) dissolved in tetrahydrofuran (5 ml) was added-drop wise at 0° C. After 15 minutes, the reaction was poured into water and extracted with ethyl acetate. The combined organics were dried over sodium sulfate, filtered, and concentrated to yield Compound 53.2 (1.65 grams, 6.01 mmol). ES (+) MS m/e=161 (M-TBDMS).

53.3 Compound 53.2 (0.560 grams, 2.04 mmol) was suspended in toluene (5 ml) and chilled to 0° C. Lithium bis(trimethylsilyl)amide 1.0M in tetrahydrofuran (2.25 ml) was added quickly and the mixture allowed to stir at 0° C. for 2 minutes at which point chlorocarbonylmethyl-carbamic acid benzyl ester (2.04 mmol, prepared by reacting benzyloxycarbonylamino-acetic acid with Vilsmeier reagent) was added in THF (2 ml). The ice bath was removed and the reaction stirred for 1 minute, acetic acid (2 ml) was added followed by ethanol (10 ml) and finally tetrahydrofuran (3 ml). Hydrazine (1.1 ml, 34.99 mmol) was added, the reaction fitted with a reflux condenser, stirred for 30 minutes, poured into 1N NaOH, extracted with ethyl acetate, washed with brine, dried over sodium sulfate, and concentrated under reduced pressure. The residue was purified by silica gel chromatography (5% methanol in dichloromethane) to yield Compound 53.3 (94 milligrams, 0.204 mmol). ES (+) MS m/e=348 (M-TBDMS).

53.4 Compound 53.3 (0.094 grams, 0.204 mmol) was dissolved in methanol (5 ml). A scoop of palladium on carbon (Degussa Type E101 NE/W wet) was added followed by 4.0M HCl p-Dioxane (1 ml). This mixture was placed on a Parr shaker at 40 psi for 48 hours, filtered through Celite, and concentrated. This residue was mixed with Compound 20.2 (54 milligrams, 0.204 mmol), N-(3-dimethylaminopropyl)-N'-ethylcarbodiimide hydrochloride (47 milligrams, 0.245 mmol) and 1-hydroxybenzotriazole monohydrate (38 milligrams, 0.245 mmol), dissolved in N,N-dimethylformamide (2 ml) and diisopropylethylamine (0.178 ml, 1.02 mmol) was added. The reaction was stirred at ambient temperature for 16 hours and then flooded with ethyl acetate, washed with saturated sodium bicarbonate, brine, dried over sodium sulfate, filtered and concentrated to yield Compound 53.4 (2.8 milligrams, 0.006 mmol). ES (+) MS m/e=461 (M+H). 1H NMR (400 MHz, MeOH-d4) δ ppm 4.60 (s, 2H) 5.14 (s, 2H) 6.49 (m, 1H) 6.60 (m, 1H) 7.11 (m, 2H) 7.23 (m, 1H) 7.37 (m, 1H) 7.83 (m, 1H) 7.96 (m, 1H) 8.29 (m, 1H) 8.40 (m, 1H) 8.69 (d, J=8.31 Hz, 1H).

Example 54

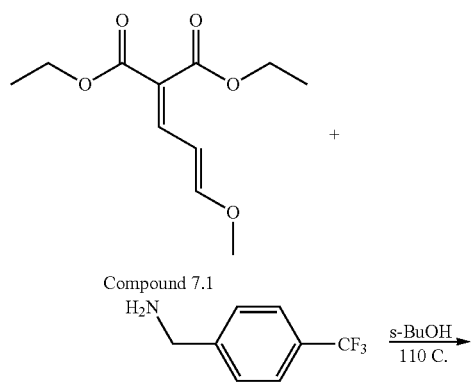

Compound 7.1

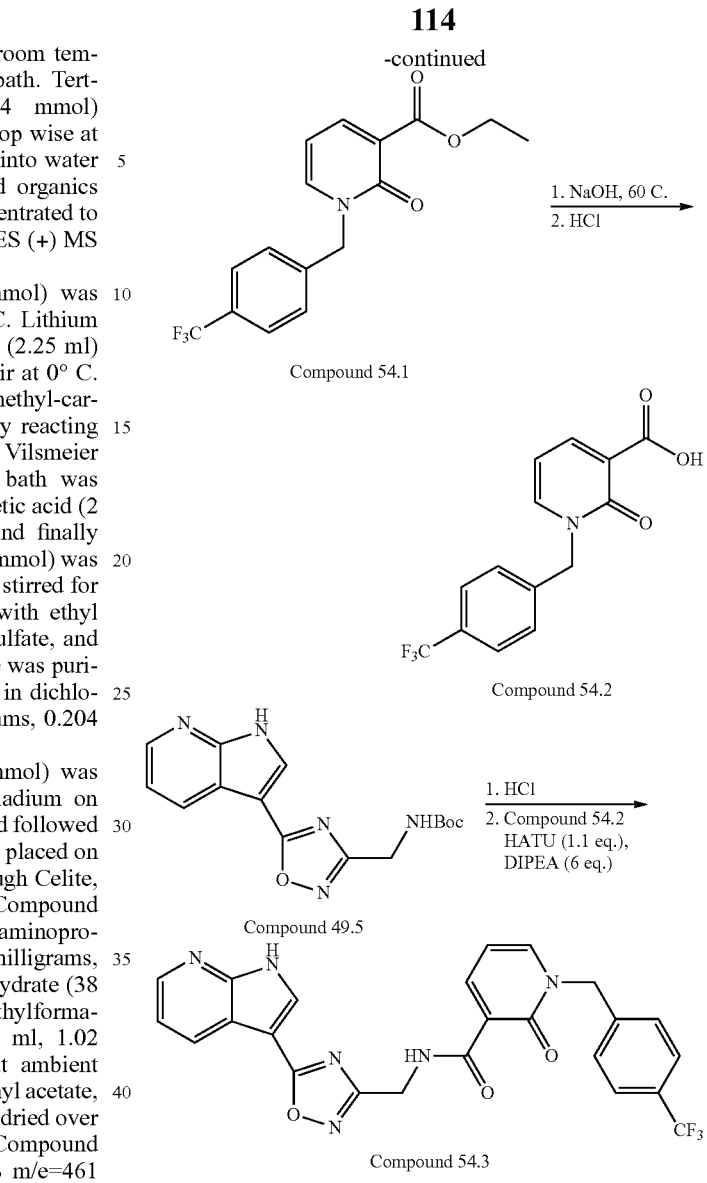

54.1 The diethyl [3-methoxypro-2-enylidene]malonate (1.0 g, 4.4 mmol), Compound 7.1, was added to a 2-dram vial in 2 ml of s-BuOH. To the mixture was added 4-trifluoromethylbenzylamine (0.74 g, 4.6 mmole). The reaction mixture was heated to 110° C. for 16 hours. When the reaction was completed, the solvent was removed using GeneVac HT-12 to give Compound 54.1. ES (+) MS m/e=326 (M+1).

54.2 To the 2-dram vial containing crude Compound 54.1 was added 1.1 equivalent of NaOH (3.0 M solution). The vial was capped and shaken at RT for 3 h. The reaction was quenched with 1.1 equivalent of HCl (3.0 M solution). The precipitate was filtered and washed with water three times. ES (+) MS m/e=298 (M+1).

54.3 To 10 dram-vial containing Compound 49.5 (0.17 mmol) and 2 ml of CH$_2$Cl$_2$ and 1 ml of MeOH was added 6 equivalents of HCl (4.0 M in dioxane). The reaction mixture was shaken at RT for 3 h. The solvent was removed under vacuum and the residue was dissolved in 2 ml of DMA. To this, Compound 54.2 (0.1 mmol) and DIPEA (6 eq.) were added followed by HATU (1.1 eq.): 2-(7-aza-1H-benzotriazole-1-yl)-1,1-3,3-tetramethyluronium hexafluorophosphate. The reaction was shaken at RT for 2 h. The solvent was concentrated using GeneVac HT-12. The crude product was dissolved in DMSO (3 ml) and purified by using HPLC (reverse phase) to give Compound 54.3. ES (+) MS m/e=495 (M+1). 1H NMR (400 MHz, DMSO-d-6) ™ 4.83 (s, 2H), 5.46 (s, 2H), 6.69 (t, J=7 Hz, 1H), 7.3-7.4 (m, 1H), 7.60 (d, J=8 Hz, 2H), 7.76 (d, J=8 Hz, 2H), 8.22 (d, J=7 Hz, 1H), 8.46 (s, 2H), 8.56 (t, J=6 Hz, 2H).

Example 55

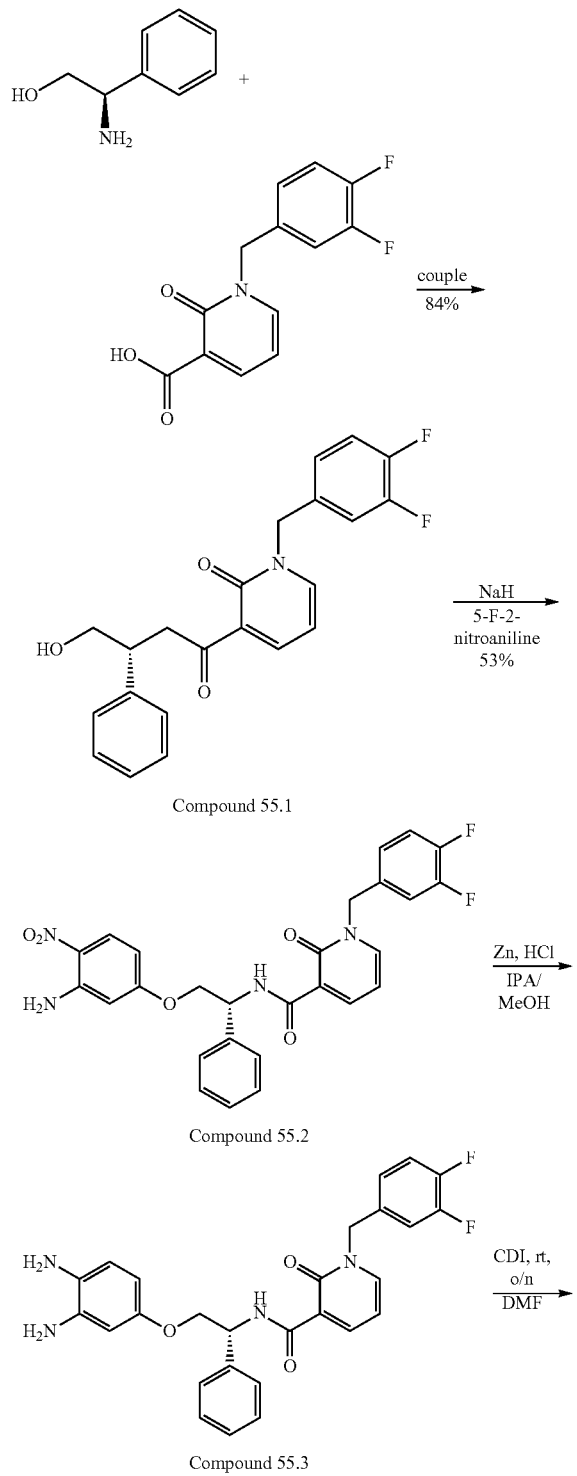

Compound 55.1

Compound 55.2

Compound 55.3

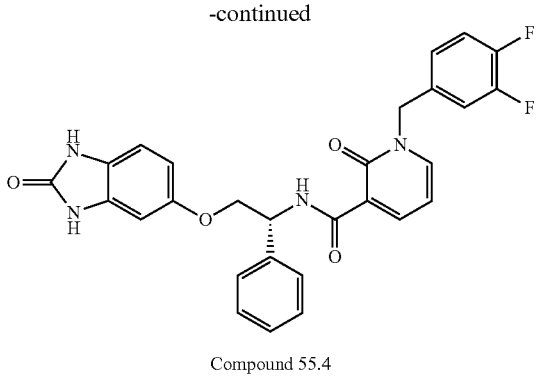

Compound 55.4

55.1 D-phenylglycinol (1.03 g, 7.5 mmol) was coupled with 1-(3,4-difluoro-benzyl)-2-oxo-1,2-dihydro-pyridine-3-carboxylic acid (1.59 g, 6 mmol, Compound 20.2), using 1-(3-Dimethylaminopropyl)-3-ethylcarbodiimide hydride (1.15 g, 6 mmol) and 1-hydroxybenzotriazole hydrate (0.92 g, 6 mmol) as coupling agent, and N,N-diisopropylethylamine (3.15 ml, 18 mmol) as base in 10 ml DMF at room temperature overnight. Then the solvent was removed under vacuum and the residue was flooded with ethyl acetate, rinsed with saturated sodium bicarbonate, brine, dried over sodium sulfate, filtered, and evaporated to dryness. This was purified using flash chromatography to give Compound 55.1 (1.94 g, 84%) as brown oil. ES (+) MS m/e=385 (M+1). $^1$H NMR (400 MHz, DMSO-d6) ™ ppm 3.65 (m, 2H) 5.01 (m, 2H) 5.23 (m, 2H) 6.57 (t, J=6.85 Hz, 1H) 7.20 (m, 2H) 7.30 (m, 4H) 7.45 (m, 2H) 8.21 (dd, J=6.85, 2.45 Hz, 1H) 8.32 (dd, J=7.34, 1.96 Hz, 1H) 10.26 (d, J=7.83 Hz, 1H).

55.2 Compound 55.1 (1.93 g, 5.02 mmol) was dissolved in 20 ml dry DMF and sodium hydride (0.81 g, 5.17 mmol) was added followed by 5-fluoro-2-nitroaniline (0.23 g, 5.77° mmol). The reaction was stirred overnight at room temperature under $N_2$. Then the solvent was removed under vacuum and the residue was flooded with ethyl acetate, rinsed with 1N sodium hydroxide, brine, dried over sodium sulfate, filtered, and evaporated to a red oil. This was purified using flash chromatography to give Compound 55.2 (1.373 g, 53%) as brown oil. ES (+) MS m/e=521 (M+1).

55.3 Compound 55.2 (0.72 g, 1.38 mmol) was dissolved in 20 ml isopropyl alcohol and 10 ml MeOH, and 1 N HCl (13.8 ml, 13.8 mmol), then Zn powder (1.8 g, 27.7 mmol) was added. After two hours, 100 ml saturated sodium bicarbonate and 80 ml ethyl acetate were added. The mixture was stirred vigorously and an intense precipitate was produced. This was filtered through Celite and the Celite was rinsed with more ethyl acetate. The organic layer of the combined filtrate was separated and then rinsed with saturated sodium bicarbonate, brine, dried over sodium sulfate, filtered, and evaporated to get 0.75 g compound 55.3 as brown oil. ES (+) MS m/e=491 (M+1).

55.4 Compound 55.3 was reacted with 1,1'-carbonyldiimidazole as described in example 15.3. Compound 55.4 was obtained as red powder after purification by reverse-phase HPLC. ES (+) MS m/e=517 (M+1). $^1$H NMR (400 MHz, DMSO-d6) ™ ppm 4.22 (m, 2H) 5.23 (dd, J=22.01, 14.18 Hz, 2H) 5.37 (m, 1H) 6.50 (m, 2H) 6.58 (t, J=6.85 Hz, 1H) 6.75 (d, J=8.31 Hz, 1H) 7.17 (m, 1H) 7.37 (m, 7H) 8.22 (dd, J=6.36, 1.96 Hz, 1H) 8.34 (dd, J=6.85, 1.96 Hz, 1H) 10.37 (m, 1H) 10.44 (d, J=7.83 Hz, 1H) 10.51 (m, 1H).

Example 56

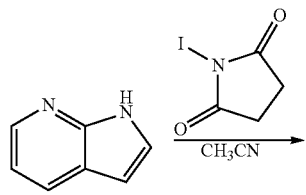

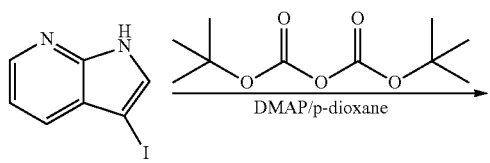

Compound 56.1

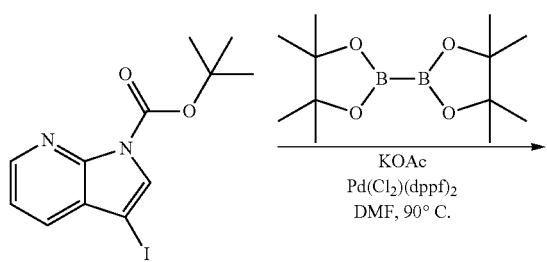

Compound 56.2

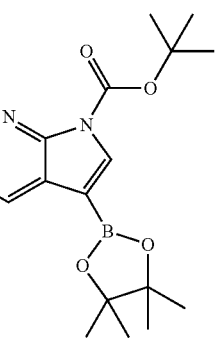

Compound 56.3

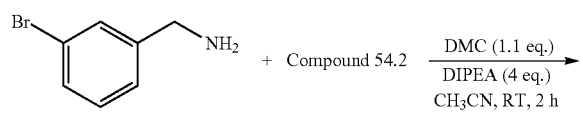

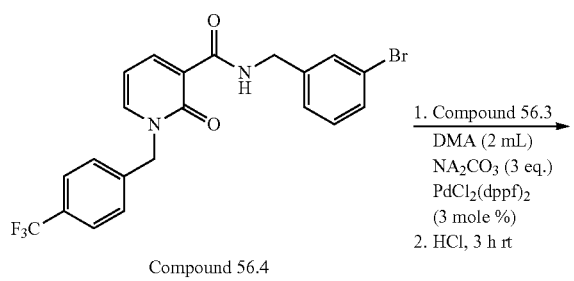

Compound 56.4

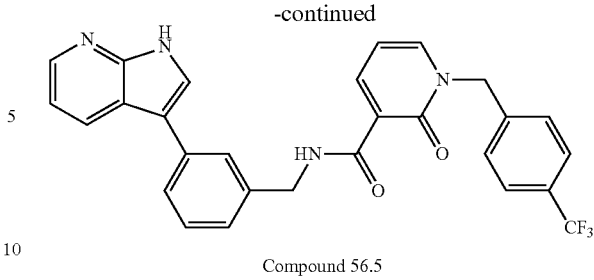

Compound 56.5
DMC = 2-Chloro-1,3-dimethylimidazolium chloride 56.1 7-Azaindole (5.33 g, 0.045 mole) was dissolved in 30 ml of acetonitrile and N-iodosuccinimide (11.18 g, 0.050 mole) was added. White precipitates formed, immediately and they were filtered through a glass frit, then washed with copious amount of acetonitrile and dried in the vacuum oven overnight. ES (+) MS m/e=246 (M+1).

56.2 Iodo-azaindole (11.0 g, 0.045 mole) was dissolved in 300 ml of p-dioxane, and 10.8 g of di-t-butyl dicarbonate (0.049 mole) and 0.5 g of 4-dimethylaminopyridine (0.004 mole) were added. The reaction was stirred at room temperature overnight, when the reaction was complete. The solvent was evaporated to dryness and the residual solid was extracted with 100 ml of ethyl acetate and 100 ml of water twice. The combined organic layer was treated with brine, dried over MgSO$_4$, filtered, and concentrated to give 15 g of solid. ES (+) MS m/e=345 (M+1).

56.3 Boc-iodo-azaindole (Compound 56.2, 7.5 g, 0.022 mole), bis(pinacolato)diboron (16.6 g, 0.065 mole), potassium acetate (12.8 g, 0.13 mole) and [1,1'-Bis(diphenylphosphino)ferrocene]palladium(II)dichloride dichloromethane complex (1:1) (1.78 g, 0.002 mole) were dissolved in 80 ml of N,N-dimethylformamide and heated at 90° C. for 3 hours. The solvent was removed by rotary evaporation, the residual solid was dissolved in dichloromethane, and purified by ISCO column purification using 15-25% ethyl acetate in hexane (10% yield). ES (+) MS m/e=345 (M+1).

56.4 To a 10-dram vial was added 3-bromobenzylamine (2 mmol) in CH$_3$CN (3 ml). To this were added Compound 54.2 (2 mmol), DIPEA (4 eq.) and DMC (1.1 eq., 2-chloro-1,3-dimethylimidazolium chloride). The reaction mixture was stirred at RT for 2 h. The reaction mixture was quenched with water and extracted with ethyl acetate. Removal of solvent provided Compound 56.4. ES (+) MS m/e=466 (M+1).

56.5 To the 10-dram vial containing Compound 56.4 was added DMA (2 ml), Na$_2$CO$_3$ (3 eq., 2.0 M solution), Compound 56.3 (1 mmol) and PdCl$_2$(dppf)$_2$ (3 mole %). The reaction mixture was stirred at 130° C. for 16 h. The reaction mixture was quenched with water and extracted with ethyl acetate. After removal of ethyl acetate, the residue was dissolved in MeOH (3 ml) in a 10-dram vial, and to this was added HCl (4.0 M in dioxane, 4 eq) and was stirred at room temperature for 3 hours. The solvent was removed under vacuum. The crude product was dissolved in DMSO (3 ml) and purified by using HPLC (reverse phase) to give Compound 56.5. ES (+) MS m/e=503 (M+1). 1H NMR (400 MHz, MeOD-d-4)$^{TM}$ 4.60 (s, 2H), 5.14 (s, 2H), 6.58 (t, J=7 Hz, 1H), 7.15 (d, J=8 Hz, 1H), 7.2-7.3 (m, 2H), 7.3-7.4 (m, 2H), 7.43 (s, 1H), 7.50 (s, 1H), 7.60 (s, 1H), 7.72 (s, 1H), 7.95 (d, J=6 Hz, 1H), 8.24 (d, J=6 Hz, 1H), 8.40 (d, J=6 Hz, 1H), 8.55 (d, J=7 Hz, 1H).

Example 57

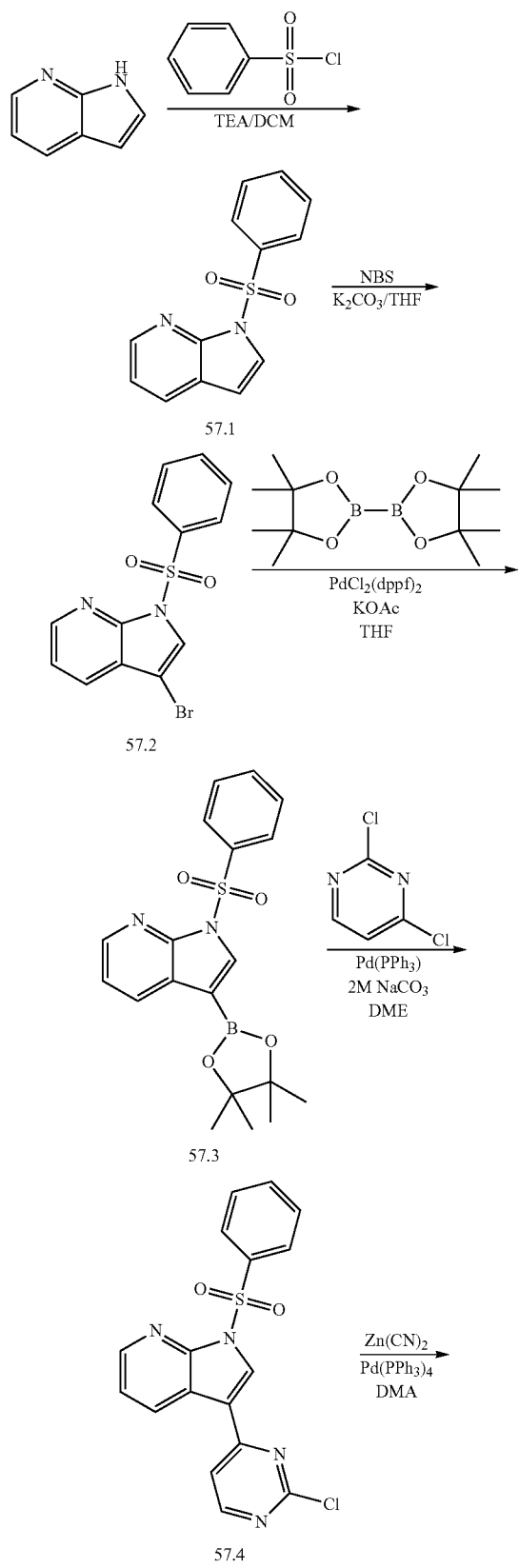

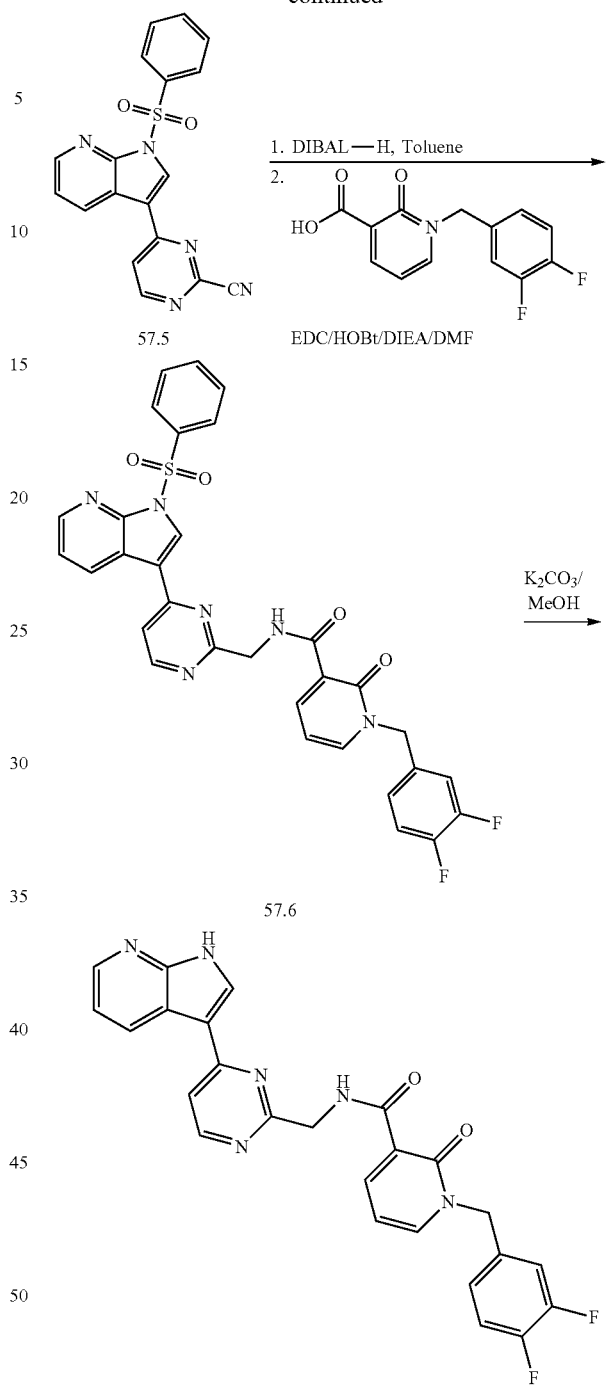

57.1 7-azaindole (18.18 grams, 154 mmol) was dissolved in dichloromethane (308 ml) and chilled to 0° C. on an ice bath. Benzenesulfonyl chloride (21.6 ml, 169 mmol) was added drop-wise at 0° C. and the reaction stirred overnight allowing to warm to ambient temperature. The mixture was filtered through a medium frit glass funnel, the filtrate was washed with saturated sodium bicarbonate, brine, dried over sodium sulfate, filtered, and concentrated. The residue was recrystallized form ethyl acetate to yield Compound 57.1 (19.76 grams, 76.5 mmol). ES (+) MS m/e=259 (M+H).

57.2 Compound 57.1 (19.72 grams, 76.5 mmol) was dissolved in tetrahydrofuran (153 ml) and chilled to 0° C. Potassium carbonate (12.67 grams, 91.66 mmol) was added followed by N-bromosuccinimide (15 grams, 84.02). The reaction was stirred overnight and allowed to warm to room temperature, quenched with water (100 ml), extracted with ethyl acetate, washed with brine, dried over sodium sulfate, filtered, and concentrated. The residue was purified by silica gel chromatography (30% hexanes in dichloromethane) to yield Compound 57.2 (4.7 grams, 13.94 mmol). ES (+) MS m/e=337 (M).

57.3 Compound 57.2 (4.63 grams, 13.73 mmol) was mixed with bis(pinacolato)diboron (3.90 grams, 15.24 mmol), potassium acetate (4.07 grams, 41.46 mmol), 1,1'-bis(diphenylphosphino)ferrocene palladium dichloride (1.12 grams, 1.37 mmol), tetrahydrofuran (70 ml) was added and the mixture refluxed under a nitrogen atmosphere for 21 hours. Water (200 ml) was added and the mixture extracted with ethyl acetate, dried over sodium sulfate, filtered and concentrated. The residue was purified by silica gel chromatography (0-2% methanol in dichloromethane) to yield Compound 57.3 (4.15 grams, 10.80 mmol). ES (+) MS m/e=385 (M+H).

57.4 Compound 57.3 (1.5 grams, 3.9 mmol), 2,4-dichloro-pyrimidine (0.756 grams, 5.07 mmol), and tetrakis(triphenylphosphine)palladium (0.451 grams, 0.39 mmol) were dissolved in dimethoxyethane (20 ml) and 2M sodium carbonate (6 ml) was added. The reaction was degassed, purged with nitrogen, and refluxed for 2.5 hours. The reaction was cooled to room temperature, water (50 ml) was added and the mixture extracted with ethyl acetate, dried over sodium sulfate, filtered, and concentrated. This residue was purified by silica gel chromatography (3% acetone in dichloromethane) to yield Compound 57.4 (0.960 grams, 2.59 mmol). ES (+) MS m/e=373 (M+3).

57.5 Compound 57.4 (0.424 grams, 1.14 mmol), zinc cyanide (0.074 grams, 0.629 mmol), and tetrakis(triphenylphosphine)palladium (0.109 grams, 0.0946 mmol) were suspended in dimethylacetamide (6 ml) and heated at 140° C. for 4 hours and then 160° C. for 3 hours. The mixture was cooled to room temperature, flooded with ethyl acetate, washed with water, brine, dried over sodium sulfate, filtered, and concentrated. The residue was purified by silica gel chromatography (5% acetone in dichloromethane) to yield compound 57.5 (0.152 grams, 0.421 mmol). ES (+) MS m/e=362 (M+H).

57.6 Compound 57.5 (0.1 grams, 0.277 mmol) was suspended in toluene (2 ml) and chilled to 0° C. 1.0M diisobutylaluminum hydride (0.304 ml) was added drop-wise and the reaction stirred overnight, allowing it to warm to room temperature. The reaction was quenched with a saturated aqueous solution of Rochelle's salt, filtered through Celite, the layers separated, the organic layer washed with brine, dried over sodium sulfate, filtered, and concentrated. This residue was mixed with 1-(3,4-Difluoro-benzyl)-2-oxo-1,2-dihydro-pyridine-3-carboxylic acid (73 milligrams, 0.277 mmol), N-(3-dimethylaminopropyl)-N'-ethylcarbodiimide hydrochloride (64 milligrams, 0.332 mmol), 1-hydroxybenzotriazole monohydrate (51 milligrams, 0.332 mmol), dissolved in N,N-dimethylformamide (2 ml) and diisopropylethylamine (0.241 ml, 1.39 mmol) was added. The reaction was stirred at ambient temperature for 16 hours and then flooded with ethyl acetate, washed with saturated sodium bicarbonate, brine, dried over sodium sulfate, filtered and concentrated to yield Compound 57.6 (90.7 milligrams, 0.148 mmol). ES (+) MS m/e=613 (M+H).

57.7 Compound 57.6 (0.091 grams, 0.148 mmol) was dissolved in methanol (1 mL), potassium carbonate (0.102 grams, 0.740 mmol) was added and the reaction refluxed for 30 minutes. The methanol was removed and the residue partitioned between water and ethyl acetate, the organic layer was dried over sodium sulfate, filtered, and concentrated. The residue was purified by prep HPLC to yield Compound 57.7 (6 milligrams, 0.0127 mmol). ES (+) MS m/e=473 (M+H). 1H NMR (400 MHz, DMSO-d6) δ ppm 4.77 (d, J=5.38 Hz, 2H) 5.30 (s, 2H) 6.62 (m, 1H) 6.79 (m, 1H) 7.23 (m, 1H) 7.43 (m, 2H) 7.84 (d, J=5.87 Hz, 1H) 8.20 (m, 1H) 8.30 (m, 1H) 8.42 (m, 1H) 8.63 (m, 2H) 8.83 (m, 1H) 10.47 (m, 1H) 12.43 (s, 1H).

Example 58

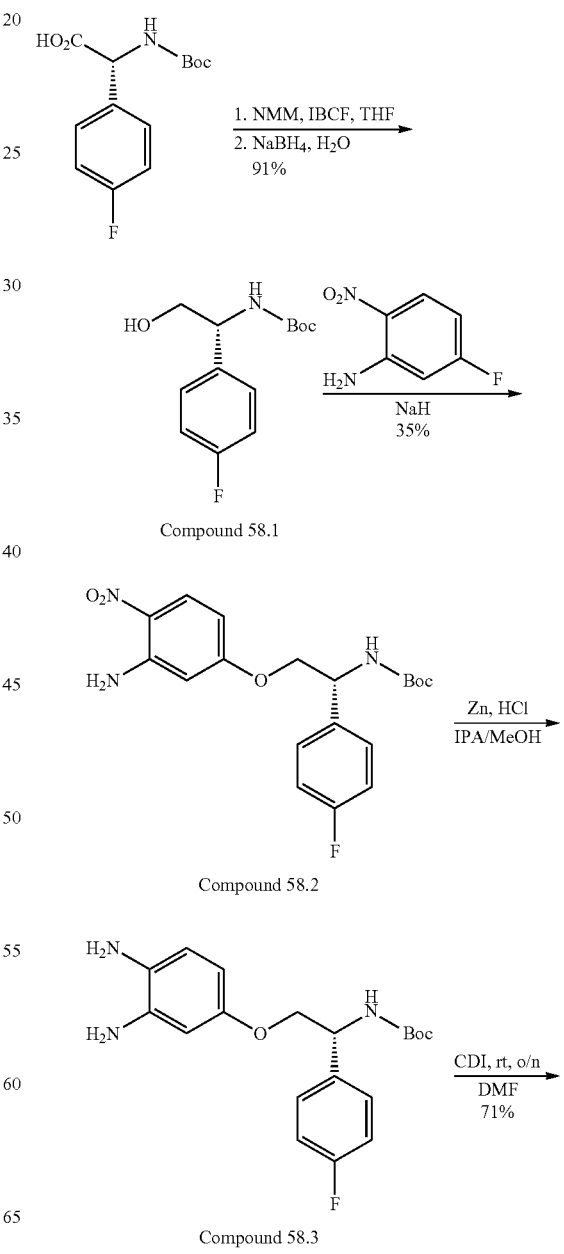

-continued

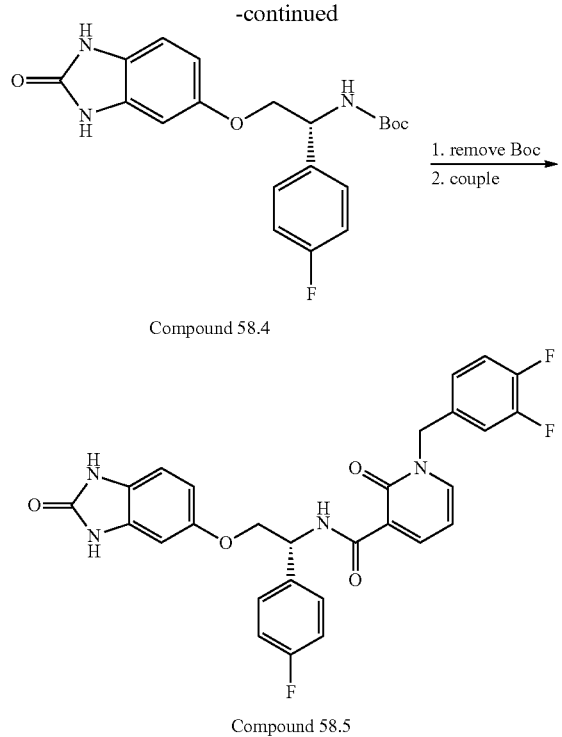

Compound 58.4

Compound 58.5

58.1 A solution of Boc-4-fluoro-D-phenylglycine (1.08 g, 4 mmol) in 20 ml dry THF under nitrogen was chilled to −30° C. N-methylmorpholine (0.44 ml, 4 mmol) was added followed by isobutyl chloroformate (0.52 ml, 4 mmol) drop-wise. After 10 minutes, NaBH$_4$ (0.46 g, 12 mmol) was added followed immediately by 1 ml H$_2$O. The reaction was allowed to warm to room temperature and stirred for 1 hour. The reaction mixture was then flooded with ethyl acetate, rinsed with 1N sodium bisulfate, saturated sodium bicarbonate, brine, and evaporated to get colorless oil. This was purified by silica gel chromatography to give Compound 58.1 (0.927 g, 91%) as colorless oil. ES (+) MS m/e=278 (M+23).

58.2 Compound 58.2 was prepared in the same way as Compound 55.2 using Compound 58.1 as starting material instead of Compound 55.1. The product was a yellow solid (0.5 g, 35%). ES (+) MS m/e=414 (M+23).

58.3 Compound 58.3 was made from Compound 58.2 using the same method as described in example 55.3 but starting from Compound 58.2 instead of Compound 55.2. The product was a yellow solid (0.5 g). ES (+) MS m/e=384 (M+23).

58.4 This was prepared with the same method described in example 55.4, using Compound 58.3 instead of Compound 55.3. The product was a yellow oil (0.35 g, 71%). ES (+) MS m/e=332 (M-Boc). $^1$H NMR (400 MHz, DMSO-d6) $^{TM}$ ppm 1.36 (m, 9H) 3.97 (m, 2H) 4.86 (m, 1H) 6.47 (m, 2H) 6.76 (m, 1H) 7.15 (t, J=8.80 Hz, 2H) 7.41 (dd, J=8.80, 5.87 Hz, 2H) 7.55 (d, J=8.80 Hz, 1H) 10.36 (m, 1H) 10.47 (m, 1H).

58.5 Compound 58.4 (0.34 g, 0.878 mmol) was deprotected with 4M HCl in dioxane for 30 minutes and then evaporated to dryness. Half of the residue (0.44 mmol) was coupled with compound 20.2 as described in example 55.1. The final product was obtained as off-white powder after purification with flash chromatography. ES (+) MS m/e=535 (M+1). $^1$H NMR (400 MHz, DMSO-d6) $^{TM}$ ppm 4.22 (m, 3H) 5.23 (dd, J=22.99, 14.67 Hz, 2H) 5.37 (m, 1H) 6.51 (m, 2H) 6.58 (t, J=6.85 Hz, 1H) 6.76 (d, J=8.31 Hz, 1H) 7.17 (m, 3H) 7.43 (m, 4H) 8.22 (dd, J=6.36, 1.96 Hz, 1H) 8.35 (dd, J=7.34, 1.96 Hz, 1H) 10.44 (m, 2H).

Example 59

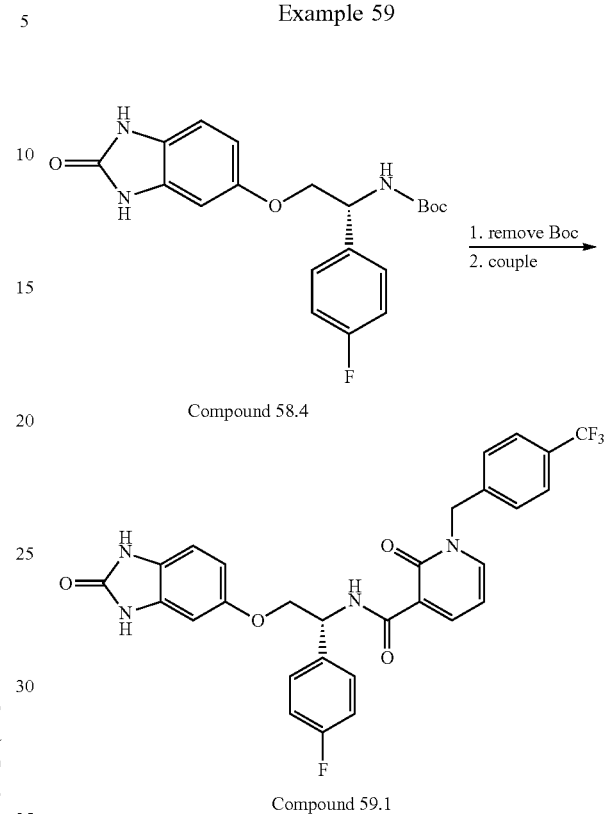

Compound 58.4

Compound 59.1

59.1 This was made with the same method described in example 58.5, using 1-(4-trifluoromethyl-benzyl)-2-oxo-1,2-dihydro-pyridine-3-carboxylic acid (Compound 49.2) instead of Compound 20.2. The final product was off-white powder. ES (+) MS m/e=567 (M+1). $^1$H NMR (400 MHz, DMSO-d6) $^{TM}$ ppm 4.22 (m, 2H) 5.35 (m, 3H) 6.49 (m, 2H) 6.61 (t, J=6.85 Hz, 1H) 6.75 (d, J=8.31 Hz, 1H) 7.17 (t, J=8.80 Hz, 2H) 7.47 (m, 4H) 7.72 (d, J=8.31 Hz, 2H) 8.24 (dd, J=6.85, 1.47 Hz, 1H) 8.38 (dd, J=7.34, 1.47 Hz, 1H) 10.40 (m, 2H) 10.51 (m, 1H).

Example 60

Compound 57.3

-continued

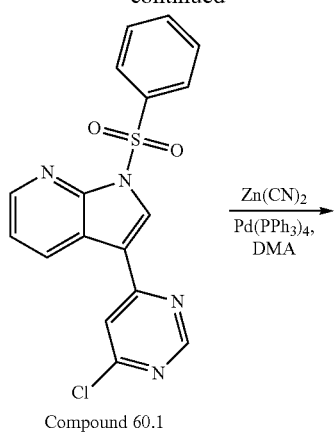
Compound 60.1

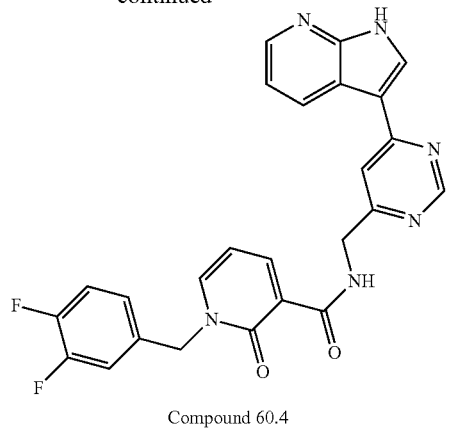
Compound 60.4

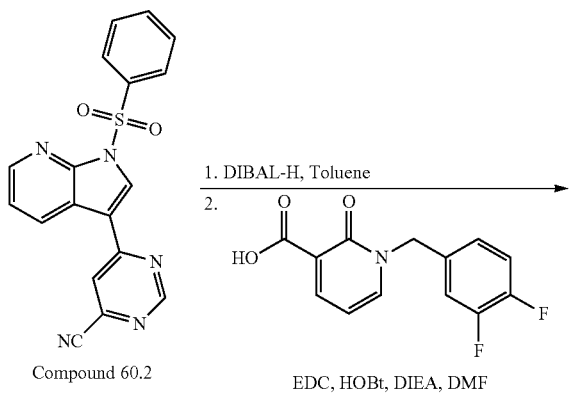
Compound 60.2

60.1 This compound was synthesized according to the procedure described in Example 57.4, except using 4,6-dichloro-pyrimidine instead of 2,4-dichloro-pyrimidine (62%). ES (+) MS m/e=373 (M+3).

60.2 This compound was synthesized according to the procedure described in Example 57.5 except using Compound 60.1 instead of Compound 57.4 (11%). ES (+) MS m/e=362 (M+H).

60.3 This compound was synthesized according to the procedure described in Example 57.6 except using Compound 60.2 instead of Compound 57.5 (14%). ES (+) MS m/e=613 (M+H).

60.4 This compound was synthesized according to the procedure described in Example 57.7 except using Compound 60.3 instead of Compound 57.6 (11%). ES (+) MS m/e=473 (M+H). 1H NMR (400 MHz, MeOH-d4) δ ppm 4.67 (s, 2H) 5.21 (s, 2H) 6.51 (m, 1H) 7.15 (m, 2H) 7.22 (m, 1H) 7.29 (m, 1H) 7.83 (m, 1H) 8.00 (m, 1H) 8.25 (m, 1H) 8.34 (m, 1H) 8.40 (m, 1H) 8.85 (m, 1H) 8.99 (s, 1H).

Example 61

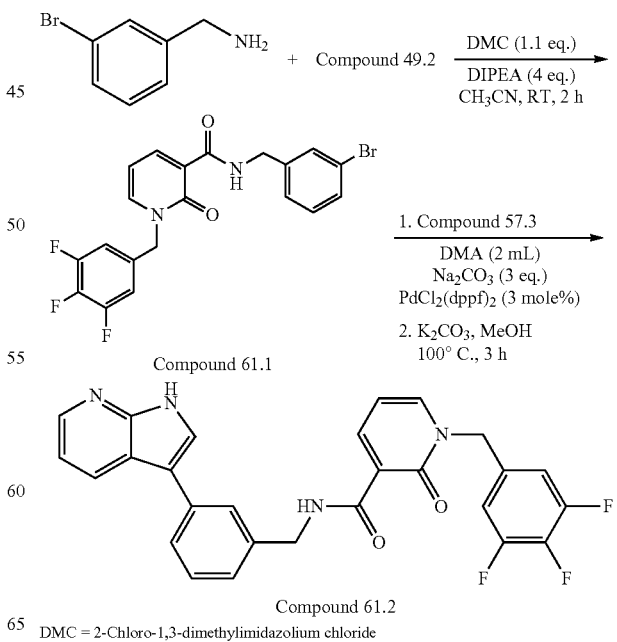
Compound 61.1

Compound 61.2

DMC = 2-Chloro-1,3-dimethylimidazolium chloride 61.1 To a 10-dram vial was added 3-bromobenzylamine (2 mmol) in CH₃CN (3 ml). To this were added Compound 49.2 (2 mmol), DIPEA (4 eq.) and DMC (1.1 eq., 2-chloro-1,3-dimethylimidazolium chloride). The reaction mixture was stirred at RT for 2 h. The reaction mixture was quenched with water and extracted with EA. Removal of solvent provided Compound 61.1. ES (+) MS m/e=452 (M+1).

61.2 To the 10-dram vial containing Compound 61.1 was added DMA (2 ml), Na₂CO₃ (3 eq., 2.0 M solution), Compound 57.3 (1 mmol) and PdCl₂(dppf)₂ (3 mole %). The reaction mixture was stirred at 130° C. for 16 h. The reaction mixture was quenched with water and extracted with EA. After removal of EA, the residue was dissolved in MeOH (3 ml) in a 10-dram vial, and to this was added K₂CO₃ (4 eqs.) and was heated at 100 C for 2-3 hours. Upon cooling to RT, the compound crashed out of the reaction solution. The solid was filtered and washed with water to remove K₂CO₃. The compound 61.2 was dried and checked for purity by using HPLC and NMR. ES (+) MS m/e=489 (M+1). 1H NMR (400 MHz, DMSO-d-6) ™ 4.58 (d, J=6 Hz, 2H), 5.20 (s, 2H), 6.61 (t, J=7 Hz, 1H), 7.0-7.1 (m, 1H), 7.19 (d, J=8 Hz, 2H), 7.3-7.4 (m, 2H), 7.39 (t, J=7 Hz, 1H), 7.59 (d, J=8 Hz, 1H), 7.69 (s, 1H), 7.85 (s, 1H), 8.2-8.3 (m, 3H), 8.41 (d, J=7 Hz, 1H), 10.05 (t, J=8 Hz, 1H), 11.92 (s (br), 1H).

Example 62

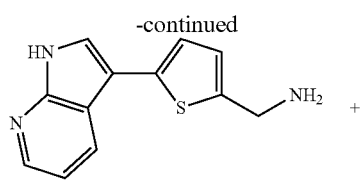

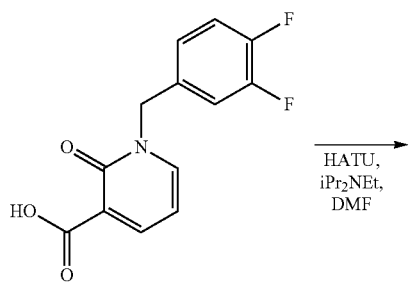

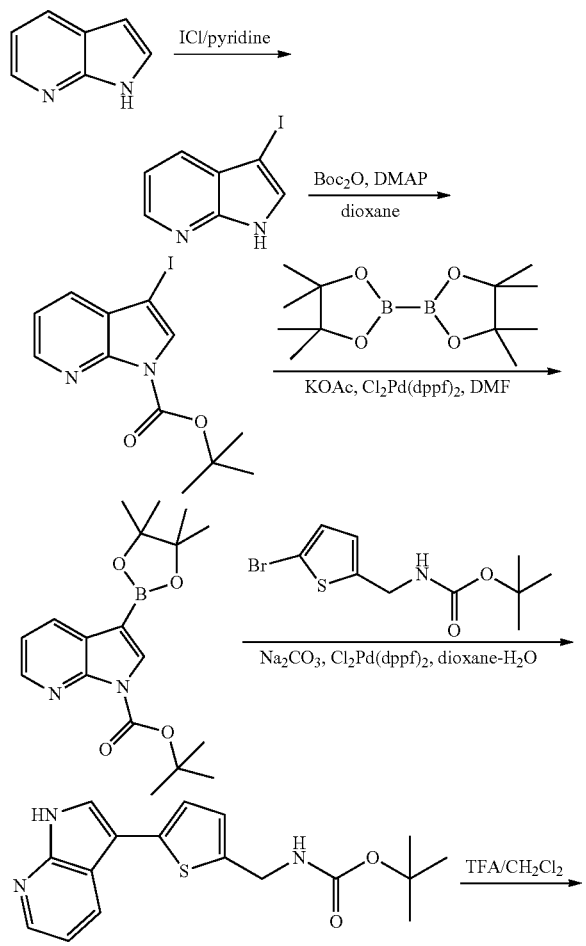

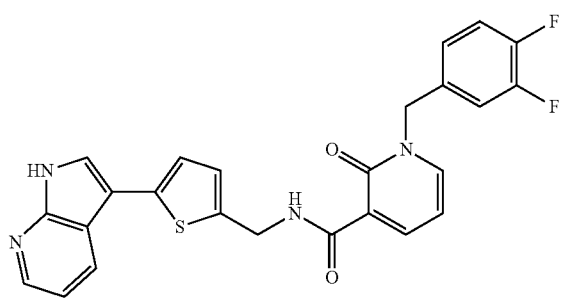

62.1 1-(3,4-Difluoro-benzyl)-2-oxo-1,2-dihydro-pyridine-3-carboxylic acid [5-(1H-pyrrolo[2,3-b]pyridin-3-yl)-thiophen-2-ylmethyl]-amide.

3-Iodo-pyrrolo[2,3-b]pyridine-1-carboxylic acid tert-butyl ester.

1H-Pyrrolo[2,3-b]pyridine (2.00 g, 0.0169 mol; Aldrich) was dissolved in pyridine (17 mL, 0.21 mol; Acros) and cooled in an ice bath. A solution of 1.00 M of iodine monochloride in methylene chloride (18.6 mL; Aldrich) was added over 5 min. After 15 min the cooling bath was removed, and after another 30 min the solution was diluted with 200 mL of ethyl acetate. The organic solution was washed sequentially with 1 N hydrogen chloride and 1 N sodium hydroxide, dried over magnesium sulfate, and concentrated. The material was dissolved in 1,4-dioxane (85 mL, 1.1 mol; Acros) and treated with di-tert-butyldicarbonate (4.07 g, 0.0186 mol; Aldrich) and 4-dimethylaminopyridine (0.216 g, 0.00177 mol; Aldrich). The mixture was stirred at room temperature for 3 days. Excess di-tert-butyldicarbonate was destroyed by the addition of N,N-dimethyl-1,2-ethanediamine (1.7 mL, 0.015 mol). After stirring for 30 min, the solution was evaporated to dryness, taken up in ethyl acetate, then washed with dilute HCl and then saturated NaCl, dried over sodium sulfate, filtered and concentrated. Purification by silica gel chromatography produced the title compound in 2.03 g (35%) yield. MS m/z=345.01 (M+1). 1H NMR (300 MHz, CDCl3) ™ ppm 8.527 (dd, J=4.8, 1.5 Hz, 1H) 7.796 (s, 1H) 7.717 (dd, J=7.9, 1.5 Hz, 1H) 7.276 (dd, J=7.9, 4.8 Hz, 1H) 1.671 (s, 9H). TLC Rf=0.50 in 3:1 hexanes/ethyl acetate.

3-(4,4,5,5-Tetramethyl-[1,3,2]dioxaborolan-2-yl)-pyrrolo[2,3-b]pyridine-1-carboxylic acid tert-butyl ester.

3-Iodo-pyrrolo[2,3-b]pyridine-1-carboxylic acid tert-butyl ester (490 mg, 0.00142 mol), bis(pinacolato)diboron (1.11 g, 0.00436 mol; Aldrich), potassium acetate (0.86 g, 0.0087 mol; Aldrich) and [1,1'-bis(diphenylphosphino)ferrocene]dichloropalladium(II), complex with dichloromethane (1:1) (0.117 g, 0.000143 mol; Strem) were dissolved in N,N-dimethylformamide (8 mL, 0.1 mol; Aldrich). The reaction was heated in a sealed tube at 80° C. for 2.5 h. The reaction was evaporated to dryness and purified by silica gel chromatography to yield the title compound (234 mg, 48%). MS m/z=345.24 (M+1). 1H NMR (300 MHz, CDCl3) $^{TM}$ ppm 8.478 (dd, J=4.6, 1.5 Hz, 1H) 8.234 (dd, J=7.7, 1.7 Hz, 1H) 8.031 (s, 1H) 7.191 (dd, J=7.9, 4.8 Hz, 1H) 1.644 (s, 9H), 1.352 (s, 12H). TLC Rf=0.43 in 3:1 hexanes/ethyl acetate.

[5-(1H-Pyrrolo[2,3-b]pyridin-3-yl)-thiophen-2-ylmethyl]-carbamic acid tert-butyl ester.

Into a vial was dissolved (5-bromo-thiophen-2-ylmethyl)-carbamic acid tert-butyl ester (115 mg, 0.000394 mol; Maybridge), 3-(4,4,5,5-tetramethyl-[1,3,2]dioxaborolan-2-yl)-pyrrolo[2,3-b]pyridine-1-carboxylic acid tert-butyl ester (119 mg, 0.000346 mol) and [1,1'-bis(diphenylphosphino)ferrocene]dichloropalladium(II), complex with dichloromethane (1:1) (28 mg, 0.000034 mol; Strem) in 1,4-dioxane (6.0 mL, 0.077 mol; Acros). To this was added 2.0 M of sodium carbonate in water (1.5 mL). The reaction was purged with Ar and sealed. The reaction was heated at 110° C. under an atmosphere of Argon for 2 hours. The reaction was diluted with methylene chloride and washed with water. The organic layer was dried with magnesium sulfate, filtered and evaporated. The residue was taken up in DMSO and purified by preparative HPLC to yield the title compound in 33.4 mg yield (22%) as the TFA salt. MS m/z=330.15 (M+1). 1H NMR (300 MHz, CDCl3) $^{TM}$ ppm 13.919 (s, 1H) 8.703 (dd, J=7.9, 1.1 Hz, 1H) 8.246 (dd, J=5.7, 1.0 Hz, 1H) 7.676 (d, J=1.7 Hz, 1H) 7.464 (dd, J=7.9, 5.8 Hz, 1H) 7.111 (d, J=3.6 Hz, 1H) 6.985 (d, J=3.6 Hz, 1H) 4.981 (s (br), 1H) 4.508 (d, J=5.7 Hz, 2H) 1.485 (s, 9H).

1-(3,4-Difluoro-benzyl)-2-oxo-1,2-dihydro-pyridine-3-carboxylic acid [5-(1H-pyrrolo[2,3-b]pyridin-3-yl)-thiophen-2-ylmethyl]-amide.

[5-(1H-Pyrrolo[2,3-b]pyridin-3-yl)-thiophen-2-ylmethyl]-carbamic acid tert-butyl ester (33.4 mg, 0.000101 mol) was dissolved in methylene chloride (2.0 mL, 0.031 mol; Aldrich) and trifluoroacetic acid (2.0 mL, 0.026 mol; Acros). The reaction was stirred for 30 minutes at room temperature. The reaction was concentrated to dryness.

The residue and 1-(3,4-difluoro-benzyl)-2-oxo-1,2-dihydro-pyridine-3-carboxylic acid (32 mg, 0.00012 mol) and HATU (54 mg, 0.00014 mol; Applied Biosystems) were dissolved in N,N-dimethylformamide (2.0 mL, 0.026 mol; Acros). To this was added N,N-diisopropylethylamine (88 uL, 0.00050 mol; Aldrich) and the reaction was stirred for 2 hours at room temperature. The reaction was diluted with ethyl acetate, washed with 5% citric acid, washed with saturated sodium chloride, dried with sodium sulfate and evaporated. The residue was taken up in DMSO and purified by preparative HPLC to yield the title compound in 35 mg yield (58%) as the TFA salt. MS m/z=477.09 (M+1). 1H NMR (300 MHz, DMSO-d6) $^{TM}$ ppm 11.933 (s (br), 1H) 10.053 (t, J=6.0 Hz, 1H) 8.399 (dd, J=7.5, 2.5 Hz, 1H) 8.387 (d, J=7.5 Hz, 1H) 8.298-8.188 (m, 3H) 7.782 (d, J=2.5 Hz, 1H) 7.533-7.334 (m, 3H) 7.250-7.122 (m, 3H) 7.008 (d, J=3.5 Hz, 1H) 6.757 (t, J=7.0 Hz, 1H) 6.594 (t, J=6.8 Hz, 1H) 5.280 (s, 1H) 5.195 (s, 2H) 4.669 (d, J=6.0 Hz, 2H).

Example 63

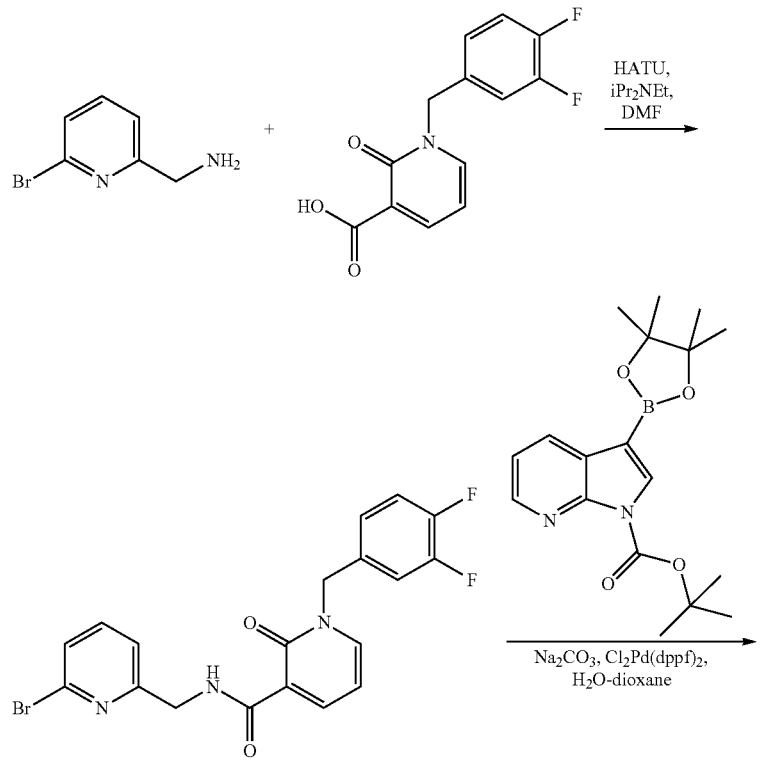

-continued

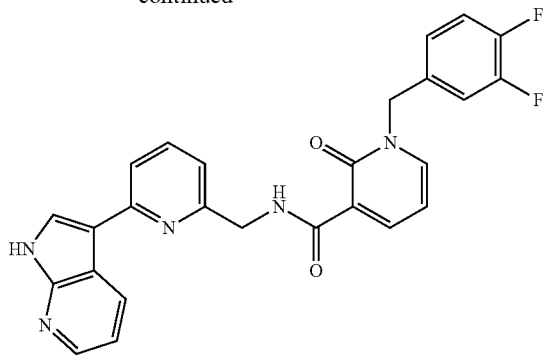

63.1  1-(3,4-Difluoro-benzyl)-2-oxo-1,2-dihydro-pyridine-3-carboxylic acid [6-(1H-pyrrolo[2,3-b]pyridin-3-yl)-pyridin-2-ylmethyl]-amide 1-(3,4-Difluoro-benzyl)-2-oxo-1,2-dihydro-pyridine-3-carboxylic acid (6-bromo-pyridin-2-ylmethyl)-amide C-(6-Bromo-pyridin-2-yl)-methylamine-HCl (8.0E1 mg; ChemPacific), 1-(3,4-difluoro-benzyl)-2-oxo-1,2-dihydro-pyridine-3-carboxylic acid (101 mg, 0.000381 mol) and HATU (164 mg, 0.000431 mol; Applied Biosystems) were dissolved in N,N-dimethylformamide (2.0 mL, 0.026 mol; Aldrich). To this was added N,N-diisopropylethylamine (280 uL, 0.00161 mol; Aldrich) and the reaction was stirred overnight at room temperature. The reaction was evaporated. The residue was taken up in DMF and purified by preparative HPLC to yield the title compound in 100. mg yield (51%) as the TFA salt. MS m/z=434.07 (M+1).

1-(3,4-Difluoro-benzyl)-2-oxo-1,2-dihydro-pyridine-3-carboxylic acid [6-(1H-pyrrolo[2,3-b]pyridin-3-yl)-pyridin-2-ylmethyl]-amide Into a vial was dissolved 1-(3,4-difluoro-benzyl)-2-oxo-1,2-dihydro-pyridine-3-carboxylic acid (6-bromo-pyridin-2-ylmethyl)-amide (1.00E2 mg, 0.000230 mol), 3-(4,4,5,5-tetramethyl-[1,3,2]dioxaborolan-2-yl)-pyrrolo[2,3-b]pyridine-1-carboxylic acid tert-butyl ester (68 mg, 0.00020 mol) and [1,1'-bis(diphenylphosphino)ferrocene]dichloropalladium(II), complex with dichloromethane (1:1) (18 mg, 0.000022 mol; Strem) in 1,4-dioxane (4.0 mL, 0.051 mol; Acros). To this was added 2.0 M of sodium carbonate in Water (1.0 mL). The reaction was purged with Ar and sealed. The reaction was heated at 110° C. under an atmosphere of Argon for 4 hours. The reaction was diluted with methylene chloride and washed with water. The organic layer was dried with magnesium sulfate, filtered and evaporated. The residue was taken up in DMF and purified by preparative HPLC to yield the title compound as the bis-TFA salt in 21.0 mg yield (15%). MS m/z=472.40 (M+1). 1H NMR (300 MHz, DMSO-d6) $^{TM}$ ppm 12.181 (s (br), 1H) 10.403 (t, J=5.6 Hz, 1H) 8.877 (d, J=7.5 Hz, 1H) 8.417 (dd, J=7.1, 1.9 Hz, 1H) 8.360 (d, J=2.6 Hz, 1H) 8-290-8.203 (m, 2H) 7.839-7.475 (m, 2H) 7.498-7.308 (m, 2H) 7.228-7.125 (m, 2H) 6.967 (dd, J=7.9, 4.7 Hz, 1H) 6.607 (t, J=6.9 Hz, 1H) 5.258 (s, 2H) 4.718 (d, J=5.4 Hz, 2H).

Example 64

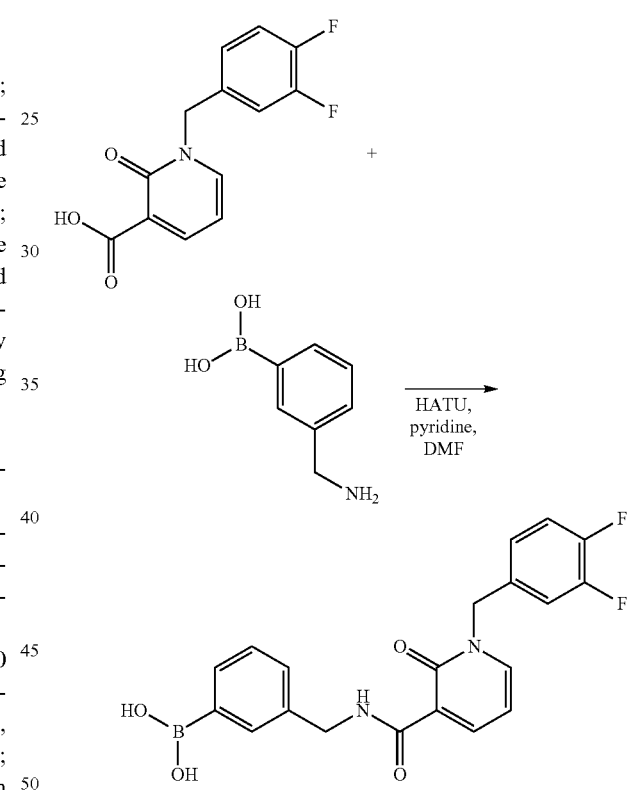

64.1  3-({[1-(3,4-Difluoro-benzyl)-2-oxo-1,2-dihydro-pyridine-3-carbonyl]-amino}-methyl)-phenylboronic acid (3-Aminomethylphenyl)boronic acid, HCl (2.14 g, 0.0142 mol; Frontier) was mixed with pyridine (23 mL, 0.28 mol; Acros) for 1 hour before adding a solution of 1-(3,4-difluoro-benzyl)-2-oxo-1,2-dihydro-pyridine-3-carboxylic acid (2.51 g, 0.00946 mol) in N,N-dimethylformamide (4.0E1 mL, 0.52 mol; Acros) and N,N,N',N'-tetramethyl-O-(7-azabenzotriazol-1-yl)uronium hexafluorophosphate (5.4 g, 0.014 mol; Applied Biosystems) was added. The reaction was stirred overnight. The reaction was evaporated to dryness, then partitioned between water, ethyl acetate. The organic layer was washed with saturated sodium chloride, dried with sodium sulfate, filtered and concentrated. The residue was purified using silica gel chromatography with 0-5% MeOH/DCM as eluent and then repurified using 0-10% MeOH/EtOAc as eluent. Appropriate fractions were combined and evaporated to give the title compound in 2.18 g yield (58%). MS m/z=398.99 (M+1). 1H NMR (400 MHz, CDCl3) $^{TM}$ ppm 10.102 (m, 1H) 8.555 (dd, J=7.1, 2.2 Hz, 1H) 7.806-7.294 (m, 4H) 7.119 (m, 2H) 7.007 (m, 1H) 6.447 (t, J=7.05 Hz, 1H) 5.488 (s (br), 1H) 5.120 (s, 2H) 4.734-4.580 (m, 2H).

Example 65

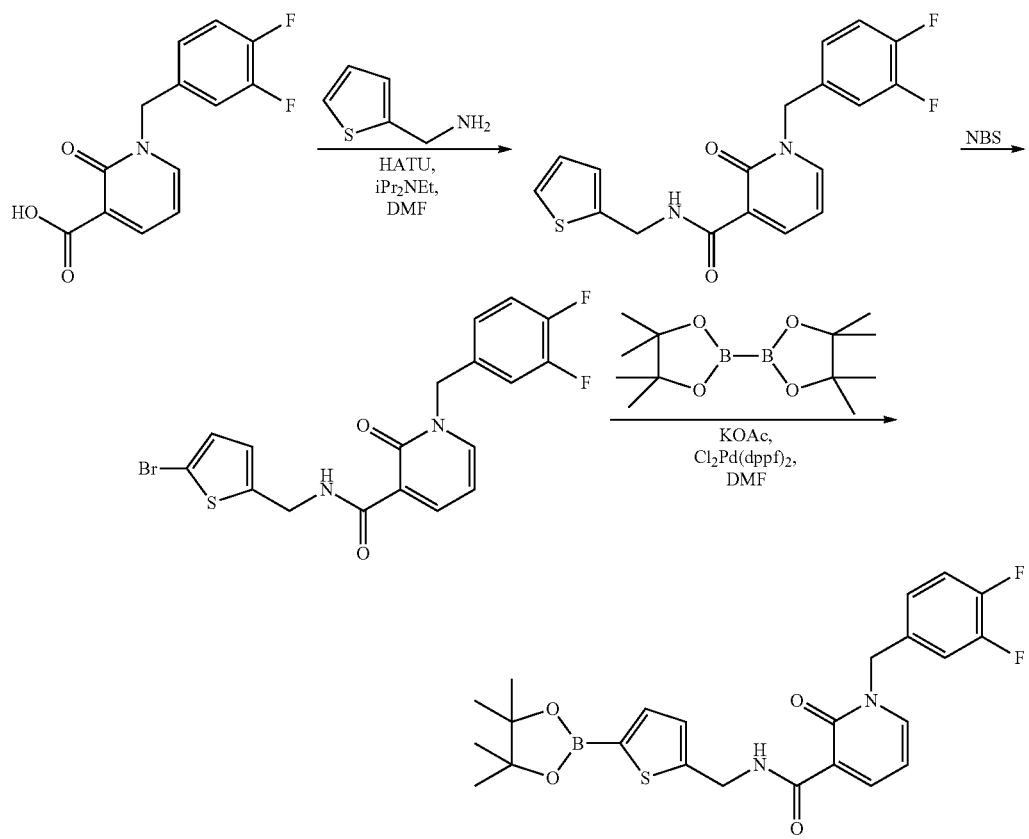

65.1  1-(3,4-Difluoro-benzyl)-2-oxo-1,2-dihydro-pyridine-3-carboxylic acid [5-(4,4,5,5-tetramethyl-1,3,2-dioxaborolan-2-yl)-thiophen-2-ylmethyl]-amide Thiophene-2-methanamine (0.562 g, 0.00496 mol; Acros) and 1-(3,4-difluoro-benzyl)-2-oxo-1,2-dihydro-pyridine-3-carboxylic acid (1.32 g, 0.00496 mol) and N,N,N',N'-tetramethyl-O-(7-azabenzotriazol-1-yl)uronium hexafluorophosphate (2.08 g, 0.00546 mol; Applied Biosystems) was dissolved in N,N-dimethylformamide (15.0 mL, Acros). To this was added N,N-diisopropylethylamine (4.32 mL, 0.0248 mol; Acros) and the reaction was stirred overnight at room temperature. The reaction was evaporated to dryness, then partitioned between 5% citric acid, ethyl acetate. The organic layer was washed with saturated sodium chloride, dried with sodium sulfate, filtered and concentrated. The residue was purified on preparative HPLC. Appropriate fractions were combined and evaporated to give the product in 1.04 g yield. MS m/z=361.06 M+H.

1-(3,4-Difluoro-benzyl)-2-oxo-1,2-dihydro-pyridine-3-carboxylic acid (thiophen-2-ylmethyl)-amide (1.04 g, 0.00288 mol) was dissolved in N,N-dimethylformamide (50. mL, Acros) and N-bromosuccinimide (0.566 g, 0.00318 mol; Aldrich) was added. The reaction was allowed to stir for 75 min. The reaction was evaporated, then taken up in methylene chloride and washed with saturated sodium bicarbonate solution, then washed with 5% citric acid, then washed with saturated sodium chloride solution. The organic layer was then dried with magnesium sulfate, filtered and concentrated to give the crude material. The residue was dissolved in methylene chloride and purified by silica gel chromatography using hexanes/ethyl acetate as eluent (Rf=0.25 in 1:1 hexanes/ethyl acetate) to give the product (1.12 g). MS m/z=438.90/441.28 M+H.

1-(3,4-Difluoro-benzyl)-2-oxo-1,2-dihydro-pyridine-3-carboxylic acid (5-bromo-thiophen-2-ylmethyl)-amide (614 mg, 0.00140 mol) and bis(pinacolato)diboron (1.77 g, 0.00699 mol; Aldrich) and potassium acetate (830 mg, 0.00846 mol; Aldrich) and [1,1'-bis(diphenylphosphino)ferrocene]dichloropalladium(II), complex with dichloromethane (1:1) (1.20E2 mg, 0.000147 mol; Strem) were dissolved in N,N-dimethylformamide (15 mL, Acros;). The reaction was heated in a sealed tube at 80° C. After 60 min, the reaction was evaporated, then taken up in DCM, washed with water, dried with magnesium sulfate, filtered and evaporated. The material was taken up in dichloromethane and purified by silica gel chromatography using hexanes/ethyl acetate as eluent (Rf=0.67 in ethyl acetate) to give the product in 650 mg yield. MS 487.33 M+H. The product contains some of the hydrolyzed product (boronic acid).

Example 66

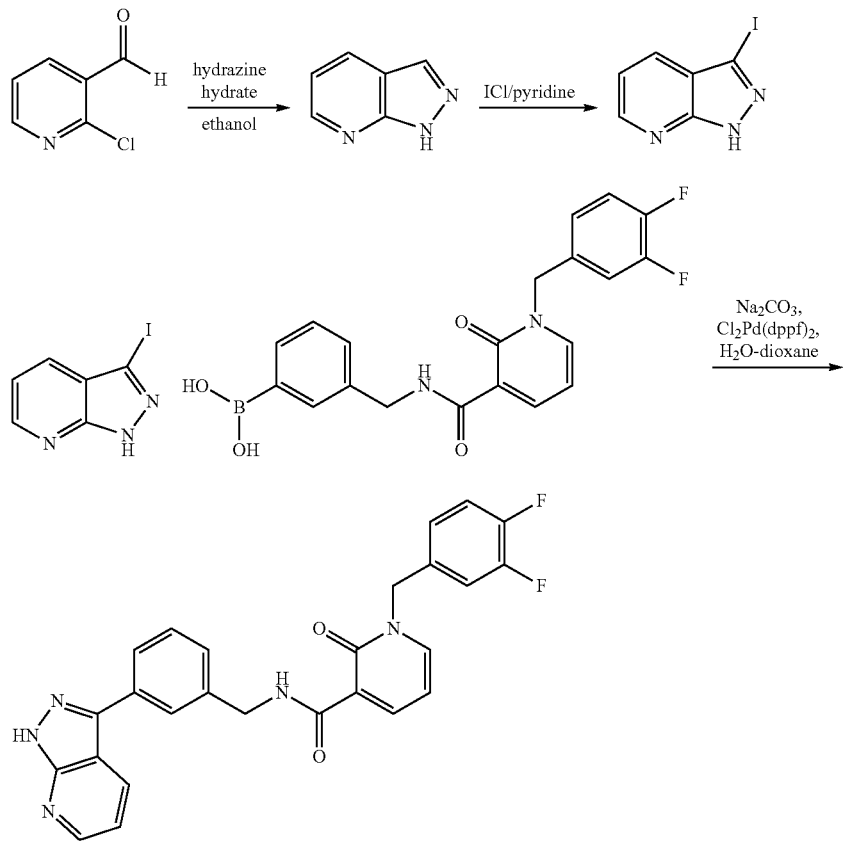

66.1 1-(3,4-Difluoro-benzyl)-2-oxo-1,2-dihydro-pyridine-3-carboxylic acid 3-(1H-pyrazolo[3,4-b]pyridin-3-yl)-benzylamide Into a round-bottom flask was added 2-chloro-pyridine-3-carbaldehyde (5.20 g, 0.0367 mol; Aldrich) and hydrazine hydrate (1.0E mL, 0.20 mol; Aldrich), and the reaction was heated for 24 hours at reflux. The solvent and excess hydrazine were removed under reduced pressure. The material was taken up in hot benzene, filtered and allowed to cool at room temperature and then cooled in a refrigerator. After 30 min, the material was filtered. The filtrate was filtered a second time and the filtrate was evaporated and purified by silica gel chromatography using hexanes/ethyl acetate as eluent to give the title compound in 225 mg yield (5%). MS m/z=120.02 (M+1). 1H NMR (300 MHz, CDCl3) ™ ppm 13.235 (s (br), 1H) 8.665 (dd, J=4.6, 1.6 Hz, 1H) 8.170 (d, J=1.5 Hz, 1H) 8.142 (s, 1H). 7.192 (dd, J=8.0, 4.4 Hz, 1H). TLC Rf=0.26 in 1:1 hexanes/ethyl acetate.

1H-Pyrazolo[3,4-b]pyridine (0.225 g, 0.00189 mol) was dissolved in pyridine (2.0 mL, 0.025 mol; Acros) and cooled in an ice bath. A solution of 1.00 M of iodine monochloride in methylene chloride (2.1 mL; Aldrich) was added over 5 min. After 15 min the cooling bath was removed, and after another 30 min the solution was diluted with 200 mL of ethyl acetate. The organic solution was washed sequentially with 1 N hydrogen chloride and 1 N sodium hydroxide, dried over magnesium sulfate, and concentrated. The residue was taken up in DMF and purified by preparative HPLC to yield the desired product as TFA salt in 55.5 mg yield (8%). MS m/z=245.87 (M+1). 1H NMR (400 MHz, DMSO-d6) ™ ppm 14.070 (s (br), 1H) 8.564 (dd, J=4.5, 1.6 Hz, 1H) 7.917 (d, J=8.0 Hz, 1H) 7.253 (dd, J=8.1, 4.5 Hz, 1H).

Into a vial was dissolved 3-({[1-(3,4-Difluoro-benzyl)-2-oxo-1,2-dihydro-pyridine-3-carbonyl]-amino}-methyl)-phenylboronic acid (62 mg, 0.00016 mol), 3-iodo-1H-pyrazolo[3,4-b]pyridine (3.0E1 mg, 0.00012 mol) and [1,1'-bis(diphenylphosphino)ferrocene]dichloropalladium(II), complex with dichloromethane (1:1) (15 mg, 0.000018 mol; Strem) in 1,4-dioxane (3.0 mL, 0.038 mol; Acros). To this was added 2.0 M of sodium carbonate in water (0.75 mL). The reaction was purged with Ar and sealed. The reaction was heated at 110° C. under an atmosphere of Argon for 75 minutes. The reaction was diluted with methylene chloride and washed with water. The organic layer was dried with magnesium sulfate, filtered and evaporated. The residue was taken up in DMF and purified by preparative HPLC to yield the title compound as the TFA salt in 25.8 mg yield (36%). MS m/z=472.38 (M+1). 1H NMR (400 MHz, DMSO-d6) ™ ppm 13.801 (s (br), 1H) 10.109 (t, J=5.8 Hz, 1H) 8.573-8.536 (m, 2H) 8.401 (dd, J=7.2, 2.2 Hz, 1H) 8.230 (dd, J=6.7, 2.2 Hz, 1H) 7.977 (m, 1H) 7.896 (dt, J=7.8, 1.4 Hz, 1H) 7.504-7.342 (m, 4H) 7.234 (m, 1H) 7.157 (m, 1H) 6.954 (t, J=6.9 Hz, 1H) 5.206 (s, 2H) 4.618 (d, J=6.0 Hz, 2H).

Example 67

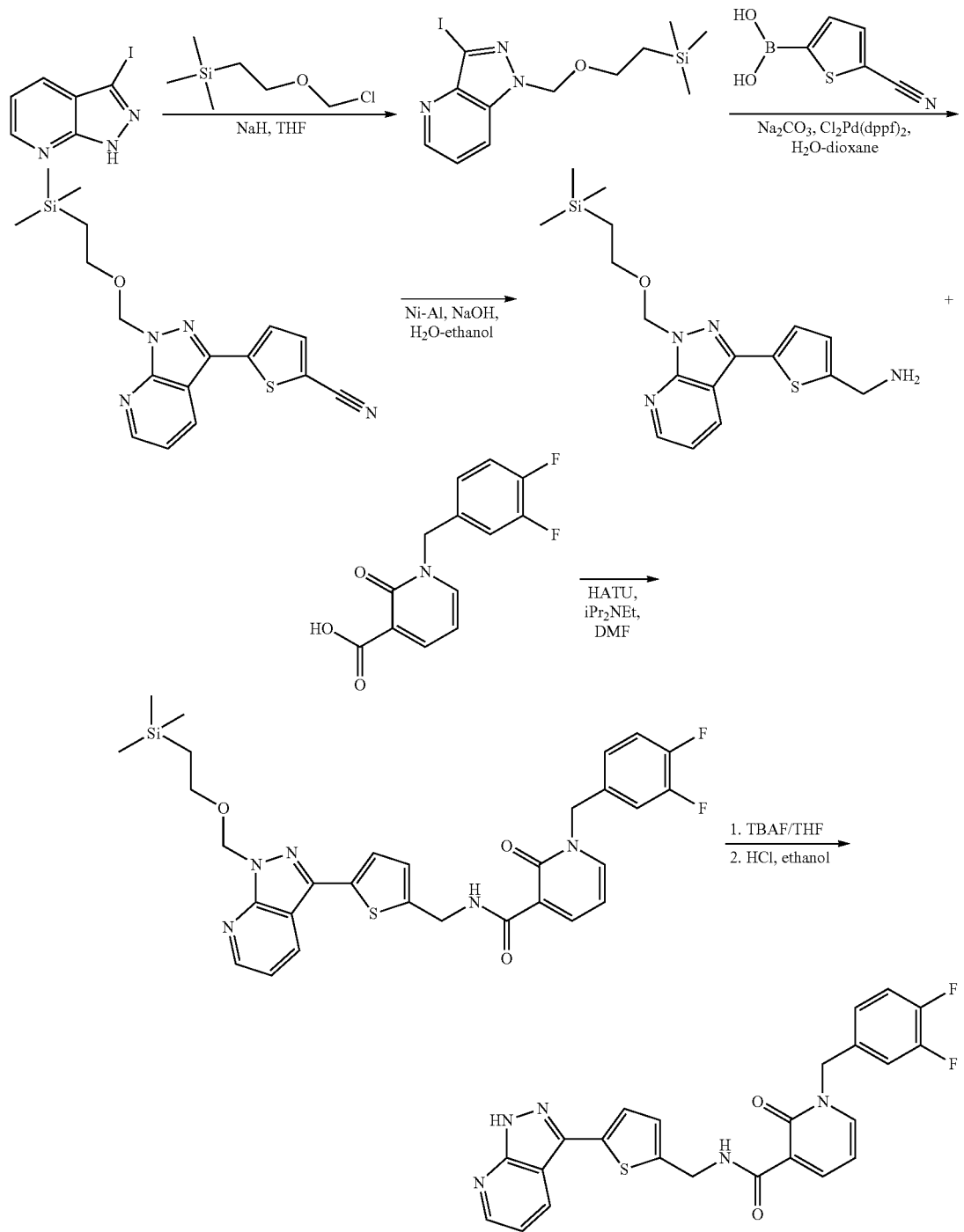

67.1 1-(3,4-Difluoro-benzyl)-2-oxo-1,2-dihydro-pyridine-3-carboxylic acid [5-(1H-pyrazolo[3,4-b]pyridin-3-yl)-thiophen-2-ylmethyl]-amide Into a round-bottom flask was dissolved 3-iodo-1H-pyrazolo[3,4-b]pyridine (0.699 g, 0.00285 mol) in tetrahydrofuran (7.5 mL, 0.092 mol; Acros). The reaction was cooled at 0 Celsius and sodium hydride, 60% in mineral oil (150 mg; Aldrich) was added. Vigorous bubbling occurred. The reaction was stirred for 10 minutes at room temperature then was cooled at 0 Celsius. [β-(Trimethylsilyl)ethoxy]methyl chloride (6.0E2 uL, 0.0034 mol; Aldrich) was added dropwise and the reaction was stirred for 1 hour at room temperature. The reaction was diluted with saturated sodium bicarbonate, extracted with ethyl acetate, washed with saturated sodium chloride, dried with sodium sulfate. The mixture was filtered and concentrated. The residue was dissolved in methylene chloride and purified by silica gel chromatography using hexanes/ethyl acetate as eluent to yield 0.351 g of the title compound (33%). MS m/z=376.14

(M+1). 1H NMR (400 MHz, CDCl3) ™ ppm 8.606 (d, J=4.5 Hz, 1H) 7.834 (d, J=7.9, 1H) 7.230 (dd, J=8.3, 4.9 Hz, 1H) 5.859 (s, 2H) 3.665 (t, J=8.3 Hz, 2H) 0.932 (t, J=8.3 Hz, 2H) −0.053 (s, 9H).

Into a vial was dissolved 5-cyanothiophene-2-boronic acid (50 mg, 0.00033 mol; Ryscor), 3-iodo-1-(2-trimethylsilanyl-ethoxymethyl)-1H-pyrazolo[4,3-b]pyridine (101 mg, 0.000269 mol) and [1,1'-bis(diphenylphosphino)ferrocene]dichloropalladium(II), complex with dichloromethane (1:1) (23 mg, 0.000028 mol; Strem) in 1,4-dioxane (6.0 mL, 0.077 mol; Acros). To this was added 2.0 M of sodium carbonate in water (1.5 mL). The reaction was purged with Ar and sealed. The reaction was heated at 110° C. under an atmosphere of Argon for 90 minutes. The reaction was diluted with methylene chloride, washed with water, dried with magnesium sulfate, filtered and evaporated. The residue was taken up in DCM and purified by silica gel chromatography to give the title compound in 32 mg yield (33%). MS m/z=357.17 (M+1). 1H NMR (400 MHz, CDCl3) ™ ppm 8.656 (d, J=3.8 Hz, 1H) 8.304 (d, J=8.0, 1H) 7.683 (d, J=3.8 Hz, 1H) 7.610 (d, J=3.8 Hz, 1H) 7.315 (dd, J=8.3, 4.5 Hz) 5.917 (s, 2H) 3.714 (t, J=8.3 Hz, 2H) 0.959 (t, J=8.3 Hz, 2H) −0.045 (s, 9H). Rf=0.30 in 3:1 hexanes/ethyl acetate.

Into a round-bottom flask was dissolved 5-[1-(2-trimethylsilanyl-ethoxymethyl)-1H-pyrazolo[3,4-b]pyridin-3-yl]-thiophene-2-carbonitrile (32 mg, 0.000090 mol) in ethanol (0.50 mL, 0.0086 mol; Fisher). To this was added 2.50 M of sodium hydroxide in Water (0.50 mL) and the mixture was cooled at 0° C. Nickel-Aluminum alloy (1:1, Nickel:Aluminum, 188 mg; Fluka) was added and the reaction was stirred at room temperature for 30 minutes. The reaction mixture was filtered through Celite. The solvent was evaporated, and the residue was partitioned between water, methylene chloride. The organic layer was dried with magnesium sulfate, filtered and concentrated to dryness to yield the title compound in 23 mg yield (crude). MS m/z=361.53 (M+1).

C-{5-[1-(2-Trimethylsilanyl-ethoxymethyl)-1H-pyrazolo[3,4-b]pyridin-3-yl]-thiophen-2-yl}-methylamine (23 mg, 0.000064 mol), 1-(3,4-difluoro-benzyl)-2-oxo-1,2-dihydro-pyridine-3-carboxylic acid (2.0E1 mg, 0.000075 mol) and HATU (44 mg, 0.00012 mol; Applied Biosystems) were dissolved in N,N-dimethylformamide (1.25 mL, 0.0161 mol; Acros). To this was added N,N-diisopropylethylamine (56 uL, 0.00032 mol; Aldrich) and the reaction was stirred for 1 hour at room temperature. The reaction was diluted with 5% citric acid in water, then extracted with ethyl acetate. Saturated sodium chloride was added to aid separation. The organic layer was washed with saturated sodium chloride, dried with sodium sulfate, filtered and evaporated to yield the crude title compound. MS m/z=608.34 (M+1).

Into a vial was dissolved 1-(3,4-difluoro-benzyl)-2-oxo-1,2-dihydro-pyridine-3-carboxylic acid {5-[1-(2-trimethylsilanyl-ethoxymethyl)-1H-pyrazolo[3,4-b]pyridin-3-yl]-thiophen-2-ylmethyl}-amide (39 mg, 0.000064 mol) in tetrahydrofuran (1.0 mL, 0.012 mol; Acros) and 1.00 M of tetra-n-butylammonium fluoride in tetrahydrofuran (1.0 mL; Aldrich). The reaction was stirred at 60° C. for 1 hour. An additional 1.0 mL TBAF solution is added (new lot, Aldrich) and the reaction was heated at 70° C. for 1 hour. LCMS showed no evidence of product after either addition. The reaction was evaporated, then taken up in ethanol (3.0 mL, 0.051 mol; Fisher). To this was added 12 M of hydrogen chloride in water (3.0 mL; Fisher) and more ethanol (3.0 mL) and the reaction was heated at 90° C. for 2.5 hours. The reaction was evaporated to dryness, taken up in DMF and purified by preparative HPLC to yield 8.4 mg (16% over three steps) of the title compound as TFA salt. MS m/z=478.02 (M+1). 1H NMR (400 MHz, DMSO-d6) ™ ppm 13.709 (s (br), 1H) 10.096 (t, J=5.9 Hz, 1H) 8.552 (dd, J=2.9, 1.5 Hz, 1H) 8.532 (m, 1H) 8.402 (dd, J=7.2, 2.2 Hz, 1H) 7.619 (d, J=3.6 Hz, 1H) 7.479-7.349 (m, 2H) 7.266 (dd, J=8.0, 4.6 Hz, 1H) 7.161 (m, 1H) 7.086 (d, J=3.6 Hz, 1H) 6.597 (t, J=7.0 Hz, 1H) 5.201 (s, 2H) 4.698 (d, J=5:8 Hz, 2H).

Example 68

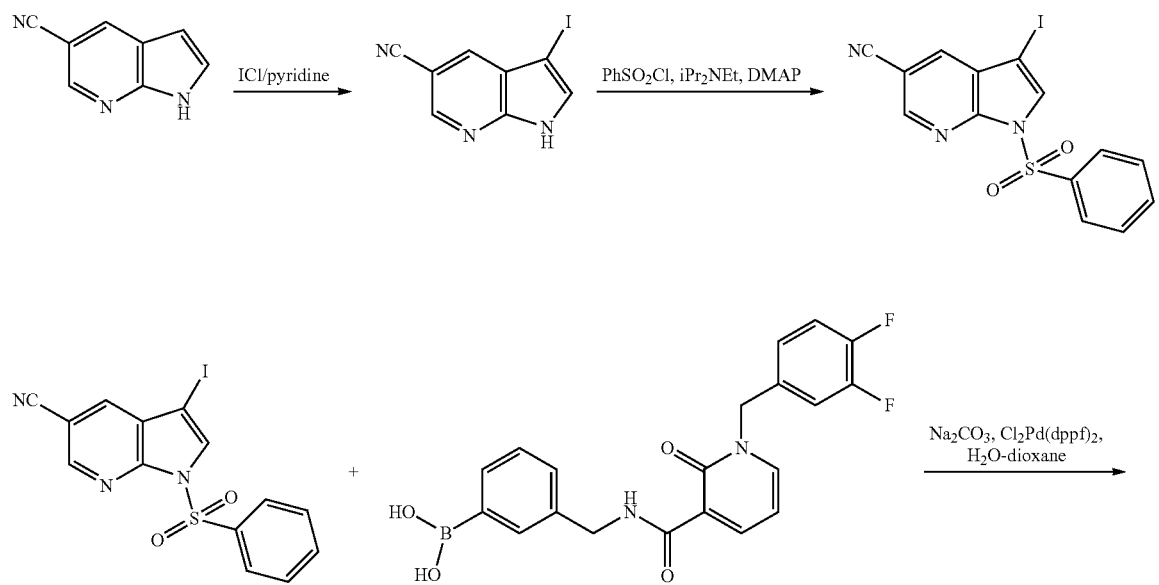

-continued

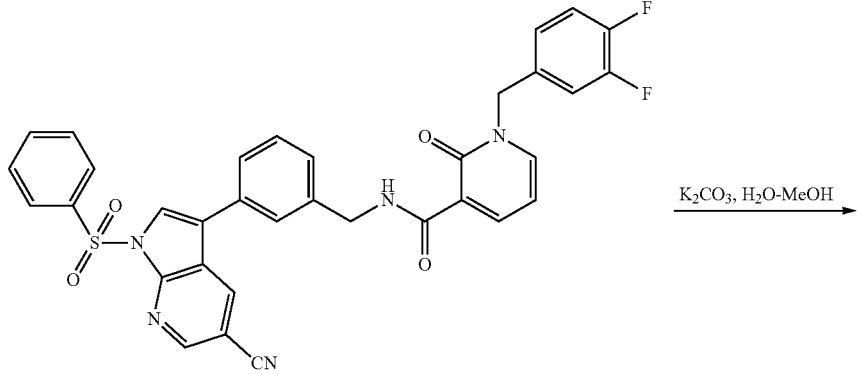

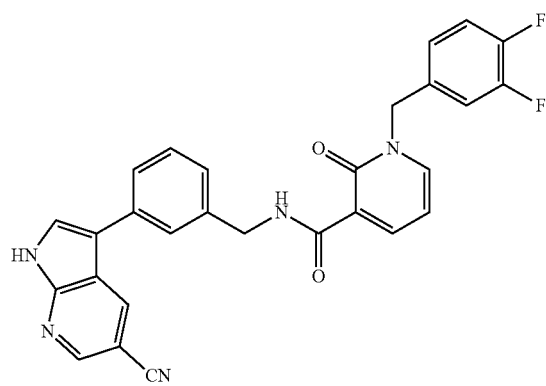

68.1 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide 1H-Pyrrolo[2,3-b]pyridine-5-carbonitrile (505 mg, 0.00353 mol; Adesis) was dissolved in pyridine (5.00 mL, 0.0618 mol; Acros) and cooled in an ice bath. 1.00 M Iodine monochloride in methylene chloride (3.88 mL, 0.00388 mol; Aldrich) was added dropwise to the reaction mixture slowly and the reaction was stirred at 0° C. for 15 minutes. The mixture was warmed to room temperature and was stirred for 30 minutes. 5 mL of pyridine (5.00 mL, 0.0618 mol; Acros) was added 15 min before completion to aid in stirring. The reaction was evaporated to dryness.

Crude 3-iodo-1H-pyrrolo[2,3-b]pyridine-5-carbonitrile (0.00353 mol) was slurried in methylene chloride (25 mL, Acros). To this was added benzenesulfonyl chloride (495 uL, 0.00388 mol; Aldrich), 4-dimethylaminopyridine (48 mg, 0.00039 mol) and N,N-diisopropylethylamine (3.07 mL, 0.0176 mol; Aldrich) and the reaction was stirred at room temperature. After 60 min, the reaction was diluted with methylene chloride, washed with water, dried with magnesium sulfate, filtered, and concentrated.

The residue was taken up in ethyl acetate/N,N-dimethylformamide, loaded onto silica gel and evaporated. The sample was purified by silica gel chromatography (using hexanes/ethyl acetate as eluent) to yield N-protected material in 1.158 g yield (80%). MS m/z=409.87 M+H.

Into a vial was dissolved 3-({[1-(3,4-Difluoro-benzyl)-2-oxo-1,2-dihydro-pyridine-3-carbonyl]-amino}-methyl)-phenylboronic acid (205 mg, 0.515 mmol) and 1-benzenesulfonyl-3-iodo-1H-pyrrolo[2,3-b]pyridine-5-carbonitrile (253 mg, 0.618 mmol) and [1,1'-bis(diphenylphosphino)ferrocene]dichloropalladium(II), complex with dichloromethane (1:1) (47 mg, 0.058 mmol; Strem) in 1,4-dioxane (6.40 mL, Acros). To this was added 2.0 M sodium carbonate in water (1.6 mL, 0.0032 mol). The reaction was purged with argon and sealed. The reaction was heated at 110° C. under an atmosphere of argon for 75 minutes. After cooling, the reaction was diluted with water and extracted with methylene chloride. The organic layer was dried with magnesium sulfate, filtered and evaporated to give the crude product.

The crude material was taken up in methylene chloride, filtered, and purified by silica gel chromatography (hexanes/ethyl acetate as eluent) to give the product in 256 mg yield (78%). MS m/z=635.98 M+H.

1-(3,4-Difluoro-benzyl)-2-oxo-1,2-dihydro-pyridine-3-carboxylic acid 3-(1-benzenesulfonyl-5-cyano-1H-pyrrolo[2,3-b]pyridin-3-yl)-benzylamide (128 mg, 0.000201 mol) was dissolved in methanol (4.5 mL; Fisher) and water (1.5 mL, Fisher). To this was added potassium carbonate (129 mg, 0.000933 mol; Fisher) and the reaction was heated at reflux for 1 hour. The reaction was evaporated, taken up in N,N-dimethylformamide, neutralized with TFA (200 uL) and purified by preparative HPLC chromatography to yield the product in 26.9 mg yield (22%). 1H NMR (400 MHz, DMSO-d6) d ppm 12.582 (s (br), 1H) 10.078 (t, J=5.7 Hz, 1H) 8.804 (s, 1H) 8.648 (s, 1H) 8.405 (d, J=7.2 Hz, 1H) 8.224 (d, J=6.4 Hz, 1H) 8.098 (d, J=1.8 Hz, 1H) 7.750 (s, 1H) 7.639 (d, J=8.0 Hz, 1H) 7.470-7.334 (m, 3H) 7.236 (d, J=7.4 Hz, 1H) 7.183-7.128 (m, 1H) 6.589 (t, J=7.2 Hz, 1H) 5.212 (s, 2H) 4.596 (d, J=6.0 Hz, 2H); MS m/z=496.02 M+H.

Example 69

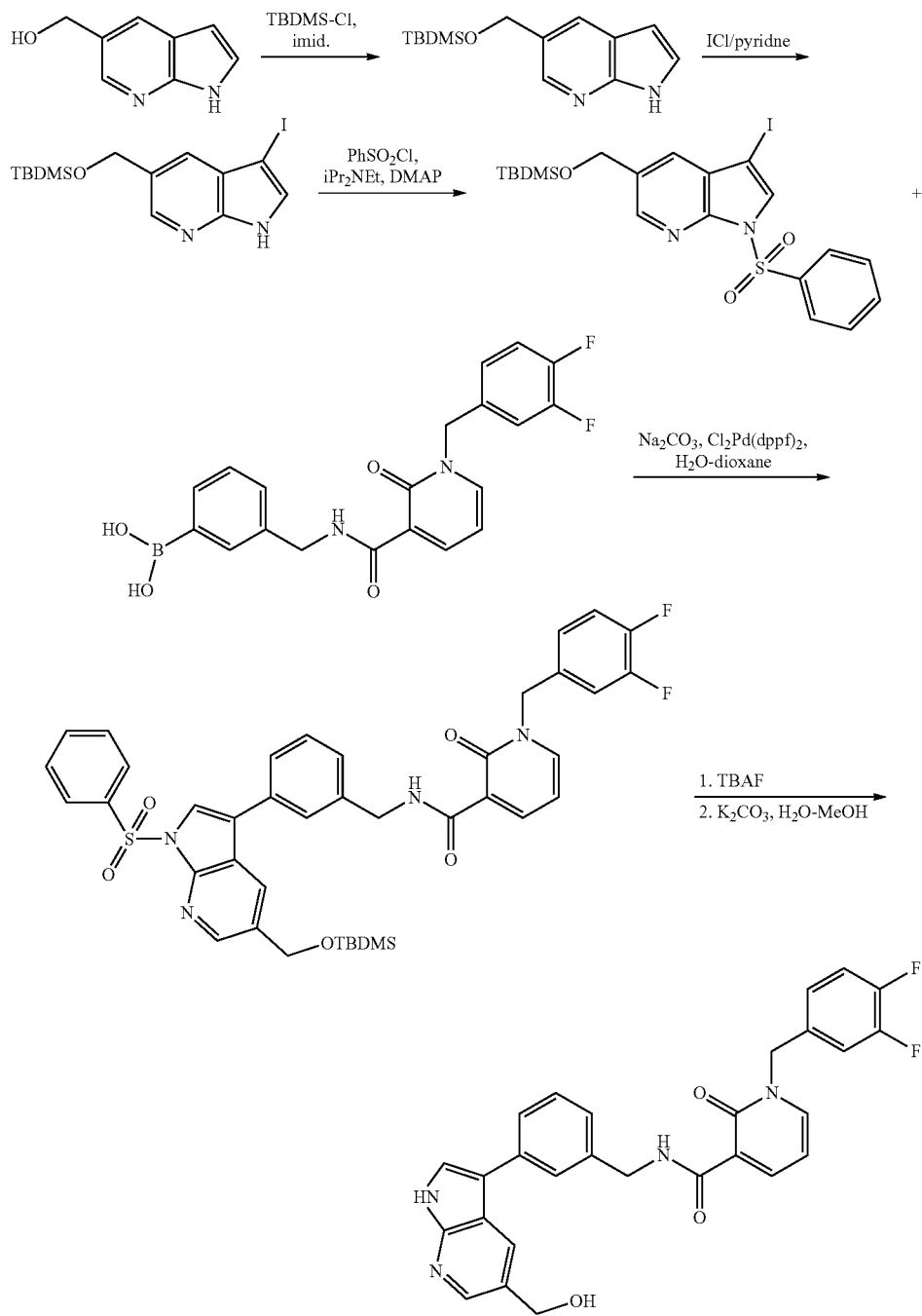

69.1 1-(3,4-Difluoro-benzyl)-2-oxo-1,2-dihydro-pyridine-3-carboxylic acid 3-(5-hydroxymethyl-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-hydroxymethyl-1H-pyrrolo[2,3-b]pyridin-3-yl)-benzylamide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 3-({[1-(3,4-Difluoro-benzyl)-2-oxo-1,2-dihydro-pyridine-3-carbonyl]-amino}-methyl)-phenylboronic acid as activated boron species and (1H-Pyrrolo[2,3-b]pyridin-5-yl)-methanol as substituted bicyclic heterocycle, to yield the title compound. 1H NMR (400 MHz, DMSO-d6) d ppm 11.935 (s, 1H) 10.072 (t, J=5.9 Hz, 1H) 8.402 (dd, J=7.4, 2.0 Hz, 1H) 8.269-8.228 (m, 2H) 8.221 (dd, J=6.7, 2.0 Hz, 1H) 7.848 (d, J=2.6 Hz, 1H) 7.679 (s, 1H) 7.594 (d, J=7.4 Hz, 1H) 7.464-7.332 (m, 3H) 7.193 (d, J=7.7 Hz, 1H) 7.175-7.120 (m, 1H) 6.589 (t, J=6.9 Hz, 1H) 5.198 (s, 2H) 4.610-4.549 (m, 4H); MS m/z=501.21 M+H.

(1H-Pyrrolo[2,3-b]pyridin-5-yl)-methanol was protected as TBS ether prior to iodination.

5-(tert-Butyl-dimethyl-silanyloxymethyl)-1H-pyrrolo[2,3-b]pyridine

Into a 1-neck round-bottom flask was dissolved (1H-pyrrolo[2,3-b]pyridin-5-yl)-methanol (0.506 g, 0.00342 mol; Adesis) and tert-butyldimethylsilyl chloride (575 mg, 0.00381 mol; Aldrich) and 1H-imidazole (355 mg, 0.00521 mol; Fluka) in N,N-dimethylformamide (2.0E1 mL, 0.25 mol; Acros). The reaction was stirred at room temperature overnight. The reaction was diluted with saturated sodium bicarbonate, extracted with ethyl acetate, washed with saturated sodium chloride. The aqueous layers were then extracted with methylene chloride. All organic layers were combined and dried with magnesium sulfate, filtered and evaporated. The residue was taken up in methylene chloride and purified by silica gel chromatography using hexanes/ethyl acetate as eluent (Rf=0.52 in 1:1 hexanes/ethyl acetate) to yield the product in 478 mg yield (53%). MS m/z=263.17 M+H.

The product of palladium-mediated coupling was subjected to TBAF deprotection prior to potassium carbonate hydrolysis.

Into a 1-neck round-bottom flask was dissolved 1-(3,4-difluoro-benzyl)-2-oxo-1,2-dihydro-pyridine-3-carboxylic acid 3-[1-benzenesulfonyl-5-(tert-butyl-dimethyl-silanyloxymethyl)-1H-pyrrolo[2,3-b]pyridin-3-yl]-benzylamide (78 mg, 0.00010 mol) in tetrahydrofuran (1.00 mL, Acros) and 1.00 M of tetra-n-butylammonium fluoride in tetrahydrofuran (1.00 mL, 0.001 mol; Aldrich). The reaction was stirred at room temperature. After 2 h, the reaction was diluted with ethyl acetate, washed with saturated sodium bicarbonate, washed with saturated sodium chloride, dried with sodium sulfate, filtered and evaporated to give 86 mg of crude material, which contained some of the doubly deprotected product.

Example 70

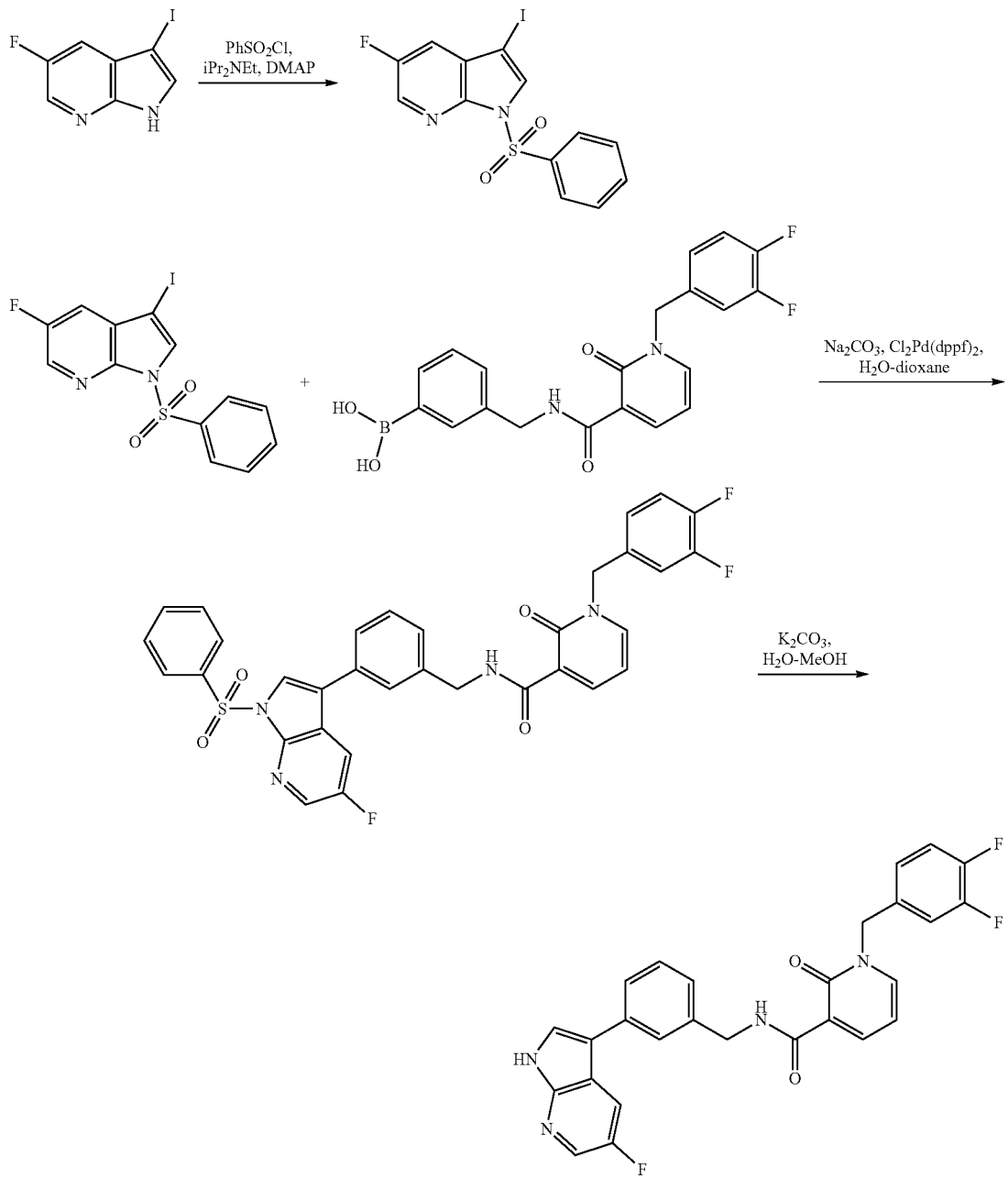 [SMILES: Fc1cnc2[nH]cc(I)c2c1 ; O=S(=O)(c1ccccc1)n1cc(I)c2cc(F)cnc21 ; O=S(=O)(c1ccccc1)n1cc(I)c2cc(F)cnc21 ; O=C(NCc1cccc(B(O)O)c1)c1cccn(Cc2ccc(F)c(F)c2)c1=O ; O=C(NCc1cccc(-c2cn(S(=O)(=O)c3ccccc3)c3ncc(F)cc23)c1)c1cccn(Cc2ccc(F)c(F)c2)c1=O ; O=C(NCc1cccc(-c2c[nH]c3ncc(F)cc23)c1)c1cccn(Cc2ccc(F)c(F)c2)c1=O]

70.1 1-(3,4-Difluoro-benzyl)-2-oxo-1,2-dihydro-pyridine-3-carboxylic acid 3-(5-fluoro-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-fluoro-1H-pyrrolo[2,3-b]pyridin-3-yl)-benzylamide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 3-({[1-(3,4-Difluoro-benzyl)-2-oxo-1,2-dihydro-pyridine-3-carbonyl]-amino}-methyl)-phenylboronic acid as activated boron species and 5-Fluoro-3-iodo-1H-pyrrolo[2,3-b]pyridine as substituted bicyclic heterocycle, to produce the title compound. 1H NMR (400 MHz, CDCl3) d ppm 12.504 (s, 1H) 10.457 (m, 1H) 8.609 (dd, J=7.3, 2.1 Hz, 1H) 8.541 (d, J=8.1 Hz, 1H) 8.259 (m, 1H) 7.788 (s, 1H) 7.605 (s, 1H) 7.576 (dd, J=6.5, 2.0 Hz, 1H) 7.522-7.366 (m, 3H) 7.221-7.094 (m, 2H) 7.044-6.993 (m, 1H) 6.517 (t, J=6.9 Hz, 1H) 5.178 (s, 2H) 4.739 (d, J=5.7 Hz, 2H); MS m/z=489.33 M+H.

Example 71

71.1 1-(3,4-Difluoro-benzyl)-2-oxo-1,2-dihydro-pyridine-3-carboxylic acid [5-(5-fluoro-1H-pyrrolo[2,3-b]pyridin-3-yl)-thiophen-2-ylmethyl]-amide Except where indicated, 1-(3,4-Difluoro-benzyl)-2-oxo-1,2-dihydro-pyridine-3-carboxylic acid [5-(5-fluoro-1H-pyrrolo[2,3-b]pyridin-3-yl)-thiophen-2-ylmethyl]-amide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 1-(3,4-Difluoro-benzyl)-2-oxo-1,2-dihydro-pyridine-3-carboxylic acid [5-(4,4,5,5-tetramethyl-1,3,2-dioxaborolan-2-yl)-thiophen-2-ylmethyl]-amide as activated boron species and 5-Fluoro-3-iodo-1H-pyrrolo[2,3-b]pyridine as substituted bicyclic heterocycle, to produce the title compound. 1H NMR (400 MHz, CDCl3-MeOH-d4) d ppm 8.570 (d, J=7.0 Hz, 1H) 8.500 (d, J=7.6 Hz, 1H) 8.287 (s, 1H) 7.744 (s, 1H) 7.555 (d, J=6.3 Hz, 1H) 7.186-6.972 (m, 5H) 6.478 (t, J=6.7 Hz, 1H) 5.135 (s, 2H) 4.788 (s, 2H); MS m/z=495.29 M+H.

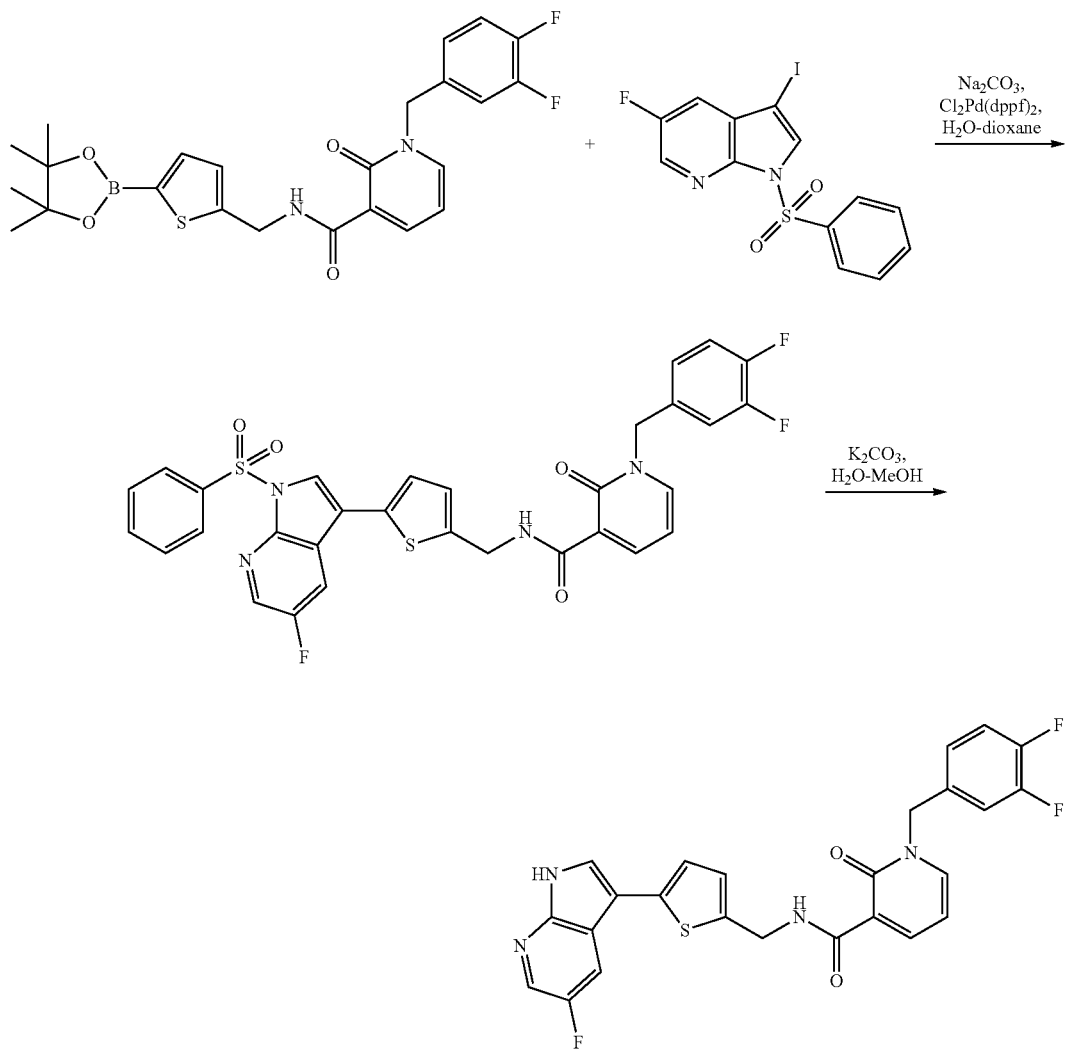 [SMILES: CC1(C)OB(c2ccc(CNC(=O)c3cccn(Cc4ccc(F)c(F)c4)c3=O)s2)OC1(C)C ; O=S(=O)(c1ccccc1)n1cc(I)c2cc(F)cnc21 ; O=C(NCc1ccc(-c2cn(S(=O)(=O)c3ccccc3)c3ncc(F)cc23)s1)c1cccn(Cc2ccc(F)c(F)c2)c1=O ; O=C(NCc1ccc(-c2c[nH]c3ncc(F)cc23)s1)c1cccn(Cc2ccc(F)c(F)c2)c1=O]

Example 72

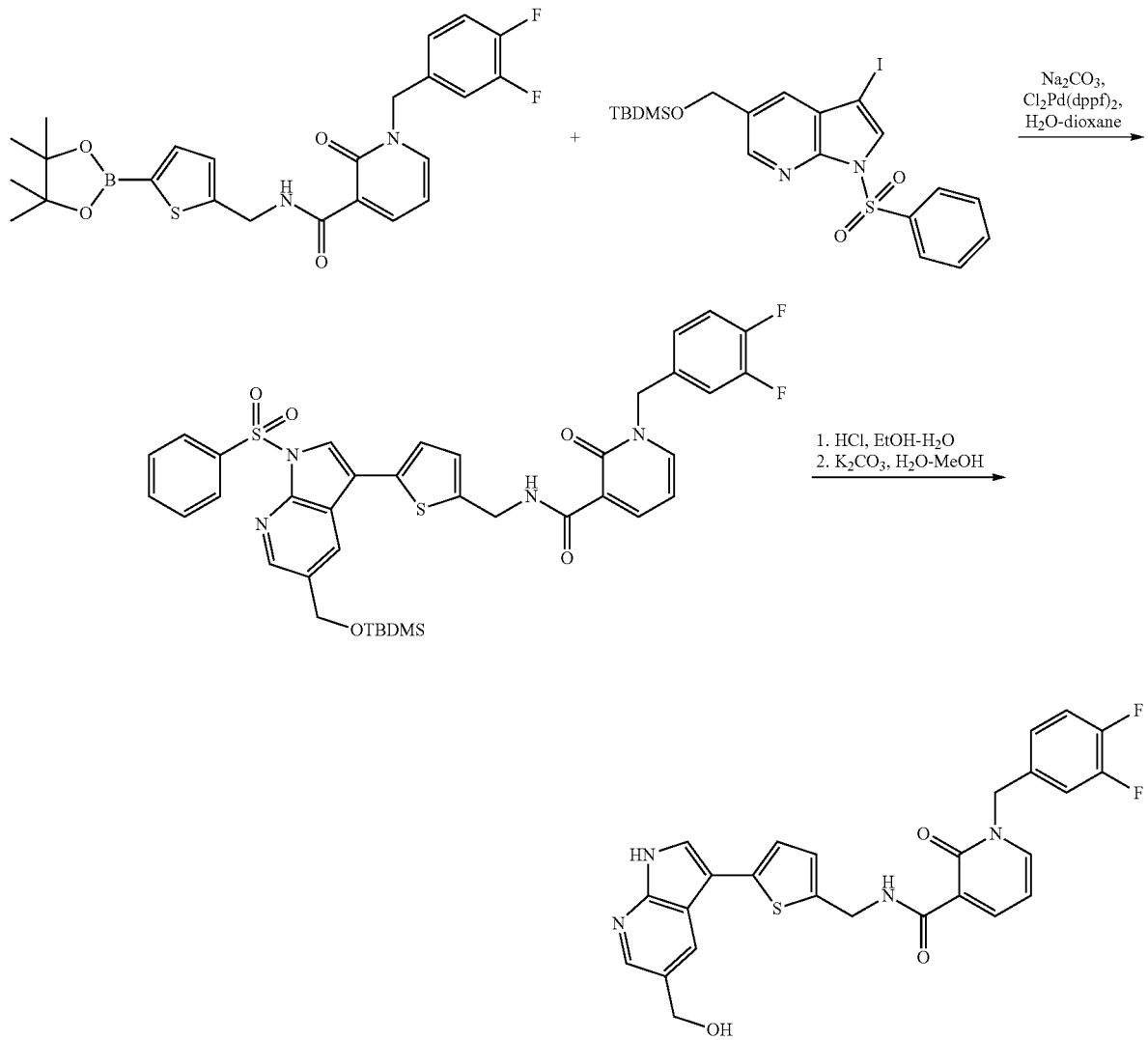

72.1 1-(3,4-Difluoro-benzyl)-2-oxo-1,2-dihydro-pyridine-3-carboxylic acid [5-(5-hydroxymethyl-1H-pyrrolo[2,3-b]pyridin-3-yl)-thiophen-2-ylmethyl]-amide Except where indicated, 1-(3,4-Difluoro-benzyl)-2-oxo-1,2-dihydro-pyridine-3-carboxylic acid [5-(5-hydroxymethyl-1H-pyrrolo[2,3-b]pyridin-3-yl)-thiophen-2-ylmethyl]-amide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 1-(3,4-Difluoro-benzyl)-2-oxo-1,2-dihydro-pyridine-3-carboxylic acid [5-(4,4,5,5-tetramethyl-1,3,2-dioxaborolan-2-yl)-thiophen-2-ylmethyl]-amide as activated boron species and (1H-Pyrrolo[2,3-b]pyridin-5-yl)-methanol as substituted bicyclic heterocycle, to yield the title compound. 1H NMR (400 MHz, DMSO-d6) d ppm 11.888 (s, 1H) 10.052 (t, J=6.0 Hz, 1H) 8.401 (dd, J=7.3, 2.1 Hz, 1H) 8.255-8.211 (m, 2H) 8.171 (d, J=1.7 Hz, 1H) 7.782 (d, J=2.5 Hz, 1H) 7.472-7.350 (m, 2H) 7.181 (d, J=3.5 Hz, 1H) 7.192-7.131 (m, 1H) 7.017 (d, J=3.5 Hz, 1H) 6.594 (t, J=6.9 Hz, 1H) 5.193 (s, 2H) 4.672 (d, J=5.8 Hz, 2H) 4.616 (s, 2H); MS m/z=507.33 M+H.

(1H-Pyrrolo[2,3-b]pyridin-5-yl)-methanol was protected as TBS ether prior to iodination [for conditions, see 1137 1-(3,4-Difluoro-benzyl)-2-oxo-1,2-dihydro-pyridine-3-carboxylic acid 3-(5-hydroxymethyl-1H-pyrrolo[2,3-b]pyridin-3-yl)-benzylamide].

The product of palladium-mediated coupling was subjected to HCl hydrolysis prior to potassium carbonate.

72.2 1-(3,4-Difluoro-benzyl)-2-oxo-1,2-dihydro-pyridine-3-carboxylic acid 3-(1-benzenesulfonyl-5-hydroxymethyl-1H-pyrrolo[2,3-b]pyridin-3-yl)-benzylamide Into a 1-neck round-bottom flask was dissolved 1-(3,4-difluoro-benzyl)-2-oxo-1,2-dihydro-pyridine-3-carboxylic acid 3-[1-benzenesulfonyl-5-(tert-butyl-dimethyl-silanyloxymethyl)-1H-pyrrolo[2,3-b]pyridin-3-yl]-benzylamide (0.17 mmol, 0.00017 mol) in ethanol (3.00 mL, Fisher;). To this was added 12 M of hydrogen chloride in water (1.00 mL, 0.012 mol; Fisher) and the reaction was stirred at room temperature for 1 h and then evaporated to give the crude product.

Example 73

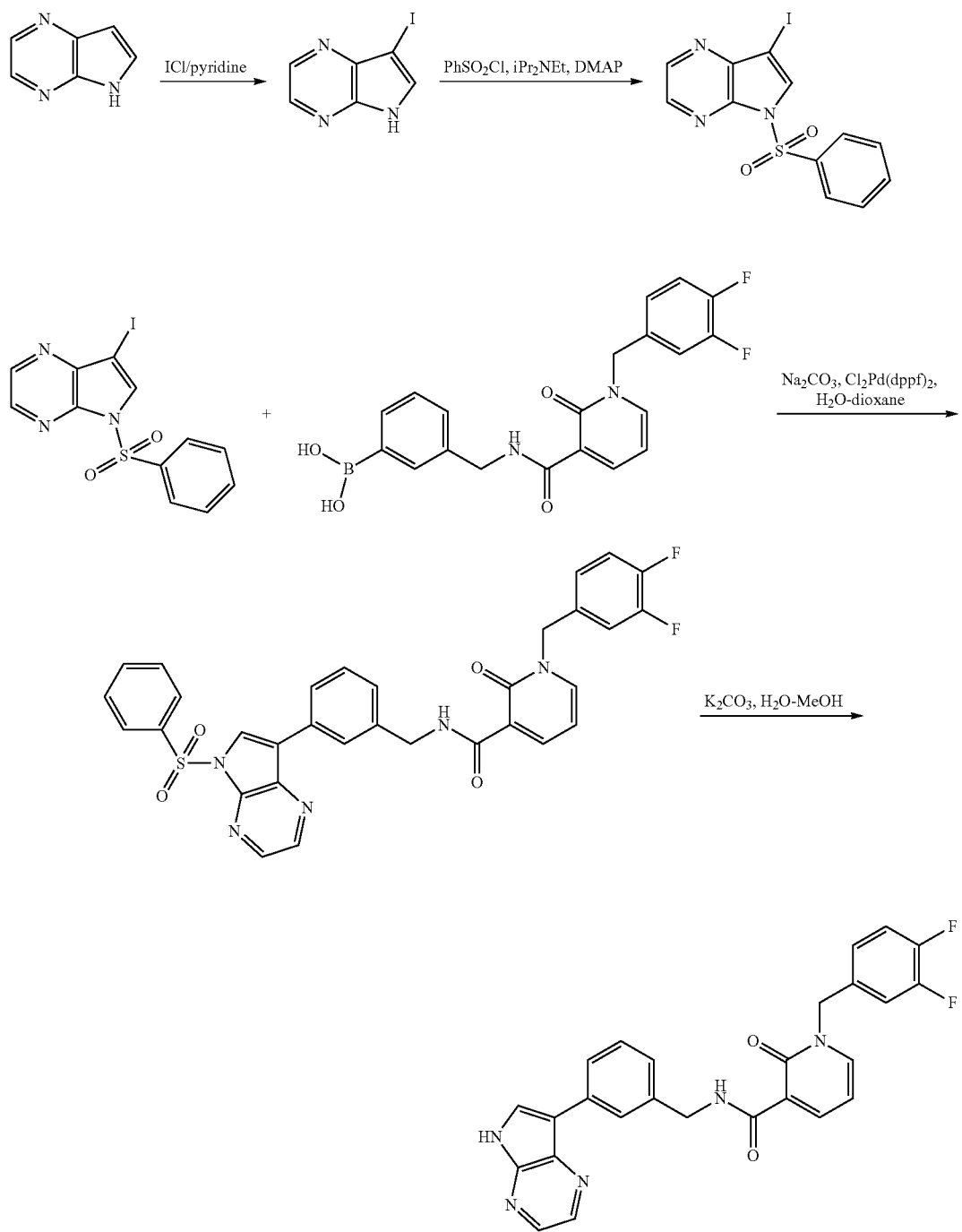

73.1 1-(3,4-Difluoro-benzyl)-2-oxo-1,2-dihydro-pyridine-3-carboxylic acid 3-(5H-pyrrolo-[2,3-b]pyrazin-7-yl)-benzylamide Except where indicated, 1-(3,4-Difluoro-benzyl)-2-oxo-1,2-dihydro-pyridine-3-carboxylic acid 3-(5H-pyrrolo[2,3-b]pyrazin-7-yl)-benzylamide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 3-({[1-(3,4-Difluoro-benzyl)-2-oxo-1,2-dihydro-pyridine-3-carbonyl]-amino}-methyl)-phenylboronic acid as activated boron species and 5H-Pyrrolo[2,3-b]pyrazine as substituted bicyclic heterocycle, to yield the product. 1H NMR (400 MHz, DMSO-d6) d ppm 12.287 (s, 1H) 10.040 (t, J=5.7 Hz, 1H) 8.448 (d, J=2.4 Hz, 1H) 8.410-8.374 (m, 1H) 8.386 (d, J=2.9 Hz, 1H) 8.286 (d, J=2.4 Hz, 1H) 8.224 (dd, J=7.0, 2.3 Hz, 1H) 8.182 (s, 1H) 8.104 (d, J=7.9 Hz, 1H) 7.462-7.337 (m, 3H) 7.170 (d, J=7.9 Hz, 1H) 7.190-7.125 (m, 1H) 6.592 (t, J=7.1 Hz, 1H) 5.192 (s, 2H) 4.556 (d, J=5.8 Hz, 2H); MS m/z=472.29 M+H.

Example 74

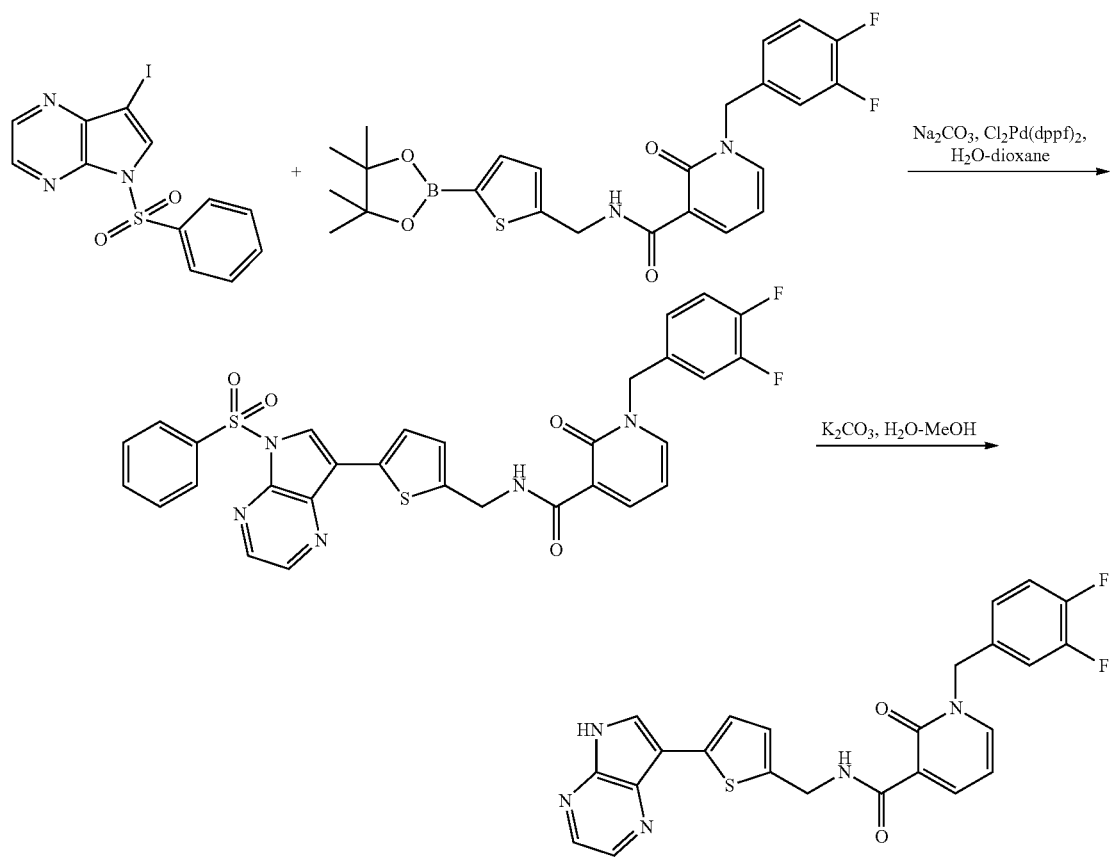

74.1 1-(3,4-Difluoro-benzyl)-2-oxo-1,2-dihydro-pyridine-3-carboxylic acid [5-(5H-pyrrolo[2,3-b]pyrazin-7-yl)-thiophen-2-ylmethyl]-amide Except where indicated, 1-(3,4-Difluoro-benzyl)-2-oxo-1,2-dihydro-pyridine-3-carboxylic acid [5-(5H-pyrrolo[2,3-b]pyrazin-7-yl)-thiophen-2-ylmethyl]-amide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide) using 1-(3,4-Difluoro-benzyl)-2-oxo-1,2-dihydro-pyridine-3-carboxylic acid [5-(4,4,5,5-tetramethyl-1,3,2-dioxaborolan-2-yl)-thiophen-2-ylmethyl]-amide as activated boron species and 5H-Pyrrolo[2,3-b]pyrazine as substituted bicyclic heterocycle, to yield the product. 1H NMR (400 MHz, DMSO-d6) d ppm 12.269 (s, 1H) 10.059 (t, J=5.8 Hz, 1H) 8.472 (d, J=2.5 Hz, 1H) 8.404 (dd, J=7.2, 2.2 Hz, 1H) 8.299 (d, J=2.8 Hz, 1H) 8.256-8.214 (m, 2H) 7.497 (d, J=3.6 Hz, 1H) 7.471-7.347 (m, 2H) 7.182-7.127 (m, 1H) 6.993 (d, J=3.6 Hz, 1H) 6.598 (t, J=6.7 Hz, 1H) 5.193 (s, 2H) 4.678 (d, J=5.8 Hz, 2H; MS m/z=478.09 M+H.

Example 75

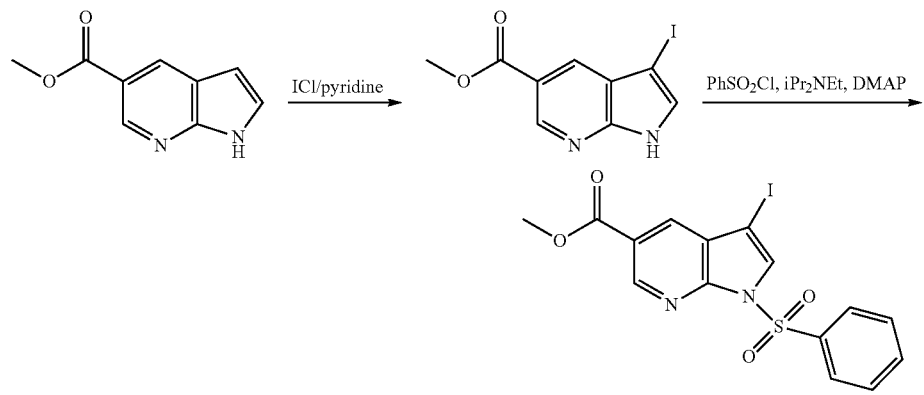

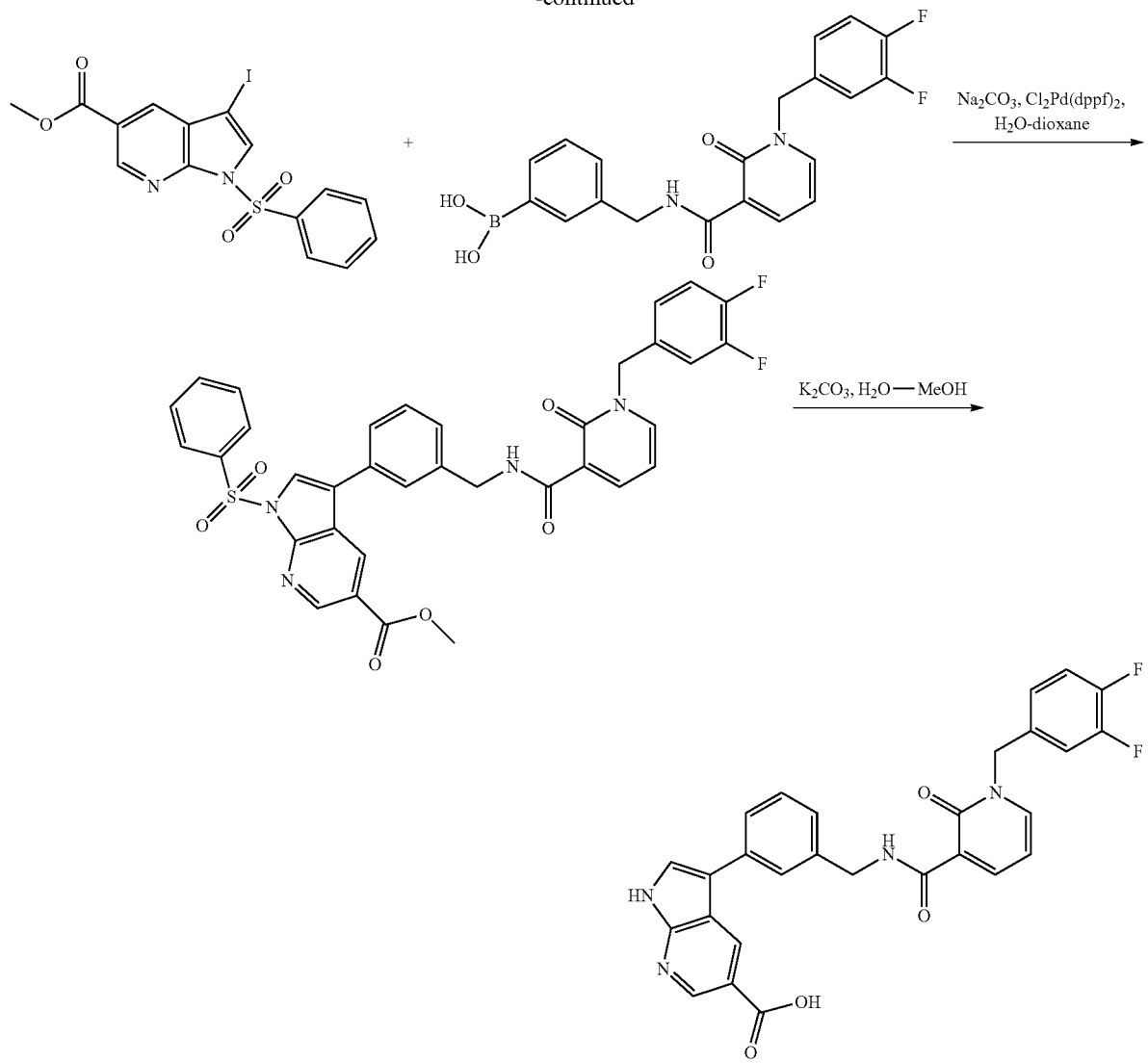

75.1 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid Except where indicated, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 3-({[1-(3,4-Difluoro-benzyl)-2-oxo-1,2-dihydro-pyridine-3-carbonyl]-amino}-methyl)-phenylboronic acid as activated boron species and 1H-Pyrrolo[2,3-b]pyridine-5-carboxylic acid methyl ester as substituted bicyclic heterocycle, to yield the product. 1H NMR (400 MHz, DMSO-d6) d ppm 12.312 (m, 1H) 10.078 (t, J=6.0 Hz, 1H) 8.829 (d, J=1.8 Hz, 1H) 8.709 (d, J=1.8 Hz, 1H) 8.400 (dd, J=7.4, 2.2 Hz, 1H) 8.211 (dd, J=6.4, 2.0 Hz, 1H) 7.954 (d, J=2.4 Hz, 1H) 7.669 (s, 1H) 7.594 (d, J=8.0 Hz, 1H) 7.462-7.328 (m, 3H) 7.236 (d, J=7.8 Hz, 1H) 7.173-7.119 (m, 1H) 6.579 (t, J=7.0 Hz, 1H) 5.188 (s, 2H), 4.582 (d, J=5.8 Hz, 2H); MS m/z=515.29 M+H.

Note that final deprotection of the benzenesulfonamide occurred with concomitant hydrolysis of the ester to the carboxylic acid.

Example 76

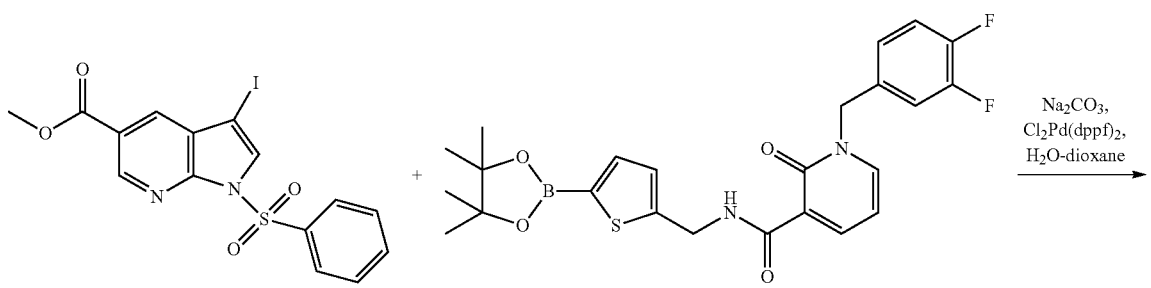

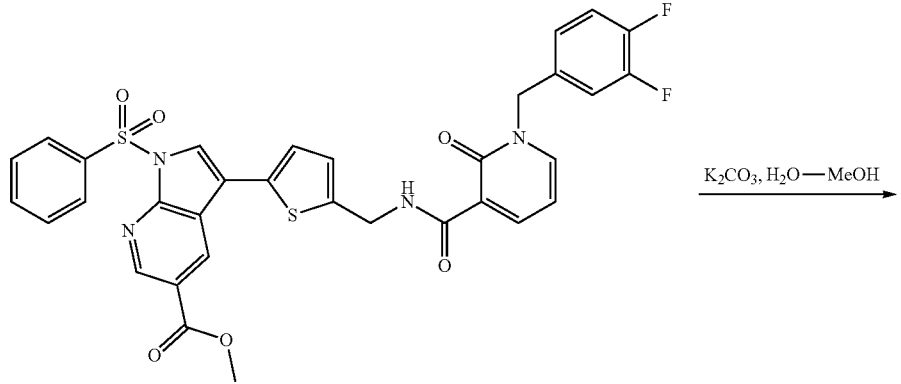

76.1 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid Except where indicated, 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 1-(3,4-Difluoro-benzyl)-2-oxo-1,2-dihydro-pyridine-3-carboxylic acid [5-(4,4,5,5-tetramethyl-1,3,2-dioxaborolan-2-yl)-thiophen-2-ylmethyl]-amide as activated boron species and 1H-Pyrrolo[2,3-b]pyridine-5-carboxylic acid methyl ester as substituted bicyclic heterocycle, to yield the product.

1H NMR (400 MHz, DMSO-d6) d ppm 12.338 (m, 1H) 10.072 (t, J=5.8 Hz, 1H) 8.829 (d, J=1.7 Hz, 1H) 8.688 (d, J=1.9 Hz, 1H) 8.403 (dd, J=7.3, 2.2 Hz, 1H) 8.234 (dd, J=6.6, 2.2 Hz, 1H) 7.944 (d, J=2.5 Hz, 1H) 7.480-7.347 (m, 2H) 7.224 (d, J=3.6 Hz, 1H) 7.188-7.134 (m, 1H) 7.040 (d, J=3.5 Hz, 1H) 6.591 (t, J=7.1 Hz, 1H) 5.194 (s, 2H), 4.685 (d, J=5.9 Hz, 2H); MS m/z=521.05 M+H.

Note that final deprotection of the benzenesulfonamide occurred with concomitant hydrolysis of the ester to the carboxylic acid.

Example 77

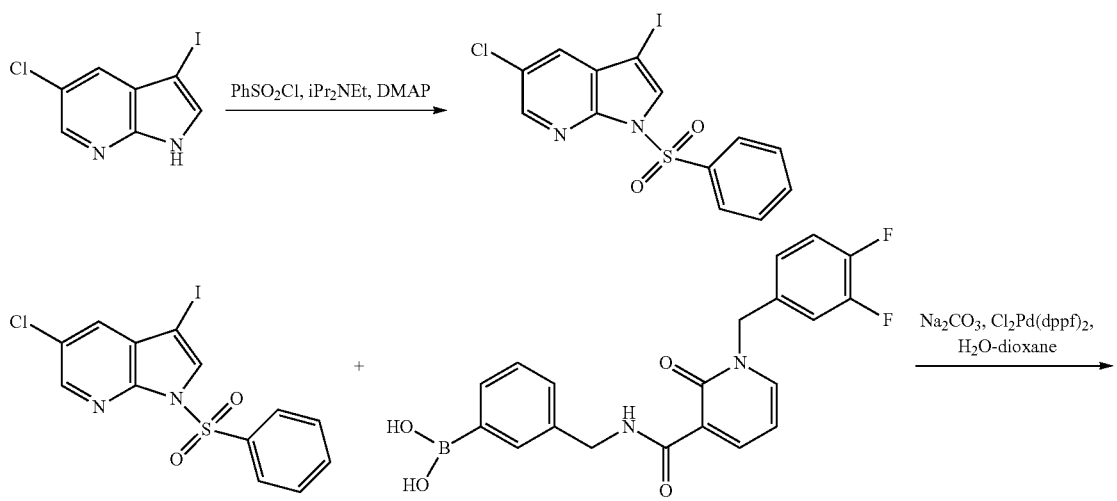

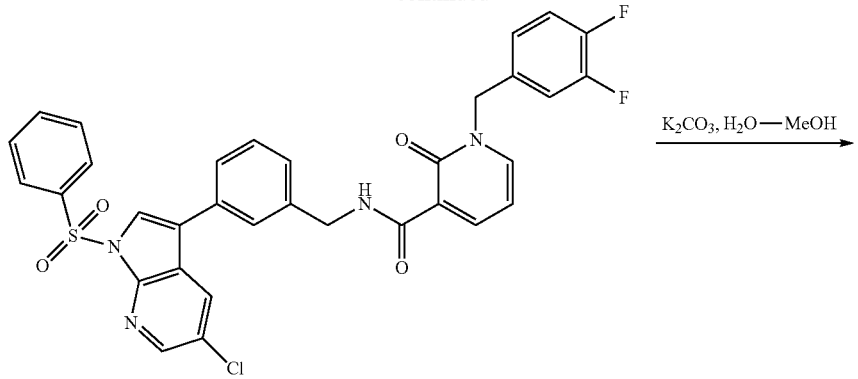

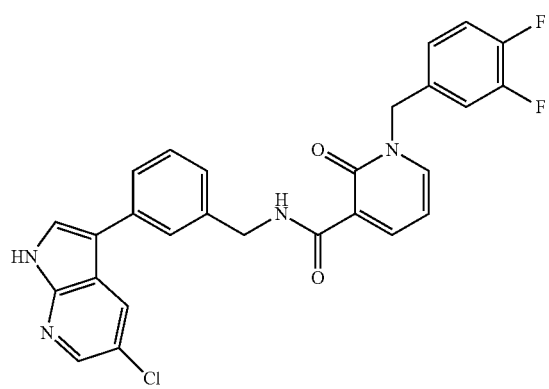

77.1 1-(3,4-Difluoro-benzyl)-2-oxo-1,2-dihydro-pyridine-3-carboxylic acid 3-(5-chloro-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-chloro-1H-pyrrolo[2,3-b]pyridin-3-yl)-benzylamide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 3-({[1-(3,4-Difluoro-benzyl)-2-oxo-1,2-dihydro-pyridine-3-carbonyl]-amino}-methyl)-phenylboronic acid as activated boron species and 5-Chloro-3-iodo-1H-pyrrolo[2,3-b]pyridine as substituted bicyclic heterocycle, to yield the product. 1H NMR (300 MHz, CDCl3-MeOH-d4) d ppm 8.564 (dd, J=7.3, 2.2 Hz, 1H) 8.332 (d, J=2.0 Hz, 1H) 8.230 (d, J=2.1 Hz, 1H) 7.584 (s, 1H) 7.565 (s (br), 1H) 7.538 (dd, J=6.8, 2.1 Hz, 1H) 7.468-7.370 (m, 2H) 7.303 (d, J=6.9 Hz, 1H) 7.168-7.061 (m, 2H) 7.027-6.955 (m, 1H) 6.461 (t, J=6.9 Hz, 1H) 5.134 (s, 2H), 4.716-4.659 (m, 2H); MS m/z=505.05 M+H.

Example 78

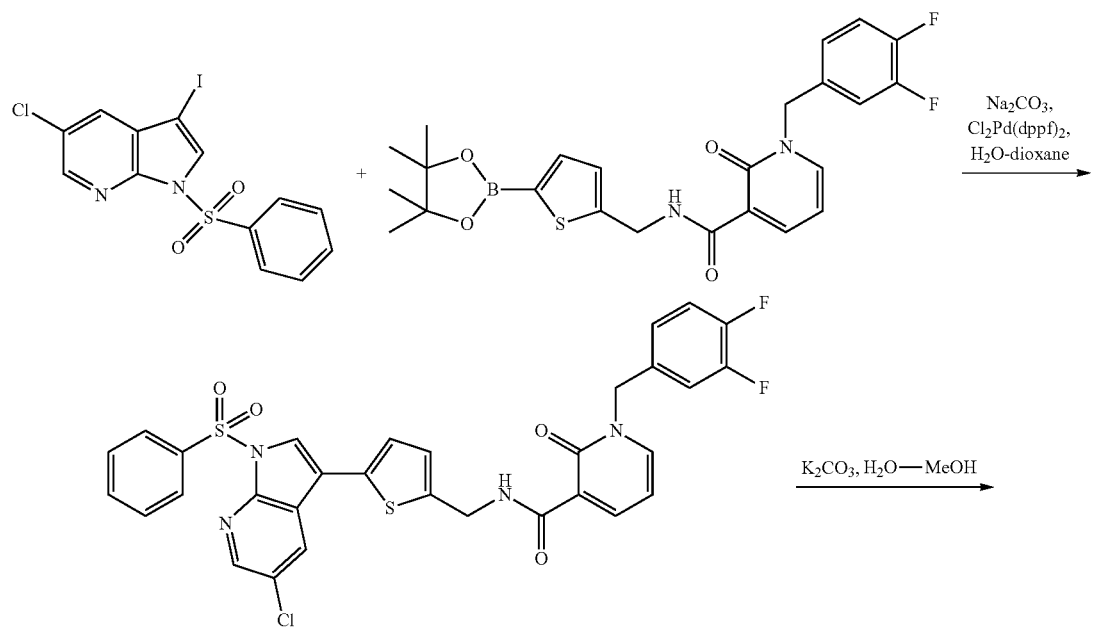

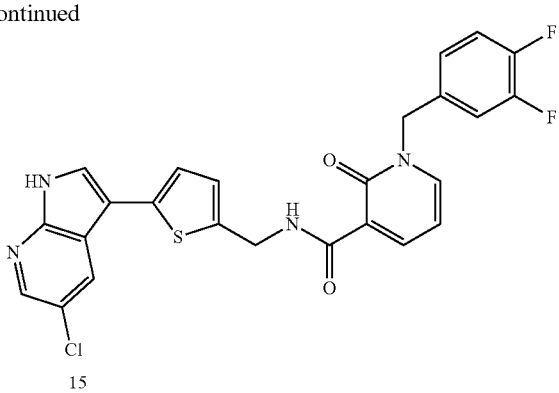

78.1  1-(3,4-Difluoro-benzyl)-2-oxo-1,2-dihydro-pyridine-3-carboxylic acid [5-(5-chloro-1H-pyrrolo[2,3-b]pyridin-3-yl)-thiophen-2-ylmethyl]-amide Except where indicated, 1-(3,4-Difluoro-benzyl)-2-oxo-1,2-dihydro-pyridine-3-carboxylic acid [5-(5-chloro-1H-pyrrolo[2,3-b]pyridin-3-yl)-thiophen-2-ylmethyl]-amide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 1-(3,4-Difluoro-benzyl)-2-oxo-1,2-dihydro-pyridine-3-carboxylic acid [5-(4,4,5,5-tetramethyl-1,3,2-dioxaborolan-2-yl)-thiophen-2-ylmethyl]-amide as activated boron species and 5-Chloro-3-iodo-1H-pyrrolo[2,3-b]pyridine as substituted bicyclic heterocycle, to yield the product. 1H NMR (300 MHz, CDCl3-MeOH-d4) d ppm 8.533 (dd, J=7.4, 2.2 Hz, 1H) 8.413 (d, J=1.7 Hz, 1H) 8.262 (s, 1H) 7.594 (s, 1H) 7.550 (dd, J=6.7, 2.3 Hz, 1H) 7.198-6.950 (m, 5H) 6.458 (t, J=6.9 Hz, 1H) 5.114 (s, 2H), 4.758 (s, 2H); MS m/z=511.13 M+H.

Example 79

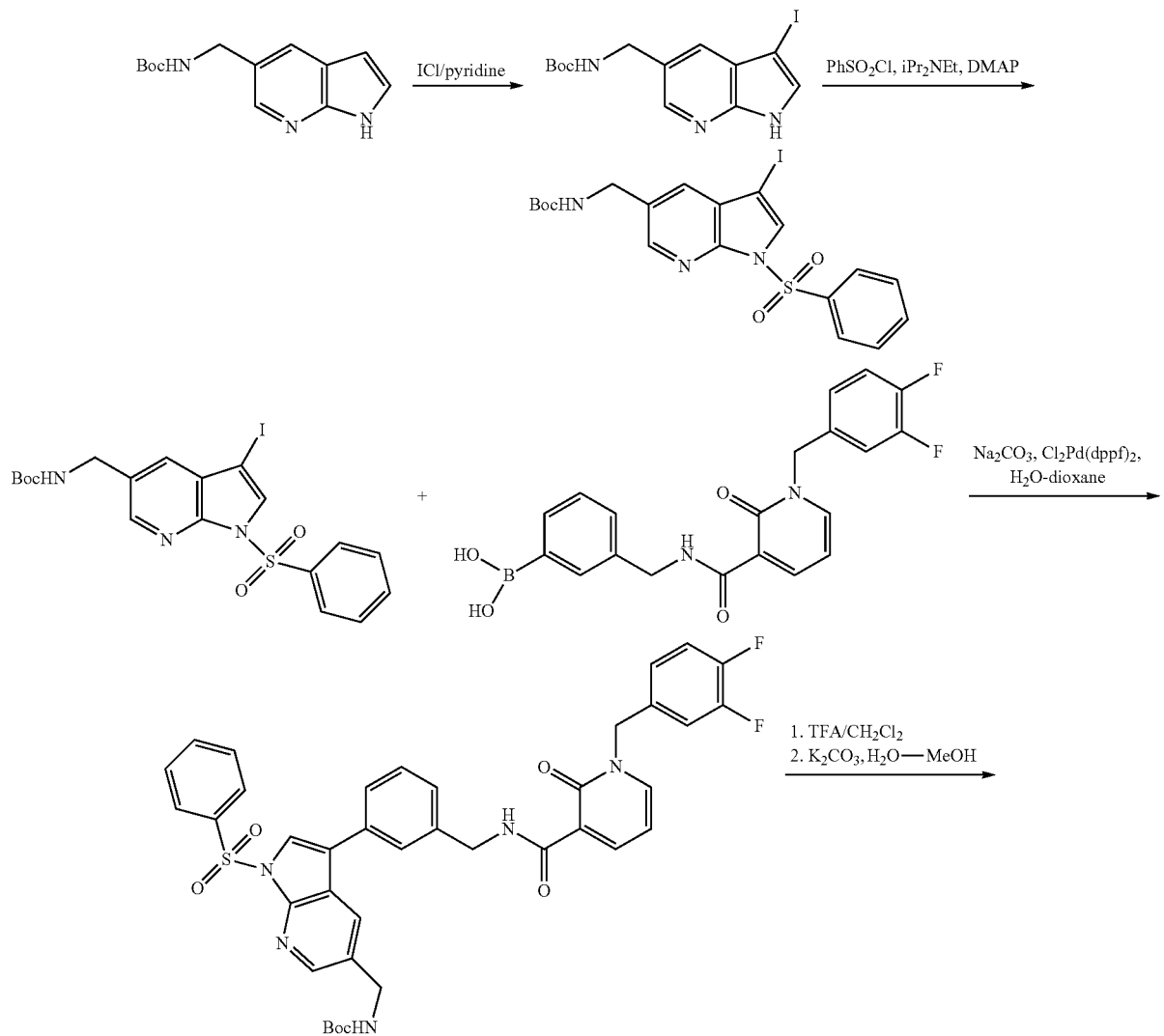

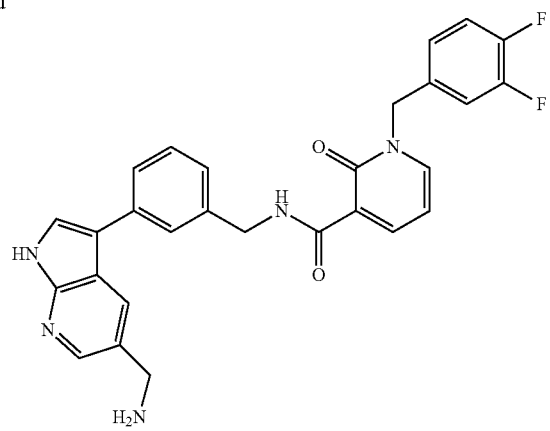

79.1 1-(3,4-Difluoro-benzyl)-2-oxo-1,2-dihydro-pyridine-3-carboxylic acid 3-(5-aminomethyl-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-aminomethyl-1H-pyrrolo[2,3-b]pyridin-3-yl)-benzylamide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 3-({[1-(3,4-Difluoro-benzyl)-2-oxo-1,2-dihydro-pyridine-3-carbonyl]-amino}-methyl)-phenylboronic acid as activated boron species and (1H-Pyrrolo[2,3-b]pyridin-5-ylmethyl)-carbamic acid tert-butyl ester as substituted bicyclic heterocycle to yield the product. 1H NMR (400 MHz, DMSO-d6) d ppm 12.034 (s, 1H) 10.051 (t, J=5.9 Hz, 1H) 8.437 (s, 1H) 8.393 (d, J=6.8 Hz, 1H) 8.334 (s, 1H) 8.230 (d, J=6.5, 1H) 8.096 (s (br), 2H) 7.917 (m, 1H) 7.687 (s, 1H) 7.630 (d, J=7.8 Hz, 1H) 7.455-7.345 (m, 3H) 7.217 (d, J=7.5 Hz, 1H) 7.169-7.119 (m, 1H) 6.596 (t, J=6.8 Hz, 1H) 5.194 (s, 2H), 4.583 (d, J=5.5 Hz, 2H) 4.209-4.142 (m, 2H); MS m/z=500.10 M+H.

The product of palladium-mediated coupling was subjected to TFA hydrolysis prior to potassium carbonate deprotection.

79.2 1-(3,4-Difluoro-benzyl)-2-oxo-1,2-dihydro-pyridine-3-carboxylic acid 3-(5-aminomethyl-1-benzenesulfonyl-1H-pyrrolo[2,3-b]pyridin-3-yl)-benzylamide Into a vial was dissolved {1-benzenesulfonyl-3-[3-({[1-(3,4-difluoro-benzyl)-2-oxo-1,2-dihydro-pyridine-3-carbonyl]-amino}-methyl)-phenyl]-1H-pyrrolo[2,3-b]pyridin-5-ylmethyl}-carbamic acid tert-butyl ester (0.259 mmol) in methylene chloride (2.00 mL, Acros) and trifluoroacetic acid (2.00 mL, 0.0260 mol; Acros). The reaction was stirred for 30 min, then the reaction was evaporated to dryness to give the crude amine.

Example 80

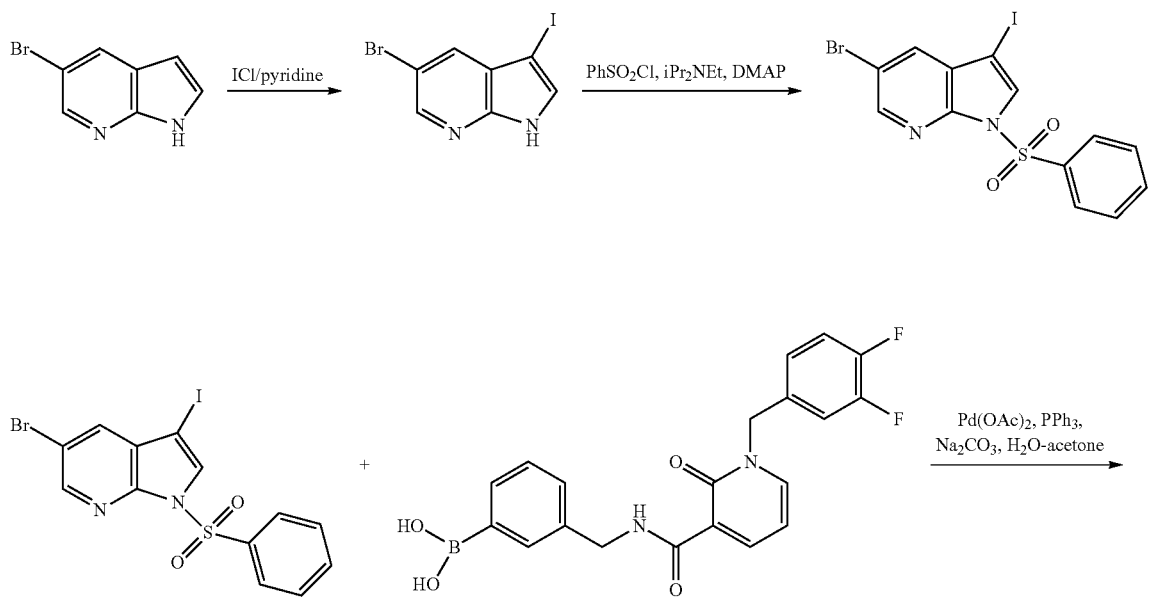

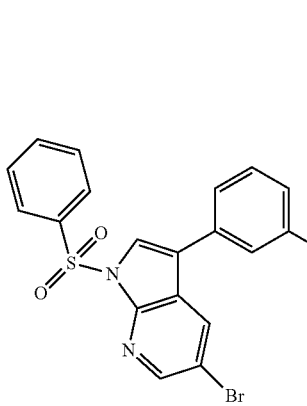
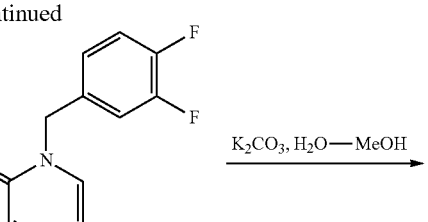

-continued

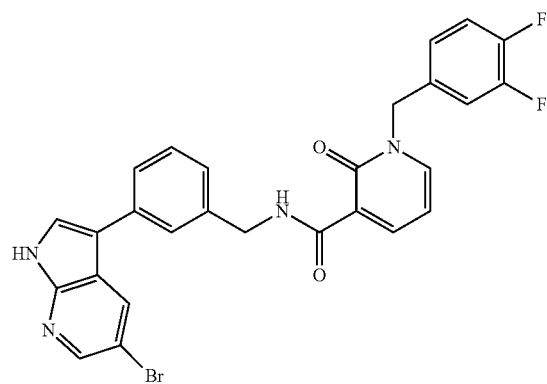

80.1  1-(3,4-Difluoro-benzyl)-2-oxo-1,2-dihydro-pyridine-3-carboxylic acid 3-(5-bromo-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-bromo-1H-pyrrolo[2,3-b]pyridin-3-yl)-benzylamide was synthesized as per Example 68, 1-(3,4-Difluoro-benzyl)-2-oxo-1,2-dihydro-pyridine-3-carboxylic acid 3-(5-cyano-1H-pyrrolo[2,3-b]pyridin-3-yl)-benzylamide using 3-({[1-(3,4-Difluoro-benzyl)-2-oxo-1,2-dihydro-pyridine-3-carbonyl]-amino}-methyl)-phenylboronic acid as activated boron species and 5-bromo-3-iodo-1H-pyrrolo[2,3-b]pyridine as substituted bicyclic heterocycle, to produce the title compound. 1H NMR (400 MHz, DMSO-d6) d ppm 12.169 (s, 1H) 10.093 (t, J=5.8 Hz, 1H) 8.422 (d, J=7.1 Hz, 1H) 8.387 (s, 1H) 8.309 (s, 1H) 8.228 (d, J=6.5, 1H) 7.943 (s, 1H) 7.672 (s, 1H) 7.580 (d, J=7.9 Hz, 1H) 7.469-7.372 (m, 3H) 7.202 (d, J=7.7 Hz, 1H) 7.183-7.130 (m, 1H) 6.602 (t, J=6.9 Hz, 1H) 5.210 (s, 2H), 4.586 (d, J=5.6 Hz, 2H); MS m/z=548.98 M+H.

Palladium-catalyzed coupling was performed using different conditions to selectively react with the 3-iodide in the presence of the 5-bromide.

80.2  1-(3,4-Difluoro-benzyl)-2-oxo-1,2-dihydro-pyridine-3-carboxylic acid 3-(1-benzenesulfonyl-5-bromo-1H-pyrrolo[2,3-b]pyridin-3-yl)-benzylamide Into a vial was dissolved 1-benzenesulfonyl-5-bromo-3-iodo-1H-pyrrolo[2,3-b]pyridine (581 mg, 0.00125 mol) and 3-({[1-(3,4-Difluoro-benzyl)-2-oxo-1,2-dihydro-pyridine-3-carbonyl]-amino}-methyl)-phenylboronic acid (453 mg, 0.00114 mol) and palladium acetate (13 mg, 0.000057 mol; Strem) and triphenylphosphine (32 mg, 0.00012 mol; Aldrich) in acetone (5.4 mL, Acros;). To this was added 2.0 M of sodium carbonate in water (1.8 mL). The vial was flushed under an atmosphere of argon and sealed and was heated at 75 Celsius for 1 hour. The reaction was evaporated then diluted with methylene chloride, washed with water, dried with magnesium sulfate, filtered, and concentrated.

The residue was taken up in methylene chloride and purified by silica gel chromatography using hexanes/ethyl acetate as eluent (Rf=0.33 in 1:3 hexanes/ethyl acetate) to yield 663.8 mg (85%) of product. MS m/z=689.09 M+H.

Example 81

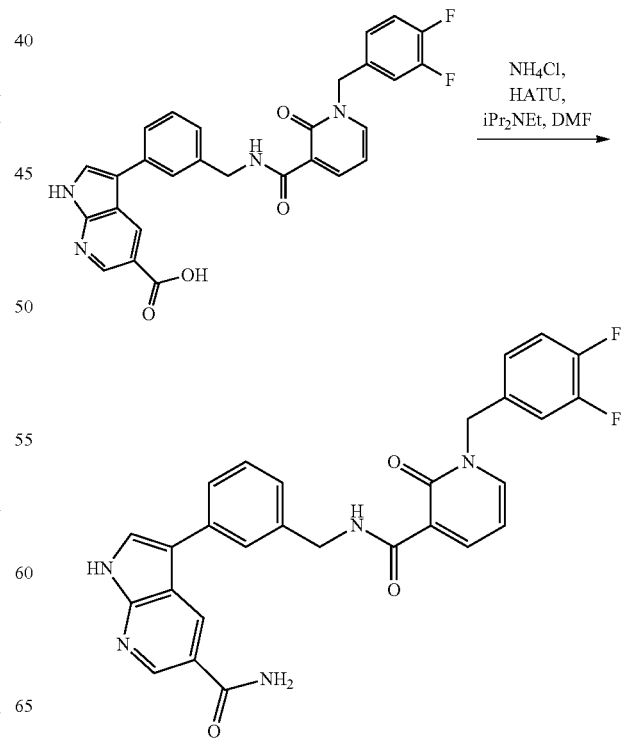

81.1 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide was prepared as per.

Into a vial was dissolved 3-[3-({[1-(3,4-difluoro-benzyl)-2-oxo-1,2-dihydro-pyridine-3-carbonyl]-amino}-methyl)-phenyl]-1H-pyrrolo[2,3-b]pyridine-5-carboxylic acid (53 mg, 0.00010 mol) and ammonium chloride (15 mg, 0.00028 mol, Aldrich) and N,N,N',N'-tetramethyl-O-(7-azabenzotriazol-1-yl)uronium hexafluorophosphate (58 mg, 0.00015 mol, Applied Biosystems) in N,N-dimethylformamide (1.0 mL, Acros). To this was added N,N-diisopropylethylamine (89 uL, 0.00051 mol, Aldrich) and the reaction was stirred at room temperature for 2 hours. The reaction was neutralized with trifluoroacetic acid (100 uL) and purified directly by preparative HPLC to yield the title compound in 30.2 mg (47%) yield. 1H NMR (400 MHz, CDCl3-MeOH-d4) d ppm 9.158 (m, 1H) 8.849 (m, 1H) 8.378 (m, 1H) 7.679 (m, 1H) 7.601-7.477 (m, 2H) 7.435-7.289 (m, 2H) 7.066-6.868 (m, 4H) 6.396 (m, 1H) 5.035 (m, 2H), 4.561 (m, 2H); MS m/z=514.29 M+H.

Example 82

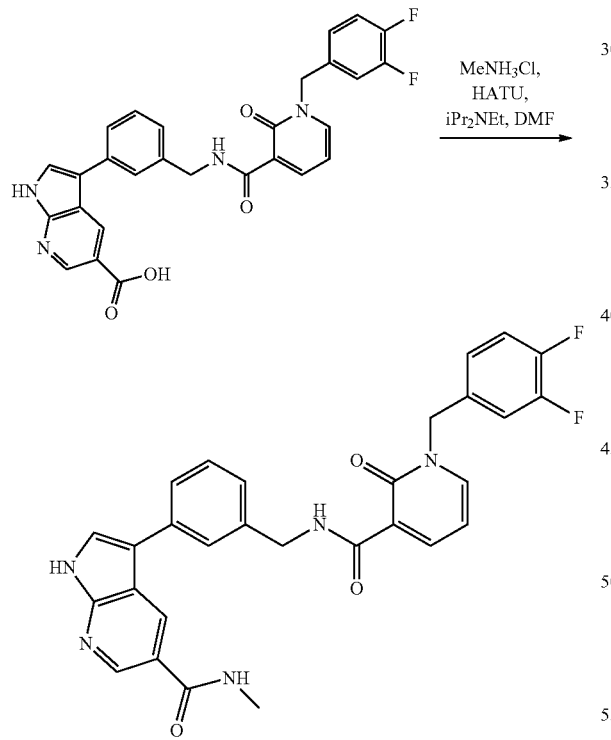

82.1 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid methylamide Except where indicated 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid methylamide was synthesized as per Example 81, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid (53 mg, 0.00010 mol) as carboxylic acid and methylammonium chloride (15 mg, 0.00022 mol; Aldrich) as amine, to yield the product. 1H NMR (400 MHz, CDCl3-MeOH-d4) d ppm 9.257 (m, 1H) 8.868 (m, 1H) 8.468 (d, J=7.2 Hz, 1H) 7.734 (m, 1H) 7.623 (s, 1H) 7.588-7.510 (m, 2H) 7.485-7.393 (m, 2H) 7.356-7.308 (m, 1H) 7.142-7.048 (m, 2H) 7.007-6.946 (m, 1H), 6.447 (m, 1H) 5.102 (s, 2H) 4.644 (s, 2H) 2.985 (obs, m, 3H); MS m/z=528.32 M+H.

Example 83

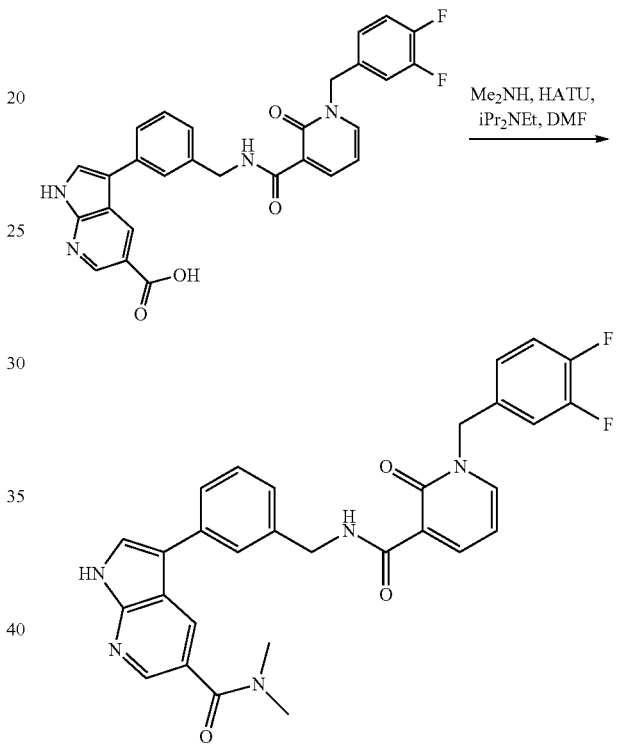

83.1 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid dimethylamide Except where indicated, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid dimethylamide was synthesized as per Example 81, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid (53 mg, 0.00010 mol) as carboxylic acid and 2.00 M of dimethylamine in tetrahydrofuran (127 uL, 0.254 mmol; Aldrich) as amine, to yield the product. 1H NMR (400 MHz, CDCl3-MeOH-d4) d ppm 8.751 (m, 1H) 8.481 (m, 1H) 8.424 (m, 1H) 7.755 (m, 1H) 7.562 (m, 1H) 7.525 (m, 1H) 7.454-7.379 (m, 2H) 7.342 (m, 1H) 7.138-7.032 (m, 2H) 7.005-6.936 (m, 1H) 6.450 (m, 1H) 5.096 (m, 2H) 4.640 (m, 2H) 3.082 (m, 6H); MS m/z=542.33 M+H.

Example 84

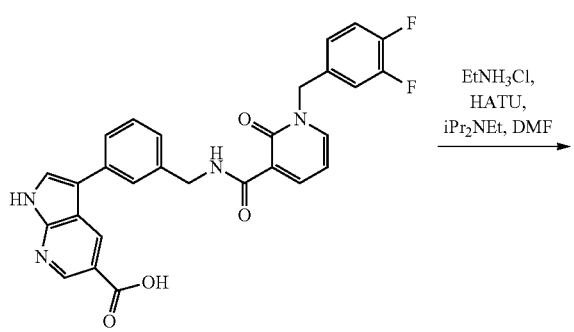
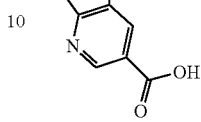

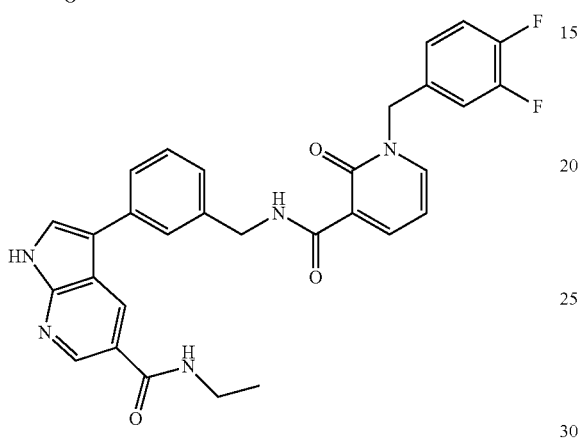

84.1 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid ethylamide Except where indicated, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid ethylamide was synthesized as per Example 81, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid (53 mg, 0.00010 mol) as carboxylic acid and ethylamine hydrochloride (15 mg, 0.00018 mol; Aldrich) as amine, to yield the product. 1H NMR (400 MHz, CDCl3) d ppm 12.550 (s, 1H) 10.727 (s (br), 1H) 9.373 (s, 1H) 9.026 (s, 1H) 8.682-8.286 (m, 2H) 7.917 (s, 1H) 7.705 (s, 1H) 7.633-7.293 (m, 4H) 7.218-7.091 (m, 2H) 7.030 (m, 1H) 6.511 (m, 1H) 5.163 (s, 2H) 4.756 (m, 2H) 3.603 (m, 2H) 1.339 (t, J=7.5 Hz, 3H); MS m/z=542.38 M+H.

Example 85

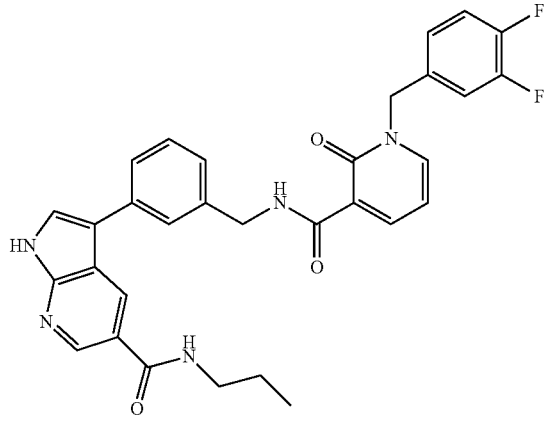

85.1 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid propylamide Except where indicated, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid propylamide was synthesized as per Example 81, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid (53 mg, 0.00010 mol) as carboxylic acid and 1-Propanamine (20 mg, 0.00034 mol; Aldrich) as amine, to yield the product. 1H NMR (400 MHz, CDCl3) d ppm 12.514 (s, 1H) 10.791 (m, 1H) 9.331 (s, 1H) 9.039 (s, 1H) 8.617 (m, 1H) 8.274 (m, 1H) 7.881-7.566 (m, 3H) 7.566-7.320 (m, 3H) 7.196-7.088 (m, 2H) 7.055-6.991 (m, 1H) 6.534 (t, J=6.5 Hz, 1H) 5.164 (s, 2H) 4.757 (d, J=5.3 Hz, 2H) 3.503 (m, 2H) 1.736 (m, 2H) 0.999 (t, J=7.4 Hz, 3H); MS m/z=556.36 M+H.

Example 86

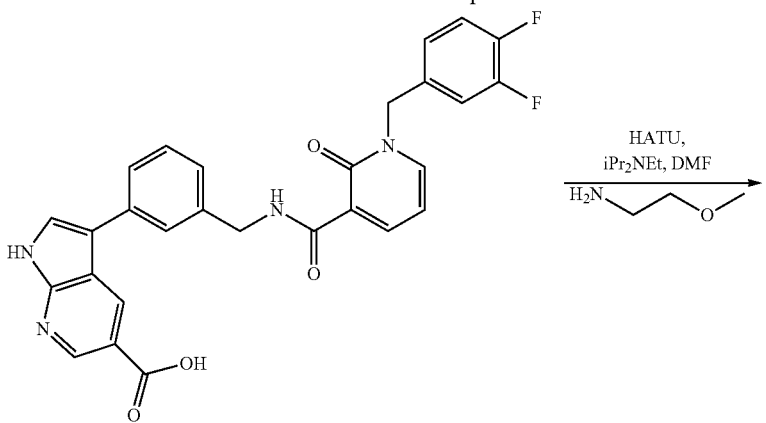

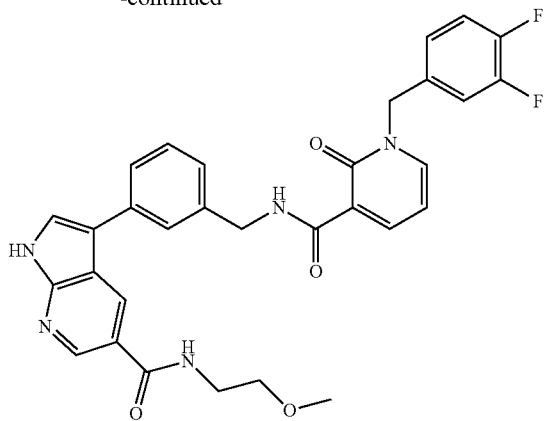

86.1 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid (2-methoxy-ethyl)-amide Except where indicated, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid (2-methoxy-ethyl)-amide was synthesized as per Example 81, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid (53 mg, 0.00010 mol) as carboxylic acid and 2-methoxyethylamine (22 uL, 0.00025 mol; Aldrich) as amine, to yield the product. 1H NMR (400 MHz, DMSO-d6) d ppm 12.168 (s, 1H) 10.063 (t, J=5.8 Hz, 1H) 8.794 (m, 1H) 8.686 (m, 1H) 8.403 (d, J=7.1 Hz, 1H) 8.236 (d, J=6.3 Hz, 1H) 8.141 (s (br), 1H) 7.855 (d, J=2.5 Hz, 1H) 7.475-7.353 (m, 3H) 7.287 (d, J=3.4 Hz, 1H) 7.184-7.131 (m, 1H) 7.046 (d, J=3.4 Hz, 1H) 6.595 (t, J=7.1 Hz, 1H) 5.194 (s, 2H) 4.683 (d, J=5.7 Hz, 2H); MS m/z=572.41 M+H.

87.1 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid amide Except where indicated 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid amide was synthesized as per Example 81, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid (43 mg, 0.000083 mol) as carboxylic acid and Ammonium chloride (14 mg, 0.00026 mol; Aldrich) as amine, to yield the product in. 1H NMR (400 MHz, DMSO-d6) d ppm 12.169 (s, 1H) 10.068 (t, J=5.7 Hz, 1H) 8.754 (s, 1H) 8.638 (s, 1H) 8.582 (m, 1H) 8.405 (d, J=7.2 Hz, 1H) 8.241 (d, J=6.8 Hz, 1H) 7.863 (s, 1H) 7.481-7.339 (m, 2H) 7.233 (d, J=3.4 Hz, 1H) 7.191-7.127 (m, 1H) 7.053 (d, J=3.4 Hz, 1H) 6.598 (t, J=6.8 Hz, 1H) 5.197 (s, 2H) 4.687 (d, J=5.3 Hz, 2H) 2.819 (d, J=3.8 Hz, 3H); MS m/z=520.06 M+H.

Example 87

Example 88

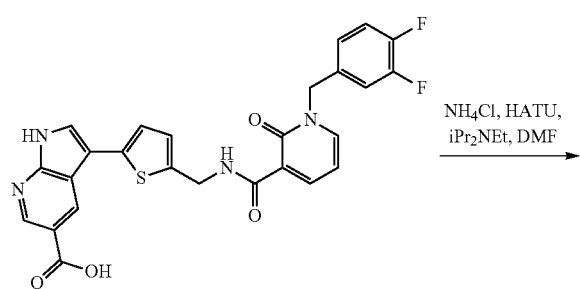

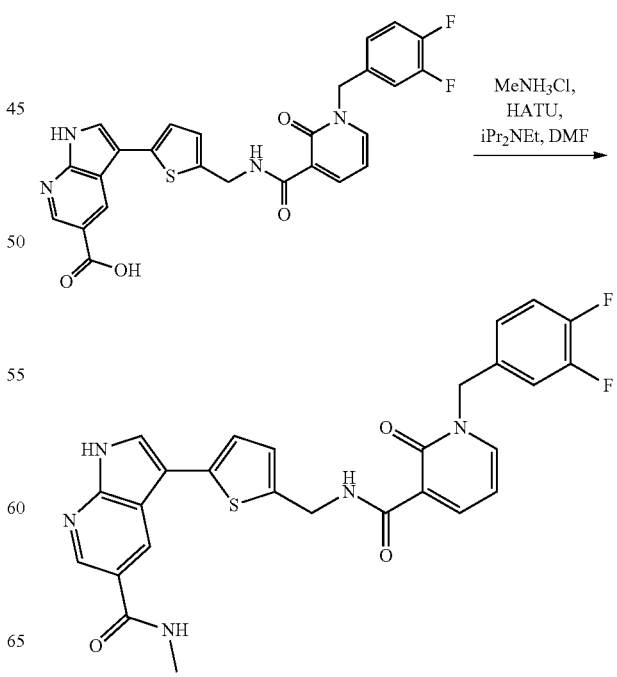

88.1 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid methylamide Except where indicated 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid methylamide was synthesized as per 1233 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid (43 mg, 0.000083 mol) as carboxylic acid and Methylammonium chloride (17 mg, 0.00025 mol; Aldrich) as amine, to yield the product. MS m/z=534.61 M+H.

Example 89

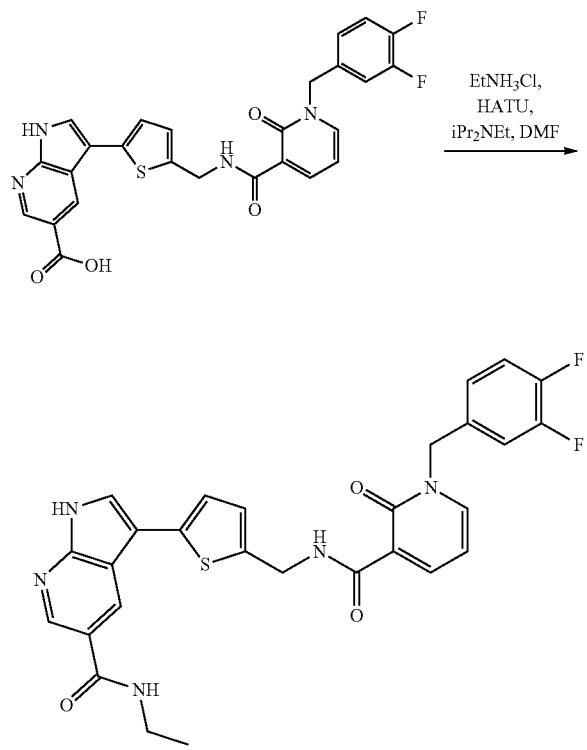 [SMILES: O=C(O)c1cnc2[nH]cc(-c3ccc(CNC(=O)c4cccn(Cc5ccc(F)c(F)c5)c4=O)s3)c2c1 ; CCNC(=O)c1cnc2[nH]cc(-c3ccc(CNC(=O)c4cccn(Cc5ccc(F)c(F)c5)c4=O)s3)c2c1]

89.1 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid ethylamide Except where indicated, 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid ethylamide was synthesized as per Example 81, 3-[3-({[1-(3,4-Difluoro-benzyl)-2-oxo-1,2-dihydro-pyridine-3-carbonyl]-amino}-methyl)-phenyl]-1H-pyrrolo[2,3-b]pyridine-5-carboxylic acid amide using 3-[5-({[1-(3,4-Difluoro-benzyl)-2-oxo-1,2-dihydro-pyridine-3-carbonyl]-amino}-methyl)-thiophen-2-yl]-1H-pyrrolo[2,3-b]pyridine-5-carboxylic acid (43 mg, 0.000083 mol) as carboxylic acid and ethylamine hydrochloride (17 mg, 0.00021 mol; Aldrich) as amine, to yield the product. 1H NMR (400 MHz, DMSO-d6) d ppm 12.161 (s, 1H) 10.066 (t, J=5.6 Hz, 1H) 8.760 (s, 1H) 8.634 (s, 1H) 8.606 (m, 1H) 8.404 (d, J=7.4 Hz, 1H) 8.237 (d, J=6.5 Hz, 1H) 7.855 (s, 1H) 7.479-7.347 (m, 2H) 7.272 (d, J=3.0 Hz, 1H) 7.187-7.129 (m, 1H) 7.055 (d, J=3.0 Hz, 1H) 6.597 (t, J=7.1 Hz, 1H) 5.195 (s, 2H) 4.686 (d, J=5.9 Hz, 2H) 3.324 (qd, J=6.5 Hz, 6.5 Hz, 2H) 1.147 (t, J=6.8 Hz, 3H); MS m/z=548.19 M+H.

Example 90

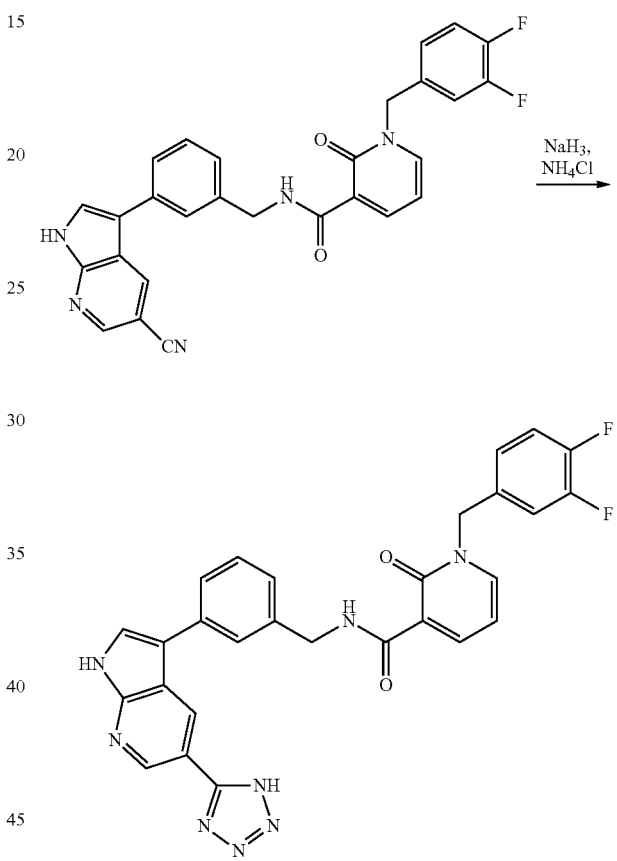

90.1 1-(3,4-Difluoro-benzyl)-2-oxo-1,2-dihydro-pyridine-3-carboxylic acid 3-[5-(1H-tetrazol-5-yl)-1H-pyrrolo[2,3-b]pyridin-3-yl]-benzylamide 1-(3,4-Difluoro-benzyl)-2-oxo-1,2-dihydro-pyridine-3-carboxylic acid 3-(1-benzenesulfonyl-5-cyano-1H-pyrrolo[2,3-b]pyridin-3-yl)-benzylamide (64 mg, 0.00010 mol) was dissolved in N,N-dimethylformamide (1.0 mL, Acros) and sodium azide (11 mg, 0.00017 mol; Aldrich) and then ammonium chloride (5 mg, 0.00009 mol; Aldrich) was added. The mixture was heated at 110° C. for 1.5 hours under an atmosphere of Argon. Additional sodium azide (29 mg, 0.00045 mol; Aldrich) and ammonium chloride (19 mg, 0.00036 mol; Aldrich) were added and the reaction was heated at 110° C. under an atmosphere of Argon. After 4 h (total), the reaction was diluted with N,N-dimethylformamide, filtered and purified by preparative HPLC to yield the product in 2.0 mg yield (3%). MS m/z=539.07 M+H.

Example 91

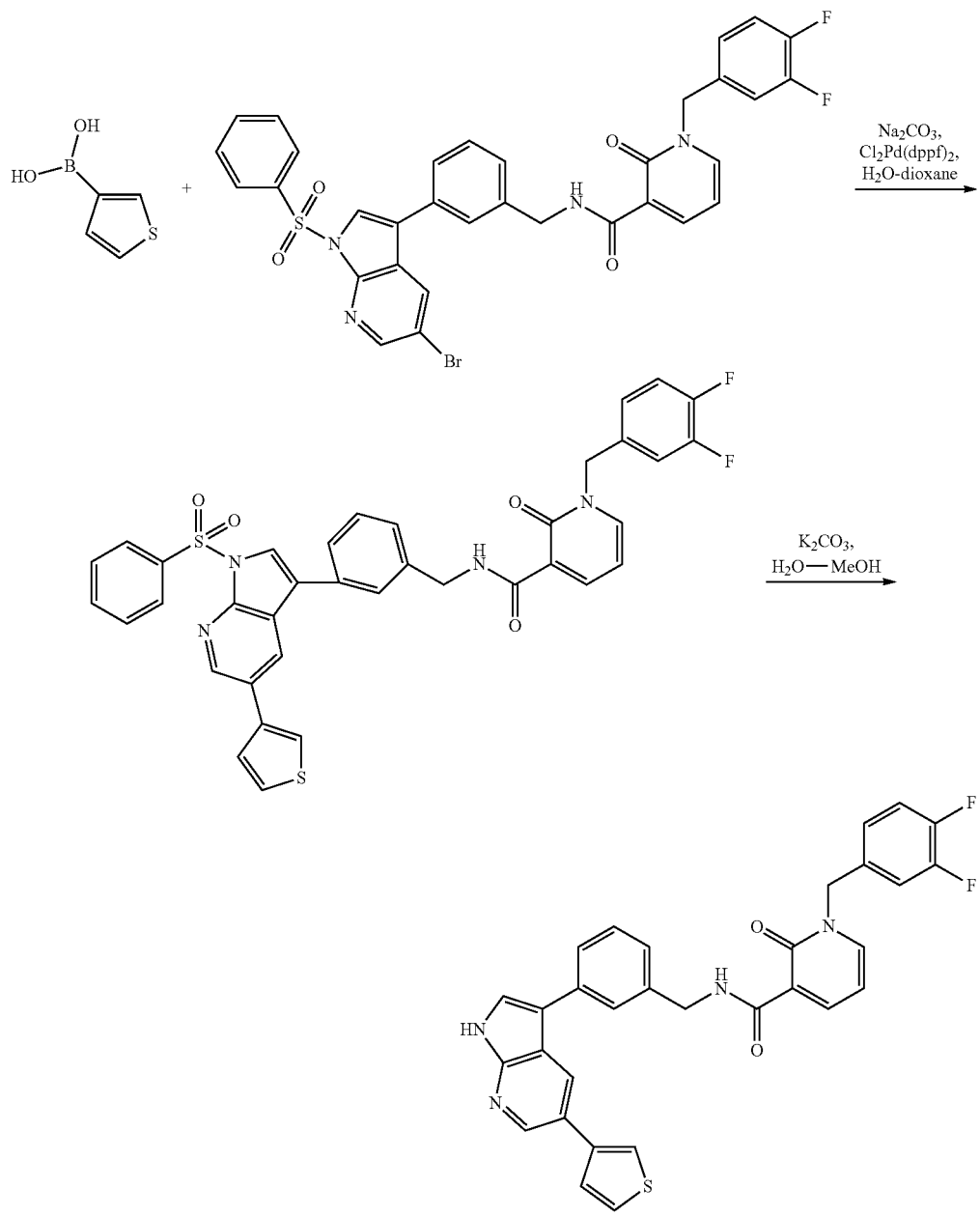

91.1 1-(3,4-Difluoro-benzyl)-2-oxo-1,2-dihydro-pyridine-3-carboxylic acid 3-(5-thiophen-3-yl-1H-pyrrolo[2,3-b]pyridin-3-yl)-benzylamide Into a vial was dissolved 1-benzenesulfonyl-5-bromo-3-iodo-1H-pyrrolo[2,3-b]pyridine (581 mg, 0.00125 mol), 3-({[1-(3,4-Difluoro-benzyl)-2-oxo-1,2-dihydro-pyridine-3-carbonyl]-amino}-methyl)-phenylboronic acid (453 mg, 0.00114 mol), palladium acetate (13 mg, 0.000057 mol; Strem) and triphenylphosphine (32 mg, 0.00012 mol; Aldrich) in acetone (5.4 mL, Acros). To this was added 2.0 M sodium carbonate in water (1.8 mL, 0.0036 mol). The vial was flushed with argon, sealed, and was heated at 75 Celsius for 1 hour. The reaction was evaporated, then was diluted with methylene chloride, washed with water, dried with magnesium sulfate, filtered, and concentrated. The residue was taken up in methylene chloride and purified by silica gel chromatography using hexanes/ethyl acetate as eluent (Rf=0.33 in 1:3 hexanes/ethyl acetate) to yield 663.8 mg (85%) of the title compound. MS m/z=689.09 M+H.

Into a vial was dissolved 3-thienylboronic acid (12 mg, 0.094 mmol; Aldrich), 1-(3,4-difluoro-benzyl)-2-oxo-1,2-dihydro-pyridine-3-carboxylic acid 3-(1-benzenesulfonyl-5-bromo-1H-pyrrolo[2,3-b]pyridin-3-yl)-benzylamide (45 mg, 0.065 mmol) and [1,1'-bis(diphenylphosphino)ferrocene]dichloropalladium(II), complex with dichloromethane (1:1) (6 mg, 0.007 mmol; Strem) in 1,4-dioxane (0.900 mL, Acros). To this was added 2.0 M sodium carbonate in water (0.22 mL, 0.00044 mol). The reaction was purged with argon and sealed. The reaction was heated at 110° C. under an atmosphere of argon for 75 minutes. After cooling, the reaction was diluted with water and extracted with methylene chloride. The organic layer was dried with magnesium sulfate, filtered and evaporated to give the crude product.

Into the reaction was dissolved crude 1-(3,4-difluoro-benzyl)-2-oxo-1,2-dihydro-pyridine-3-carboxylic acid 3-(1-benzenesulfonyl-5-thiophen-3-yl-1H-pyrrolo[2,3-b]pyridin-3-yl)-benzylamide (0.065 mmol) in methanol (1.50 mL, Fisher) and water (0.50 mL, Fisher). To this was added potassium carbonate (43 mg, 0.00031 mol; Fisher) and the reaction was heated at reflux for 1 hour. The reaction was evaporated, taken up in N,N-dimethylformamide, neutralized with TFA (100 uL) and purified by preparative HPLC chromatography to yield the product in 27.6 mg yield (64%). 1H NMR (400 MHz, DMSO-d6) d ppm 11.973 (s, 1H) 10.108 (t, J=6.2 Hz, 1H) 8.659 (s, 1H) 8.471 (s, 1H) 8.404 (d, J=7.3 Hz, 1H) 8.211 (d, J=6.5 Hz, 1H) 7.915 (m, 1H) 7.868 (s, 1H) 7.777 (s, 1H) 7.688-7.611 (m, 3H) 7.437-7.294 (m, 3H) 7.205 (d, J=7.6 Hz, 1H) 7.152-7.086 (m, 1H) 6.580 (t, J=6.7 Hz, 1H) 5.161 (s, 2H) 4.597 (d, J=5.6 Hz, 2H); MS m/z=553.29 M+H.

Example 92

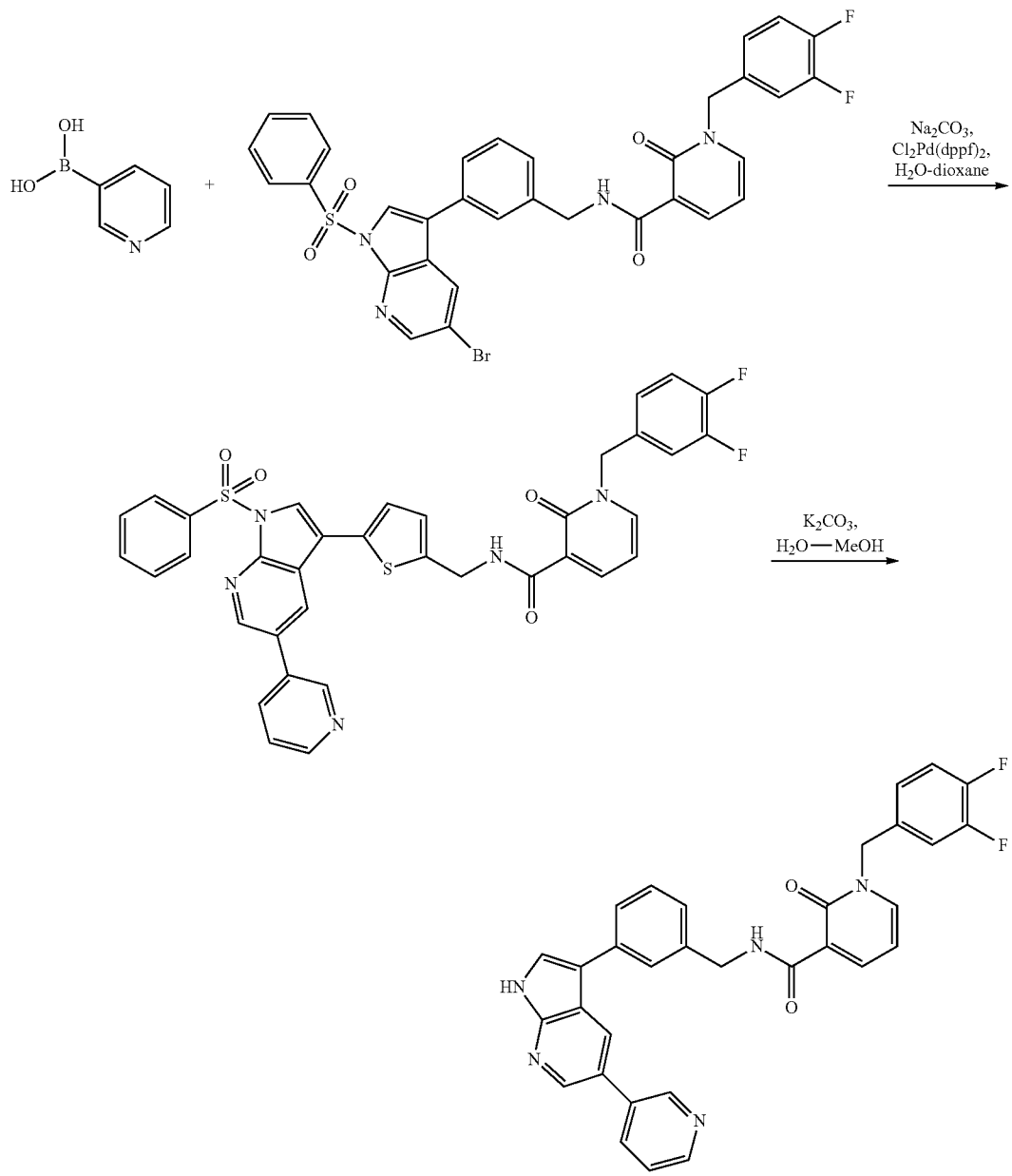

92.1 1-(3,4-Difluoro-benzyl)-2-oxo-1,2-dihydro-pyridine-3-carboxylic acid 3-(5-pyridin-3-yl-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-pyridin-3-yl-1H-pyrrolo[2,3-b]pyridin-3-yl)-benzylamide was synthesized as per Example 91, 1-(3,4-Difluoro-benzyl)-2-oxo-1,2-dihydro-pyridine-3-carboxylic acid 3-(5-thiophen-3-yl- 1H-pyrrolo[2,3-b]pyridin-3-yl)-benzylamide (Scheme 10) using 3-Pyridylboronic acid as boronic acid to yield the product. 1H NMR (400 MHz, DMSO-d6) d ppm 12.153 (s, 1H) 10.089 (t, J=5.8 Hz, 1H) 9.177 (s, 1H) 8.714 (d, J=4.9 Hz, 1H) 8.670 (s, 1H) 8.603 (s, 1H) 8.546 (d, J=7.3 Hz, 1H) 8.374 (d, J=7.3 Hz, 1H) 8.197 (d, J=6.8 Hz, 1H) 7.954 (s, 1H) 7.797 (s, 1H) 7.813-7.742 (m, 1H) 7.684 (d, J=7.3 Hz, 1H) 7.440-7.307 (m, 3H) 7.220 (d, J=7.3 Hz, 1H) 7.142-7.083 (m, 1H) 6.555 (t, J=6.8 Hz, 1H) 5.147 (s, 2H) 4.594 (d, J=5.8 Hz, 2H); MS m/z=548.07 M+H.

Example 93

93.1 1-(3,4-Difluoro-benzyl)-2-oxo-1,2-dihydro-pyridine-3-carboxylic acid 3-(5-pyridin-4-yl-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-pyridin-4-yl-1H-pyrrolo[2,3-b]pyridin-3-yl)-benzylamide was synthesized as per Example 91, 1-(3,4-Difluoro-benzyl)-2-oxo-1,2-dihydro-pyridine-3-carboxylic acid 3-(5-thiophen-3-yl-1H-pyrrolo[2,3-b]pyridin-3-yl)-benzylamide using 4-Pyridylboronic acid as boronic acid to yield the product. 1H NMR (400 MHz, DMSO-d6) d ppm 12.280 (s, 1H) 10.090 (t, J=6.0 Hz, 1H) 8.864-8.712 (m, 4H) 8.384 (d, J=7.4 Hz, 1H) 8.302-8.233 (m, 2H) 8.201 (d, J=6.5 Hz, 1H) 7.983 (s, 1H) 7.797 (s, 1H) 7.694 (d, J=7.4 Hz, 1H) 7.458-7.302 (m, 3H) 7.239 (d, J=7.0 Hz, 1H) 7.134-7.079 (m, 1H) 6.567 (t, J=7.0 Hz, 1H) 5.146 (s, 2H) 4.605 (d, J=5.6 Hz, 2H); MS m/z/z=548.29 M+H.

Example 94

94.1 1-(3,4-Difluoro-benzyl)-2-oxo-1,2-dihydro-pyridine-3-carboxylic acid 3-(5-furan-3-yl-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-furan-3-yl-1H-pyrrolo[2,3-b]pyridin-3-yl)-benzylamide was synthesized as per Example 91, 1-(3,4-Difluoro-benzyl)-2-oxo-1,2-dihydro-pyridine-3-carboxylic acid 3-(5-thiophen-3-yl-1H-pyrrolo[2,3-b]pyridin-3-yl)-benzylamide using Furan-3-boronic acid as boronic acid to yield the product. 1H NMR (500 MHz, DMSO-d6) d ppm 11.973 (s, 1H) 10.118 (t, J=5.7 Hz, 1H) 8.568 (s, 1H) 8.400 (d, J=7.2 Hz, 1H) 8.374 (s, 1H) 8.248 (s, 1H) 8.221 (d, J=6.7 Hz, 1H) 7.863 (d, J=2.6 Hz, 1H) 7.755 (m, 2H) 7.622 (d, J=7.7 Hz, 1H) 7.439-7.308 (m, 3H) 7.198 (d, J=7.7 Hz, 1H) 7.144-7.100 (m, 1H) 7.073 (s, 1H) 6.586 (t, J=6.7 Hz, 1H) 5.168 (s, 2H) 4.593 (d, J=6.2 Hz, 2H); MS m/z=537.36 M+H.

Example 95

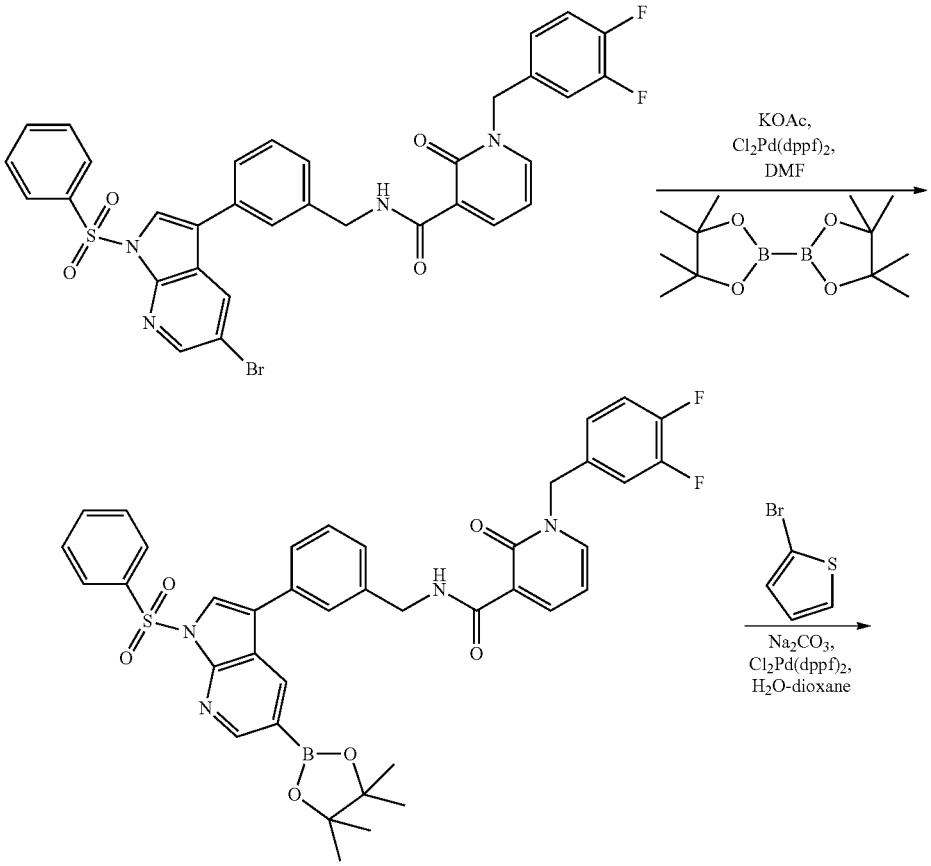

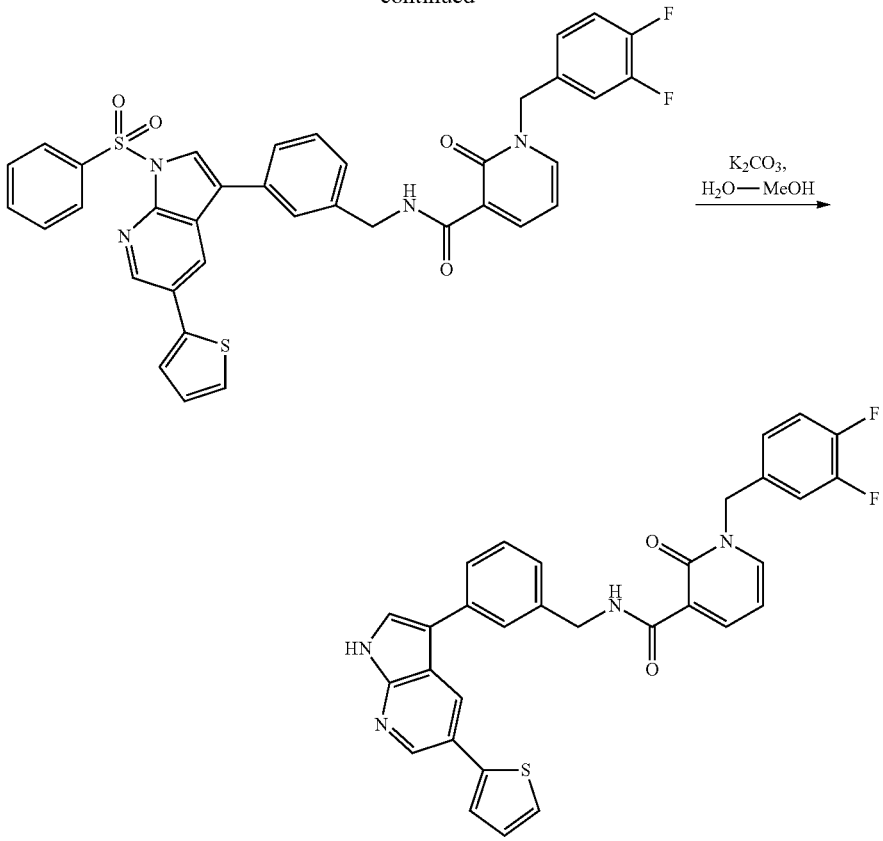

95.1  1-(3,4-Difluoro-benzyl)-2-oxo-1,2-dihydro-pyridine-3-carboxylic acid 3-(5-thiophen-2-yl-1H-pyrrolo[2,3-b]pyridin-3-yl)-benzylamide 1-(3,4-Difluoro-benzyl)-2-oxo-1,2-dihydro-pyridine-3-carboxylic acid 3-(1-benzenesulfonyl-5-bromo-1H-pyrrolo[2,3-b]pyridin-3-yl)-benzylamide (297 mg, 0.000431 mol), bis(pinacolato)diboron (224 mg, 0.000882 mol; Aldrich), potassium acetate (253 mg, 0.00258 mol; Aldrich) and [1,1'-bis(diphenylphosphino)ferrocene]dichloropalladium (II), complex with dichloromethane (1:1) (37 mg, 0.000045 mol; Strem) were dissolved in N,N-dimethylformamide (5.00 mL, Acros). The reaction was heated in a sealed tube at 80° C. under Argon. After 60 min, additional bis(pinacolato)diboron (242 mg, 0.000953 mol; Aldrich) was added and the reaction was heated at 80° C. for 1 hour. Additional [1,1'-bis(diphenylphosphino)ferrocene]dichloropalladium (II), complex with dichloromethane (1:1) (35 mg, 0.000043 mol; Strem) was added and the reaction was heated at 80° C. under an atmosphere of Argon for 1 hour. The reaction was evaporated, then taken up in dichloromethane, filtered and purified by silica gel chromatography using hexanes/ethyl acetate as eluent. Appropriate fractions are combined and evaporated to give 116 mg of product (contains 20% bromide starting material). MS m/z=737.00 M+H.

Into a vial was dissolved 1-(3,4-difluoro-benzyl)-2-oxo-1,2-dihydro-pyridine-3-carboxylic acid 3-[1-benzenesulfonyl-5-(4,4,5,5-tetramethyl-1,3,2-dioxaborolan-2-yl)-1H-pyrrolo[2,3-b]pyridin-3-yl]-benzylamide (58 mg, 0.079 mmol) and [1,1'-bis(diphenylphosphino)ferrocene]dichloropalladium(II), complex with dichloromethane (1:1) (6.4 mg, 0.0079 mmol; Strem) in 1,4-dioxane (1.20 mL, Acros). To this was added 2-bromothiophene (12 uL, 0.12 mmol; Aldrich) and then 2.0 M sodium carbonate in water (0.30 mL, 0.0006 mol). The reaction was purged with argon and sealed. The reaction was heated at 110° C. under an atmosphere of argon for 75 minutes. The reaction was diluted with water and extracted with methylene chloride. The organic layer was dried with magnesium sulfate, filtered and evaporated to give the crude product.

1-(3,4-Difluoro-benzyl)-2-oxo-1,2-dihydro-pyridine-3-carboxylic acid 3-(1-benzenesulfonyl-5-thiophen-2-yl-1H-pyrrolo[2,3-b]pyridin-3-yl)-benzylamide (0.079 mmol, 0.000079 mol) was dissolved in methanol (1.8 mL, Fisher;) and water (0.60 mL, Fisher). To this was added potassium carbonate (46 mg, 0.00033 mol; Fisher) and the reaction was heated at reflux for 1 hour. The reaction was evaporated, taken up in N,N-dimethylformamide, neutralized with TFA (100 uL) and purified by preparative HPLC chromatography to yield the product in 3.4 mg yield. 1H NMR (500 MHz, CDCl3-MeOH-d4) d ppm 10.244 (s, 1H) 8.734 (s, 1H) 8.550-8.480 (m, 2H) 7.677 (s, 1H) 7.604 (s, 1H) 7.537 (s, 1H) 7.506-7.393 (m, 3H) 7.390-7.326 (m, 2H) 7.144-7.035 (m, 3H) 6.999-6.938 (m, 1H) 6.442 (m, 1H) 5.070 (s, 2H) 4.689 (m, 2H); MS m/z=552.95 M+H.

Example 96

96.1  1-(3,4-Difluoro-benzyl)-2-oxo-1,2-dihydro-pyridine-3-carboxylic acid 3-(5-furan-2-yl-1H-pyrrolo[2,3-b]pyridin-3-yl)-benzylamide Except where indicated, 1-(3,4-Difluoro-benzyl)-2-oxo-1,2-dihydro-pyridine-3-carboxylic acid 3-(5-furan-2-yl-1H-pyrrolo[2,3-b]pyridin-3-yl)-benzylamide was synthesized as per Example 95, 1-(3,4-Difluoro-benzyl)-2-oxo-1,2-dihydro-pyridine-3-carboxylic acid 3-(5-thiophen-2-yl-1H-pyrrolo[2,3-b]pyridin-3-yl)-benzylamide using 2-Bromofuran as bromide in the second palladium coupling, to yield the product. 1H NMR (400 MHz, CDCl3-MeOH-d4) δ ppm 10.237 (m, 1H) 8.813 (s, 1H) 8.594 (s, 1H) 8.510 (d, J=7.0 Hz, 1H) 7.669 (s, 1H) 7.587 (s, 1H) 7.543 (d, J=6.1

Hz, 1H) 7.508 (s, 1H) 7.490-7.391 (m, 2H) 7.346 (d, J=6.7 Hz, 1H) 7.132-7.014 (m, 2H) 6.991-6.925 (m, 1H) 6.868 (d, J=2.9 Hz, 1H) 6.495 (m, 1H) 6.440 (t, J=6.7 Hz, 1H) 5.079 (s, 2H) 4.677 (m, 2H); MS m/z=537.31 M+H.

Example 97

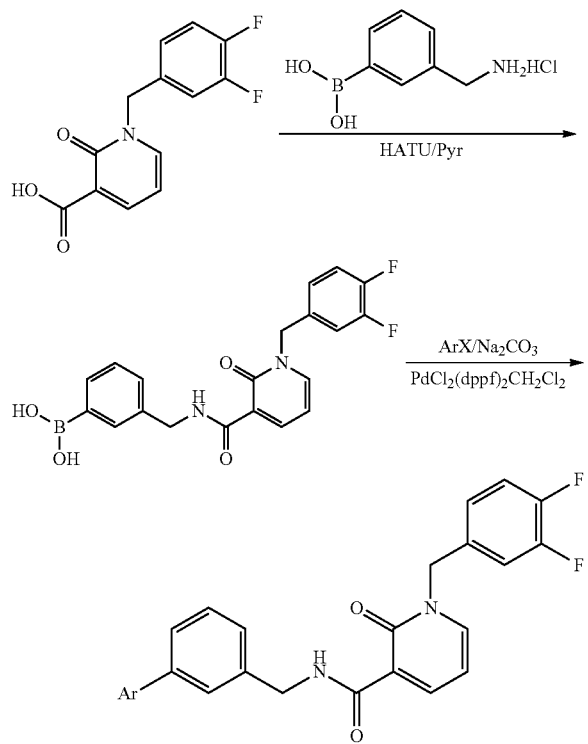

97.1  3-({[1-(3,4-Difluoro-benzyl)-2-oxo-1,2-dihydro-pyridine-3-carbonyl]-amino}-methyl)-boronic acid was produced according to the methods set forth in Example 64 above.

97.2  1-(3,4-Difluoro-benzyl)-2-oxo-1,2-dihydro-pyridine-3-carboxylic acid 3-[1,2,4]triazolo[1,5-a]pyridin-6-yl-benzylamide

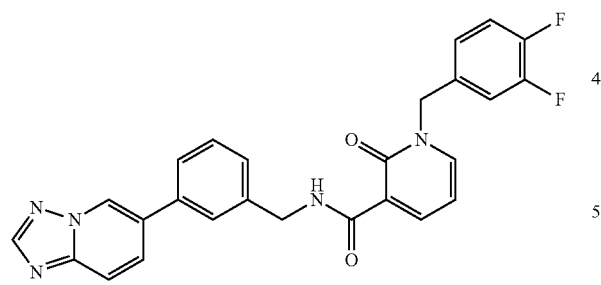

MS (ES+) m/z 472.26 (M+1).

1HNMR (MeOH-d4, 300 MHz): ™ 9.36 (s, 1H), 8.79 (s, 1H), 8.71 (dd, 1H), 8.33 (dd, 1H), 8.27 (dd, 1H), 8.12 (d, 1H), 7.96 (s, 1H), 7.85 (t, 1H), 7.77-7.65 (m, 2H), 7.60-7.35 (m, 3H), 6.81 (t, 1H), 5.46 (s, 2H), 4.8 (s, 2H)

97.3  1-(3,4-Difluoro-benzyl)-2-oxo-1,2-dihydro-pyridine-3-carboxylic acid 3-(1H-indazol-5-yl)-benzylamide

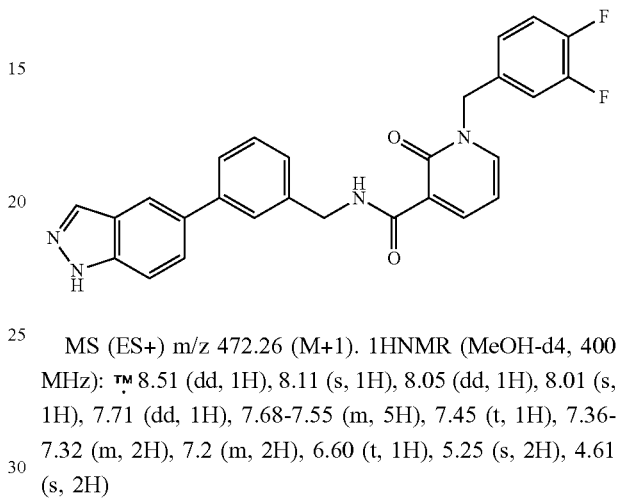

MS (ES+) m/z 472.26 (M+1). 1HNMR (MeOH-d4, 400 MHz): ™ 8.51 (dd, 1H), 8.11 (s, 1H), 8.05 (dd, 1H), 8.01 (s, 1H), 7.71 (dd, 1H), 7.68-7.55 (m, 5H), 7.45 (t, 1H), 7.36-7.32 (m, 2H), 7.2 (m, 2H), 6.60 (t, 1H), 5.25 (s, 2H), 4.61 (s, 2H)

97.4  methyl 4-(3-((1-(3,4-difluorobenzyl)-2-oxo-1,2-dihydropyridine-3-carboxamido)methyl)phenyl)-1H-pyrrole-2-carboxylate

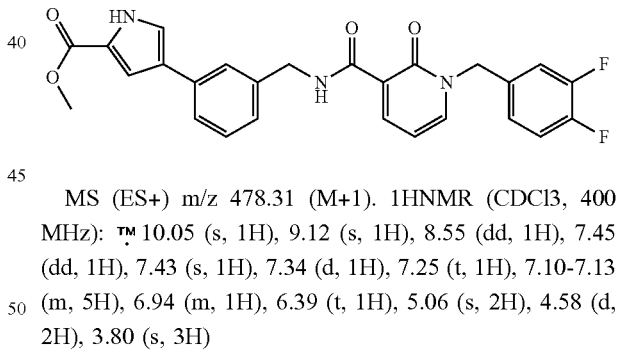

MS (ES+) m/z 478.31 (M+1). 1HNMR (CDCl3, 400 MHz): ™ 10.05 (s, 1H), 9.12 (s, 1H), 8.55 (dd, 1H), 7.45 (dd, 1H), 7.43 (s, 1H), 7.34 (d, 1H), 7.25 (t, 1H), 7.10-7.13 (m, 5H), 6.94 (m, 1H), 6.39 (t, 1H), 5.06 (s, 2H), 4.58 (d, 2H), 3.80 (s, 3H)

Example 98

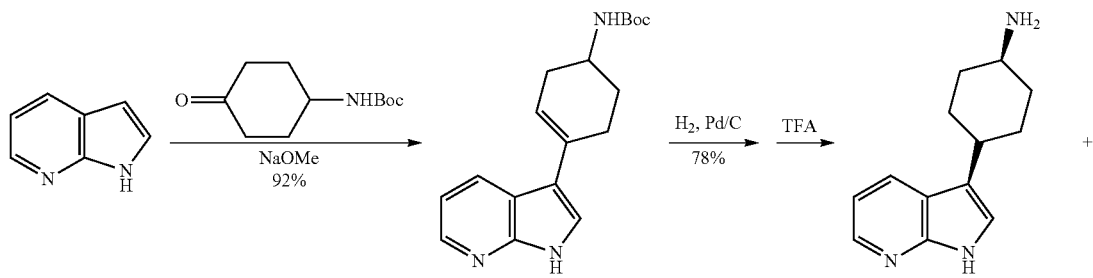

-continued

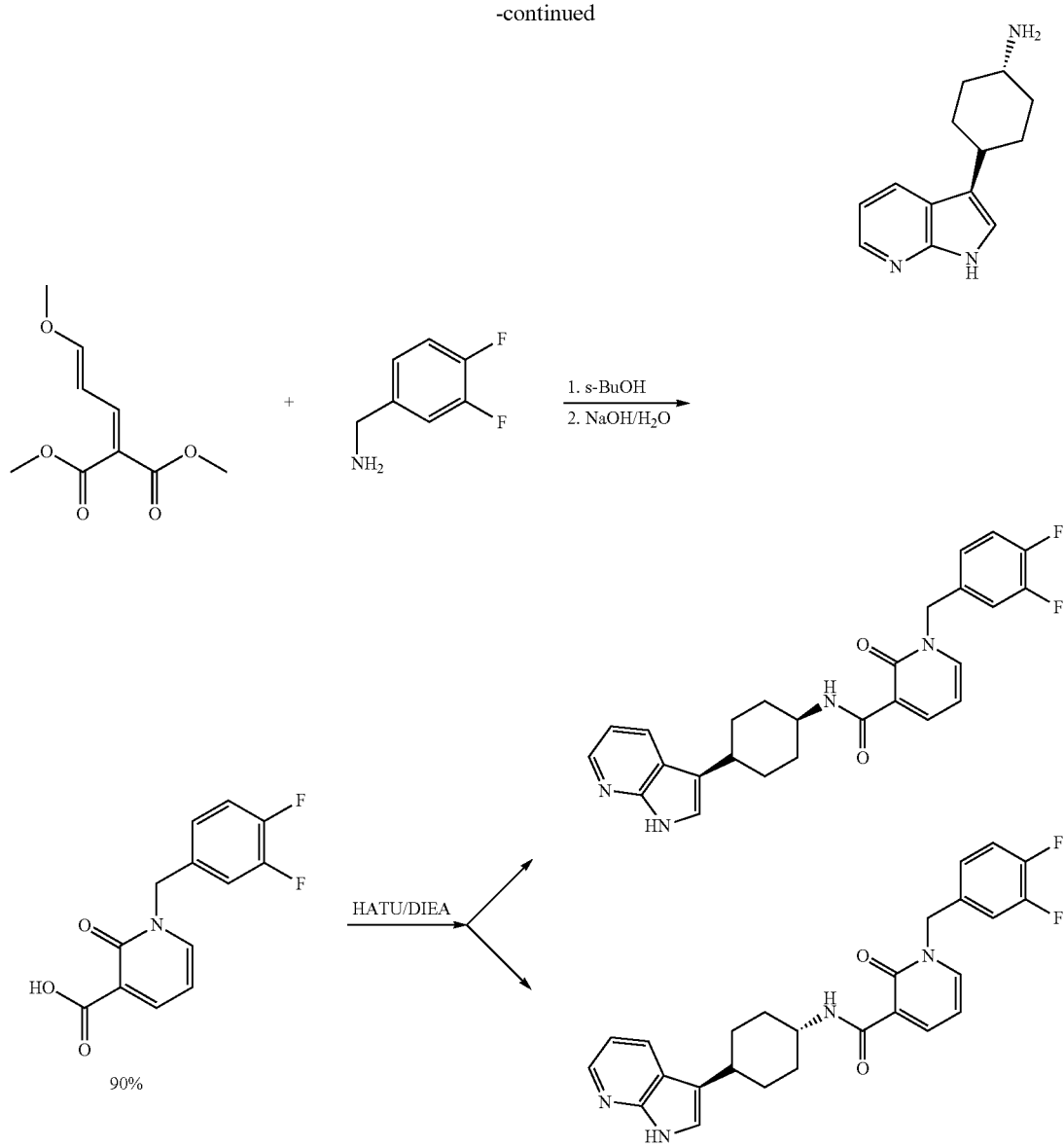

N-4-Boc-aminocyclohexanone (2.2 g, 0.010 mol; Astatech0 was added to a mixture of 1H-pyrrolo[2,3-b]pyridine (0.60 g, 0.0051 mol; Aldrich) and 21% Sodium ethoxide in ethanol (10 mL; Aldrich) and heated to reflux for overnight. LC-MS showed formation of the desired product. The reaction mix was then cooled to room temperature and concentrated in vacuo. The residue was carefully neutralized to pH ~7-8 and then extracted with EtOAc. Dried over MgSO4 and concentrated. Purified on silica gel column with 50-100% in hexane to give the desired product as an offwhite solid (1.6 g, 92% yield). MS (ES+) m/z 314.10 (M+1). 1HNMR (CDCl3, 300 MHz): ™ 11.09 (s, 1H), 8.21 (d, 1H), 8.11 (d, 1H), 7.24 (s, 1H), 7.02 (dd, 1H), 6.05 (t, 1H), 4.70 (m, 1H), 3.52 (m, 1H), 2.50 (m, 2H), 1.95 (m, 2H), 1.55 (m, 1H), 1.39-1.33 (m, 9H)

A mixture of [4-(1H-Pyrrolo[2,3-b]pyridin-3-yl)-cyclohex-3-enyl]-carbamic acid tert-butyl ester (750 mg, 0.0024 mol) and palladium hydroxide (150 mg, 0.0011 mol) in methanol (20 mL) and tetrahydrofuran (20 mL) was hydrogenated under 1 atmosphere of hydrogen for overnight and LC-MS showed complete reaction. Filtered off the catalyst through a Celite cake and concentrated. Purified on silica gel column with 10-100% EtOAc in methylene chloride to give the desired product as a white solid (0.59 g, 78% yield). MS (ES+) m/z 316.12 (M+1).

A mixture of [4-(1H-Pyrrolo[2,3-b]pyridin-3-yl)-cyclohexyl]-carbamic acid tert-butyl ester (0.5 g, 0.002 mol) and trifluoroacetic acid (10 mL) in methylene chloride (10 mL) was stirred at room temperature for 1 h until LC-MS showed complete removal of Boc. Evaporated off the solvents and purified on semi-preparative HPLC to give cis- and trans-4-(1H-Pyrrolo[2,3-b]pyridin-3-yl)-cyclohexylamine as separated products. cis enantiomer: MS (ES+) m/z 216.12 (M+1). 1HNMR (MeOH-d4, 300 MHz): ™ 8.76 (d, 1H), 8.48 (d, 1H), 7.55 (dd, 1H), 7.51 (s, 1H), 3.25 (m, 1H), 2.93 (m, 1H), 2.22 (m, 4H), 1.73 (m, 4H) Trans enantiomer: MS (ES+) m/z 216.08 (M+1). 1HNMR (MeOH-d4, 300 MHz): ™ 8.71 (d, 1H), 8.37 (d, 1H), 7.55 (s, 1H), 7.50 (dd, 1H), 3.50 (m, 1H), 3.05 (m, 1H), 2.01 (m, 8H)

98.1 1-(3,4-Difluoro-benzyl)-2-oxo-1,2-dihydro-pyridine-3-carboxylic acid [4-(1H-pyrrolo[2,3-b]pyridin-3-yl)-cis-cyclohexyl]-amide

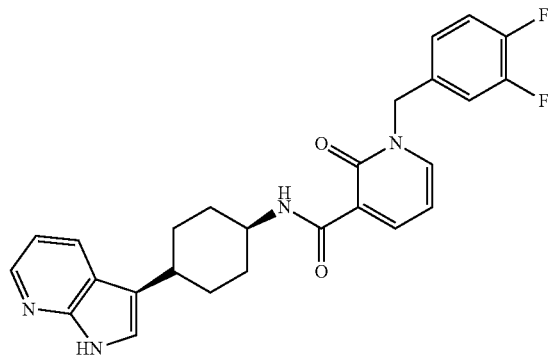

To a solution of 4-(1H-Pyrrolo[2,3-b]pyridin-3-yl)-cyclohexylamine (cis-/12615-3-a, TFA salt) (50.0 mg, 0.23 mmol) in methanol was stirred with MP-carbonate resin (200 mg) at room temperature for overnight. Filtered off the resin and concentrated in vacuo. The residue was then dissolved in anhydrous DMF (10 mL) and then added 1-(3,4-Difluoro-benzyl)-2-oxo-1,2-dihydro-pyridine-3-carboxylic acid (74 mg, 0.28 mmol), DIEA (0.2 mL, 1.2 mmol), and HATU (220 mg, 0.58 mmol) and stirred for overnight. Worked up with water and EtOAc. Dried over MgSO4. Purified on Gilson HPLC with 5-75% B to give the desired product as a TFA salt (65 mg, 60% yield). MS (ES+) m/z 463.50 (M+1). 1HNMR (DMSO-d6, 300 MHz): ™ 11.75 (s, 1H), 10.21 (d, 1H), 8.40 (dd, 1H), 8.37 (d, 1H), 8.28 (d, 1H), 8.22 (dd, 1H), 7.48-7.42 (m, 2H), 7.34 (d, 1H), 7.22 (m, 1H), 7.12 (dd, 1H), 6.61 (t, 1H), 4.22 (s, 1H), 2.92 (s, 1H), 1.95-1.7 (m, 8H)

98.2 1-(3,4-Difluoro-benzyl)-2-oxo-1,2-dihydro-pyridine-3-carboxylic acid [4-(1H-pyrrolo[2,3-b]pyridin-3-yl)-trans-cyclohexyl]-amide

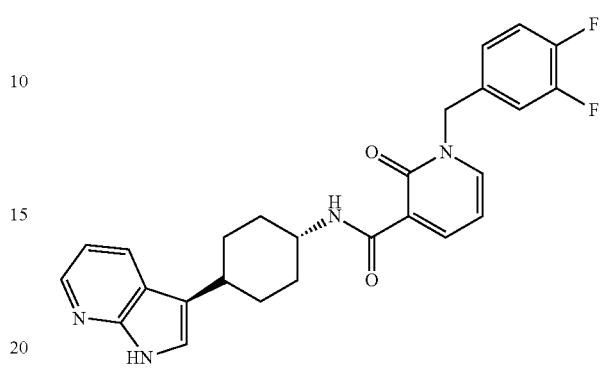

MS (ES+) m/z 463.49 (M+1). 1HNMR (DMSO-d6, 300 MHz): ™ 1.62 (s, 1H), 9.66 (d, 1H), 8.40 (dd, 1H), 8.37 (d, 1H), 8.25-8.19 (m, 2H), 7.48-7.42 (m, 2H), 7.31 (s, 1H), 7.19 (m, 1H), 7.14 (dd, 1H), 6.59 (t, 1H), 3.85 (m, 1H), 2.82 (t, 1H), 2.05 (d, 4H), 1.63 (q, 2H), 1.45 (q, 2H)

Example 99

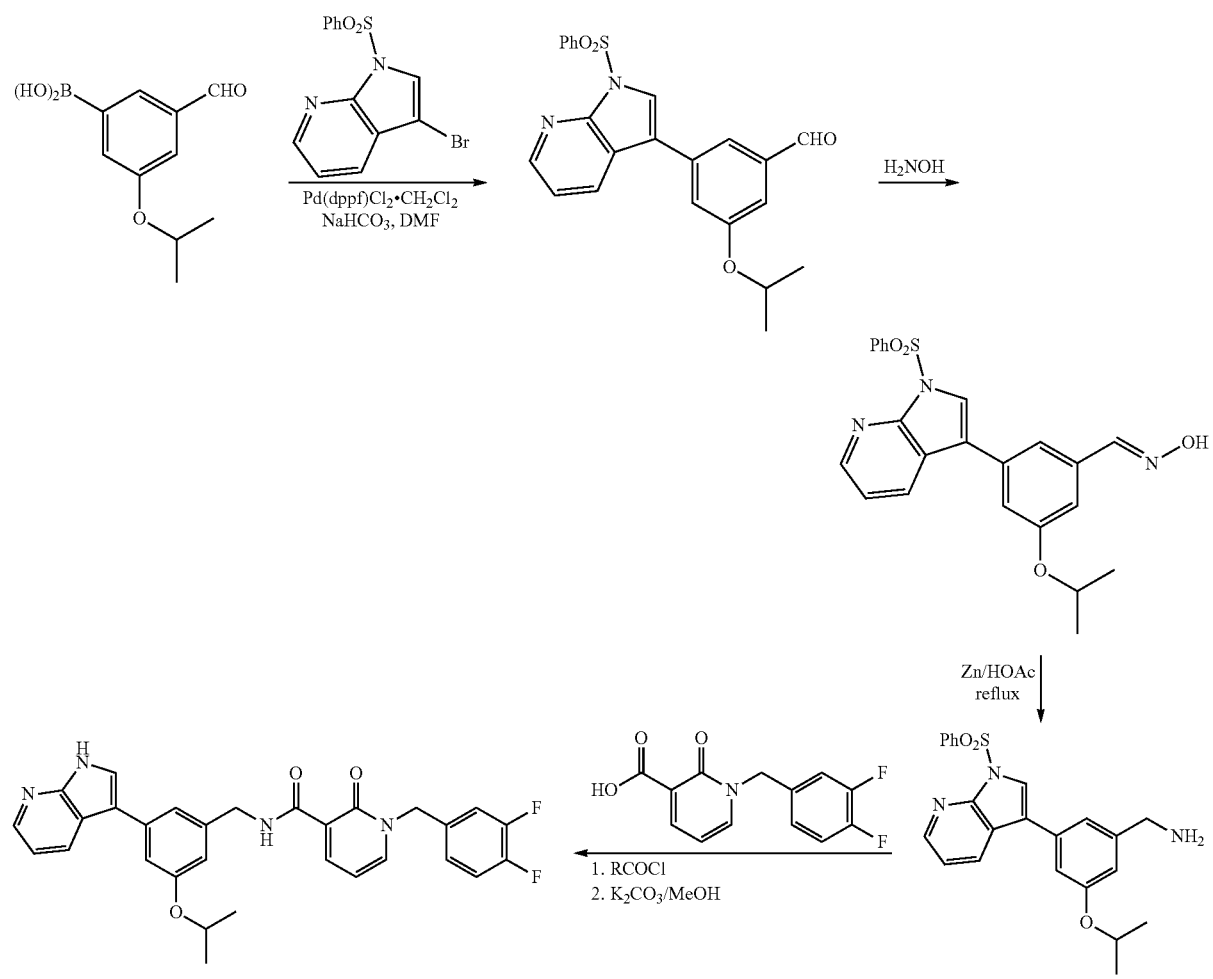

3-isopropoxy-5-(1-(phenylsulfonyl)-1H-pyrrolo[2,3-b]pyridin-3-yl)benzaldehyde

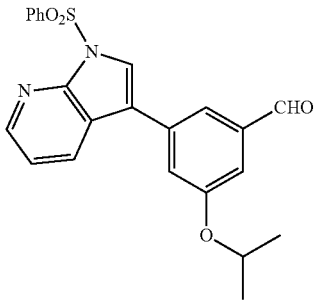

3-bromo-1-(phenylsulfonyl)-1H-pyrrolo[2,3-b]pyridine (750 mg, 0.0022 mol) and 3-formyl-5-isopropoxyphenylboronic acid (510 mg, 0.0024 mol) were dissolved in N,N-Dimethylformamide (10 mL, 0.2 mol) and then added 1.2 M of Sodium bicarbonate in water (6 mL) and [1,1'-Bis(diphenylphosphino)ferrocene]dichloropalladium(II), complex with dichloromethane (1:1) (20 mg, 0.00002 mol). Flushed with nitrogen and The reaction was microwaved on 50 watts, 120° C. for 15 minutes. LC-MS showed complete reaction (1.99 min, ES+/421.07) Worked up with DCM and water. Dried over MgSO4. Purified on silica gel column with 0-100% EtOAc to give the desired product as a yellow syrup (665 mg, 71%) MS (ES+) m/z 421.07 (M+1). 1HNMR (CDCl3, 400 MHz): ™ 10.03 (s, 1H), 8.50 (d, 1H), 8.26 (d, 2H), 8.13 (d, 1H), 7.97 (s, 1H), 7.66 (s, 1H), 7.60 (t, 1H), 7.51 (t, 2H), 7.38 (s, 2H) 7.26 (dd, 1H), 4.72 (qd, 1H), 1.41 (d, 6H)

(3-isopropoxy-5-(1-(phenylsulfonyl)-1H-pyrrolo[2,3-b]pyridin-3-yl)phenyl)-methanamine

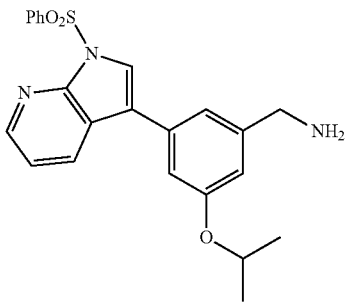

Hydroxylamine hydrochloride (3000 mg, 0.04 mol) was added to a solution of 3-(1-benzenesulfonyl-1H-pyrrolo[2,3-b]pyridin-3-yl)-5-isopropoxy-benzaldehyde (3500 mg, 0.0083 mol) in Methanol (130 mL, 3.3 mol) and stirred for overnight. LC-MS showed the major formation of the desired oxime (1.88 min, ES+/436.20). Evaporated off the solvents and worked up with DCM and sat. NaHCO3. Dried over MgSO4 and concentrated. Purified on silica gel column with 0-100% EtOAc to give the product as a white solid (3.5 g, 96%). This material and zinc (1 g, 0.02 mol) in acetic acid (50 mL, 0.9 mol) was heated at 100° C. for overnight. LC-MS showed complete reaction (1.33 min, ES+/422.14). Cooled to room temperature and filtered off the solids. Concentrated and then worked up with EtOAc and saturated Na2CO3. Dried over MgSO4 and concentrated. No further purifications. MS (ES+) m/z 422.14 (M+1). 1HNMR (MeOH-d4, 400 MHz): ™ 8.38 (dd, 1H), 8.13 (d, 2H), 8.03 (dd, 1H), 7.80 (s, 1H), 7.48 (t, 1H), 7.40 (t, 2H), 7.14 (dd, 1H), 7.04 (s, 1H), 6.91 (s, 1H), 6.82 (s, 1H), 4.54 (m, 1H), 3.84 (s, 2H), 2.30 (br, 2H), 1.28 (d, 6H)

99.1 1-(3,4-difluorobenzyl)-N-(3-isopropoxy-5-(1-(phenylsulfonyl)-1H-pyrrolo[2,3-b]pyridin-3-yl)benzyl)-2-oxo-1,2-dihydropyridine-3-carboxamide

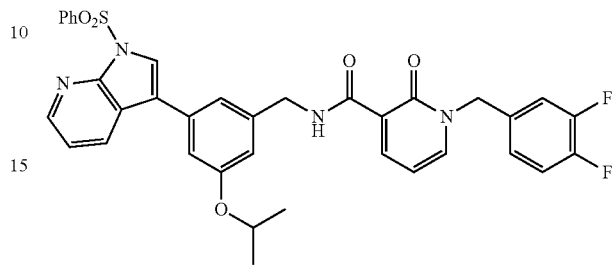

A solution of [A] 3-(1-Benzenesulfonyl-1H-pyrrolo[2,3-b]pyridin-3-yl)-5-isopropoxy-benzylamine (1.7 g, 0.0040 mol;), [B] 1-(3,4-Difluoro-benzyl)-2-oxo-1,2-dihydro-pyridine-3-carboxylic acid (1.1 g, 0.0040 mol;), N,N-Diisopropylethylamine (4 mL, 0.02 mol;) and N,N,N',N'-Tetramethyl-O-(7-azabenzotriazol-1-yl)uronium Hexafluorophosphate (2.3 g, 0.0060 mol;) in N,N-Dimethylformamide (20 uL, 0.0002 mol;) was stirred for 1 hour. LC-MS showed complete reaction (2.03 min, ES+/669.19). Worked up with water and EtOAc and dried over MgSO4. Concentrated and purified on silica gel column with 0-100% EtOAc to give the desired product as a pinkish solid (1.65 g, 61%); MS (ES+) m/z 669.19 (M+1); 1HNMR (CDCl3, 400 MHz): ™ 8.60 (d, 1H), 8.50 (d, 1H), 8.23 (d, 2H), 8.21 (d, 1H), 7.88 (s, 1H), 7.62-7.52 (m, 4H), 7.28 (s, 2H), 7.18-7.12 (m, 3H), 7.05 (m, 1H), 6.99 (s, 1H), 6.92 (s, 1H), 6.49 (t, 1H), 5.17 (s, 2H), 4.67 (d, 2H), 4.63 (m, 1H), 1.37 (d, 6H).

99.2 1-(3,4-difluorobenzyl)-N-(3-isopropoxy-5-(1H-pyrrolo[2,3-b]pyridin-3-yl)benzyl)-2-oxo-1,2-dihydropyridine-3-carboxamide

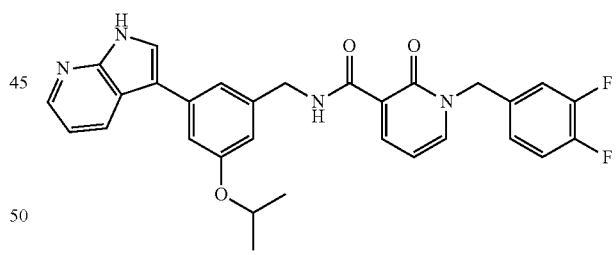

A mix of [A] 1-(3,4-Difluoro-benzyl)-2-oxo-1,2-dihydro-pyridine-3-carboxylic acid 3-(1-benzenesulfonyl-1H-pyrrolo[2,3-b]pyridin-3-yl)-5-isopropoxy-benzylamide (60 mg, 0.00009 mol;) and Potassium carbonate (60 mg, 0.0004 mol;) in Methanol (10 mL, 0.2 mol;) was heated to reflux for 30 min and LC-MS showed complete removal of PhSO2. Evaporated off the solvents and worked up with DCM and sat. ammonium chloride. Dried over MgSO4 and concentrated. Purified on Gilson HPLC to give the desired product as A TFA salt (10 mg, 60%); MS (ES+) m/z 529.30 (M+1); 1HNMR (CDCl3, 400 MHz): ™ 13.20 (s, 1H), 10.10 (s, 1H), 8.67 (d, 1H), 8.53 (dd, 1H), 8.20 (d, 1H), 7.62 (s, 1H), 7.50 9dd, 1H), 7.38 9t, 1H), 7.19 (s, 1H), 7.10-7.02 (m, 3H), 6.98-6-92 (m, 2H), 6.91 (s, 1H), 6.84 (s, 1H), 6.42 (t, 1H), 5.09 (s, 2H), 4.61 (d, 2H), 4.55 (m, 1H), 1.30 (d, 6H).

Example 100

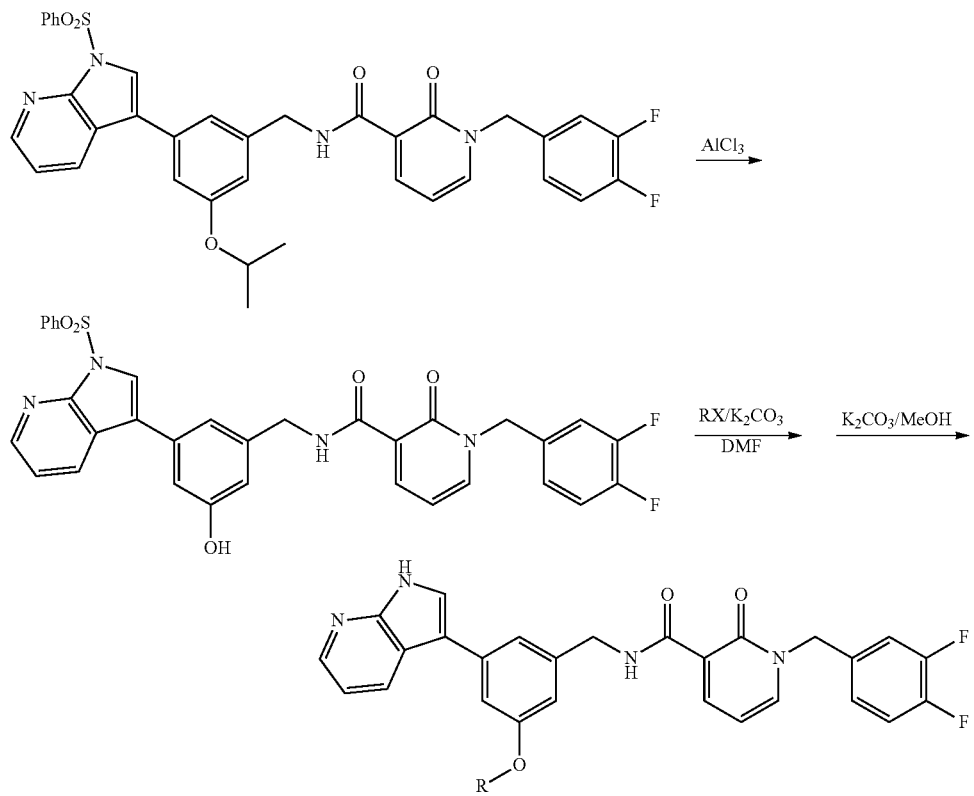

100.1 1-(3,4-difluorobenzyl)-N-(3-hydroxy-5-(1-(phenylsulfonyl)-1H-pyrrolo[2,3-b]pyridin-3-yl)benzyl)-2-oxo-1,2-dihydropyridine-3-carboxamide

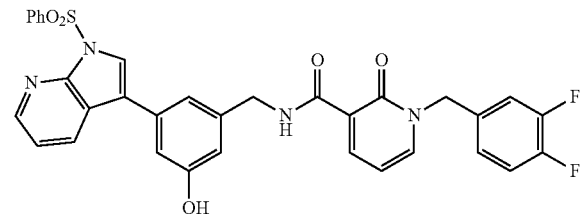

A mix of [A] 1-(3,4-Difluoro-benzyl)-2-oxo-1,2-dihydropyridine-3-carboxylic acid 3-(1-benzenesulfonyl-1H-pyrrolo[2,3-b]pyridin-3-yl)-5-isopropoxy-benzylamide (500 mg, 0.0007 mol;) and Aluminum trichloride (500 mg, 0.004 mol;) in Methylene chloride (50 mL, 0.8 mol;) was stirred at room temperature for 1 hour. LC-MS showed the formation of the desired product (1.73 min, ES+/627.09). Worked up with saturated ammonium chloride and DCM. Dried over MgSO4 and concentrated. Purified on silica gel column with 0-100% EtOAc in hexane to give the desired product (120 mg, 20%) MS (ES+) m/z 627.09 (M+1).

100.2 1-(3,4-difluorobenzyl)-N-(3-hydroxy-5-(1H-pyrrolo[2,3-b]pyridin-3-yl)benzyl)-2-oxo-1,2-dihydropyridine-3-carboxamide

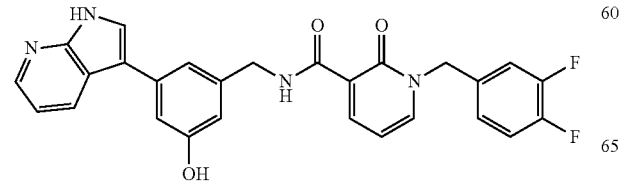

A mix of 1-(3,4-difluorobenzyl)-N-(3-hydroxy-5-(1-(phenylsulfonyl)-1H-pyrrolo[2,3-b]pyridin-3-yl)benzyl)-2-oxo-1,2-dihydropyridine-3-carboxamide (120 mg, 0.00019 mol;) and Potassium carbonate (100 mg, 0.001 mol;) in Methanol (15 mL, 0.37 mol;) was heated to reflux for 30 min. LC-mS showed complete reaction (ES+487.2). Evaporated off the solvents and purified on Gilson HPLC to give the product as a TFA salt (45 mg, 48%) MS (ES+) m/z 487.2 (M+1). 1HNMR (MeOD, 400 MHz): ™ 8.82 (s, 1H), 8.48 (d, 1H), 8.42 (s, 1H), 8.03 (d, 1H), 7.84 (s, 1H), 7.51 (s, 1H), 7.28 (t, 1H), 7.22-7.12 (m, 3H), 7.18 (s, 1H), 6.80 (s, 1H), 6.60 (t, 1H), 5.23 (s, 2H), 4.61 (s, 2H)

100.3 1-(3,4-difluorobenzyl)-2-oxo-N-(3-(2-(morpholino-1-yl)ethoxy)-5-(1H-pyrrolo[2,3-b]pyridin-3-yl)benzyl)-1,2-dihydropyridine-3-carboxamide

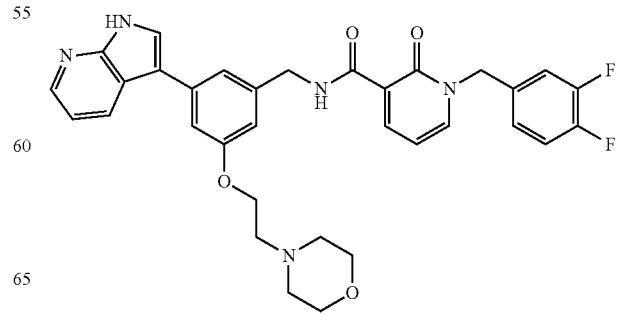

A mix of 1-(3,4-difluorobenzyl)-N-(3-hydroxy-5-(1-(phenylsulfonyl)-1H-pyrrolo[2,3-b]pyridin-3-yl)benzyl)-2-oxo-1,2-dihydropyridine-3-carboxamide (70 mg, 0.0001 mol;), 4-(2-chloroethyl)morpholine (30 mg, 0.0001 mol), and Potassium carbonate (100 mg, 0.001 mol;) in Acetonitrile (19 mL, 0.37 mol;) N,N-Dimethylformamide (3 mL, 0.04 mol;) was heated at 80° C. for overnight. LC-MS showed complete reaction (1.50 min, ES+/739.97). Methanol (10 mL) was then added and heated to reflux for 1 h and LC-MS showed complete reaction (1.11 min, ES+/600.08). Evaporated off the solvents and worked up with EtOAc and water. Dried over MgSO4 and concentrated. Purified on Gilson HPLC to give the desired product as a bis-TFA salt (25 mg, 40%) MS (ES+) m/z 600.08 (M+1). 1HNMR (MeOD, 400 MHz): ᵀᴹ 8.40 (dt, 2H), 8.20 (dd, 1H), 7.97 (dd, 1H), 7.67 (s, 1H), 7.29 (s, 1H), 7.17-7.05 (m, 5H), 6.88 (s, 1H), 6.51 (t, 1H), 5.15 (s, 2H), 4.57 (d, 2H), 4.38 (t, 2H), 3.96 (br, 2H), 3.73 (br, 2H), 3.57 (t, 2H), 3.50 (br, 2H)

100.4  1-(3,4-difluorobenzyl)-N-(3-(2-(dimethylamino)ethoxy)-5-(1H-pyrrolo[2,3-b]pyridin-3-yl)benzyl)-2-oxo-1,2-dihydropyridine-3-carboxamide

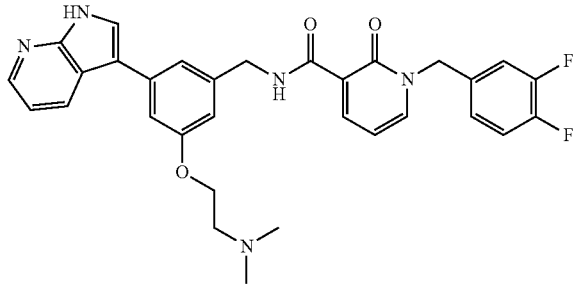 [SMILES: CN(C)CCOc1cc(CNC(=O)c2cccn(Cc3ccc(F)c(F)c3)c2=O)cc(-c2c[nH]c3ncccc23)c1]

MS (ES+) m/z 487.2 (M+1). 1HNMR (MeOD, 400 MHz): ᵀᴹ 8.40 (dd, 1H), 8.25-8.22 (m, 2H), 7.95 (dd, 1H), 7.63 (s, 1H), 7.21 (m, 1H), 7.13-7.05 (m, 4H), 6.92 (s, 1H), 6.64 (s, 1H), 6.48 (t, 1H), 5.14 (s, 2H), 4.63 (t, 2H), 4.50 (s, 2H), 3.63 (t, 2H), 2.94 (s, 6H)

Example 101

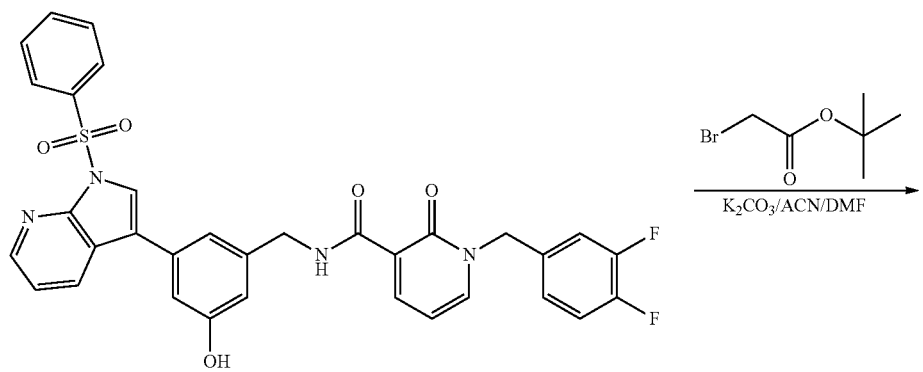

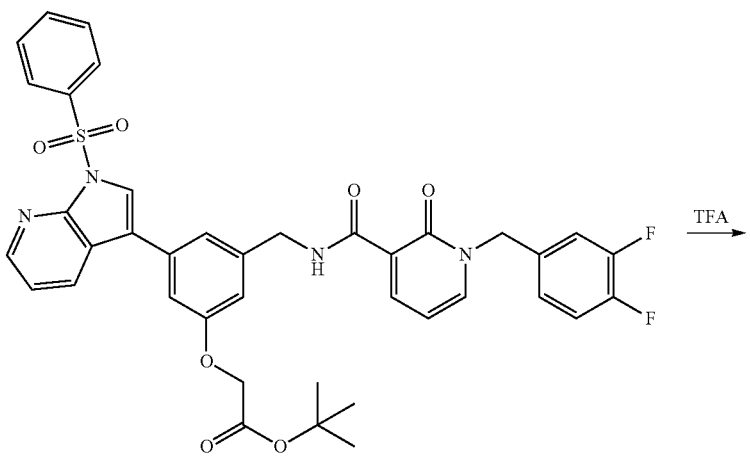

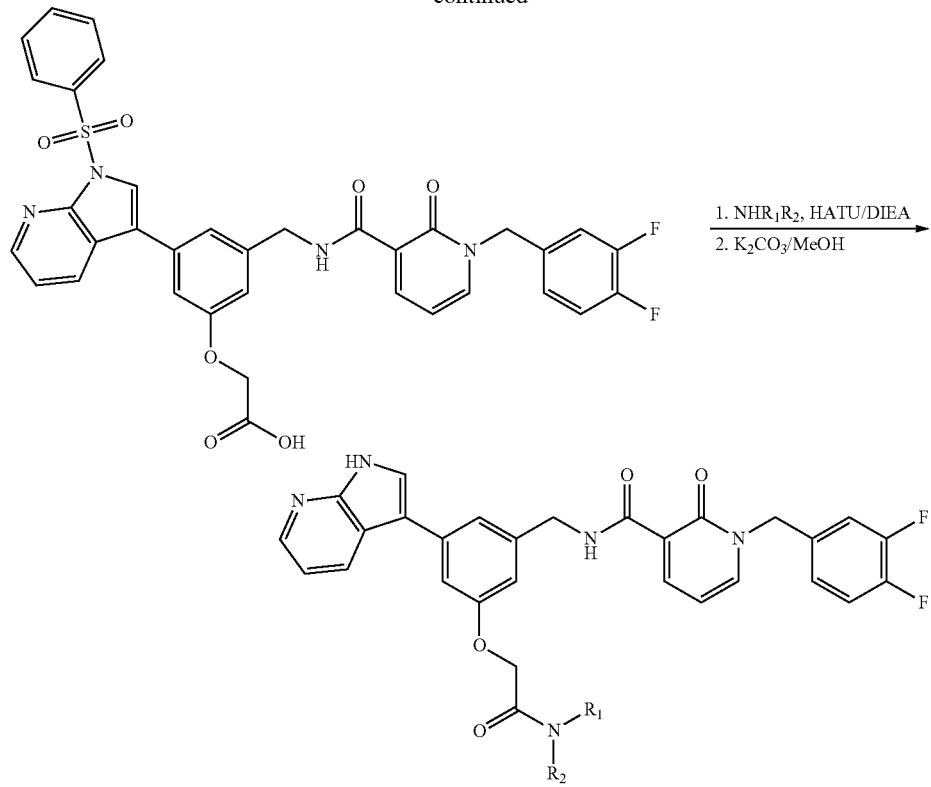

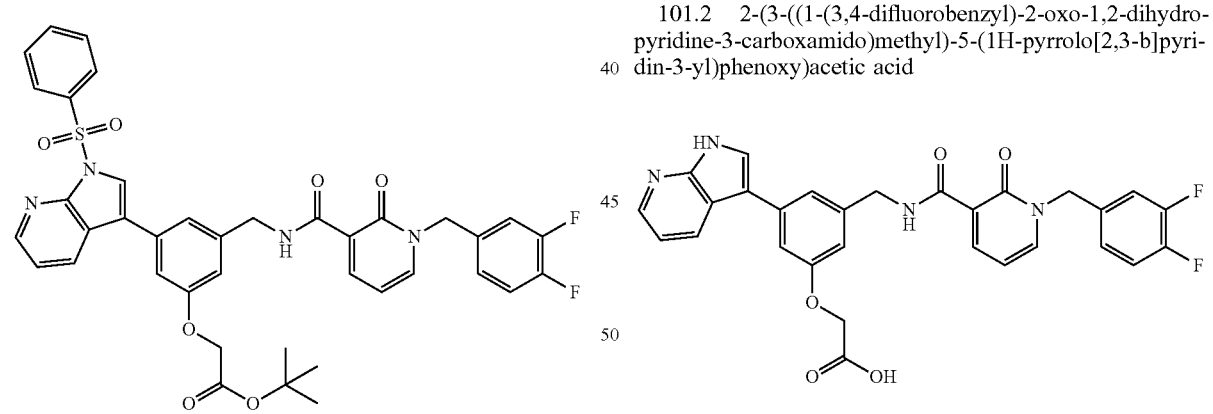

101.1 tert-butyl 2-(3-((1-(3,4-difluorobenzyl)-2-oxo-1,2-dihydropyridine-3-carboxamido)methyl)-5-(1-(phenylsulfonyl)-1H-pyrrolo[2,3-b]pyridin-3-yl)phenoxy)acetate A mix of 1-(3,4-difluorobenzyl)-N-(3-hydroxy-5-(1-(phenylsulfonyl)-1H-pyrrolo[2,3-b]pyridin-3-yl)benzyl)-2-oxo-1,2-dihydropyridine-3-carboxamide (155 mg, 0.000247 mol;) and Potassium carbonate (200 mg, 0.001 mol;) in Acetonitrile (10 mL, 0.2 mol;) and N,N-Dimethylformamide (5 mL, 0.06 mol;) was heated at 80° C. for overnight and LC-MS showed complete reaction (2.03 min, ES+/741.51). Cooled to room temperature and worked up with Et2O and water. Dried over MgSO4 and concentrated. Purified on silica gel column with 0-100% EtOAc in hexane to give the desired product (180 mg, 98%) MS (ES+) m/z 741.51 (M+1); 1HNMR (CDCl3, 400 MHz): ™ 10.05 (t, 1H), 8.48 (dd, 1H), 8.36 (d, 1H), 8.13 (dd, 2H), 8.03 (d, 1H), 7.91 (s, 2H), 7.78 (s, 1H), 7.52 (dd, 1H), 7.48 (d, 1H), 7.39 (t, 2H), 7.12-7.00 (m, 4H), 6.95 (m, 1H), 6.93 (s, 1H), 6.81 (s, 1H), 6.36 (t, 1H), 5.07 (s, 2H), 4.58 (d, 2H), 4.48 (s, 2H), 1.40 (s, 9H).

101.2 2-(3-((1-(3,4-difluorobenzyl)-2-oxo-1,2-dihydropyridine-3-carboxamido)methyl)-5-(1H-pyrrolo[2,3-b]pyridin-3-yl)phenoxy)acetic acid A mix of [3-(1-Benzenesulfonyl-1H-pyrrolo[2,3-b]pyridin-3-yl)-5-({[1-(3,4-difluoro-benzyl)-2-oxo-1,2-dihydro-pyridine-3-carbonyl]-amino}-methyl)-phenoxy]-acetic acid tert-butyl ester (20 mg, 0.00003 mol) and Trifluoroacetic Acid (20 mg, 0.0001 mol;) in Methylene chloride (8 mL, 0.1 mol) was stirred for overnight. LC-MS showed only formation of the des-phSO 2 and saponified product C (1.24 min, ES+/545.64). Evaporated off the solvents and dissolved in DMSO and water and purified on Gilson HPLC to give the desired product (6 mg, 40%) MS (ES+) m/z 545.64 (M+1). 1HNMR (DMSO, 400 MHz): δ8.41 (dd, 1H), 8.26 (d, 2H), 8.24 (dd, 1H), 7.88 (s, 2H), 7.45-7.35 (m, 2H), 7.30 (s, 2H), 7.18 (m, 1H), 7.10-7.07 (m, 2H), 6.77 (s, 2H), 6.60 (t, 1H), 5.22 (s, 2H), 4.75 (s, 2H), 4.55 (d, 2H), 101.3 2-(3-((1-(3,4-difluorobenzyl)-2-oxo-1,2-dihydro-pyridine-3-carboxamido)methyl)-5-(1-(phenylsulfonyl)-1H-pyrrolo[2,3-b]pyridin-3-yl)phenoxy)acetic acid

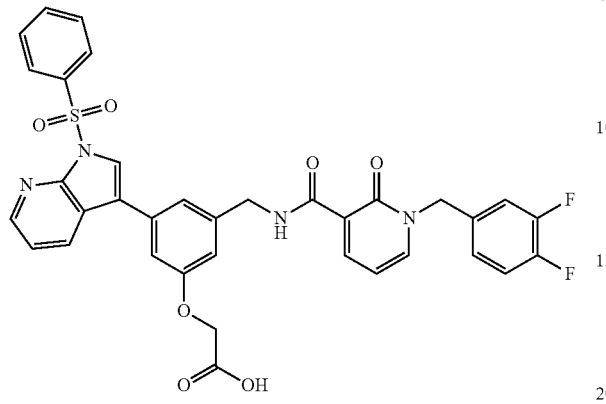

A solution of [A] [3-(1-Benzenesulfonyl-1H-pyrrolo[2,3-b]pyridin-3-yl)-5-({[1-(3,4-difluoro-benzyl)-2-oxo-1,2-dihydro-pyridine-3-carbonyl]-amino}-methyl)-phenoxy]-acetic acid tert-butyl ester (150 mg, 0.00020 mol;) in Trifluoroacetic Acid (2 mL, 0.02 mol;) and Methylene chloride (2 mL, 0.03 mol;) was stirred at room temperature for overnight. LC-MS showed complete reaction (1.75 min, ES+/685.36). Evaporated off the solvents. No further purifications. MS (ES+) m/z 685.36 (M+1).

101.4 N-(3-(2-amino-2-oxoethoxy)-5-(1H-pyrrolo[2,3-b]pyridin-3-yl)benzyl)-1-(3,4-difluorobenzyl)-2-oxo-1,2-dihydropyridine-3-carboxamide

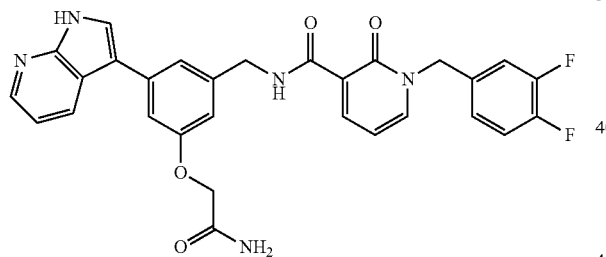

A mix of 2-(3-((1-(3,4-difluorobenzyl)-2-oxo-1,2-dihydropyridine-3-carboxamido)methyl)-5-(1-(phenylsulfonyl)-1H-pyrrolo[2,3-b]yridine-3-yl)phenoxy)acetic acid (50 mg, 0.00007 mol;), Ammonium chloride (20 mg, 0.0004 mol;), and N,N,N',N'-Tetramethyl-O-(7-azabenzotriazol-1-yl)yridin Hexafluorophosphate (0.06 g, 0.0001 mol;) in N,N-Dimethylformamide (5 mL, 0.06 mol;) N,N-Diisopropylethylamine (0.06 mL, 0.0004 mol;) was stirred for overnight and LC-MS showed complete amide formation (1.71 min, ES+/684.37). Worked up with EtOAc and water. Dried over MgSO4 and concentrated. The residue was then dissolved in Methanol (10 mL, 0.2 mol;) and added Potassium carbonate (50 mg, 0.0004 mol;) and heated to reflux for 1 h. LC-MS showed the formation of the des-PhSO2 product C (1.24 min, ES+/544.53). Evaporated off the solvents and dissolved in DMSO and water and purified on Gilson HPLC to give the desired product (15 mg, 40%) MS (ES+) m/z 544.53 4 (M+1). 1HNMR (DMSO, 400 MHz): δ 8.41 (dd, 1H), 8.29 (d, 1H), 8.27 (dd, 1H), 8.24 (dd, 1H), 7.88 (s, 1H), 7.45-7.35 (m, 2H), 7.31 (s, 2H), 7.18 (m, 2H), 7.11 (dd, 1H), 6.83 (s, 1H), 6.60 (t, 1H), 5.22 (s, 2H), 4.55 (s, 2H), 4.49 (s, 2H), 101.5 1-(3,4-difluorobenzyl)-N-(3-(2-(dimethylamino)-2-oxoethoxy)-5-(1H-pyrrolo[2,3-b]yridine-3-yl)benzyl)-2-oxo-1,2-dihydropyridine-3-carboxamide

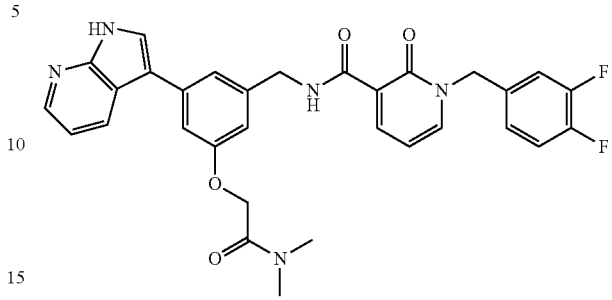

MS (ES+) m/z 544.53 4 (M+1). 1HNMR (DMSO, 400 MHz): δ 852 (dd, 1H), 8.38 (dd, 1H), 8.23 (d, 1H), 7.94 (dd, 1H), 7.72 (s, 1H), 7.26-7.19 (m, 3H), 7.14-7.04 (m, 3H), 6.83 (s, 1H), 6.49 (t, 1H), 5.14 (s, 2H), 4.78 (s, 2H), 4.55 (s, 2H), 3.01 (s, 3H), 2.88 (s, 3H).

Example 102

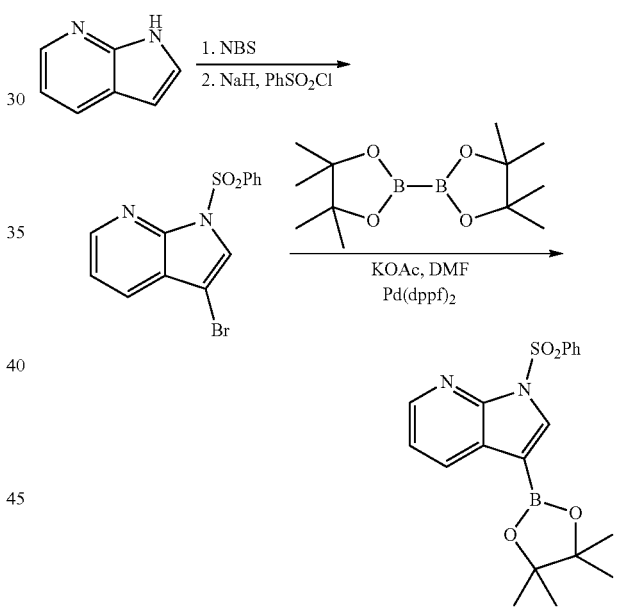

102.1 1-Benzenesulfonyl-3-(4,4,5,5-tetramethyl-1,3,2-dioxaborolan-2-yl)-1H-pyrrolo[2,3-b]pyridine 1H-Pyrrolo[2,3-b]pyridine (7.07 g, 0.0598 mol;) was dissolved in Tetrahydrofuran (100 mL, 1 mol;) and N-Bromosuccinimide (12 g, 0.066 mol;) was added. The reaction was allowed to stir at RT o/n. LCMS showed the appearance of the product at 0.84 198.92 and an unidentified impurity at 1.73. The reaction was worked up by dilution with methylene chloride and washing 1× with saturated sodium bicarbonate and 1× with brine before drying with magnesium sulfate and concentration. About half of the crude was dissolved in ethyl acetate and silica was added for solid loading onto a 120 g column for purification by combiflash. A 0-100% hexanes ethyl acetate gradient was used. Upon purification some of the impurity remained, but it was taken to the next step without further purification. ES (+) MS m/e=197.03

3-bromo-1H-pyrrolo[2,3-b]pyridine (4.37 g, 0.0222 mol;) was dissolved in Tetrahydrofuran (100 mL, 1 mol;) and the reaction was cooled to 0 degrees. sodium hydride, 60% in mineral oil (60:40, Sodium hydride:Mineral Oil, 2.2 g) was then added in two portions and the reaction was stirred for 5-10 minutes before Benzenesulfonyl chloride (3.4 mL, 0.027 mol;) was added. The reaction was then allowed to warm to room temperature o/n. LC-MS showed formation of product at 1.78 338.89. The reaction was worked up by dilution with methylene chloride then washing 1× with saturated bicarbonate, 1× with 5% citric acid, and 1× with brine then drying with magnesium sulfate and concentration to give the crude product which was taken directly into the next step. ES (+) MS m/e=338.89.

3-bromo-1-(phenylsulfonyl)-1H-pyrrolo[2,3-b]pyridine (300 mg, 0.0009 mol;), bis(pinacolato)diboron (0.678 g, 0.00267 mol; Aldrich;), Potassium acetate (0.52 g, 0.0053 mol; Aldrich;) and [1,1'-Bis(diphenylphosphino)ferrocene]dichloropalladium(II), complex with dichloromethane (1:1) (0.085 g, 0.00010 mol; Strem;) was dissolved in N,N-Dimethylformamide (8.5 mL, 0.11 mol; Acros;). The reaction was heated in a sealed tube at 80° C., after 2 hours, LCMS shows complete conversion to a new peak consistent with product (2.03 384.92). The reaction was concentrated and then taken up in DCM, washed with water, dried with magnesium sulfate, filtered and evaporated. The DCM solution was purified by silica gel chromatography using hexanes/ethyl acetate as eluent to yield the product. ES (+) MS m/e=384.92

Example 103 was filtered and washed several times with ether and briefly with acetone. It is somewhat soluble in acetone. The crude solid was then taken on to the next step. ES (+) MS m/e=136.05

4-Aminopyrazolo[3,4-d]pyrimidine (1 g, 0.007 mol), crude from last step, was dissolved in N,N-Dimethylformamide (25 mL, 0.32 mol) (only partially soluble) and N-Iodosuccinimide (1.8 g, 0.0081 mol) was added. The reaction was heated at 50 degrees for 4 hours. LC-MS showed the appearance of product, but a large amount of starting material appeared to remain, therefore an additional 0.5 equivalents of NIS was added and the reaction was heated for another hour. Starting material still remained, but the reaction was worked up anyway. The reaction was first concentrated and then a small portion was isolated by first dissolving in ethyl acetate and washing with saturated bicarbonate. Most of the product did not go into either solution. After sonication the compound went into the saturated bicarbonate and then was extracted with ethyl acetate. Concentration gave the crude product that was brought directly on to the next step. ES (+) MS m/e=261.93

3-Iodo-1H-pyrazolo[3,4-d]pyrimidin-4-ylamine (0.08 g, 0.0003 mol;) was dissolved in 1,4-Dioxane (2 mL, 0.02 mol;) and N,N-Dimethylformamide (1 mL, 0.01 mol;). 3-({[1-(3,4-Difluoro-benzyl)-2-oxo-1,2-dihydro-pyridine-3-carbonyl]-amino}-methyl)-boronic acid (scheme x) (0.2 g, 0.0006 mol;), [1,1'-Bis(diphenylphosphino)ferrocene]dichloropalladium(II), complex with dichloromethane (1:1) (0.05 g, 0.00006 mol;), and Potassium phosphate (0.2 g, 0.0009 mol;) were then added and the reaction was microwaved at 180 for 10 min. Purification was performed by direct injection of the reaction onto the Gilson and concen-

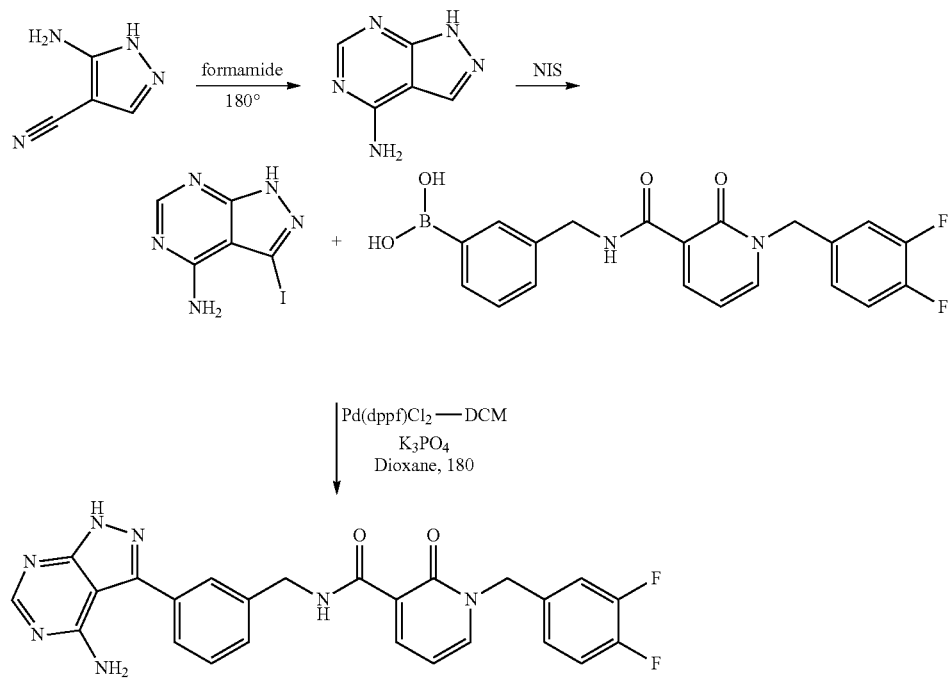

103.1 1-(3,4-Difluoro-benzyl)-2-oxo-1,2-dihydro-pyridine-3-carboxylic acid 3-(4-amino-1H-pyrazolo[3,4-d]pyrimidin-3-yl)-benzylamides 5-Amino-1H-pyrazole-4-carbonitrile (1 g, 0.009 mol) was dissolved in Formamide (10 mL, 0.3 mol) and heated at 180 degrees overnight. Upon cooling a precipitate formed that tration of the pure fractions gave the product. ES (+) MS m/e=488.14 NMR (400 MHz, DMSO-d6) δ ppm 4.58 (d, 2H, J=7 Hz), 5.22 (s, 2H), 6.60 (t, 1H, J=8 Hz), 7.17 (m, 1H), 7.30-7.50 (m, 5H), 7.55-7.62 (m, 2H), 7.69 (s, 1H), 8.02 (s, 1H), 8.24 (m, 1H), 8.41 (m, 1H), 10.05 (t. 1H, J=6 Hz), 12.55 (s, 1H).

Example 104

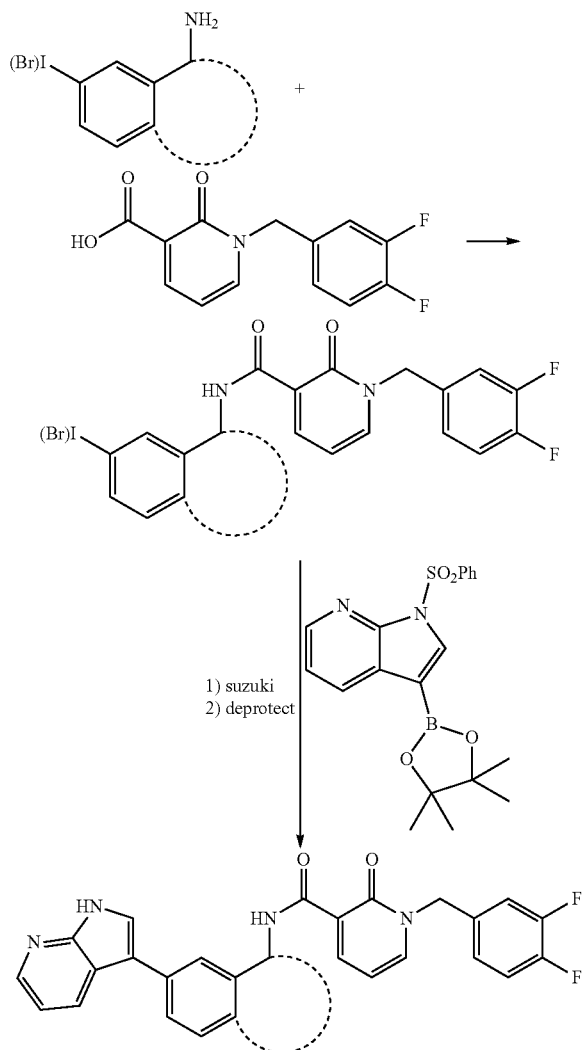

1) suzuki
2) deprotect 104.1  1-(3,4-Difluoro-benzyl)-2-oxo-1,2-dihydro-pyridine-3-carboxylic acid [7-(1H-pyrrolo[2,3-b]pyridin-3-yl)-1,2,3,4-tetrahydro-naphthalen-1-yl]-amide 7-Bromo-1,2,3,4-tetrahydro-naphthalen-1-ylamine (Chembridge) (0.0938 g, 0.000415 mol;), 1-(3,4-Difluoro-benzyl)-2-oxo-1,2-dihydro-pyridine-3-carboxylic acid (0.100 g, 0.000377 mol;), N,N,N',N'-Tetramethyl-O-(7-azabenzotriazol-1-yl)uronium Hexafluorophosphate (0.16 g, 0.00041 mol;), N,N-Diisopropylethylamine (0.2 g, 0.002 mol;), and Methylene chloride (3.6 mL, 0.056 mol;) were added to a 50 mL round and stirred for 2 to 3 hours. LC-MS showed the formation of product at 2.04. The reaction was worked up by diluting with methylene chloride and washing 1× with 5% citric acid, 1× with saturated bicarbonate, and 1× with brine before drying and concentration to give the crude material. The crude was then taken up in dichloromethane and purified by combiflash using a 0-100 percent hexanes/ethyl acetate gradient to give the pure product (0.150 g 84%). ES (+) MS m/e=472.83

Into a Vial was dissolved 1-(3,4-Difluoro-benzyl)-2-oxo-1,2-dihydro-pyridine-3-carboxylic acid (7-bromo-1,2,3,4-tetrahydro-naphthalen-1-yl)-amide (0.074 g, 0.16 mmol;), 1-Benzenesulfonyl-3-(4,4,5,5-tetramethyl-1,3,2-dioxaborolan-2-yl)-1H-pyrrolo[2,3-b]pyridine (50 mg, 0.1 mmol;) and [1,1'-Bis(diphenylphosphino)ferrocene]dichloropalladium (II), complex with dichloromethane (1:1) (17 mg, 0.021 mmol; Strem;) in 1,4-Dioxane (2.21 mL, 28.4 mmol; Acros;). To this was added 2.0 M of Sodium carbonate in water (0.55 mL). The reaction was purged with Ar and sealed. The reaction was heated at 100° C. under an atmosphere of Argon for 2 hours. The reaction showed complete conversion to product at 2.16 with the correct mass 651.03. The reaction was diluted with dichloromethane and washed 1× with 5% citric acid, 1× with saturated bicarbonate, and 1× with brine before drying with magnesium sulfate and concentrating to give the crude material. The crude material was then dissolved in methylene chloride and purified by combiflash using a 0-100% hexanes/ethyl acetate gradient to give the pure product. ES (+) MS m/e=651.03

1-(3,4-Difluoro-benzyl)-2-oxo-1,2-dihydro-pyridine-3-carboxylic acid [7-(1-benzenesulfonyl-1H-pyrrolo[2,3-b]pyridin-3-yl)-1,2,3,4-tetrahydro-naphthalen-1-yl]-amide (0.063 g, 0.000097 mol;) was dissolved in 0.5 M of Sodium methoxide in methanol (3 mL) and Methylene chloride (3 g, 0.04 mol;) and heated at 75 C for 1 hour. LC-MS showed the disappearance of starting material and the appearance of product. The reaction was concentrated and dissolved in DMSO and methanol 1:1 for purification by Gilson Preparative HPLC. Pure fractions were combined and concentrated to give the pure product. ES (+) MS m/e=511.37; (400 MHz, DMSO-d6) δ ppm 1.84 (m, 3H), 2.07 (m, 1H), 2.80 (m, 2H), 5.22 (d, 2H, 5 Hz), 5.25 (m, 1H), 6.62 (t, 1H, J=8 Hz), 6.99 (m, 1H), 7.12 (m, 1H), 7.20 (d, 1H, J=8 Hz), 7.30-7.45 (m, 2H), 7.52 (m, H), 7.60 (s, 1H), 7.78 (s, 1H), 8.16 (d, 1H, J=8 Hz), 8.22 (m, 2H), 8.46 (m, 1H), 10.10 (d. 1H, J=8 Hz), 12.55 (s, 1H).

104.2  1-(3,4-Difluoro-benzyl)-2-oxo-1,2-dihydro-pyridine-3-carboxylic acid [7-(1H-pyrrolo[2,3-b]pyridin-3-yl)-naphthalen-1-yl]-amide 1-(3,4-Difluoro-benzyl)-2-oxo-1,2-dihydro-pyridine-3-carboxylic acid (0.17 g, 0.00063 mol;) was dissolved in Methylene chloride (10 mL, 0.2 mol;) and N,N-Diisopropylethylamine (500 uL, 0.003 mol;) and N,N,N',N'-Tetramethyl-O-(7-azabenzotriazol-1-yl)uronium Hexafluorophosphate (0.31 g, 0.00082 mol;) were added. The reaction was allowed to stir until the solution was almost clear, then 8-Amino-naphthalen-2-ol (0.100 g, 0.000628 mol;) was added. After stirring o/n product was formed at 1.75 407.03. The reaction was diluted with methylene chloride and washed once with citric acid then the organic layer was dried with magnesium sulfate and concentrated. The crude was then purified by dilution with methylene chloride then purification by combiflash using a 0-100 gradient of hexanes/ethyl acetate. ES (+) MS m/e=407.03

1-(3,4-Difluoro-benzyl)-2-oxo-1,2-dihydro-pyridine-3-carboxylic acid (7-hydroxy-naphthalen-1-yl)-amide (0.085 g, 0.00021 mol;) was dissolved in Methylene chloride (10 mL, 0.2 mol;) and Pyridine (30 uL, 0.0004 mol;) and Trifluoromethanesulfonic anhydride (42 uL, 0.00025 mol;) were added. After one hour the reaction was not complete therefore 2 eq of Trifluoromethanesulfonic anhydride and 4 eq of Pyridine were added and the reaction then proceeded to completion with product appearing at 2.21 539.08. The reaction was concentrated and diluted in methylene chloride for purification by combiflash using a 0-100 percent hexanes/ethyl acetate gradient to give pure product. ES (+) MS m/e=539.08

Into a Vial was dissolved Trifluoro-methanesulfonic acid 8-{[1-(3,4-difluoro-benzyl)-2-oxo-1,2-dihydro-pyridine-3-carbonyl]-amino}-naphthalen-2-yl ester (0.092 g, 0.17 mmol;) and 1-Benzenesulfonyl-3-(4,4,5,5-tetramethyl-1,3, 2-dioxaborolan-2-yl)-1H-pyrrolo[2,3-b]pyridine (60 mg, 0.2 mmol;) and [1,1'-Bis(diphenylphosphino)ferrocene]dichloropalladium(II), complex with dichloromethane (1:1) (17 mg, 0.021 mmol; Strem;) in 1,4-Dioxane (2.20 mL, 28.2 mmol; Acros;). To this was added 2.0 M of Sodium carbonate in water (0.55 mL). The reaction was purged with Ar and sealed. The reaction was heated at 100° C. under an atmosphere of Argon for 2 hours. LC-MS showed the formation of product at 2.31 with the correct mass 647.30. The reaction was worked up by dissolving in methylene chloride then washing 1× with citric acid, 1× with saturated bicarbonate and 1× with brine before drying with magnesium sulfate and concentrating to give the crude product. The crude was dissolved in methylene chloride and purified by combiflash using a 0-100 hexanes/ethyl acetate gradient. ES (+) MS m/e=647.30.

1-(3,4-Difluoro-benzyl)-2-oxo-1,2-dihydro-pyridine-3-carboxylic acid [7-(1-benzenesulfonyl-1H-pyrrolo[2,3-b]pyridin-3-yl)-naphthalen-1-yl]-amide (0.035 g, 0.000054 mol;) was dissolved in Methylene chloride (2 g, 0.02 mol;) and 0.5 M of Sodium methoxide in methanol (2 mL) then heated at 80 degrees for 1 hour. LC-MS showed the appearance of product at 1.64 506.91. The crude was concentrated and dissolved in a mixture of methanol and DMSO then directly injected onto the gilson for purification. The pure fractions were combined and concentrated to give the product. ES (+) MS m/e=506.91; (400 MHz, DMSO-d6) δ ppm 5.43 (s, 2H), 6.76 (t, 1H, J=8 Hz), 6.98 (d, 1H, J=8 Hz), 7.08 (m, 1H), 7.25 (m, 1H), 7.36-7.6 (m, 3H), 8.01 (d, 1H, J=8 Hz), 8.14 (s, 1H), 8.27 (m, 2H), 8.35 (m, 2H), 8.49 (s, 1H), 8.60 (m, 1H), 8.80 (d, 1H, J=8 Hz), 12.10 (s. 1H), 12.63 (s, 1H).

104.3 1-(3,4-Difluoro-benzyl)-2-oxo-1,2-dihydro-pyridine-3-carboxylic acid [5-(1H-pyrrolo[2,3-b]pyridin-3-yl)-1H-indazol-3-yl]-amide 1-(3,4-Difluoro-benzyl)-2-oxo-1,2-dihydro-pyridine-3-carboxylic acid (0.150 g, 0.000566 mol;), N,N,N',N'-Tetramethyl-O-(7-azabenzotriazol-1-yl)uronium Hexafluorophosphate (0.24 g, 0.00062 mol;), N,N-Diisopropylethylamine (500 uL, 0.003 mol;), and N,N-Dimethylformamide (6.6 mL, 0.085 mol;) were added to a 50 mL round bottom and stirred for 10 to 15 minutes then 5-Bromo-1H-indazol-3-ylamine (JW pharmlab) (0.12 g, 0.00056 mol;) was added. LC-MS showed the formation of product at 1.77 458.80. The crude was directly injected onto the Gilson for purification to give 135 mgs of pure product. ES (+) MS m/e=458.80

1-(3,4-Difluoro-benzyl)-2-oxo-1,2-dihydro-pyridine-3-carboxylic acid (5-bromo-1H-indazol-3-yl)-amide (0.135 g, 0.000294 mol;) was dissolved in Tetrahydrofuran (10 mL, 0.1 mol;) and cooled to 0 C then sodium hydride, 60% in mineral oil (60:40, Sodium hydride:Mineral Oil, 29 mg) was added. The reaction was allowed to stir for a couple of minutes then [β-(Trimethylsilyl)ethoxy]methyl chloride (57 uL, 0.00032 mol;) was added. After 2 hours LC-MS showed completion of the reaction 2.40 589.07. The reaction was worked up by dilution with methylene chloride then washing 1× with saturated bicarbonate, 1× with 5% citric acid and 1× with brine. The organic layer was dried with magnesium sulfate and then concentrated. The concentrated material was dissolved in methylene chloride and then purified by combiflash using a 0-100 hexanes/ethyl acetate gradient to give 123 mgs of pure product. ES (+) MS m/e=589.07

1-(3,4-Difluoro-benzyl)-2-oxo-1,2-dihydro-pyridine-3-carboxylic acid [5-(1-benzenesulfonyl-1H-pyrrolo[2,3-b]pyridin-3-yl)-1-(2-trimethylsilanyl-ethoxymethyl)-1H-indazol-3-yl]-amide Into a Vial was dissolved 1-(3,4-Difluoro-benzyl)-2-oxo-1,2-dihydro-pyridine-3-carboxylic acid [5-bromo-1-(2-trimethylsilanyl-ethoxymethyl)-1H-indazol-3-yl]-amide (0.123 g, 0.209 mmol;) and 1-Benzenesulfonyl-3-(4,4,5,5-tetramethyl-1,3,2-dioxaborolan-2-yl)-1H-pyrrolo[2,3-b]pyridine (88 mg, 0.23 mmol;) and [1,1'-Bis(diphenylphosphino)ferrocene]dichloropalladium(II), complex with dichloromethane (1:1) (21 mg, 0.025 mmol; Strem;) in 1,4-Dioxane (2.69 mL, 34.4 mmol; Acros;). To this was added 2.0 M of Sodium carbonate in water (0.67 mL). The reaction was purged with Ar and sealed. The reaction was heated at 100° C. under an atmosphere of Argon for 2 hours. LC-MS showed the formation of product at 2.41 with the correct mass 767.28. The reaction was worked up by dissolving in methylene chloride then washing 1× with citric acid, 1× with saturated bicarbonate and 1× with brine before drying with magnesium sulfate and concentrating to give the crude product. The crude was then purified by combiflash using a 0-100 percent hex/ea gradient to give 66 mg of pure product. ES (+) MS m/e=767.28

1-(3,4-Difluoro-benzyl)-2-oxo-1,2-dihydro-pyridine-3-carboxylic acid [5-(1H-pyrrolo[2,3-b]pyridin-3-yl)-1-(2-trimethylsilanyl-ethoxymethyl)-1H-indazol-3-yl]-amide 1-(3,4-Difluoro-benzyl)-2-oxo-1,2-dihydro-pyridine-3-carboxylic acid [5-(1-benzenesulfonyl-1H-pyrrolo[2,3-b]pyridin-3-yl)-1-(2-trimethylsilanyl-ethoxymethyl)-1H-indazol-3-yl]-amide (0.066 g, 0.000086 mol;) was dissolved in Methylene chloride (4 mL, 0.06 mol;) and 0.5 M of Sodium methoxide in methanol (4 mL). The reaction was heated at 80 C for 1 hour and LC-MS showed the formation of product at 1.81 627.21. The crude material was concentrated and dissolved in a mixture of methanol and DMSO and the injected on the Gilson for purification. ES (+) MS m/e=627.21

1-(3,4-Difluoro-benzyl)-2-oxo-1,2-dihydro-pyridine-3-carboxylic acid [5-(1H-pyrrolo[2,3-b]pyridin-3-yl)-1-(2-trimethylsilanyl-ethoxymethyl)-1H-indazol-3-yl]-amide (40 mg, 0.00006 mol;) was dissolved in Ethanol (3 mL, 0.05 mol;) and Hydrogen chloride (1 mL, 0.03 mol;) was added. The reaction was heated at 100 C. for 1.5 hours. A precipitate was formed that was assayed by LC-MS. The precipitate contained product and it was therefore filtered and an NMR was taken indicating the precipitate was pure product. ES (+) MS m/e=496.56; (400 MHz, DMSO-d6) δ ppm 5.33 (s, 2H), 6.72 (t, 1H, J=8 Hz), 7.27 (m, 2H), 7.41-7.58 (m, 3H), 7.72 (d, 1H, J=8 Hz), 7.87 (s, 1H), 8.32-8.45 (m, 4H), 8.60 (m, 1H), 12.10 (s. 1H), 12.35 (s, 1H).

Example 105

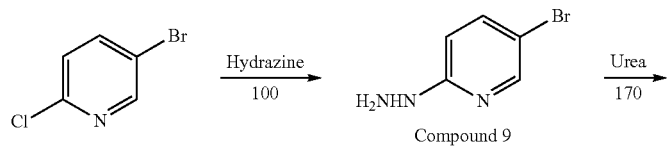

Compound 9

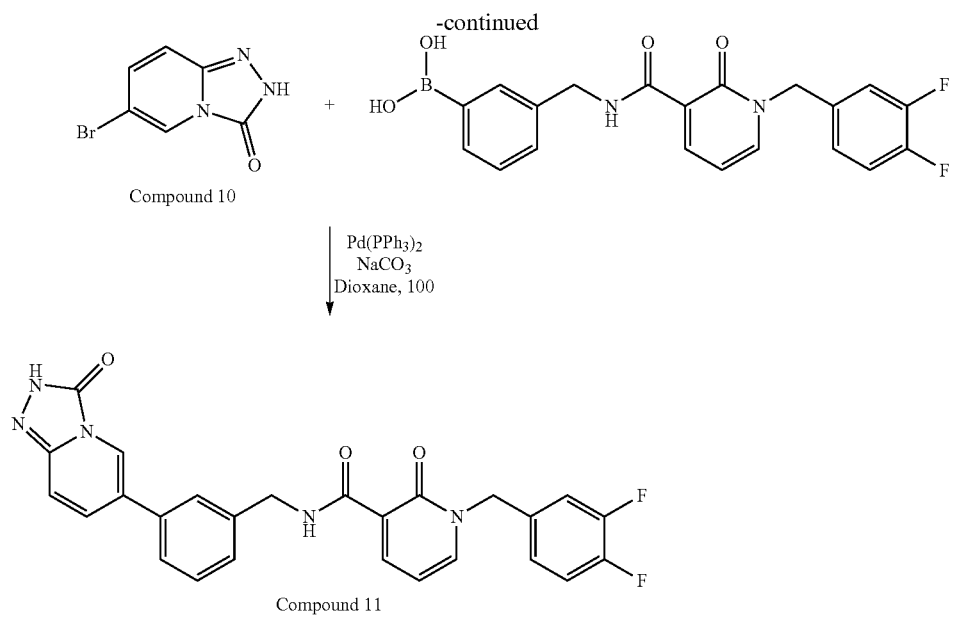

Compound 10

Pd(PPh₃)₂
NaCO₃
Dioxane, 100

Compound 11

105.1 1-(3,4-Difluoro-benzyl)-2-oxo-1,2-dihydro-pyridine-3-carboxylic acid 3-(3-oxo-2,3-dihydro-[1,2,4]triazolo[4,3-a]pyridin-6-yl)-benzylamide 5-Bromo-2-chloro-pyridine (3.5 g, 0.018 mol) was dissolved in hydrazine (20 mL) and heated at 100 degrees for 6 hours. The reaction was then diluted with water and extracted with ether 2×. The aqueous was then dried to remove the hydrazine then brought back up in water. The pH was made basic by addition of solid KOH then extracted 2× with ether. The ether layers were then combined, dried with magnesium sulfate, and concentrated to give 2.25 grams of product which was brought on directly to the next step. ES (+) MS m/e=189.01

(5-Bromo-pyridin-2-yl)-hydrazine (2.25 g, 0.021 mol) was placed in a sealed tube with urea and heated for 2 hrs at 170. The crude was dissolved in methanol and purified by preparative HPLC using a 5-40% 0.1% TFA water/0.1% TFA acetonitrile gradient. ES (+) MS m/e=213.88

3-({[1-(3,4-Difluoro-benzyl)-2-oxo-1,2-dihydro-pyridine-3-carbonyl]-amino}-methyl)-boronic acid (0.150 g, 0.000377 mol) was dissolved in dioxane and 6-Bromo-2H-[1,2,4]triazolo[4,3-a]pyridin-3-one (54 mg, 0.00025 mol), Tetrakis(triphenylphosphine)palladium(0) (0.03 g, 0.00002 mol), and 2 M of Sodium carbonate in Water (0.4 mL) were added. The reaction was then placed over a bed of argon and capped. The reaction was heated at 100 degrees for 4-5 hours. LC-MS shows the appearance of product, at approximately the same retention time as the boronic acid. To push the reaction to completion more bromide was added and the reaction was stirred o/n. Some of the boronic acid still remained but purification was attempted anyway. Purification was done by direct injection onto the gilson preparative HPLC using a 30-90 gradient over 14 minutes. Separation was seen and several clean fractions were combined and dried to give the pure product. ES (+) MS m/e=488.07 NMR (400 MHz, DMSO-d6) ™ ppm 4.54 (d, 2H, J=7 Hz), 5.88 (s, 1H), 5.21 (s, 2H), 6.60 (t, 1H, J=8 Hz), 7.17 (m, 1H), 7.26 (m, 1H), 7.30-7.50 (m, 3H), 7.56 (m, 1H), 7.64 (s, 1H), 8.24 (m, 1H), 8.41 (m, 1H), 10.04 (t, 1H, J=6 Hz).

105.2 1-(3,4-Difluoro-benzyl)-2-oxo-1,2-dihydro-pyridine-3-carboxylic acid 3-imidazo[1,2-a]pyridin-6-yl-benzylamide 3-({[1-(3,4-Difluoro-benzyl)-2-oxo-1,2-dihydro-pyridine-3-carbonyl]-amino}-methyl)-boronic acid (Scheme X) (0.0758 g, 0.000190 mol;) was dissolved in dioxane and 6-Bromoimidazo[1,2-a]pyridine (25 mg, 0.00013 mol;), Tetrakis(triphenylphosphine)palladium(0) (0.01 g, 0.00001 mol;), and 2 M of Sodium carbonate in water (0.2 mL) were added. The reaction was then placed over a bed of argon and capped. The reaction was heated at 100 degrees for 4-5 hours. LC-MS shows the appearance of product at 1.22 with the correct mass 471.08. Purification was done by direct injection onto the Gilson preparative HPLC using a 10-90 gradient over 14 minutes. Separation was seen and several clean fractions were combined and dried to give the pure product. ES (+) MS m/e=471.08; NMR (400 MHz, DMSO-d6) δ ppm 4.63 (d, 2H, J=7 Hz), 5.22 (s, 2H), 6.60 (t, 1H, J=8 Hz), 7.17 (m, 1H), 7.30-7.50 (m, 3H), 7.54 (t, 1H, J=8 Hz), 7.67 (m, 1H), 7.73 (m, 1H), 8.01 (d, 1H, J=8 Hz), 8.3-8.15 (m, 4H), 8.4 (dd. 1H), 9.24 (s, 1H), 10.09 (t, 1H, J=7 Hz).

Example 106

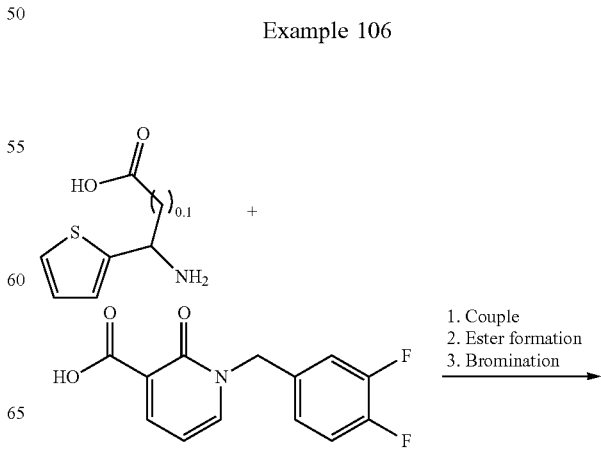

1. Couple
2. Ester formation
3. Bromination

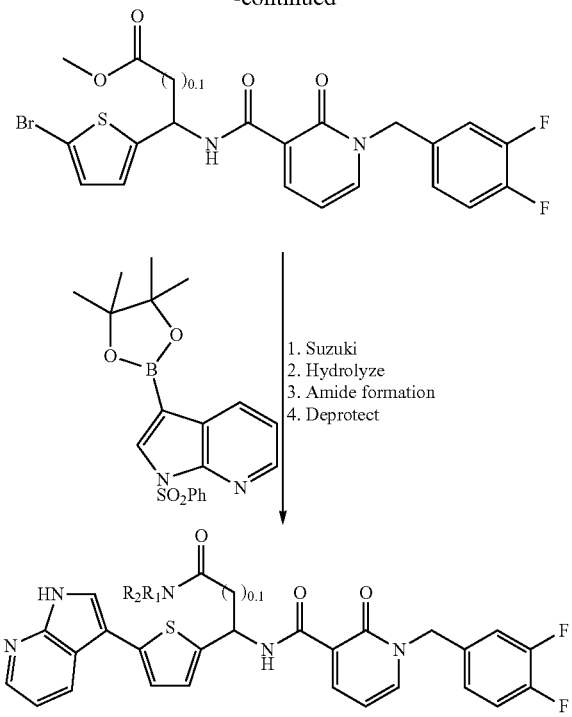

(R)-3-(1-(3,4-difluorobenzyl)-2-oxo-1,2-dihydropyridine-3-carboxamido)-3-(thiophen-2-yl)propanoic acid Into a round bottom was added 1-(3,4-Difluoro-benzyl)-2-oxo-1,2-dihydro-pyridine-3-carboxylic acid (0.400 g, 0.00151 mol;), N,N,N',N'-Tetramethyl-O-(7-azabenzotriazol-1-yl)uronium Hexafluorophosphate (0.573 g, 0.00151 mol;), Methylene chloride (14 mL, 0.23 mol;), and N,N-Diisopropylethylamine (1310 uL, 0.00754 mol;). The reaction was stirred until all contents were dissolved and pre-activation was complete. (R)-3-Amino-3-thiophen-2-yl-propionic acid (0.28 g, 0.0016 mol;) was added and the reaction was allowed to stir for 1-2 hours then an LC-MS was taken which showed product at 1.47. The reaction was worked up by washing with citric acid and brine then drying with magnesium sulfate. The crude concentrated reaction was taken on directly to the next step. ES (+) MS m/e=419.08

(R)-3-{[1-(3,4-Difluoro-benzyl)-2-oxo-1,2-dihydro-pyridine-3-carbonyl]-amino}-3-thiophen-2-yl-propionic acid methyl ester (R)-3-(1-(3,4-difluorobenzyl)-2-oxo-1,2-dihydropyridine-3-carboxamido)-3-(thiophen-2-yl)propanoic acid (0.631 g, 0.00151 mol;) was dissolved in Methanol (10 mL, 0.2 mol;) and cooled to 0 C. Thionyl chloride (600 uL, 0.008 mol;) was then added and the reaction was allowed to warm up o/n. LC-MS showed the formation of product at 1.63 432.97. The reaction was diluted with methylene chloride then washed 1× with sodium bicarbonate and 1× with brine before drying and concentration. The reaction was then concentrated and dissolved in methylene chloride for purification by combiflash using a 0-100 hexanes/ethyl acetate gradient. ES (+) MS m/e=432.97

(R)-3-(5-Bromo-thiophen-2-yl)-3-{[1-(3,4-difluoro-benzyl)-2-oxo-1,2-dihydro-pyridine-3-carbonyl]-amino}-propionic acid methyl ester (R)-3-{[1-(3,4-Difluoro-benzyl)-2-oxo-1,2-dihydro-pyridine-3-carbonyl]-amino}-3-thiophen-2-yl-propionic acid methyl ester (0.420 g, 0.000971 mol;) was dissolved in N,N-Dimethylformamide (20 mL, 0.2 mol;) and N-Bromosuccinimide (0.19 g, 0.0011 mol;) was added. The reaction was allowed to stir o/n and LC-MS showed formation of product at 1.87 510.95. The reaction was diluted with methylene chloride and washed 1× with saturated bicarbonate, 1× with 5% citric acid, and 1× with brine. The organic layer was then dried with magnesium sulfate and concentrated to give the crude material. The crude was dissolved in methylene chloride and purified by combiflash 0-100% hexanes/ethyl acetate to give the pure product. ES (+) MS m/e=510.95

(R)-3-[5-(1-Benzenesulfonyl-1H-pyrrolo[2,3-b]pyridin-3-yl)-thiophen-2-yl]-3-{[1-(3,4-difluoro-benzyl)-2-oxo-1,2-dihydro-pyridine-3-carbonyl]-amino}-propionic acid methyl ester Into a Vial was dissolved (R)-3-(5-Bromo-thiophen-2-yl)-3-{[1-(3,4-difluoro-benzyl)-2-oxo-1,2-dihydro-pyridine-3-carbonyl]-amino}-propionic acid methyl ester (0.080 g, 0.16 mmol;), 1-Benzenesulfonyl-3-(4,4,5,5-tetramethyl-1,3,2-dioxaborolan-2-yl)-1H-pyrrolo[2,3-b]pyridine (50 mg, 0.1 mmol;) and [1,1'-Bis(diphenylphosphino)ferrocene]dichloropalladium(II), complex with dichloromethane (1:1) (17 mg, 0.021 mmol; Strem;) in 1,4-Dioxane (2.21 mL, 28.4 mmol; Acros;). To this was added 2.0 M of Sodium carbonate in water (0.55 mL). The reaction was purged with Argon and sealed. The reaction was heated at 100° C. under an atmosphere of Argon for 2 hours. LC-MS showed the formation of product at 1.97 with the correct mass 689.16. The reaction was worked up by dissolving in methylene chloride then washing 1× with citric acid, 1× with saturated bicarbonate, and 1× with brine before drying with magnesium sulfate and concentrating to give the crude product. The crude was dissolved in dichloromethane and the purified by combiflash using a 0-100 percent hexanes/ea gradient to give the pure product. ES (+) MS m/e=689.16

(R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (R)-3-[5-(1-Benzenesulfonyl-1H-pyrrolo[2,3-b]pyridin-3-yl)-thiophen-2-yl]-3-{[1-(3,4-difluoro-benzyl)-2-oxo-1,2-dihydro-pyridine-3-carbonyl]-amino}-propionic acid methyl ester (0.050 g, 0.000072 mol;) was dissolved in 0.5 M of Sodium methoxide in methanol (3 mL) and Methylene chloride (3 g, 0.04 mol;). The reaction was heated at 75 C for 1 hour. LC-MS showed the disappearance of starting material and the appearance of product at 1.25 535.55. Some methyl ester and acid were seen but by the time it was injected on gilson only acid was present. The reaction was concentrated and dissolved in DMSO and methanol 1:1 for purification by Gilson Preparative HPLC. Pure fractions were combined and concentrated. ES (+) MS m/e=535.55; NMR (400 MHz, DMSO-d6) δ ppm 2.98 (d, 2H, J=7 Hz), 5.22 (s, 2H,), 5.66 (m, 1H), 6.66 (t, 1H, J=8 Hz), 7.03 (d, 1H, J=3 Hz), 7.14-7.20 (m, 2H), 7.22 (d, 1H, J=4 Hz), 7.38-7.49 (m, 2H), 7.81 (m, 1H), 8.2-8.25 (m, 2H), 8.29 (m, 1H), 8.4 (dd. 1H), 10.27 (d, 1H)

1-(3,4-Difluoro-benzyl)-2-oxo-1,2-dihydro-pyridine-3-carboxylic acid {(R)-2-dimethylcarbamoyl-1-[5-(1H-pyrrolo[2,3-b]pyridin-3-yl)-thiophen-2-yl]-ethyl}-amide (R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (0.026 g, 0.000049 mol;) was dissolved in N,N-Dimethylformamide (2 mL, 0.03 mol;) and 2.0 M of Dimethylamine in Tetrahydrofuran (0.243 mL) then N,N,N',N'-Tetramethyl-O-(7-azabenzotriazol-1-yl)uronium Hexafluorophosphate (0.024 g, 0.000063 mol;) was added. The reaction was allowed to stir for 2 hours and LC-MS showed disappearance of starting material and appearance of product at 1.28 562.10. The reaction was purified by Gilson Preparative HPLC and the pure fractions were concentrated. ES (+) MS m/e=562.10; NMR (400 MHz, DMSO-d6) δ ppm 2.79 (s, 3H), 3.00 (s, 3H), 3.06 (d, 2H, J=7 Hz), 5.22 (d, 2H, J=5 Hz), 5.7 (m, 1H), 6.60 (t, 1H, J=8 Hz), 7.00 (d, 1H, J=3 Hz), 7.14-7.21 (m, 3H), 7.38-7.49 (m, 2H), 7.54 (t, 1H, J=8 Hz), 7.79 (m, 1H), 8.2-8.25 (m, 2H), 8.29 (m, 1H), 8.4 (dd. 1H), 10.29 (d, 1H)

1-(3,4-Difluoro-benzyl)-2-oxo-1,2-dihydro-pyridine-3-carboxylic acid {(R)-2-methylcarbamoyl-1-[5-(1H-pyrrolo[2,3-b]pyridin-3-yl)-thiophen-2-yl]-ethyl}-amide (R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (0.026 g, 0.000049 mol;) was dissolved in N,N-Dimethylformamide (2 mL, 0.03 mol;) and 2.0 M of Methylamine in Tetrahydrofuran (0.2432 mL) and N,N,N',N'-Tetramethyl-O-(7-azabenzotriazol-1-yl) uronium Hexafluorophosphate (0.024 g, 0.000063 mol;) were added. The reaction was checked after 2 hours and it showed that both product and starting material were present. The reaction was pushed by further addition of methylamine and HATU, but the reaction could not be pushed past 60-70 percent completion. The reaction was therefore worked up by concentration then dissolving in methylene chloride and washing 1× with saturated bicarbonate, and 1× with brine before drying with magnesium sulfate and concentration. The crude showed very little starting material left after workup, the acid was most likely removed by the bicarb wash. The crude was dissolved in DMSO and injected onto the Gilson for HPLC purification to give the pure product at 1.20 548.54. ES (+) MS m/e=548.54; NMR (400 MHz, DMSO-d6) δ ppm 2.55 (s, 3H), 2.78 (d, 2H, J=7 Hz), 5.22 (m, 2H), 6.66 (t, 1H, J=8 Hz), 6.97 (d, 1H, J=3 Hz), 7.14-7.21 (m, 3H), 7.38-7.49 (m, 2H), 7.79 (m, 1H), 8.2-8.25 (m, 2H), 8.29 (m, 1H), 8.4 (dd. 1H), 10.25 (d, 1H), 11.97 (s, 1H)

1-(3,4-Difluoro-benzyl)-2-oxo-1,2-dihydro-pyridine-3-carboxylic acid {(R)-2-carbamoyl-1-[5-(1H-pyrrolo[2,3-b]pyridin-3-yl)-thiophen-2-yl]-ethyl}-amide (R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (0.026 g, 0.000049 mol;) was dissolved in N,N-Dimethylformamide (2 g, 0.03 mol;) and Ammonium chloride (0.0065 g, 0.00012 mol;), N,N-Diisopropylethylamine (42.4 uL, 0.000243 mol;), and N,N,N',N'-Tetramethyl-O-(7-azabenzotriazol-1-yl)uronium Hexafluorophosphate (0.024 g, 0.000063 mol;) were added. After 2 hours the reaction was found to be complete by LC-MS 1.17 534.06. The crude reaction was directly injected onto the Gilson for purification to give the pure product. ES (+) MS m/e=534.06; NMR (400 MHz, DMSO-d6) δ ppm 2.78 (d, 2H, J=7 Hz), 5.22 (m, 2H), 5.66 (m, 1H), 6.66 (t, 1H, J=8 Hz), 6.99 (d, 1H, J=3 Hz), 7.14-7.21 (m, 3H), 7.38-7.49 (m, 3H), 7.79 (m, 1H), 8.2-8.25 (m, 2H), 8.29 (m, 1H), 8.4 (dd. 1H), 10.22 (d, 1H), 11.95 (s, 1H)

1-(3,4-Difluoro-benzyl)-2-oxo-1,2-dihydro-pyridine-3-carboxylic acid {(R)-2-ethylcarbamoyl-1-[5-(1H-pyrrolo[2,3-b]pyridin-3-yl)-thiophen-2-yl]-ethyl}-amide (R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (0.040 g, 0.000075 mol;) was dissolved in N,N-Dimethylformamide (3 mL, 0.04 mol;) and Ethylamine (7 mg, 0.0001 mol;) then N,N,N',N'-Tetramethyl-O-(7-azabenzotriazol-1-yl)uronium Hexafluorophosphate (0.037 g, 0.000097 mol;) was added. The reaction was allowed to stir for 2 hours and LC-MS showed disappearance of starting material and appearance of product at 1.28 562.10. The reaction was purified by Gilson Preparative HPLC and the pure fractions were concentrated. ES (+) MS m/e=562.10; NMR (400 MHz, DMSO-d6) δ ppm 0.92 (t, 3H, J=7 Hz), 2.76 (m, 2H), 2.95 (m, 2H), 5.22 (m, 2H), 5.66 (m, 1H), 6.66 (t, 1H, J=8 Hz), 6.99 (d, 1H, J=3 Hz), 7.14-7.21 (m, 3H), 7.38-7.49 (m, 2H), 7.79 (m, 1H), 8.2-8.25 (m, 2H), 8.29 (m, 1H), 8.4 (dd. 1H), 10.22 (d, 1H), 11.95 (s, 1H)

1-(3,4-Difluoro-benzyl)-2-oxo-1,2-dihydro-pyridine-3-carboxylic acid {(R)-2-propylcarbamoyl-1-[5-(1H-pyrrolo[2,3-b]pyridin-3-yl)-thiophen-2-yl]-ethyl}-amide (R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (0.040 g, 0.000075 mol;) was dissolved in N,N-Dimethylformamide (3 mL, 0.04 mol;) and 1-Propanamine (9 mg, 0.0001 mol;) then N,N,N',N'-Tetramethyl-O-(7-azabenzotriazol-1-yl)uronium Hexafluorophosphate (0.037 g, 0.000097 mol;) was added. The reaction was allowed to stir for 2 hours and LC-MS showed disappearance of starting material and appearance of product at 1.28 575.98. ES (+) MS m/e=575.98; NMR (400 MHz, DMSO-d6) δ ppm 0.72 (t, 3H, J=7 Hz), 1.31 (q, 2H, J=7 Hz), 2.76 (m, 2H), 2.95 (m, 2H), 5.22 (m, 2H), 5.66 (m, 1H), 6.66 (t, 1H, J=8 Hz), 6.99 (d, 1H, J=3 Hz), 7.14-7.21 (m, 3H), 7.38-7.49 (m, 2H), 7.79 (m, 1H), 8.2-8.25 (m, 2H), 8.29 (m, 1H), 8.4 (dd. 1H), 10.22 (d, 1H), 11.95 (s, 1H)

1-(3,4-Difluoro-benzyl)-2-oxo-1,2-dihydro-pyridine-3-carboxylic acid {(R)-2-cyclopropylcarbamoyl-1-[5-(1H-pyrrolo[2,3-b]pyridin-3-yl)-thiophen-2-yl]-ethyl}-amide (R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (0.040 g, 0.000075 mol;) was dissolved in N,N-Dimethylformamide (3 mL, 0.04 mol;) and Cyclopropylamine (20 uL, 0.0004 mol;) then N,N,N',N'-Tetramethyl-O-(7-azabenzotriazol-1-yl)uronium Hexafluorophosphate (0.037 g, 0.000097 mol;) was added. The reaction was allowed to stir for 2 hours and LC-MS showed disappearance of starting material and appearance of product at 1.28 573.87. The reaction was purified by Gilson Preparative HPLC and the pure fractions were concentrated. ES (+) MS m/e=573.87; NMR (400 MHz, DMSO-d6) δ ppm 0.28 (m, 2H), 0.54 (m, 2H), 2.55 (m, 1H), 2.72 (m, 2H), 5.22 (m, 2H), 5.66 (m, 1H), 6.60 (t, 1H, J=8 Hz), 6.96 (d, 1H, J=3 Hz), 7.14-7.21 (m, 3H), 7.38-7.49 (m, 2H), 7.79 (m, 1H), 8.2-8.25 (m, 2H), 8.29 (m, 1H), 8.4 (dd. 1H), 10.22 (d, 1H), 11.95 (s, 1H)

1-(3,4-Difluoro-benzyl)-2-oxo-1,2-dihydro-pyridine-3-carboxylic acid {(R)-2-(2-methoxy-ethylcarbamoyl)-1-[5-(1H-pyrrolo[2,3-b]pyridin-3-yl)-thiophen-2-yl]-ethyl}-amide (R)-3-{[1-(3,4-Difluoro-benzyl)-2-oxo-1,2-dihydro-pyridine-3-carbonyl]-amino}-3-[5-(1H-pyrrolo[2,3-b]pyridin-3-yl)-thiophen-2-yl]-propionic acid (0.040 g, 0.000075 mol;) was dissolved in N,N-Dimethylformamide (3 mL, 0.04 mol;) and 2-Methoxyethylamine (30 uL, 0.0004 mol;) then N,N,N',N'-Tetramethyl-O-(7-azabenzotriazol-1-yl)uronium Hexafluorophosphate (0.037 g, 0.000097 mol;) was added. The reaction was allowed to stir for 2 hours and LC-MS showed disappearance of starting material and appearance of product at 1.28 592.07. The reaction was purified by Gilson Preparative HPLC and the pure fractions were concentrated. ES (+) MS m/e=592.07; NMR (400 MHz, DMSO-d6) δ ppm 2.80 (m, 2H), 3.17 (m, 5H), 3.25 (t, 2H, J=7 Hz), 5.22 (m, 2H), 5.66 (m, 1H), 6.60 (t, 1H, J=8 Hz), 6.96 (d, 1H, J=3

Hz), 7.14-7.21 (m, 3H), 7.38-7.49 (m, 2H), 7.79 (m, 1H), 8.2-8.25 (m, 2H), 8.29 (m, 1H), 8.4 (dd. 1H), 10.22 (d, 1H), 11.95 (s, 1H)

{[1-(3,4-Difluoro-benzyl)-2-oxo-1,2-dihydro-pyridine-3-carbonyl]-amino}-thiophen-2-yl-acetic acid 1-(3,4-Difluoro-benzyl)-2-oxo-1,2-dihydro-pyridine-3-carboxylic acid (0.23 g, 0.00088 mol;) was dissolved in N,N-Dimethylformamide (9 mL, 0.1 mol;) and N,N-Diisopropylethylamine (800 uL, 0.004 mol;), and N,N,N',N'-Tetramethyl-O-(7-azabenzotriazol-1-yl)uronium Hexafluorophosphate (0.37 g, 0.00097 mol;) were added. After 5 minutes preactivation Amino-thiophen-2-yl-acetic acid (0.266 g, 0.00169 mol;) was added. Workup consisted of rinsing with 5% citric acid then brine after dissolving the crude in ethyl acetate. The organic layer was then dried with magnesium sulfate and concentrated. The crude material was brought on directly to the next step. ES (+) MS m/e=404.81

{[1-(3,4-Difluoro-benzyl)-2-oxo-1,2-dihydro-pyridine-3-carbonyl]-amino}-thiophen-2-yl-acetic acid methyl ester {[1-(3,4-Difluoro-benzyl)-2-oxo-1,2-dihydro-pyridine-3-carbonyl]-amino}-thiophen-2-yl-acetic acid (0.360 g, 0.000890 mol;) was dissolved in Methanol (10 mL, 0.2 mol;) then cooled to 0. Thionyl chloride (325 uL, 0.00445 mol;) was added and the reaction was allowed to stir o/n. The crude was concentrated then dissolved in ethyl acetate and washed with 1× citric acid, 1× saturated bicarbonate, and 1× brine. The ethyl acetate was then dried with magnesium sulfate and concentrated. The crude was then dissolved in methylene chloride and injected onto the combiflash for purification. The compound eluted at almost 100% EA using a 0-100% hexanes ethyl acetate gradient. Pure fractions were concentrated to give the pure product. ES (+) MS m/e=418.86.

(5-Bromo-thiophen-2-yl)-{[1-(3,4-difluoro-benzyl)-2-oxo-1,2-dihydro-pyridine-3-carbonyl]-amino}-acetic acid methyl ester {[1-(3,4-Difluoro-benzyl)-2-oxo-1,2-dihydro-pyridine-3-carbonyl]-amino}-thiophen-2-yl-acetic acid methyl ester (0.190 g, 0.000454 mol;) was dissolved in N,N-Dimethylformamide (6 mL, 0.07 mol;) and N-Bromosuccinimide (0.089 g, 0.00050 mol;) was added. The reaction was allowed to stir at room temperature o/n. LC-MS showed the formation of product at 1.89 498.45. The reaction was concentrated and dissolved in ethyl acetate. The reaction was then washed 1× with saturated bicarbonate and 1× with brine before drying with magnesium sulfate and concentrating. The crude was then dissolved in methylene chloride and injected onto the combiflash and eluted using a 0-100% hexanes ethyl acetate gradient. The pure fractions were combined and concentrated to give the product. ES (+) MS m/e=498.45

[5-(1-Benzenesulfonyl-1H-pyrrolo[2,3-b]pyridin-3-yl)-thiophen-2-yl]-{[1-(3,4-difluoro-benzyl)-2-oxo-1,2-dihydro-pyridine-3-carbonyl]-amino}-acetic acid Into a Vial was dissolved (5-Bromo-thiophen-2-yl)-{[1-(3,4-difluoro-benzyl)-2-oxo-1,2-dihydro-pyridine-3-carbonyl]-amino}-acetic acid methyl ester (0.173 g, 0.348 mmol;) and [A] 1-Benzenesulfonyl-3-(4,4,5,5-tetramethyl-1,3,2-dioxaborolan-2-yl)-1H-pyrrolo[2,3-b]pyridine (160 mg, 0.42 mmol;) and [1,1'-Bis(diphenylphosphino)ferrocene]dichloropalladium(II), complex with dichloromethane (1:1) (45 mg, 0.056 mmol; Strem;) in 1,4-Dioxane (5.92 mL, 75.8 mmol; Acros;). To this was added 2.0 M of Sodium carbonate in water (1.5 mL). The reaction was purged with Ar and sealed. The reaction was heated at 100° C. under an atmosphere of Argon for 2 hours. LC-MS showed the formation of the acid product at 1.80 with the correct mass 660.93, the methyl ester was hydrolyzed under the reaction conditions. The reaction was worked up by dissolving in methylene chloride then washing 1× with citric acid, and 1× with brine before drying with magnesium sulfate and concentrating to give the crude product. The crude was dissolved in dichloromethane and the purified by combiflash using a 0-100 percent hexanes/ea gradient to give the pure product. ES (+) MS m/e=660.93

{[1-(3,4-Difluoro-benzyl)-2-oxo-1,2-dihydro-pyridine-3-carbonyl]-amino}-[5-(1H-pyrrolo[2,3-b]pyridin-3-yl)-thiophen-2-yl]-acetic acid

[5-(1-Benzenesulfonyl-1H-pyrrolo[2,3-b]pyridin-3-yl)-thiophen-2-yl]-{[1-(3,4-difluoro-benzyl)-2-oxo-1,2-dihydro-pyridine-3-carbonyl]-amino}-acetic acid methyl ester (0.085 g, 0.00012 mol;) was dissolved in Methylene chloride (3 mL, 0.05 mol;) then 0.5 M of Sodium methoxide in methanol (3 mL) was added and the reaction was heated at 75 C for 1 hour. LC-MS showed the disappearance of starting material and the appearance of product at 1.34 520.75. The reaction was concentrated and dissolved in DMSO and methanol 1:1 for purification by Gilson Preparative HPLC. ES (+) MS m/e=520.75

1-(3,4-Difluoro-benzyl)-2-oxo-1,2-dihydro-pyridine-3-carboxylic acid {carbamoyl-[5-(1H-pyrrolo[2,3-b]pyridin-3-yl)-thiophen-2-yl]-methyl}-amide {[1-(3,4-Difluoro-benzyl)-2-oxo-1,2-dihydro-pyridine-3-carbonyl]-amino}-[5-(1H-pyrrolo[2,3-b]pyridin-3-yl)-thiophen-2-yl]-acetic acid (0.039 g, 0.000075 mol;) was dissolved in N,N-Dimethylformamide (3 g, 0.04 mol;) and Ammonium chloride (0.010 g, 0.00019 mol;), N,N-Diisopropylethylamine (65.2 uL, 0.000374 mol;), and N,N,N',N'-Tetramethyl-O-(7-azabenzotriazol-1-yl)uronium Hexafluorophosphate (0.037 g, 0.000097 mol;) were added. After 2 hours the reaction was found to be complete by LC-MS 1.18 520.03. The crude reaction was directly injected onto the Gilson for purification to give the pure product. ES (+) MS m/e=520.03; NMR (400 MHz, DMSO-d6) δ ppm 5.22 (m, 2H), 5.83 (d, 1H, J=8 Hz), 6.60 (t, 1H, J=8 Hz), 7.07 (d, 1H, J=4 Hz), 7.14-7.21 (m, 2H), 7.23 (d, 1H, J=4 Hz) 7.38-7.49 (m, 3H), 7.81 (m, 1H), 8.19-8.30 (m, 3H), 8.37 (dd. 1H), 10.53 (d, 1H), 11.95 (s, 1H)

Example 107

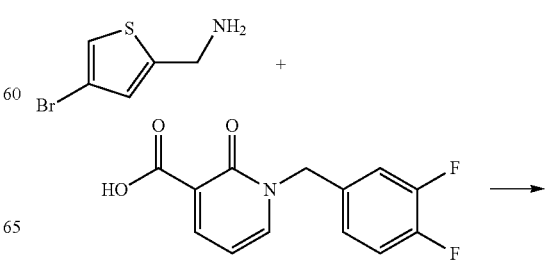

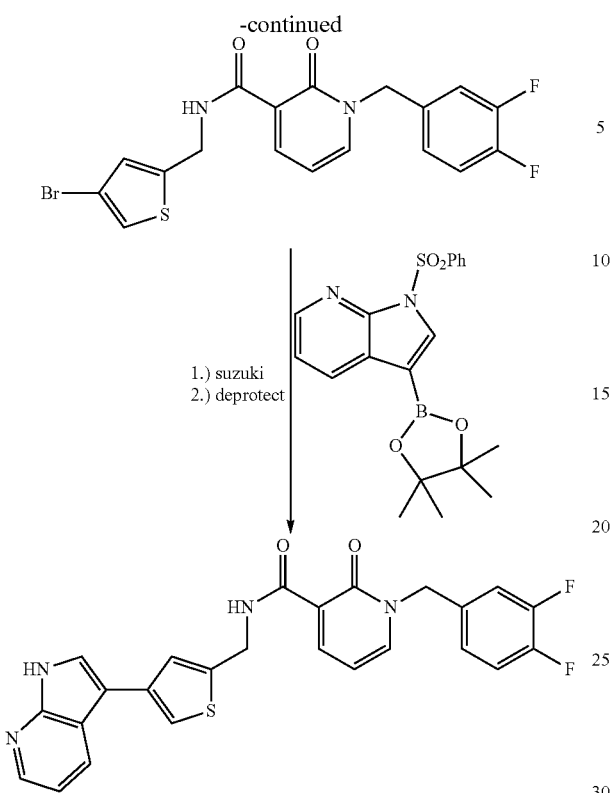

1-(3,4-Difluoro-benzyl)-2-oxo-1,2-dihydro-pyridine-3-carboxylic acid (4-bromo-thiophen-2-ylmethyl)-amide C-(4-Bromo-thiophen-2-yl)-methylamine (0.200 g, 0.00104 mol;), 1-(3,4-Difluoro-benzyl)-2-oxo-1,2-dihydro-pyridine-3-carboxylic acid (0.251 g, 0.000946 mol;), N,N,N',N'-Tetramethyl-O-(7-azabenzotriazol-1-yl)uronium Hexafluorophosphate (0.40 g, 0.0010 mol;), N,N-Diisopropylethylamine (800 uL, 0.005 mol;), and Methylene chloride (9.1 mL, 0.14 mol;) were added to a 50 mL round bottom and stirred for 2 to 3 hours. LC-MS showed the formation of product at 1.78 438.92. Workup consisted of dilution with methylene chloride washing 1× with citric acid, 1× with saturated bicarbonate, and 1× with brine before drying and concentration to give the crude material. The crude was then purified by combiflash 0-100 percent hexanes/Ethyl acetate to give pure material. ES (+) MS m/e=438.92

1-(3,4-Difluoro-benzyl)-2-oxo-1,2-dihydro-pyridine-3-carboxylic acid [4-(1-benzenesulfonyl-1H-pyrrolo[2,3-b]pyridin-3-yl)-thiophen-2-ylmethyl]-amide Into a Vial was dissolved 1-(3,4-Difluoro-benzyl)-2-oxo-1,2-dihydro-pyridine-3-carboxylic acid (4-bromo-thiophen-2-ylmethyl)-amide (0.0953 g, 0.217 mmol;), 1-Benzenesulfonyl-3-(4,4,5,5-tetramethyl-1,3,2-dioxaborolan-2-yl)-1H-pyrrolo[2,3-b]pyridine (100 mg, 0.3 mmol;) and [1,1'-Bis(diphenylphosphino)ferrocene]dichloropalladium(II), complex with dichloromethane (1:1) (28 mg, 0.035 mmol; Strem;) in 1,4-Dioxane (3.69 mL, 47.3 mmol; Acros;). To this was added 2.0 M of Sodium carbonate in water (0.92 mL). The reaction was purged with Ar and sealed. The reaction was heated at 100° C. under an atmosphere of Argon for 2 hours. LC-MS showed the formation of product at 1.80 with the correct mass 661.13. The reaction was worked up by dissolving in methylene chloride then washing 1× with citric acid, 1× with saturated bicarbonate and 1× with brine before drying with magnesium sulfate and concentrating to give the crude product. The crude was then purified by combiflash using a 0-100 percent hex/ea gradient to give pure product. ES (+) MS m/e=661.13

1-(3,4-Difluoro-benzyl)-2-oxo-1,2-dihydro-pyridine-3-carboxylic acid [4-(1H-pyrrolo[2,3-b]pyridin-3-yl)-thiophen-2-ylmethyl]-amide 1-(3,4-Difluoro-benzyl)-2-oxo-1,2-dihydro-pyridine-3-carboxylic acid [4-(1-benzenesulfonyl-1H-pyrrolo[2,3-b]pyridin-3-yl)-thiophen-2-ylmethyl]-amide (0.050 g, 0.000081 mol;) was dissolved in Methylene chloride (3 mL, 0.05 mol;) then 0.5 M of Sodium methoxide in methanol (3 mL) was added and the reaction was heated at 75 C for 1 hour. LC-MS showed the disappearance of starting material and the appearance of product at 1.34 477.10. The reaction was concentrated and dissolved in DMSO and methanol 1:1 for purification by Gilson Preparative HPLC. Pure fractions were combined and concentrated. ES (+) MS m/e=477.10; NMR (400 MHz, DMSO-d6) δ ppm 4.72 (m, 2H), 5.21 (s, 2H), 6.60 (t, 1H, J=8 Hz), 7.19 (m, 2H), 7.37-7.50 (m, 3H), 7.62 (s, 1H), 7.86 (m, 1H), 7.64 (s, 1H), 8.24 (m, 1H), 8.41 (m, 1H), 10.04 (t, 1H, J=6 Hz).

Example 108

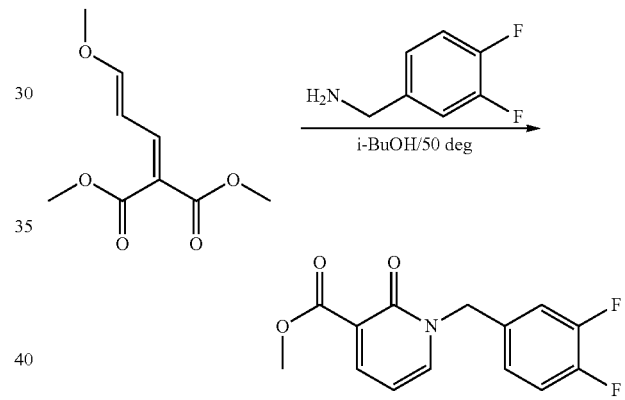

The dimethyl 2-(3-methoxyallylidene) malonate (2.00 g, 10 mmol) was added to a flask in 20 ml of i-BuOH. To the mixture was added 3,4-difluorobenzylamine (1.43 g, 10 mmol). The reaction mixture was heated to 50° C. for 3 h and monitored by LC-MS. The reaction solution was use for the next step reaction without further purification.

Example 109

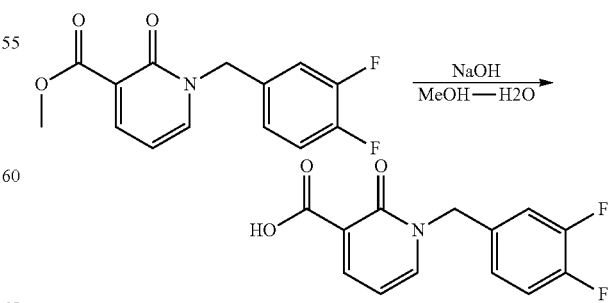

A mixture solvent of methanol in water (50%) was added to the previous reaction solution. 1.1 eq. of 6.0 M NaOH was added and the mixture was heated to 60° C. for overnight. To this mixture was added 1.2 eq. of 4.0 M HCl, and the precipitate was collected and washed three times with water. The solid was dried under vacuum. 2.14 g of product compound was obtained (yield: 94.3%). m/z 266 (M+H$^+$).

Example 110

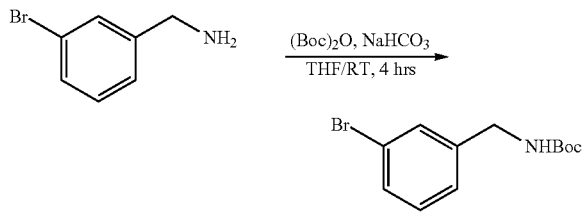

A 100-mL round-bottomed flask, equipped with magnetic stirring bar, was charged with THF (10 mL) and (3-bromophenyl)methanamine (1.86 g, 10 mmol) and sodium bicarbonate (1.68 g, 20 mmol), the di-tert-butyl dicarbonate (2.4 g, 11 mmol) was added. The resulted solution was stirred at room temperature for 3 h. The reaction mixture was filtered and the solvents are then removed under reduced pressure, the residue was pure enough for next step without further purification (2.86 g, yield: 100%). m/z 286 (M+H$^+$).

Example 111 tert-butyl 3-(4,4,5,5-tetramethyl-1,3,2-dioxaborolan-2-yl) benzylcarbamate

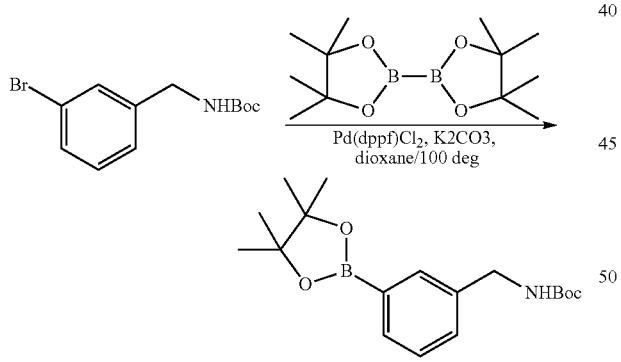

Bis(pinacolato) diboron (588 mg, 2.0 mmol), reactant (286 mg, 1.0 mmol), potassium carbonate (276 mg, 2.0 mmol) and PdCl2(dppf)CH$_2$Cl$_2$ (25 mg, 0.03 mmol) were added to a reaction flask which was purged thoroughly with N$_2$. 10 ml of dried dioxane was added via syringe and the reaction was heated to 80° C. for overnight. After LC-MS showed the reaction was complete, the solution was then cooled to room temperature and filtered and concentrated. Purification by chromatography (0-10% EtOAc:hexane), giving 288 mg of product as a white solid, yield: 86.5%. m/z 334 (M+H+).

Example 112

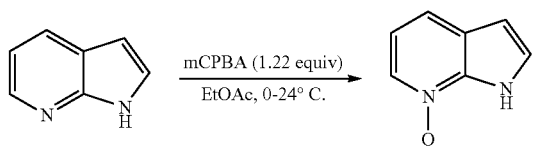

A solution of 1H-pyrrolo[2,3-b]pyridine (3 g) in ethyl acetate (20 ml) was cooled to 0-50° C., to the cooled solution was added 7 g of mCPBA, the resulting solution was warmed to room temperature, and allowed to stir at this temperature until the azaindole had been completely consumed, the reaction mixture was then cooled to 0° C., filtered and collected, the solid was washed with addition ethyl acetate and then dried, the resulted solid in de-ionized water at rt was treated with a sufficient amount of an aqueous solution containing K$_2$CO$_3$ to raise the PH of the slurry to about 10, addition water was added to the mixture and the slurry was cooled to 0° C. for 2 h, filtered and dried to afford 2.2 g of product, yield: 64.7%.

Example 113

A solution of 2 g of reactant in DMF was heated to about 50° C. and 4.5 g of Methanesulfonyl chloride was added to the heated solution at such a rate as to about 80° C. until the reaction was judged completed by reversed phase HPLC analysis. The reaction mixture was cooled to about 30° C., and then quenched with water. Upon cooling the quenched reaction mixture to 5° C., sufficient 10N NaOH solution was added to adjust the pH of the solution to about 7. The resulted slurry was warmed to 25° C., agitated for approximately 1 h, and then filtered to collect the solid. The product was washed with additional water, and dried under high vacuum to afford 1.3 g of product, yield: 57.2%.

Example 114

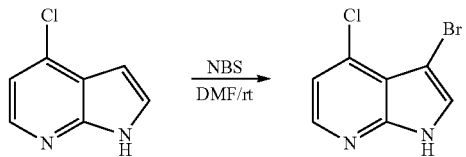

A 50 ml of flask was charged with 1.52 g of 4-chloro-1H-pyrrolo[2,3-b]pyridine (prepared according to Tetrahedron Letters (2007), 48(9), 1527-1529), 2.7 g NBS and 29 ml DMF. The mixture was stirred at rt for 6 h. The solvent was evaporated off and purified by chromatography to give the 2.11 g of product, yield: 90.9%.

Example 115

3-bromo-4-chloro-1H-pyrrolo[2,3-b]pyridine (2.32 g) was dissolved in anhydrous THF and cooled to 0° C., the NaH (60%, 1.2 g) was added slowly and the mixture stirred at 0° C. for 40 min. The benzenesulfonyl chloride was added, and the mixture was allowed to warm to room temperature and stirred at room temperature for 3 h. The reaction mixture was quenched with H₂O, and extracted with EtOAc. The organic layer was dried over Na₂SO₄. Ater the solvent evaporated under reduced pressure, the residue was purified with chromatography on silica gel to give 3-bromo-4-chloro-1-(phenylsulfonyl)-1H-pyrrolo[2,3-b]pyridine: (2.63 g), yield: 71%.

Example 116 tert-butyl 3-(4-chloro-1-(phenylsulfonyl)-1H-pyrrolo[2,3-b]pyridin-3-yl)benzylcarbamate

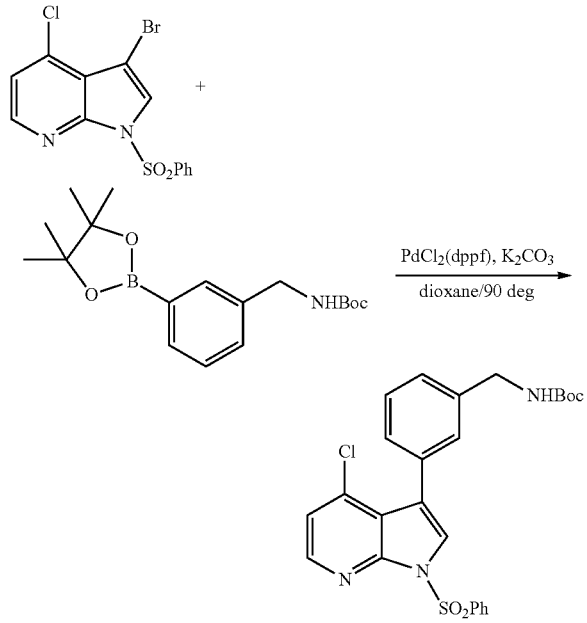

tert-butyl 3-(4,4,5,5-tetramethyl-1,3,2-dioxaborolan-2-yl)benzylcarbamate (333 mg, 1.0 mmol), 3-bromo-4-chloro-1-(phenylsulfonyl)-1H-pyrrolo[2,3-b]pyridine (372 mg, 1.0 mmol), potassium carbonate (270 mg, 2 mmol) and PdCl₂(dppf)CH₂Cl₂ (41 mg, 0.05 mmol) were added to a reaction flask which was purged thoroughly with N2. 10 ml of dried dioxane was added via syringe and the reaction was heated to 90° C. for overnight. After LC-MS showed the reaction was complete, the solution was then cooled to room temperature and filtered and concentrated. The residue was purified by chromatography (0-50% EtOAc:hexane), giving 201 mg of tert-butyl 3-(4-chloro-1-(phenylsulfonyl)-1H-pyrrolo[2,3-b]pyridin-3-yl)benzylcarbamate as a white solid, yield: 40.4%.

Example 117

(3-(4-chloro-1-(phenylsulfonyl)-1H-pyrrolo[2,3-b]pyridin-3-yl)phenyl)methanamine

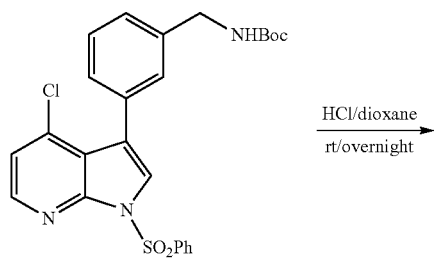

-continued

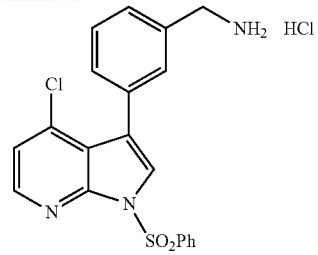

tert-butyl 3-(4-chloro-1-(phenylsulfonyl)-1H-pyrrolo[2,3-b]pyridin-3-yl)benzylcarbamate (50 mg) was dissolved in a solution of HCl in ethyl acetate, the reaction solution was stirred at room temperature overnight, the most of solvent was removed on a rotary evaporator and filtered to give the 31 mg of (3-(4-chloro-1-(phenylsulfonyl)-1H-pyrrolo[2,3-b]pyridin-3-yl)phenyl)methanamine as HCl salt. yield: 72.1%.

Example 118

1-(3,4-difluorobenzyl)-2-oxo-1,2-dihydropyridine-3-carbonyl chloride

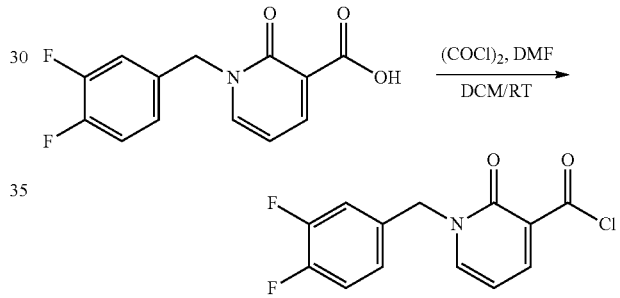

The flask was charged with dichloromethane, 20 mg of 1-(3,4-difluorobenzyl)-2-oxo-1,2-dihydropyridine-3-carboxylic acid, DMF, (COCl)₂ was added slowly via syringe. Then the resulted mixture was allowed to stir at room temperature for 3 h. After TLC show the reaction was complete, the solvent was removed under high vacuum to give 25 mg of crude product, which was used for the next step reaction without further purification.

Example 119

N-(3-(4-chloro-H-pyrrolo[2,3-b]pyridin-3-yl)benzyl)-1-(3,4-difluorobenzyl)-2-oxo-1,2-dihydropyridine-3-carboxamide

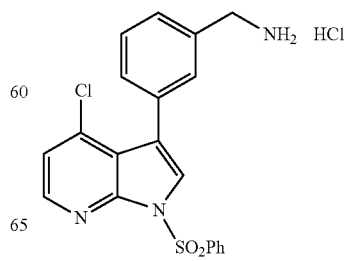

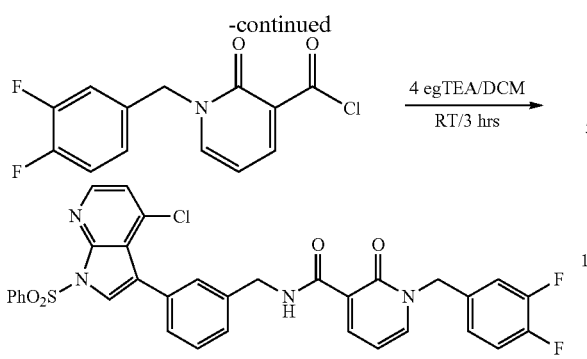

43 mg of (3-(4-chloro-1-(phenylsulfonyl)-1H-pyrrolo[2,3-b]pyridin-3-yl)phenyl)methanamine, 32 mg of crude 1-(3,4-difluorobenzyl)-2-oxo-1,2-dihydropyridine-3-carbonyl chloride were dissolved in DCM, TEA was added, then the resulted mixture was stirred at room temperature for overnight. The solvent was removed on a rotary evaporator and the crude was purified by chromatography to give 32 mg of N-(3-(4-chloro-1-(phenylsulfonyl)-1H-pyrrolo[2,3-b]pyridin-3-yl)benzyl)-1-(3,4-difluorobenzyl)-2-oxo-1,2-dihydropyridine-3-carboxamide, yield: 50%.

120 mg of the above product was dissolved in 20 ml of MeOH, 123 mg of $K_2CO_3$ was added and the resulting mixture was heated to reflux. After TLC showed reaction was complete. The solvent was removed on a rotary evaporator, and the residue was purified on silica gel to give the 77 mg of N-(3-(4-chloro-1H-pyrrolo[2,3-b]pyridin-3-yl)benzyl)-1-(3,4-difluorobenzyl)-2-oxo-1,2-dihydropyridine-3-carboxamide. yield: 81.9%. m/z: 505 (M+H+). 1H-NMR (CDCl3, 300 MHz): δ 8.600 (s, 1H), 8.124 (s, 1H), 7.540-7.451 (m, 3H), 7.386 (m, 3H), 7.257 (m, 2H), 7.164-7.104 (m, 2H), 7.029 (s, 1H), 6.461 (d, 1H), 5.137 (d, 2H), 4.708-4.688 (d, 2H).

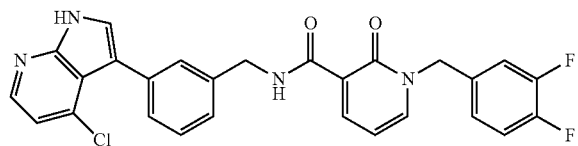 [SMILES: O=C(NCc1cccc(-c2c[nH]c3nccc(Cl)c23)c1)c1cccn(Cc2ccc(F)c(F)c2)c1=O]

The following compounds were similarly prepared.

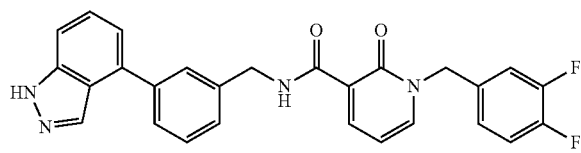 [SMILES: O=C(NCc1cccc(-c2cccc3[nH]ncc23)c1)c1cccn(Cc2ccc(F)c(F)c2)c1=O]

m/z: 611 (M+H+); $^1$H-NMR (DMSO-d$_6$, 300 MHz): $^{TM}$ 10.212 (s, 1H), 8.604-8.583 (s, 1H), 8.246 (s, 1H), 7.707-7.439 (m, 7H), 7.269-7.028 (m, 5H), 6.442 (s, 1H), 5.132 (d, 2H), 4.759-4.749 (d, 2H).

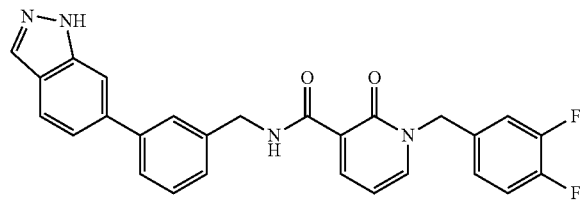 [SMILES: O=C(NCc1cccc(-c2ccc3cn[nH]c3c2)c1)c1cccn(Cc2ccc(F)c(F)c2)c1=O]

m/z: 611 (M+H+); 1H-NMR (CDCl3, 300 MHz): $^{TM}$ 10.129 (s, 1H), 8.616-8.515 (d, 1H), 8.097 (s, 1H), 7.804-7.775 (d, 1H), 7.656-7.624 (d, 2H), 7.544-7.498 (m, 2H), 7.444-7.360 (m, 3H), 7.177-7.008 (m, 3H), 6.480-6.434 (t, 1H), 5.132 (d, 2H), 4.731-4.711 (d, 2H).

Example 120

6,8-dibromoimidazo[1,2-a]pyrazine

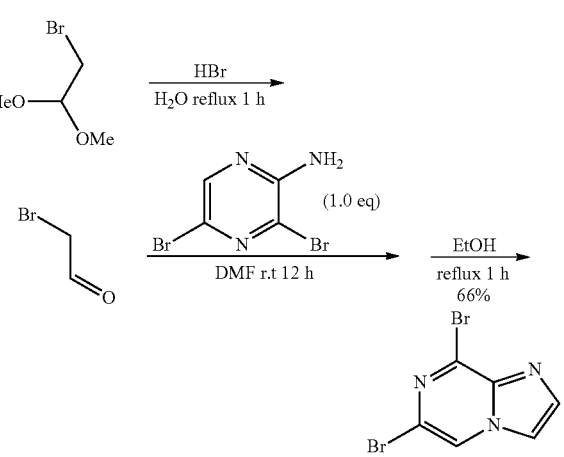

A mixture of 5.0 g (30 mmol) of bromoacetaldehyde dimethyl acetal 1.0 ml of concentrated aqueous HBr solution and 4.0 ml of distilled water was brought to reflux for 1 h. After reaction, the mixture was alkalinized and extracted with ether. This organic phase was added to a solution of 1.0 g (4.0 mmol) of 3,5-dibromopyrazin-2-amine in 2 ml of DMF. The ether was removed and the mixture was stirred under a stream of nitrogen for 12 h. After reaction, the DMF was removed and the residue was dissolved in 5 ml of anhydrous ethanol and then it was brought to reflux for 1 h. The alcohol was then removed and the residue was dissolved in water, alkalinized with Na2CO3 and extracted with dichloromethane. After chromatography with alumina column (eluted with ether), 900 mg (yield: 82%) of 6,8-dibromoimidazo[1,2-a]pyrazine was obtained. ESI-MS (M+H$^+$): 278.

Example 121

8-bromo-6-methylaminoimidazo[1,2-a]pyrazine

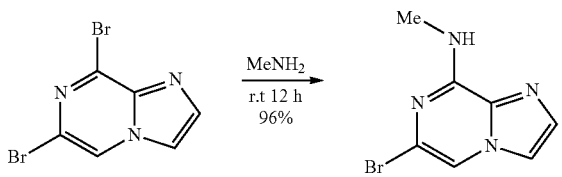 [SMILES: "MeNH2" ; Brc1cn2ccnc2c(Br)n1 ; CNc1nc(Br)cn2ccnc12]

A mixture of 100 mg (0.36 mmol) of 6,8-dibromoimidazo[1,2-a]pyrazine in 5 ml of a 25% aqueous methylamine solution was stirred for 12 h. After the removal of solvent, the residue was purified by chromatography (silica column eluted with ether) to provide 78 mg (yield: 96%) of 8-bromo-6-methylaminoimidazo[1,2-a]pyrazine. ESI-MS (M+H+): 227.

Example 122 tert-butyl 6-bromoimidazo[1,2-a]pyrazin-8-yl(methyl)carbamate

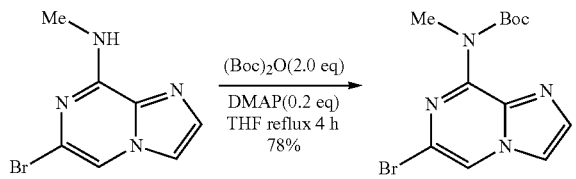 [SMILES: CNc1nc(Br)cn2ccnc12 ; CN(C(=O)OC(C)(C)C)c1nc(Br)cn2ccnc12]

8-bromo-6-methylaminoimidazo[1,2-a]pyrazine (100 mg, 0.442 mmol) and N,N-dimethyl-4-aminopyridine (10 mg, 0.0884 mmol) was dissolved in THF (2 ml). Di-tert-butyl dicarbonate (193 mg, 0.884 mmol) was added, and the mixture was heated to reflux for 4 h. After the solution was cooled to room temperature, and the solvent was removed. The residue was purity by chromatography with alumina column to give 78 mg (yield: 95%) of pure product. ESI-MS (M+H$^+$): 327.

Example 123

1-(3,4-difluorobenzyl)-N-((5-(8-(methylamino)imidazo[1,2-a]pyrazin-6-yl)thiophen-2-yl)methyl)-2-oxo-1,2-dihydropyridine-3-carboxamide

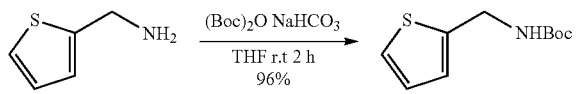 [SMILES: NCc1cccs1 ; CC(C)(C)OC(=O)NCc1cccs1]

To a solution of thiephen-2-ylmethanamine (5 g, 44.18 mmol) in THF (20 ml), was added NaHCO$_3$ (3.712 g, 44.18 mmol) and (Boc)$_2$O (10.12 g, 46.38 mmol) slowly. The resulted mixture was stirred at room temperature for two hours. After TLC showed the starting material was disappeared. The reaction was filtrate through a 3.0 g of silica and concentrated to give 9.03 g of product, yield: 96%.

Example 124

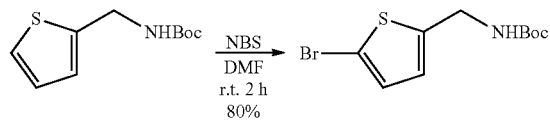

The mixture of reactant (11 g, 51.57 mmol), NBS (10.09 g, 56.72 mmol) in DMF (20 ml) was stirred at room temperature for 2 h. The reaction was monitored by LC-MS, after the reaction was complete, it was diluted with ethyl acetate and washed with water for three times. The organic layer was dried over MgSO$_4$ and concentrated in vacuum. The residue was purified by chromatography with silica gel to give 12.01 g (80%) of product.

Example 125

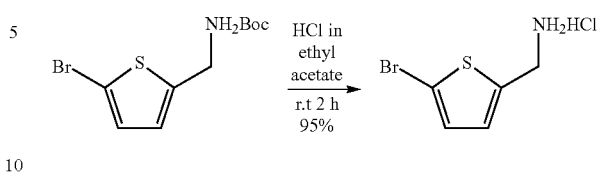

Reactant (8.322 g, 0.0285 mmol) was dissolved in 150 ml of anhydrous ethyl acetate. The dried HCl was induced continuously for two hours and a large amount of precipitate formed. The solvent was removed and the residue was washed with anhydrous ethyl acetate (3×50 ml), ether (3×50 ml) in turn to give the product 01-0034-1 (5.862 g), yield: 95%.

Example 126

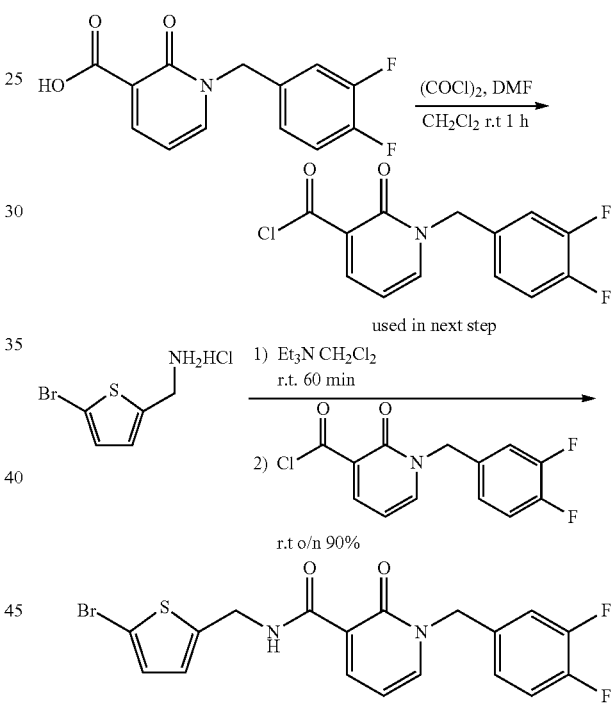

To a solution of reactant (3.0 g, 11.3 mmol) in anhydrous dichloromethane (100 ml) and DMF (83 mg, 1.13 mmol) was added oxalyl chloride (2.88 g, 22.6 mmol) dropwise. The resulted mixture was stirred at room temperature for 60 min. The solvent was evaporated to give corresponding acetyl chloride, which was used for next step without further purification.

To a solution of c-(S-Bromo-thiphen-2-yl)-methyl amine hydrochoric acid (4.0 g, 15.6 mmol) in anhydrous dichloromethane (100 ml) was added triethylamine (2.88 g, 28 mmol) dropwise. After the reaction mixture was stirred at room temperature for 30 min., the acid chloride prepared above was dissolved in anhydrous dichloromethane (100 ml) and added dropwise with an ice-water bath. The resulted mixture was stirred at room temperature for 4 h. The solvent was removed and the residue was purified by column chromatography to afford compound product (4.455 g) as a white solid, yield: 90%.

Example 127

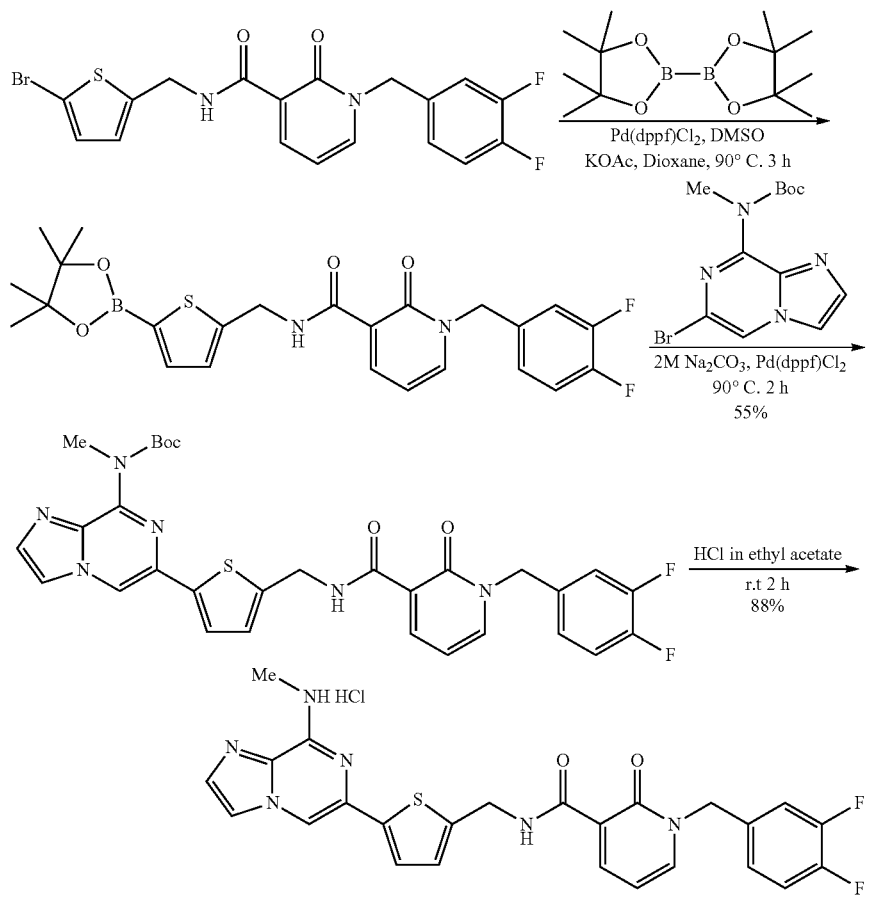

A flask charged with reactant (300 mg, 0.68 mmol), bis(pinacolato) diboron (691 mg, 2.72 mmol), KOAc (133 mg, 1.36 mmol), Pd(dppf) Cl2 (16.6 mg, 0.0204 mmol) and 0.04 ml of DMSO was flushed with nitrogen. 1,4-Dioxane (15 ml) was added and the reaction was stirred at 90° C. for 2 h. After cooling the solution to room temperature, the Boc-protected 8-bromo-6-methylamnoimidazo[1,2-a]pyrazine (148 mg, 0.45 mmol), PdCl2(dppf) (16 mg, 0.020 mmol) and 2M Na2CO3 (0.45 ml, 2.0 eq) were added and the resulted mixture was stirred at 90° C. under nitrogen for another 2 h. The solution was cooled to room temperature, The solvent was removed and the residue was purified by column chromatography to give the product Boc-protected pyridinone compound 150 mg (yield: 55%). ESI-MS (M+H+): 607.

tert-butyl 6-(5-((1-(3,4-difluorobenzyl)-2-oxo-1,2-dihydropyridine-3-carboxamido)methyl)thiophen-2-yl)imidazo[1,2-a]pyrazin-8-yl(methyl)carbamate (102 mg, 0.168 mmol was prepared similarly to Example 68 but using tert-butyl 6-bromoimidazo[1,2-a]pyrazin-8-yl(methyl)carbamate) dissolved in 2 ml of anhydrous ethyl acetate. The dried HCl was induced continuously for two hours and a large amount of precipitate formed. The solvent was removed under vacuum and the residue was washed with anhydrous ethyl acetate (3×50 ml), ether (3×50 ml) in turn to give the product (82 mg), yield: 88%. 1H NMR (DMSO-d6, 300 MHz): δ 10.068 (s, 1H), 8.467-8.387 (t, 2H), 8.368-8.363 (d, 1H), 8.271-8.249 (d, 1H), 8.092-8.037 (d, 2H), 7.455-7.362 (m, 3H), 7.159-7.021 (t, 2H), 6.603-6.557 (t, 1H), 5.191 (s, 2H), 4.670-4.651 (d, 2H), 3.025 (s, 3H) ESI-MS (M+H+): 608. HPLC: 98%.

Example 128

N-((5-(4-chloro-1H-pyrrolo[2,3-b]pyridin-3-yl)thiophen-2-yl)methyl)-1-(3,4-difluorobenzyl)-2-oxo-1,2-dihydropyridine-3-carboxamide

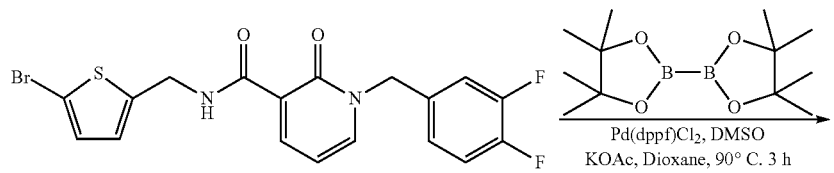

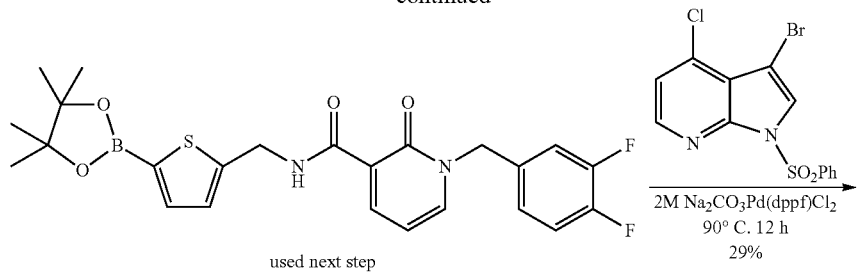

used next step

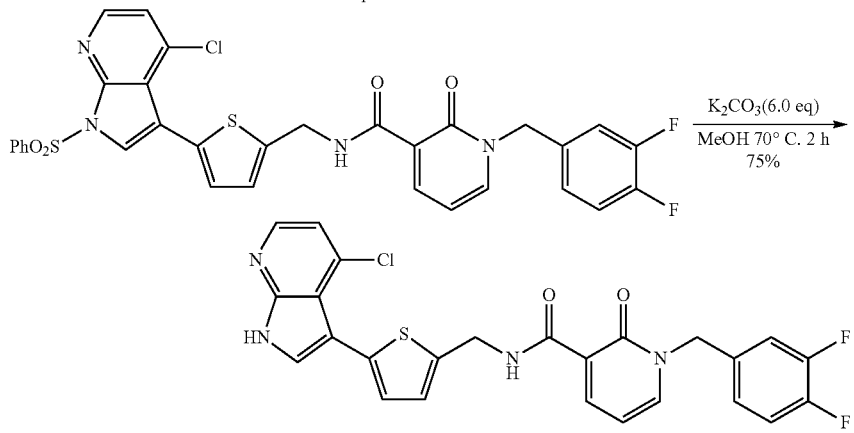

The compound was prepared similarly to Example 68 but using 3-bromo-4-chloro-1-(phenylsulfonyl)-1H-pyrrolo[2,3-b]pyridine.

A flask charged with reactant (100 mg, 0.24 mmol), bis(pinacolato) diboron (240 mg, 0.94 mmol), KOAc (48 mg, 0.48 mmol), Pd(dppf)Cl2 (6.0 mg, 0.0072 mmol) and 1 ml of DMSO was flushed with nitrogen. 1,4-Dioxane (5 ml) was added and the reaction was stirred at 90° C. for 2 h. After cooling the solution to room temperature, brominated pyrrolo-pyridine (84 mg, 0.36 mmol), PdCl2 (dppf) (6.0 mg, 0.0072 mmol) and 2M Na2CO3 (51 mg, 0.48 mmol) were added and the mixture was stirred at 90° C. under nitrogen for another 2 h. The solution was cooled to room temperature, The solvent was removed and the residue was purified by column chromatography to give the resulting N-protected pyrrolo-pyridine pyridinone compound 43 mg (yield: 29%). ESI-MS (M+H+): 652.

Potassium carbonate (101 mg, 0.736 mmol, 6.0 eq) was added to a solution of compound 10-0005-1 (80 mg, 0.123 mmol, 1.0 eq) in MeOH (10 ml). The reaction mixture was heated to reflux and stirred for 3 h. After the reaction was cooled to room temperature, the solvent was removed and the residue was purified by column chromatography to give the product 10-0005 (47 mg) as a white solid, yield 75%.

1H NMR (300 MHz, DMSO-d6): δ 13.072 (s, 1H), 10.048-10.027 (d, 1H), 8.405-8.373 (m, 1H), 8.231-8.201 (m, 1H), 8.052 (s, 1H), 7.929 (s, 1H), 7.608-7.336 (m, 4H), 7.272, 7.258 (d, 2H), 7.173-7.160 (d, 2H), 7.000-6.988 (d, 1H). 6.606-6.561 (t, 1H), 5.192 (s, 2H), 4.665-4.645 (d, 2H). ESI-MS (M+H+): 477.

The following compounds were prepared similarly.

Example 129

N-((5-(1H-indazol-5-yl)thiophen-2-yl)methyl)-1-(3,4-difluorobenzyl)-2-oxo-1,2-dihydropyridine-3-carboxamide

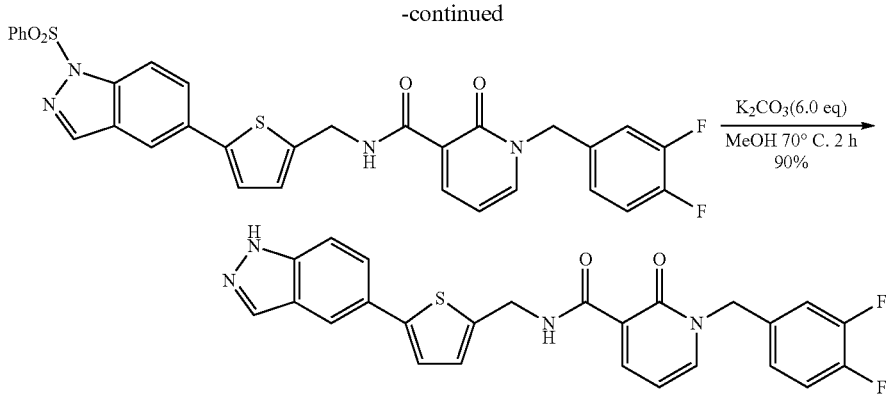
1H NMR (300 MHz, DMSO-d6): δ 13.072 (s, 1H), 10.048-10.027 (d, 1H), 8.405-8.373 (m, 1H), 8.231-8.201 (m, 1H), 8.052 (s, 1H), 7.929 (s, 1H), 7.608-7.336 (m, 4H), 7.272-7.258 (d, 2H), 7.173-7.160 (d, 2H), 7.000-6.988 (d, 1H), 6.606-6.561 (t, 1H), 5.192 (s, 2H), 4.665-4.645 (d, 2H). ESI-MS (M+H+): 477.
Example 130
N-((5-(1H-indazol-4-yl)thiophen-2-yl)methyl)-1-(3,4-difluorobenzyl)-2-oxo-1,2-dihydropyridine-3-carboxamide
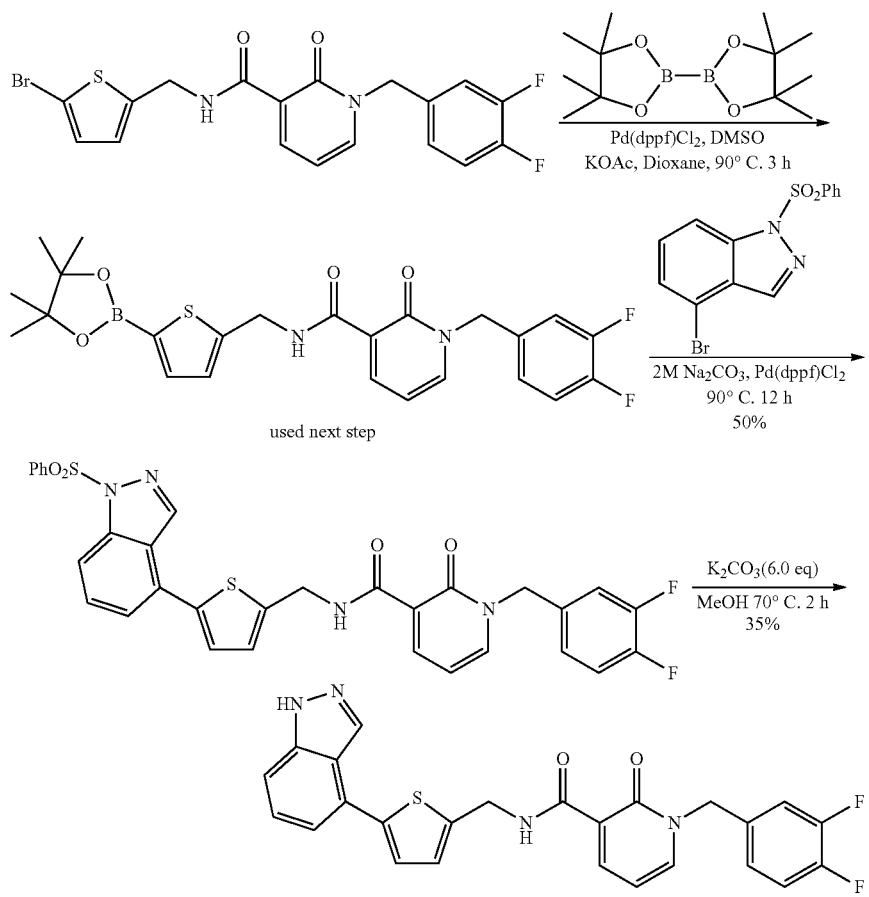
1H-NMR (DMSO-d6, 300 MHz) δ: 13.27 (s, 1H), 10.10 (s, 1H), 8.21-8.40 (m, 3H), 7.20-7.50 (m, 6H), 7.09-7.20 (m, 2H), 6.58 (s, 1H), 5.18 (s, 2H), 4.69-4.70 (s, 2H). LCMS (ESI-MS): m/z=477.1 (M+1); HPLC (purity): 99.14%.

Example 131
N-((5-(1H-indazol-6-yl)thiophen-2-yl)methyl)-1-(3,4-di-fluorobenzyl)-2-oxo-1,2-dihydropyridine-3-carboxamide
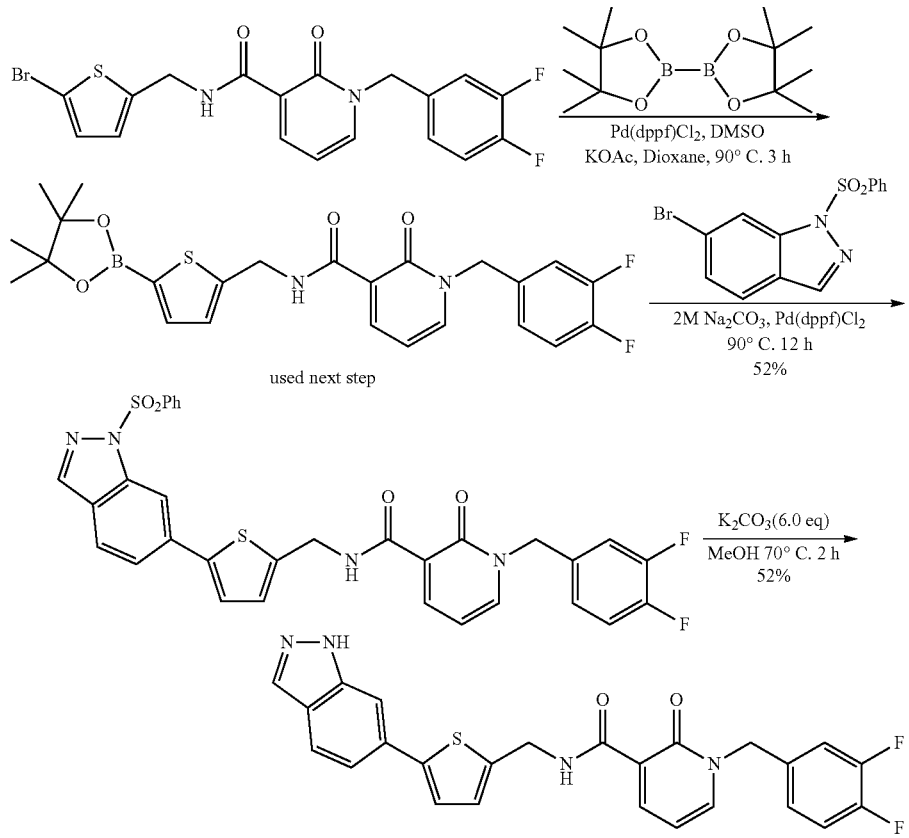
$^1$H NMR (DMSO-d$_6$, 300 MHz) δ: 13.02 (s, 1H), 10.06 (s, 1H), 8.40 (m, 1H), 8.22 (m, 1H), 8.03 (m, 1H), 7.64-7.73 (m, 2H), 7.34-7.46 (m, 4H), 7.16 (m, 1H), 7.03 (m, 1H), 6.58 (m, 1H), 5.19 (s, 2H), 4.66 (s, 2H); LCMS (ESI-MS): m/z=477.1 (M+1).
Example 132
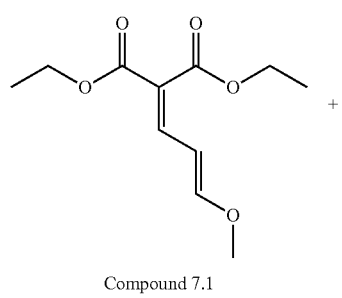
Compound 7.1
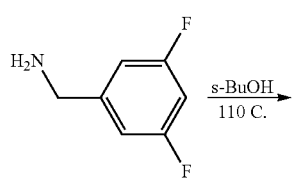
s-BuOH
110 C.
-continued
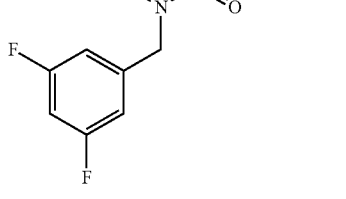
Compound 132.1
1. NaOH, 60 C.
2. HCl
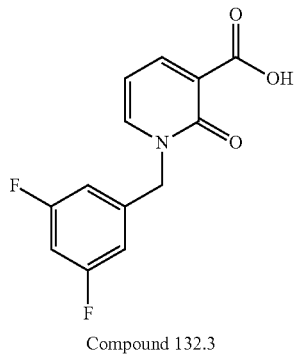
Compound 132.3

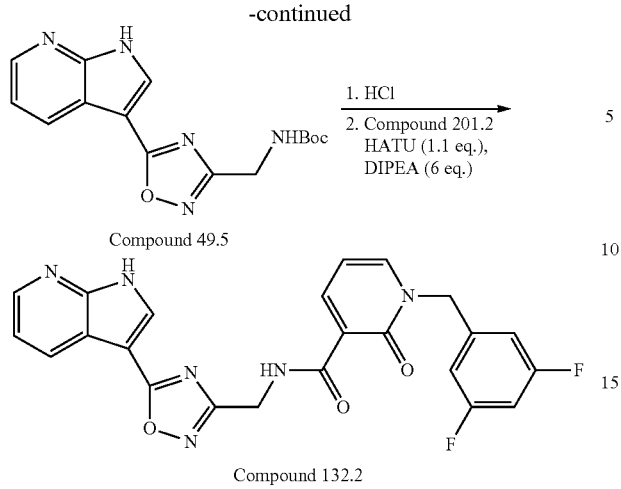

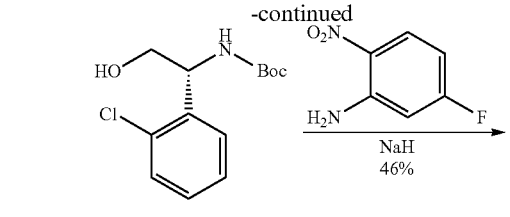

132.1 The diethyl [3=-methoxypro-2-enylidene]malonate (1.0 g, 4.4 mmol), Compound 7.1, was added to a 2-dram vial in 2 ml of s-BuOH. To the mixture was added 3,5-difluoromethylbenzylamine (0.74 g, 4.6 mmol). The reaction mixture was heated to 110° C. for 16 hours. When the reaction was completed, the solvent was removed using GeneVac HT-12 to give Compound 132.1. ES (+) MS m/e=294 (M+1). 132.1

132.2 To the 2-dram vial containing crude Compound 132.1 was added 1.1 equivalent of NaOH (3.0 M solution). The vial was capped and shaken at 60° C. for 3 h. The reaction was quenched with 1.1 equivalents of HCl (3.0 M solution). The precipitate was filtered and washed with water three times. ES (+) MS m/e=266 (M+1).

132.3 To 10 dram-vial containing Compound 49.5 (0.5 mmol) and 2 mL of $CH_2Cl_2$ and 1 mL of MeOH was added 6 equivalents of HCl (4.0 M in dioxane). The reaction mixture was shaken at RT for 3 h. The solvent was removed under reduced pressure, and the residue was dissolved in 2 mL of DMF. To this, Compound 132.2 (0.5 mmol) and DIPEA (6 equivalents) were added followed by HATU (1.1 equivalents): 2-(7-aza-1H-benzotriazole-1-yl)-1,1-3,3-tetramethyluronium hexafluorophosphate. The reaction was shaken at RT for 2 h. The solvent was concentrated using GeneVac HT-12. The crude product was dissolved in DMSO (3 ml) and purified by using HPLC (reverse phase) to give Compound 132.3. ES (+) MS m/e=463 (M+1). 1H NMR (400 MHz, DMSO-d-6) $^{TM}$ 4.73 (d, J=5 Hz, 2H), 5.28 (s, 2H), 6.63 (t, J=7 Hz, 1H), 7.07 (s, 1H), 7.09 (s, 1H), 7.20 (t, J=10 Hz, 1H), 7.32 (dd, J=6 and 7 Hz, 1H), 8.28 (dd, J=4 and 2 Hz, 1H), 8.4-8.5 (m, 3H), 8.54 (d, J=3 Hz, 1H), 10.21 (s, 1H), 12.83 (s, 1H).

Example 133

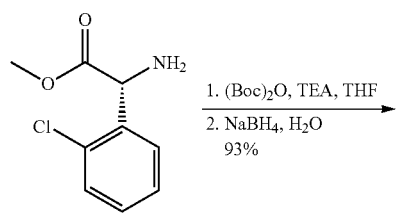

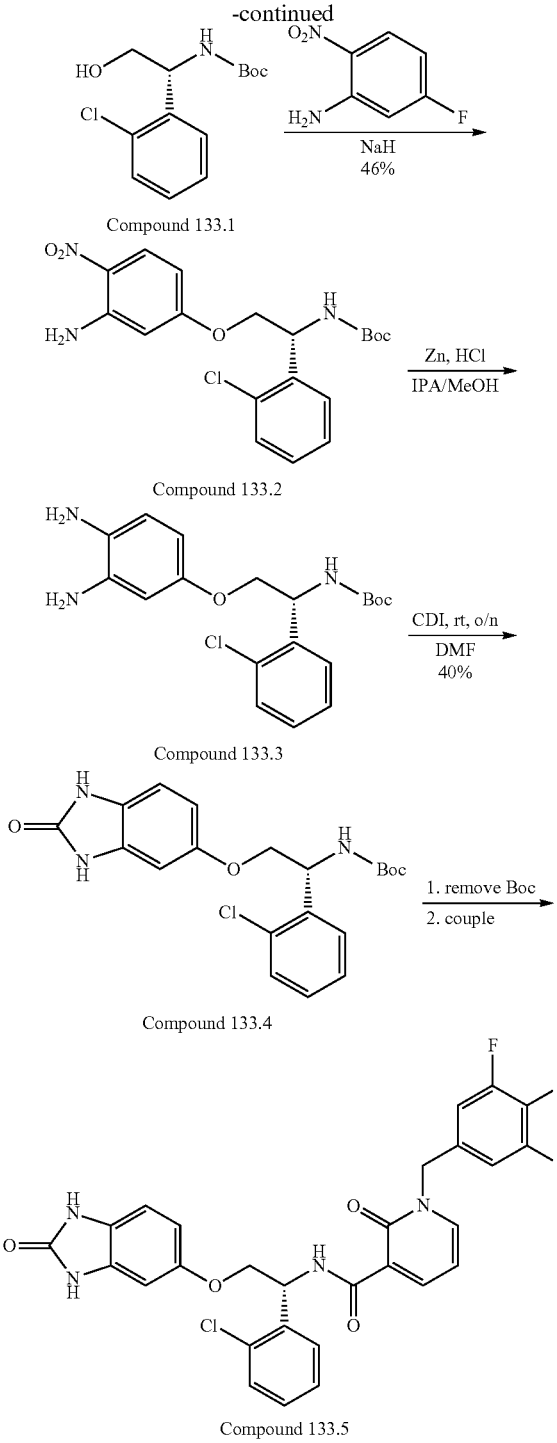

133.1 A mixture of (R)-(–)-2-chlorophenylglycine methyl ester (2.0 g, 10 mmol) and di-tert-butyl dicarbonate (2.19 g, 10 mmol) was dissolved in 80 ml THF plus 5 ml methanol. Then triethylamine (2.8 ml, 20 mmol) was added and the mixture was heated at 50° C. overnight. TLC showed that the reaction was done. At this point N,N-dimethylethylenediamine (330 μl, 3 mmol) was added and stirred for 30 minutes. Then the solvent was removed under vacuum and the residue was flooded with ethyl acetate, rinsed with 0.1N HCl, brine, dried over sodium sulfate, filtered, and evaporated to dryness to get 2.71 g crude compound. This crude was dissolved in 30 ml MeOH and solid $NaBH_4$ (3.14 g, 8.3 mmol) was added and the mixture was stirred at room temperature overnight. More solid NaBH$_4$ (1.57 g, 4.15 mmol) was added and the reaction was left stirring over the weekend. Then the solvent was removed under vacuum and the residue was flooded with ethyl acetate, rinsed with saturated sodium bicarbonate, brine, dried over sodium sulfate, filtered, and evaporated to get compound 133.1 as a white solid (2.28 g, 93%). ES (+) MS m/e=294 (M+23).

after purification with flash chromatography. ES (+) MS nm/e=569 (M+1). $^1$H NMR (400 MHz, DMSO-d6)$^{TM}$ ppm 4.22 (m, 2H) 5.24 (dd, J=25.43, 14.18 Hz, 2H) 5.71 (m, 1H) 6.51 (m, 2H) 6.59 (t, J=6.85 Hz, 1H) 6.75 (d, J=8.31 Hz, 1H) 7.33 (m, 4H) 7.47 (m, 2H) 8.21 (dd, J=6.36, 1.96 Hz, 1H) 8.32 (dd, J=7.34, 1.96 Hz, 1H) 10.38 (m, 1H) 10.52 (m, 2H).

Example 134

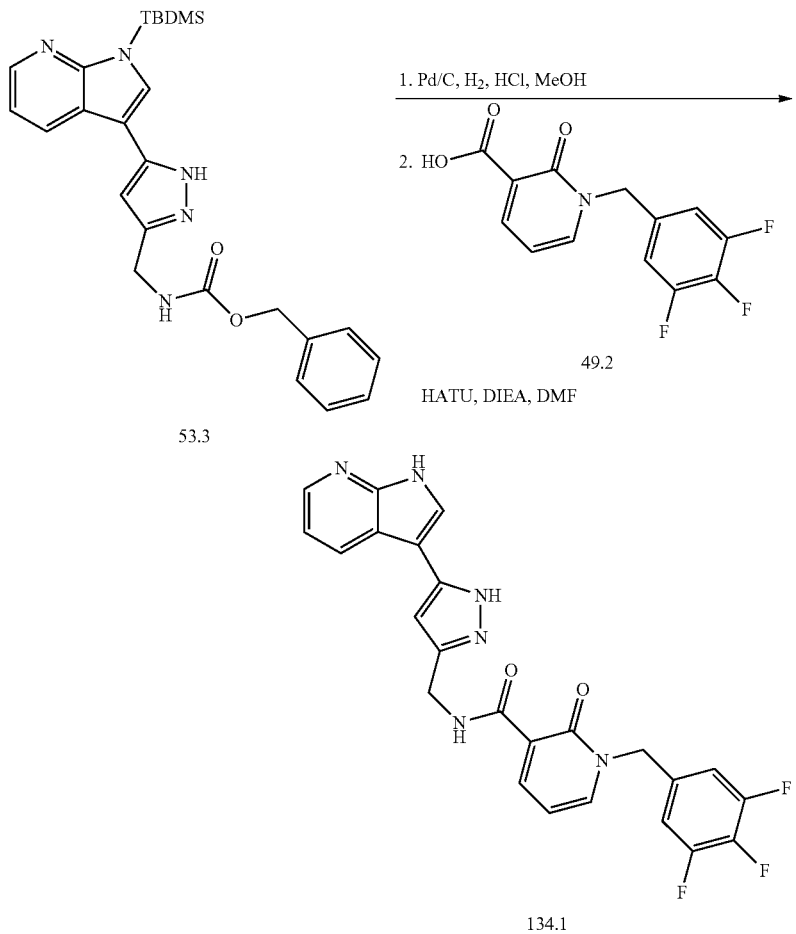

133.2 Compound 133.2 was prepared in the same way as Example 55.2 using Compound 133.1 as starting material. It was a yellow solid (1.56 g, 46%). ES (+) MS m/e=430 (M+23).

133.3 Compound 133.3 was made from Compound 133.2 using the same method as described in Example 55.3. It was a brown oil (1.344 g). ES (+) MS m/e=384 (M+23).

133.4 This was prepared with the same method described in example 55.4, using Compound 133.3 instead of Compound 55.3. It was a brown oil (0.56 g, 40%). $^1$H NMR (400 MHz, DMSO-d6)$^{TM}$ ppm 1.36 (m, 9H) 3.93 (m, 2H) 5.30 (m, 1H) 6.50 (m, 2H) 6.76 (d, J=8.31 Hz, 1H) 7.30 (m, 1H) 7.36 (t, J=6.85 Hz, 1H) 7.43 (d, J=7.83 Hz, 1H) 7.54 (dd, J=7.83, 1.47 Hz, 1H) 7.74 (d, J=8.31 Hz, 1H) 10.37 (m, 1H) 10.50 (m, 1H).

133.5 Compound 133.4 (0.56 g, 1.386 mmol) was deprotected with 4M HCl in dioxane for 30 minutes and then evaporated to dryness. One-third of the residue (0.46 mmol) was coupled with Compound 49.2 as described in Example 55.1. The final product was obtained as an off-white powder 134.1 Compound 53.3 (0.276 grams, 0.599 mmol) was dissolved in methanol (3 ml). A scoop of palladium on carbon (Degussa Type E101 NE/W wet) was added followed by 4.0M HCl in p-dioxane (1 ml). This mixture was placed on a Parr shaker at 40 psi for 48 hours, filtered through Celite, and concentrated. This residue was mixed with Compound 49.2 (0.146 grams, 0.516 mmol), O-(7-Azabenzotriazole-1-yl)-N,N,N'N'-tetramethyluronium hexafluorophosphate (0.235 grams, 0.619 mmol) and diisopropylethylamine (0.450 ml, 2.58 mmol) in DMF (2 ml) and stirred at ambient temperature for 1 hour. The mixture was flooded with ethyl acetate, washed with saturated sodium bicarbonate solution, brine, dried over sodium sulfate, filtered and concentrated. The residue was purified by silica gel column chromatography eluting with 5-10% 2 M methanolic ammonia in dichloromethane to yield Compound 134.1. (0.128 grams, 0.268 mmol) ES (+) MS m/e=479 (M+H). 1H NMR (400 MHz, CD$_3$OD) δ ppm 4.56 (m, 2H) 5.07 (m, 2H) 6.46 (m, 1H) 6.50 (m, 1H) 7.02 (m, 2H) 7.08 (m, 1H) 7.63 (m, 1H) 7.89 (m, 1H) 8.14 (m, 1H) 8.38 (m, 1H).

Example 135

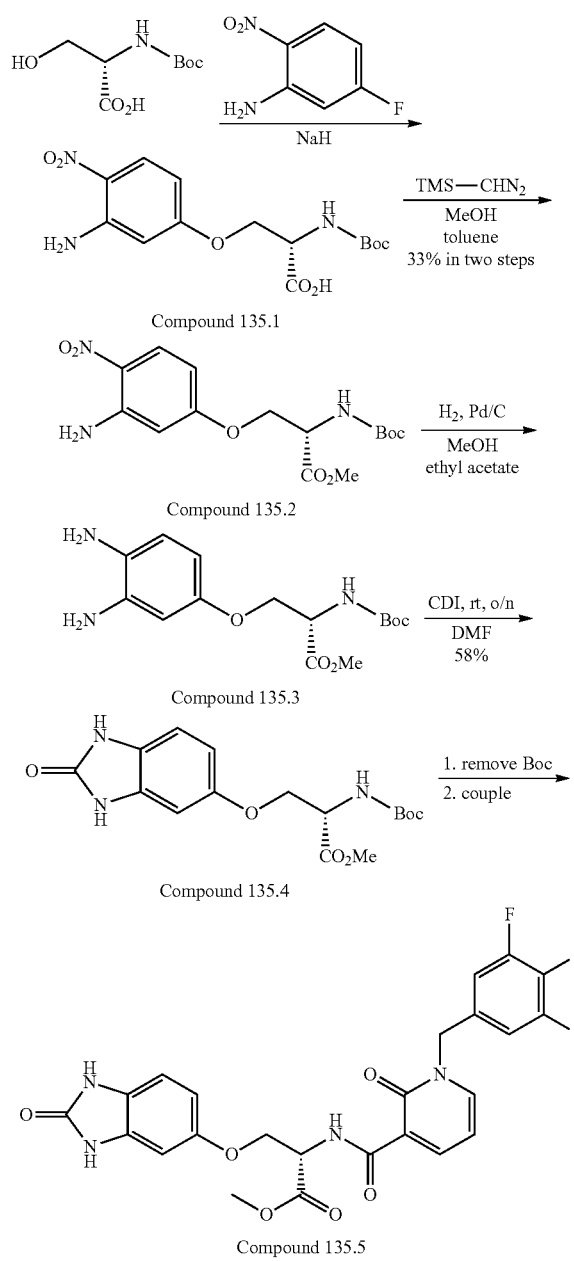

135.1 Compound 135.1 was prepared in the same way as Compound 55.2 using Boc-L-serine as starting material. The crude product was a brown oil (16.2 g, 46%) which was used in next step without further purification. ES (+) MS m/e=342 (M+1).

135.2 Compound 135.2 was made from Compound 135.1 using the same method as described in Example 31.2. The resulting brown oil was purified by chromatography (twice) to afford Compound 135.2 (5.58 g, 33% for two steps). ES (+) MS m/e=356 (M+1).

135.3 Compound 204.2 (3.75 g, 10.56 mmol) was suspended in a mixture of 25 ml MeOH and 25 ml ethyl acetate and 1.12 g 10% Pd/C (1.056 mmol) was added. This was hydrogenated ($H_2$ balloon) overnight. The mixture was filtered through Celite, the filtrate was evaporated to give Compound 135.3 as a black oil (3.24 g). ES (+) MS m/e=326 (M+1).

135.4 This was made as in Example 55.4 to give a light brown solid (2.02 g, 58%). ES (+) MS m/e=352 (M+1). $^1$H NMR (400 MHz, DMSO-d6) $^{TM}$ ppm 1.38 (m, 9H) 3.65 (m, 3H) 4.11 (m, 2H) 4.40 (m, 1H) 6.50 (m, 2H) 6.78 (d, J=7.83 Hz, 1H) 7.39 (d, J=8.31 Hz, 1H) 10.39 (m, 1H) 10.52 (m, 1H).

135.5 Compound 135.4 (2.0 g, 5.69 mmol) was deprotected with 4M HCl in dioxane for 30 minutes and then evaporated to dryness. This was coupled with Compound 49.2 as described in Example 55.1. The final product was obtained as a yellow solid (2.52 g, 86%) after purification with flash chromatography. ES (+) MS m/e=517 (M+1). $^1$H NMR (400 MHz, DMSO-d6) $^{TM}$ ppm 3.67 (m, 3H) 4.20 (dd, J=9.78, 3.42 Hz, 1H) 4.37 (dd, J=10.27, 3.91 Hz, 1H) 4.93 (m, 1H) 5.22 (m, 2H) 6.52 (m, 2H) 6.60 (t, J=6.85 Hz, 1H) 6.77 (d, J=8.31 Hz, 1H) 7.32 (m, 2H) 8.24 (dd, J=6.36, 1.96 Hz, 1H) 8.37 (dd, J=6.85, 1.47 Hz, 1H) 10.34 (d, J=7.83 Hz, 1H) 10.41 (m, 1H) 10.54 (m, 1H).

Example 136

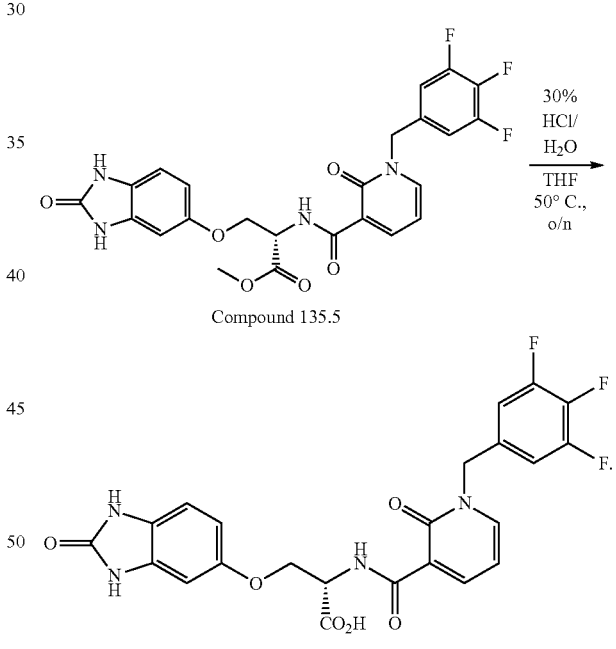

Compound 136 was prepared by heating Compound 135.5 in a mixture of 30% HCl and THF (1:2 v/v) at 50° C. overnight. The mixture was concentrated and then purified by HPLC (reverse phase) to give Compound 136. ES (+) MS m/e=503 (M+1). $^1$H NMR (400 MHz, Methanol-d4) $^{TM}$ ppm 4.30 (dd, J=9.78, 3.42 Hz, 1H) 4.50 (dd, J=9.78, 3.42 Hz, 1H) 4.96 (t, J=2.93 Hz, 1H) 5.22 (dd, J=22.50, 14.67 Hz, 2H) 6.57 (m, 1H) 6.68 (dd, J=8.31, 2.45 Hz, 1H) 6.72 (d, J=1.96 Hz, 1H) 6.90 (d, J=8.31 Hz, 1H) 7.17 (m, 2H) 8.03 (dd, J=6.36, 1.96 Hz, 1H) 8.45 (dd, J=7.34, 1.96 Hz, 1H).

Example 137

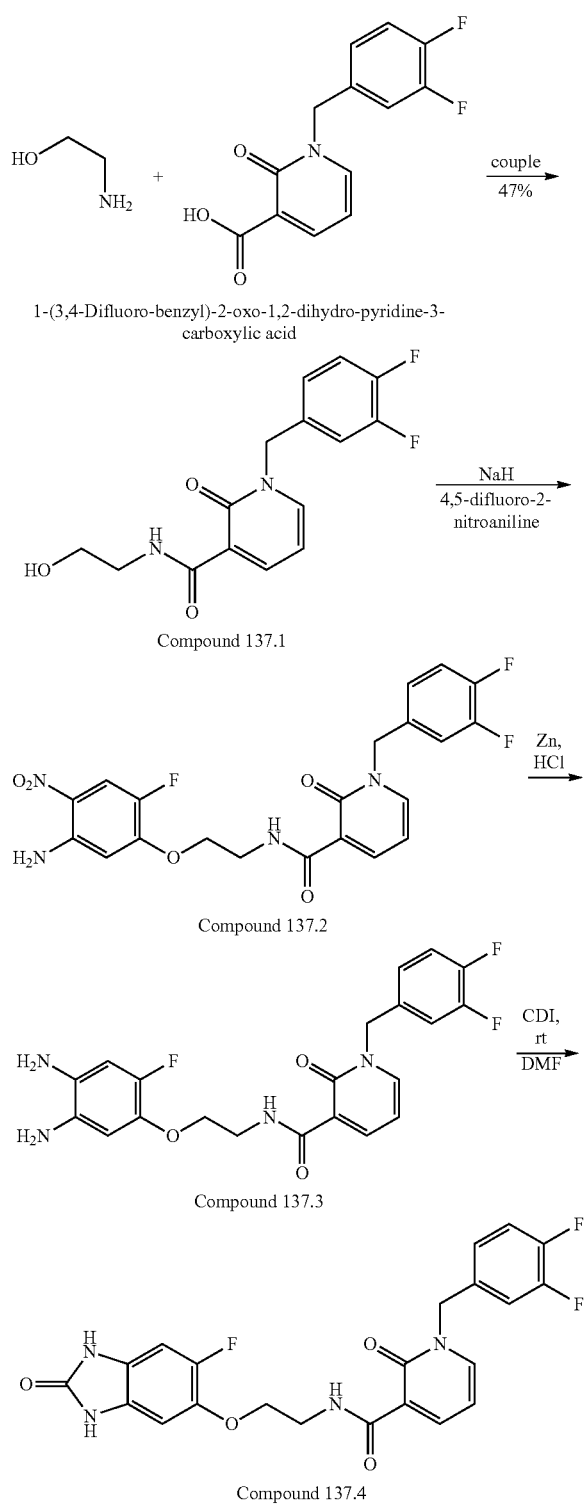

triethylamine (23.7 mmol total) was added. After one week the reaction was concentrated by rotary evaporation, flooded with 100 ml EtOAc, rinsed with 2×50 ml 1 M HCl, 2×50 ml 1 M NaOH, 50 ml brine, dried over sodium sulfated, and evaporated to dryness to yield Compound 137.1 as a salmon-colored solid (1.115 g, 3.62 mmol, 47%). ES (+) MS m/e=309 (M+1).

137.2 A mixture of Compound 137.1 (369 mg, 1.198 mmol) and 4,5-difluoro-2-nitroaniline (220 mg, 1.26 mmol) was dissolved in 5 ml dry DMF, sodium hydride (60 mg of 60% in mineral oil suspension, 1.5 mmol) was added, followed by an additional 5 ml of dry DMF. The reaction was stirred overnight at room temperature, then flooded with 80 ml EtOAc, rinsed with 2×40 ml water, 40 ml brine, dried over sodium sulfate, and evaporated to dryness to yield compound 137.2 as an orange solid that was used without further purification. ES (+) MS m/e=463 (M+1).

137.3 Crude compound 137.2 was suspended in 20 ml methanol and then 1 M HCl in water (12 ml) was added, followed by 40 ml isopropanol and zinc dust (3.195 g, 49 mmol). The heterogeneous reaction was stirred vigorously for two hours, then 50 ml of saturated sodium biocarbonate was added and the reaction was filtered through Celite with 70 ml EtOAc. The aqueous layer was drained, and the organic layer rinsed with 50 ml saturated sodium bicarbonate, 50 ml brine, dried over sodium sulfated, and evaporated to dryness to yield compound 137.3 as a blackish foam that was used without further purification (471 mg, 91% yield, two steps). ES (+) MS m/e=433 (M+1).

137.4 Compound 137.3 (471 mg, 1.09 mmol) was dissolved in 10 ml dry DMF and CDI (188 mg, 1.16 mmol) was added. The reaction was allowed to proceed for 1 hour at room temperature, and then flooded with 80 ml EtOAc, rinsed with 2×40 ml saturated sodium bicarbonate, 40 ml brine, dried over sodium sulfate, filtered, and evaporated to dryness to yield a black oil. This was purified by silica gel chromatography using initially 97.5:2.5 DCM:MeOH on a 15.5×2.5 cm column, followed by 95:5 DCM:MeOH. The product-containing fractions were dried to a brown film which was further purified by reverse-phase HPLC to yield Compound 137.4 as a pale violet solid. ES (+) MS m/e=459 (M+1).

Example 138

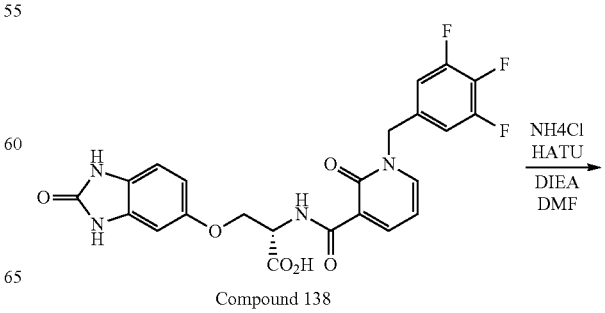

137.1 A mixture of EDC (1.49 g, 7.77 mmol), HOBT (1.073 g, 7.95 mmol) and Compound 20.2 was suspended in 10 ml dry DMF, to which was added ethanolamine (0.47 ml, 7.81 mmol) and triethylamine (2.2 ml, 15.8 mmol) followed by 30 ml more DMF. After two hours an additional 1.1 ml

239
-continued

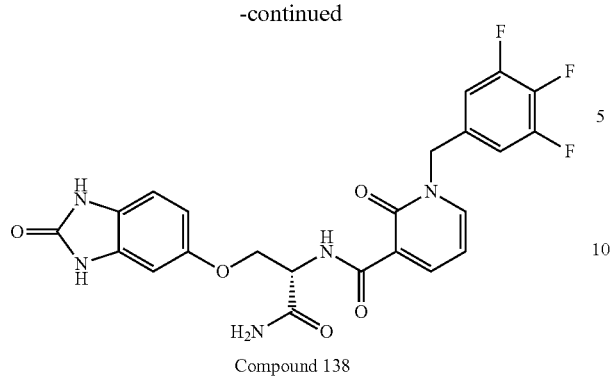
Compound 138

Compound 136 (0.25 g, 0.5 mmol) was coupled with ammonium chloride (0.054 g, 1 mmol), using 2-(7-Aza-1H-benzotriazole-1-yl)-1,1,3,3,-tetramethyluroniumhexafluorophosphate (0.285 g, 0.75 mmol) as the coupling agent, and N,N-diisopropylethylamine (0.26 ml, 1.5 mmol) as base in DMF overnight. The mixture was concentrated and then purified by reverse-phase HPLC to give Compound 138 as an off-white powder. ES (+) MS m/e=503 (M+1). $^1$H NMR (400 MHz, ACETIC ACID-d4) $^{TM}$ ppm 3.50 (m, 1H) 3.56 (m, 1H) 3.67 (m, 1H) 4.29 (m, 1H) 4.55 (m, 1H) 5.10 (m, 1H) 5.26 (m, 3H) 6.63 (t, J=6.85 Hz, 1H) 6.80 (dd, J=8.31, 1.96 Hz, 1H) 6.95 (d, J=1.96 Hz, 1H) 7.11 (m, 4H) 7.95 (dd, J=6.85, 1.96 Hz, 1H) 8.62 (dd, J=7.34, 1.96 Hz, 1H).

Example 139

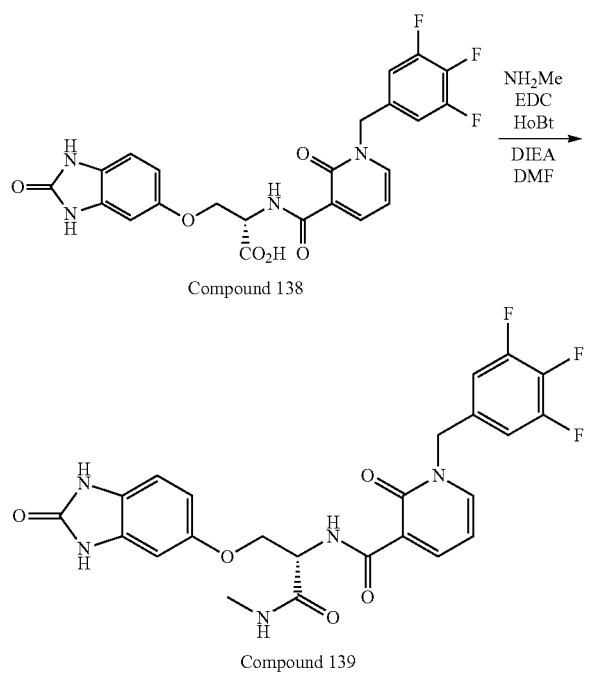
Compound 139

Compound 136 (0.25 g, 0.5 mmol) was coupled with methylamine (2 M in THF, 0.25 ml, 0.5 mmol), using HOBt and EDC as the coupling agent. Compound 139 was obtained as an off-white powder after purification by reverse-phase HPLC. ES (+) MS m/e=516 (M+1). $^1$H NMR (400 MHz, DMSO-d6) $^{TM}$ ppm 2.60 (d, J=4.40 Hz, 3H) 4.05 (m, 1H) 4.21 (m, 1H) 4.73 (m, 1H) 5.20 (m, 2H) 6.53 (m, 2H) 6.59 (m, 1H) 6.77 (m, 1H) 7.31 (m, 2H) 8.10 (m, 1H) 8.22 (m, 1H) 8.36 (m, 1H) 10.19 (m, 1H) 10.39 (m, 1H) 10.53 (m, 1H).

240

Example 140

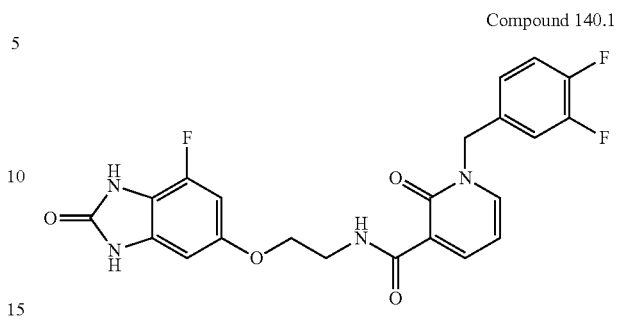
Compound 140.1

140.1 This was made analogously to compound 137.4, using the same sequence except substituting 3,5 difluoro-2-nitroaniline for 4,5-difluoro-2-nitroaniline in the second step. ES (+) MS m/e=459 (M+1).

Example 141

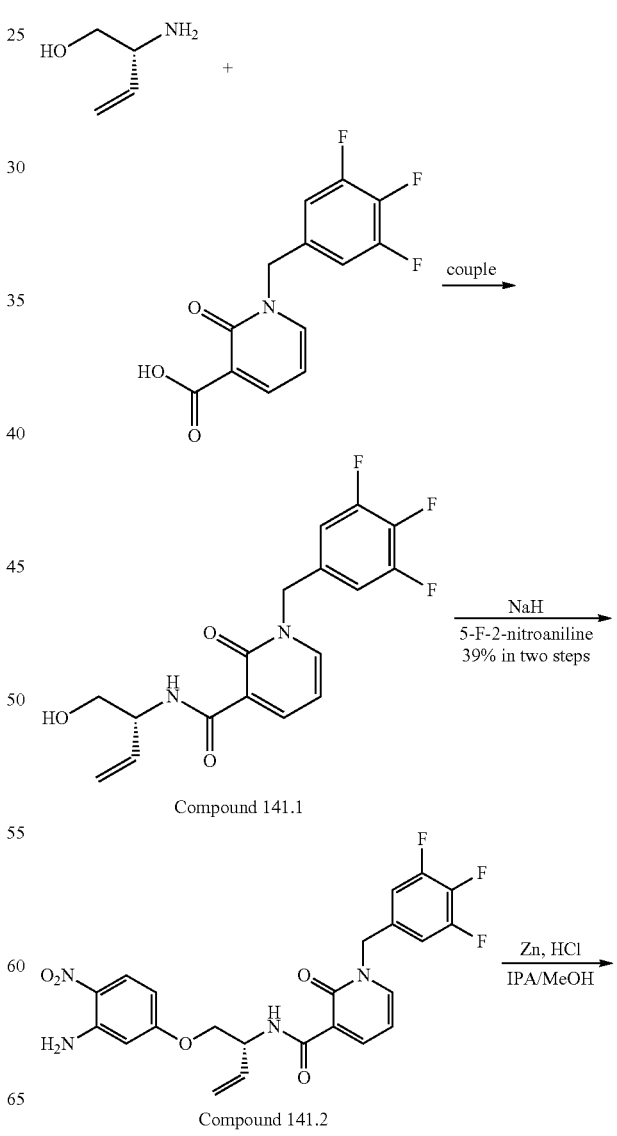

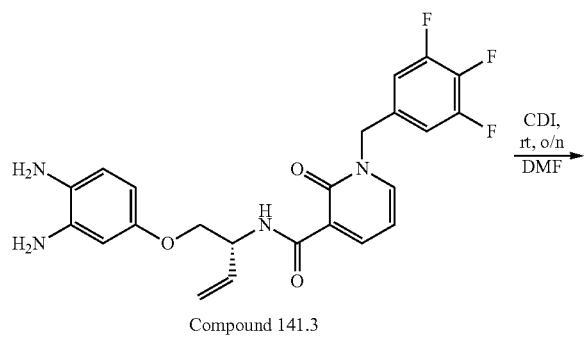

Compound 141.3

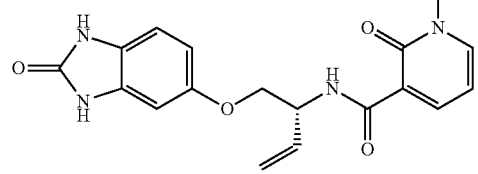

Compound 141.4

141.1 This was made as in Example 55.1 except using (R)-2-amino-but-3-en-1-ol (0.5 g, 4 mmol) and Compound 49.2 as starting material. It was a red oil. ES (+) MS m/e=353 (M+1).

141.2 This was prepared in the same way as Compound 55.2 using Compound 210.1. It was a yellow oil (0.78 g, 39% in two steps). ES (+) MS m/e=489 (M+1).

141.3 This was made from Compound 141.2 using the same method described in Example 55.3. It was a brown oil (0.43 g). ES (+) MS m/e=459 (M+1).

141.4 This was prepared as in Example 55.4 using Compound 141.3 instead of Compound 55.3. ES (+) MS m/e=485 (M+1). $^1$H NMR (400 MHz, Methanol-d4) $^{TM}$ ppm 4.08 (m, 2H) 4.95 (m, 1H) 5.23 (m, 4H) 6.04 (m, 1H) 6.55 (m, 1H) 6.67 (m, 2H) 6.87 (d, J=8.31 Hz, 1H) 7.11 (m, 2H) 7.98 (d, J=5.87 Hz, 1H) 8.43 (d, J=6.36 Hz, 1H).

Example 142

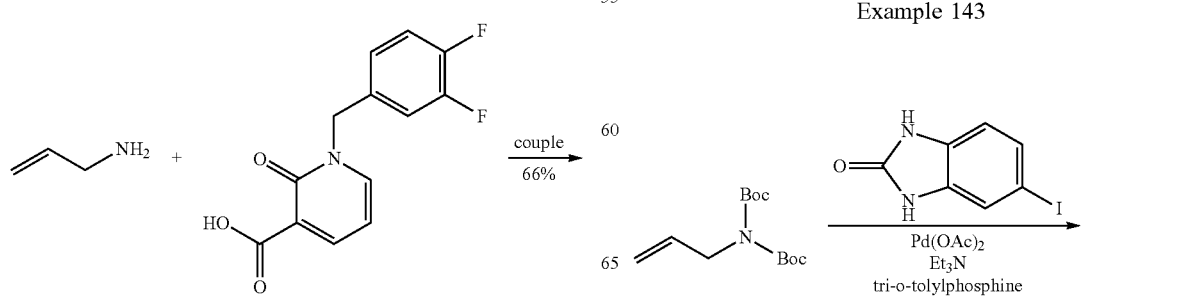

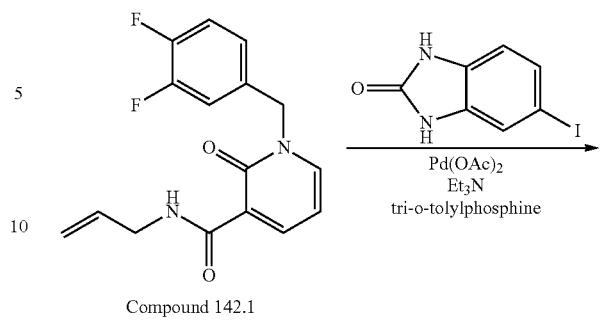

Compound 142.1

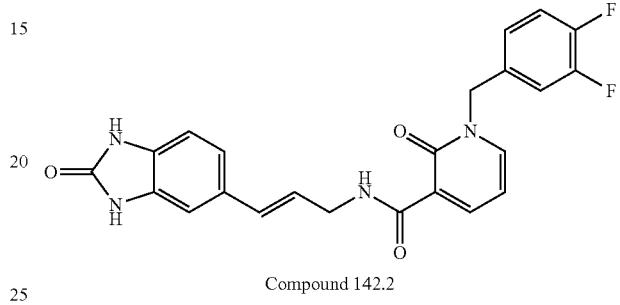

Compound 142.2

142.1 Compound 20.2 (2.506 g, 9.46 mmol), EDC (1.835 g, 9.57 mmol), and HOBT (1.293 g, 9.56 mmol) were suspended in 20 ml dry DMF, to which was then added allylamine (0.72 ml, 9.6 mmol) and triethylamine (2.8 ml, 20.1 mmol). The reaction was stirred for three days, then flooded with 100 ml EtOAc, rinsed with 2×50 ml 1 M sodium hydrogen sulfate, 2×50 ml 1 M NaOH, and 50 ml brine, dried over sodium sulfate, filtered, and evaporated to dryness to yield Compound 142.1 as a yellow solid (1.91 g, 66%). ES (+) MS m/e=305 (M+1).

142.2 Compound 142.1 (172 mg, 0.566 mmol), 5-iodo-1,3-dihydro-benzimidazole-2-one (146 mg, 0.561 mmol), palladium (II) acetate (6 mg, 0.027 mmol), and tri-(ortho-tolyl)phosphine (22 mg, 0.072 mmol) were dissolved in 2 ml dry DMF, triethylamine (0.16 ml, 1.15 mmol) was added, and the reaction was heated at 95° C. under nitrogen overnight. The reaction was then flooded with 50 ml EtOAc, rinsed with 2×25 ml 1 M HCl, 2×25 ml saturated sodium bicarbonate, 25 ml brine, dried over sodium sulfate, filtered, and evaporated to dryness to yield a brown solid that was then purified by silica gel chromatography using 95:5 DCM: MeOH on a 15×2.5 cm column to yield a yellow solid that was further purified using reverse-phase HPLC to obtain Compound 142.2 as an off-white solid (11.4 mg). ES (+) MS m/e=437 (M+1).

Example 143

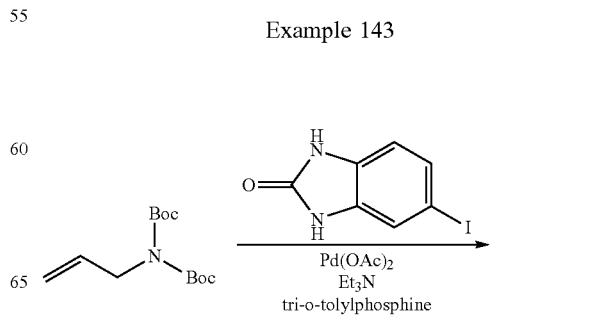

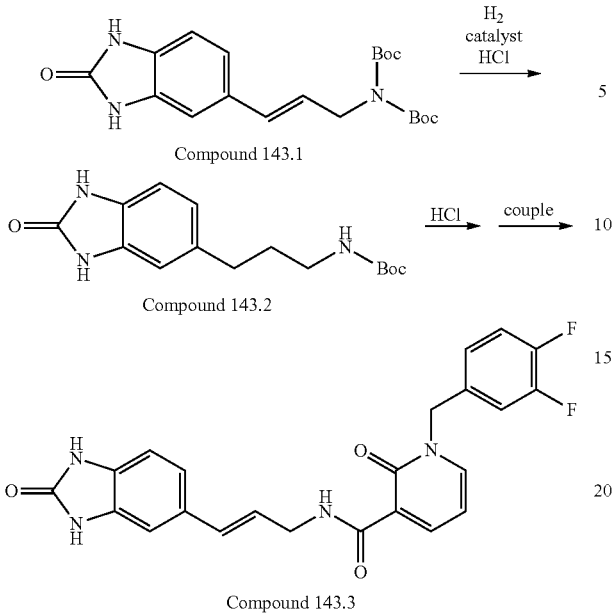

Compound 143.1

Compound 143.2

Compound 143.3

143.1 This compound was made analogously to compound 142.2 except using N,N-bis-Boc-N-allylamine instead of compound 142.1. ES (+) MS m/e=390 (M+1).

143.2 Compound 143.1 (97 mg, 0.249 mmol) was dissolved in 2 ml methanol and 2 ml EtOAc, and then 10% wet palladium on carbon was added (25 mg). The mixture was sparged and put under a hydrogen balloon for four hours. Then an additional 1 ml EtOAc was added, followed by 0.15 ml 4 M HCl in dioxane. The following day the reaction was transferred to a Parr apparatus with 5 ml methanol and an additional 82 mg palladium on carbon, 8 mg platinum (IV) oxide, and 88 mg Pearlman's catalyst was added and the reaction was hydrogenated overnight at 47 PSI. The following day the reaction was filtered through an 0.45 µM filter and evaporated to dryness to yield compound 143.2 as a beige foam (68 mg, 94%). ES (+) MS m/e=236 (M-55).

143.3 Compound 143.2 (68 mg, 0.234 mmol) was deprotected in 4 M HCl in dioxane for 75 minutes, evaporated to dryness, and co-evaporated twice from DCM. Then Compound 20.2 (61 mg, 0.230 mmol), EDC (42 mg, 0.219 mmol), and HOBT (33 mg, 0.244 mmol) was added, the reaction was dissolved in 2 ml dry DMF, and triethylamine (0.12 ml, 0.863 mmol) was added, followed by an additional 1 ml dry DMF. After 1 hour the reaction was heated under nitrogen to 60° C. overnight, then flooded with 50 ml EtOAc, rinsed with 2×25 ml 1 M HCl, 2×25 ml 1 M NaOH, 25 ml brine, dried over sodium sulfate, filtered, and evaporated to dryness. The residue was then purified by reverse-phase HPLC to yield compound 143.3 as a white solid (10 mg, 0.023 mmol, 10%). ES (+) MS m/e=439 (M+1).

Example 144

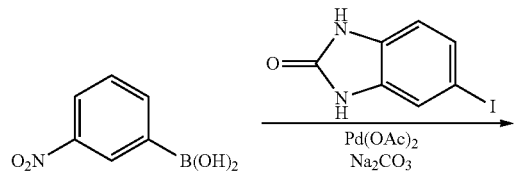

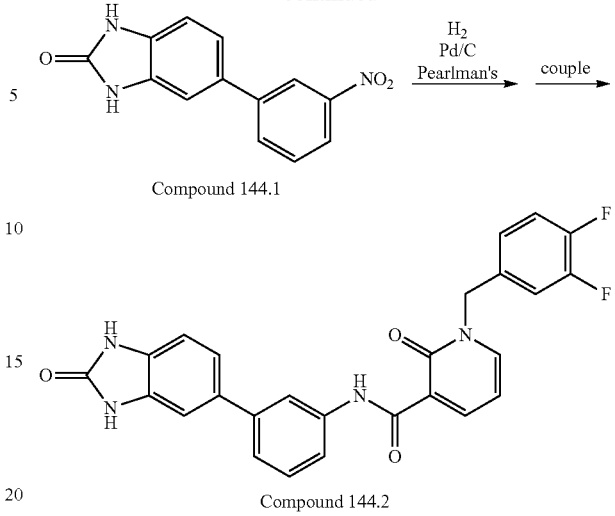

Compound 144.1

Compound 144.2

144.1 5-Iodo-1,3-dihydro-benzoimidazol-2-one (209 mg, 0.804 mmol) and 3-nitro-benzene boronic acid (135 mg, 0.809 mmol) were dissolved in 3 ml DMF, and then 1 ml of 2 M sodium carbonate in water was added, followed by palladium (II) acetate (17 mg, 0.076 mmol), and the reaction was heated under nitrogen to 80° C. for 3 hours. Then, tri-orthotolyl-phosphine (101 mg, 0.33 mmol) and more palladium (II) acetate (18 mg, 0.156 mmol) were added, as well as 3 ml DMF, and 3 ml water. After several days 50 ml EtOAc was added, the reaction was partially concentrated under reduced pressure, and then filtered through a medium glass frit. The precipitate was rinsed with 2×25 ml water, resuspended in 50 ml diethyl ether, filtered, and dried to yield Compound 144.1 as a fine brown powder (141 mg, 0.553 mmol, 69%). ES (+) MS m/e=256 (M+1).

144.2 Compound 144.1 (141 mg, 0.553 mmol) was suspended in 10 ml ethanol, and 10% wet palladium on carbon was added (110 mg), followed by an additional 10 ml ethanol. The reaction was sparged and put under a hydrogen balloon. After two hours 0.2 ml of 4 M HCl in dioxane was added, along with 90 mg of Pearlman's catalyst. The following day the reaction was filtered through Celite and evaporated to yield a red oil. This was resuspended in 50 ml 1 N NaOH and extracted with 3×25 ml EtOAc, the combined organics were dried over sodium sulfate, filtered, and evaporated to yield a yellow solid which was coupled with Compound 20.2 as in Example 212.3 to yield, after reverse-phase HPLC purification, Compound 144.2. ES (+) MS m/e=473 (M+1).

Example 145

Compound 145

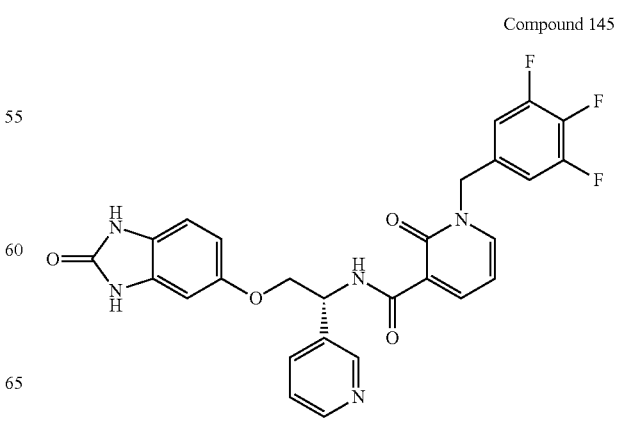

Compound 145 was made as Compound 141.4 but starting with 1-(3-pyridinyl)-2-hydroxy ethylamine. ES (+) MS m/e=536 (M+1). $^1$H NMR (400 MHz, DMSO-d6)$^{TM}$ ppm 4.34 (m, 2H) 5.23 (m, 2H) 5.50 (m, 1H) 6.52 (m, 2H) 6.60 (t, J=6.85 Hz, 1H) 6.76 (d, J=8.31 Hz, 1H) 7.32 (m, 2H) 7.79 (dd, J=7.83, 5.38 Hz, 1H) 8.23 (dd, J=6.85, 2.45 Hz, 1H) 8.33 (m, 2H) 8.70 (d, J=4.89 Hz, 1H) 8.86 (m, 1H) 10.41 (m, 1H) 10.55 (m, 2H).

Example 146

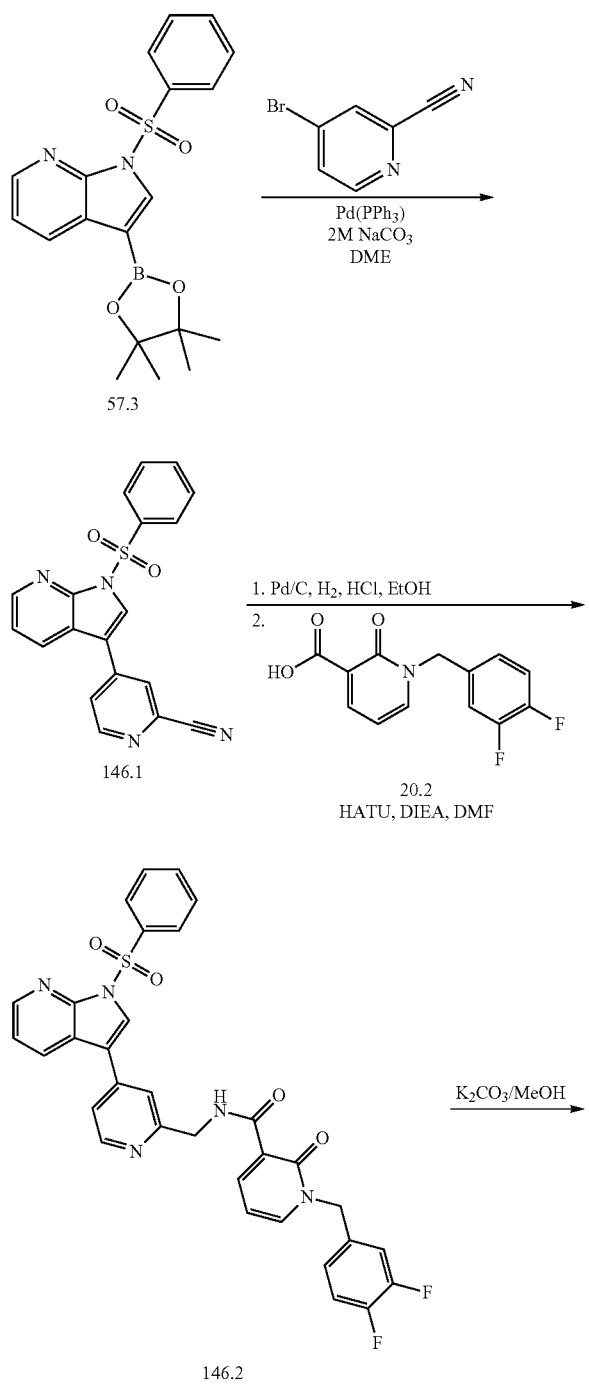

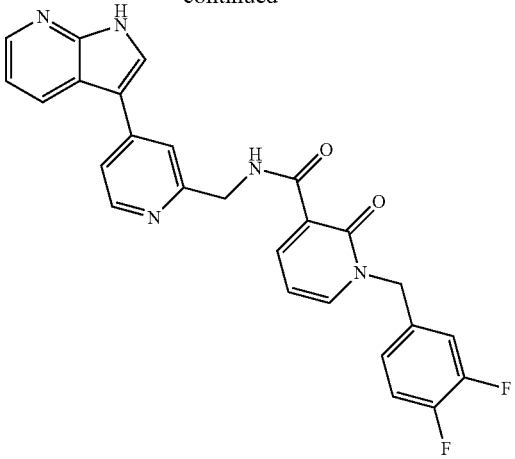

146.1 Compound 57.3 (4.94 grams, 12.85 mmol) was combined with 4-bromo-pyridine-2-carbonitrile (1.96 grams, 210.71 mmol), tetrakis(triphenylphosphine)palladium (1.36 grams, 1.18 mmol) and dissolved in dimethoxyethane (54 ml). The mixture was purged with nitrogen and a 2 M sodium carbonate solution (27 ml, 53.55 mmol) was added. The reaction was sealed and stirred at 50° C. for 1 hour. The reaction was cooled to ambient temperature, flooded with water, extracted with ethyl acetate, washed with brine, dried over sodium sulfate, filtered and concentrated under reduced pressure. The residue was purified by silica gel column chromatography eluting with 7:5 hexane: ethyl acetate to yield Compound 146.1 (1.96 grams, 5.44 mmol). ES (+) MS m/e=361 (M+H).

146.2 Compound 146.1 (1.41 grams, 3.09 mmol) was dissolved in ethanol (20 ml), mixed with palladium on carbon (Degussa Type E101 NE/W wet, 0.152 grams) and 12 N HCl (12 ml) was added. The mixture was placed on a Parr shaker at 45 psi for 16 hours. The mixture was filtered through Celite and concentrated under reduced pressure. This residue was triturated with diethyl ether and dried. ES (+) MS m/e=365 (M+H). This intermediate (55 mg, 0.151 mmol) was combined with Compound 20.2 (0.188 grams, 0.708 mmol), O-(7-Azabenzotriazole-1-yl)-N,N,N'N'-tetramethyluronium hexafluorophosphate (0.350 grams, 0.920 mmol) and diisopropylethylamine (0.617 ml, 3.54 mmol) in DMF (2 ml) and stirred at ambient temperature for 30 minutes. The mixture was flooded with ethyl acetate, washed with saturated sodium bicarbonate, brine, dried over sodium sulfate, filtered and concentrated to yield crude Compound 146.2. ES (+) MS m/e=612 (M+H).

146.3 Compound 146.2 (0.708 mmol) was dissolved in methanol (1 ml) and potassium carbonate (0.490 grams, 3.54 mmol) was added. The mixture was stirred at 50° C. for 30 minutes and flooded with ethyl acetate, washed with water, brine, dried over sodium sulfate, filtered, and concentrated. The residue was purified by silica gel column chromatography, eluting with 5-10% 2M methanolic ammonia in dichloromethane to yield Compound 146.3 (0.042 grams, 0.089 mmol). ES (+) MS m/e=472 (M+H). 1H NMR (400 MHz, CD$_3$OD) δ ppm 4.66 (m, 2H) 5.15 (m, 2H) 6.48 (m, 1H) 7.07 (m, 2H) 7.23 (m, 1H) 7.54 (m, 1H) 7.67 (m, 1H) 7.88 (m, 1H) 7.94 (m, 1H) 8.16 (m, 1H) 8.28 (m, 1H) 8.38 (m, 2H).

Example 147
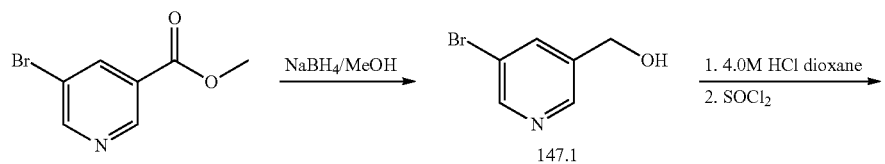
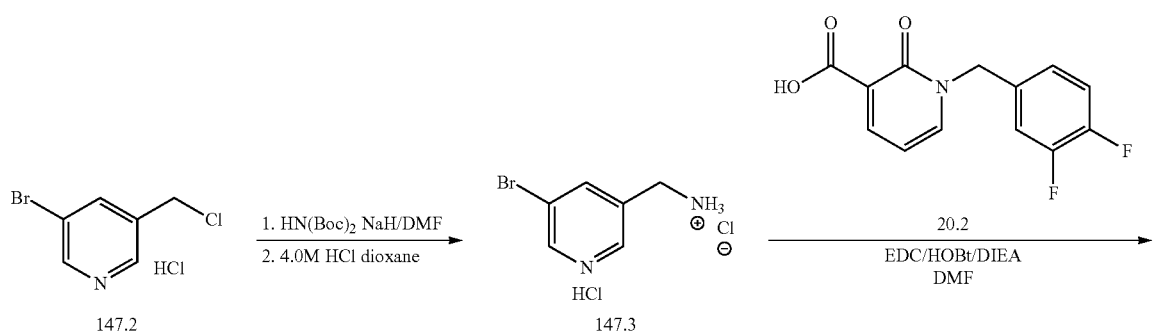
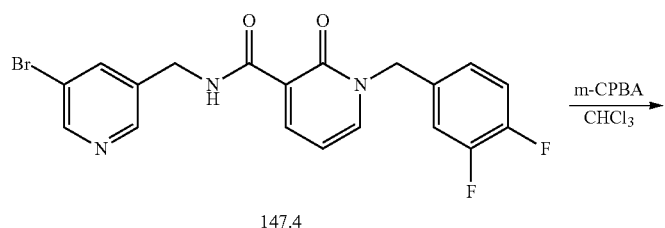
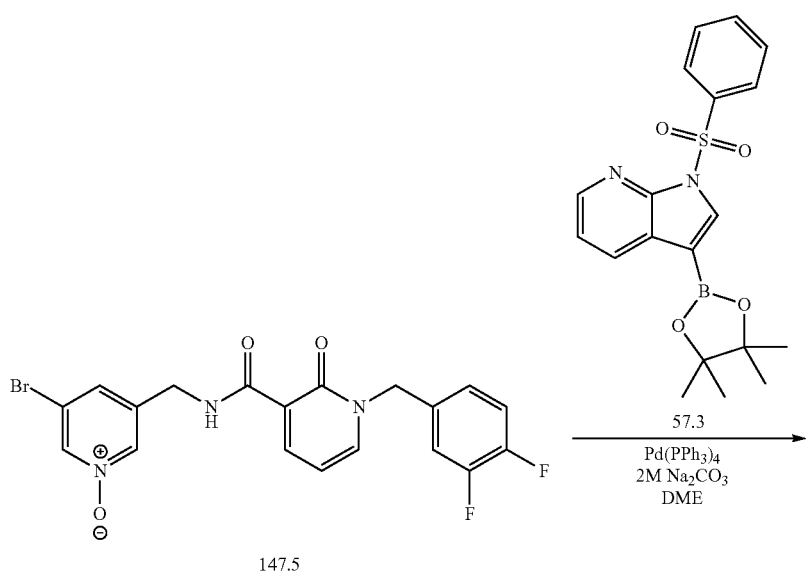

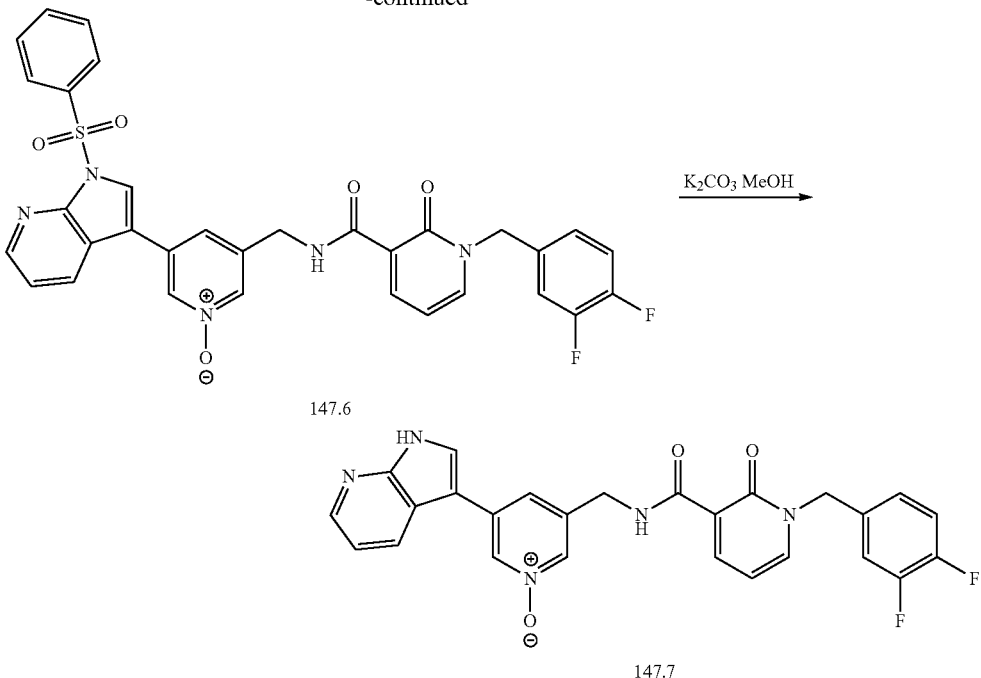

147.1 5-Bromo-nicotinic acid methyl ester (3.0 grams, 13.89 mmol) was dissolved in methanol (70 ml), chilled on an ice bath to 0° C., and sodium borohydride (5.25 grams, 139 mmol) was added portion-wise. The ice bath was removed and the mixture stirred at ambient temperature for 16 hours at which point it was cooled to 0° C. and quenched with water. The mixture was extracted with ethyl acetate, dried over sodium sulfate, filtered and evaporated under reduced pressure. The residue was purified by silica gel column chromatography eluting with 5-10% 2 M methanolic ammonia in dichloromethane to yield Compound 147.1 (1.14 grams, 6.06 mmol). ES (+) MS m/e=190 (M+2).

147.2 Compound 147.1 (1.14 grams, 6.06 mmol) was dissolved in dichloromethane (10 ml) and 4.0 M HCl in p-dioxane (15 ml) was added. The mixture was stirred for 15 minutes and then concentrated under reduced pressure. To this residue was added thionyl chloride (4.23 ml, 9.91 mmol) at 0° C. The mixture was heated to reflux for 2 hours, cooled to ambient temperature, hexane (25 ml) was added and the mixture filtered. The cake was dried under reduced pressure to yield Compound 147.2. ES (+) MS m/e=208 (M+2).

147.3 Di-tert-butyl iminodicarboxylate (1.72 grams, 7.9 mmol) was dissolved in DMF (26 ml) and sodium hydride (0.380 grams, 9.49 mmol) was added portion-wise. The mixture was stirred at ambient temperature for 30 minutes at which point Compound 147.2 (1.28 grams, 5.27 mmol) dissolved in DMF (5 ml) was added drop-wise. The reaction was stirred at ambient temperature for 2 hours at which point another 0.5 equiv of sodium hydride was added. The reaction continued stirring for 1.5 hours at which point it was flooded with water (200 ml), extracted with ethyl acetate, washed with brine, dried over sodium sulfate, filtered and concentrated. ES (+) MS m/e=389 (M+2). This residue (1.0 grams, 2.58 mmol) was dissolved in dichloromethane (15 ml) and 4.0 M HCl in p-dioxane was added. The mixture was stirred at ambient temperature for 21 hours and concentrated under reduced pressure to yield Compound 147.3 (0.629 grams, 2.4 mmol). ES (+) MS m/e=189 (M+2).

147.4 This was made as in example 4.4, using Compound 147.3 as the amine. ES (+) MS m/e=436 (M+2).

147.5 Compound 147.4 (0.768 grams, 1.77 mmol) was dissolved in chloroform (10 ml), meta-chloroperoxybenzoic acid (0.481 grams, 1.95 mmol) was added, the reaction stirred at ambient temperature for 18 hours and concentrated under reduced pressure. The residue was dissolved in dichloromethane and washed with 1N NaOH, saturated sodium bicarbonate, brine, dried over sodium sulfate, filtered and concentrated under reduced pressure to yield Compound 147.5 (0.731 grams, 1.6 mmol). ES (+) MS m/e=452 (M+2).

147.6 This was made as in example 215.1 except using compound 147.5. ES (+) MS m/e=628 (M+1).

147.7 This was made as in example 215.3 except using Compound 147.6. ES (+) MS m/e=488 (M+H). 1H NMR (400 MHz, DMSO-D6) δ ppm 4.53 (d, J=5.87 Hz, 2H) 5.21 (m, 2H) 6.58 (m, 1H) 7.15 (m, 2H) 7.41 (m, 2H) 7.71 (m, 1H) 8.02 (m, 1H) 8.13 (m, 1H) 8.23 (m, 1H) 8.30 (m, 2H) 8.37 (m, 1H) 8.52 (m, 1H) 10.11 (m, 1H) 12.19 (m, 1H).

Example 148

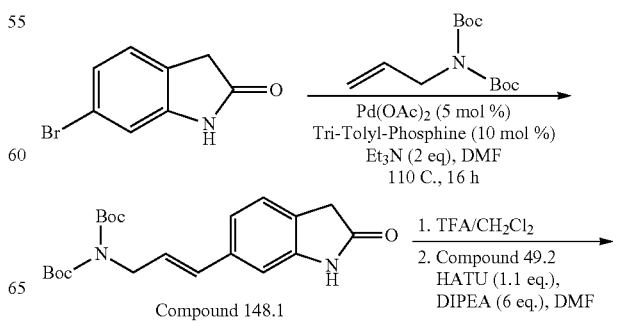

Compound 148.1

251
-continued

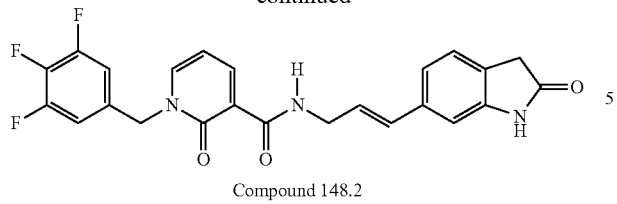

Compound 148.2

148.1 To a 10-dram vial containing 6-bromo-oxoindole (1 mmol, 212 mg), allyl-carbamic acid di-tert-butyl ester (1.16 mmol, 300 mg), Pd(OAc)$_2$ (5 mol %, 5 mg), tri-tolyl-phosphine (10 mol %, 10 mg), and Et$_3$N (2 mmol, 202 mg, 0.278 mL) was added 2 ml of DMF. The reaction mixture was heated to 110° C. for 16 h. The mixture was quenched with water, extracted with ethyl acetate. The solvent was removed under reduced pressure and chromatographed (silica gel, hexane:EA, 4:1) to give Compound 148.1 (270 mg, 69% yield). ES (+) MS m/e=389 (M+1).

148.2 To the 2-dram vial containing Compound 148.1 (0.2 mmol) in 2 ml of CH$_2$Cl$_2$ was added TFA (excess). The reaction mixture was shaken at RT for 1 h. The solvents were removed under reduced pressure. To the vial containing the intermediate in DMF (1 ml) were added Compound 49.2 (1 equivalent), HATU (1.1 equivalents), DIPEA (6 equivalents). The reaction mixture was shaken at RT for 1 h, quenched with water, extracted with EA, and chromatographed (silica gel, hexane:EA, 4:1) to give Compound 148.2 (65 mg, 70% yield). ES (+) MS m/e=454 (M+1). 1H NMR (400 MHz, DMSO-d-6) $^{TM}$ 4.44 (s, 2H), 4.08 (t, J=6 Hz, 2H), 5.21 (s, 2H), 6.2-6.3 (m, 1H), 6.59 (d, J=16 Hz, 1H), 6.61 (d, J=7 Hz, 1H), 6.83 (s, 1H), 6.69 (d, J=8 Hz, 1H), 7.13 (d, J=8 Hz, 1H), 7.32 (t, J=7 Hz, 2H), 8.23 (d, J=5 Hz, 1H), 8.39 (d, J=5 Hz, 1H), 9.75 (t, J=6 Hz, 1H), 10.37 (s, 1H).

Example 149

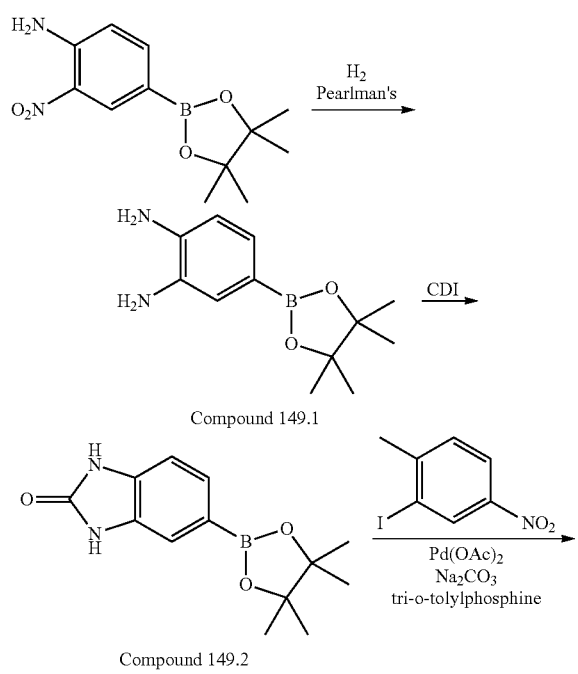

252
-continued

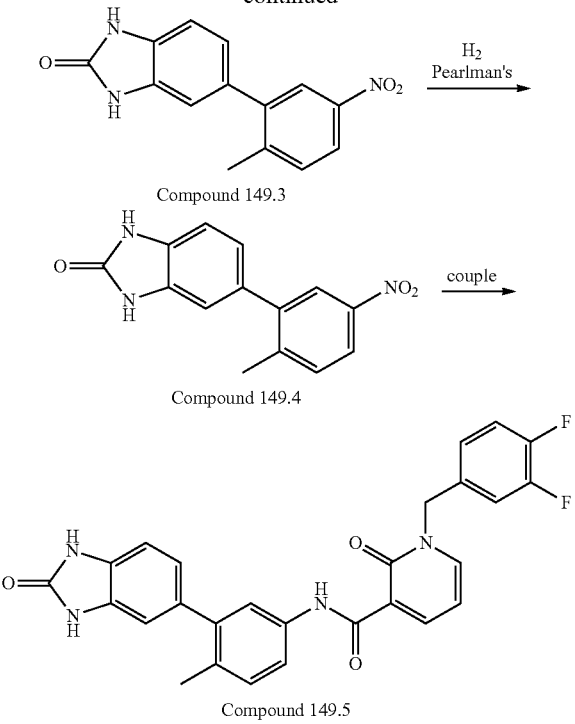

149.1 4-amino-3-nitrophenylboronic acid pinacol ester (2.283 g, 8.64 mmol) was dissolved in 20 ml ethanol and 30 ml EtOAc, Pearlman's catalyst (1.21 g of 20% dry weight) was added, the reaction was sparged, and placed under a hydrogen-filled balloon for 3 hours. The reaction was then filtered through Celite with methanol and EtOAc and evaporated to give compound 149.1 as a brown foam (2.204 g, 8.65 mmol, 100%). ES (+) MS m/e=235 (M+1).

149.2 Compound 149.1 was dissolved in 80 ml dry DMF, and CDI (1.404 g, 8.67 mmol) was added in portions, followed by an additional 20 ml DMF. After three days the reaction was evaporated under reduced pressure, suspended in 50 ml water, and filtered through a medium glass frit. The precipitate was rinsed with 2×25 ml water and dried to yield compound 149.2 as a pale violet solid (1.02 g, 3.9 mmol, 45%). ES (+) MS m/e=261 (M+1).

149.3 Compound 149.2 (212 mg, 0.815 mmol), 2-iodo-4-nitrotoluene (214 mg, 0.814 mmol), palladium (II) acetate (21 mg, 0.094 mmol), and tri-ortho-tolyl-phosphine (52 mg, 0.171 mmol) were suspended in 1.5 ml DMF, followed by 1.2 ml of 2 M sodium carbonate in water, and the reaction was heated to 95° C. under nitrogen for 150 minutes. The reaction was then evaporated to dryness, suspended in 10 ml water, and filtered through a medium glass frit. The precipitate was resuspended in 10 ml diethyl ether and filtered through a medium glass flit and rinsed with 2×10 ml diethyl ether. The precipitate was then rinsed through the frit with methanol and EtOAc and concentrated to dryness to yield a brown solid that was used without further purification. ES (+) MS m/e=270 (M+1).

149.4 Compound 149.3 was suspended in 20 ml methanol and 10 ml EtOAc, and then Pearlman's catalyst was added (127 mg). The reaction was hydrogenated on a Parr apparatus at 48 PSI overnight, filtered through a 0.45 μM filter, evaporated to dryness, and purified by silica gel chromatography using 95:5 DCM:MeOH on a 15×2.5 cm column to yield Compound 149.4 as a brown solid (29 mg, 15%, 2 steps). ES (+) MS m/e=240 (M+1).

149.5 Compound 149.4 (29 mg, 0.121 mmol), Compound 20.2 (32 mg, 0.121 mmol), HOBT (19 mg, 0.141 mmol), and EDC (23 mg, 0.120 mmol) were dissolved in 1.5 ml dry DMF, and triethylamine (0.06 ml, 0.431 mmol) was added. The reaction was stirred at 60° C. overnight under nitrogen, flooded with 40 ml EtOAc, rinsed with 2×20 ml 1 M HCl, 2×20 ml 1 M NaOH, 20 ml brine, dried over sodium sulfate, filtered, evaporated, and purified by reverse-phase HPLC to yield compound 149.5 as a yellow solid (28 mg). ES (+) MS m/e=487 (M+1).

Example 150

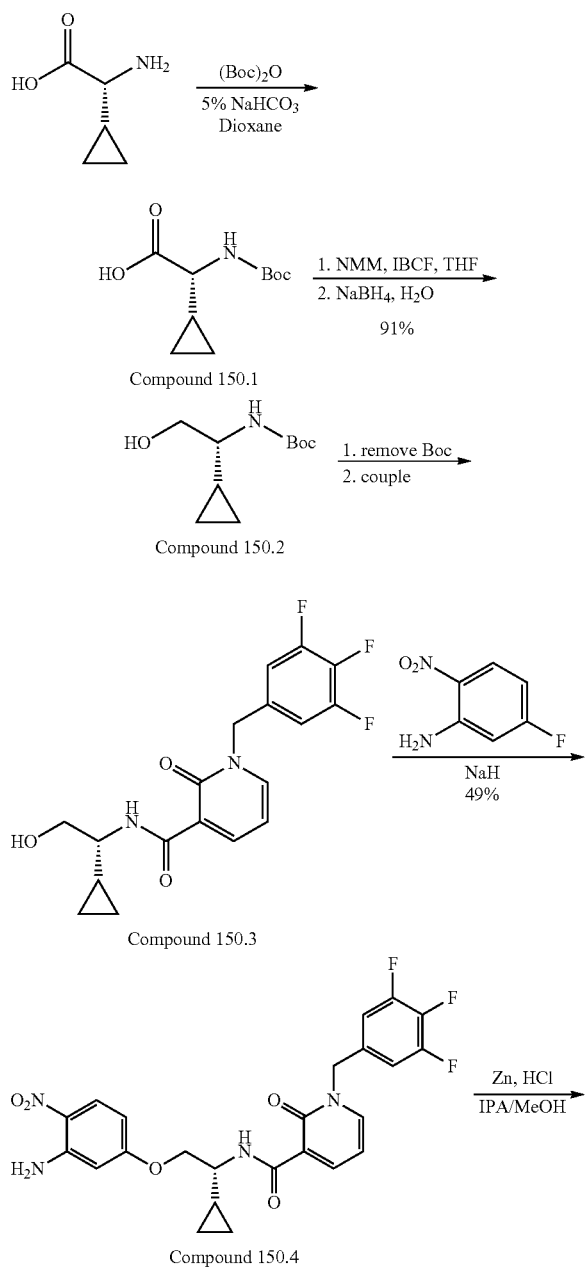

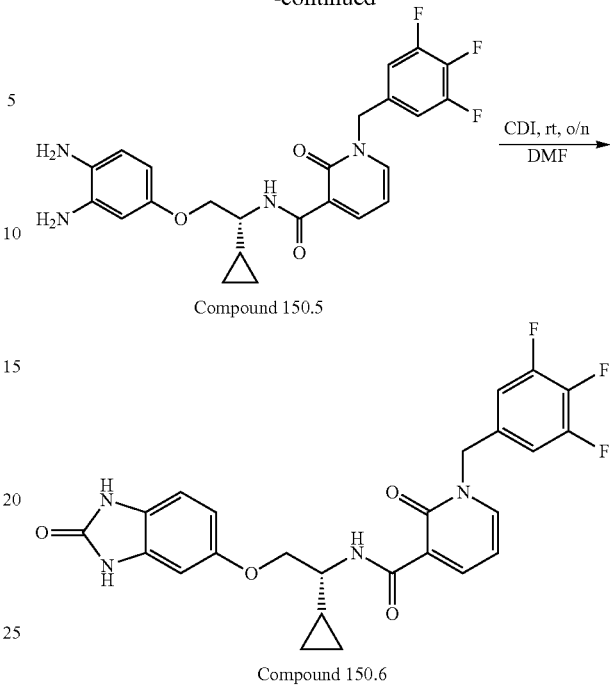

150.1 A solution of di-tert-butyl dicarbonate (1.9 g, 8.7 mmol) in dioxane (20 ml) was added to a suspension of D-cyclopropylglycine in 5% aqueous sodium bicarbonate (30 ml) and the mixture was stirred at room temperature overnight. Then more di-tert-butyl dicarbonate (0.7 g, 3.2 mmol) was added and the stirring was continued overnight. The mixture was then concentrated and the residue was re-dissolved in ethyl acetate, rinsed with 1N sodium hydrogensulfate, brine, dried over sodium sulfate, filtered, and evaporated to get a white solid. ES (+) MS m/e=238 (M+23). $^1$H NMR (400 MHz, DMSO-d6)$^{TM}$ ppm 0.26 (m, 1H) 0.33 (m, 1H) 0.40 (m, 1H) 0.48 (m, 1H) 1.01 (m, 1H) 1.36 (m, 9H) 3.29 (t, J=7.83 Hz, 1H) 7.17 (d, J=7.83 Hz, 1H) 12.38 (m, 1H).

150.2 A solution of crude compound 150.1 (8.7 mmol) in 40 ml dry THF under nitrogen was chilled to −30° C. N-methylmorpholine (0.95 ml, 8.7 mmol) was added followed by isobutyl chloroformate (1.13 ml, 8.7 mmol) dropwise. After 10 minutes, neat NaBH$_4$ (0.99 g, 26.1 mmol) was added followed immediately by 1.5 ml H$_2$O. The reaction was allowed to warm to room temperature and stirred for 1 hour. The reaction mixture was then flooded with ethyl acetate, rinsed with 1N sodium bisulfate, saturated sodium bicarbonate, brine and concentrated. The residue was purified by chromatography to give Compound 150.2 (1.7 g, 97% in two steps) as a colorless oil. $^1$H NMR (400 MHz, DMSO-d6)$^{TM}$ ppm 0.10 (m, 1H) 0.23 (m, 1H) 0.35 (m, 1H) 0.80 (m, 1H) 1.36 (m, 9H) 2.97 (m, 1H) 3.36 (m, 3H) 4.52 (t, J=5.87 Hz, 1H) 6.48 (m, 1H).

150.3 Compound 150.2 (0.56 g, 1.386 mmol) was deprotected with 4M HCl in dioxane for 30 minutes and then evaporated to dryness. This was coupled with compound 49.2 as described in Example 55.1. Compound 150.3 was obtained as a brown oil after purification with flash chromatography (2.95 g, 96%). ES (+) MS m/e=367 (M+1).

150.4 This was made in the same way as Compound 55.2 using Compound 150.3 as starting material. It was a brown solid (1.56 g, 49%). ES (+) MS m/e=503 (M+1).

150.5 This was made from Compound 150.4 using the same method as described in Example 55.3. It was a brown oil ES (+) MS m/e=473 (M+1).

150.6 This was prepared with the same method in Example 55.4, using Compound 150.5 instead of Compound 55.3 as starting material. It was a pale red powder. ES (+) MS m/e=499 (M+1). $^1$H NMR (400 MHz, DMSO-d6)$^{TM}$ ppm 0.32 (m, 2H) 0.45 (m, 2H) 1.15 (m, 1H) 3.68 (m, 1H) 3.99 (m, 1H) 4.08 (m, 1H) 5.20 (m, 2H) 6.52 (m, 2H) 6.58 (t, J=6.85 Hz, 1H) 6.76 (d, J=8.31 Hz, 1H) 7.31 (m, 2H) 8.19 (dd, J=6.36, 1.96 Hz, 1H) 8.36 (dd, J=7.34, 1.96 Hz, 1H) 9.91 (d, J=8.31 Hz, 1H) 10.36 (m, 1H) 10.49 (m, 1H).

Example 151

Compound 151.1

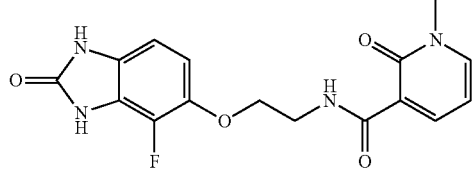

151.1 This was made analogously to compound 151.4, using the same sequence except substituting 2,3 difluoro-6-nitroaniline for 4,5-difluoro-2-nitroaniline in the second step. ES (+) MS m/e=459 (M+1).

Example 152

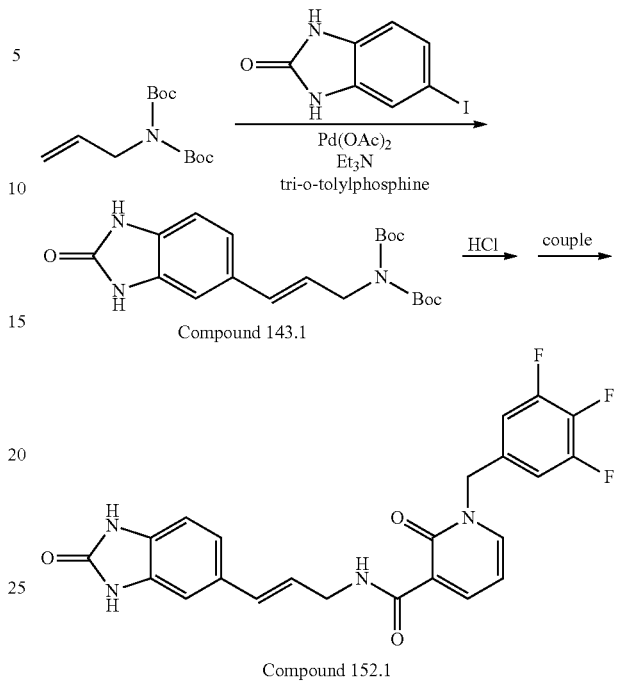

Compound 143.1

Compound 152.1

152.1 This was made analogously to compound 143.3, except substituting Compound 143.1 for Compound 143.2 and substituting Compound 49.2 for Compound 20.2. The product was a pale violet solid. ES (+) MS m/e=455 (M+1).

Example 153

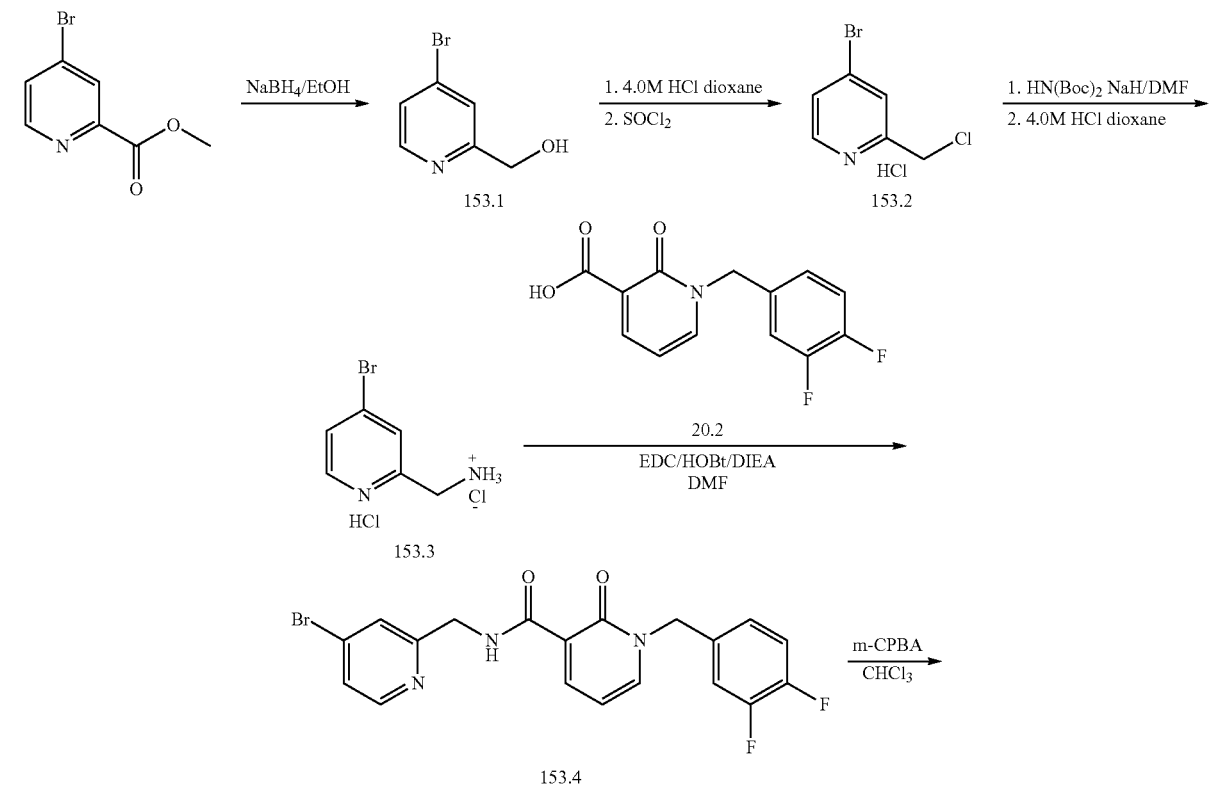

-continued

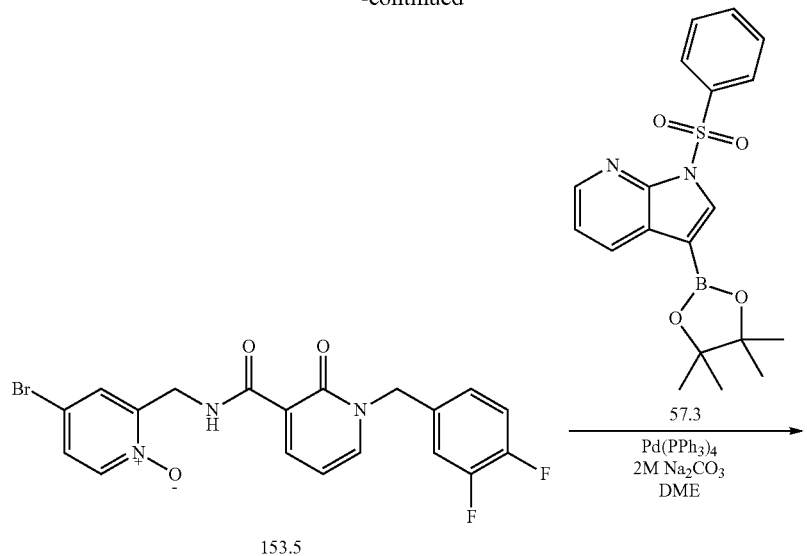

153.5

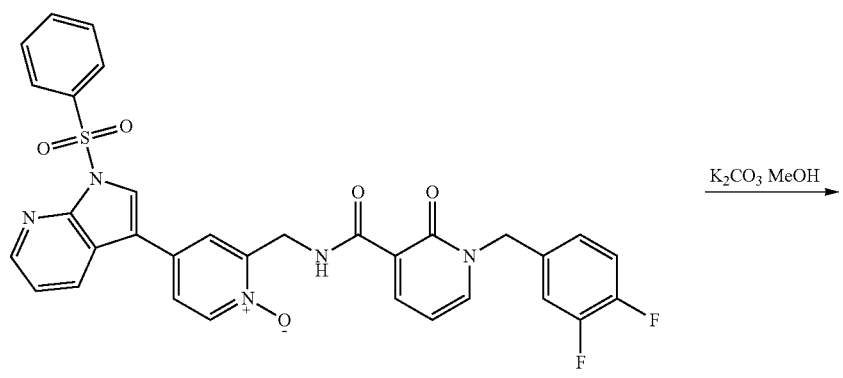

153.6

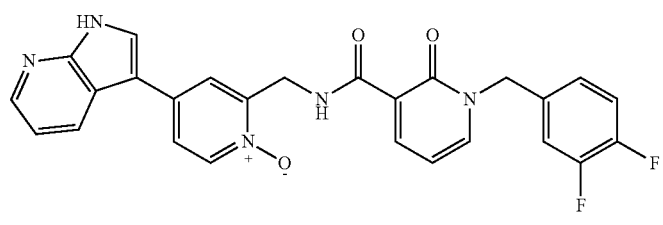

153.7

153.1 4-Bromo-pyridine-2-carboxylic acid methyl ester (1.06 grams, 4.9 mmol) was dissolved in ethanol (25 ml) and sodium borohydride (0.426 grams, 11.27 mmol) was added portion-wise. The reaction was heated to reflux for 15 minutes and then cooled to ambient temperature and acetone (5 ml) was added. The mixture was vigorously stirred for 15 minutes and the volatiles were removed under reduced pressure. The residue was purified by silica gel column chromatography eluting with 5-10% 2 M methanolic ammonia in dichloromethane to yield Compound 153.1 (0.638 grams, 3.39 mmol). ES (+) MS m/e=190 (M+2).

153.2 This was made as in example 147.2, using Compound 153.1. ES (+) MS m/e=207 (M+1).

153.3 This was made as in example 147.3, using Compound 153.2. ES (+) MS m/e=189 (M+2).

153.4 This was made as in Example 147.4, using Compound 153.3. ES (+) MS m/e=436 (M+2).

153.5 This was made as in Example 147.5, using Compound 153.4. ES (+) MS m/e=452 (M+2).

153.6 This was made as in Example 146.1, using Compound 153.5. ES (+) MS m/e=628 (M+1).

153.7 This was made as in Example 146.3, using Compound 153.6. ES (+) MS m/e=488 (M+H). 1H NMR (400 MHz, DMSO-D6) δ ppm 4.66 (m, 2H) 5.24 (m, 2H) 6.58 (m, 1H) 7.05 (m, 1H) 7.18 (m, 1H) 7.41 (m, 2H) 7.73 (m, 2H) 8.13 (m, 1H) 8.25 (m, 4H) 8.37 (m, 1H) 10.22 (m, 1H) 12.20 (m, 1H).

Example 154
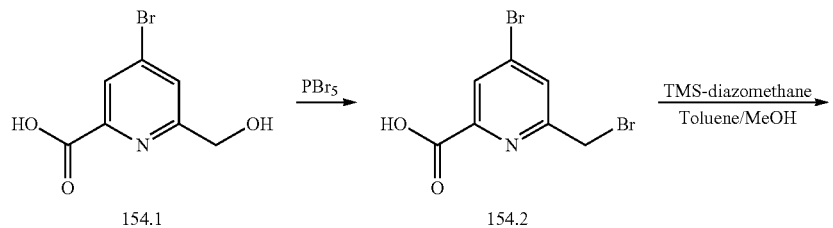
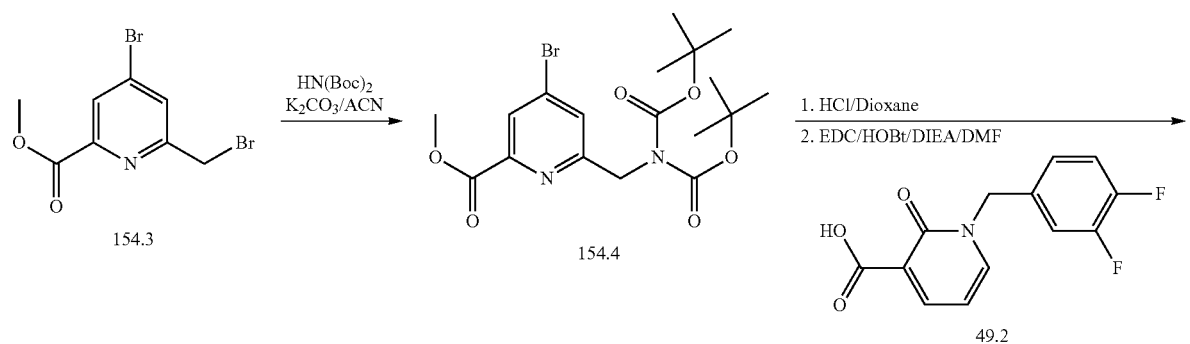
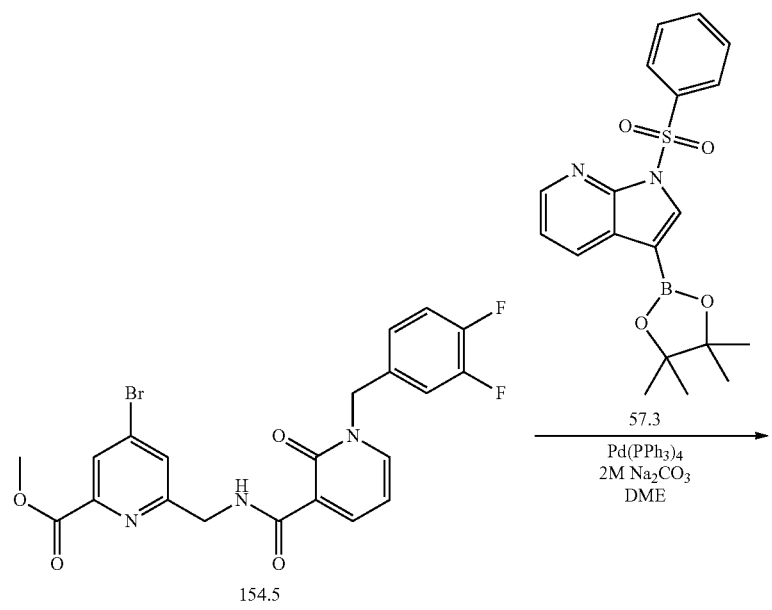

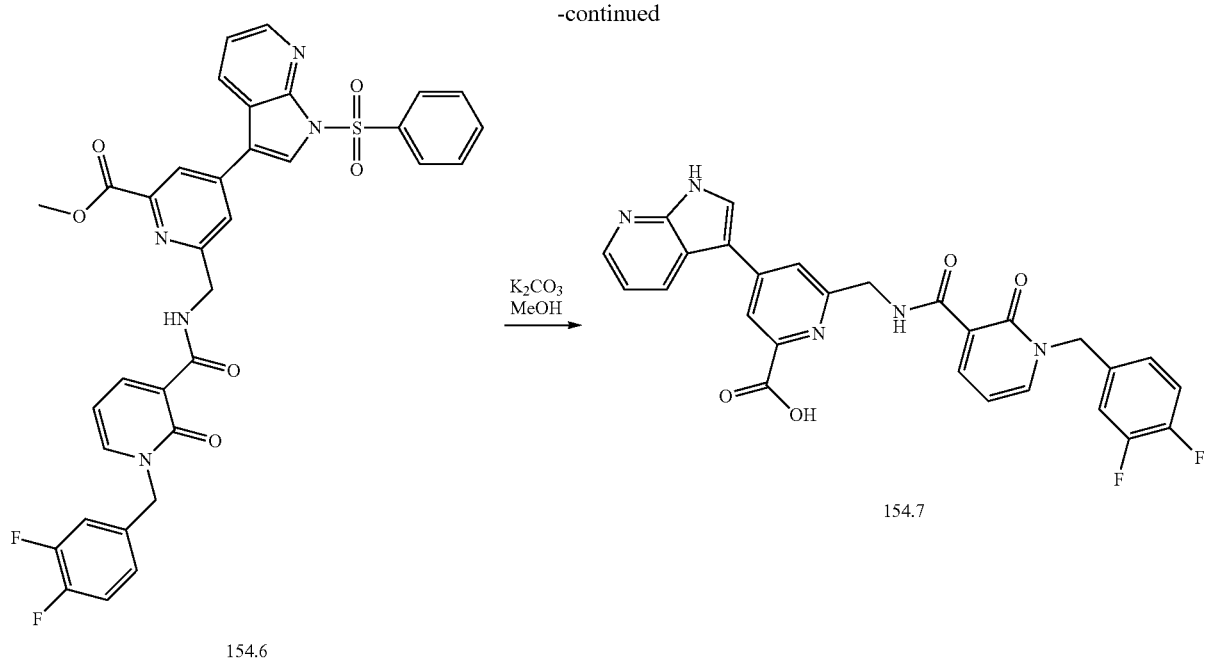

154.6

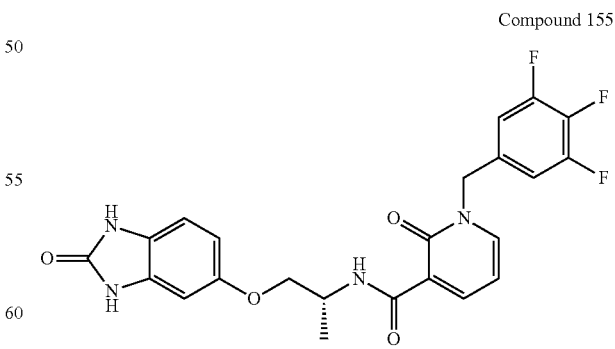

154.7

154.1 Compound 154.1 was prepared as described in Takalo et al. Helv. Chim. Acta. 1996 (79) 789-802.

154.2 Compound 154.1 (2.19 grams, 9.44 mmol) was mixed with phosphorus pentabromide (8.13 grams, 18.88 mmol) and stirred at 90° C. for 1.5 hours. This mixture was allowed to stand open to air at ambient temperature for 3 days to yield crude Compound 154.2. (0.788 grams, 2.67 mmol) ES (+) MS m/e=296 (M+2).

154.3 Compound 154.2 (0.788 grams, 2.67 mmol) was dissolved in a mixture of toluene (11.2 ml) and methanol (2.8 ml) and trimethylsilyldiazomethane (3.0 ml, 5.34 mmol) was added drop-wise. The reaction was stirred at ambient temperature for 15 minutes and then concentrated under reduced pressure. The residue was purified by silica gel column chromatography eluting with 7:3 hexane:ethyl acetate to yield Compound 154.3 (0.362 grams, 1.17 mmol). ES (+) MS m/e=310 (M+2).

154.4 Compound 154.3 (0.308 grams, 0.996 mmol) was dissolved in acetonitrile (10 ml), then di-tert-butyl iminodicarboxylate (0.216 grams, 0.996 mmol), and potassium carbonate (0.688 grams, 4.98 mmol) were added. The reaction was stirred for 16 hours at ambient temperature and then filtered and concentrated under reduced pressure. The residue was purified by silica gel column chromatography eluting with 10-20% ethyl acetate in hexane to yield Compound 154.4 (0.399 grams, 0.898 mmol). ES (+) MS m/e=447 (M+2).

154.5 Compound 154.4 was deprotected as described in Example 147.3 and coupled as in Example 147.4. ES (+) MS m/e=494 (M+2).

154.5 Compound 154.6 was prepared as described in Example 146.1. ES (+) MS m/e=670 (M+1).

154.6 Compound 154.6 (0.118 grams, 0.176 mmol) was dissolved in methanol (1 ml), potassium carbonate (0.122 grams, 0.881 mmol) was added and the mixture was stirred at 50° C. for 30 minutes. The solvent was removed under reduced pressure and the residue was partitioned between ethyl acetate and water. The aqueous layer was concentrated and the residue was purified by preparative HPLC eluting with acetonitrile/water to yield Compound 154.7. ES (+) MS m/e=516 (M+H). 1H NMR (400 MHz, DMSO-D6) δ ppm 4.73 (d, J=5.87 Hz, 2H) 5.24 (m, 2H) 6.60 (m, 1H) 7.13 (m, 1H) 7.20 (m, 1H) 7.42 (m, 2H) 7.96 (m, 1H) 8.25 (m, 2H) 8.32 (m, 2H) 8.39 (m, 2H) 10.27 (m, 1H) 12.38 (m, 1H).

Example 155

Compound 155

Compound 155 was made as Compound 141.4 but starting with (R)-(−)-2-amino-1-propanol. ES (+) MS m/e=473 (M+1). $^1$H NMR (400 MHz, DMSO-d6) $^{TM}$ ppm 1.24 (d, J=6.85 Hz, 3H) 3.88 (m, 1H) 3.97 (m, 1H) 4.29 (m, 1H) 5.19

(m, 2H) 6.52 (m, 2H) 6.58 (t, J=6.85 Hz, 1H) 6.77 (d, J=8.31 Hz, 1H) 7.30 (m, 2H) 8.19 (dd, J=6.36, 1.96 Hz, 1H) 8.36 (dd, J=6.85, 1.96 Hz, 1H) 9.79 (d, J=7.83 Hz, 1H) 10.36 (m, 1H) 10.50 (m, 1H).

Example 156

Compound 156

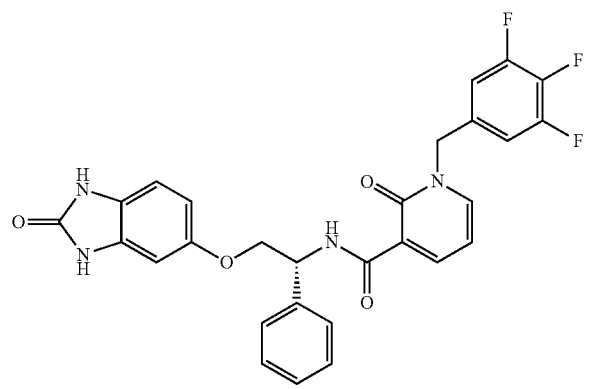

Compound 156 was made as Compound 55.4 except using Compound 49.2 instead of Compound 20.2. ES (+) MS m/e=535 (M+1). ¹H NMR (400 MHz, DMSO-d6) ppm 4.19 (m, 1H) 4.25 (m, 1H) 5.22 (m, 2H) 5.36 (m, 1H) 6.50 (m, 2H) 6.59 (t, J=6.85 Hz, 1H) 6.75 (d, J=7.83 Hz, 1H) 7.30 (m, 5H) 7.41 (m, 2H) 8.20 (dd, J=6.85, 2.45 Hz, 1H) 8.35 (dd, J=6.85, 1.96 Hz, 1H) 10.37 (m, 1H) 10.41 (d, J=7.83 Hz, 1H) 10.50 (m, 1H).

Example 157

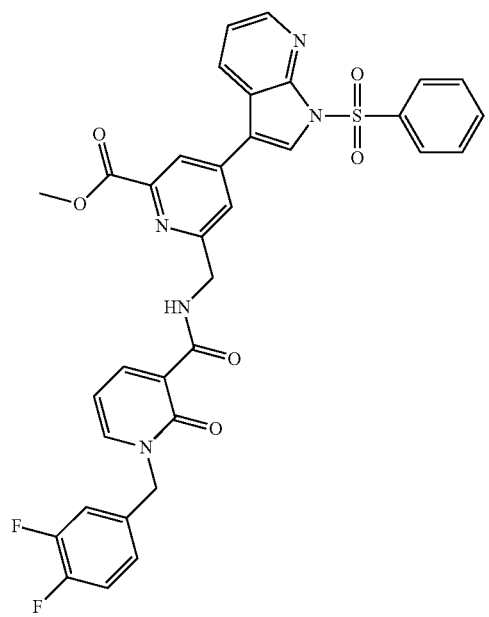

154.6

-continued

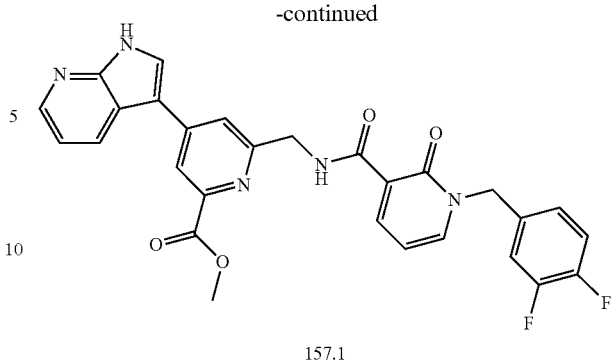

157.1

157.1 The organic layer from the workup of Example 154.7 was dried over sodium sulfate, filtered and concentrated under reduced pressure. The residue was purified by preparative HPLC eluting with acetonitrile/water to yield Compound 157.1. ES (+) MS m/e=530 (M+H). 1H NMR (400 MHz, DMSO-D6) δ ppm 3.91 (m, 3H) 4.71 (m, 2H) 5.24 (m, 2H) 6.59 (m, 1H) 7.13 (m, 1H) 7.19 (m, 1H) 7.42 (m, 2H) 7.94 (m, 1H) 8.25 (m, 2H) 8.35 (m, 4H) 10.25 (m, 1H) 12.35 (m, 1H)

Example 158

Compound 158.1

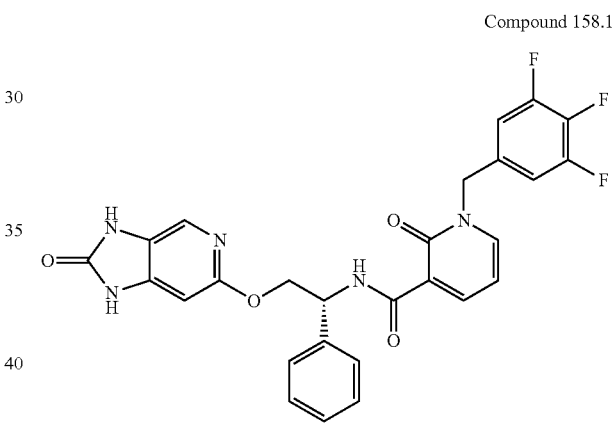

158.1 This was made analogously to Compound 137.4, using the same sequence except substituting D-phenylglycinol for ethanolamine and Compound 49.2 for Compound 20.2 in the first step and 2-chloro-5-nitro-pyridin-4-ylamine for 4,5-difluoro-2-nitroaniline in the second step. ES (+) MS m/e=536 (M+1).

Example 159

Compound 159.1

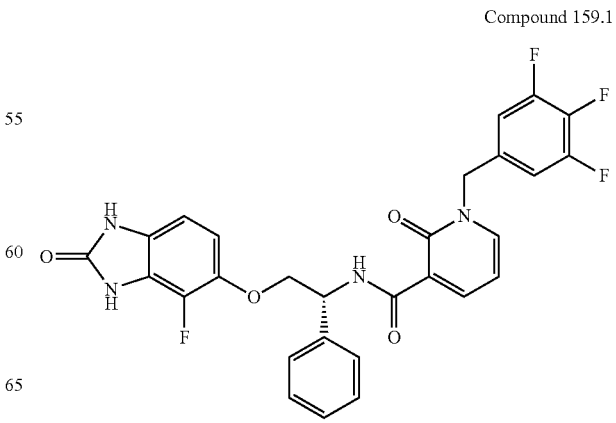

159.1 This was made analogously to compound 151.1, using the same sequence except substituting D-phenylglycinol for ethanolamine and Compound 49.2 for Compound 20.2 in the first step. ES (+) MS m/e=553 (M+1).

Example 160

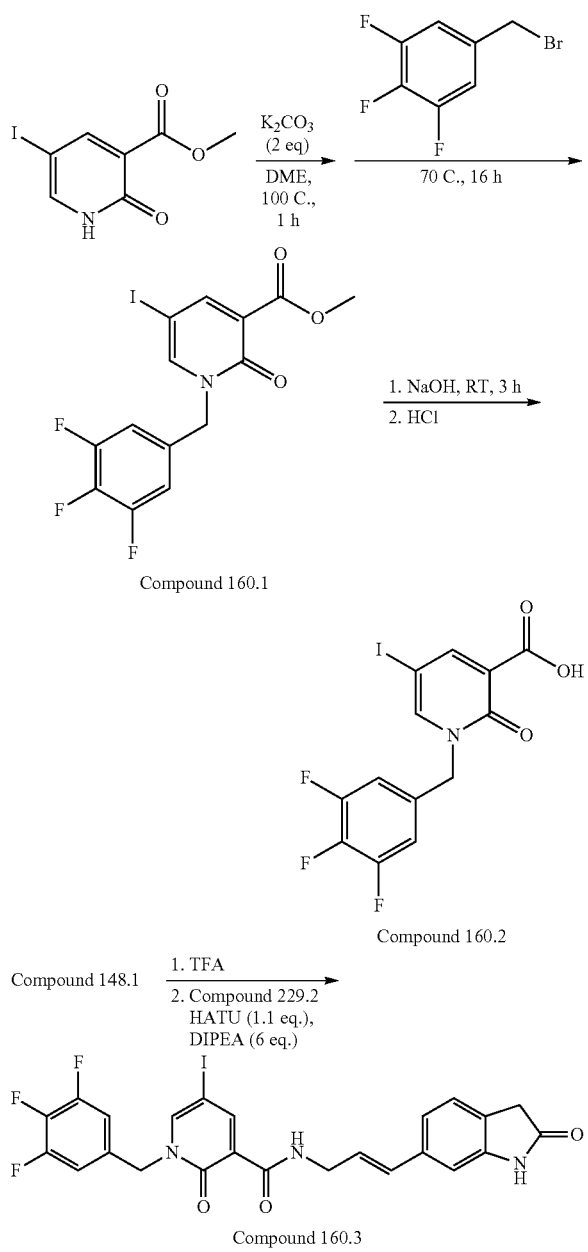

Compound 160.1

Compound 160.2

Compound 148.1

Compound 160.3

160.1 To a 10-dram vial containing 5-iodo-2-oxo-1,2-dihydro-pyridine-3-carboxylic acid methyl ester (1 mmol) in 3 ml of DME was added 2 equivalents of K₂CO₃. The suspension of reaction mixture was stirred at 100° C. for 1 h. The reaction mixture was cooled to RT and 5-bromomethyl-1,2,3-trifluoro-benzene (1 mmol) was added. It was stirred at 70° C. for 16 h. It was quenched with water, extracted with EA. The solvent was removed under reduced pressure to give Compound 160.1. ES (+) MS m/e=424 (M+1).

160.2 To the 2-dram vial containing crude Compound 160.1 was added 1.1 equivalents of NaOH (3.0 M solution). The vial was capped and shaken at RT for 3 h. The reaction was quenched with 1.1 equivalents of HCl (3.0 M solution). The precipitate was filtered and washed with water three times. ES (+) MS m/e=410 (M+1).

160.3 To the 2-dram vial containing Compound 148.1 (0.2 mmol) in CH₂Cl₂ was added TFA (excess). The reaction mixture was shaken at RT for 1 h. The solvents were removed under reduced pressure. To the vial containing the intermediate in DMF (1 ml) were added Compound 160.2 (1 equivalent), HATU (1.1 equivalents), DIPEA (6 equivalents). The reaction mixture was shaken at RT for 1 h, quenched with water, extracted with EA, and chromatographed (silica gel, hexane:EA, 4:1) to give Compound 160.3. ES (+) MS m/e=580 (M+1). 1H NMR (400 MHz, DMSO-d-6) ™ 3.44 (s, 2H), 4.07 (t, J=6 Hz, 2H), 5.15 (s, 2H), 6.2-6.3 (m, 1H), 6.49 (d, J=16 Hz, 1H), 6.83 (s, 1H), 6.95 (d, J=8 Hz, 1H), 7.13 (d, J=8 Hz, 1H), 7.36 (t, J=7 Hz, 2H), 8.40 (d, J=5 Hz, 1H), 8.57 (d, J=5 Hz, 1H), 9.62 (t, J=6 Hz, 1H), 10.37 (s, 1H).

Example 161

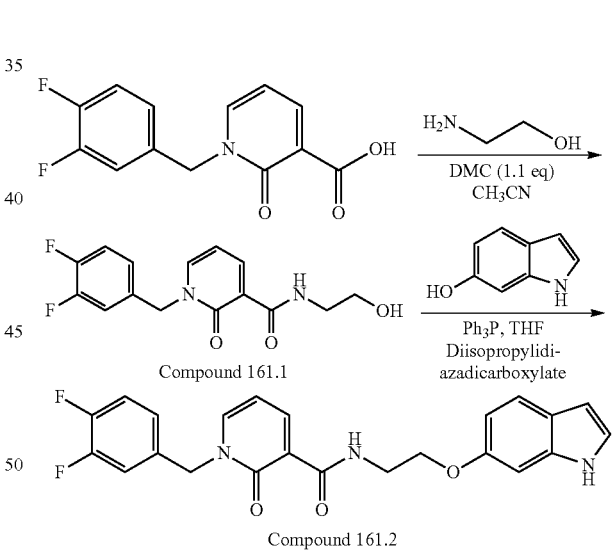

Compound 161.1

Compound 161.2

161.1 The Compound 20.2 (10 mmol) was added to a flask containing 2-amino-ethanol (10 mmol) in CH₃CN (50 ml). To this was added DMC (2-chloro-1,3-dimethylimidazolinium chloride, 12 mmol) and Et₃N (2 equivalents). The reaction mixture was stirred at RT for 16 hours. It was quenched with water and extracted CH₂Cl₂. The solvent was removed under reduced pressure to give Compound 161.1. ES (+) MS m/e=309 (M+1).

161.2 To the 2-dram vial containing crude Compound 161.1 (0.318 mmol) in THF (3 mL) was added 1.0 equivalent of 6-hydroxy-indole. To this were added Ph₃P (1 equiva-

267 lent) and di-isopropyl-diazodicarboxylate (1.2 equivalents) at 0° C. The reaction mixture was warmed to RT and shaken for 16 h. The solvent was removed under reduced pressure, and crude product was dissolved in DMSO (3 ml) and purified by using HPLC (reverse phase) to give Compound 161.2. ES (+) MS m/e=424 (M+1). 1H NMR (400 MHz, DMSO-d-6) ™ 3.68 (t, J=5 Hz, 2H), 4.07 (t, J=5 Hz, 2H), 5.22 (s, 2H), 6.32 (s, 1H), 6.58 (t, J=7 Hz, 1H), 6.6-6.7 (m, 1H), 6.92 (s, 1H), 7.1-7.2 (m, 2H), 7.3-7.5 (m, 3H), 8.22 (d, J=7 Hz, 1H), 8.38 (d, J=7 Hz, 1H), 9.91 (t, J=6 Hz, 1H), 10.87 (s, 1H).

Example 162

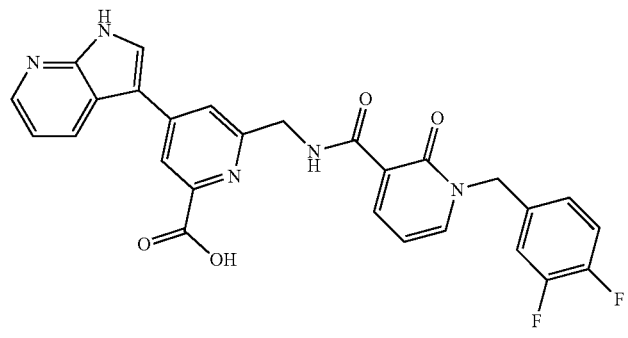

154.7

Compound 154.7 (0.080 grams, 0.155 mmol) and O-(7-Azabenzotriazole-1-yl)-N,N,N'N'-tetramethyluronium hexafluorophosphate (0.076 grams, 0.202 mmol) were dissolved in DMF and 2.0 M methylamine in THF (0.776 ml, 1.56 mmol) was added followed by diisopropylethylamine (0.135 ml, 0.755 mmol). Five minutes later the reaction was diluted with DMSO and purified by preparative HPLC eluting with acetonitrile/water to yield Compound 162.1. ES (+) MS m/e=529 (M+H). 1H NMR (400 MHz, DMSO-D6) δ ppm 2.88 (d, J=4.40 Hz, 3H) 4.77 (m, 2H) 5.32 (m, 2H) 6.64 (m, 1H) 7.18 (m, 2H) 7.44 (m, 2H) 7.96 (m, 1H) 8.25 (m, 2H) 8.31 (m, 1H) 8.35 (m, 1H) 8.43 (m, 2H) 8.82 (m, 1H) 10.85 (m, 1H) 12.33 (m, 1H).

268

Example 163

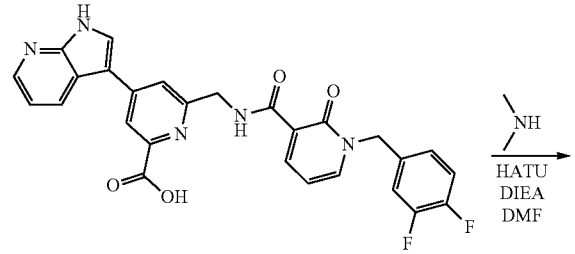

154.7

-continued

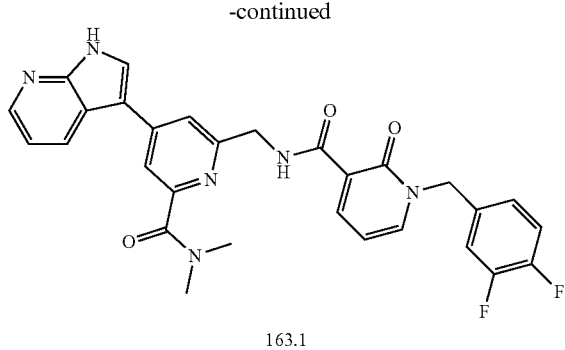

163.1

163.1 Compound 163.1 was prepared as in Example 162.1, using dimethylamine in THF. ES (+) MS m/e=542 (M+H). 1H NMR (400 MHz, Solvent) δ ppm 3.00 (m, 3H) 3.07 (m, 3H) 4.73 (m, 2H) 5.18 (m, 2H) 6.50 (m, 1H) 7.13 (m, 2H) 7.25 (m, 2H) 7.83 (m, 2H) 7.99 (m, 1H) 8.10 (m, 1H) 8.27 (m, 1H) 8.39 (m, 1H) 8.53 (m, 1H).

Example 164

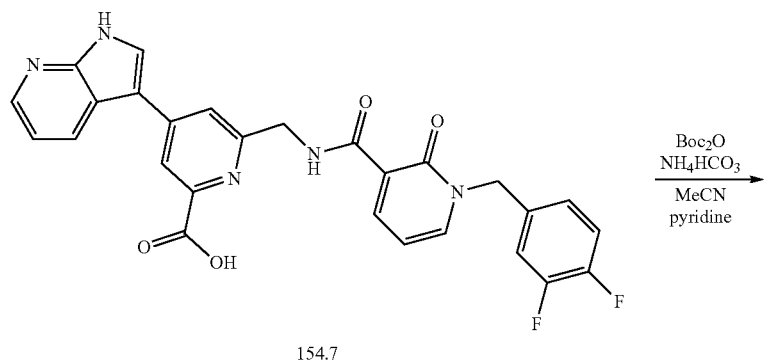

154.7

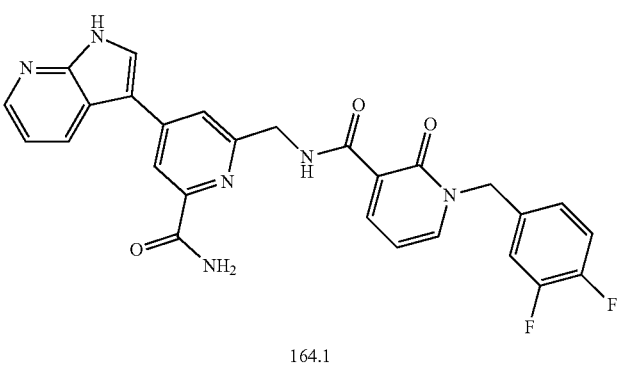

164.1

164.1 Compound 154.7 (0.188 grams, 0.365 mmol), ammonium bicarbonate (0.036 grams, 0.449 mmol), t-butoxycarbonyl anhydride (0.104 grams, 0.478 mmol), and DMF (3 ml) were combined in a round bottom flask and flushed with nitrogen. Pyridine (0.018 ml, 0.226 mmol) was added drop-wise and the reaction stirred at ambient temperature for 16 hours. Water (1 ml) was added, the reaction diluted with DMSO and purified by preparative HPLC eluting with acetonitrile/water to yield Compound 164.1. ES (+) MS m/e=515 (M+H). 1H NMR (400 MHz, DMSO-D6) δ ppm 4.76 (m, 2H) 5.24 (m, 2H) 6.63 (m, 1H) 7.21 (m, 1H) 7.26 (m, 1H) 7.42 (m, 1H) 7.51 (m, 1H) 7.92 (m, 1H) 7.98 (m, 1H) 8.30 (m, 3H) 8.36 (m, 2H) 8.43 (m, 2H) 10.94 (m, 1H) 12.34 (m, 1H).

Example 165

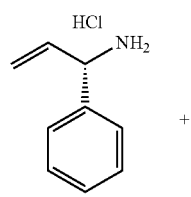

Compound 165.1

+

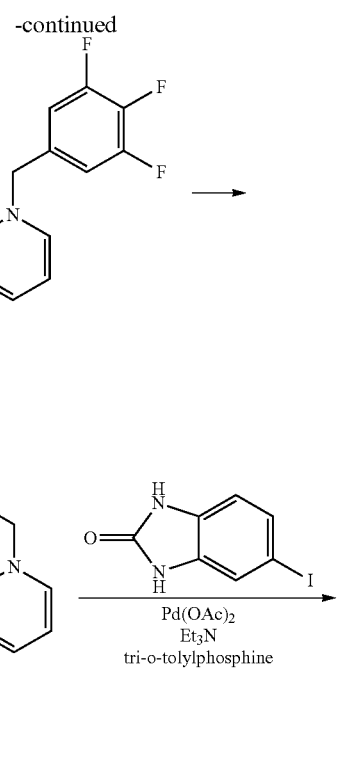

Compound 165.2

-continued

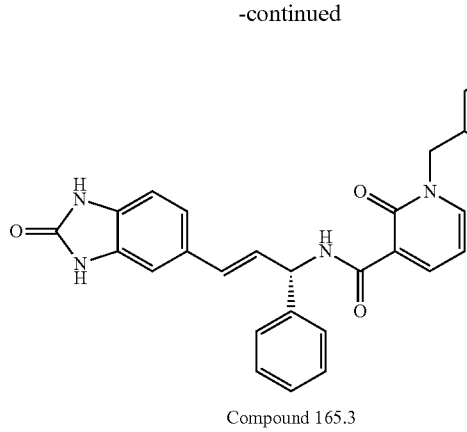

Compound 165.3

165.1 Compound 165.1 was made as described in Liu et al. (J. Am. Chem. Soc. 1997 (119) 9913-9914).

165.2 Compound 165.2 was made as described for Compound 142.1, except using compound 165.1 instead of allylamine and using Compound 49.2 instead of Compound 20.2. ES (+) MS m/e=399 (M+1).

165.3 Compound 165.3 was made as described for Compound 142.2, except using compound 165.2 instead of compound 142.1. ES (+) MS m/e=531 (M+1).

Example 166

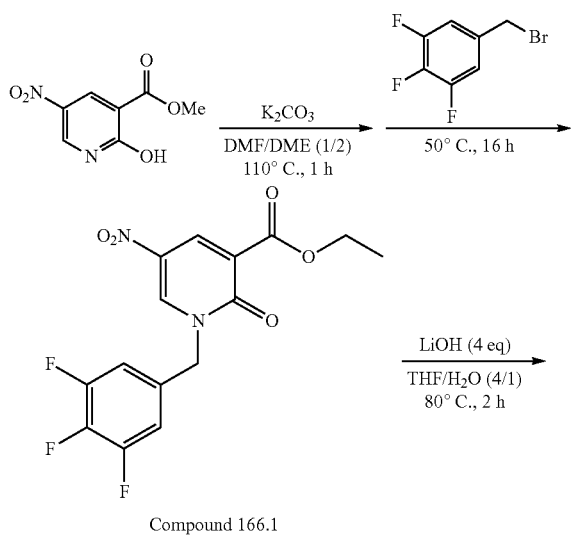

-continued

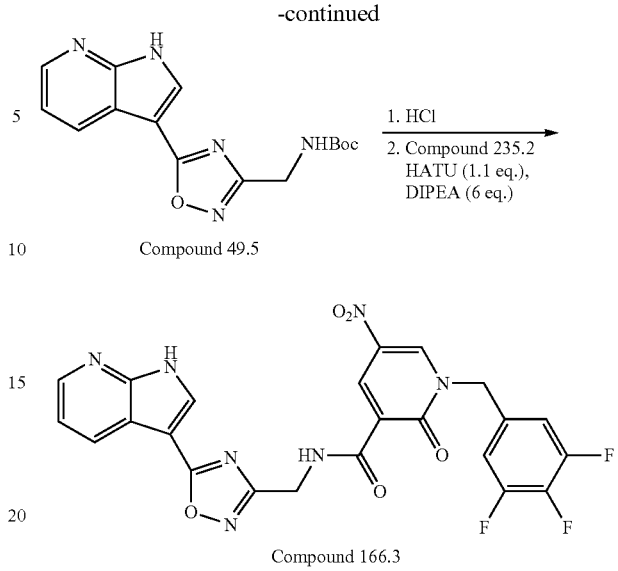

166.1 To a 10-dram vial containing 5-nitro-2-oxo-1,2-dihydro-pyridine-3-carboxylic acid methyl ester (1 mmol) in 3 ml of DME was added 2 equivalents of $K_2CO_3$. The suspension of the reaction mixture was stirred at 100° C. for 1 h. The reaction mixture was cooled to RT and 5-bromomethyl-1,2,3-trifluoro-benzene (1 mmol) was added. It was stirred at 70° C. for 16 h. It was quenched with water, extracted with EA. The solvent was removed under reduced pressure to give Compound 166.1. ES (+) MS m/e=357 (M+1).

166.2 To the 2-dram vial containing crude Compound 166.1 in $THF/H_2O$ (4/1) was added 4 equivalents of LiOH (1.0 M solution). The vial was capped and shaken at 80° C. for 2 h. The reaction was quenched with 4.1 equivalent of HCl (3.0 M solution). The precipitate was filtered and washed with water three times. ES (+) MS m/e=329 (M+1).

166.3 To 10 dram-vial containing Compound 49.5 (0.5 mmol) and 2 ml of $CH_2Cl_2$ and 1 ml of MeOH was added 6 equivalents of HCl (4.0 M in dioxane). The reaction mixture was shaken at RT for 3 h. The solvent was removed under vacuum and the residue was dissolved in 2 ml of DMF. To this, Compound 166.2 (0.5 mmol) and DIPEA (6 equivalents) were added followed by HATU (1.1 equivalents) and 2-(7-aza-1H-benzotriazole-1-yl)-1,1-3,3-tetramethyluronium hexafluorophosphate. The reaction was shaken at RT for 2 h, quenched with water, extracted with EA, and chromatographed (silica gel, hexane/EA, 4/1) to give Compound 166.3. ES (+) MS m/e=526 (M+1). 1H NMR (400 MHz, DMSO-d-6) $^{TM}$ 4.74 (d, J=5 Hz, 2H), 5.36 (s, 2H), 7.32 (t, J=6 Hz, 1H), 7.46 (t, J=6 Hz, 2H), 8.40 (s, 1H), 8.41 (s, 1H), 8.53 (s, 1H), 8.90 (d, J=3 Hz, 1H), 9.68 (d, J=3 Hz, 1H), 9.71 (t, J=6 Hz, 1H), 12.83 (s, 1H).

Example 167

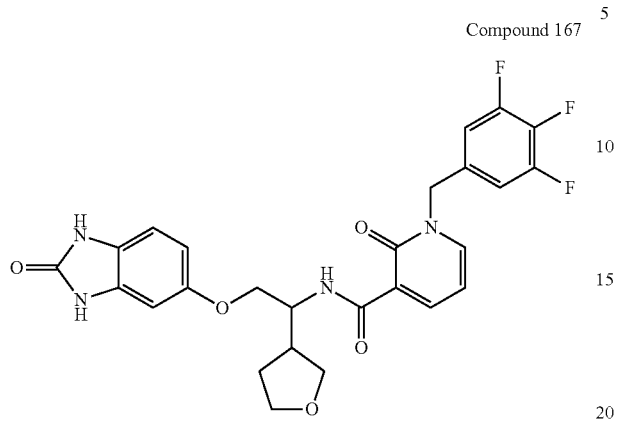

Compound 167

Compound 167 was made as Compound 141.4 but starting with 2-amino-2-(tetrahydrofuran-3-yl)-ethanol. It was a yellow solid. ES (+) MS m/e=529 (M+1). $^1$H NMR (400 MHz, DMSO-d6) $^{TM}$ ppm 1.66 (m, 1H) 1.94 (m, 1H) 2.60 (m, 1H) 3.47 (m, 1H) 3.60 (m, 1H) 3.73 (m, 2H) 3.98 (m, 2H) 4.29 (m, 1H) 5.19 (m, 2H) 6.51 (m, 2H) 6.58 (m, 1H) 6.76 (d, J=8.31 Hz, 1H) 7.31 (m, 2H) 8.19 (m, 1H) 8.37 (m, 1H) 9.96 (d, J=8.80 Hz, 1H) 10.37 (m, 1H) 10.50 (m, 1H).

Example 168

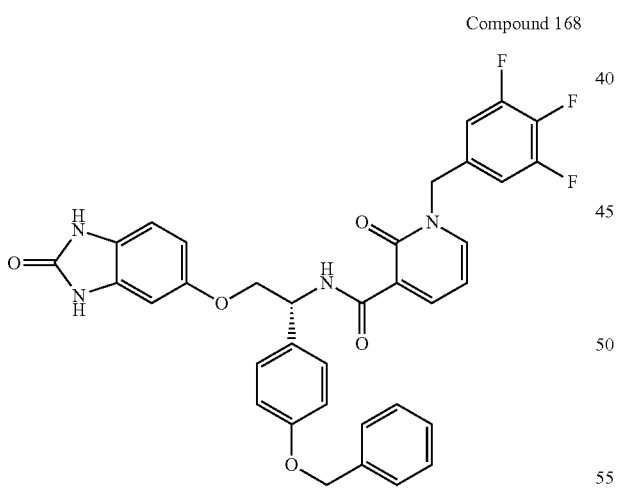

Compound 168

Compound 168 was made as Compound 141.4 but starting with 2-amino-2-[4-(benzyloxy)phenyl]ethanol. It was a light yellow solid. ES (+) MS m/e=641 (M+1). $^1$H NMR (400 MHz, DMSO-d6) $^{TM}$ ppm 4.16 (m, 1H) 4.22 (m, 1H) 5.07 (m, 2H) 5.21 (m, 2H) 5.31 (m, 1H) 6.50 (m, 2H) 6.58 (t, J=6.85 Hz, 1H) 6.75 (d, J=8.31 Hz, 1H) 6.98 (d, J=8.31 Hz, 2H) 7.35 (m, 9H) 8.19 (dd, J=6.85, 2.45 Hz, 1H) 8.35 (dd, J=7.34, 1.96 Hz, 1H) 10.33 (d, J=7.83 Hz, 1H) 10.37 (m, 1H) 10.50 (m, 1H).

Example 169

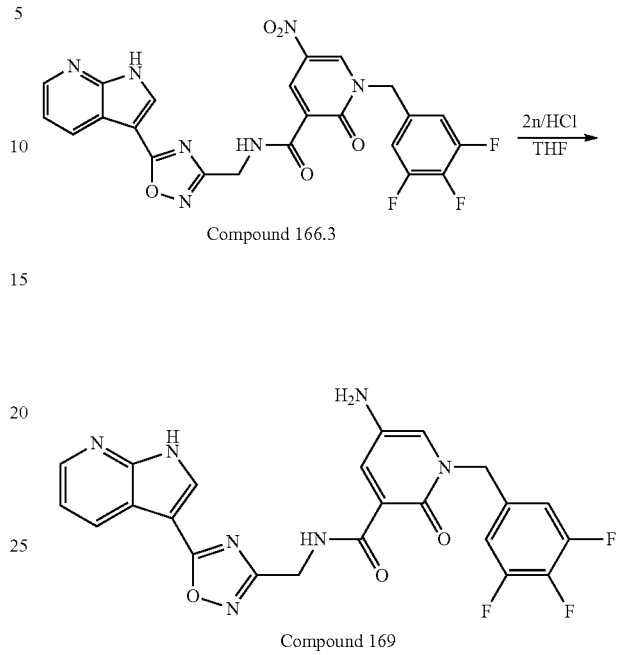

Compound 166.3 (0.6 mmol) was dissolved in THF (2 ml) and to this was added Zn dust (10 equivalents) followed by HCl (20 equivalents, 1.0 M solution). The reaction was shaken at RT for 1 h. The mixture was filtered to remove Zn dust. The solvent was removed under reduced pressure and the crude was dissolved in DMSO for purification using HPLC (reverse phase) to give Compound 169. (ES (+) MS m/e=496 (M+1). 1H NMR (400 MHz, DMSO-d-6) $^{TM}$ 4.72 (d, J=5 Hz, 2H), 5.21 (s, 2H), 7.3-7.4 (m, 4H), 7.64 (s, 1H), 8.20 (s, 1H)), 8.4-8.5 (m, 3H), 8.54 (s, 1H), 10.47 (s, 1H), 12.84 (s, 1H)

Examples 170 and 171

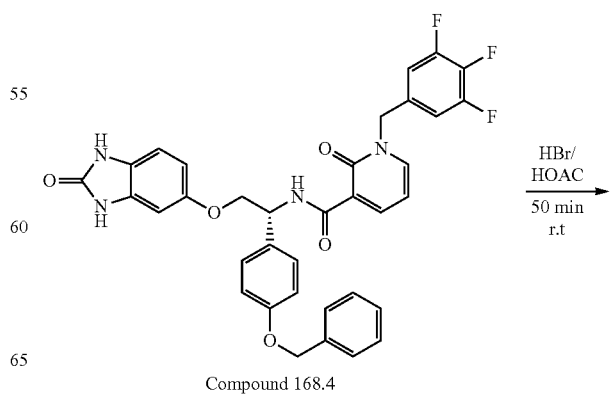

Compound 168.4

-continued

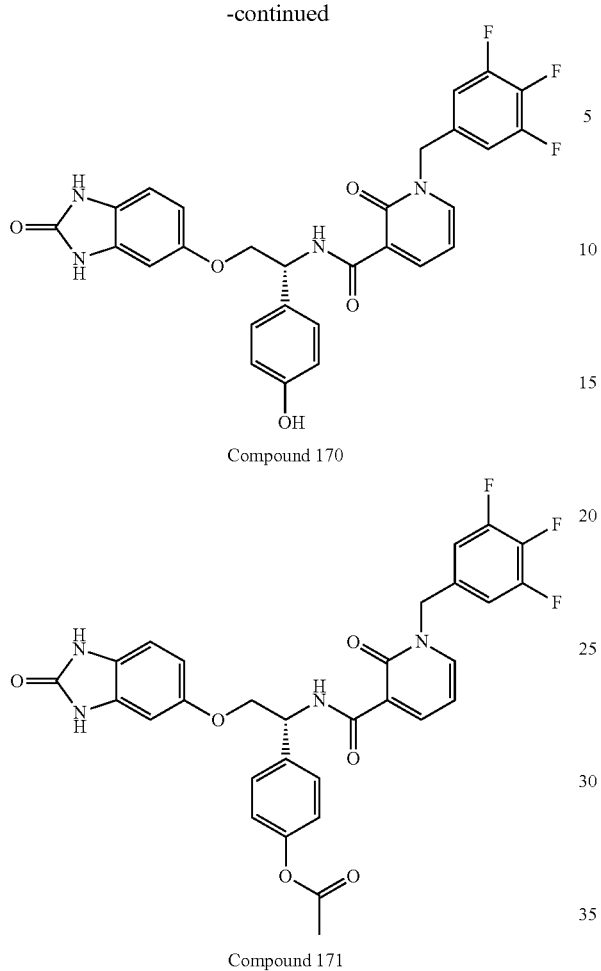

Compound 170

Compound 171

Compound 168 (0.328 g, 0.51 mmol) was treated with 6 ml hydrobromic acid solution (33 wt %) in glacial acetic acid at room temperature for 50 min. The mixture was concentrated and then co-evaporated with toluene twice. The resulted residue was purified by HPLC (reverse phase) to give both Compound 170 and Compound 171.

Compound 170 ES (+) MS m/e=551 (M+1). $^1$H NMR (400 MHz, DMSO-d6) $^{TM}$ ppm 4.12 (m, 1H) 4.19 (m, 1H) 5.22 (m, 3H) 6.50 (m, 2H) 6.59 (m, 1H) 6.73 (m, 3H) 7.20 (d, J=8.31 Hz, 2H) 7.31 (m, 2H) 8.19 (dd, J=6.85, 1.96 Hz, 1H) 8.35 (dd, J=7.34, 1.96 Hz, 1H) 9.36 (m, 1H) 10.27 (d, J=7.83 Hz, 1H) 10.37 (m, 1H) 10.49 (m, 1H).

Compound 171 ES (+) MS m/e=593 (M+1). $^1$H NMR (400 MHz, DMSO-d6) $^{TM}$ ppm 2.24 (m, 3H) 4.20 (m, 1H) 4.26 (m, 1H) 5.22 (m, 2H) 5.37 (m, 1H) 6.51 (m, 2H) 6.59 (t, J=6.85 Hz, 1H) 6.75 (d, J=7.83 Hz, 1H) 7.09 (d, J=8.31 Hz, 2H) 7.32 (m, 2H) 7.45 (d, J=8.31 Hz, 2H) 8.20 (dd, J=6.85, 1.47 Hz, 1H) 8.35 (dd, J=6.85, 1.47 Hz, 1H) 10.37 (m, 1H) 10.42 (d, J=7.83 Hz, 1H) 10.50 (m, 1H).

Examples 172 and 173

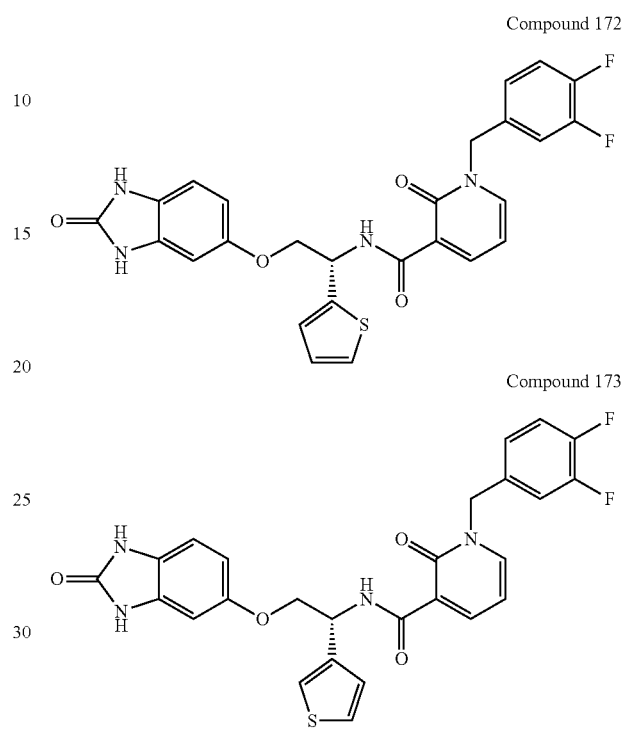

Compound 172

Compound 173

Compound 172 and Compound 173 were prepared according to the method described for Compound 150.6 but using Boc-(s)-2-thienylglycine and Boc-(R)-3-thienylglycine as starting material respectively instead of Compound 150.1.

Compound 172 ES (+) MS m/e=523 (M+1). $^1$H NMR (400 MHz, DMSO-d6) $^{TM}$ ppm 4.27 (m, 3H) 5.21 (m, 2H) 5.65 (m, 1H) 6.57 (m, 3H) 6.78 (d, J=8.31 Hz, 1H) 6.99 (t, J=4.89 Hz, 1H) 7.12 (m, 1H) 7.16 (m, 1H) 7.42 (m, 2H) 8.23 (dd, J=6.36, 1.96 Hz, 1H) 8.38 (dd, J=7.34, 1.96 Hz, 1H) 10.40 (m, 2H) 10.52 (m, 1H).

Compound 173 ES (+) MS m/e=523 (M+1). $^1$H NMR (400 MHz, DMSO-d6) $^{TM}$ ppm 4.20 (m, 1H) 4.27 (m, 1H) 5.21 (m, 2H) 5.47 (m, 1H) 6.52 (m, 2H) 6.58 (t, J=6.85 Hz, 1H) 6.75 (d, J=7.83 Hz, 1H) 7.16 (m, 2H) 7.41 (m, 3H) 7.50 (m, 1H) 8.21 (dd, J=6.85, 2.45 Hz, 1H) 8.37 (dd, J=6.85, 1.96 Hz, 1H) 10.31 (d, J=8.31 Hz, 1H) 10.37 (m, 1H) 10.51 (m, 1H).

Example 174

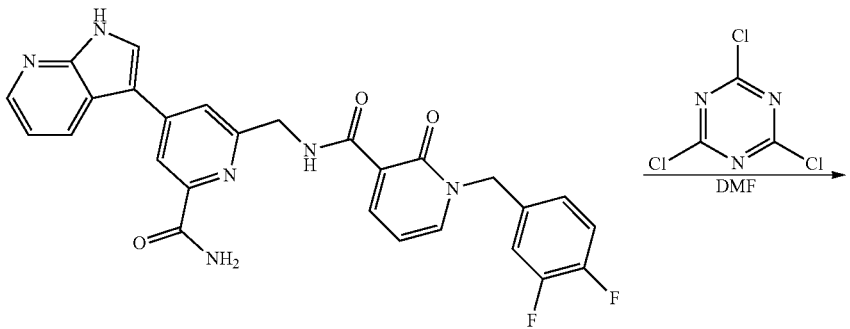

164.1

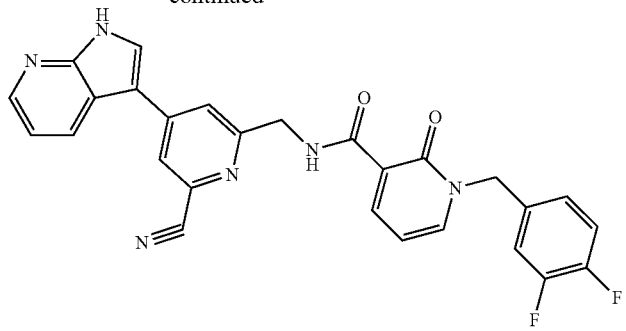

174.1

174.1 Compound 164.1 (0.020 grams, 0.0388 mmol) was dissolved in DMF (1 ml) and chilled on an ice bath. Cyanuric chloride (5 mg, 0.0252 mmol) was added and the reaction was stirred for 16 hours warming to ambient temperature. The mixture was concentrated under reduced pressure and the residue was purified by silica gel column chromatography eluting with 1-10% 2.0 M methanolic ammonia in dichloromethane to yield Compound 174.1. ES (+) MS m/e=497 (M+H). 1H NMR (400 MHz, CD$_3$OD) δ ppm 4.71 (m, 2H) 5.20 (m, 2H) 6.51 (m, 1H) 7.12 (m, 2H) 7.26 (m, 1H) 7.91 (m, 2H) 7.98 (m, 1H) 8.04 (m, 1H) 8.21 (m, 1H) 8.34 (m, 1H) 8.41 (m, 1H) 8.58 (m, 1H).

Example 175

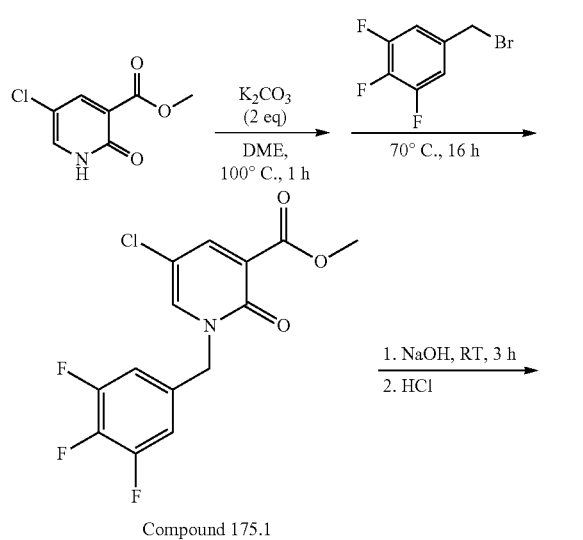

Compound 175.1

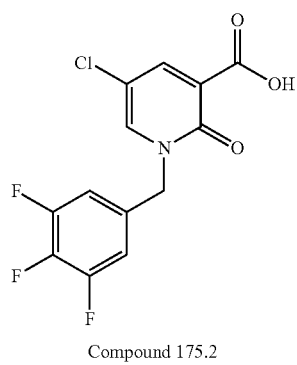

Compound 175.2

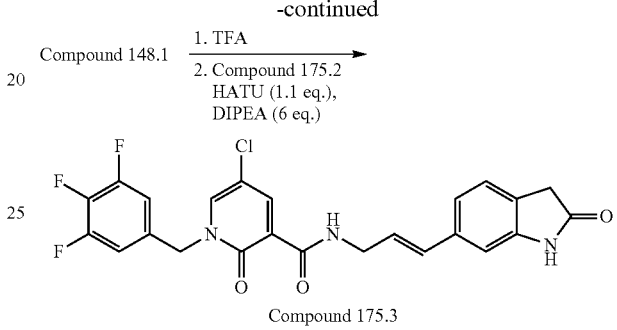

Compound 175.3

175.1 To a 10-dram vial containing 5-chloro-2-oxo-1,2-dihydro-pyridine-3-carboxylic acid methyl ester (1 mmol) in 3 ml of DME was added 2 equivalents of K$_2$CO$_3$. The suspension of the reaction mixture was stirred at 100° C. for 1 h. The reaction mixture was cooled to RT and 5-bromomethyl-1,2,3-trifluoro-benzene (1 mmol) was added. It was stirred at 70° C. for 16 h. It was quenched with water, extracted with EA. The solvent was removed under reduced pressure to give Compound 175.1. ES (+) MS nm/e=332 (M+1).

175.2 To the 2-dram vial containing Compound 175.1 was added 1.1 equivalents of NaOH (3.0 M solution). The vial was capped and shaken at RT for 3 h. The reaction was quenched with 1.1 equivalents of HCl (3.0 M solution). The precipitate was filtered and washed with water three times. ES (+) MS m/e=318 (M+1).

175.3 To the 2-dram vial containing Compound 148.1 (0.2 mmol) in CH$_2$Cl$_2$ was added TFA (excess). The reaction mixture was shaken at RT for 1 h. The solvents were removed under reduced pressure. To the vial containing the intermediate in DMF (1 ml) were added Compound 175.2 (1 equivalent), HATU (1.1 equivalents), and DIPEA (6 equivalents). The reaction mixture was shaken at RT for 1 h, quenched with water, extracted with EA, and chromatographed (silica gel, hexane/EA, 4/1) to give Compound 175.3. ES (+) MS m/e=488 (M+1). 1H NMR (400 MHz, DMSO-d-6) $^{TM}$ 3.44 (s, 2H), 4.07 (t, J=5 Hz, 2H), 5.17 (s, 2H), 6.2-6.3 (m, 1H), 6.49 (d, J=16 Hz, 1H), 6.83 (s, 1H), 6.95 (d, J=7 Hz, 1H), 7.13 (d, J=7 Hz, 1H), 7.38 (t, J=8 Hz, 2H), 8.28 (d, J=3 Hz, 1H), 8.55 (d, J=3 Hz, 1H), 9.64 (t, J=5 Hz, 1H), 10.37 (s, 1H).

Example 176

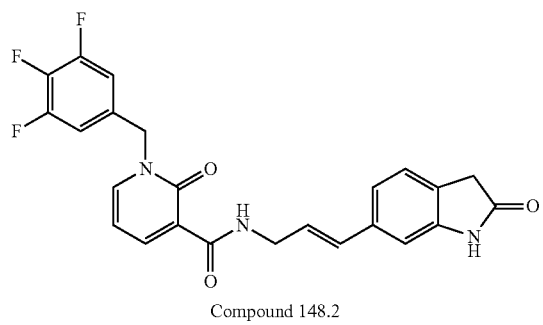

Compound 148.2

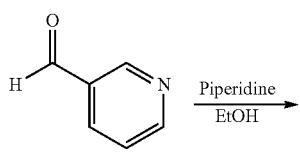

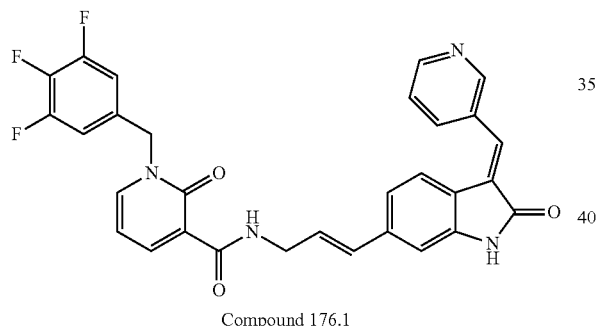

Compound 176.1

176.1 To a 2-dram vial was added Compound 148.2 (104 mg, 0.23 mmol), ethanol (250 µL), piperidine (45 µL, 0.46 mmol) and 3-pyridinecarboxaldehyde (24 µL, 0.25 mmol). The vial was sealed and the mixture was stirred at 80° C. Additional ethanol (750 µL) was added after 40 minutes. The reaction was heated for a total of 2 hours then cooled to room temperature and water (2 ml) was added dropwise. The mixture was filtered and the solids were washed with water (3×2 ml). The solids were dissolved in a mixture of MeOH/DCM, dried ($Na_2SO_4$), filtered and evaporated to obtain a black solid. The crude product was purified using flash chromatography (silica gel, hexanes to ethyl acetate to 7% MeOH/ethyl acetate) to obtain Compound 176.1 as a brown solid (49 mg, 39% yield). ES (+) MS m/e=543 (M+1). $^1$H NMR (400 MHz, $CDCl_3$) $^{TM}$ 9.81 (br. s, 1H), 8.91 (br. s, 1H), 8.70-8.54 (m, 2H), 7.99-7.90 (m, 1H), 7.68 (s, 1H), 7.54 (d, J=6.9 Hz, 1H), 7.50-7.35 (m, 3H), 6.98-6.81 (m, 4H), 6.56-6.46 (m, 2H), 6.37-6.26 (m, 1H), 5.13 (s, 2H), 4.23 (t, J=5.9 Hz, 2H).

Example 177

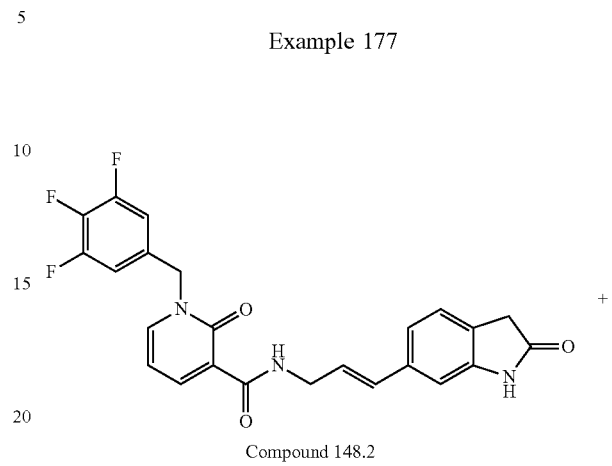

Compound 148.2

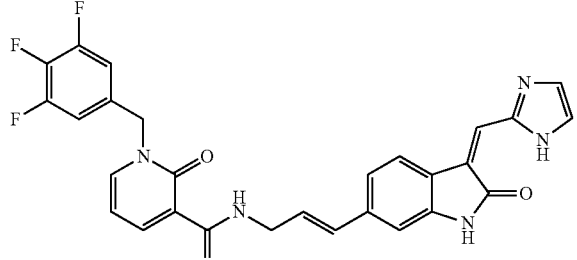

Compound 177.1

177.1 To a 2-dram vial was added Compound 148.2 (173 mg, 0.38 mmol), ethanol (1.6 mL), piperidine (75 µL, 0.76 mmol) and 2-imidazolecarboxaldehyde (40 µL, 0.43 mmol). The vial was sealed and the mixture was stirred at 80° C. for 1 hour. The reaction mixture was cooled to room temperature then water (1.5 ml) was added. The mixture was filtered and the solids were washed with a 1:1 mixture of ethanol/water (2×2 ml) and dried under vacuum. The crude product was purified by column chromatography (hexanes to ethyl acetate to 7% MeOH/ethyl acetate) to obtain Compound 177.1 as a yellow solid (182 mg, 90% yield). ES (+) MS m/e=532 (M+1). $^1$H NMR (400 MHz, DMSO-d6) $^{TM}$ 14.03 (s, 1H), 11.16 (br. s, 1H), 9.77 (t, J=5.6 Hz, 1H), 8.39 (dd, J=7.3 Hz, J=2.0 Hz, 1H), 8.22 (dd, J=6.4 Hz, J=2.0 Hz, 1H), 7.78 (d, J=7.8 Hz, 1H), 7.75 (s, 1H), 7.54 (s, 1H), 7.37-7.28 (m, 3H), 7.08 (d, J=8.3 Hz, 1H), 6.94 (s, 1H), 6.64-6.52 (m, 2H), 6.40-6.31 (m, 1H), 5.21 (s, 2H), 4.10 (t, J=5.6 Hz, 2H).

Example 178

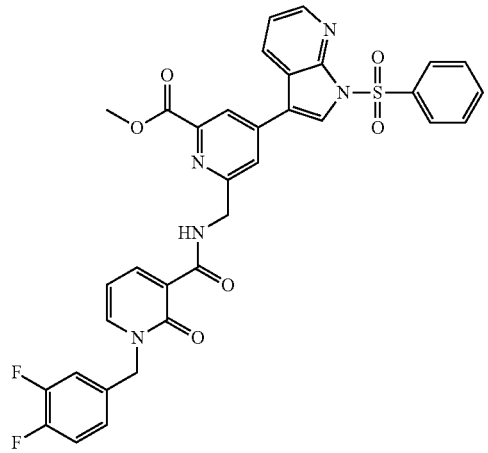

154.6

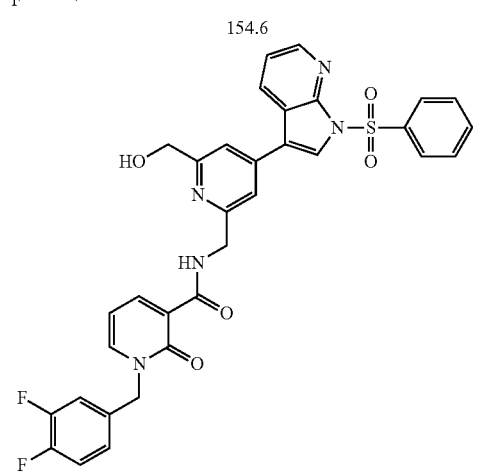

178.1

178.1 Compound 154.6 (0.100 grams, 0.149 mmol) was dissolved in dry THF under nitrogen. Lithium aluminum hydride 1.0 M in hexanes (0.167 ml, 0.167 mmol) was added drop-wise and the reaction stirred at ambient temperature for 30 minutes. An aqueous saturated ammonium chloride solution (1 ml) was added and the mixture stirred for 30 minutes, extracted with ethyl acetate, dried over sodium sulfate, filtered, and concentrated under reduced pressure to yield Compound 178.1 (0.069 grams, 0.108 mmol). ES (+) MS m/e=642 (M+H).

178.2 Compound 178.2 was prepared as in Example 146.3. ES (+) MS nm/e=502 (M+H). 1H NMR (400 MHz, DMSO-D6) δ ppm 4.58 (m, 2H) 4.63 (m, 2H) 5.23 (m, 2H) 5.42 (m, 1H) 6.58 (m, 1H) 7.13 (m, 1H) 7.18 (m, 1H) 7.37 (m, 1H) 7.46 (m, 1H) 7.57 (m, 1H) 7.69 (m, 1H) 8.15 (m, 1H) 8.23 (m, 1H) 8.28 (m, 1H) 8.34 (m, 1H) 8.39 (m, 1H) 10.26 (m, 1H) 12.19 (m, 1H).

Example 179

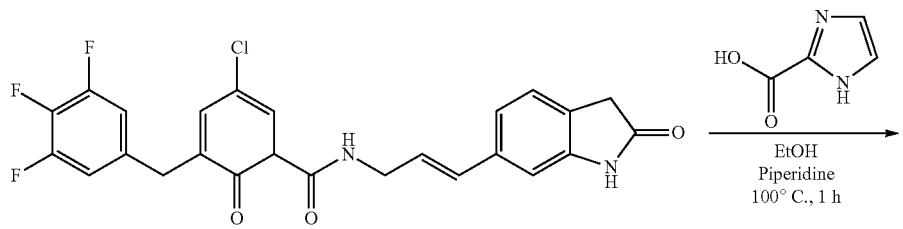

Compound 175.3

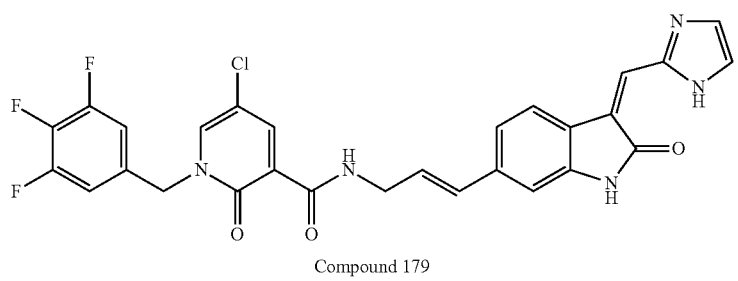

Compound 179

179 To a 2-dram vial containing Compound 175.3 (0.3 mmol) in 2 ml of ethanol were added 1H-imidazole-2-carbaldehyde (1.1 equivalents) and piperidine (2 equivalents). The reaction mixture was heated at 100° C. for 1 h. It was quenched with water. Solid was filtered and washed with hot water three times. The solid was dried under vacuum for three days. ES (+) MS m/e=566 (M+1). 1H NMR (400 MHz, CDCl$_3$, Me$_4$Si) $^{TM}$ 4.24 (t, J=6 Hz, 2H), 5.09 (s, 2H), 6.2-6.3 (m, 1H), 6.58 (d, J=16 Hz, 1H), 6.94 (s, 1H), 7.0-7.1 (m, 2H), 7.11 (d, J=8 Hz, 1H), 7.29 (s, 1H), 7.41 (s, 1H), 7.48 (d, J=8 Hz, 1H), 7.52 (s, 1H), 7.55 (d, J=3 Hz, 1H), 7.57 (s, 1H), 7.63 (s, 1H), 8.55 (d, J=3 Hz, 1H), 9.71 (s, 1H).

Example 180

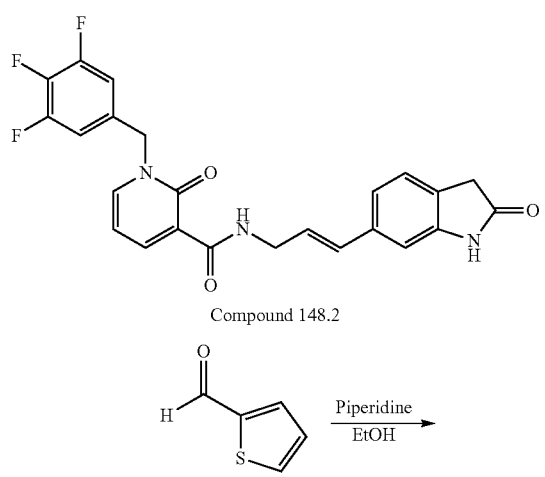

Compound 148.2

Piperidine
EtOH

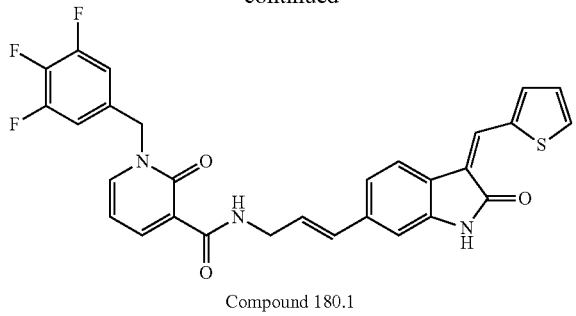

Compound 180.1

180.1 To a 2-dram vial containing 2-thiophenecarboxaldehyde (37 mg, 0.33 mmol) was added Compound 148.2 (136 mg, 0.30 mmol) as a slurry in ethanol (1.6 ml) followed by addition of piperidine (59 µL, 0.60 mmol). The vial was sealed and the mixture was stirred at 80° C. for 1 hour. While the mixture was still hot, water (2 ml) was slowly added and then allowed to cool for 15 minutes. The mixture was filtered and the solids were washed with 1:1 ethanol/water (2×2 ml) and dried under vacuum. The crude product was purified by column chromatography (1:1 hexanes/DCM to DCM to 4% MeOH/DCM) to obtain Compound 180.1 as an orange solid (151 mg, 92% yield). ES (+) MS m/e=548 (M+1). NMR indicates a mixture of the E and Z isomers in about a 3:2 ratio. NMR assignments are for the major isomer. $^1$H NMR (400 MHz, DMSO-d6) $^{TM}$ 10.63 (s, 1H), 9.81-9.73 (m, 1H), 8.38 (dd, J=7.3 Hz, J=2.0 Hz, 1H), 8.23 (dd, J=6.7 Hz, J=1.7 Hz, 1H), 8.10 (d, J=7.8 Hz, 1H), 7.98 (d, J=4.9 Hz, 1H), 7.80 (d, J=3.9 Hz, 1H), 7.74 (s, 1H), 7.37-7.26 (m, 3H), 7.07 (d, J=8.8 Hz, 1H), 6.93 (s, 1H) 6.61 (t, J=6.9 Hz, 1H), 6.55 (d, J=16.1 Hz, 1H), 6.43-6.27 (m, 1H), 5.21 (s, 2H), 4.11 (t, J=5.7 Hz, 2H).

Example 181

Compound 148.1
1. TFA
2. Compound 20.2, HATU (1.1 eq.), DIPEA (6 eq.)

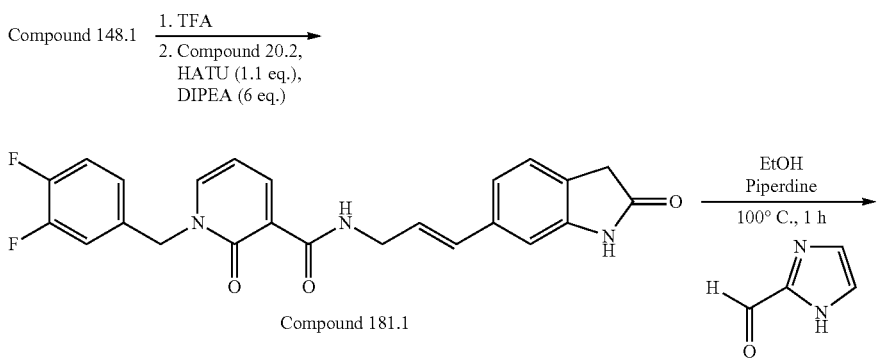

Compound 181.1

EtOH
Piperdine
100° C., 1 h

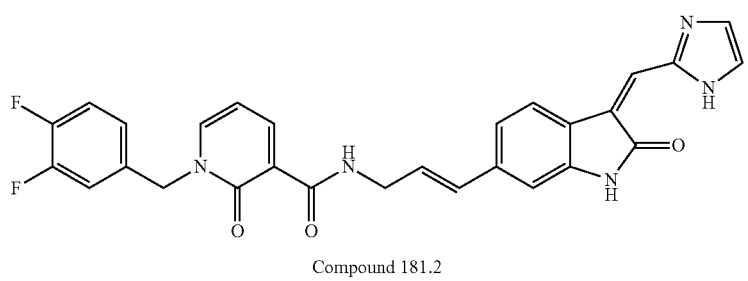

Compound 181.2

181.1 To the 2-dram vial containing Compound 148.1 (0.2 mmol) in CH$_2$Cl$_2$ was added TFA (excess). The reaction mixture was shaken at RT for 1 h. The solvents were removed under reduced pressure. To the vial containing the intermediate in DMF (1 ml) were added Compound 20.2 (1 equivalent), HATU (1.1 equivalents), and DIPEA (6 equivalents). The reaction mixture was shaken at RT for 1 h, quenched with water, extracted with EA, and chromatographed (silica gel, hexane/EA, 4/1) to give Compound 181.1. ES (+) MS m/e=436 (M+1).

181.2 To a 2-dram vial containing Compound 181.1 (0.3 mmol) in 2 ml of ethanol were added 1H-imidazole-2-carbaldehyde (1.1 equivalents) and piperidine (2 equivalents). The reaction mixture was heated at 100° C. for 1 h. It was quenched with water. Solid was filtered and washed with hot water three times. The solid was dried under vacuum for three days to give. Compound 181.2. ES (+) MS m/e=514 (M+1). 1H NMR (400 MHz, DMSO-d-6) $^{TM}$ 4.09 (s, 2H), 5.21 (s, 2H), 6.35 (s, 1H), 6.5-6.6 (m, 2H), 6.93 (s, 1H), 7.08 (s, 1H), 7.18 (s, 1H) 7.32 (s, 1H) 7.4-7.5 (m, 2H), 7.54 (s, 1H), 7.7-7.8 (m, 2H), 8.23 (s, 1H), 8.37 (s, 1H), 9.80 (s, 1H), 11.15 (s, 1H), 14.02 (s, 1H).

Example 182

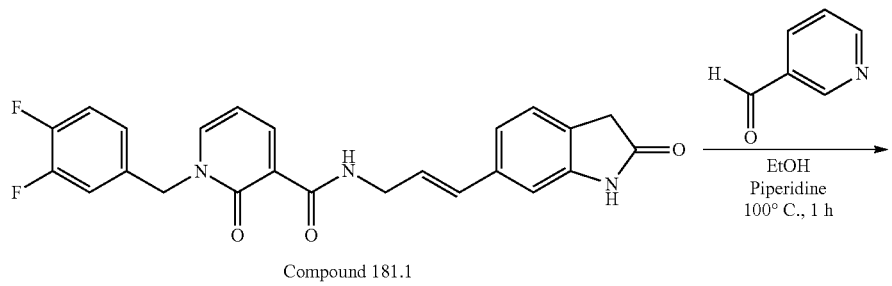

Compound 181.1

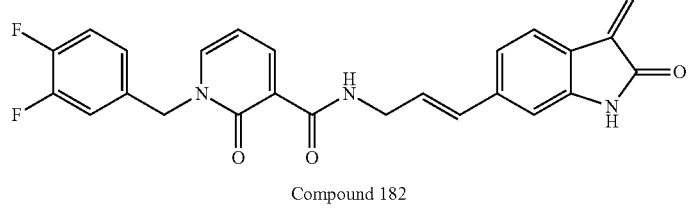

Compound 182

182 To a 2-dram vial containing Compound 181.1 (0.3 mmol) in 2 ml of ethanol were added pyridine-3-carbaldehyde (1.1 equivalents) and piperidine (2 equivalents). The reaction mixture was heated at 100° C. for 1 h. It was quenched with water. Solid was filtered and washed with hot water three times. The solid was dried under vacuum for three days to give Compound 182. ES (+) MS m/e=525 (M+1). 1H NMR (400 MHz, DMSO-d-6) $^{TM}$ 4.09 (s, 2H), 5.21 (s, 2H), 6.3-6.4 (m, 1H), 6.50 (d, J=16 Hz, 1H), 6.59 (s, 1H), 6.90 (s, 2H), 7.18 (s, 1H), 7.3-7.6 (m, 5H), 8.10 (s, 1H), 8.23 (s, 1H), 8.37 (s, 1H), 8.64 (s, 1H), 8.86 (s, 1H), 9.79 (s, 1H), 10.69 (s, 1H).

Example 183

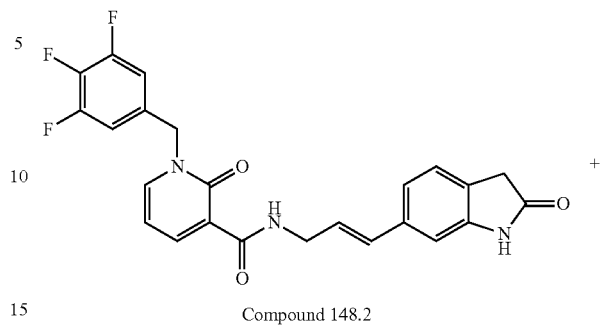

Compound 148.2

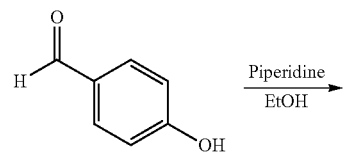

-continued

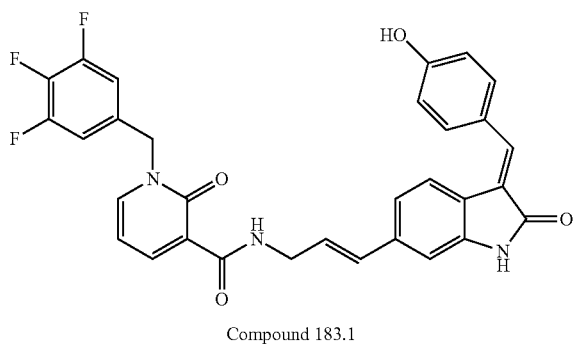

Compound 183.1

183.1 To a 2-dram vial containing 4-hydroxybenzaldehyde (40 mg, 0.33 mmol) was added Compound 148.2 (136 mg, 0.30 mmol) as a slurry in ethanol (1.6 ml) followed by addition of piperidine (59 μL, 0.60 mmol). The vial was sealed and the mixture was stirred at 80° C. for 1 hour. The reaction mixture was evaporated to dryness and the residue was dissolved in DMSO (5 ml) then purified by reverse phase preparative HPLC to obtain Compound 183.1 as a yellow solid (17 mg, 10% yield). ES (+) MS m/e=558 (M+1). NMR indicates approximately 35% of the Z isomer present. NMR assignments are for the major isomer. $^1$H NMR (400 MHz, DMSO-d6) $^{TM}$ 10.53 (s, 1H), 10.13 (s, 1H), 9.76 (t, J=5.6 Hz, 1H), 8.38 (d, J=6.9 Hz, 1H), 8.22 (d, J=6.7 Hz, 1H), 7.67-7.57 (m, 3H), 7.48 (s, 1H), 7.31 (t, J=7.6 Hz, 2H), 6.94-6.81 (m, 4H) 6.60 (t, J=6.9 Hz, 1H), 6.51 (d, J=15.7 Hz, 1H), 6.36-6.25 (m, 1H), 5.20 (s, 2H), 4.09 (t, J=5.6 Hz, 2H).

Example 184 and 185

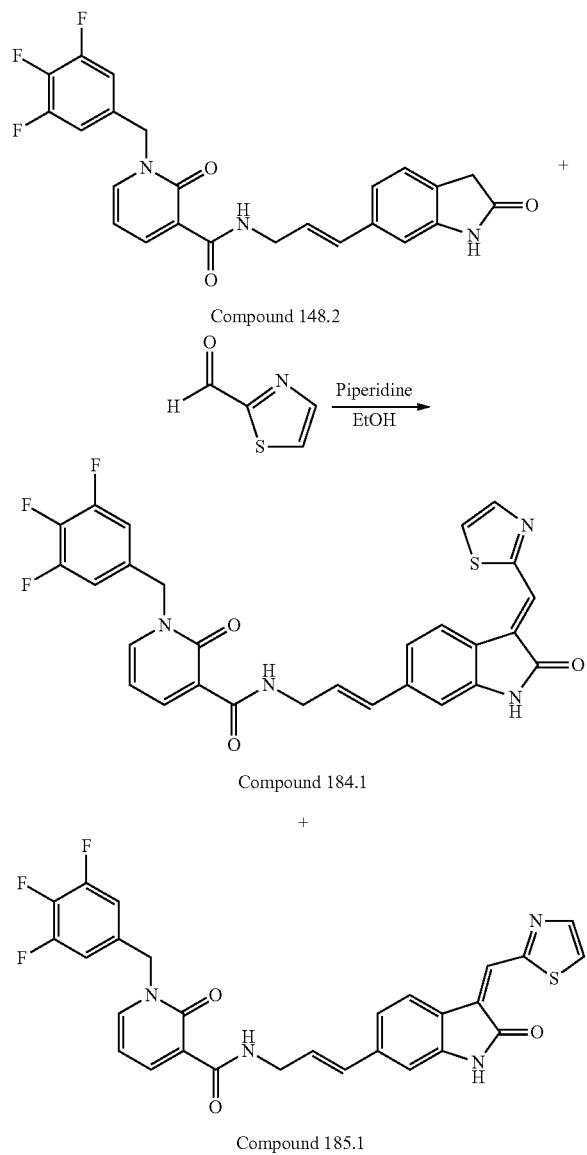

Compound 148.2

Compound 184.1

Compound 185.1

184.1 and 185.1 To a 2-dram vial containing 2-thiazole-carboxaldehyde (37 mg, 0.33 mmol) was added Compound 148.2 (136 mg, 0.30 mmol) as a slurry in ethanol (1.6 ml) followed by addition of piperidine (59 μL, 0.60 mmol). The vial was sealed and the mixture was stirred at 80° C. for 1 hour. The reaction mixture was evaporated to dryness and the residue was dissolved in DMSO (5 ml) then purified by reverse phase preparative HPLC to obtain isomers 184.1 and 185.1.

184.1 Compound 184.1 was isolated as an orange-brown solid (8 mg, 5% yield). ES (+) MS m/e=549 (M+1). $^1$H NMR (400 MHz, DMSO-d6) $^{TM}$ 10.85 (s, 1H), 9.97 (t, J=5.6 Hz, 1H), 8.38 (dd, J=7.3 Hz, J=2.0 Hz, 1H), 8.22 (dd, J=6.4 Hz, J=2.0 Hz, 1H), 8.10 (d, J=2.9 Hz, 1H), 8.08 (s, 1H), 8.01 (d, J=2.9 Hz, 1H), 7.80 (d, J=7.8 Hz, 1H), 7.32 (t, J=7.8 Hz, 2H), 7.07 (d, J=7.8 Hz, 1H), 6.91 (s, 1H), 6.64-6.52 (m, 2H), 6.43-6.33 (m, 1H), 5.20 (s, 2H), 4.10 (t, J=5.4 Hz, 2H).

185.1 Compound 185.1 was isolated as an orange-brown solid (25 mg, 15% yield). ES (+) MS m/e=549 (M+1). $^1$H NMR (400 MHz, DMSO-d6) $^{TM}$ 10.70 (s, 1H), 9.78 (t, J=5.6 Hz, 1H), 9.05 (d, J=8.3 Hz, 1H) 8.38 (dd, J=7.3 Hz, J=2.0 Hz, 1H), 8.27 (d, J=2.9 Hz, 1H), 8.22 (dd, J=6.9 Hz, J=2.0 Hz, 1H), 8.12 (d, J=3.4 Hz, 1H), 7.57 (s, 1H), 7.32 (t, J=7.6 Hz, 2H), 7.06 (d, J=7.8 Hz, 1H), 6.91 (s, 1H), 6.64-6.51 (m, 2H), 6.45-6.35 (m, 1H), 5.21 (s, 2H), 4.12 (t, J=5.4 Hz, 2H).

Example 186

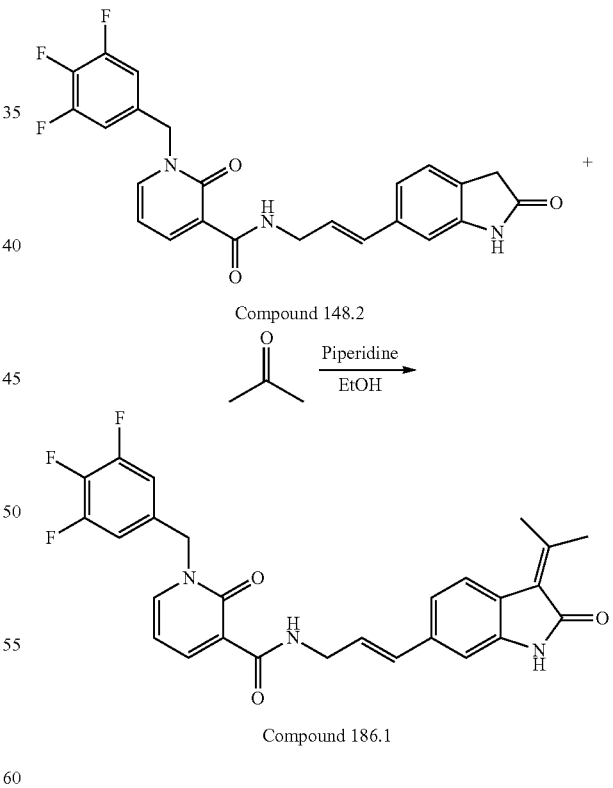

Compound 148.2

Compound 186.1

186.1 To a 2-dram vial was added Compound 148.2 (136 mg, 0.30 mmol) as a slurry in ethanol (1.6 ml). Acetone (29 μL, 0.39 mmol) and piperidine (59 μL, 0.60 mmol) were added, the vial was sealed and the mixture was stirred at 50° C. for 4 days then additional acetone (9 μL, 0.12 mmol) was added and the mixture was stirred at 50° C. for an additional 4 days. Water (2 ml) was slowly added and the mixture was filtered. The solids were washed with 1:1 ethanol/water (2×2 mL) and dried under vacuum. The crude product was purified by column chromatography (DCM to 4% MeOH/DCM) to obtain Compound 186.1 as a yellow solid (60 mg, 41% yield). ES (+) MS m/e=494 (M+1). $^1$H NMR (400 MHz, DMSO-d6) $^{TM}$ 10.42 (s, 1H), 9.76 (t, J=5.7 Hz, 1H), 8.38 (dd, J=6.8 Hz, J=1.7 Hz, 1H), 8.22 (dd, J=6.9 Hz, J=1.7 Hz, 1H), 7.46 (d, J=7.8 Hz, 1H), 7.32 (t, J=7.9 Hz, 2H), 6.97 (d, J=7.8 Hz, 1H), 6.83 (s, 1H), 6.60 (t, J=6.9 Hz, 1H), 6.51 (d, J=15.7 Hz, 1H), 6.33-6.23 (m, 1H), 5.20 (s, 2H), 4.08 (t, J=5.7 Hz, 2H), 2.49 (s, 3H), 2.29 (s, 3H).

Example 187

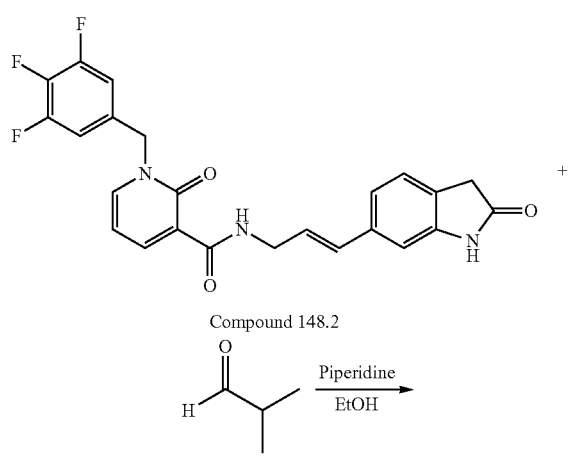

Compound 148.2

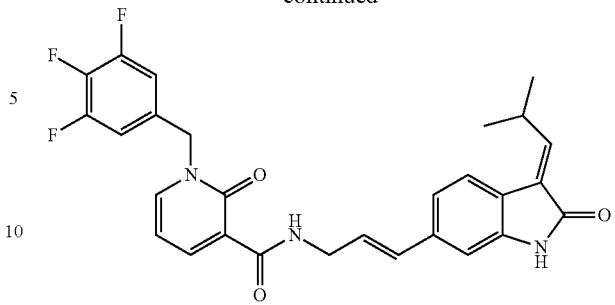

Compound 187.1

187.1 To a 2-dram vial was added Compound 148.2 (136 mg, 0.30 mmol) as a slurry in ethanol (1.6 ml). Isobutyraldehyde (33 µL, 0.36 mmol) and piperidine (59 µL, 0.60 mmol) were added, the vial was sealed and the mixture was stirred at 50° C. for 1 hour. The reaction mixture was filtered and the solids were washed with ethanol (1 ml) followed by diethyl ether (1 ml) to obtain Compound 187.1 as a tan powder (115 mg, 76% yield). ES (+) MS m/e=508 (M+1). NMR indicates there is approximately 15% of the Z isomer present. NMR assignments are for the major isomer. $^1$H NMR (400 MHz, DMSO-d6) $^{TM}$ 10.46 (s, 1H), 9.76 (t, J=5.4 Hz, 1H), 8.38 (d, J=7.3 Hz, 1H), 8.22 (d, J=6.4 Hz, 1H), 7.49 (d, J=7.8 Hz, 1H), 7.31 (t, J=7.8 Hz, 2H), 7.00 (d, J=7.8 Hz, 1H), 6.86 (s, 1H), 6.63-6.48 (m, 3H), 6.37-6.25 (m, 1H), 5.20 (s, 2H), 4.09 (t, J=5.4 Hz, 2H), 3.26-3.15 (m, 1H), 1.14 (s, 3H), 1.12 (s, 3H).

Example 188

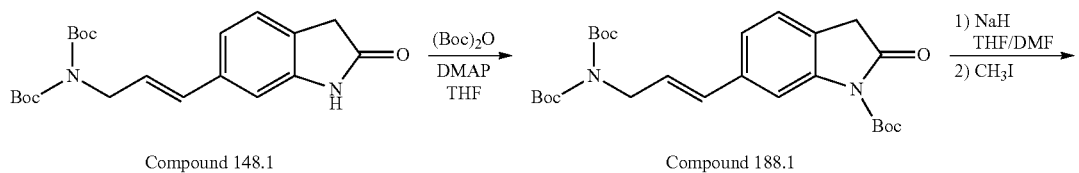

Compound 148.1 → Compound 188.1

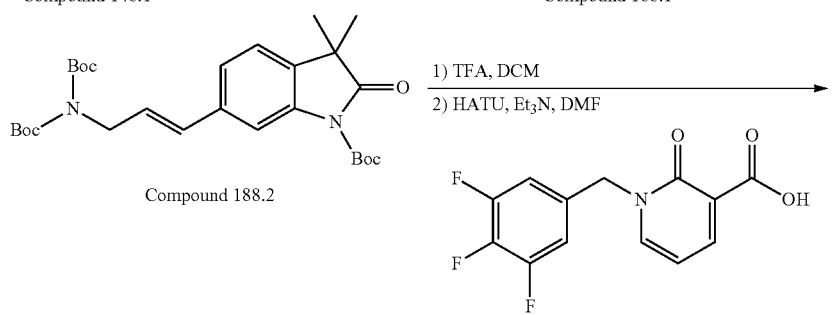

Compound 188.2

Compound 49.2

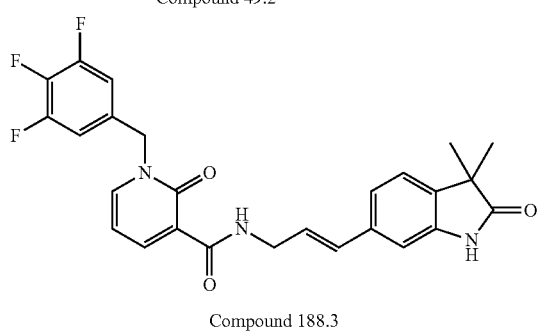

Compound 188.3

188.1 To a mixture of Compound 148.1 (500 mg, 1.29 mmol), di-t-butyl dicarbonate (295 mg, 1.35 mmol) and 4-(dimethylamino)-pyridine (158 mg, 1.29 mmol) THF was carefully added (1.3 ml). Vigorous bubbling was observed. Additional THF (3 ml) and DCM (3 ml) were added after about 15 minutes to completely dissolve the solids. The mixture was stirred at room temperature for 16 hours then diluted with ethyl acetate (20 ml) and washed with water (20 ml), dried (Na$_2$SO$_4$), filtered and evaporated. The crude product was presorbed onto silica and column chromatography was performed (hexanes to 60% ethyl acetate/hexanes) to obtain Compound 188.1 as a mauve solid (185 mg, 29% yield). ES (+) MS m/e=511 (M+23).

188.2 To oven dried glassware was added sodium hydride (60% dispersion in mineral oil, 18 mg, 0.44 mmol). THF (500 µL) then DMF (500 µL) was added and the mixture was purged with nitrogen then cooled to 0° C. Compound 188.1 (98 mg, 0.20 mmol) in DMF (1 ml) was added drop-wise over 5 minutes. The resulting mixture was stirred at 0° C. for 1 hour then methyl iodide (28 µL, 0.44 mmol) in DMF (500 µL) was added dropwise over 2 minutes. The mixture was stirred at room temperature for 4 hours then carefully quenched with a few drops of water. Additional water (8 mL) was added drop-wise until no additional material precipitated. The solution was filtered and the resulting gum was dissolved in ethyl acetate (10 ml) and washed with brine (7 ml), dried (Na$_2$SO$_4$), filtered and evaporated to obtain Compound 188.2 as a brown wax. ES (+) MS m/e=539 (M+23).

188.3 Crude Compound 188.2 was dissolved in DCM (4 ml) then trifluoroacetic acid (154 µL, 2.0 mmol) was carefully added. The mixture was stirred at room temperature for 3 hours then evaporated under reduced pressure. The resulting black gum was dissolved in DMF (1 ml) then Compound 49.2 (57 mg, 0.2 mmol) was added followed by triethylamine (139 µL, 1.0 mmol) and 2-(1H-7-azabenzotriazol-1-yl)-1,1,3,3-tetramethyl uronium hexafluorophosphate methanaminium (HATU) (84 mg, 0.22 mmol). The mixture was stirred at room temperature for 30 minutes then water (2 ml) was added drop-wise. The resulting mixture was stirred an additional 10 minutes then filtered and washed with water (2 ml). The isolated material was dried under high vacuum then purified by column chromatography on silica (DCM to 4% MeOH/DCM) to obtain Compound 188.3 as a tan to light brown solid (18 mg, 18% yield from Compound 188.1 to Compound 188.3). ES (+) MS m/e=482 (M+1). $^1$H NMR (400 MHz, CDCl$_3$) $^{TM}$ 9.78 (br. s, 1H), 8.60 (dd, J=7.3 Hz, J=2.0 Hz, 1H), 7.57-7.47 (m, 2H), 7.10 (d, J=7.8 Hz, 1H), 7.01 (d, J=7.3 Hz, 1H), 6.97-6.88 (m, 2H), 6.58-6.46 (m, 2H), 6.31-6.21 (m, 1H), 5.12 (s, 2H), 4.22 (t, J=5.9 Hz, 2H), 1.38 (s, 6H).

Example 189

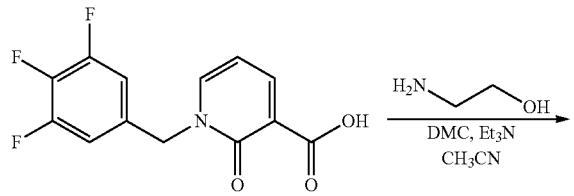

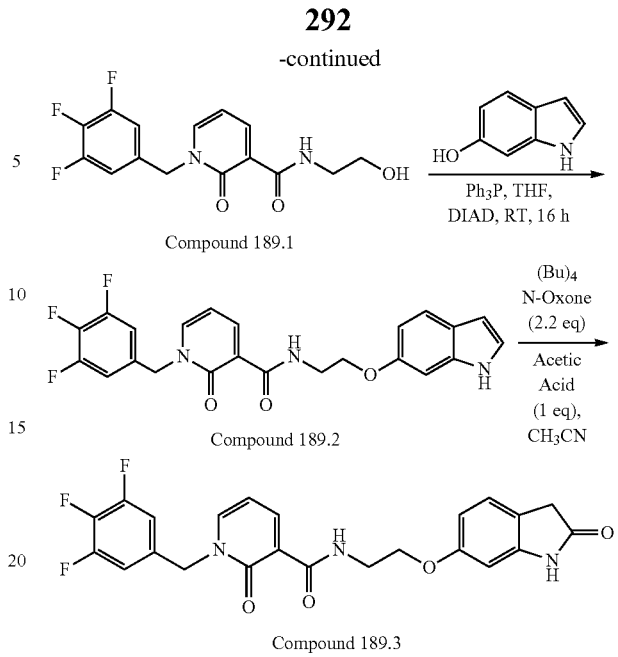

189.1 The 1-(3,4,5-trifluoro-benzyl)-2-oxo-1,2-dihydro-pyridine-3-carboxylic acid (10 mmol) was added to a flask containing 2-amino-ethanol (10 mmol) in CH$_3$CN (50 ml). To this was added DMC (2-chloro-1,3-dimethylimidazolinium chloride, 12 mmol) and Et$_3$N (2 equivalents). The reaction mixture was stirred at RT for 16 hours. It was quenched with water and extracted with CH$_2$Cl$_2$. The solvent was removed under reduced pressure to give Compound 189.1 in 65% yield. ES (+) MS m/e=327 (M+1).

189.2 To the 2-dram vial containing Compound 189.1 (1.12 mmol) in THF (3 mL) was added 1.0 equivalent of 6-hydroxy-indole. To this were added Ph$_3$P (1 equivalent) and di-isopropyl-diazodicarboxylate (1.2 equivalents) at 0° C. The reaction mixture was warmed to RT and shaken for 16 h. The solvent was removed under reduced pressure, and the crude product was purified using flash chromatography (CH$_2$Cl$_2$/MeOH, 2%) to give Compound 189.2. ES (+) MS m/e=442 (M+1).

189.3 To a 10 dram-vial containing Compound 189.2 (0.272 mmol) and 3 ml of CH$_3$CN were added 1.0 equivalent of acetic acid and 2.3 equivalents of Bu$_4$N-Oxone. The reaction mixture was stirred at RT for three days. The crude product was purified using flash chromatography (CH$_2$Cl$_2$/MeOH, 2%) to give Compound 189.3. ES (+) MS m/e=458 (M+1). 1H NMR (400 MHz, MeOD-d-4) $^{TM}$ 3.29 (s, 1H), 3.36 (s, 2H), 3.73 (t, J=5 Hz, 2H), 4.06 (t, J=5 Hz, 2H), 5.15 (s, 2H), 5.40 (s, 1H), 6.50 (d, J=7 Hz, 2H), 6.53 (t, J=2 Hz, 1H), 7.04 (d, J=8 Hz, 1H), 7.09 (t, J=7 Hz, 2H), 7.95 (d, J=6 Hz, 1H), 8.41 (d, J=6 Hz, 1H).

Example 190

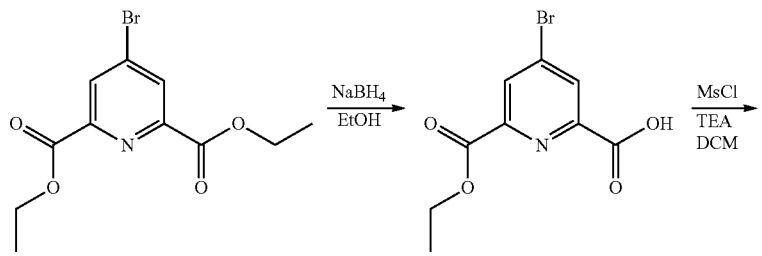

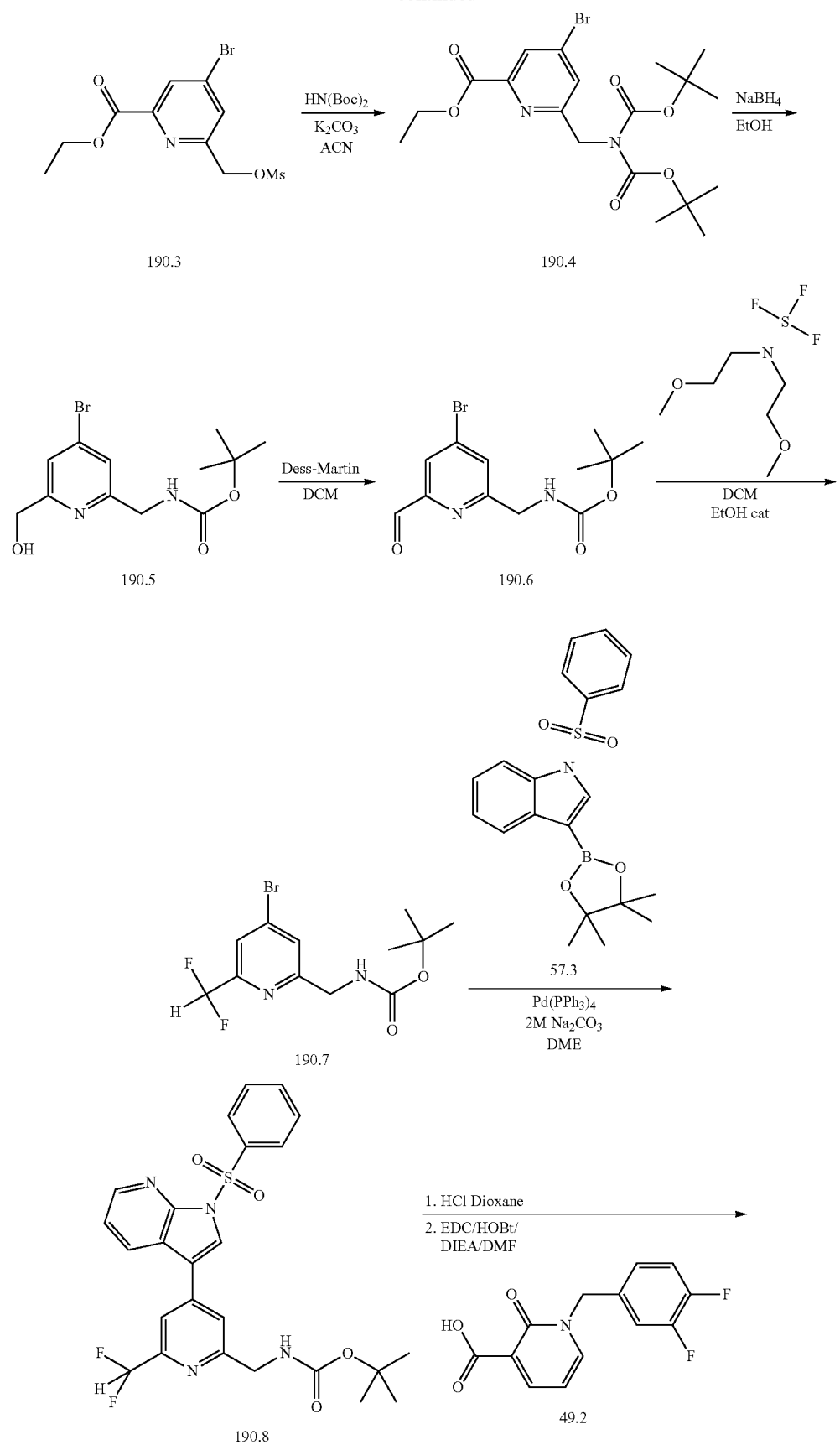

-continued

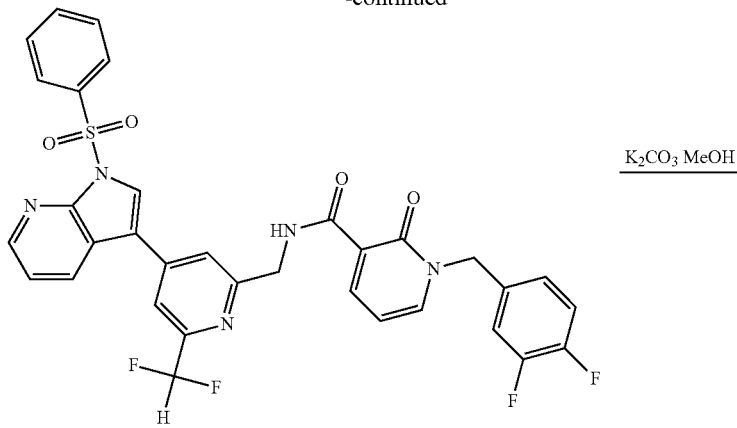

190.9

K₂CO₃ MeOH →

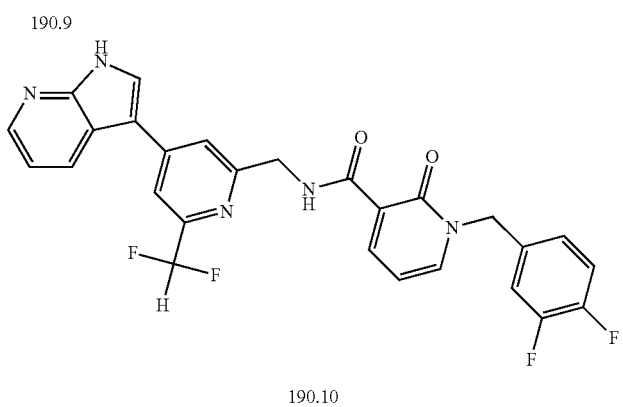

190.10

Compound 190.1 was prepared as described in Takalo et al. Helv. Chim. Acta. 1996 (79) 789-802.

Compound 190.2 was prepared as in Example 153.1, using Compound 190.1. ES (+) MS m/e=262 (M+2).

Compound 190.2 (4.20 grams, 16.15 mmol) was dissolved in dichloromethane (81 ml) under a nitrogen atmosphere, triethylamine (4.5 ml, 32.3 mmol) was added and the solution cooled to 0° C. Methanesulfonyl chloride (1.5 ml, 19.38 mmol) was added drop-wise and the reaction stirred at 0° C. for 10 minutes. The reaction was diluted with dichloromethane, washed with water, saturated sodium bicarbonate, brine, dried over sodium sulfate, filtered, and concentrated under reduced pressure to yield Compound 190.3 (5.01 grams, 14.82 mmol). ES (+) MS m/e=340 (M+2).

Compound 190.4 was prepared as in Example 154.4, using Compound 190.3. ES (+) MS m/e=461 (M+2).

Compound 190.5 was prepared as in Example 153.1, using Compound 190.4. ES (+) MS m/e=319 (M+2).

190.6 Compound 190.5 (0.663 grams, 2.09 mmol) was dissolved in dichloromethane (11 ml) and chilled to 0° C. Dess-Martin periodinane (0.976 grams, 2.30 mmol) was added and the reaction stirred at 0° C. for 1 hour, filtered through Celite and the solvent removed under reduced pressure. The crude residue was purified by silica gel column chromatography eluting with 8:2 hexane:ethyl acetate to yield Compound 190.6 (0.308 grams, 0.977 mmol). ES (+) MS m/e=317 (M+2).

190.7 Compound 190.6 (0.308 grams, 0.977 mmol) was dissolved in dichloromethane (0.3 ml) and placed in a plastic tube with a nitrogen inlet, and bis-(2-methoxyethyl)aminosulfur trifluoride (0.306 ml, 1.66 mmol) was added in dichloromethane (0.2 ml). The reaction was stirred at ambient temperature for 17 hours, poured into saturated sodium bicarbonate and extracted with dichloromethane. The combined organics were dried over sodium sulfate, filtered, and concentrated under reduced pressure. The residue was purified by silica gel column chromatography eluting with 8:2 hexane/ethyl acetate to yield Compound 190.7 (0.125 grams, 0.371 mmol). ES (+) MS m/e=339 (M+2).

190.8 Compound 190.8 was prepared as described in Example 146.1, using Compound 190.7. ES (+) MS m/e=515 (M+1).

190.9 Compound 190.9 was prepared as described in Example 154.5, using Compound 190.8. ES (+) MS m/e=662 (M+1).

190.10 Compound 190.10 was prepared as described in Example 146.3. ES (+) MS m/e=522 (M+H). 1H NMR (400 MHz, CD₃OD) δ ppm 4.25 (m, 1H) 4.72 (m, 2H) 5.19 (m, 2H) 6.51 (m, 1H) 7.10 (m, 2H) 7.24 (m, 1H) 7.38 (m, 1H) 7.72 (m, 1H) 7.79 (m, 2H) 7.98 (m, 1H) 8.19 (m, 1H) 8.30 (m, 1H) 8.41 (m, 1H).

Example 191

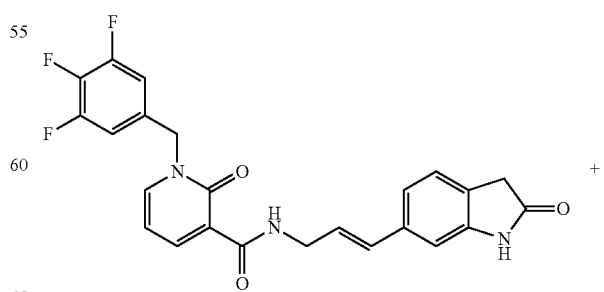

Compound 148.2

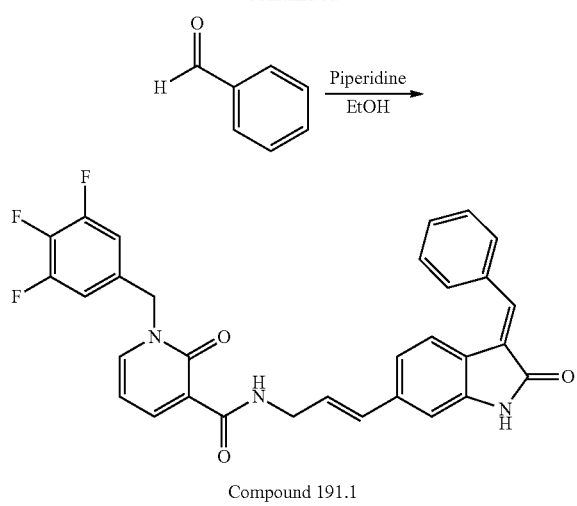

Compound 191.1

191.1 To a 2-dram vial was added Compound 148.2 (136 mg, 0.30 mmol) as a slurry in ethanol (1.6 ml). Benzaldehyde (34 μL, 0.33 mmol) and piperidine (59 μL, 0.60 mmol) were added, and the vial was sealed and the mixture was stirred at 80° C. for 1 hour. Water (2 ml) was slowly added and the mixture was filtered. The solids were washed with 1:1 ethanol/water (2 ml) followed by 1:1 ethanol/diethyl ether (2 ml) and the solids dried under vacuum. The crude product was purified by column chromatography on silica (DCM to 4% MeOH/DCM) to obtain Compound 191.1 as a yellow solid (108 mg, 67% yield). ES (+) MS m/e=542 (M+1). NMR indicates there is approximately 15% of the Z isomer present. NMR assignments are for the major isomer. $^1$H NMR (400 MHz, DMSO-d6) $^{TM}$ 10.62 (s, 1H), 9.75 (t, J=5.6 Hz, 1H), 8.37 (d, J=7.3 Hz, 1H), 8.22 (dd, J=6.4 Hz, J=2.0 Hz, 1H), 7.69 (d, J=7.3 Hz, 2H), 7.58 (s, 1H), 7.55-7.42 (m, 4H), 7.31 (t, J=7.6 Hz, 2H), 6.89 (s, 2H), 6.60 (t, J=6.9 Hz, 1H), 6.50 (d, J=15.7 Hz, 1H), 6.38-6.27 (m, 1H), 5.20 (s, 2H), 4.09 (t, J=5.4 Hz, 2H).

Example 192

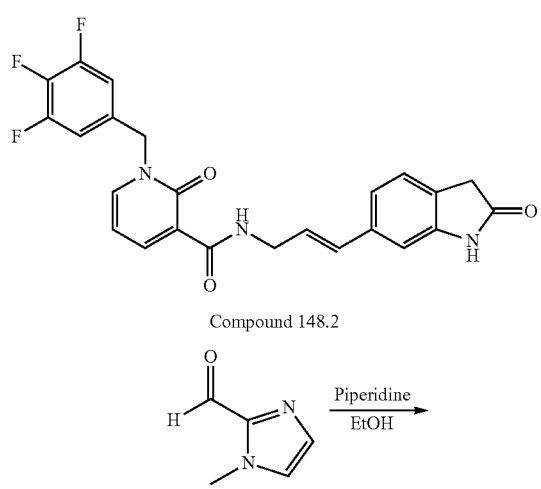

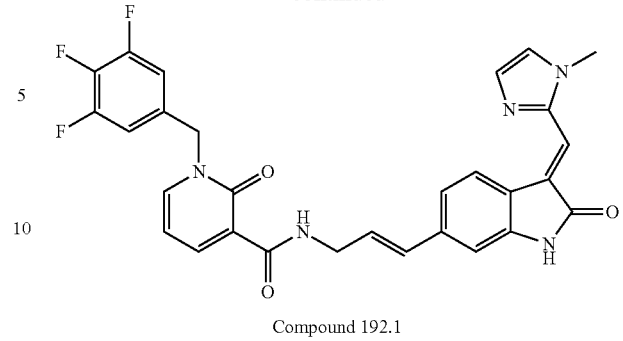

Compound 192.1

192.1 To a 2-dram vial was added Compound 148.2 (91 mg, 0.20 mmol), 1-methyl-2-imidazolecarboxaldehyde (24 mg, 0.22 mmol), ethanol (1.3 ml) and piperidine (40 μL, 0.40 mmol). The vial was sealed and the reaction was stirred at 50° C. for 2 hours then allowed to cool to room temperature upon which time solids precipitated out of solution. The solids were filtered and washed with diethyl ether (2×2 ml) and dried under vacuum to obtain Compound 192.1 as an orange-brown powder (83 mg, 76% yield). ES (+) MS m/e=546 (M+1). $^1$H NMR (400 MHz, DMSO-d6) $^{TM}$ 10.57 (s, 1H), 9.77 (t, J=5.6 Hz, 1H), 9.27 (d, J=7.8 Hz, 1H), 8.38 (dd, J=6.9 Hz, J=1.7 Hz, 1H), 8.22 (dd, J=6.9 Hz, J=1.7 Hz, 1H), 7.49 (s, 1H), 7.37-7.28 (m, 4H), 7.03 (d, J=8.3 Hz, 1H), 6.87 (s, 1H), 6.60 (t, J=6.8 Hz, 1H), 6.54 (d, J=16.1 Hz, 1H), 6.40-6.31 (m, 1H), 5.20 (s, 2H), 4.10 (t, J=5.6 Hz, 2H), 3.87 (s, 3H).

Example 193

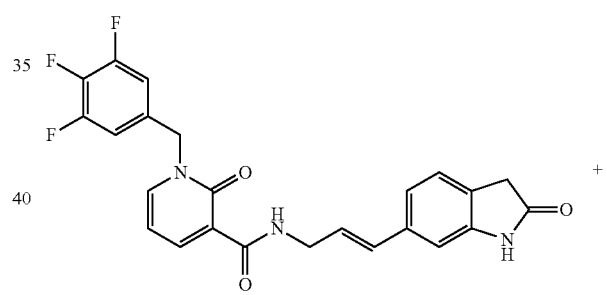

Compound 148.2

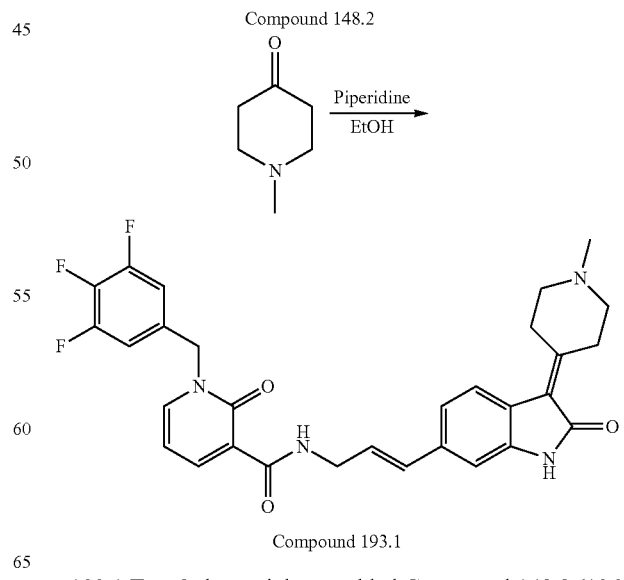

Compound 193.1

193.1 To a 2-dram vial was added Compound 148.2 (136 mg, 0.30 mmol) as a slurry in ethanol (1.6 ml). 1-methyl- 4-piperidone (38 μL, 0.33 mmol) and piperidine (59 μL, 0.60 mmol) were added, the vial was sealed and the mixture was stirred at 80° C. for 19 hours. Water (2 ml) was slowly added and the mixture was filtered. The solids were washed with 1:1 ethanol/water (2×2 ml) and then dried under vacuum. The crude product was purified by column chromatography (DCM to 7% MeOH/DCM) to obtain Compound 193.1 as a brown solid (40 mg, 24% yield). ES (+) MS m/e=549 (M+1). $^1$H NMR (400 MHz, CDCl$_3$) $^{TM}$ 9.80 (br. s, 1H), 8.62 (dd, J=7.3 Hz, J=1.5 Hz, 1H), 7.55 (br. d, J=6.4 Hz, 1H), 7.50 (d, J=8.3 Hz, 1H), 7.03-6.91 (m, 3H), 6.87 (s, 1H), 6.59-6.48 (m, 2H), 6.37-6.25 (m, 1H), 5.14 (s, 2H), 4.24 (t, J=5.9 Hz, 2H), 3.53 (t, J=5.6 Hz, 1H), 3.02 (t, J=5.6 Hz, 1H) 2.69-2.43 (m, 4H), 2.35 (s, 3H), 2.28-2.18 (m, 1H), 2.10-1.98 (m, 1H).

Example 194

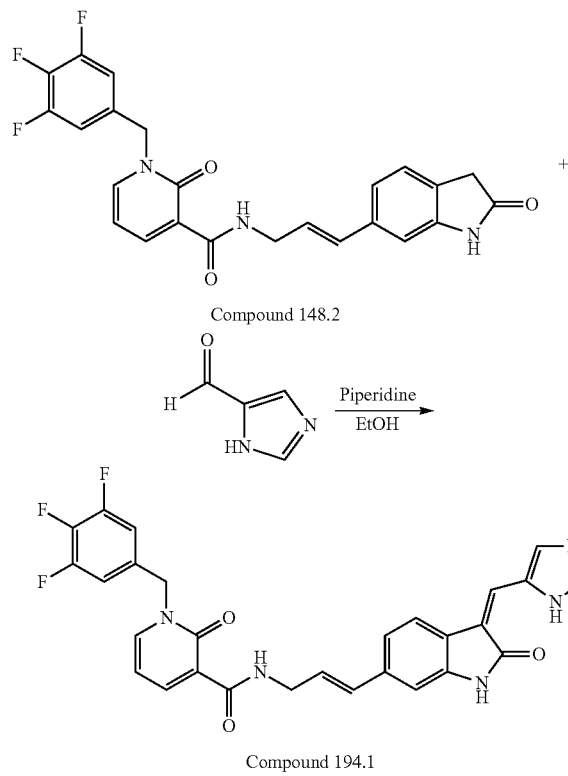

194.1 To a 2-dram vial containing 4(5)-imidazolecarboxaldehyde (32 mg, 0.33 mmol) was added Compound 148.2 (136 mg, 0.30 mmol) as a slurry in ethanol (1.6 ml) followed by addition of piperidine (59 μL, 0.60 mmol). The vial was sealed and the mixture was stirred at 80° C. for 1 hour. The mixture was allowed to cool to room temperature and the solids were filtered and washed with 1:1 ethanol/diethyl ether (2×2 ml) and dried under vacuum to obtain Compound 194.1 as an orange to brown powder (67 mg, 42% yield). ES (+) MS m/e=532 (M+1). NMR indicates approximately 20% of the E isomer present. NMR assignments are for the major isomer. $^1$H NMR (400 MHz, DMSO-d6) $^{TM}$ 13.66 (br. s, 1H), 11.02 (br. s, 1H), 9.76 (t, J=5.6 Hz, 1H), 8.38 (d, J=7.3 Hz, 1H), 8.22 (dd, J=6.4 Hz, J=1.7 Hz, 1H), 8.01 (d, J=2.9 Hz, 1H), 7.81 (s, 1H), 7.61 (s, 2H), 7.32 (t, J=7.8 Hz, 2H), 7.07 (d, J=7.8 Hz, 1H), 6.91 (s, 1H), 6.60 (t, J=6.8 Hz, 1H), 6.55 (d, J=16.1 Hz, 1H), 6.38-6.26 (m, 1H), 5.21 (s, 2H), 4.10 (t, J=5.6 Hz, 2H).

Example 195

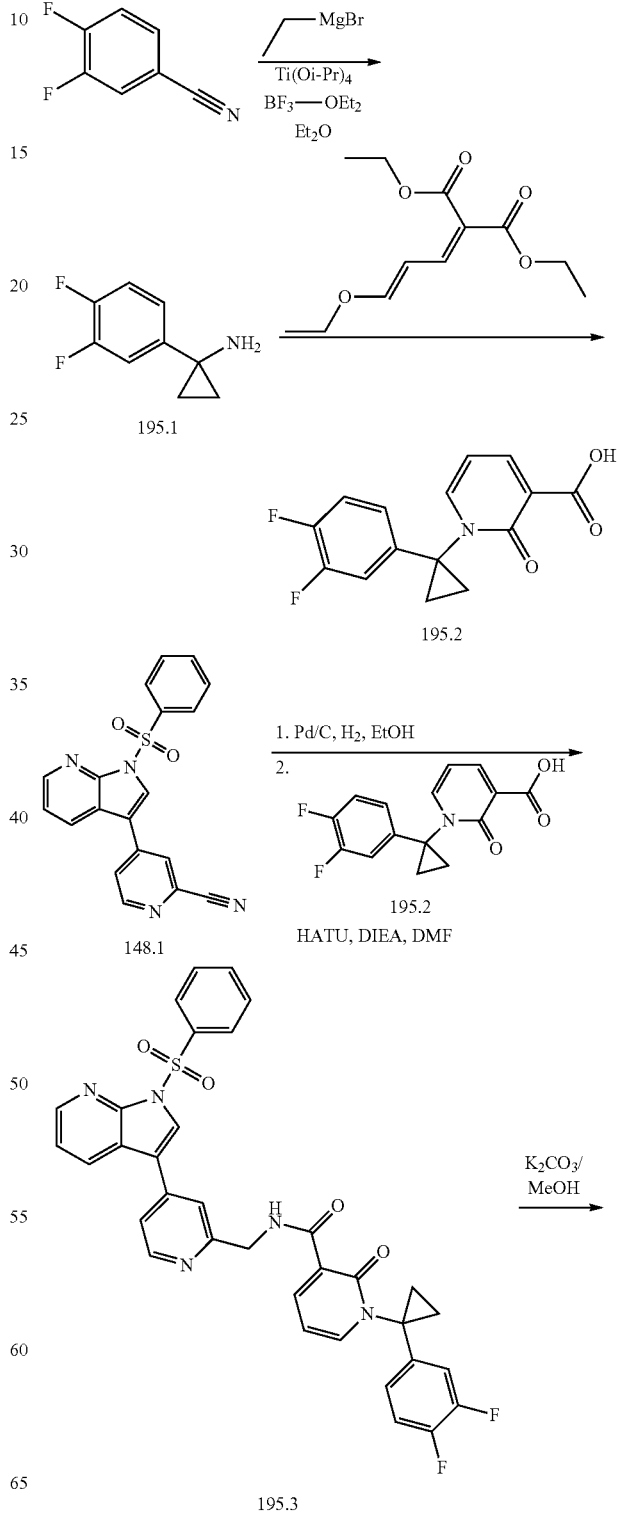

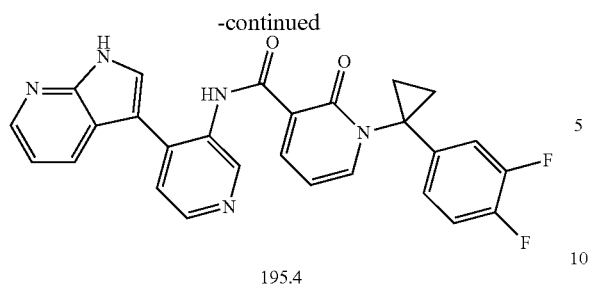

195.4

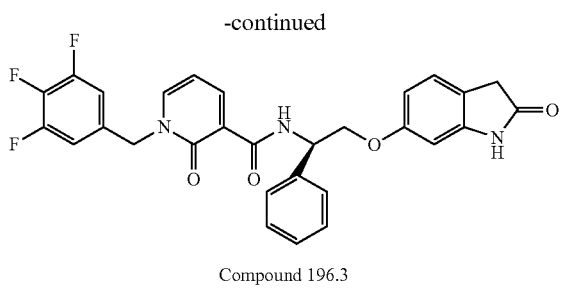

Compound 196.3

195.1 3,4-Difluoro-benzonitrile (0.139 grams, 1.0 mmol) was dissolved in diethyl ether (5 ml) under nitrogen and chilled to −78° C. Titanium isopropoxide (0.322 ml, 1.1 mmol) was added followed by drop-wise addition of ethyl magnesium bromide (3.0 M in diethyl ether, 0.733 ml, 2.2 mmol). After 10 minutes, the cooling bath was removed and the reaction warmed to ambient temperature at which point boron trifluoride etherate (0.253 ml, 2.0 mmol) was added and the reaction stirred for an additional hour. 1 N HCl (1 ml) and diethyl ether (5 ml) were added followed by 10% NaOH (10 ml). The mixture was extracted with ethyl acetate, dried over sodium sulfate, filtered and concentrated under reduced pressure to yield Compound 195.1. ES (+) MS m/e=170 (M+H).

195.2 Compound 195.2 is made following the route in Example 9.2

195.3 Compound 195.3 is made following the route in Example 146.2

195.4 Compound 195.4 is made following the route in Example 146.3

Example 196

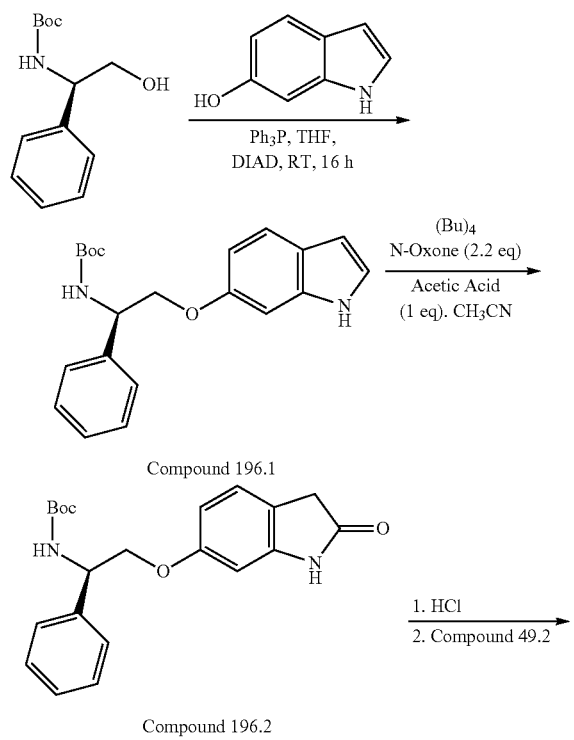

196.1 To the 2-dram vial containing D-(2-hydroxy-1-phenyl-ethyl)-carbamic acid tert-butyl ester (1.12 mmol) in THF (3 mL) is added 1.0 equivalent of 6-hydroxy-indole. To this vial are added $Ph_3P$ (1 equivalent) and di-isopropyl-diazodicarboxylate (1.2 equivalents) at 0° C. The reaction mixture is warmed to RT and shaken for 16 h. The solvent is removed under reduced pressure, and crude product is purified using flash chromatography ($CH_2Cl_2$/MeOH, 2%) to give Compound 196.1.

196.2 To a vial containing Compound 196.1 (1.12 mmol) and 3 mL of $CH_3CN$ are added 1.0 equivalent of acetic acid, and 2.3 equivalents of $Bu_4N$-Oxone. The reaction mixture is stirred at RT for three days. The crude product is purified using flash chromatography ($CH_2Cl_2$/MeOH, 2%) to give Compound 196.2.

196.3 Compound 196.2 is treated with HCl in $CH_2Cl_2$ for 2 h and concentrated followed by treatment with Compound 49.2 (1 equivalent), HATU (1 equivalent), and DIPEA (6 equivalents) in DMF (2 ml) to form the product. The product is purified using flash chromatography ($CH_2Cl_2$/MeOH, 2%) to give Compound 196.3.

Example 197

A Phospho-T308 Akt detection using immunoblot (western blot) analysis was performed as described below.

PC-3 prostate cells were plated in a 6 well plate in F12K media (Invitrogen, Carlsbad, Calif.) plus 10% FBS (Invitrogen) and placed in incubator overnight. The stock of compound A was a 50 mM solution in DMSO. 1000× dilutions of the compound were made in DMSO. The 1000× dilutions include, 35 mM, 25 mM, 15 mM, 10 mM, 7 mM, 5 mM, and 1 mM. 1 µl of the 1000× dilutions was added to 1 ml F12K media without serum for final concentrations of 35 µl, 25 µl, 15 µl, 10 µl, 7 µl, 5 µl and 1 µl. 1 µl of DMSO was added to 1 ml media with no serum for a control. The 1 ml DMSO or compound plus media was then added to the cells. Following a 2 hour incubation at 37° C., cells were harvested and washed in PBS and subjected to centrifugation at 3,300 rpm for 5 minutes. Cells were lysed in 100 µl of Bio Rad Bioplex buffer containing protease inhibitors (BioRad, Hercules, Calif.) for 30 minutes on ice followed by centrifugation at 13,000 rpm for 5 minutes. The protein content of the supernatant was assayed using DC Protein Assay (BioRad). 25 µl of protein was added to 4× sample buffer (Invitrogen) and sample reducer (Invitrogen) and run on a 4-12% NuPage gel (Invitrogen). Proteins were then transferred to nitrocellulose (Invitrogen). The membrane was blocked in Tris-buffered saline (Sigma, St. Louis, Mo.) plus 0.1% Tween (Sigma) (T-TBS) plus 5% blotting grade milk (BioRad) for 60 minutes. Membranes were then incubated in T-TBS plus 5% BSA (Sigma) plus 1:1000 of anti-phospho akt (Thr 308) (Cell Signaling Technology, Beverly, Mass.) overnight at 4° C. Membranes were washed in T-TBS then incubated in 1:2000 of anti-rabbit-HRP (Cell Signaling) in TTBS plus 5% milk. Membranes were washed again and proteins were visualized with Super Signal West Pico (Pierce, Rockford, Ill.) and using Kodak BioMax MR film (Kodak, Rochester, N.Y.).

Phospho-akt 308 protein bands on the film were quantified using densitometry. An Alpha Imager (Alpha Innotech Corp, San Leandro, Calif.) using AlphaEase FC software version 4.1.0 (Alpha Innotech Corp.) was used to quantitate protein bands. Briefly, a rectangle of equal size was placed around each protein band as well as a background spot on the film. The densitometry values (IDV=Integrated Density Value) obtained for the background spot was then subtracted from the values obtained for the protein bands. These values were used to obtain an EC50 value using non-linear regression analysis in GraphPad Prism Version 4.00 (Graph Pad Prism, San Diego, Calif.). Percent decrease in expression of phosphoh-akt 308 were also measured specifically at 2 µM and 5 µM levels of inhibitor.

Results are set forth in Tables 2 and 3.

Example 198

Determination of EC50s for the inhibition of phospho-akt (Thr308) was accomplished by treating PC-3 cells with subject inhibitors for 2 hours in no serum then using the Meso Scale Discovery (MSD) phospho-akt 308 ELISA kit to detect p-akt (Thr308) levels.

PC-3 cells were harvested by trypsin and counted. Cells were plated in coated 96-well flat bottom plates (plate 15,000 cells/well in 100 ul growth media (10% FBS, 1× pen-strep) an place in an incubator overnight.

Subject inhibitors were stocked at 50 mM, then diluted to 30 mM (4.8 µl cpd plus 1.6 ul DMSO) in 100% DMSO. Three-fold dilutions were performed from 30 mM stock. (4 µl into 8 ul 100% DMSO). Aliquots of 1.0 µl of inhibitor solution were transferred into SF Medium (using deep well block).

Control wells were prepared as follows. For DMSO high controls, 1.0 µl of 100% DMSO was added into 1.0 ml SF. For low controls for PC-3 cells, 5 µM of Wortmannin (10 µl of 1 mM Wortmannin stock was added into 2 ml SF Medium. The supernatant media was removed and the plate was blotted. 100 µl of controls/media or compound/media were added to cells and placed in incubator for 2 hours. The supernatant media was removed and the plate was blotted. 55 µl of the MSD complete lysis buffer was added (10 mls Tris Lysis buffer, 200 ul protease inhibitor, 100 ul phosphatase inhibitor 1, and 100 ul phosphatase inhibitor II). The plate was placed on a plate shaker for 60 mins at 4 deg.

MSD plates were blocked for 1 hour by adding 150 µl of Blocking Solution (3% BSA) to each well. The MSD plates were washed 4× with TBST, and 50 µl lysates were transferred to MSD plate and place on plate shaker shake at 4 degrees O/N, light shaking (speed 3.5). The plate was washed 4× with TBST.

For detection, the following detection antibody solution was used: 1 ml Blocking Solution (3% BSA stock, 1% BSA final); 2 mls TBST; and 91 µl of stock (0.33 uM) detection antibody (final concentration 10 nM). 25 µl of Ab detection solution was added to each well. The plate was sealed and incubated 1 hr RT, light shaking (speed 3.5). The plate was washed 4 times with TBST. 150 µl of Read Buffer was added (5 mls 4×MSD Read Buffer+15 mls water). Finally the plate was read immediately on the MSD plate reader.

Materials: PC-3 (cultured in F12K media—Invitrogen cat#21127-030 plus 10% FBS and 1× pen-strep); Mesoscale Discovery phospho-akt (Thr 308) kit—cat#K151DYD-1 (includes MSD plate, Tris Wash Buffer, Blocking Solution A, Read buffer, Tris Lysis Buffer, protease inhibitor, phosphatase inhibitor I, phosphatase inhibitor II, and detection); Wortmannin—Calbiochem, cat#681675 (1 mM stock, aliquoted and stored at −20 deg); and 96 well Poly-L-Lysine coated plates—Becton Dickinson cat#35-4516 (stored at room temp).

Percent decrease in expression of phospho-akt 308 was also measured specifically at 1 µM and 10 µM inhibitor levels. Results are set forth in Tables 2 and 3.

Example 199

A PDK1 kinase assay was performed as follows. PDK1 (amino acids 51-360) and AKT2 (amino acids 140-467 fused to PIFtide, amino acids EEQEMFRDFDYIADW) were expressed as N-terminally tagged GST fusion proteins in insect cells and purified to greater than 90% homogeneity. PDK1 protein was divided into two fractions, one of which was subsequently dephosphorylated. To generate dephosphorylated PDK1, the PDK1 was reacted with GST-tagged lambda-phosphatase in vitro. GST was subsequently cleaved proteolytically for both phosphorylated and dephosphorylated PDK1. Protein preparations were run on glutathione Sepharose columns to remove GST and GST-tagged lambda-phosphatase, if present. Phosphorylated PDK1 and dephosphorylated PDK1 were verified by mass-spectrometry. Enzyme activity was determined in a coupled PDK1/AKT/FAM-crosstide assay using either phosphorylated or unphosphorylated PDK1 and phosphorylation of FAM-crosstide was determined by standard IMAP protocol (Molecular Devices). For inhibition studies, compounds were titrated 3-fold in DMSO and diluted 40-fold into assay buffer (10 mM Tris HCl pH7.2; 10 mM $MgCl_2$; 0.01% Triton X-100; 1 mM DTT) containing PDK1, AKT2, and FAM-crosstide. (final concentrations: 25 nM un-phosphorylated PDK1 or 0.5 nM phosphorylated PDK1, 30 nM unphosphorylated AKT2, and 100 nM crosstide substrate). The kinase reaction was initiated by adding ATP to a final concentration of 24 µM for both forms of PDK1 and incubated at 25° C. for 30 min. To detect assay product, the kinase reaction was combined with Progressive Binding Solution (1:600 Progressive Binding Reagent, 50% Buffer A, 50% Buffer B, Molecular Devices) in a 1:3 ratio. The mixture was incubated for 2 hours at 25° C. and the plate was scanned on an Analyst AD with excitation at 485 nm and emission at 530 nm. The fluorescence polarization value "P" is defined by the equation below. The value "mP" is generated by multiplying the P value for each reaction well by a factor of 1000. The value "ΔmP" for each well is the mP value for that well minus the mP value for the average negative control.

$$P=(F\text{par}-F\text{perp})/(F\text{par}+F\text{perp}) \qquad \text{Eq.:}$$

Where "par" is fluorescence intensity parallel to the excitation plane; and "perp" is fluorescence intensity perpendicular to the excitation plane. ΔmP values were plotted as a function of compound concentration and the data were analyzed with a 4-parameter fit using GraphPad Prism software.

Results of the in vitro tests are presented in Table 2.

Example 200

The Phospho-PKC Detection was performed using immunoblot analysis as follows. The cell activity of test compounds, were assessed using immunoblot analysis for phospho-akt (thr308), phospho-PKC delta (thr505), phospho-PKC (thr538) and phospho-PKC zeta (thr410).

PC-3 prostate cells were plated in a 100 mm tissue culture dish in F12K media (Invitrogen, Carlsbad, Calif.) plus 10% FBS (Invitrogen) and placed in incubator overnight. The stocks of test compounds were a 50 mM solution in DMSO. For some test compounds a 5 mM solution was made in DMSO then directly diluted (1 µM and 5 µM final concentration) into fresh media with no serum. For other test compounds the 50 mM stock was directly diluted (10 µM and 30 µM final concentrations) into fresh media with no serum. For the control, DMSO was added to media with no serum at a final concentration of 0.1%. Cells were incubated with compound for 2 hrs or 18 hrs at 37° C. Cells were harvested and washed in PBS and subjected to centrifugation at 3,300 rpm for 5 minutes. The cell pellet was lysed in 150 µl Pierce (Rockford, Ill.) M-PER lysis buffer plus protease inhibitors and phosphatase inhibitors (Sigma, St. Louis, Mo.) for 30 minutes on ice followed by centrifugation at 13,000 rpm for 5 minutes. The protein content of the supernatant was assayed using DC Protein Assay (BioRad, Hercules, Calif.). 35 µg of protein was added to 4× sample buffer (Invitrogen) and sample reducer (Invitrogen) and run on a 4-12% NuPage gel (Invitrogen). Proteins were then transferred to nitrocellulose (Invitrogen). The membrane was blocked in Tris-buffered saline (Sigma, St. Louis, Mo.) plus 0.1% Tween (Sigma) (T-TBS) plus 5% blotting grade milk (BioRad) for 60 minutes. Membranes were then incubated in T-TBS plus 5% BSA (Sigma) plus 1:1000 of either anti-akt, anti-phospho akt (thr 308), anti-PKC delta, anti-phospho-PKC delta (thr505), anti-PKC theta, anti-phospho-PKC theta (thr538), anti-PKC zeta and anti-phospho-PKC zeta (thr410) (all from Cell Signaling Technology, Beverly, Mass.) overnight at 40° C. Membranes were washed in T-TBS then incubated in 1:2000 of anti-rabbit-HRP (Cell Signaling) in T-TBS plus 5% milk. Membranes were washed again and proteins were visualized with Super Signal West Pico (Pierce) and using Kodak BioMax MR film (Kodak, Rochester, N.Y.).

Figure 2:
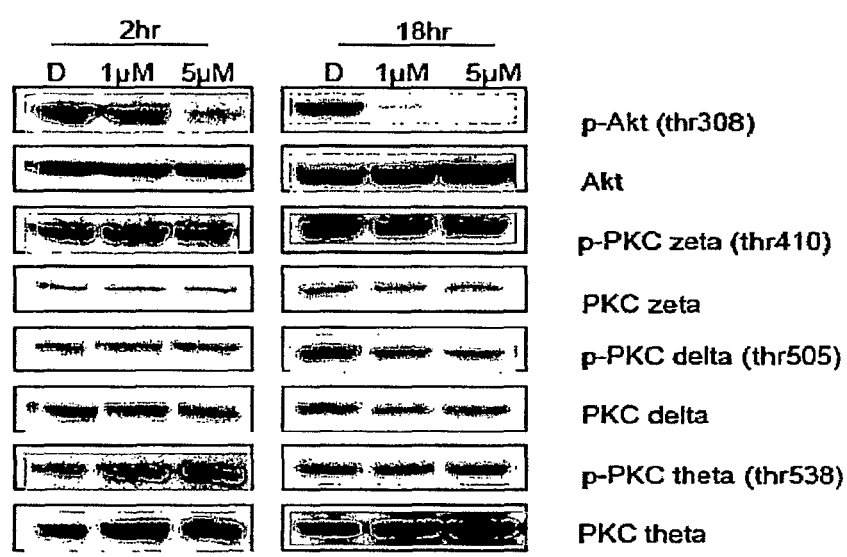
FIG. 2 illustrates selective inhibition of PDK1 mediated phosphorylation of Akt relative to PDK1 mediated phosphorylation of PKC isoforms using a compound of the present invention (compound 144 of Table 2) at 2 hours and 18 hours.

Results are presented in FIG. 1 and FIG. 2 (setting forth data from Compound 144 in Table 1).

Example 201

PDK phosphorylation of two different substrates, AKT and PKC-PIFtide, was measured in presence of pre-formed phophoinositol lipid PIP3 vesicles. 5 nM full-length PDK1 and was incubated with 100 nM substrate (unphosphorylated, full-length AKT2 or PKC-PIFtide, Invitrogen cat#P2925) in presence of test compound or DMSO at room temperature for 3 hours. Final buffer conditions were 10 mM Tris pH 7.5 buffer containing 10 mM $MgCl_2$, 0.002% Triton X-100, 1 mM DTT, 0.2 mg/ml BSA, 10 uM PtdIns(3,4,5)P3 (Matreya, Inc), 100 uM DOPC:DOPS (Avanti Polar Lipids), and 0.5 uCi $\gamma^{33}$P-ATP (3000 Ci/mmol, Perkin-Elmer.)

Kinase reactions were stopped with addition of 50 uM non-labelled ATP and 5 mM EDTA, then acidified with 0.5% final concentration phosphoric acid. Labeled proteins were collected in Whatman P81 filter plates and washed with three 150 ul volumes of 0.5% phosphoric acid. 125 uL of Wallac Optiphase 'SuperMix' scintillation fluid (Perkin Elmer) was added, and plates were read in a Wallac 1450 Microbeta liquid scintillation counter (Perkin Elmer) according to manufacturer's instructions.

Lipid vesicles were pre-formed as follows. 15 mg (3 ampules) DOPC:DOPS was resuspended in 898 ul 10 mM HEPES pH 7.4. 1 mg PIP3 was resuspended in 1000 ul 10 mM HEPES pH 7.4. 964 ul of PIP3 was mixed with 800 ul DOPC:DOPS and diluted with 18.2 ml 10 mM HEPES pH 7.4 and mixed by vortexing. The lipid mixture was subjected to 5 cycles of freeze/thaw using liquid nitrogen and a 50° C. water bath. Aliquot of lipids were flash frozen and stored at −20° C. Results are provided in Table 1 below.

TABLE 1

| Cpd No | Ratio of PIP3 IC50 with PKCtide to PIP3 IC50 with AKT |
|---|---|
| 2 | 36.7 |
| 102 | 19.1 |
| 109 | 51.8 |
| 110 | 13.5 |
| 112 | 71.9 |
| 129 | 16.6 |
| 144 | 14.6 |
| BX-320 | 1.83 |

The compound numbers in Table 1 correspond to the structures set forth in Table 2.

TABLE 2

| Cpd No. | Structure | Inhibition of phospo-PDK1 in vitro IC50 (µM) | Inhibition of dephospo-PDK1 in vitro IC50 (µM) | Inhibition of P308 Akt in cells using MSD EC50 (µM) | Reduction of Cellular Levels of Akt p308 By Western |
|---|---|---|---|---|---|
| 1 | 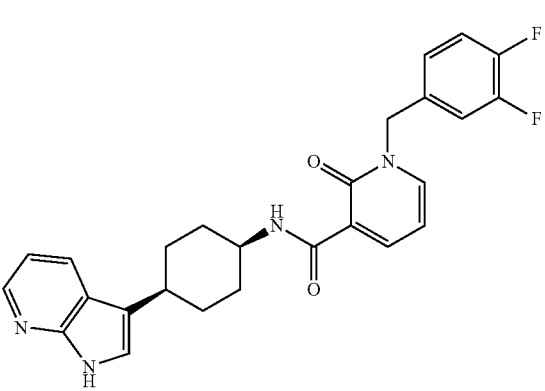 [SMILES: O=C(N[C@H]1CC[C@@H](c2c[nH]c3ncccc32)CC1)c1cccn(Cc2ccc(F)c(F)c2)c1=O] | +++ | +++ | a | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 2 | 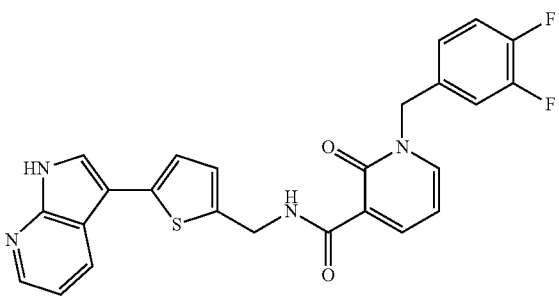 [SMILES: O=C(NCc1ccc(-c2c[nH]c3ncccc23)s1)c1cccn(Cc2ccc(F)c(F)c2)c1=O] | +++ | +++ | aa | |
| 3 | 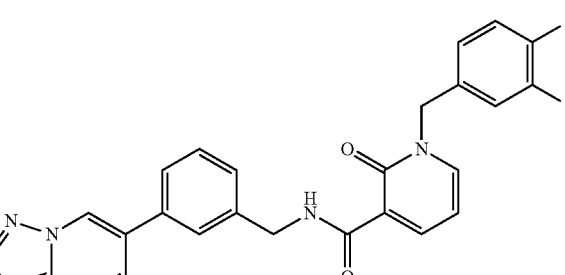 | +++ | +++ | | |
| 4 | 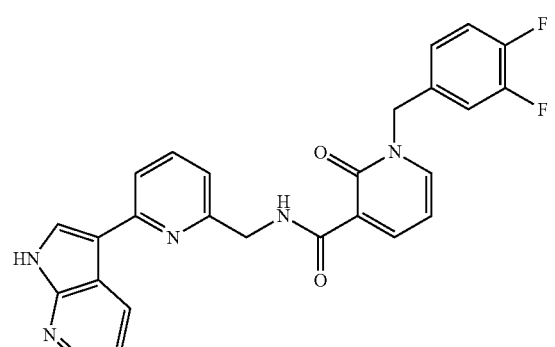 | +++ | | aa | |
| 5 | 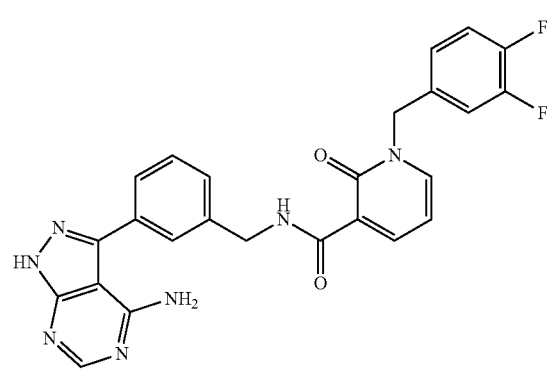 [SMILES: Nc1ncnc2[nH]nc(-c3cccc(CNC(=O)c4cccn(Cc5ccc(F)c(F)c5)c4=O)c3)c12] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 6 | 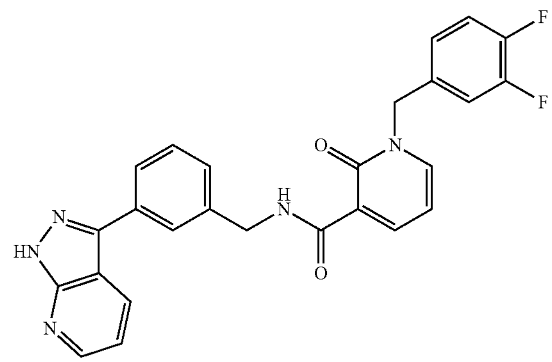 [SMILES: O=C(NCc1cccc(-c2n[nH]c3ncccc23)c1)c1cccn(Cc2ccc(F)c(F)c2)c1=O] | +++ | | aa | |
| 7 | 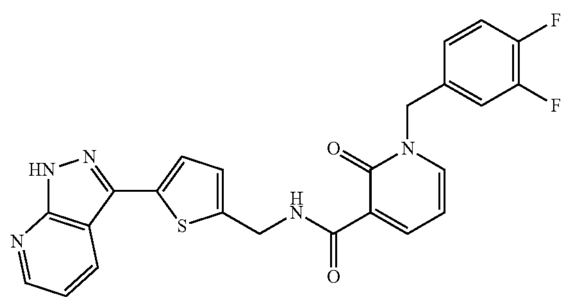 [SMILES: O=C(NCc1ccc(-c2n[nH]c3ncccc23)s1)c1cccn(Cc2ccc(F)c(F)c2)c1=O] | +++ | +++ | aaa | |
| 8 | 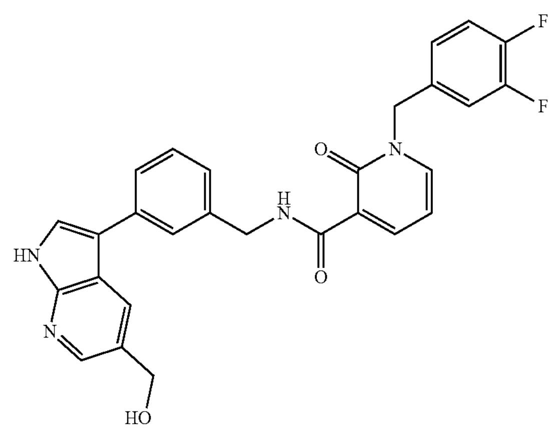 [SMILES: O=C(NCc1cccc(-c2c[nH]c3ncc(CO)cc23)c1)c1cccn(Cc2ccc(F)c(F)c2)c1=O] | +++ | | aaa | |
| 9 | 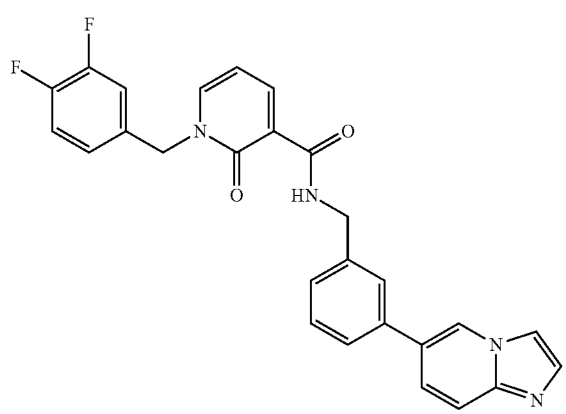 [SMILES: O=C(NCc1cccc(-c2ccc3nccn3c2)c1)c1cccn(Cc2ccc(F)c(F)c2)c1=O] | +++ | +++ | bbb | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 10 | 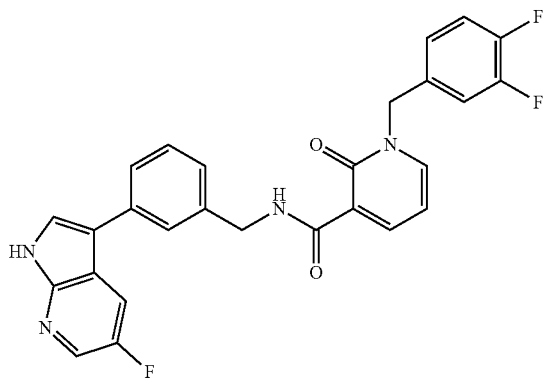 [SMILES: O=C(NCc1cccc(-c2c[nH]c3ncc(F)cc23)c1)c1cccn(Cc2ccc(F)c(F)c2)c1=O] | +++ | | aa | bbb |
| 11 | 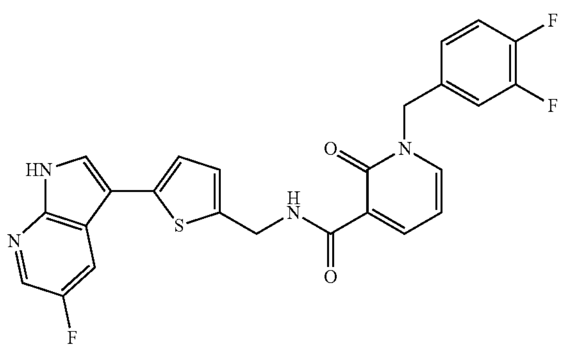 [SMILES: O=C(NCc1ccc(-c2c[nH]c3ncc(F)cc23)s1)c1cccn(Cc2ccc(F)c(F)c2)c1=O] | +++ | | aaa | bbb |
| 12 | 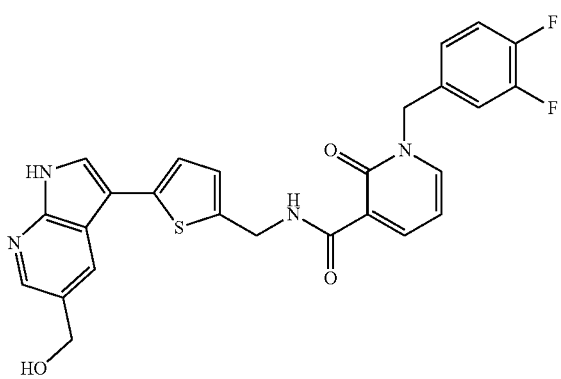 [SMILES: O=C(NCc1ccc(-c2c[nH]c3ncc(CO)cc23)s1)c1cccn(Cc2ccc(F)c(F)c2)c1=O] | +++ | | aaa | bb |
| 13 | 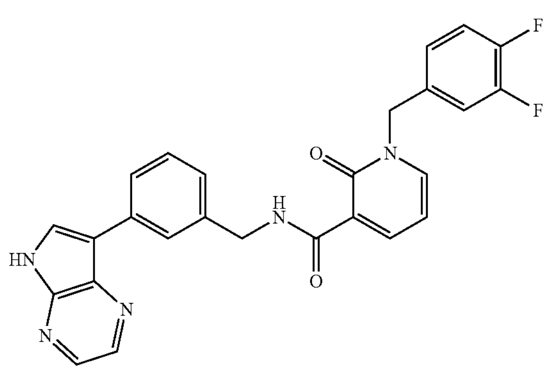 | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 14 | 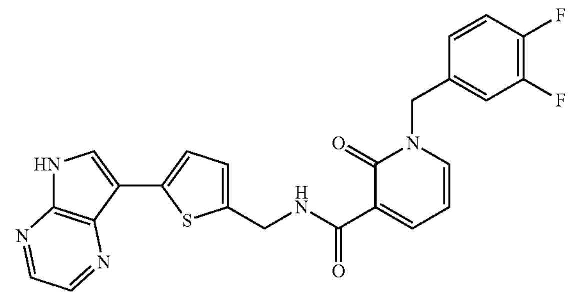 [SMILES: O=C(NCc1ccc(-c2c[nH]c3nccnc23)s1)c1cccn(Cc2ccc(F)c(F)c2)c1=O] | +++ | +++ | | bb |
| 15 | Chiral | +++ | +++ | | |
| 16 | 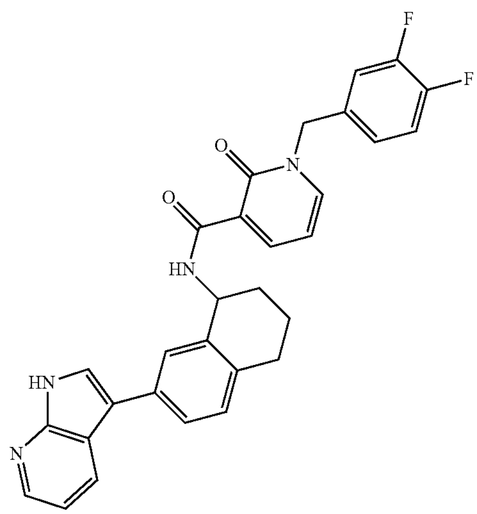 [SMILES: O=C(NC1CCCc2ccc(-c3c[nH]c4ncccc34)cc21)c1cccn(Cc2ccc(F)c(F)c2)c1=O] | +++ | +++ | a | bb |
| 17 | 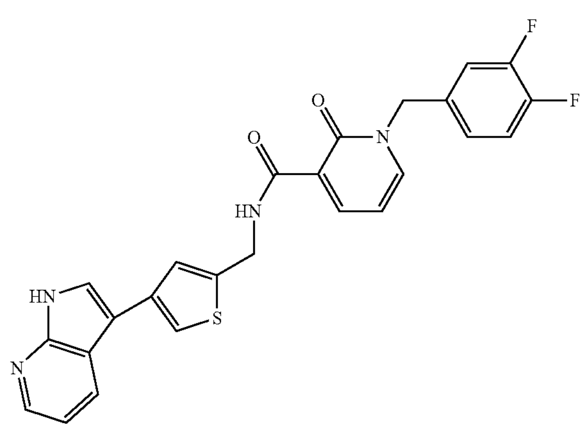 [SMILES: O=C(NCc1cc(-c2c[nH]c3ncccc23)cs1)c1cccn(Cc2ccc(F)c(F)c2)c1=O] | +++ | | aa | bbb |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 18 | Chiral 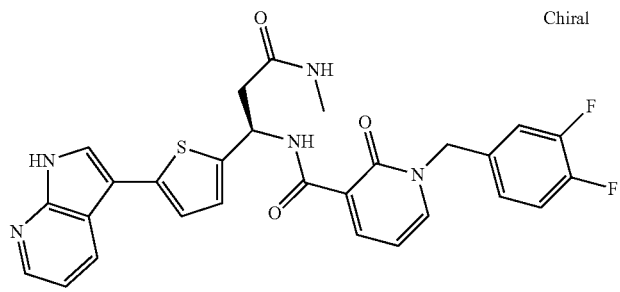 [SMILES: CNC(=O)C[C@@H](NC(=O)c1cccn(Cc2ccc(F)c(F)c2)c1=O)c1ccc(-c2c[nH]c3ncccc23)s1 ; "Chiral"] | +++ | | aa | bb |
| 19 | Chiral 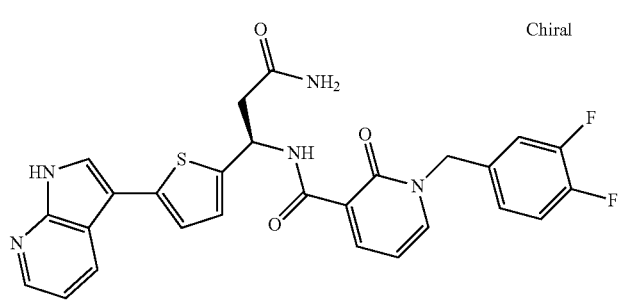 [SMILES: NC(=O)C[C@@H](NC(=O)c1cccn(Cc2ccc(F)c(F)c2)c1=O)c1ccc(-c2c[nH]c3ncccc23)s1 ; "Chiral"] | +++ | | aa | bbb |
| 20 | 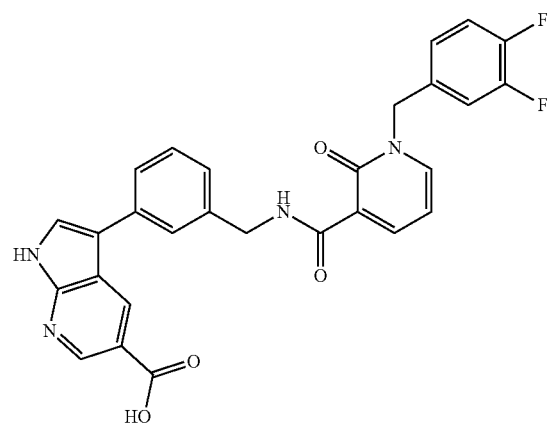 [SMILES: O=C(O)c1cnc2[nH]cc(-c3cccc(CNC(=O)c4cccn(Cc5ccc(F)c(F)c5)c4=O)c3)c2c1] | +++ | | | |
| 21 | 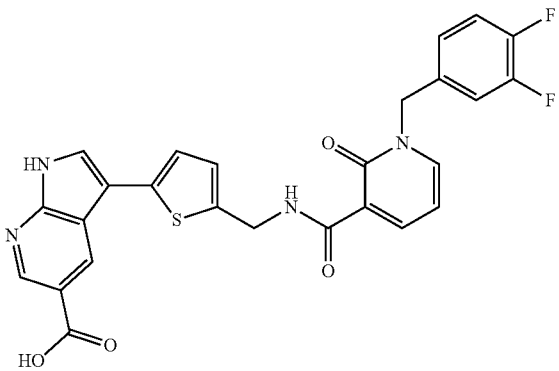 [SMILES: O=C(O)c1cnc2[nH]cc(-c3ccc(CNC(=O)c4cccn(Cc5ccc(F)c(F)c5)c4=O)s3)c2c1] | +++ | | | b |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 22 | 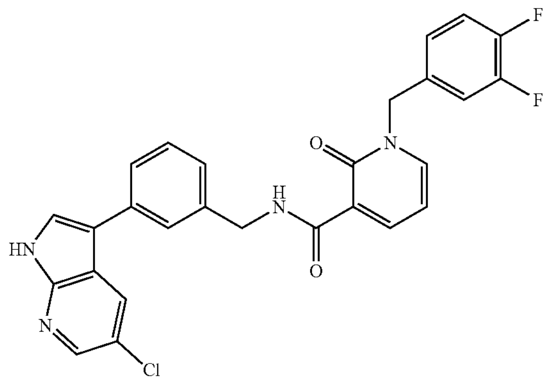 [SMILES: O=C(NCc1cccc(-c2c[nH]c3ncc(Cl)cc23)c1)c1cccn(Cc2ccc(F)c(F)c2)c1=O] | +++ | | aa | |
| 23 | 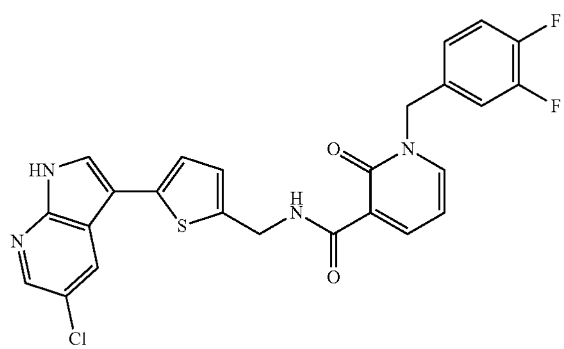 | +++ | +++ | a | |
| 24 | 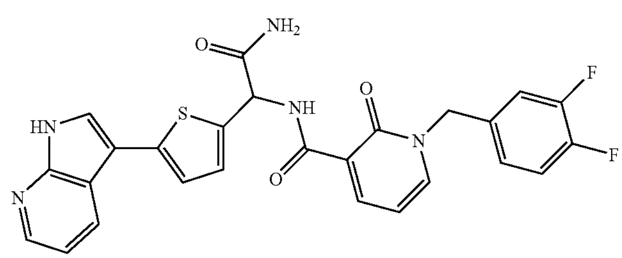 [SMILES: NC(=O)C(NC(=O)c1cccn(Cc2ccc(F)c(F)c2)c1=O)c1ccc(-c2c[nH]c3ncccc23)s1] | +++ | +++ | aa | |
| 25 | 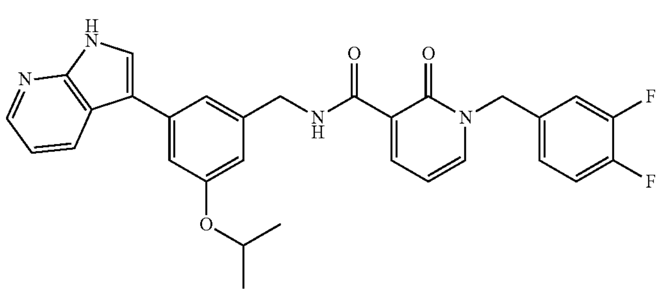 [SMILES: CC(C)Oc1cc(CNC(=O)c2cccn(Cc3ccc(F)c(F)c3)c2=O)cc(-c2c[nH]c3ncccc23)c1] | +++ | | aaa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 26 | 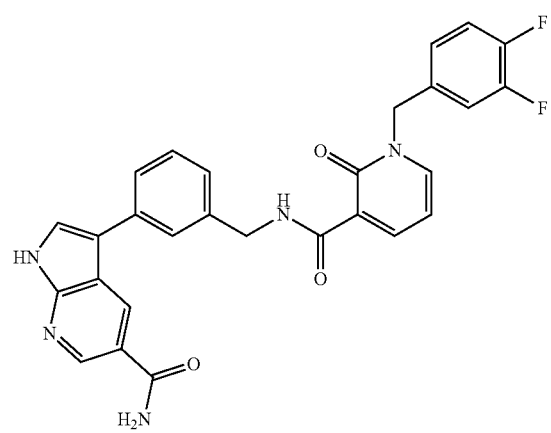 [SMILES: NC(=O)c1cnc2[nH]cc(-c3cccc(CNC(=O)c4cccn(Cc5ccc(F)c(F)c5)c4=O)c3)c2c1] | +++ | | aaa | |
| 27 | 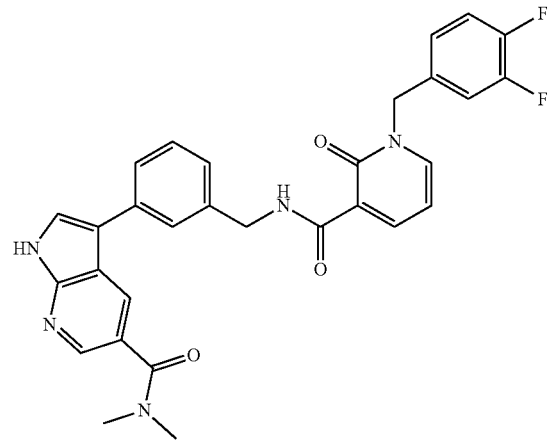 [SMILES: CN(C)C(=O)c1cnc2[nH]cc(-c3cccc(CNC(=O)c4cccn(Cc5ccc(F)c(F)c5)c4=O)c3)c2c1] | +++ | | aaa | |
| 28 | 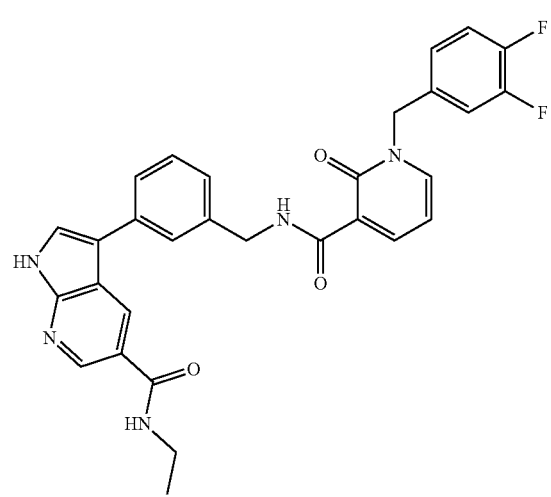 [SMILES: CCNC(=O)c1cnc2[nH]cc(-c3cccc(CNC(=O)c4cccn(Cc5ccc(F)c(F)c5)c4=O)c3)c2c1] | +++ | | aaa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 29 | 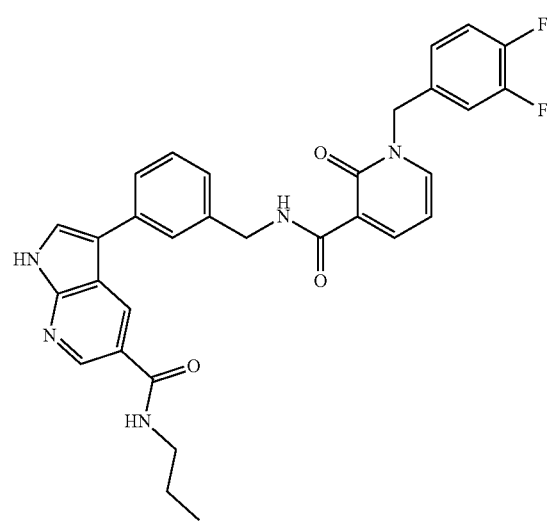 [SMILES: CCCNC(=O)c1cnc2[nH]cc(-c3cccc(CNC(=O)c4cccn(Cc5ccc(F)c(F)c5)c4=O)c3)c2c1] | | | +++ | aaa |
| 30 | 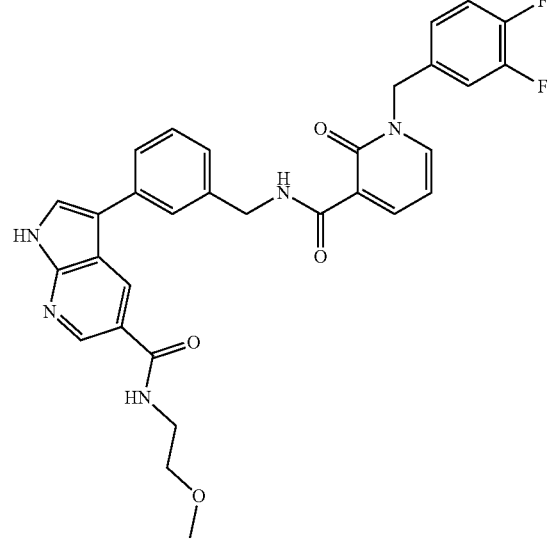 [SMILES: COCCNC(=O)c1cnc2[nH]cc(-c3cccc(CNC(=O)c4cccn(Cc5ccc(F)c(F)c5)c4=O)c3)c2c1] | | | +++ | aaa |
| 31 | 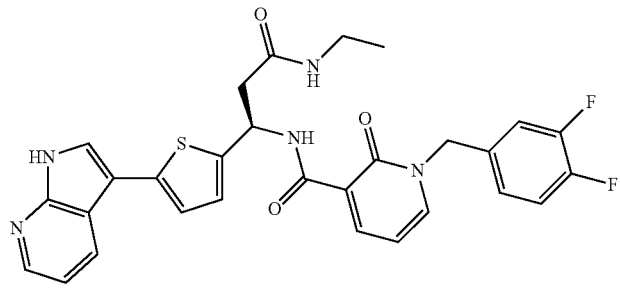 [SMILES: CCNC(=O)C[C@@H](NC(=O)c1cccn(Cc2ccc(F)c(F)c2)c1=O)c1ccc(-c2c[nH]c3ncccc23)s1] | | | +++ | aa |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 32 | 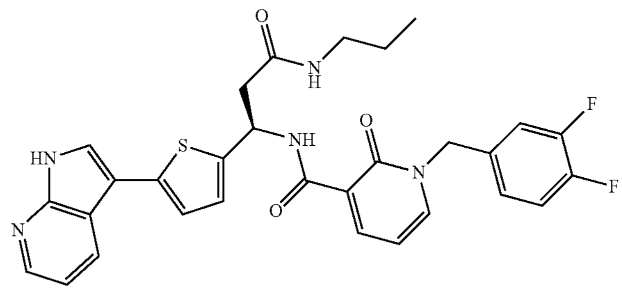 [SMILES: CCCNC(=O)C[C@@H](NC(=O)c1cccn(Cc2ccc(F)c(F)c2)c1=O)c1ccc(-c2c[nH]c3ncccc23)s1] | +++ | | aa | |
| 33 | 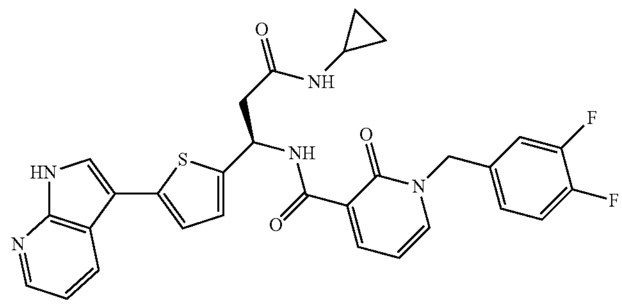 [SMILES: O=C(C[C@@H](NC(=O)c1cccn(Cc2ccc(F)c(F)c2)c1=O)c1ccc(-c2c[nH]c3ncccc23)s1)NC1CC1] | +++ | | aa | |
| 34 | 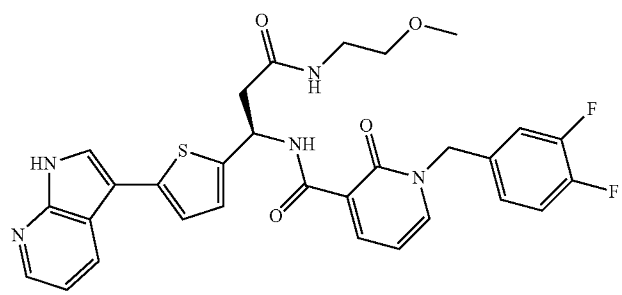 [SMILES: COCCNC(=O)C[C@@H](NC(=O)c1cccn(Cc2ccc(F)c(F)c2)c1=O)c1ccc(-c2c[nH]c3ncccc23)s1] | +++ | | aa | |
| 35 | 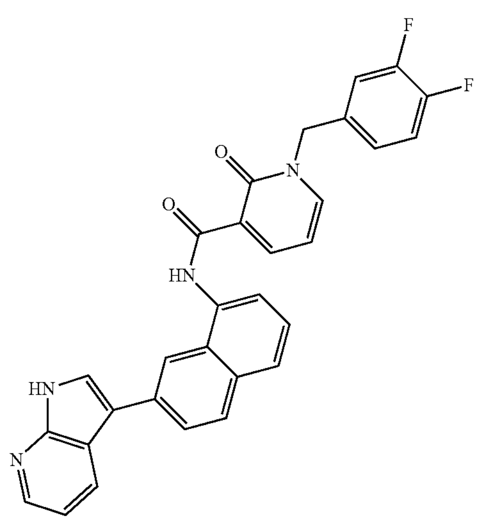 [SMILES: O=C(Nc1cccc2ccc(-c3c[nH]c4ncccc34)cc12)c1cccn(Cc2ccc(F)c(F)c2)c1=O] | +++ | | a | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 36 | 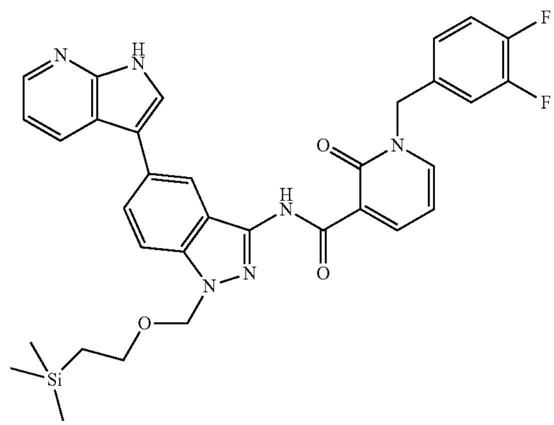 [SMILES: C[Si](C)(C)CCOCn1nc(NC(=O)c2cccn(Cc3ccc(F)c(F)c3)c2=O)c2cc(-c3c[nH]c4ncccc34)ccc21] | +++ | | a | |
| 37 | 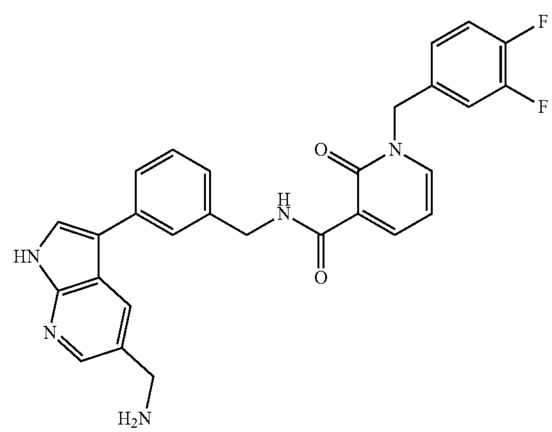 [SMILES: NCc1cnc2[nH]cc(-c3cccc(CNC(=O)c4cccn(Cc5ccc(F)c(F)c5)c4=O)c3)c2c1] | +++ | | aa | |
| 38 | 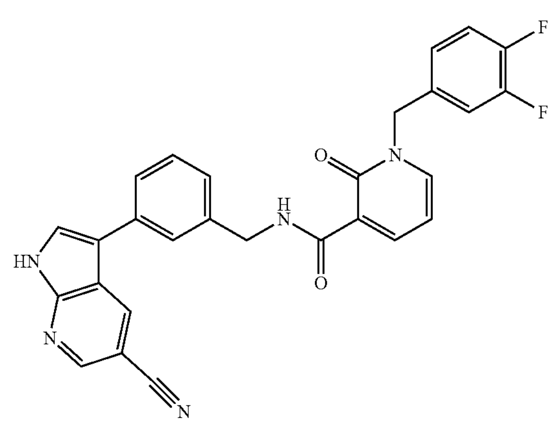 [SMILES: N#Cc1cnc2[nH]cc(-c3cccc(CNC(=O)c4cccn(Cc5ccc(F)c(F)c5)c4=O)c3)c2c1] | +++ | | aaa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 39 | 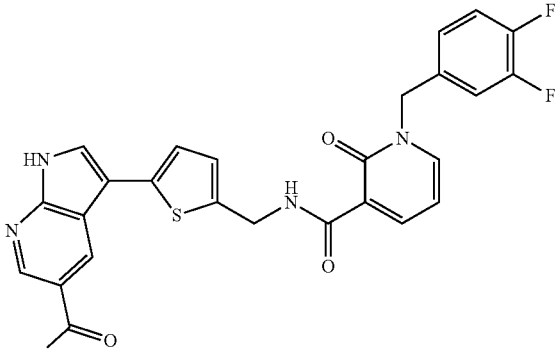 | +++ | | aaa | |
| 40 | 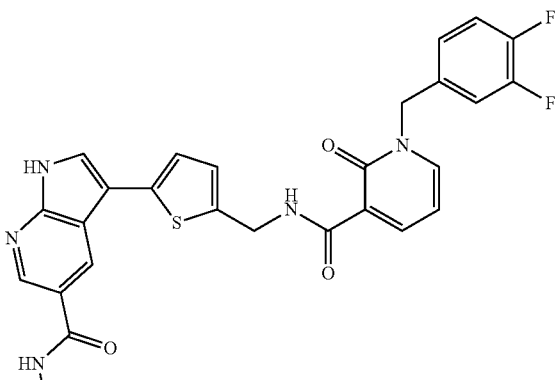 | +++ | | aa | |
| 41 | 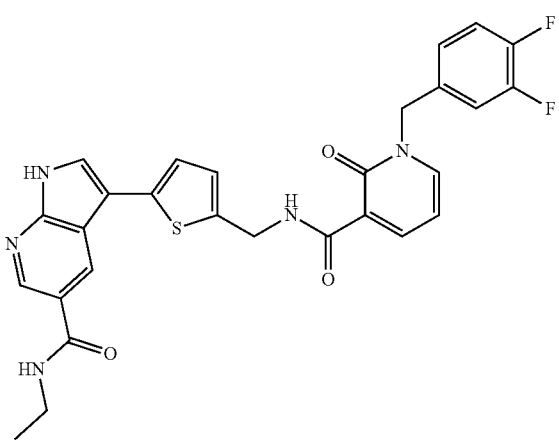 [SMILES: CCNC(=O)c1cnc2[nH]cc(-c3ccc(CNC(=O)c4cccn(Cc5ccc(F)c(F)c5)c4=O)s3)c2c1] | +++ | | aaa | |
| 42 | 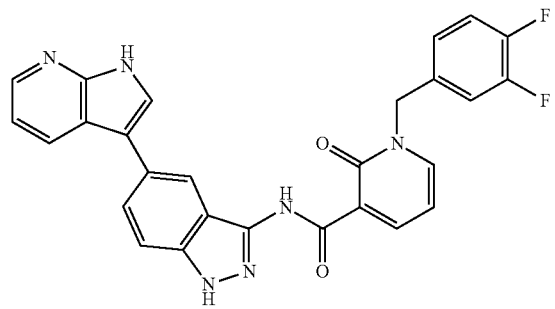 [SMILES: O=C(Nc1n[nH]c2ccc(-c3c[nH]c4ncccc34)cc12)c1cccn(Cc2ccc(F)c(F)c2)c1=O] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 43 | 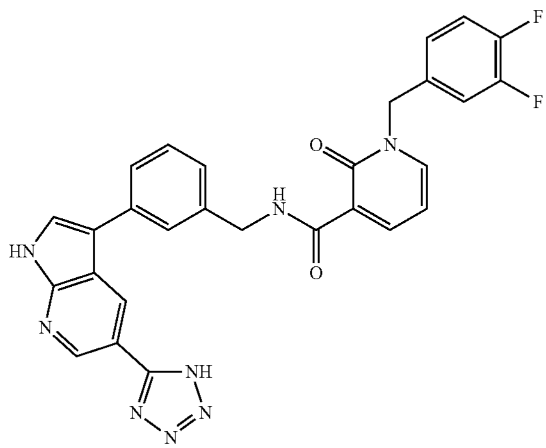 [SMILES: O=C(NCc1cccc(-c2c[nH]c3ncc(-c4nnn[nH]4)cc23)c1)c1cccn(Cc2ccc(F)c(F)c2)c1=O] | +++ | | | |
| 44 | 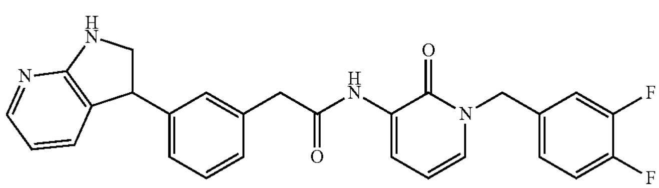 [SMILES: O=C(Cc1cccc(C2CNc3ncccc32)c1)Nc1cccn(Cc2ccc(F)c(F)c2)c1=O] | +++ | | aa | |
| 45 | 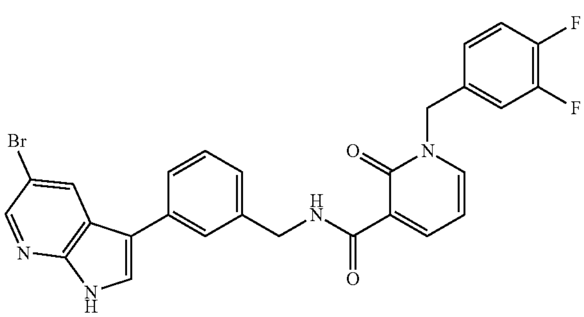 [SMILES: O=C(NCc1cccc(-c2c[nH]c3ncc(Br)cc23)c1)c1cccn(Cc2ccc(F)c(F)c2)c1=O] | +++ | | aa | |
| 46 | 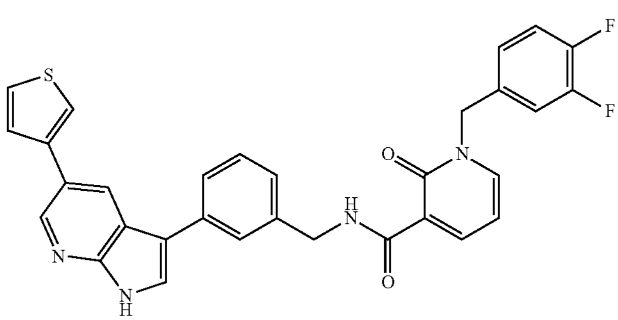 [SMILES: O=C(NCc1cccc(-c2c[nH]c3ncc(-c4ccsc4)cc23)c1)c1cccn(Cc2ccc(F)c(F)c2)c1=O] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 47 | 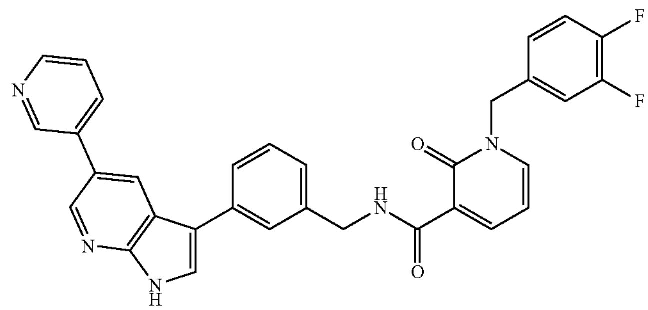 [SMILES: O=C(NCc1cccc(-c2c[nH]c3ncc(-c4cccnc4)cc23)c1)c1cccn(Cc2ccc(F)c(F)c2)c1=O] | +++ | | aaa | |
| 48 | 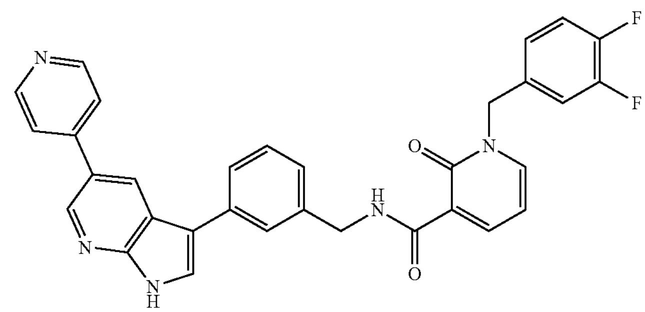 [SMILES: O=C(NCc1cccc(-c2c[nH]c3ncc(-c4ccncc4)cc23)c1)c1cccn(Cc2ccc(F)c(F)c2)c1=O] | +++ | | aaa | |
| 49 | 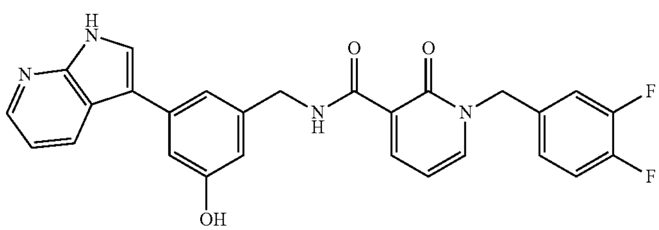 [SMILES: O=C(NCc1cc(O)cc(-c2c[nH]c3ncccc23)c1)c1cccn(Cc2ccc(F)c(F)c2)c1=O] | +++ | | aa | |
| 50 | 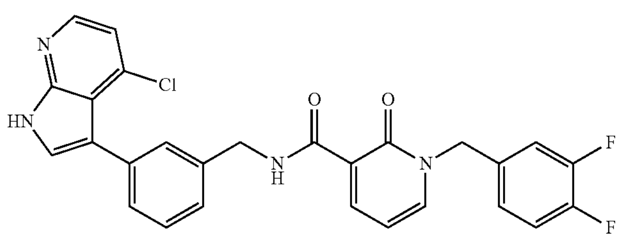 [SMILES: O=C(NCc1cccc(-c2c[nH]c3nccc(Cl)c23)c1)c1cccn(Cc2ccc(F)c(F)c2)c1=O] | +++ | | aa | |
| 51 | 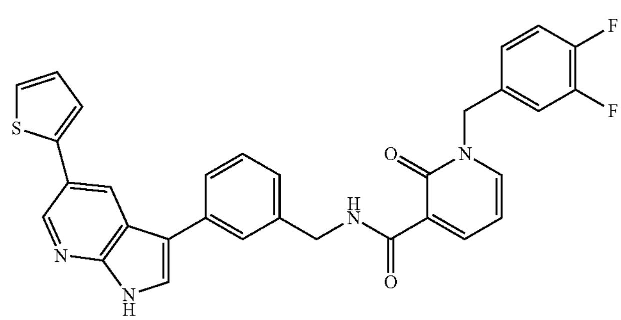 [SMILES: O=C(NCc1cccc(-c2c[nH]c3ncc(-c4cccs4)cc23)c1)c1cccn(Cc2ccc(F)c(F)c2)c1=O] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 52 | 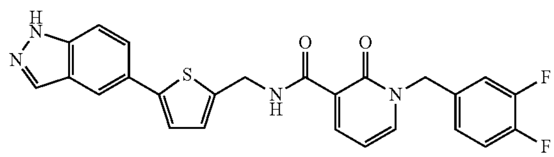 [SMILES: O=C(NCc1ccc(-c2ccc3[nH]ncc3c2)s1)c1cccn(Cc2ccc(F)c(F)c2)c1=O] | +++ | +++ | aa | |
| 53 | 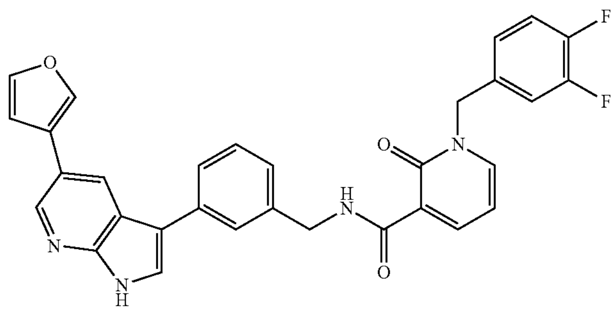 [SMILES: O=C(NCc1cccc(-c2c[nH]c3ncc(-c4ccoc4)cc23)c1)c1cccn(Cc2ccc(F)c(F)c2)c1=O] | +++ | | aaa | |
| 54 | 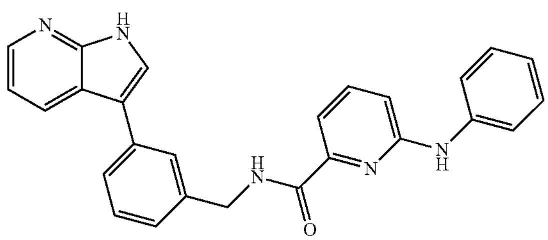 [SMILES: O=C(NCc1cccc(-c2c[nH]c3ncccc23)c1)c1cccc(Nc2ccccc2)n1] | +++ | +++ | | |
| 55 | 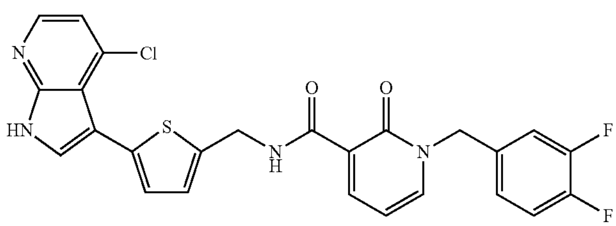 [SMILES: O=C(NCc1ccc(-c2c[nH]c3nccc(Cl)c23)s1)c1cccn(Cc2ccc(F)c(F)c2)c1=O] | +++ | | aa | |
| 56 | 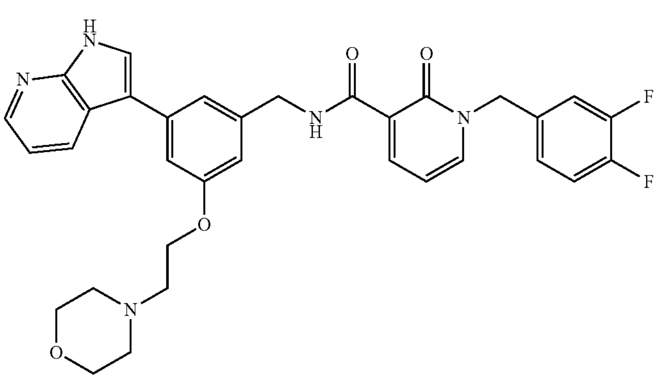 [SMILES: O=C(NCc1cc(OCCN2CCOCC2)cc(-c2c[nH]c3ncccc23)c1)c1cccn(Cc2ccc(F)c(F)c2)c1=O] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 57 | 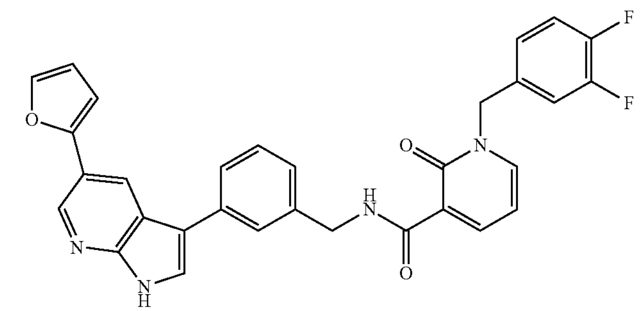 | +++ | +++ | | |
| 58 | 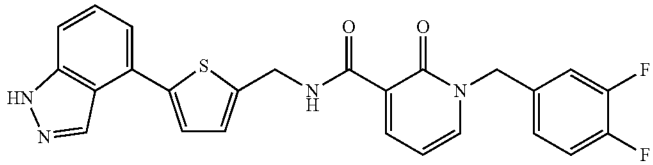 [SMILES: O=C(NCc1ccc(-c2cccc3[nH]ncc23)s1)c1cccn(Cc2ccc(F)c(F)c2)c1=O] | +++ | +++ | aa | |
| 59 | 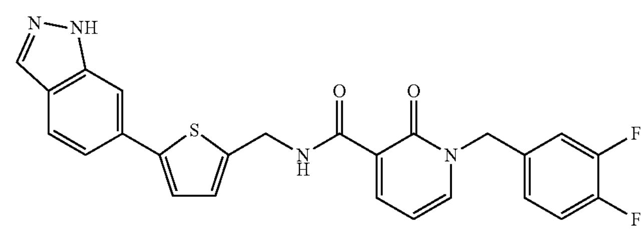 [SMILES: O=C(NCc1ccc(-c2ccc3cn[nH]c3c2)s1)c1cccn(Cc2ccc(F)c(F)c2)c1=O] | | +++ | aa | |
| 60 | 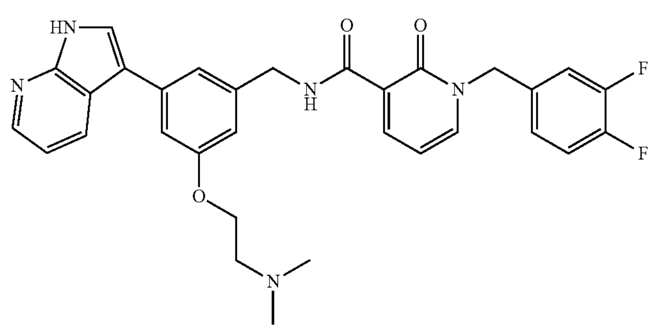 [SMILES: CN(C)CCOc1cc(CNC(=O)c2cccn(Cc3ccc(F)c(F)c3)c2=O)cc(-c2c[nH]c3ncccc23)c1] | | +++ | aa | |
| 61 | 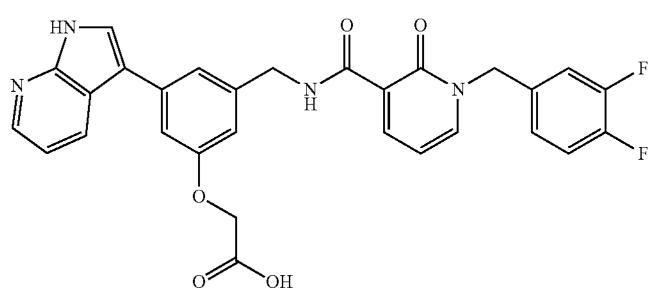 [SMILES: O=C(O)COc1cc(CNC(=O)c2cccn(Cc3ccc(F)c(F)c3)c2=O)cc(-c2c[nH]c3ncccc23)c1] | | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 62 | 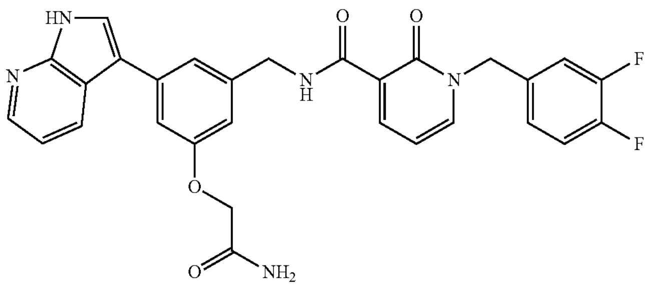 [SMILES: NC(=O)COc1cc(CNC(=O)c2cccn(Cc3ccc(F)c(F)c3)c2=O)cc(-c2c[nH]c3ncccc23)c1] | +++ | | aaa | |
| 63 | 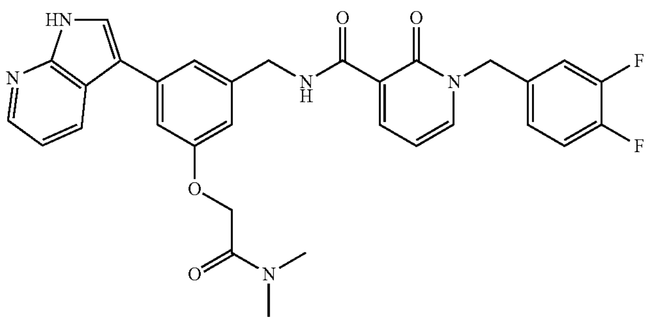 [SMILES: CN(C)C(=O)COc1cc(CNC(=O)c2cccn(Cc3ccc(F)c(F)c3)c2=O)cc(-c2c[nH]c3ncccc23)c1] | +++ | | aaa | |
| 64 | 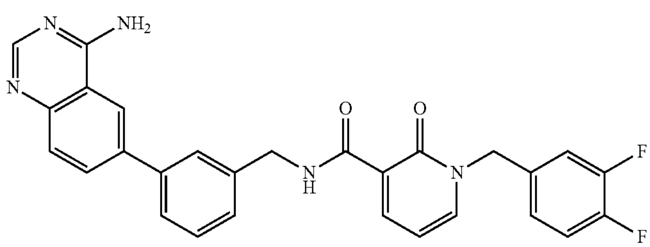 [SMILES: Nc1ncnc2ccc(-c3cccc(CNC(=O)c4cccn(Cc5ccc(F)c(F)c5)c4=O)c3)cc12] | +++ | +++ | a | |
| 65 | 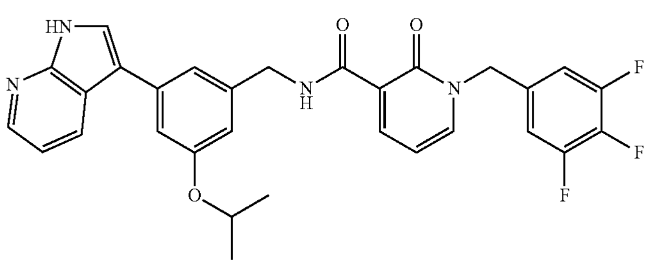 [SMILES: CC(C)Oc1cc(CNC(=O)c2cccn(Cc3cc(F)c(F)c(F)c3)c2=O)cc(-c2c[nH]c3ncccc23)c1] | +++ | | aaa | |
| 66 | 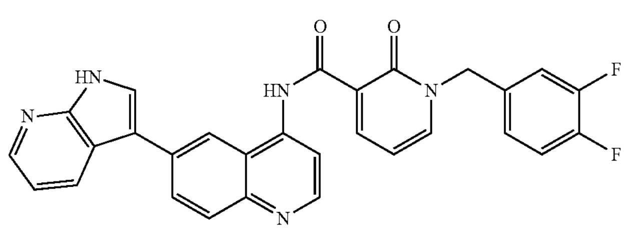 [SMILES: O=C(Nc1ccnc2ccc(-c3c[nH]c4ncccc34)cc12)c1cccn(Cc2ccc(F)c(F)c2)c1=O] | +++ | | aaa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 67 | 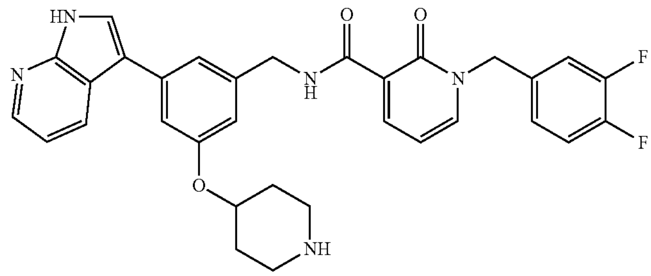 [SMILES: O=C(NCc1cc(OC2CCNCC2)cc(-c2c[nH]c3ncccc23)c1)c1cccn(Cc2ccc(F)c(F)c2)c1=O] | +++ | | aaa | |
| 68 | 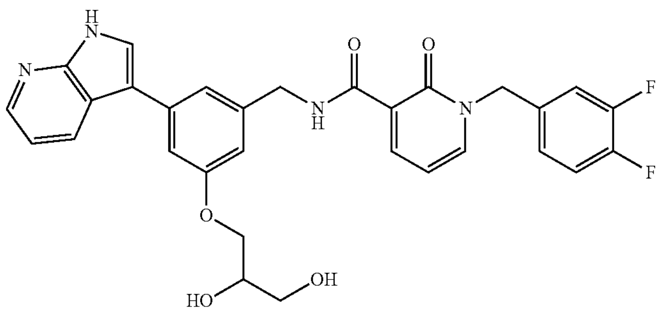 [SMILES: O=C(NCc1cc(OCC(O)CO)cc(-c2c[nH]c3ncccc23)c1)c1cccn(Cc2ccc(F)c(F)c2)c1=O] | +++ | | aa | |
| 69 | 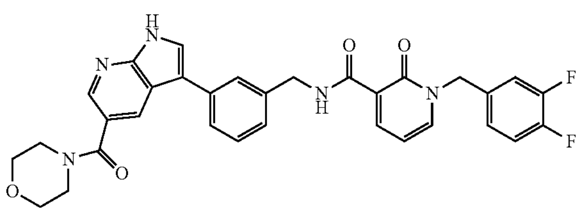 [SMILES: O=C(NCc1cccc(-c2c[nH]c3ncc(C(=O)N4CCOCC4)cc23)c1)c1cccn(Cc2ccc(F)c(F)c2)c1=O] | +++ | | aaa | |
| 70 | 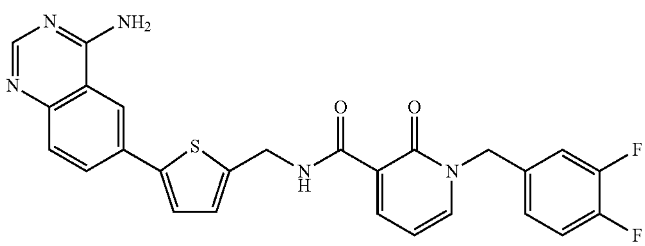 [SMILES: Nc1ncnc2ccc(-c3ccc(CNC(=O)c4cccn(Cc5ccc(F)c(F)c5)c4=O)s3)cc12] | +++ | | aaa | |
| 71 | 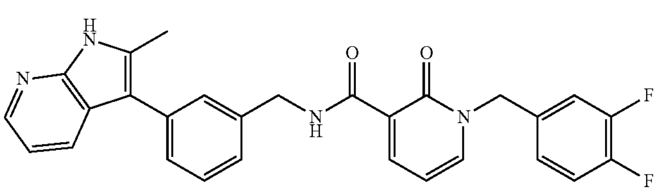 [SMILES: Cc1[nH]c2ncccc2c1-c1cccc(CNC(=O)c2cccn(Cc3ccc(F)c(F)c3)c2=O)c1] | +++ | +++ | | |
| 72 | 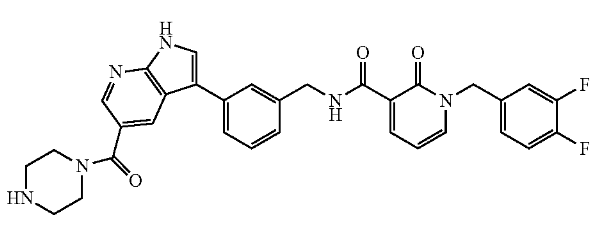 [SMILES: O=C(NCc1cccc(-c2c[nH]c3ncc(C(=O)N4CCNCC4)cc23)c1)c1cccn(Cc2ccc(F)c(F)c2)c1=O] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 73 | 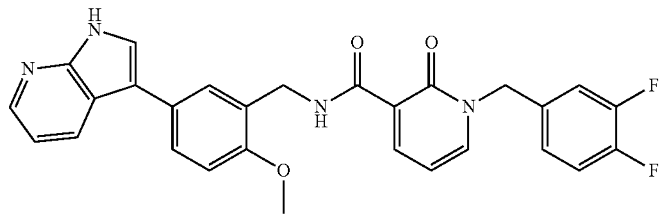 [SMILES: COc1ccc(-c2c[nH]c3ncccc23)cc1CNC(=O)c1cccn(Cc2ccc(F)c(F)c2)c1=O] | +++ | | aaa | |
| 74 | 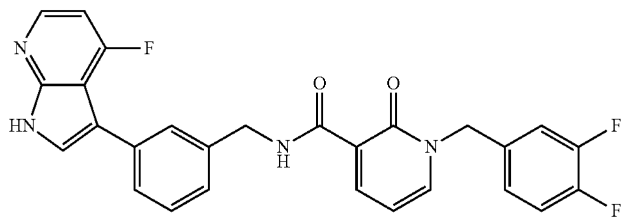 [SMILES: O=C(NCc1cccc(-c2c[nH]c3nccc(F)c23)c1)c1cccn(Cc2ccc(F)c(F)c2)c1=O] | +++ | | aa | |
| 75 | 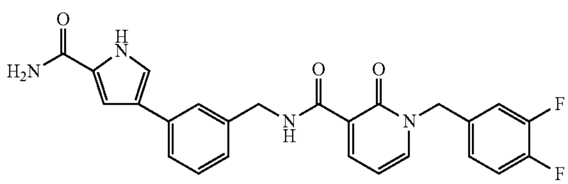 [SMILES: NC(=O)c1cc(-c2cccc(CNC(=O)c3cccn(Cc4ccc(F)c(F)c4)c3=O)c2)c[nH]1] | +++ | | aa | |
| 76 | 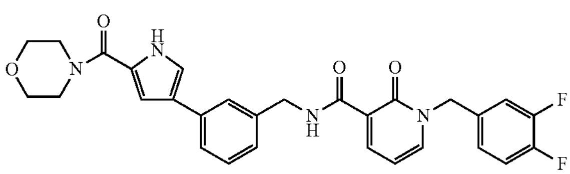 [SMILES: O=C(NCc1cccc(-c2c[nH]c(C(=O)N3CCOCC3)c2)c1)c1cccn(Cc2ccc(F)c(F)c2)c1=O] | +++ | +++ | aa | |
| 77 | 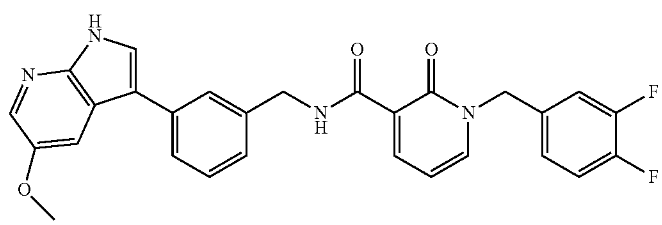 [SMILES: COc1cnc2[nH]cc(-c3cccc(CNC(=O)c4cccn(Cc5ccc(F)c(F)c5)c4=O)c3)c2c1] | +++ | | aaa | |
| 78 | 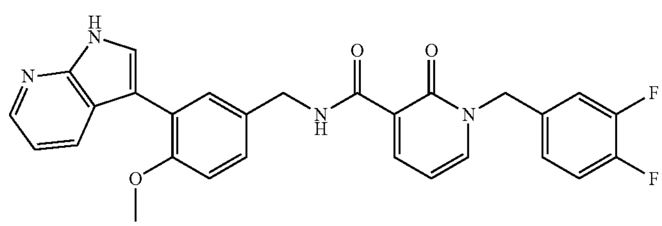 [SMILES: COc1ccc(CNC(=O)c2cccn(Cc3ccc(F)c(F)c3)c2=O)cc1-c1c[nH]c2ncccc12] | +++ | | aa | |
| 79 | 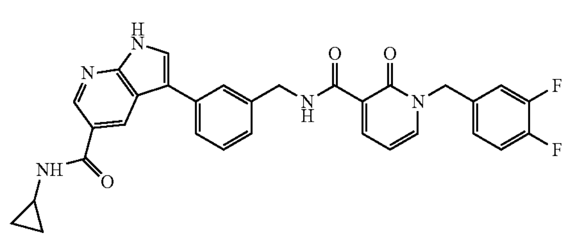 [SMILES: O=C(NC1CC1)c1cnc2[nH]cc(-c3cccc(CNC(=O)c4cccn(Cc5ccc(F)c(F)c5)c4=O)c3)c2c1] | +++ | | aaa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 80 | 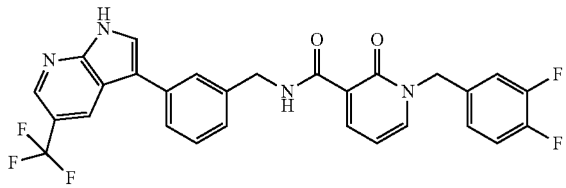 [SMILES: O=C(NCc1cccc(-c2c[nH]c3ncc(C(F)(F)F)cc23)c1)c1cccn(Cc2ccc(F)c(F)c2)c1=O] | +++ | | aa | |
| 81 | 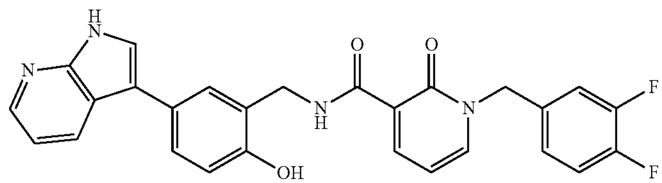 [SMILES: O=C(NCc1cc(-c2c[nH]c3ncccc23)ccc1O)c1cccn(Cc2ccc(F)c(F)c2)c1=O] | +++ | | aaa | |
| 82 | 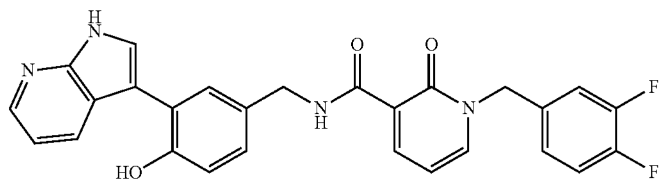 [SMILES: O=C(NCc1ccc(O)c(-c2c[nH]c3ncccc23)c1)c1cccn(Cc2ccc(F)c(F)c2)c1=O] | +++ | | aa | |
| 83 | 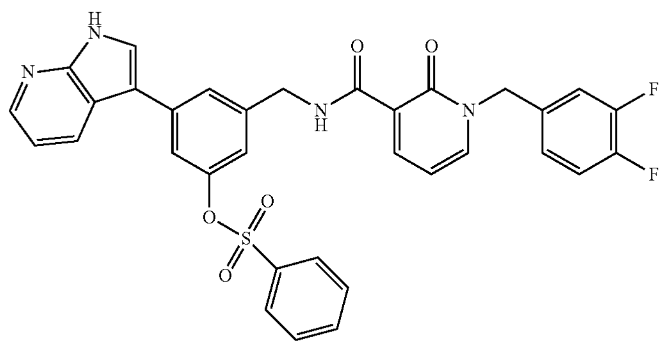 [SMILES: O=C(NCc1cc(OS(=O)(=O)c2ccccc2)cc(-c2c[nH]c3ncccc23)c1)c1cccn(Cc2ccc(F)c(F)c2)c1=O] | +++ | | aa | |
| 84 | 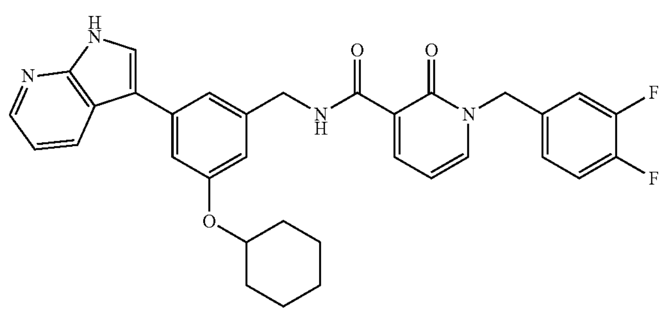 [SMILES: O=C(NCc1cc(OC2CCCCC2)cc(-c2c[nH]c3ncccc23)c1)c1cccn(Cc2ccc(F)c(F)c2)c1=O] | +++ | | a | |
| 85 | 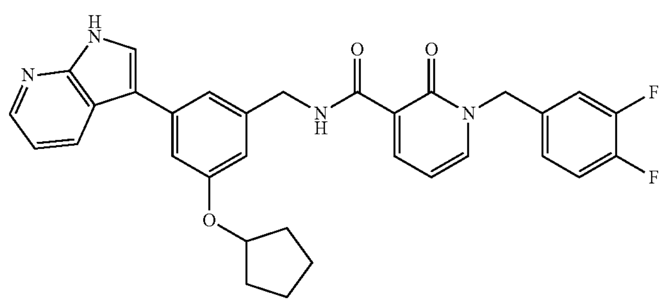 [SMILES: O=C(NCc1cc(OC2CCCC2)cc(-c2c[nH]c3ncccc23)c1)c1cccn(Cc2ccc(F)c(F)c2)c1=O] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 86 | 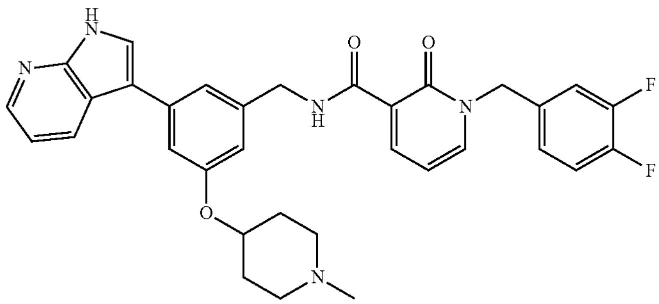 [SMILES: CN1CCC(Oc2cc(CNC(=O)c3cccn(Cc4ccc(F)c(F)c4)c3=O)cc(-c3c[nH]c4ncccc34)c2)CC1] | | | +++ | aa |
| 87 | 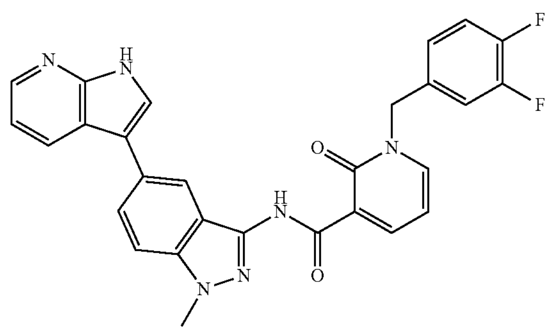 [SMILES: Cn1nc(NC(=O)c2cccn(Cc3ccc(F)c(F)c3)c2=O)c2cc(-c3c[nH]c4ncccc34)ccc21] | | | +++ | aaa |
| 88 | 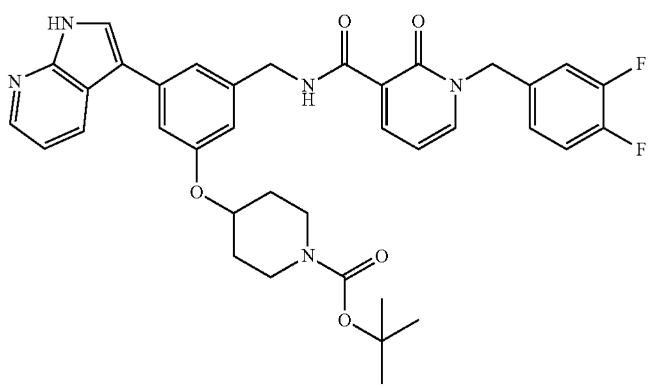 [SMILES: CC(C)(C)OC(=O)N1CCC(Oc2cc(CNC(=O)c3cccn(Cc4ccc(F)c(F)c4)c3=O)cc(-c3c[nH]c4ncccc34)c2)CC1] | | | +++ | a |
| 89 | 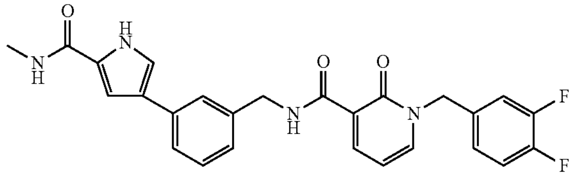 [SMILES: CNC(=O)c1cc(-c2cccc(CNC(=O)c3cccn(Cc4ccc(F)c(F)c4)c3=O)c2)c[nH]1] | | | +++ | aa |
| 90 | 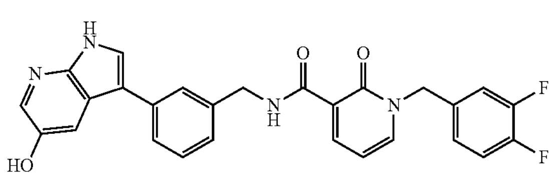 [SMILES: O=C(NCc1cccc(-c2c[nH]c3ncc(O)cc23)c1)c1cccn(Cc2ccc(F)c(F)c2)c1=O] | | | +++ | aaa |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 91 | 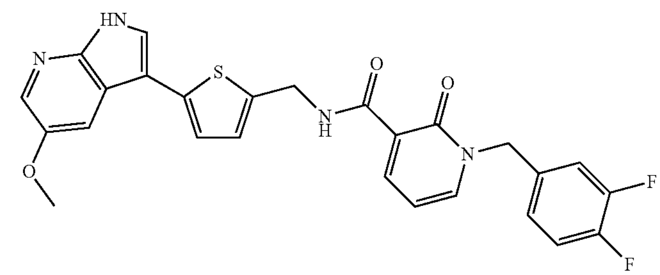 [SMILES: COc1cnc2[nH]cc(-c3ccc(CNC(=O)c4cccn(Cc5ccc(F)c(F)c5)c4=O)s3)c2c1] | | +++ | | |
| 92 | 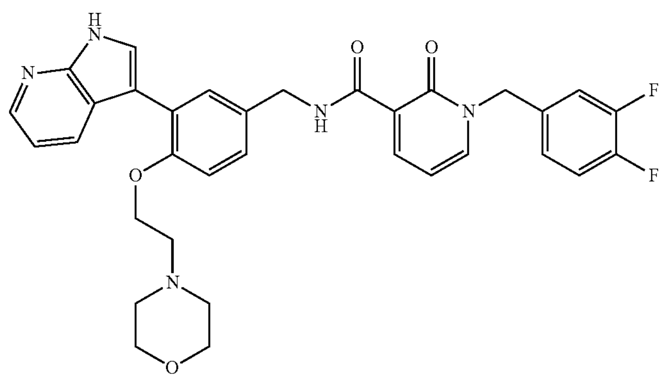 [SMILES: O=C(NCc1ccc(OCCN2CCOCC2)c(-c2c[nH]c3ncccc23)c1)c1cccn(Cc2ccc(F)c(F)c2)c1=O] | | +++ | | aa |
| 93 | 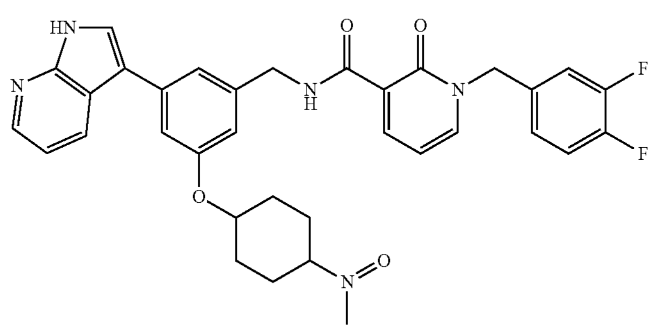 | | +++ | | aaa |
| 94 | 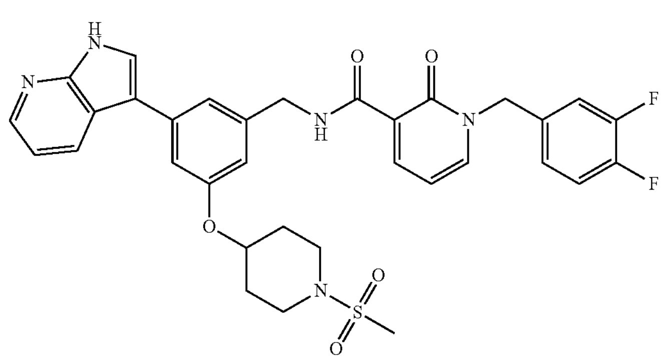 [SMILES: CS(=O)(=O)N1CCC(Oc2cc(CNC(=O)c3cccn(Cc4ccc(F)c(F)c4)c3=O)cc(-c3c[nH]c4ncccc34)c2)CC1] | | +++ | | aaa |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 95 | 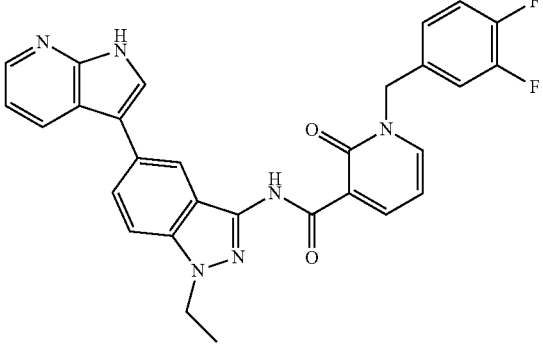 | +++ | | aa | |
| 96 | 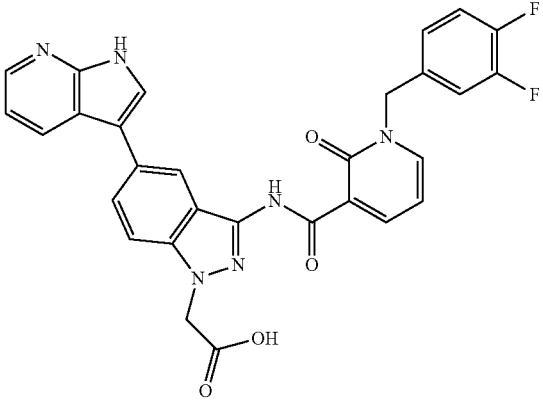 [SMILES: O=C(O)Cn1nc(NC(=O)c2cccn(Cc3ccc(F)c(F)c3)c2=O)c2cc(-c3c[nH]c4ncccc34)ccc21] | +++ | | | |
| 97 | 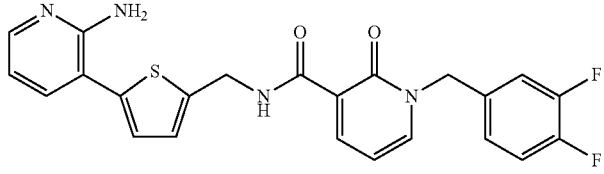 [SMILES: Nc1ncccc1-c1ccc(CNC(=O)c2cccn(Cc3ccc(F)c(F)c3)c2=O)s1] | +++ | | aa | |
| 98 | 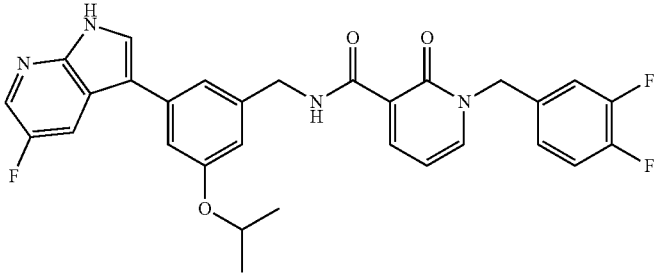 [SMILES: CC(C)Oc1cc(CNC(=O)c2cccn(Cc3ccc(F)c(F)c3)c2=O)cc(-c2c[nH]c3ncc(F)cc23)c1] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 99 | 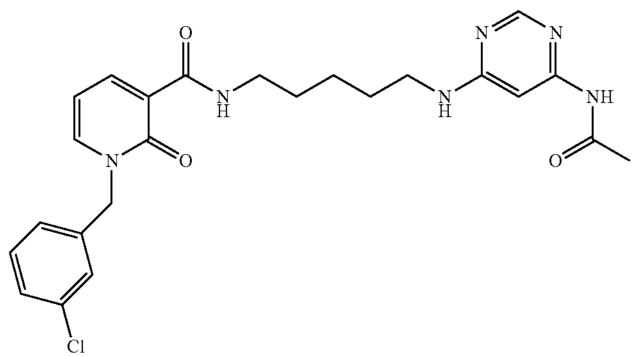 [SMILES: CC(=O)Nc1cc(NCCCCCNC(=O)c2cccn(Cc3cccc(Cl)c3)c2=O)ncn1] | + | ++ | | |
| 100 | 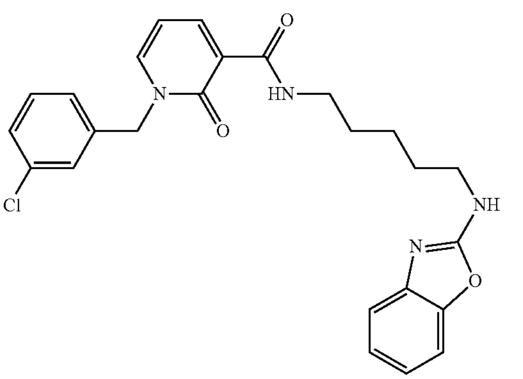 [SMILES: O=C(NCCCCCNc1nc2ccccc2o1)c1cccn(Cc2cccc(Cl)c2)c1=O] | + | ++ | | |
| 101 | 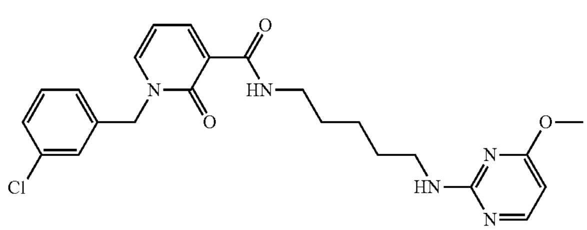 [SMILES: COc1ccnc(NCCCCCNC(=O)c2cccn(Cc3cccc(Cl)c3)c2=O)n1] | ++ | ++ | | |
| 102 | 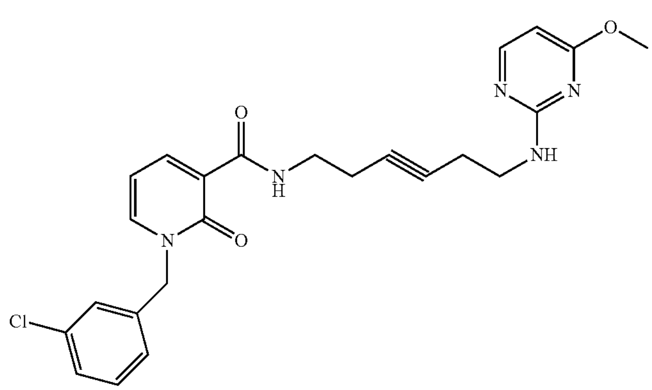 [SMILES: COc1ccnc(NCCC#CCCNC(=O)c2cccn(Cc3cccc(Cl)c3)c2=O)n1] | ++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 103 | 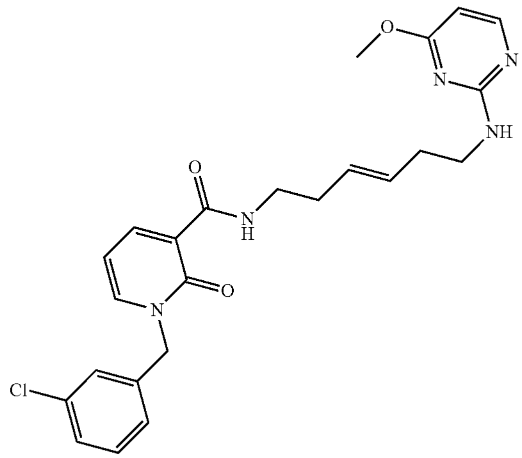 [SMILES: COc1ccnc(NCC/C=C/CCNC(=O)c2cccn(Cc3cccc(Cl)c3)c2=O)n1] | | | ++ | +++ |
| 104 | 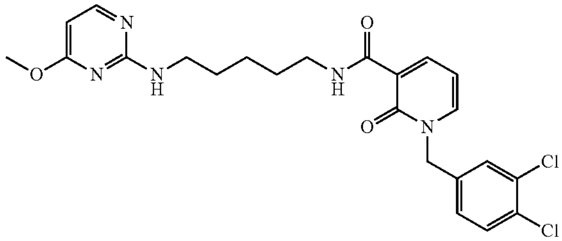 [SMILES: COc1ccnc(NCCCCCNC(=O)c2cccn(Cc3ccc(Cl)c(Cl)c3)c2=O)n1] | | | ++ | +++ |
| 105 | 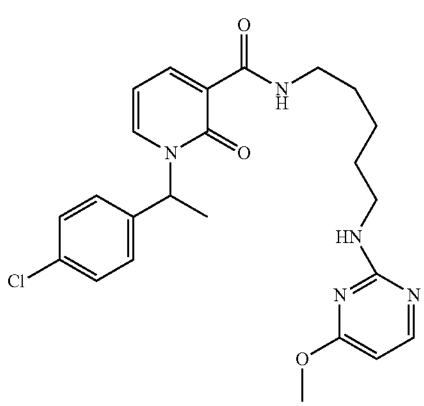 [SMILES: COc1ccnc(NCCCCCNC(=O)c2cccn(C(C)c3ccc(Cl)cc3)c2=O)n1] | | | ++ | +++ |

TABLE 2-continued
| Cpd No. | Structure | Inhibition of phospo- PDK1 in vitro | Inhibition of dephospo- PDK1 in vitro | Inhibition of P308 Akt in cells using MSD | Reduction of Cellular Levels of Akt p308 By Western |
|---|---|---|---|---|---|
| 106 | 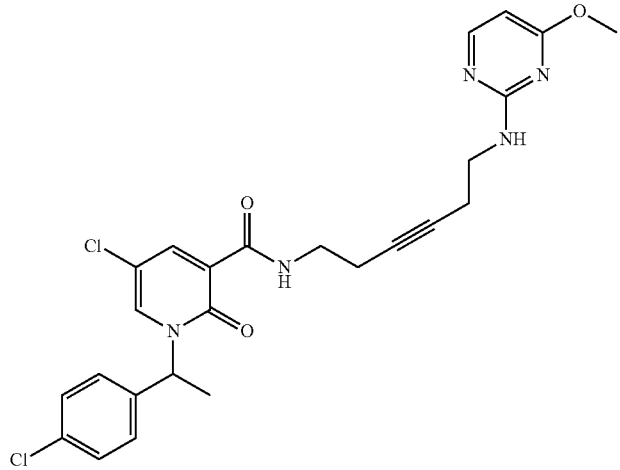 [SMILES: COc1ccnc(NCCC#CCCNC(=O)c2cc(Cl)cn(C(C)c3ccc(Cl)cc3)c2=O)n1] | +++ | +++ | | |
| 107 | 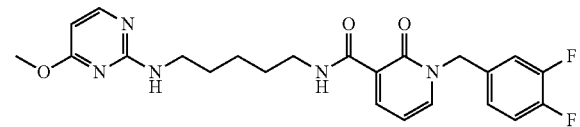 [SMILES: COc1ccnc(NCCCCCNC(=O)c2cccn(Cc3ccc(F)c(F)c3)c2=O)n1] | ++ | +++ | | |
| 108 | 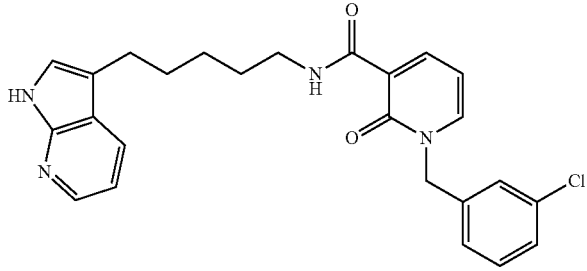 [SMILES: O=C(NCCCCCc1c[nH]c2ncccc12)c1cccn(Cc2cccc(Cl)c2)c1=O] | ++ | ++ | | |
| 109 | 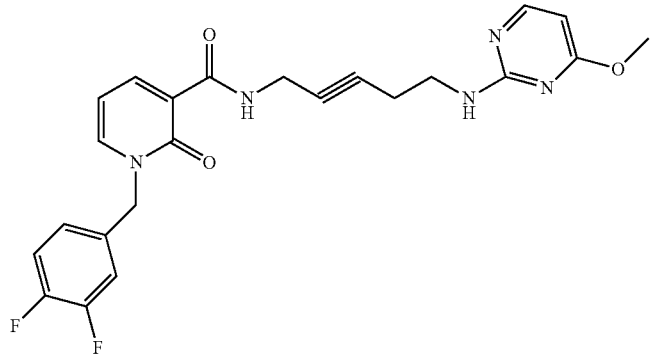 [SMILES: COc1ccnc(NCCC#CCNC(=O)c2cccn(Cc3ccc(F)c(F)c3)c2=O)n1] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 110 | 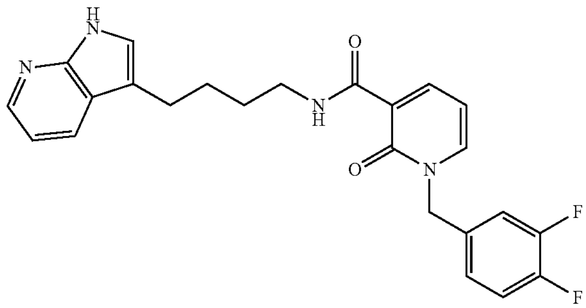 [SMILES: O=C(NCCCCc1c[nH]c2ncccc12)c1cccn(Cc2ccc(F)c(F)c2)c1=O] | +++ | +++ | | |
| 111 | 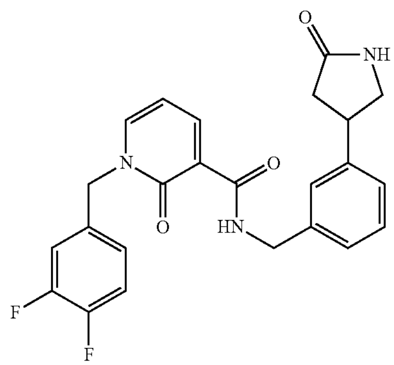 [SMILES: O=C1CC(c2cccc(CNC(=O)c3cccn(Cc4ccc(F)c(F)c4)c3=O)c2)CN1] | ++ | ++ | | |
| 112 | 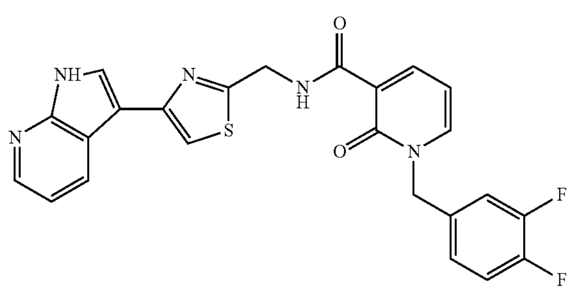 [SMILES: O=C(NCc1nc(-c2c[nH]c3ncccc23)cs1)c1cccn(Cc2ccc(F)c(F)c2)c1=O] | +++ | +++ | aaa | |
| 113 | 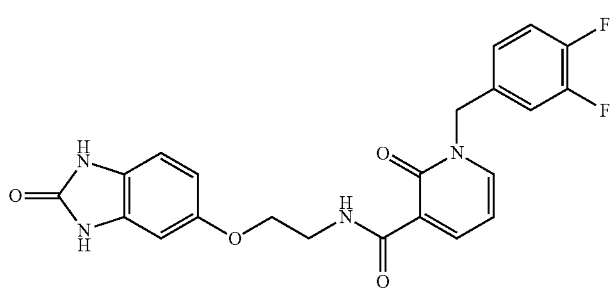 | +++ | +++ | a | |
| 114 | 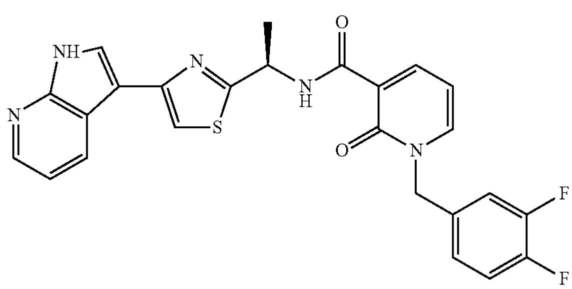 [SMILES: C[C@@H](NC(=O)c1cccn(Cc2ccc(F)c(F)c2)c1=O)c1nc(-c2c[nH]c3ncccc23)cs1] | +++ | +++ | | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 115 | 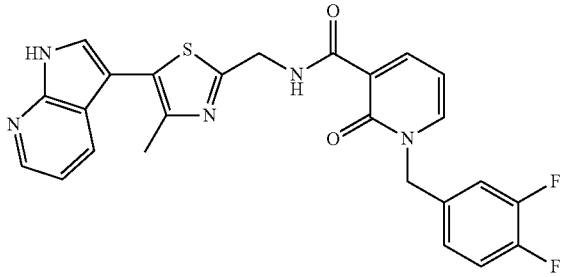 [SMILES: Cc1nc(CNC(=O)c2cccn(Cc3ccc(F)c(F)c3)c2=O)sc1-c1c[nH]c2ncccc12] | ++ | +++ | | |
| 116 | 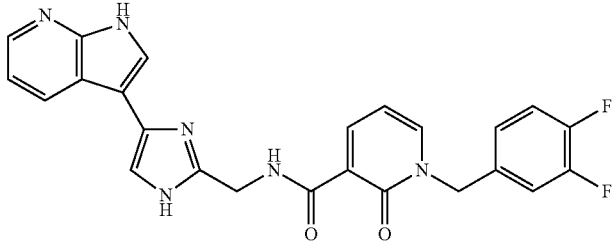 [SMILES: O=C(NCc1nc(-c2c[nH]c3ncccc23)c[nH]1)c1cccn(Cc2ccc(F)c(F)c2)c1=O] | ++ | +++ | | |
| 117 | 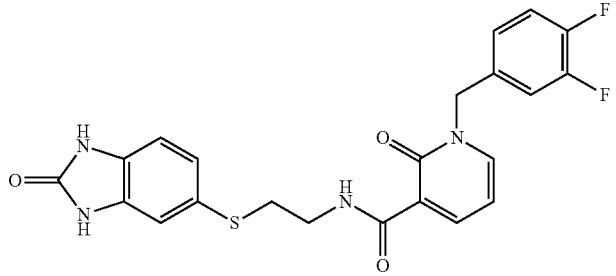 [SMILES: O=C(NCCSc1ccc2[nH]c(=O)[nH]c2c1)c1cccn(Cc2ccc(F)c(F)c2)c1=O] | ++ | ++ | | |
| 118 | 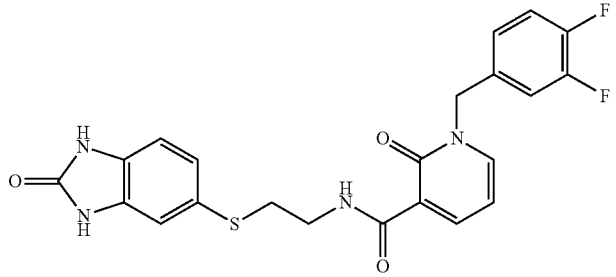 | ++ | +++ | | |
| 119 | 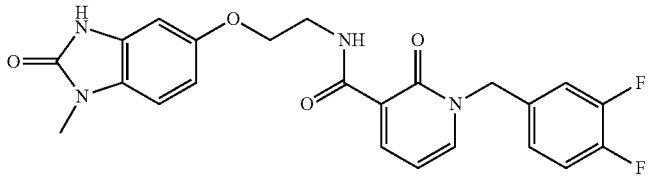 [SMILES: Cn1c(=O)[nH]c2cc(OCCNC(=O)c3cccn(Cc4ccc(F)c(F)c4)c3=O)ccc21] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 120 | 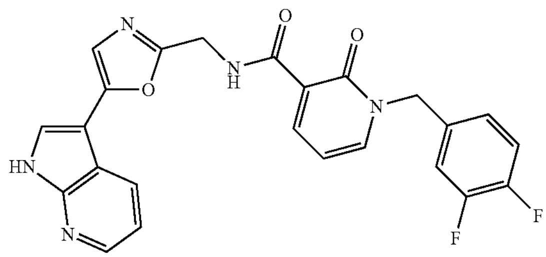 [SMILES: O=C(NCc1ncc(-c2c[nH]c3ncccc23)o1)c1cccn(Cc2ccc(F)c(F)c2)c1=O] | +++ | +++ | | |
| 121 | 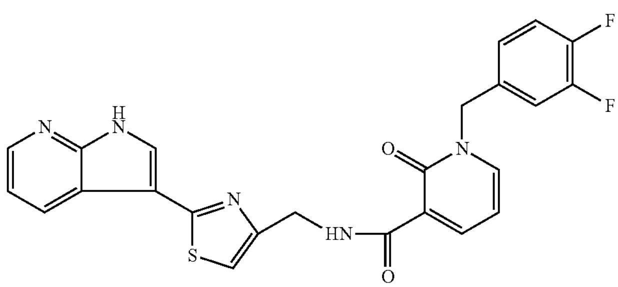 [SMILES: O=C(NCc1csc(-c2c[nH]c3ncccc23)n1)c1cccn(Cc2ccc(F)c(F)c2)c1=O] | +++ | +++ | aaa | |
| 122 | 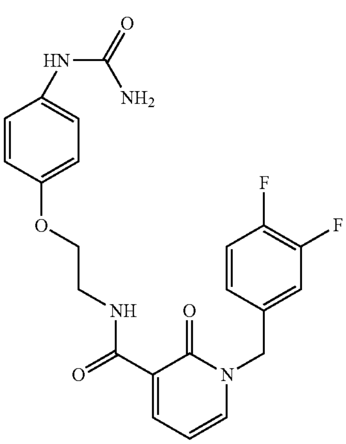 [SMILES: NC(=O)Nc1ccc(OCCNC(=O)c2cccn(Cc3ccc(F)c(F)c3)c2=O)cc1] | ++ | +++ | | |
| 123 | 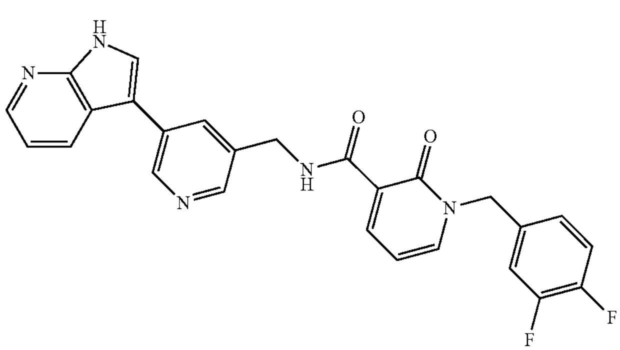 [SMILES: O=C(NCc1cncc(-c2c[nH]c3ncccc23)c1)c1cccn(Cc2ccc(F)c(F)c2)c1=O] | +++ | | aaa | |

TABLE 2-continued

| Cpd No. | Structure | Inhibition of phospo- PDK1 in vitro | Inhibition of dephospo- PDK1 in vitro | Inhibition of P308 Akt in cells using MSD | Reduction of Cellular Levels of Akt p308 By Western |
|---|---|---|---|---|---|
| 124 | 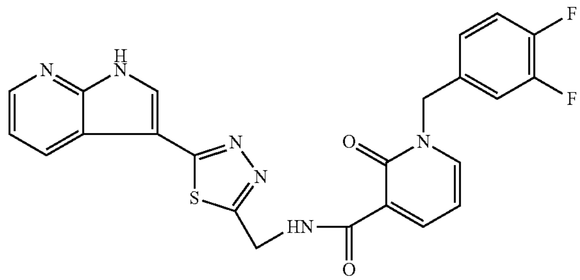 [SMILES: O=C(NCc1nnc(-c2c[nH]c3ncccc23)s1)c1cccn(Cc2ccc(F)c(F)c2)c1=O] | +++ | +++ | | |
| 125 | 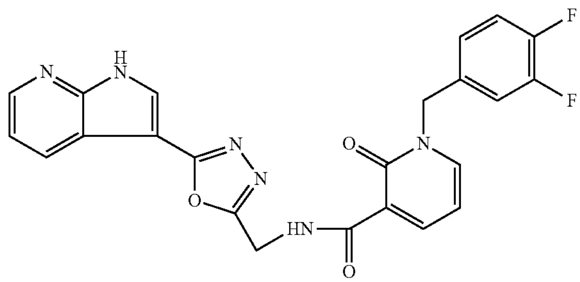 | +++ | +++ | aa | |
| 126 | 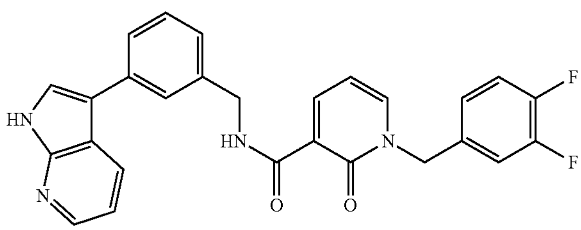 [SMILES: O=C(NCc1cccc(-c2c[nH]c3ncccc23)c1)c1cccn(Cc2ccc(F)c(F)c2)c1=O] | +++ | | aa | |
| 127 | 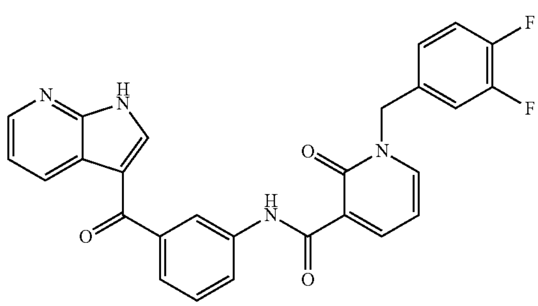 [SMILES: O=C(Nc1cccc(C(=O)c2c[nH]c3ncccc23)c1)c1cccn(Cc2ccc(F)c(F)c2)c1=O] | +++ | | | |
| 128 | 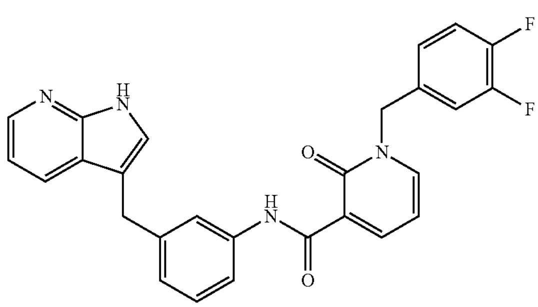 [SMILES: O=C(Nc1cccc(Cc2c[nH]c3ncccc23)c1)c1cccn(Cc2ccc(F)c(F)c2)c1=O] | ++ | +++ | a | |

TABLE 2-continued

| Cpd No. | Structure | Inhibition of phospho-PDK1 in vitro | Inhibition of dephospho-PDK1 in vitro | Inhibition of P308 Akt in cells using MSD | Reduction of Cellular Levels of Akt p308 By Western |
|---|---|---|---|---|---|
| 129 | 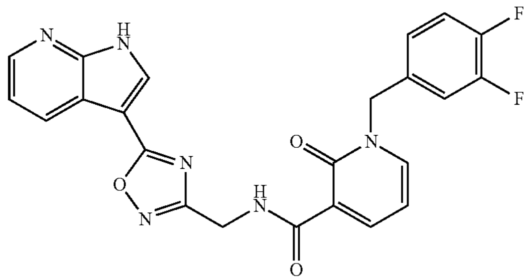 [SMILES: O=C(NCc1noc(-c2c[nH]c3ncccc23)n1)c1cccn(Cc2ccc(F)c(F)c2)c1=O] | +++ | +++ | | |
| 130 | 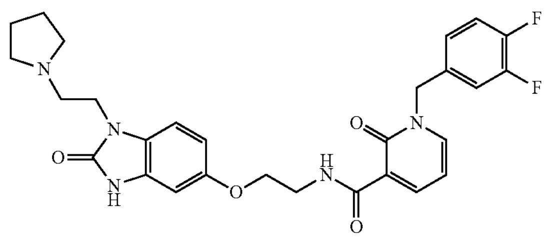 [SMILES: O=C(NCCOc1ccc2c(c1)[nH]c(=O)n2CCN1CCCC1)c1cccn(Cc2ccc(F)c(F)c2)c1=O] | ++ | ++ | | |
| 131 | 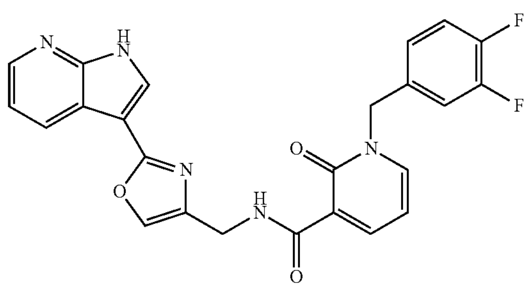 [SMILES: O=C(NCc1coc(-c2c[nH]c3ncccc23)n1)c1cccn(Cc2ccc(F)c(F)c2)c1=O] | +++ | +++ | aa | |
| 132 | 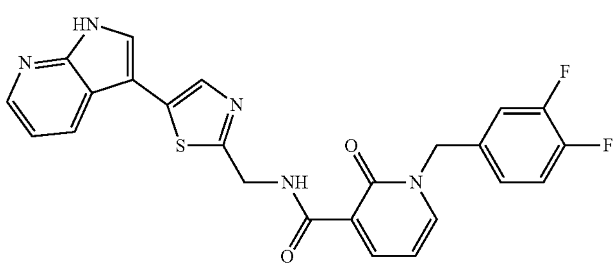 [SMILES: O=C(NCc1ncc(-c2c[nH]c3ncccc23)s1)c1cccn(Cc2ccc(F)c(F)c2)c1=O] | +++ | | aaa | bbb |
| 133 | 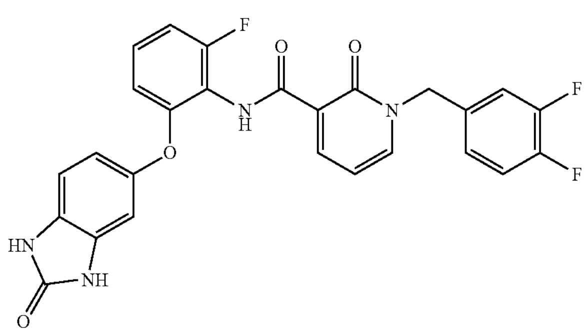 [SMILES: O=C(Nc1c(F)cccc1Oc1ccc2[nH]c(=O)[nH]c2c1)c1cccn(Cc2ccc(F)c(F)c2)c1=O] | +++ | +++ | | bbb |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 134 | 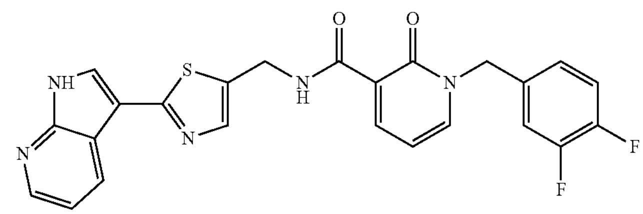 [SMILES: O=C(NCc1cnc(-c2c[nH]c3ncccc23)s1)c1cccn(Cc2ccc(F)c(F)c2)c1=O] | +++ | +++ | | bbb |
| 135 | 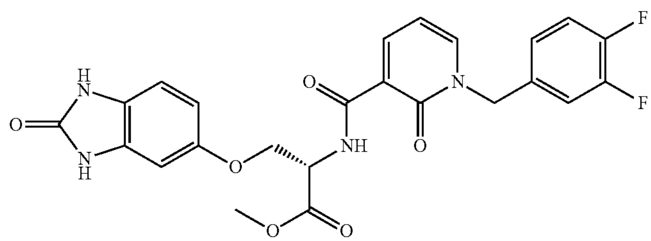 [SMILES: COC(=O)[C@H](COc1ccc2[nH]c(=O)[nH]c2c1)NC(=O)c1cccn(Cc2ccc(F)c(F)c2)c1=O] | +++ | +++ | aa | bbb |
| 136 | 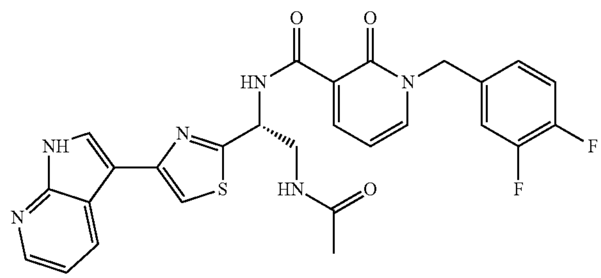 [SMILES: CC(=O)NC[C@@H](NC(=O)c1cccn(Cc2ccc(F)c(F)c2)c1=O)c1nc(-c2c[nH]c3ncccc23)cs1] | +++ | +++ | | bb |
| 137 | 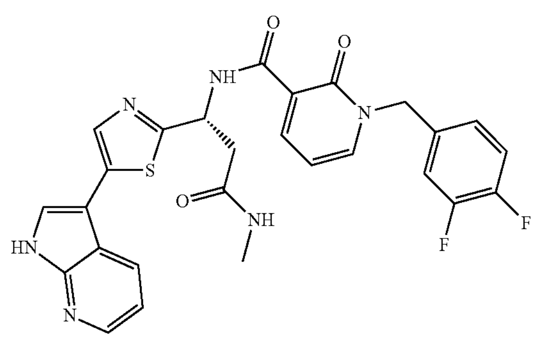 [SMILES: CNC(=O)C[C@@H](NC(=O)c1cccn(Cc2ccc(F)c(F)c2)c1=O)c1ncc(-c2c[nH]c3ncccc23)s1] | +++ | +++ | a | bbb |
| 138 | 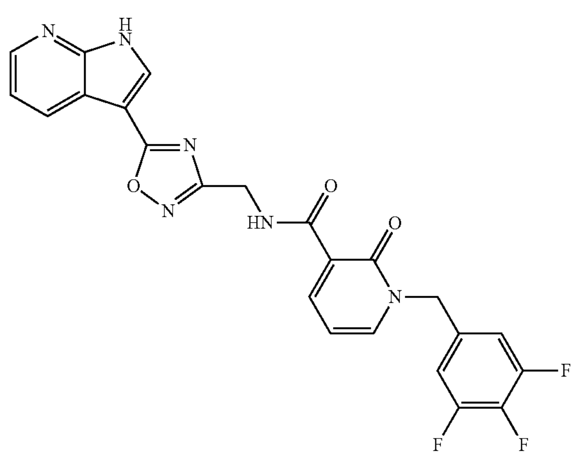 [SMILES: O=C(NCc1noc(-c2c[nH]c3ncccc23)n1)c1cccn(Cc2cc(F)c(F)c(F)c2)c1=O] | +++ | +++ | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 139 | 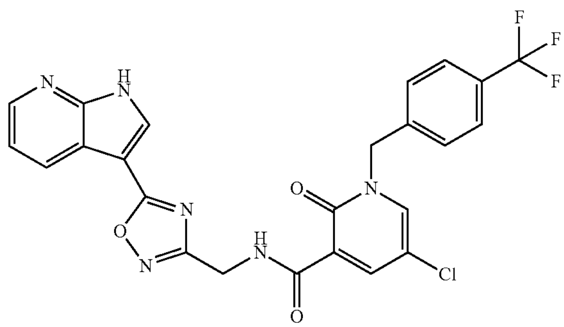 [SMILES: O=C(NCc1noc(-c2c[nH]c3ncccc23)n1)c1cc(Cl)cn(Cc2ccc(C(F)(F)F)cc2)c1=O] | +++ | +++ | | |
| 140 | 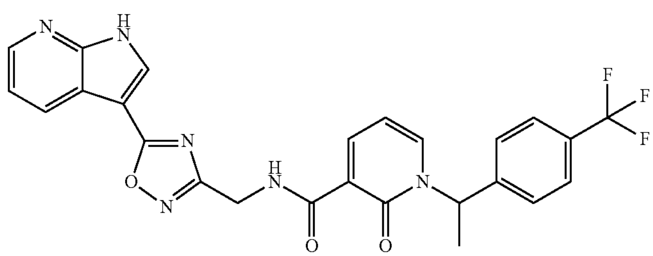 [SMILES: CC(c1ccc(C(F)(F)F)cc1)n1cccc(C(=O)NCc2noc(-c3c[nH]c4ncccc34)n2)c1=O] | +++ | +++ | aa | |
| 141 | 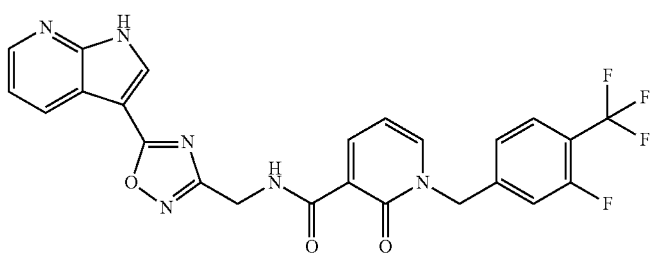 [SMILES: O=C(NCc1noc(-c2c[nH]c3ncccc23)n1)c1cccn(Cc2ccc(C(F)(F)F)c(F)c2)c1=O] | +++ | +++ | aa | |
| 142 | 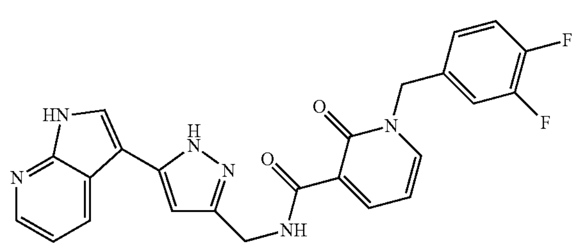 [SMILES: O=C(NCc1cc(-c2c[nH]c3ncccc23)[nH]n1)c1cccn(Cc2ccc(F)c(F)c2)c1=O] | +++ | +++ | | |
| 143 | 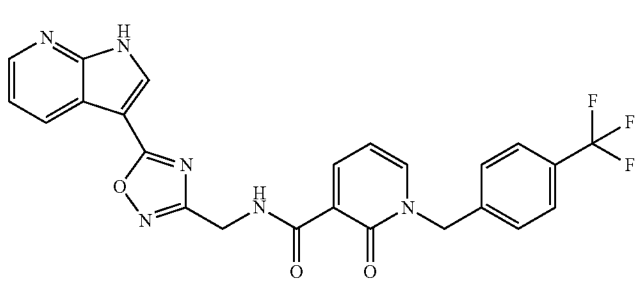 [SMILES: O=C(NCc1noc(-c2c[nH]c3ncccc23)n1)c1cccn(Cc2ccc(C(F)(F)F)cc2)c1=O] | +++ | +++ | a | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 144 | 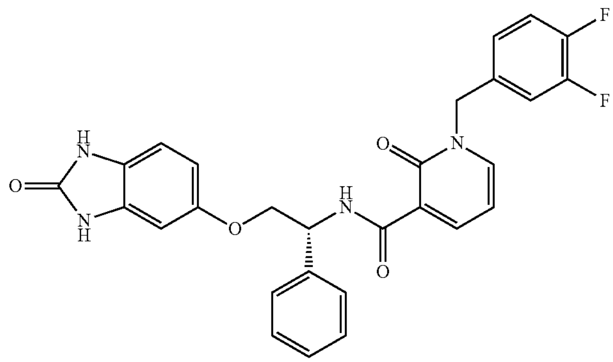 [SMILES: O=C(N[C@@H](COc1ccc2[nH]c(=O)[nH]c2c1)c1ccccc1)c1cccn(Cc2ccc(F)c(F)c2)c1=O] | +++ | | aaa | bbb |
| 145 | 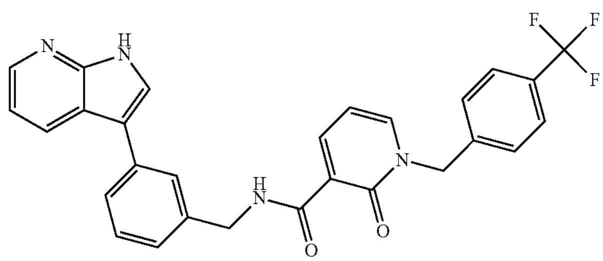 [SMILES: O=C(NCc1cccc(-c2c[nH]c3ncccc23)c1)c1cccn(Cc2ccc(C(F)(F)F)cc2)c1=O] | +++ | +++ | a | |
| 146 | 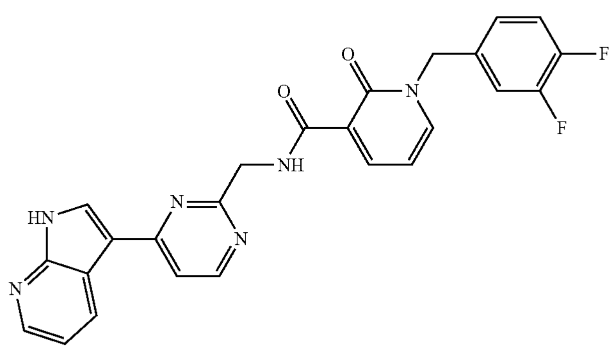 [SMILES: O=C(NCc1nccc(-c2c[nH]c3ncccc23)n1)c1cccn(Cc2ccc(F)c(F)c2)c1=O] | +++ | | a | |
| 147 | 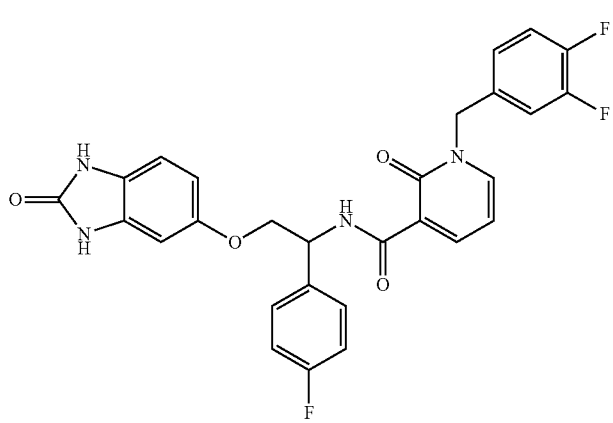 [SMILES: O=C(NC(COc1ccc2[nH]c(=O)[nH]c2c1)c1ccc(F)cc1)c1cccn(Cc2ccc(F)c(F)c2)c1=O] | +++ | | aaa | |

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 148 | 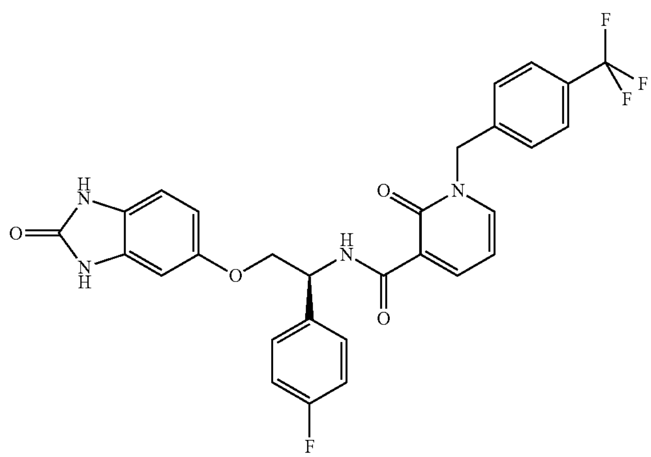 [SMILES: O=C(N[C@H](COc1ccc2[nH]c(=O)[nH]c2c1)c1ccc(F)cc1)c1cccn(Cc2ccc(C(F)(F)F)cc2)c1=O] | +++ | +++ | aa | |
| 149 | 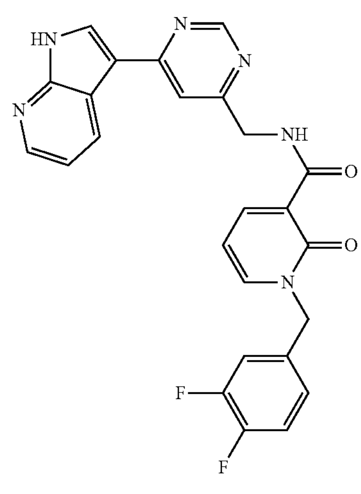 [SMILES: O=C(NCc1cc(-c2c[nH]c3ncccc23)ncn1)c1cccn(Cc2ccc(F)c(F)c2)c1=O] | | +++ | | |
| 150 | 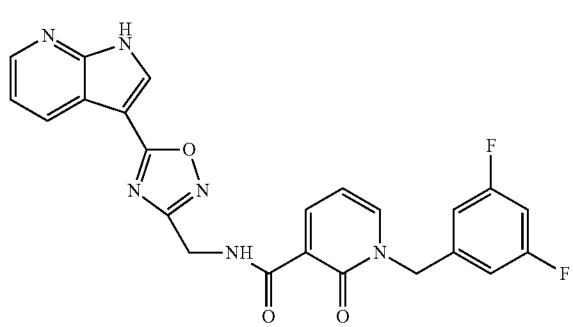 [SMILES: O=C(NCc1noc(-c2c[nH]c3ncccc23)n1)c1cccn(Cc2cc(F)cc(F)c2)c1=O] | +++ | +++ | a | |

TABLE 2-continued

| Cpd No. | Structure | Inhibition of phospho-PDK1 in vitro | Inhibition of dephospho-PDK1 in vitro | Inhibition of P308 Akt in cells using MSD | Reduction of Cellular Levels of Akt p308 By Western |
|---|---|---|---|---|---|
| 151 | 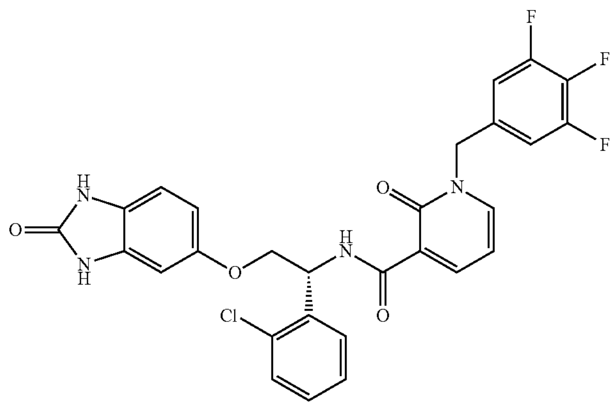 [SMILES: O=C(N[C@@H](COc1ccc2[nH]c(=O)[nH]c2c1)c1ccccc1Cl)c1cccn(Cc2cc(F)c(F)c(F)c2)c1=O] | +++ | | aaa | |
| 152 | 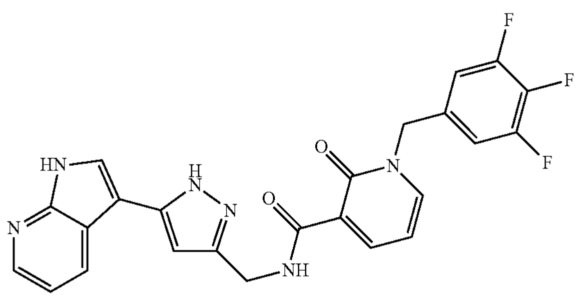 [SMILES: O=C(NCc1cc(-c2c[nH]c3ncccc23)[nH]n1)c1cccn(Cc2cc(F)c(F)c(F)c2)c1=O] | +++ | +++ | aa | |
| 153 | 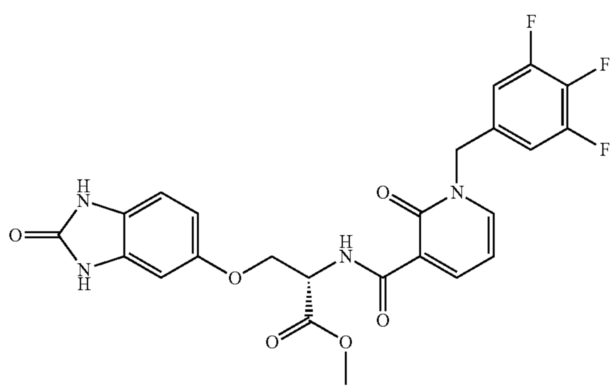 [SMILES: COC(=O)[C@H](COc1ccc2[nH]c(=O)[nH]c2c1)NC(=O)c1cccn(Cc2cc(F)c(F)c(F)c2)c1=O] | +++ | | aaa | |
| 154 | 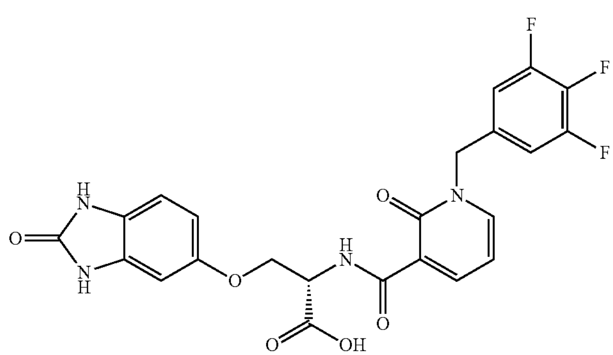 [SMILES: O=C(N[C@@H](COc1ccc2[nH]c(=O)[nH]c2c1)C(=O)O)c1cccn(Cc2cc(F)c(F)c(F)c2)c1=O] | +++ | | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 155 | 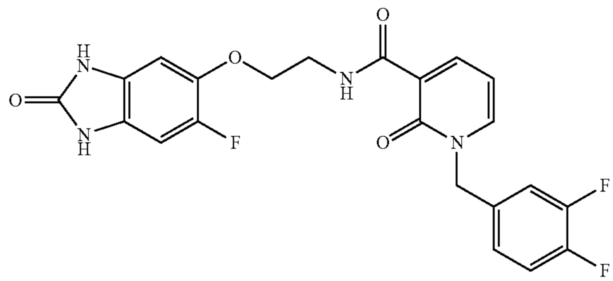 [SMILES: O=C(NCCOc1cc2[nH]c(=O)[nH]c2cc1F)c1cccn(Cc2ccc(F)c(F)c2)c1=O] | ++ | +++ | | |
| 156 | 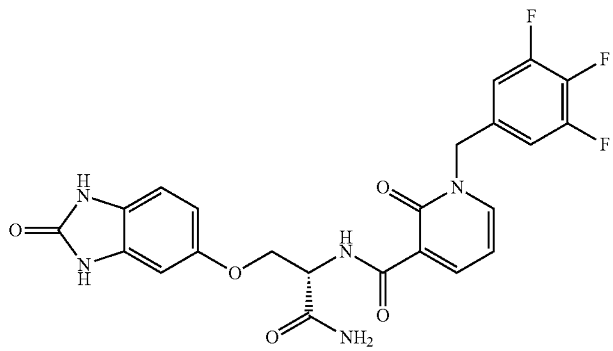 [SMILES: NC(=O)[C@H](COc1ccc2[nH]c(=O)[nH]c2c1)NC(=O)c1cccn(Cc2cc(F)c(F)c(F)c2)c1=O] | | +++ | | |
| 157 | 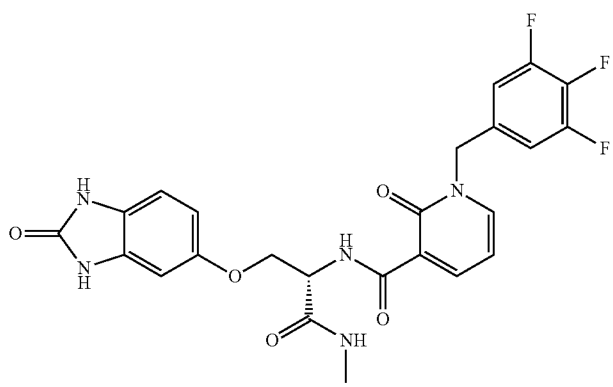 [SMILES: CNC(=O)[C@H](COc1ccc2[nH]c(=O)[nH]c2c1)NC(=O)c1cccn(Cc2cc(F)c(F)c(F)c2)c1=O] | +++ | +++ | | |
| 158 | 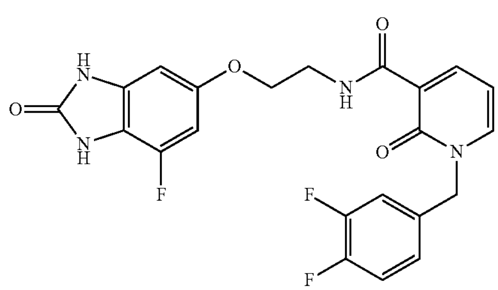 [SMILES: O=C(NCCOc1cc(F)c2[nH]c(=O)[nH]c2c1)c1cccn(Cc2ccc(F)c(F)c2)c1=O] | ++ | +++ | | |

TABLE 2-continued
| Cpd No. | Structure | Inhibition of phospho-PDK1 in vitro | Inhibition of dephospho-PDK1 in vitro | Inhibition of P308 Akt in cells using MSD | Reduction of Cellular Levels of Akt p308 By Western |
|---|---|---|---|---|---|
| 159 | 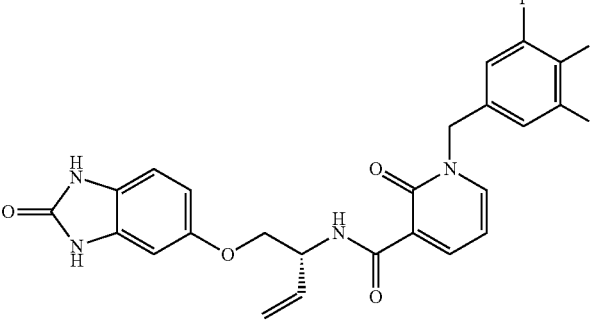 | +++ | | aa | |
| 160 | 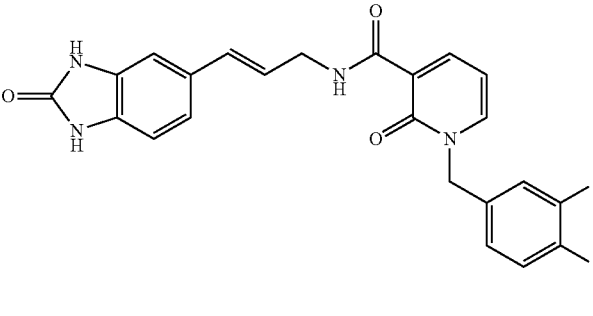 | +++ | | a | |
| 161 | 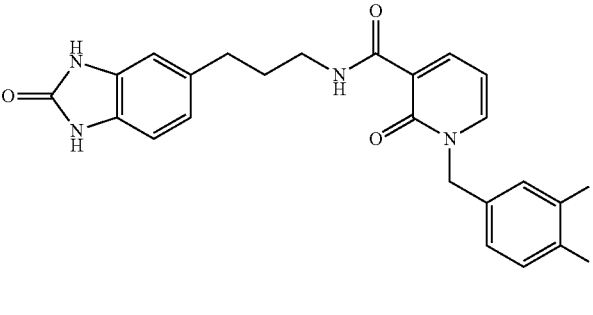 | +++ | | | |
| 162 | 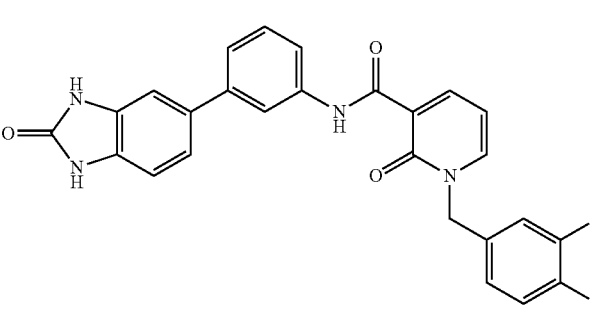 | ++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 163 | 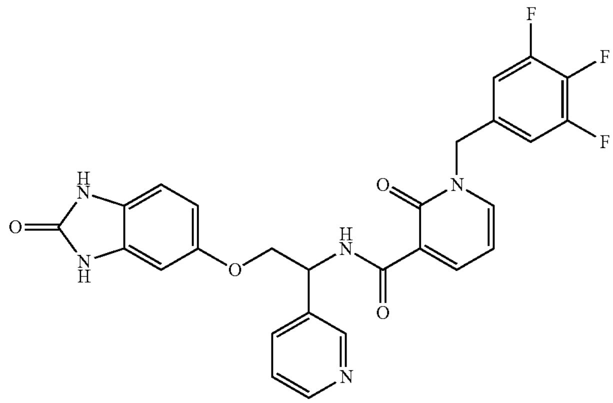 [SMILES: O=C(NC(COc1ccc2[nH]c(=O)[nH]c2c1)c1cccnc1)c1cccn(Cc2cc(F)c(F)c(F)c2)c1=O] | +++ | | | aa |
| 164 | 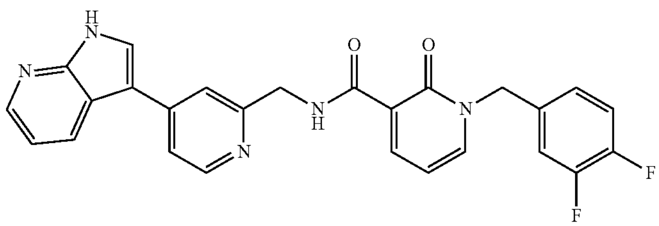 [SMILES: O=C(NCc1cc(-c2c[nH]c3ncccc23)ccn1)c1cccn(Cc2ccc(F)c(F)c2)c1=O] | +++ | | | aaa |
| 165 | 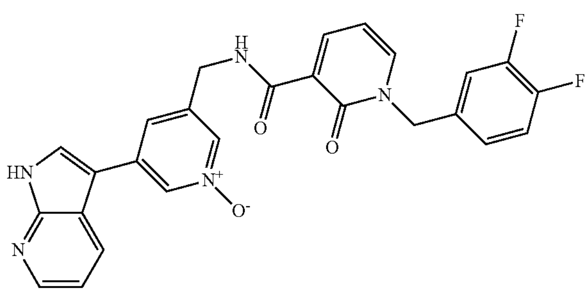 [SMILES: O=C(NCc1cc(-c2c[nH]c3ncccc23)c[n+]([O-])c1)c1cccn(Cc2ccc(F)c(F)c2)c1=O] | +++ | | | a |
| 166 | 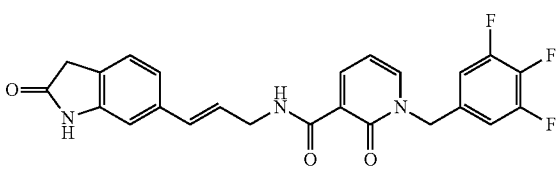 [SMILES: O=C1Cc2ccc(/C=C/CNC(=O)c3cccn(Cc4cc(F)c(F)c(F)c4)c3=O)cc2N1] | +++ | +++ | | a |
| 167 | 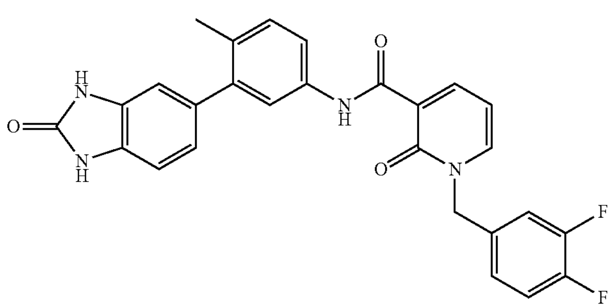 [SMILES: Cc1ccc(NC(=O)c2cccn(Cc3ccc(F)c(F)c3)c2=O)cc1-c1ccc2[nH]c(=O)[nH]c2c1] | ++ | ++ | | a |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 168 | 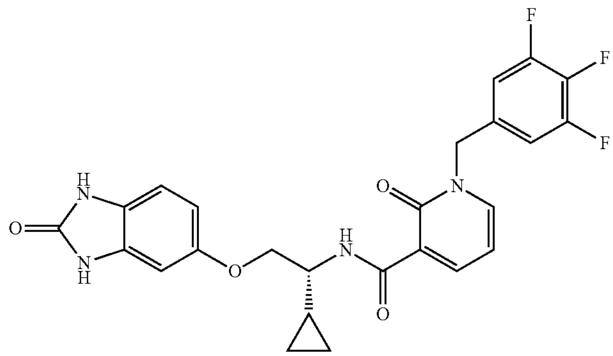 [SMILES: O=C(N[C@@H](COc1ccc2[nH]c(=O)[nH]c2c1)C1CC1)c1cccn(Cc2cc(F)c(F)c(F)c2)c1=O] | +++ | +++ | aa | |
| 169 | 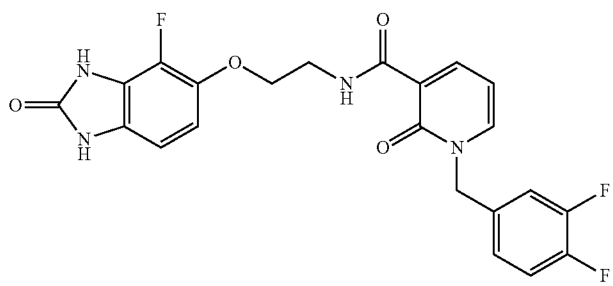 [SMILES: O=C(NCCOc1ccc2[nH]c(=O)[nH]c2c1F)c1cccn(Cc2ccc(F)c(F)c2)c1=O] | +++ | | aa | |
| 170 | 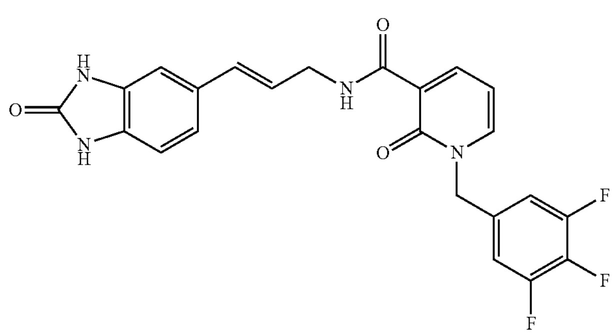 [SMILES: O=C(NC/C=C/c1ccc2[nH]c(=O)[nH]c2c1)c1cccn(Cc2cc(F)c(F)c(F)c2)c1=O] | +++ | | aa | |
| 171 | 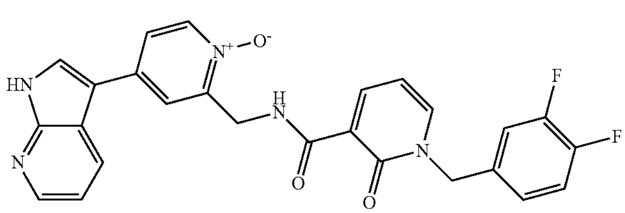 [SMILES: O=C(NCc1cc(-c2c[nH]c3ncccc23)cc[n+]1[O-])c1cccn(Cc2ccc(F)c(F)c2)c1=O] | +++ | | | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 172 | 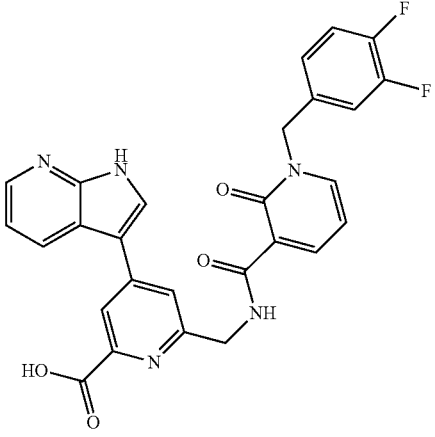 [SMILES: O=C(O)c1cc(-c2c[nH]c3ncccc23)cc(CNC(=O)c2cccn(Cc3ccc(F)c(F)c3)c2=O)n1] | +++ | | a | |
| 173 | 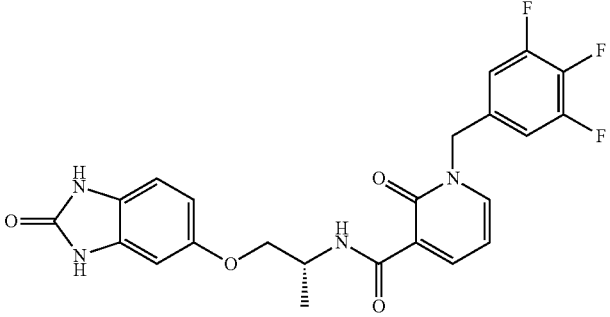 [SMILES: C[C@H](COc1ccc2[nH]c(=O)[nH]c2c1)NC(=O)c1cccn(Cc2cc(F)c(F)c(F)c2)c1=O] | +++ | +++ | aa | |
| 174 | 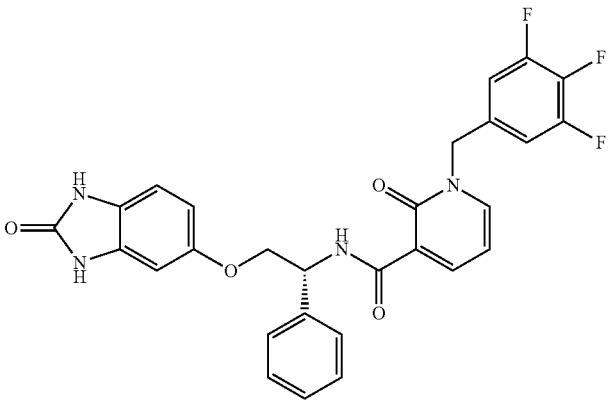 [SMILES: O=C(N[C@@H](COc1ccc2[nH]c(=O)[nH]c2c1)c1ccccc1)c1cccn(Cc2cc(F)c(F)c(F)c2)c1=O] | +++ | | aa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 175 | 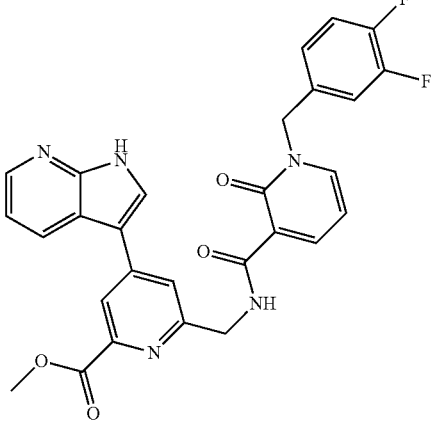 | +++ | +++ | aaa | |
| 176 | 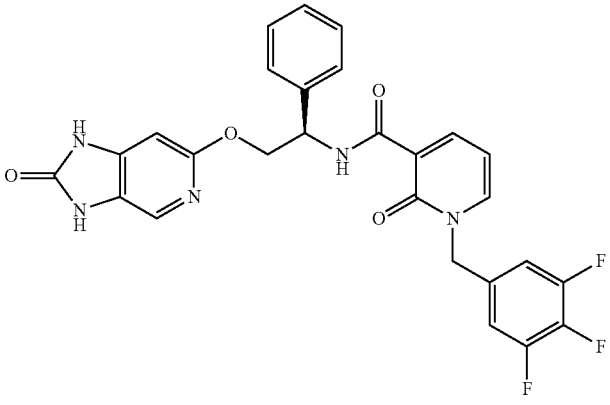 [SMILES: O=C(N[C@@H](COc1cc2[nH]c(=O)[nH]c2cn1)c1ccccc1)c1cccn(Cc2cc(F)c(F)c(F)c2)c1=O] | | +++ | | |
| 177 | 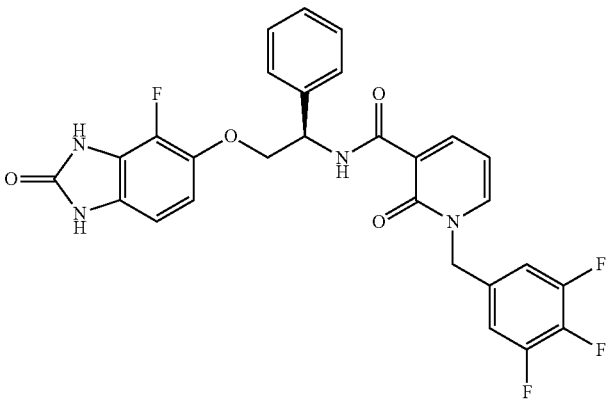 [SMILES: O=C(N[C@@H](COc1ccc2[nH]c(=O)[nH]c2c1F)c1ccccc1)c1cccn(Cc2cc(F)c(F)c(F)c2)c1=O] | | +++ | aaa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 178 | 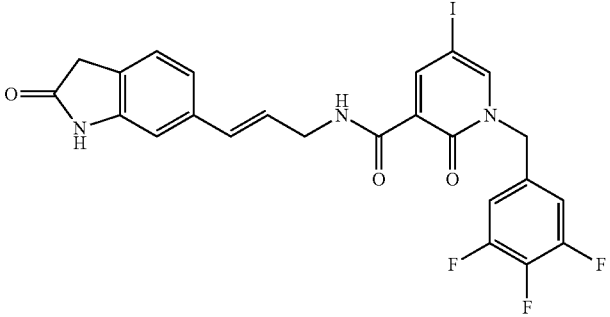 [SMILES: O=C1Cc2ccc(/C=C/CNC(=O)c3cc(I)cn(Cc4cc(F)c(F)c(F)c4)c3=O)cc2N1] | +++ | +++ | | |
| 179 | 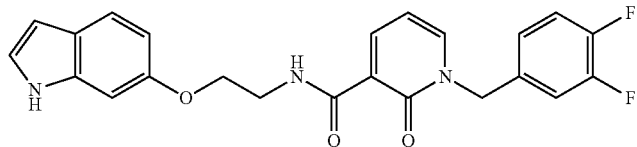 [SMILES: O=C(NCCOc1ccc2cc[nH]c2c1)c1cccn(Cc2ccc(F)c(F)c2)c1=O] | ++ | ++ | a | |
| 180 | 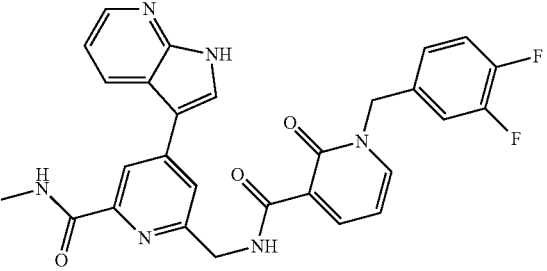 [SMILES: CNC(=O)c1cc(-c2c[nH]c3ncccc23)cc(CNC(=O)c2cccn(Cc3ccc(F)c(F)c3)c2=O)n1] | +++ | | aaa | |
| 181 | 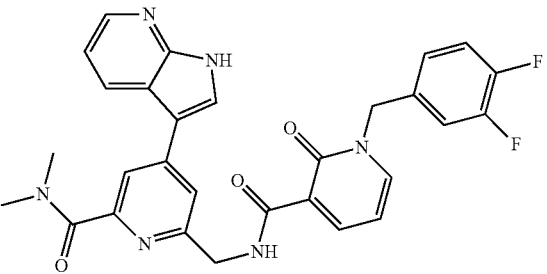 [SMILES: CN(C)C(=O)c1cc(-c2c[nH]c3ncccc23)cc(CNC(=O)c2cccn(Cc3ccc(F)c(F)c3)c2=O)n1] | +++ | | aa | |
| 182 | 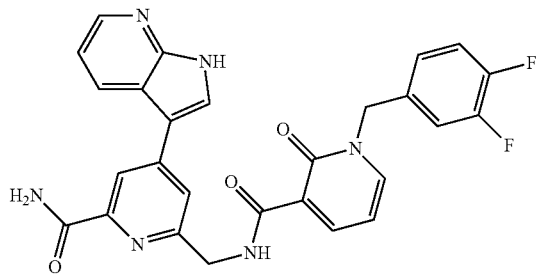 [SMILES: NC(=O)c1cc(-c2c[nH]c3ncccc23)cc(CNC(=O)c2cccn(Cc3ccc(F)c(F)c3)c2=O)n1] | +++ | | | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
| --- | --- | --- | --- | --- | --- |
| 183 | 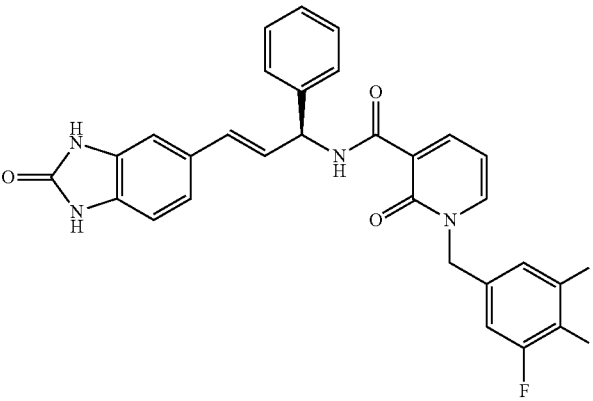 | | +++ | aa | |
| 184 | 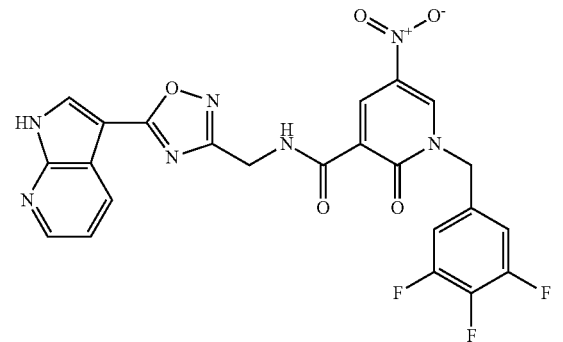 [SMILES: O=C(NCc1noc(-c2c[nH]c3ncccc23)n1)c1cc([N+](=O)[O-])cn(Cc2cc(F)c(F)c(F)c2)c1=O] | | +++ | aa | |
| 185 | 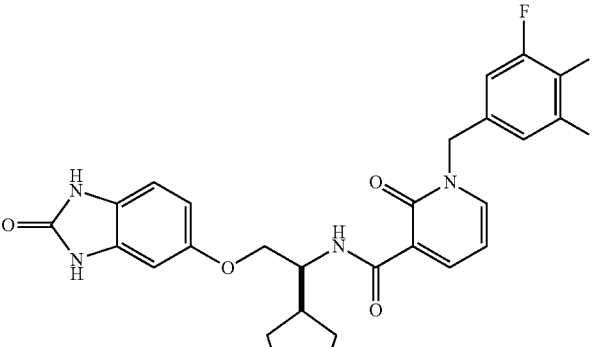 | | +++ | +++ | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 186 | 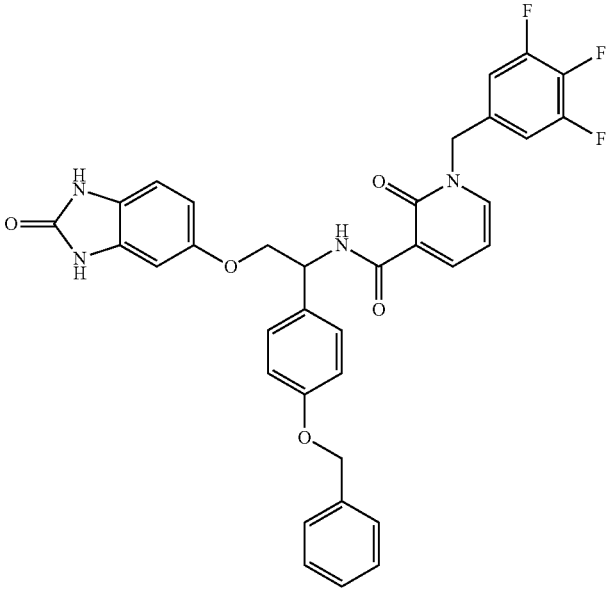 [SMILES: O=C(NC(COc1ccc2[nH]c(=O)[nH]c2c1)c1ccc(OCc2ccccc2)cc1)c1cccn(Cc2cc(F)c(F)c(F)c2)c1=O] | +++ | | a | |
| 187 | 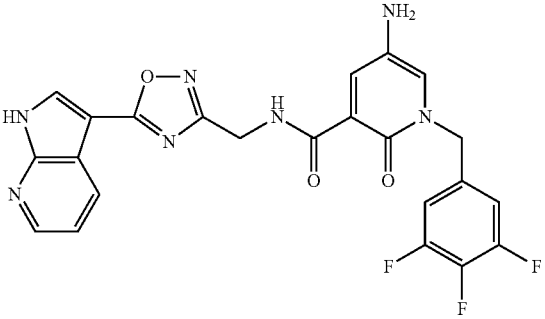 [SMILES: Nc1cc(C(=O)NCc2noc(-c3c[nH]c4ncccc34)n2)c(=O)n(Cc2cc(F)c(F)c(F)c2)c1] | +++ | +++ | a | |
| 188 | 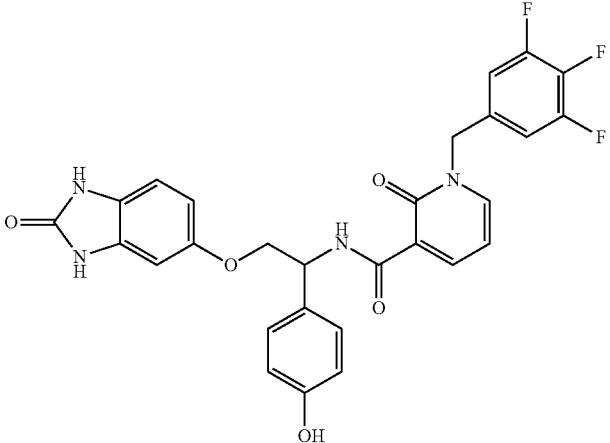 [SMILES: O=C(NC(COc1ccc2[nH]c(=O)[nH]c2c1)c1ccc(O)cc1)c1cccn(Cc2cc(F)c(F)c(F)c2)c1=O] | +++ | | aa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 189 | 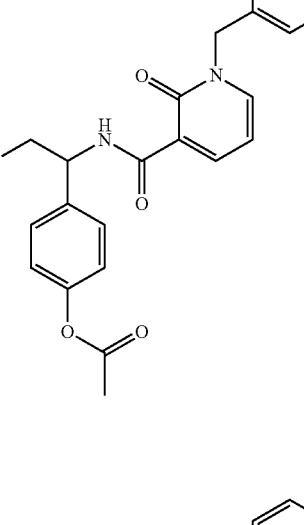 | +++ | | aaa | |
| 190 | 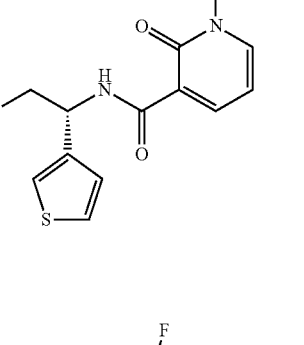 | +++ | | aaa | |
| 191 | 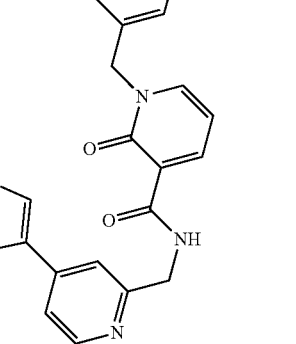 | +++ | | aaa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 192 | 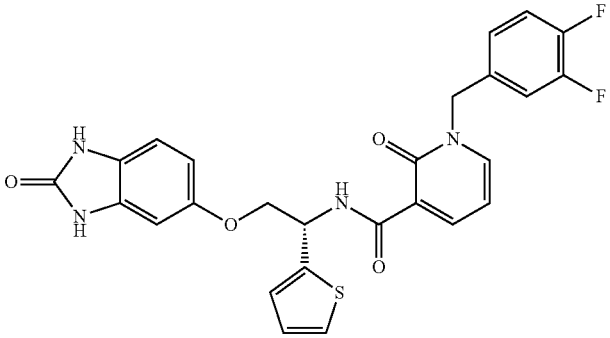 [SMILES: O=C(N[C@@H](COc1ccc2[nH]c(=O)[nH]c2c1)c1cccs1)c1cccn(Cc2ccc(F)c(F)c2)c1=O] | +++ | | aaa | |
| 193 | 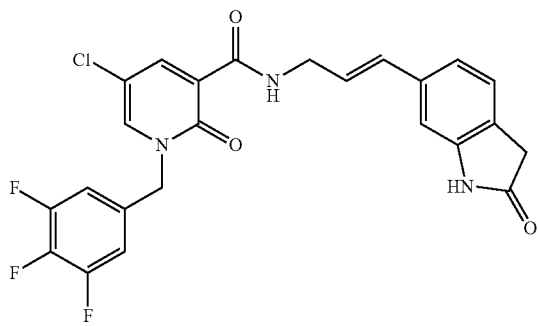 [SMILES: O=C1Cc2ccc(/C=C/CNC(=O)c3cc(Cl)cn(Cc4cc(F)c(F)c(F)c4)c3=O)cc2N1] | +++ | +++ | a | |
| 194 | 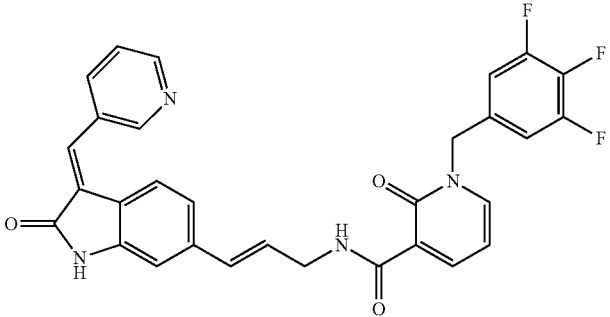 [SMILES: O=C1Nc2cc(/C=C/CNC(=O)c3cccn(Cc4cc(F)c(F)c(F)c4)c3=O)ccc2/C1=C\c1cccnc1] | +++ | | aaa | |
| 195 | 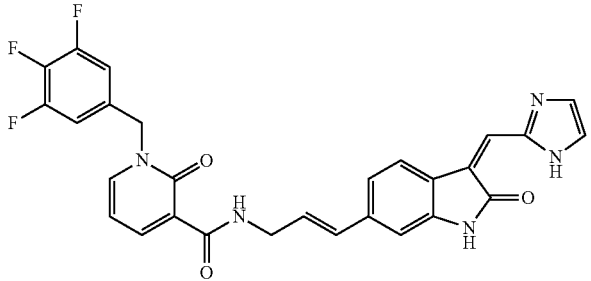 [SMILES: O=C1Nc2cc(/C=C/CNC(=O)c3cccn(Cc4cc(F)c(F)c(F)c4)c3=O)ccc2/C1=C/c1ncc[nH]1] | +++ | | aaa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 196 | 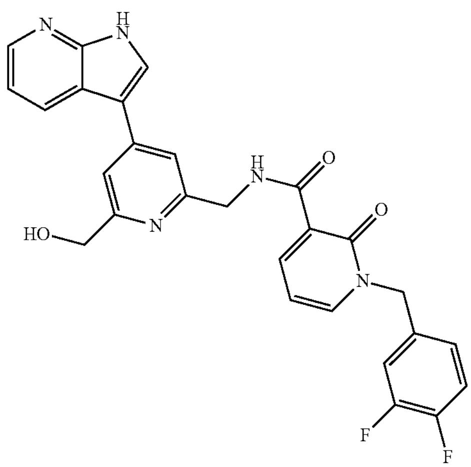 [SMILES: O=C(NCc1cc(-c2c[nH]c3ncccc23)cc(CO)n1)c1cccn(Cc2ccc(F)c(F)c2)c1=O] | | +++ | aa | |
| 197 | 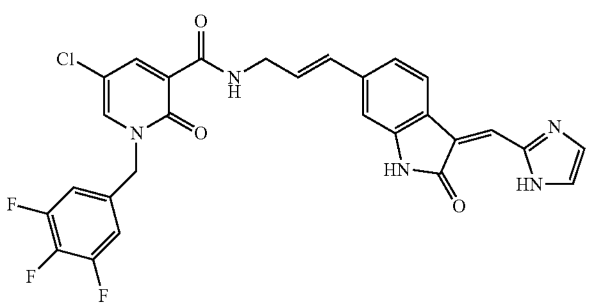 [SMILES: O=C1Nc2cc(/C=C/CNC(=O)c3cc(Cl)cn(Cc4cc(F)c(F)c(F)c4)c3=O)ccc2/C1=C/c1ncc[nH]1] | | +++ | aaa | |
| 198 | 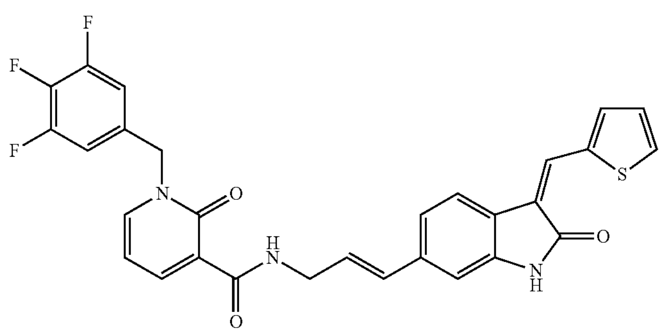 | | +++ | aa | |
| 199 | 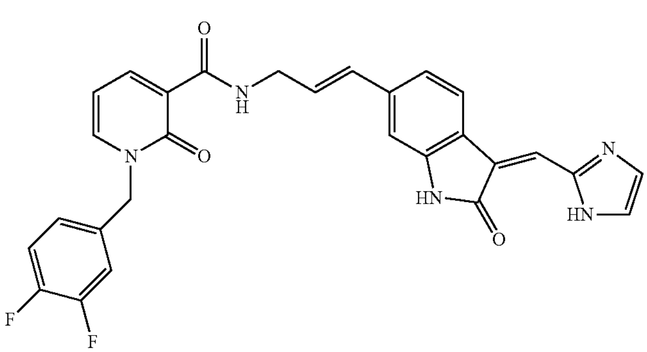 [SMILES: O=C1Nc2cc(/C=C/CNC(=O)c3cccn(Cc4ccc(F)c(F)c4)c3=O)ccc2/C1=C/c1ncc[nH]1] | | +++ | aaa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 200 | 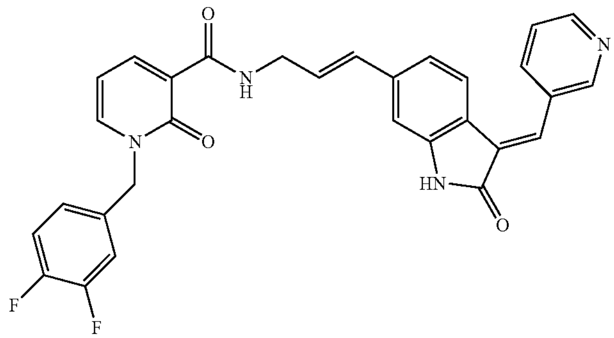 [SMILES: O=C1Nc2cc(/C=C/CNC(=O)c3cccn(Cc4ccc(F)c(F)c4)c3=O)ccc2/C1=C\c1cccnc1] | +++ | | aa | |
| 201 | 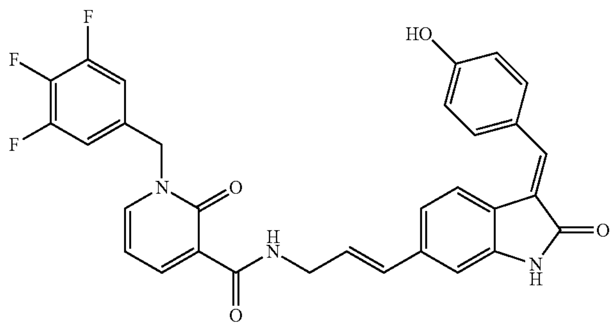 [SMILES: O=C1Nc2cc(/C=C/CNC(=O)c3cccn(Cc4cc(F)c(F)c(F)c4)c3=O)ccc2/C1=C\c1ccc(O)cc1] | +++ | | aaa | |
| 202 | 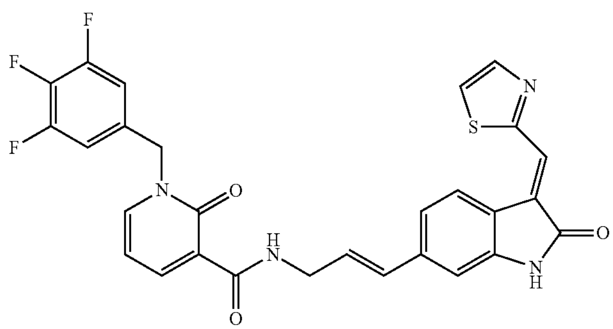 [SMILES: O=C1Nc2cc(/C=C/CNC(=O)c3cccn(Cc4cc(F)c(F)c(F)c4)c3=O)ccc2/C1=C\c1nccs1] | +++ | | aa | |
| 203 | 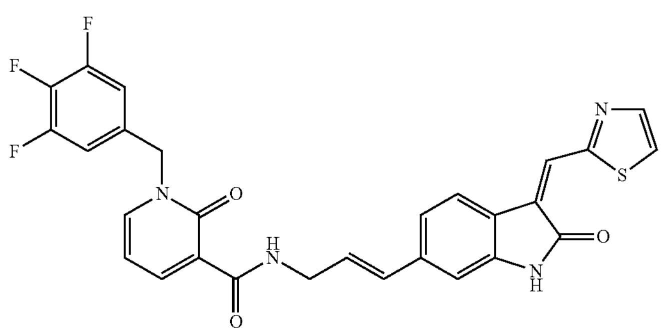 [SMILES: O=C1Nc2cc(/C=C/CNC(=O)c3cccn(Cc4cc(F)c(F)c(F)c4)c3=O)ccc2/C1=C/c1nccs1] | +++ | | aa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 204 | 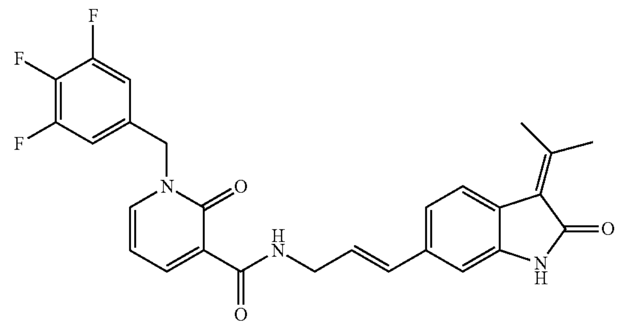 [SMILES: CC(C)=C1C(=O)Nc2cc(/C=C/CNC(=O)c3cccn(Cc4cc(F)c(F)c(F)c4)c3=O)ccc21] | +++ | | aa | |
| 205 | 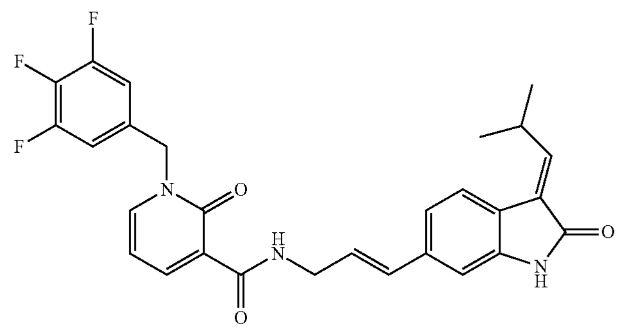 [SMILES: CC(C)/C=C1/C(=O)Nc2cc(/C=C/CNC(=O)c3cccn(Cc4cc(F)c(F)c(F)c4)c3=O)ccc21] | +++ | | a | |
| 206 | 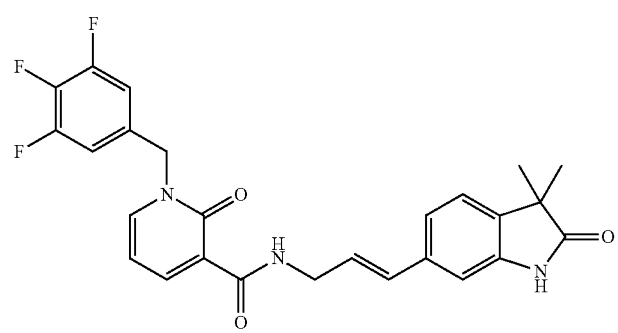 [SMILES: CC1(C)C(=O)Nc2cc(/C=C/CNC(=O)c3cccn(Cc4cc(F)c(F)c(F)c4)c3=O)ccc21] | ++ | +++ | aa | |
| 207 | 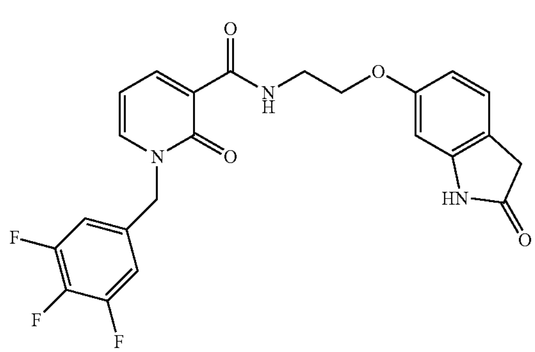 [SMILES: O=C1Cc2ccc(OCCNC(=O)c3cccn(Cc4cc(F)c(F)c(F)c4)c3=O)cc2N1] | +++ | | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 208 | 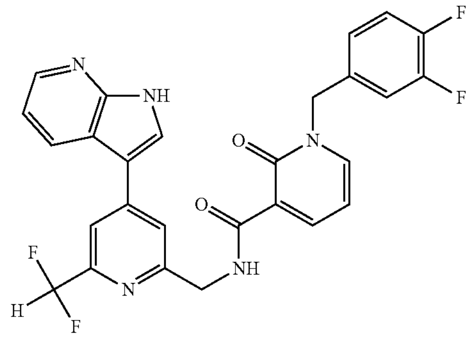 [SMILES: O=C(NCc1cc(-c2c[nH]c3ncccc23)cc(C(F)F)n1)c1cccn(Cc2ccc(F)c(F)c2)c1=O] | +++ | | aaa | |
| 209 | 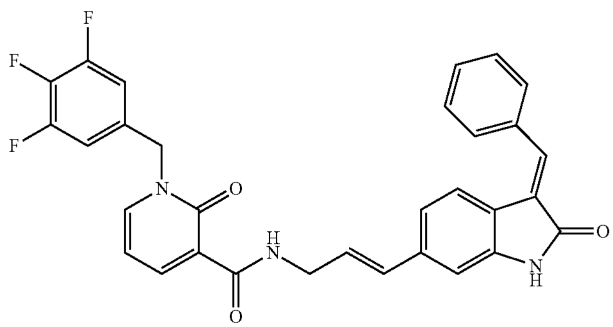 [SMILES: O=C1Nc2cc(/C=C/CNC(=O)c3cccn(Cc4cc(F)c(F)c(F)c4)c3=O)ccc2/C1=C\c1ccccc1] | +++ | | a | |
| 210 | 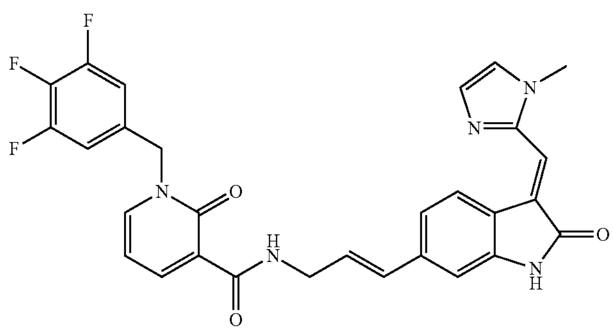 [SMILES: Cn1ccnc1/C=C1/C(=O)Nc2cc(/C=C/CNC(=O)c3cccn(Cc4cc(F)c(F)c(F)c4)c3=O)ccc21] | +++ | | | |
| 211 | 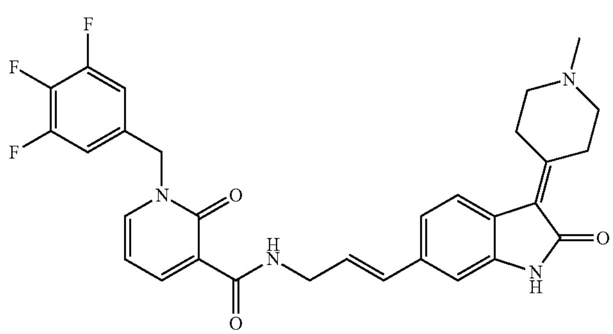 [SMILES: CN1CCC(=C2C(=O)Nc3cc(/C=C/CNC(=O)c4cccn(Cc5cc(F)c(F)c(F)c5)c4=O)ccc32)CC1] | +++ | | | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 212 | 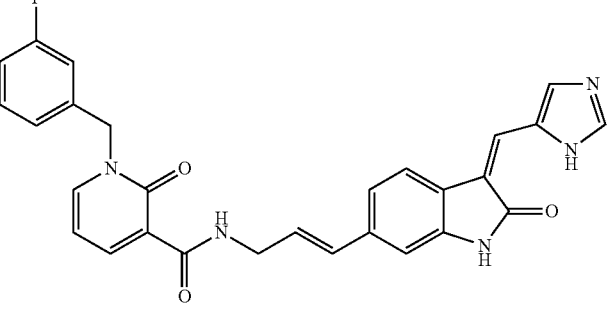 | | | +++ | aa |
| 213 | 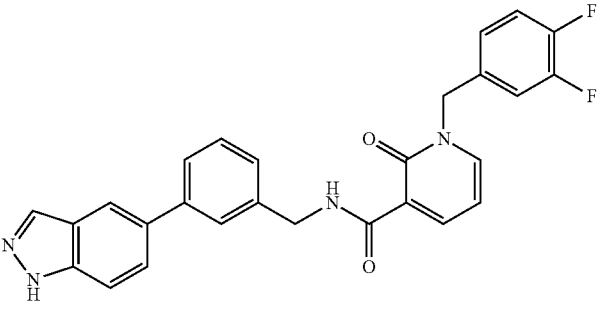 [SMILES: O=C(NCc1cccc(-c2ccc3[nH]ncc3c2)c1)c1cccn(Cc2ccc(F)c(F)c2)c1=O] | +++ | +++ | | |
| 214 | 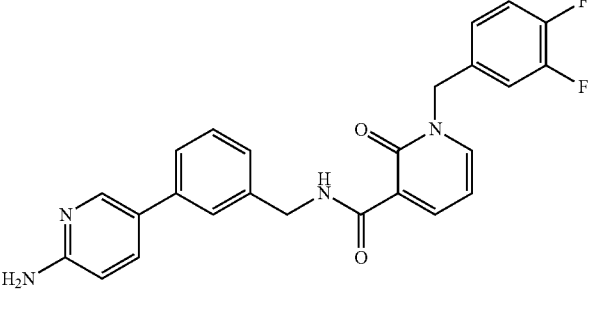 [SMILES: Nc1ccc(-c2cccc(CNC(=O)c3cccn(Cc4ccc(F)c(F)c4)c3=O)c2)cn1] | | | ++ | |
| 215 | 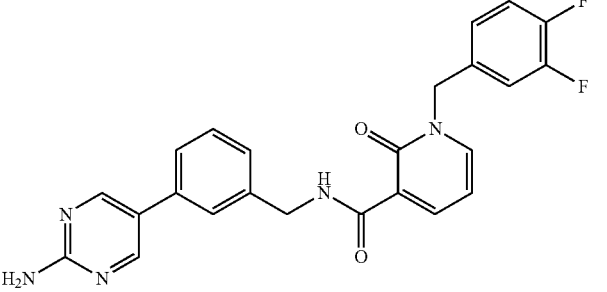 | | | + | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 216 | 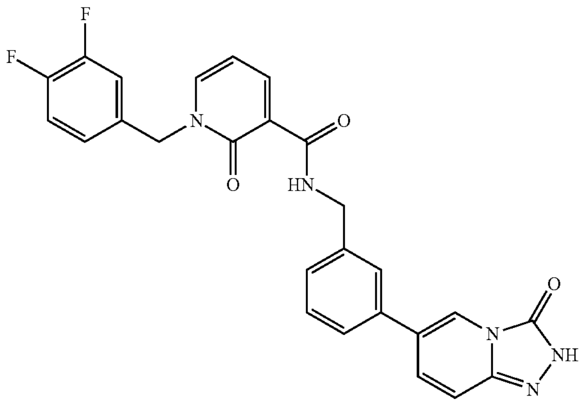 [SMILES: O=C(NCc1cccc(-c2ccc3n[nH]c(=O)n3c2)c1)c1cccn(Cc2ccc(F)c(F)c2)c1=O] | ++ | +++ | | bb |
| 217 | 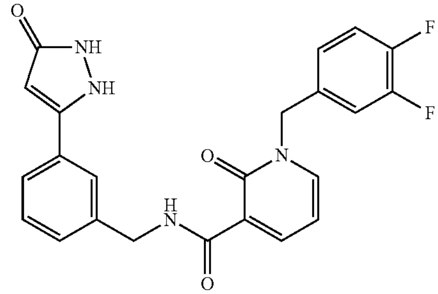 [SMILES: O=C(NCc1cccc(-c2cc(=O)[nH][nH]2)c1)c1cccn(Cc2ccc(F)c(F)c2)c1=O] | + | ++ | | |
| 218 | 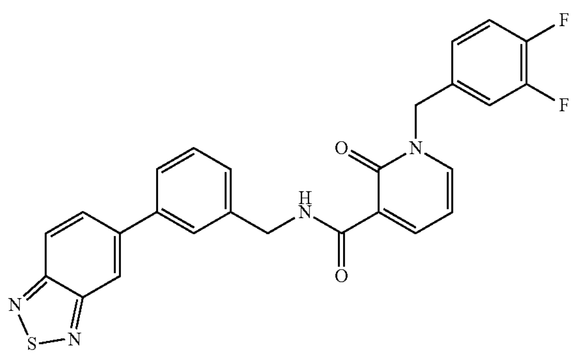 | + | ++ | | |
| 219 | 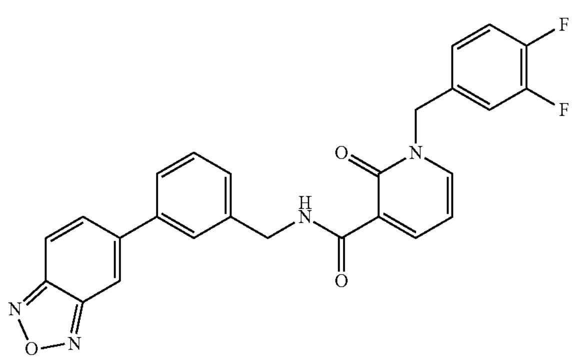 [SMILES: O=C(NCc1cccc(-c2ccc3nonc3c2)c1)c1cccn(Cc2ccc(F)c(F)c2)c1=O] | + | ++ | | |

TABLE 2-continued

| Cpd No. | Structure | Inhibition of phospo- PDK1 in vitro | Inhibition of dephospo- PDK1 in vitro | Inhibition of P308 Akt in cells using MSD | Reduction of Cellular Levels of Akt p308 By Western |
|---|---|---|---|---|---|
| 220 | 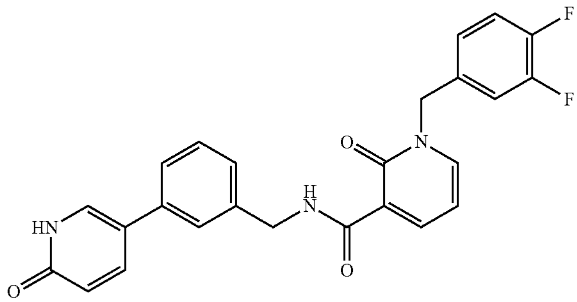 [SMILES: O=C(NCc1cccc(-c2ccc(=O)[nH]c2)c1)c1cccn(Cc2ccc(F)c(F)c2)c1=O] | ++ | ++ | | |
| 221 | 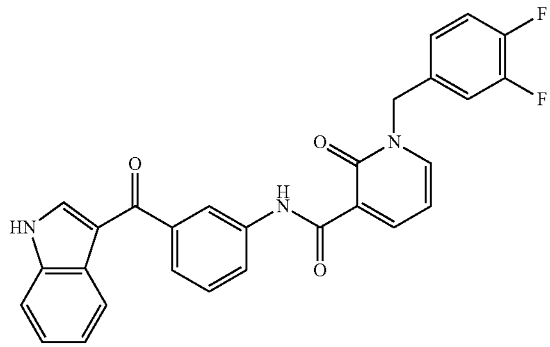 [SMILES: O=C(Nc1cccc(C(=O)c2c[nH]c3ccccc23)c1)c1cccn(Cc2ccc(F)c(F)c2)c1=O] | + | | | |
| 222 | 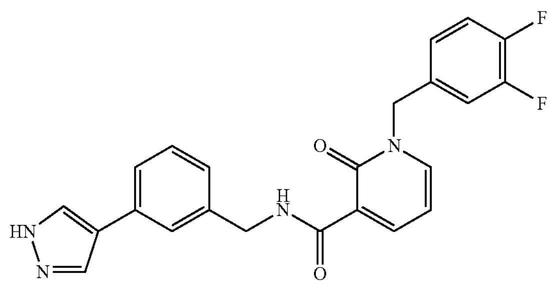 [SMILES: O=C(NCc1cccc(-c2cn[nH]c2)c1)c1cccn(Cc2ccc(F)c(F)c2)c1=O] | ++ | +++ | | bb |
| 223 | 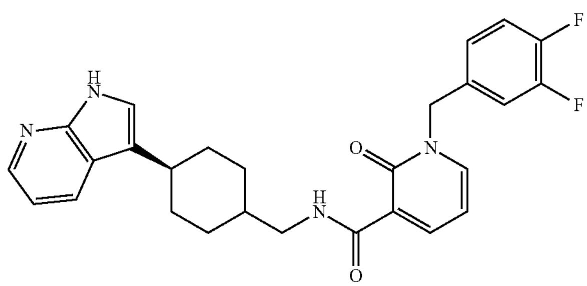 | + | | | |
| 224 | 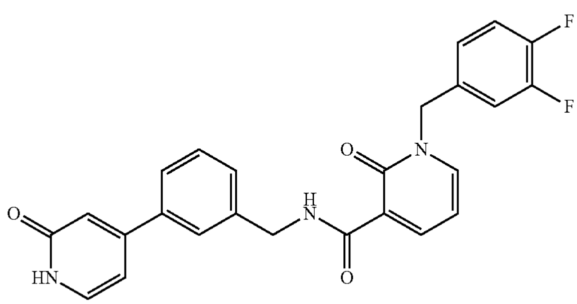 [SMILES: O=C(NCc1cccc(-c2cc[nH]c(=O)c2)c1)c1cccn(Cc2ccc(F)c(F)c2)c1=O] | | ++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 225 | 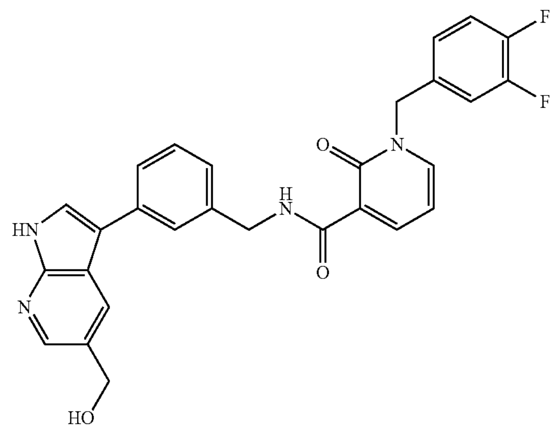 [SMILES: O=C(NCc1cccc(-c2c[nH]c3ncc(CO)cc23)c1)c1cccn(Cc2ccc(F)c(F)c2)c1=O] | +++ | +++ | | bbb |
| 226 | 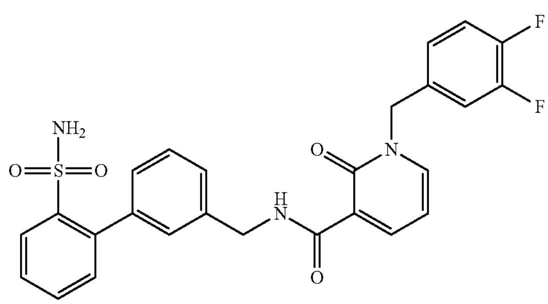 [SMILES: NS(=O)(=O)c1ccccc1-c1cccc(CNC(=O)c2cccn(Cc3ccc(F)c(F)c3)c2=O)c1] | + | | | |
| 227 | 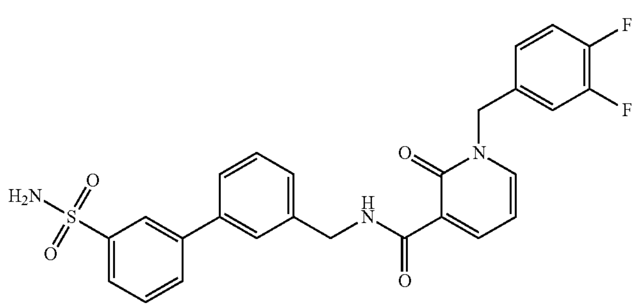 [SMILES: NS(=O)(=O)c1cccc(-c2cccc(CNC(=O)c3cccn(Cc4ccc(F)c(F)c4)c3=O)c2)c1] | + | | | |
| 228 | 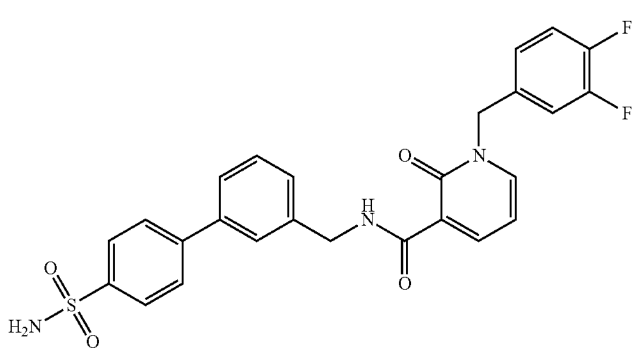 [SMILES: NS(=O)(=O)c1ccc(-c2cccc(CNC(=O)c3cccn(Cc4ccc(F)c(F)c4)c3=O)c2)cc1] | + | | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 229 | 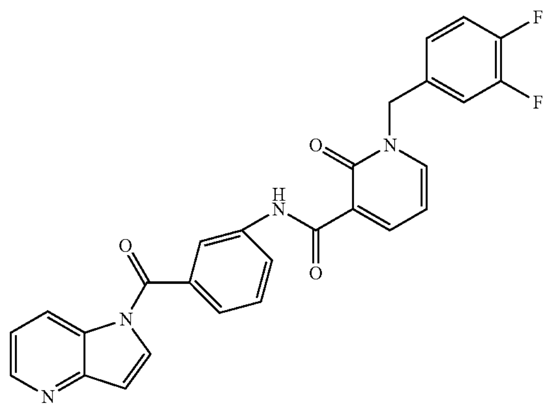 [SMILES: O=C(Nc1cccc(C(=O)n2ccc3ncccc32)c1)c1cccn(Cc2ccc(F)c(F)c2)c1=O] | + | | | |
| 230 | 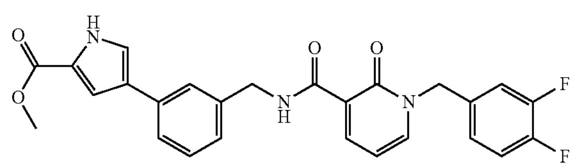 [SMILES: COC(=O)c1cc(-c2cccc(CNC(=O)c3cccn(Cc4ccc(F)c(F)c4)c3=O)c2)c[nH]1] | +++ | +++ | | b |
| 231 | 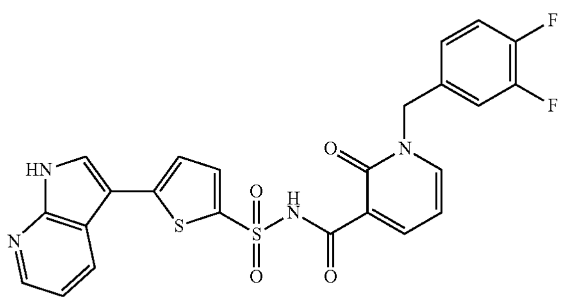 [SMILES: O=C(NS(=O)(=O)c1ccc(-c2c[nH]c3ncccc23)s1)c1cccn(Cc2ccc(F)c(F)c2)c1=O] | ++ | ++ | | |
| 232 | 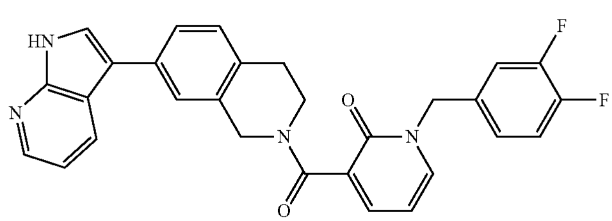 [SMILES: O=C(c1cccn(Cc2ccc(F)c(F)c2)c1=O)N1CCc2ccc(-c3c[nH]c4ncccc34)cc2C1] | ++ | ++ | a | |
| 233 | 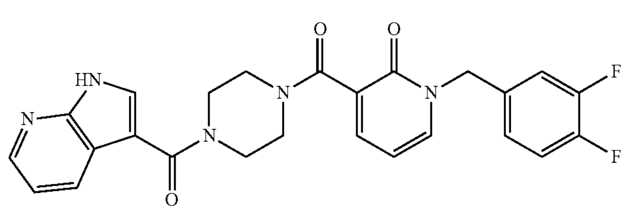 [SMILES: O=C(c1cccn(Cc2ccc(F)c(F)c2)c1=O)N1CCN(C(=O)c2c[nH]c3ncccc23)CC1] | + | | | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 234 | 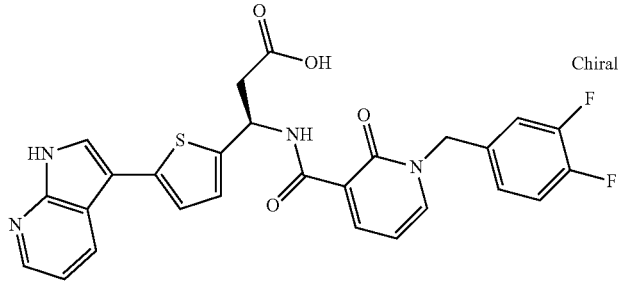 Chiral | +++ | +++ | | |
| 235 | 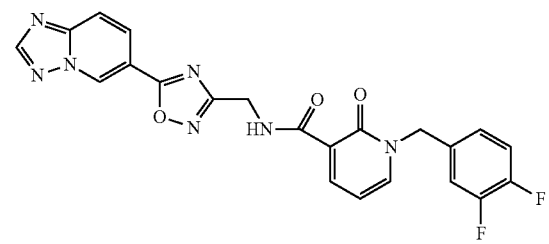 [SMILES: O=C(NCc1noc(-c2ccc3ncnn3c2)n1)c1cccn(Cc2ccc(F)c(F)c2)c1=O] | ++ | +++ | | |
| 236 | 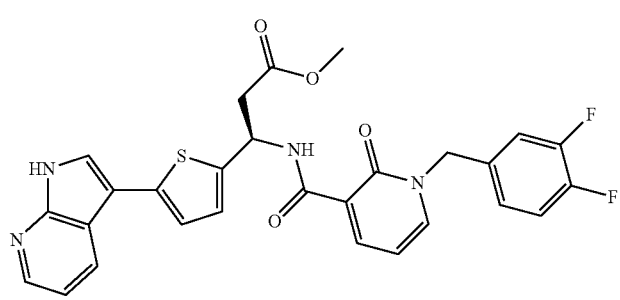 [SMILES: COC(=O)C[C@@H](NC(=O)c1cccn(Cc2ccc(F)c(F)c2)c1=O)c1ccc(-c2c[nH]c3ncccc23)s1] | ++ | +++ | | |
| 237 | 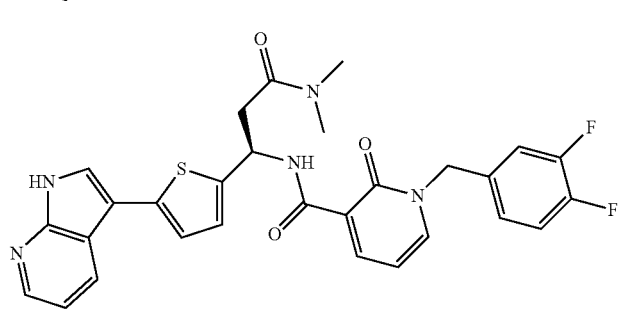 | +++ | +++ | a | |
| 238 | 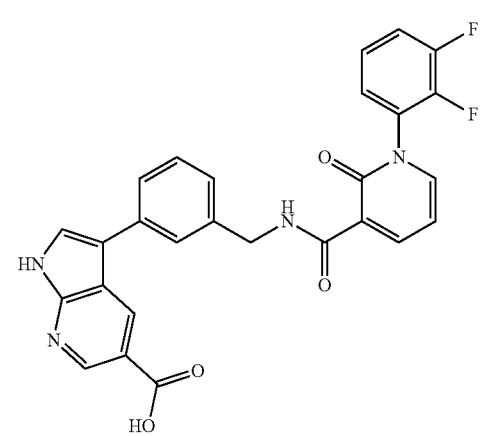 [SMILES: O=C(O)c1cnc2[nH]cc(-c3cccc(CNC(=O)c4cccn(-c5cccc(F)c5F)c4=O)c3)c2c1] | +++ | | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 239 | 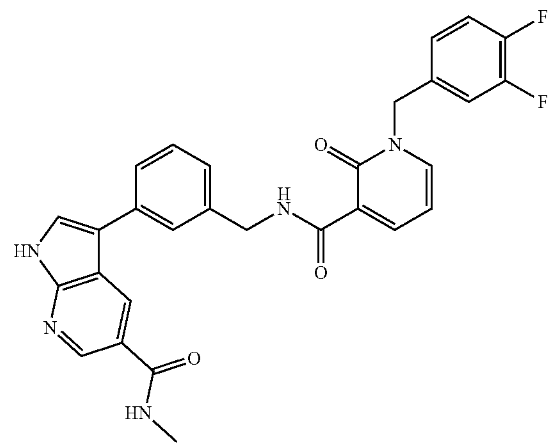 [SMILES: CNC(=O)c1cnc2[nH]cc(-c3cccc(CNC(=O)c4cccn(Cc5ccc(F)c(F)c5)c4=O)c3)c2c1] | +++ | | aa | |
| 240 | 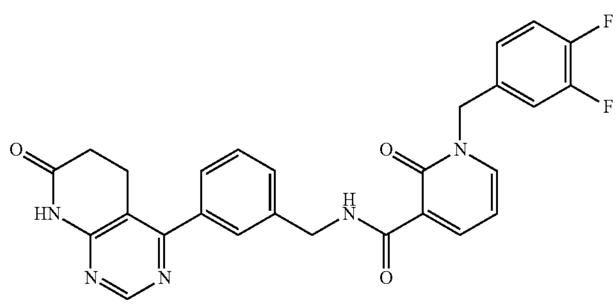 [SMILES: O=C1CCc2c(ncnc2-c2cccc(CNC(=O)c3cccn(Cc4ccc(F)c(F)c4)c3=O)c2)N1] | + | | | |
| 241 | 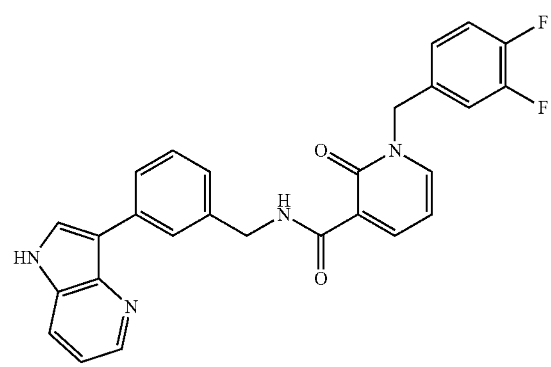 [SMILES: O=C(NCc1cccc(-c2c[nH]c3cccnc23)c1)c1cccn(Cc2ccc(F)c(F)c2)c1=O] | ++ | | | |
| 242 | 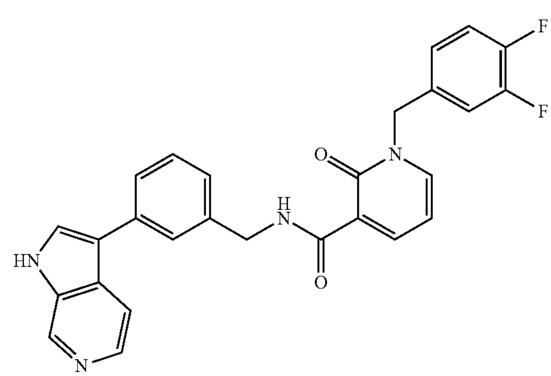 [SMILES: O=C(NCc1cccc(-c2c[nH]c3cnccc23)c1)c1cccn(Cc2ccc(F)c(F)c2)c1=O] | ++ | +++ | | |

TABLE 2-continued

| Cpd No. | Structure | Inhibition of phospo- PDK1 in vitro | Inhibition of dephospo- PDK1 in vitro | Inhibition of P308 Akt in cells using MSD | Reduction of Cellular Levels of Akt p308 By Western |
|---|---|---|---|---|---|
| 243 | 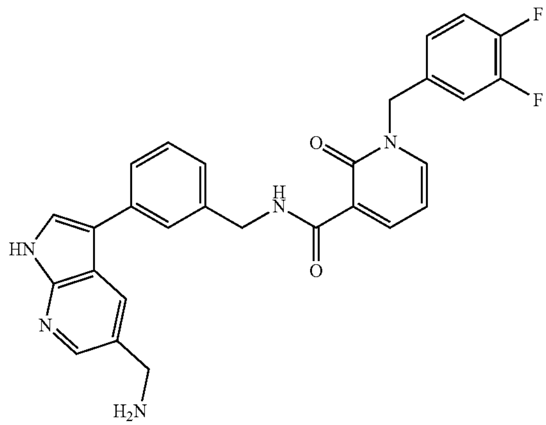 [SMILES: NCc1cnc2[nH]cc(-c3cccc(CNC(=O)c4cccn(Cc5ccc(F)c(F)c5)c4=O)c3)c2c1] | +++ | | aaa | |
| 244 | 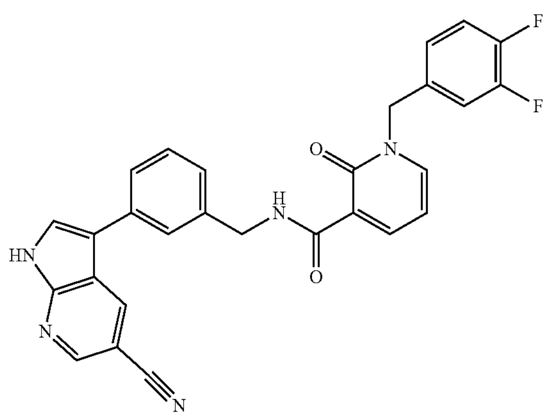 [SMILES: N#Cc1cnc2[nH]cc(-c3cccc(CNC(=O)c4cccn(Cc5ccc(F)c(F)c5)c4=O)c3)c2c1] | +++ | | aaa | |
| 245 | 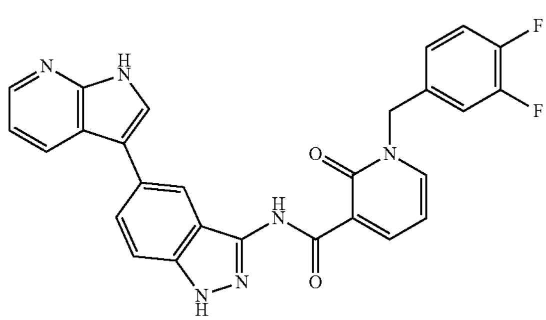 [SMILES: O=C(Nc1n[nH]c2ccc(-c3c[nH]c4ncccc34)cc12)c1cccn(Cc2ccc(F)c(F)c2)c1=O] | +++ | | aa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 246 | 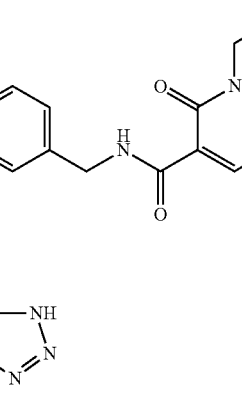 | +++ | | | |
| 247 | 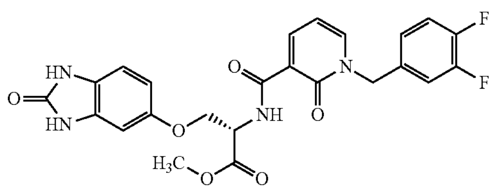 | +++ | | | |
| 248 | 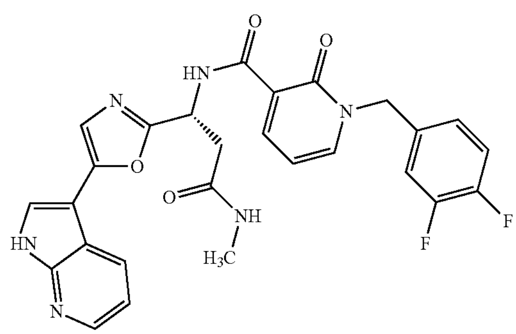 [SMILES: CNC(=O)C[C@@H](NC(=O)c1cccn(Cc2ccc(F)c(F)c2)c1=O)c1ncc(-c2c[nH]c3ncccc23)o1] | +++ | | | |
| 249 | 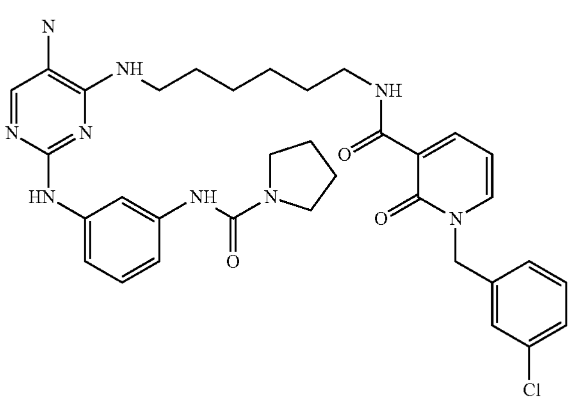 [SMILES: Nc1cnc(Nc2cccc(NC(=O)N3CCCC3)c2)nc1NCCCCCCNC(=O)c1cccn(Cc2cccc(Cl)c2)c1=O] | + | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 250 | 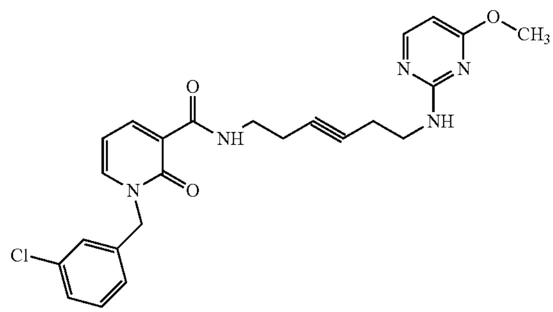 [SMILES: COc1ccnc(NCCC#CCCNC(=O)c2cccn(Cc3cccc(Cl)c3)c2=O)n1] | ++ | +++ | | |
| 251 | 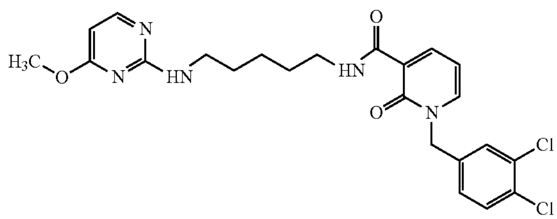 [SMILES: COc1ccnc(NCCCCCNC(=O)c2cccn(Cc3ccc(Cl)c(Cl)c3)c2=O)n1] | ++ | +++ | | |
| 252 | 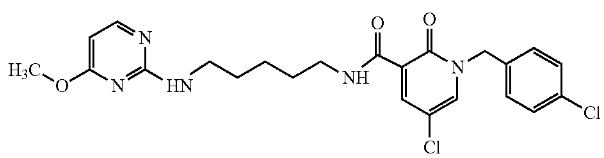 [SMILES: COc1ccnc(NCCCCCNC(=O)c2cc(Cl)cn(Cc3ccc(Cl)cc3)c2=O)n1] | ++ | +++ | | |
| 253 | 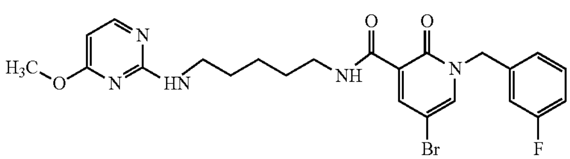 [SMILES: COc1ccnc(NCCCCCNC(=O)c2cc(Br)cn(Cc3cccc(F)c3)c2=O)n1] | ++ | +++ | | |
| 254 | 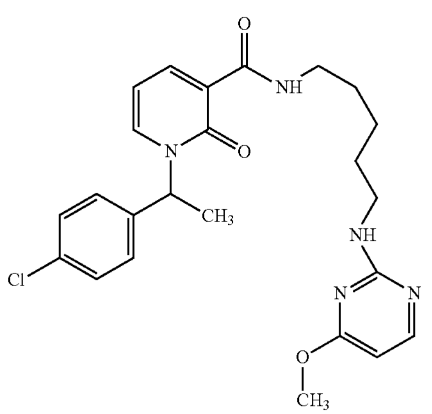 [SMILES: COc1ccnc(NCCCCCNC(=O)c2cccn(C(C)c3ccc(Cl)cc3)c2=O)n1] | ++ | +++ | | |
| 255 | 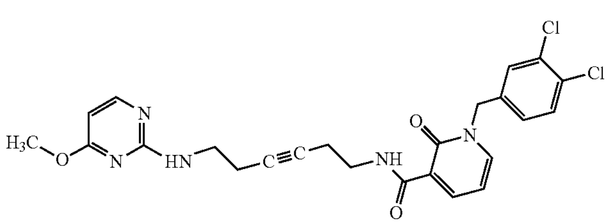 [SMILES: COc1ccnc(NCCC#CCCNC(=O)c2cccn(Cc3ccc(Cl)c(Cl)c3)c2=O)n1] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 256 | 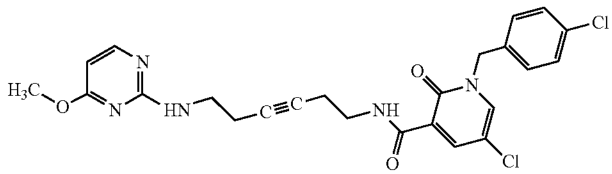 [SMILES: COc1ccnc(NCCC#CCCNC(=O)c2cc(Cl)cn(Cc3ccc(Cl)cc3)c2=O)n1] | ++ | +++ | | |
| 257 | 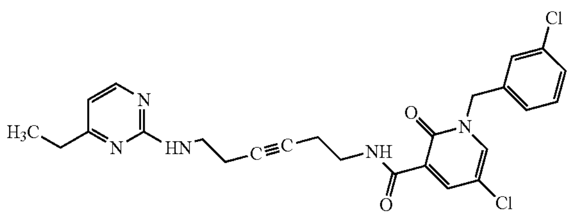 [SMILES: CCc1ccnc(NCCC#CCCNC(=O)c2cc(Cl)cn(Cc3cccc(Cl)c3)c2=O)n1] | +++ | +++ | | |
| 258 | 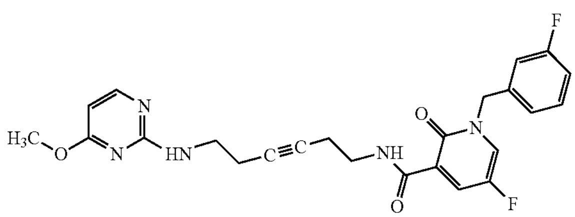 [SMILES: COc1ccnc(NCCC#CCCNC(=O)c2cc(F)cn(Cc3cccc(F)c3)c2=O)n1] | +++ | +++ | | |
| 259 | 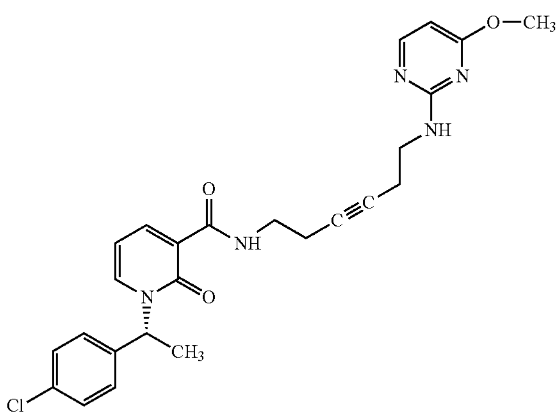 [SMILES: COc1ccnc(NCCC#CCCNC(=O)c2cccn([C@H](C)c3ccc(Cl)cc3)c2=O)n1] | +++ | +++ | | |
| 260 | 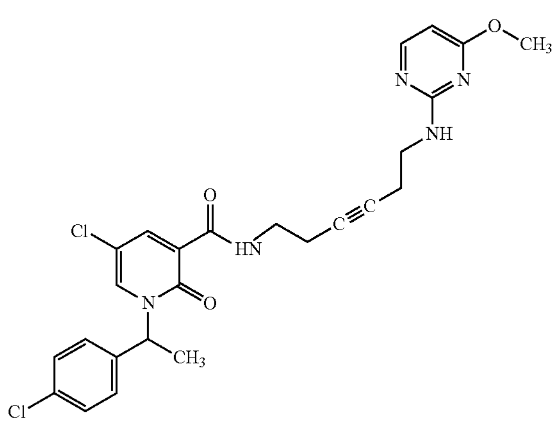 [SMILES: COc1ccnc(NCCC#CCCNC(=O)c2cc(Cl)cn(C(C)c3ccc(Cl)cc3)c2=O)n1] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 261 | 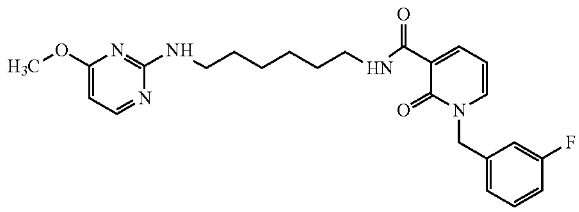 [SMILES: COc1ccnc(NCCCCCCNC(=O)c2cccn(Cc3cccc(F)c3)c2=O)n1] | ++ | +++ | | |
| 262 | 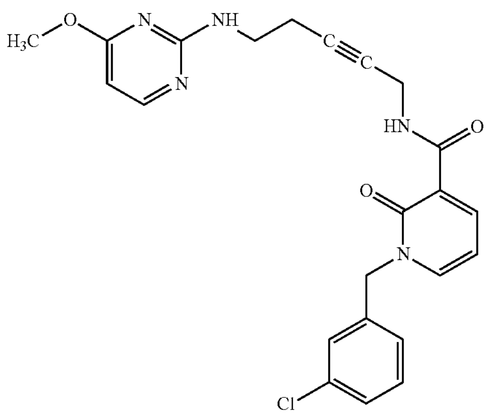 [SMILES: COc1ccnc(NCCC#CCNC(=O)c2cccn(Cc3cccc(Cl)c3)c2=O)n1] | +++ | +++ | | |
| 263 | 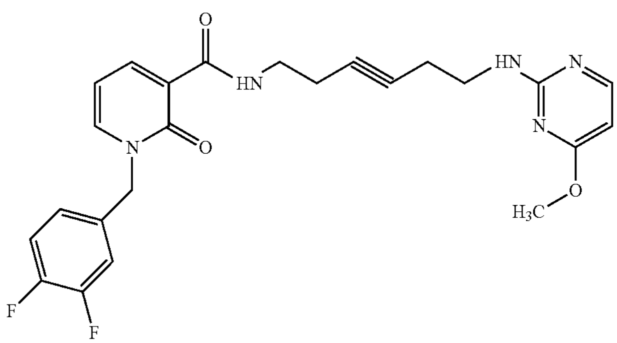 [SMILES: COc1ccnc(NCCC#CCCNC(=O)c2cccn(Cc3ccc(F)c(F)c3)c2=O)n1] | +++ | +++ | | |
| 264 | 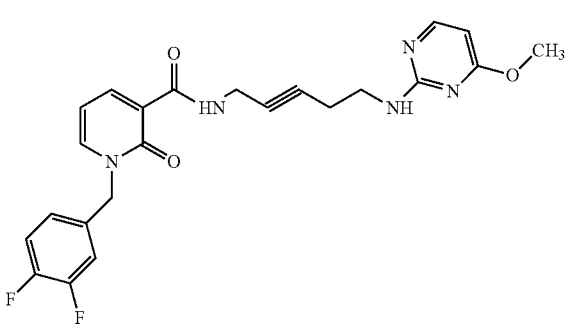 [SMILES: COc1ccnc(NCCC#CCNC(=O)c2cccn(Cc3ccc(F)c(F)c3)c2=O)n1] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
| --- | --- | --- | --- | --- | --- |
| 265 | 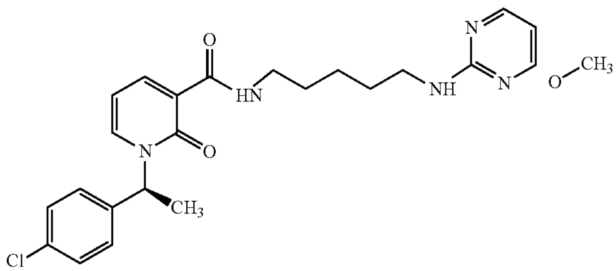 | ++ | +++ | | |
| 266 | 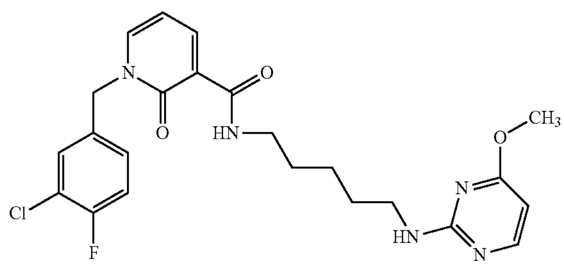 [SMILES: COc1ccnc(NCCCCCNC(=O)c2cccn(Cc3ccc(F)c(Cl)c3)c2=O)n1] | ++ | +++ | | |
| 267 | 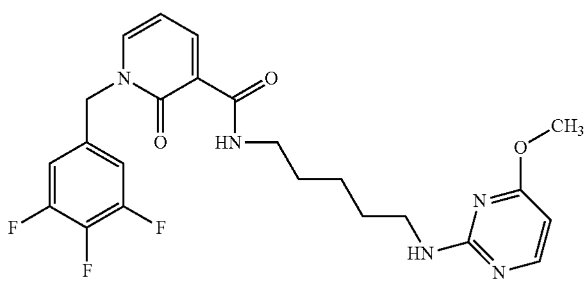 [SMILES: COc1ccnc(NCCCCCNC(=O)c2cccn(Cc3cc(F)c(F)c(F)c3)c2=O)n1] | | +++ | | |
| 268 | 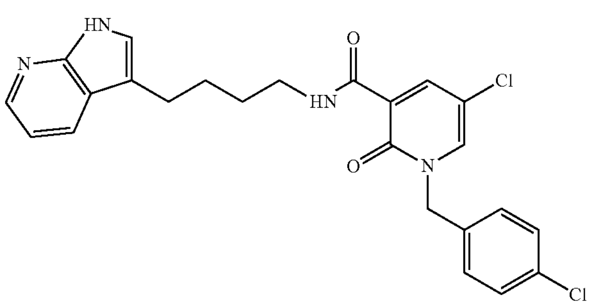 [SMILES: O=C(NCCCCc1c[nH]c2ncccc12)c1cc(Cl)cn(Cc2ccc(Cl)cc2)c1=O] | | +++ | | |
| 269 | 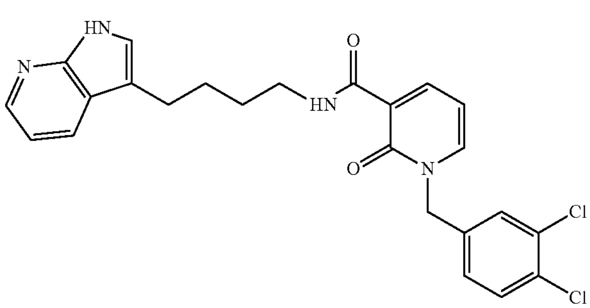 [SMILES: O=C(NCCCCc1c[nH]c2ncccc12)c1cccn(Cc2ccc(Cl)c(Cl)c2)c1=O] | | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 270 | 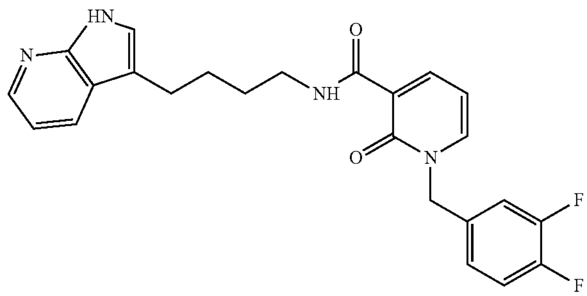 [SMILES: O=C(NCCCCc1c[nH]c2ncccc12)c1cccn(Cc2ccc(F)c(F)c2)c1=O] | +++ | +++ | | |
| 271 | 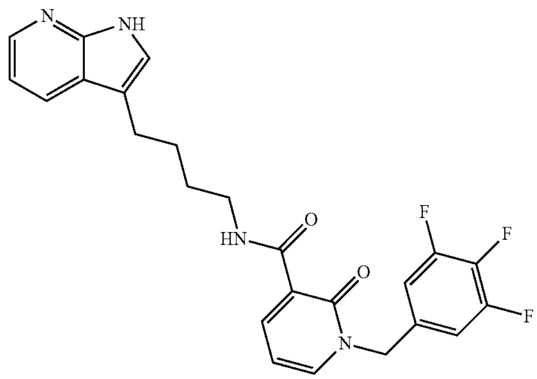 [SMILES: O=C(NCCCCc1c[nH]c2ncccc12)c1cccn(Cc2cc(F)c(F)c(F)c2)c1=O] | +++ | +++ | | |
| 272 | 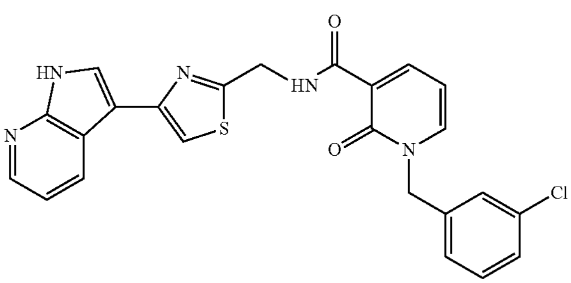 [SMILES: O=C(NCc1nc(-c2c[nH]c3ncccc23)cs1)c1cccn(Cc2cccc(Cl)c2)c1=O] | +++ | +++ | | |
| 273 | 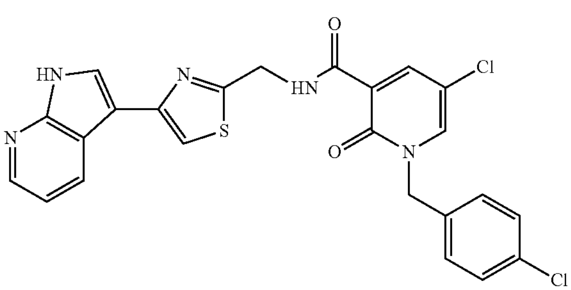 [SMILES: O=C(NCc1nc(-c2c[nH]c3ncccc23)cs1)c1cc(Cl)cn(Cc2ccc(Cl)cc2)c1=O] | +++ | +++ | | |
| 274 | 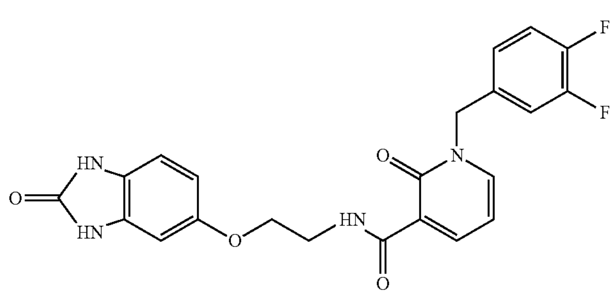 [SMILES: O=C(NCCOc1ccc2[nH]c(=O)[nH]c2c1)c1cccn(Cc2ccc(F)c(F)c2)c1=O] | +++ | +++ | a | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 275 | 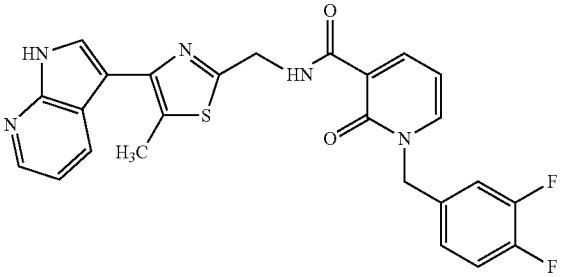 [SMILES: Cc1sc(CNC(=O)c2cccn(Cc3ccc(F)c(F)c3)c2=O)nc1-c1c[nH]c2ncccc12] | ++ | +++ | | |
| 276 | 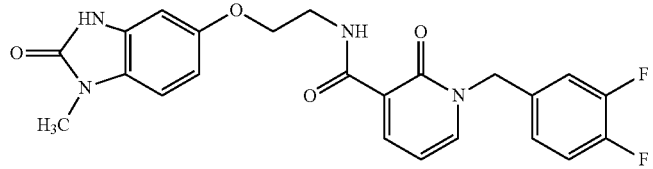 [SMILES: Cn1c(=O)[nH]c2cc(OCCNC(=O)c3cccn(Cc4ccc(F)c(F)c4)c3=O)ccc21] | +++ | +++ | | |
| 277 | 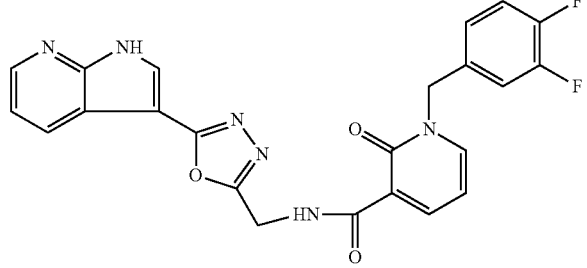 | +++ | +++ | | |
| 278 | 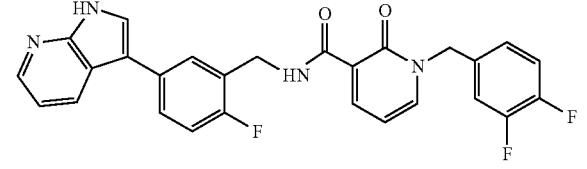 [SMILES: O=C(NCc1cc(-c2c[nH]c3ncccc23)ccc1F)c1cccn(Cc2ccc(F)c(F)c2)c1=O] | +++ | | | |
| 279 | 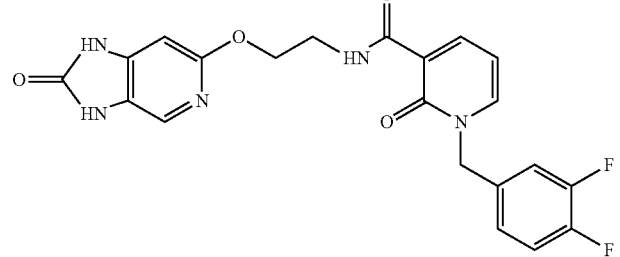 | +++ | +++ | | |
| 280 | 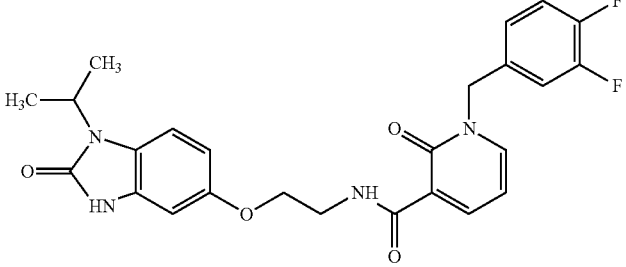 | +++ | +++ | a | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 281 | 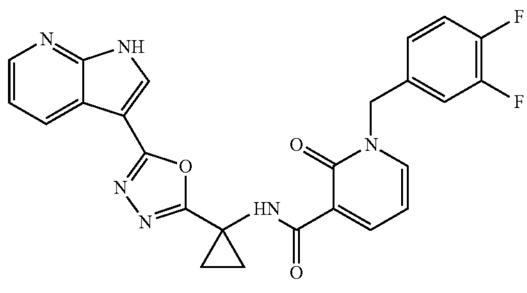 [SMILES: O=C(NC1(c2nnc(-c3c[nH]c4ncccc34)o2)CC1)c1cccn(Cc2ccc(F)c(F)c2)c1=O] | +++ | +++ | | |
| 282 | 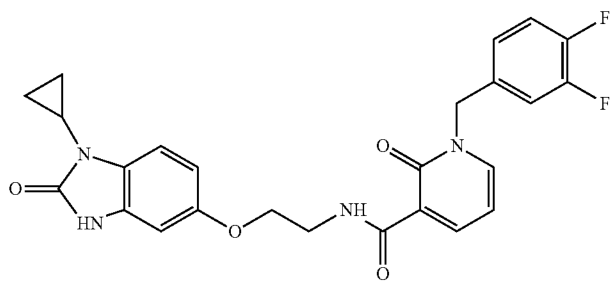 [SMILES: O=C(NCCOc1ccc2c(c1)[nH]c(=O)n2C1CC1)c1cccn(Cc2ccc(F)c(F)c2)c1=O] | +++ | +++ | a | |
| 283 | 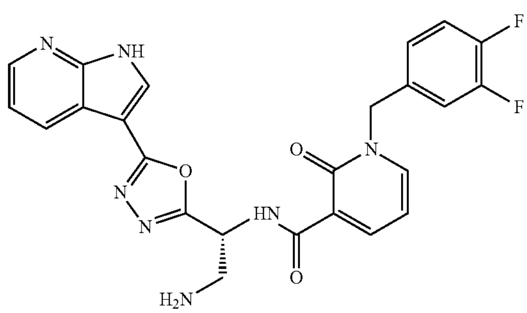 [SMILES: NC[C@@H](NC(=O)c1cccn(Cc2ccc(F)c(F)c2)c1=O)c1nnc(-c2c[nH]c3ncccc23)o1] | +++ | +++ | aa | bb |
| 284 | 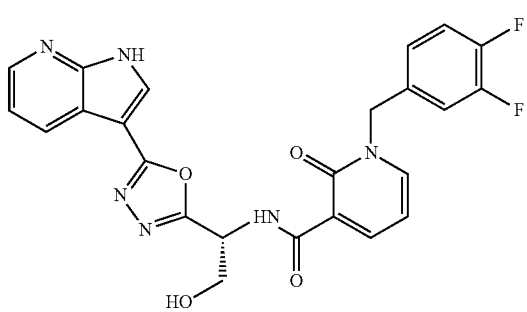 [SMILES: O=C(N[C@H](CO)c1nnc(-c2c[nH]c3ncccc23)o1)c1cccn(Cc2ccc(F)c(F)c2)c1=O] | +++ | | aa | |
| 285 | 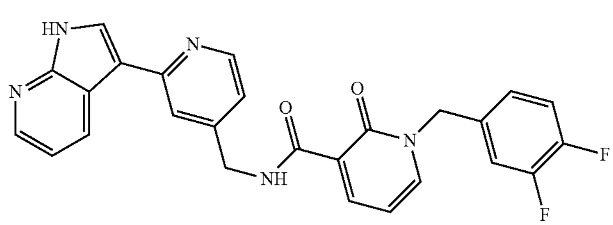 [SMILES: O=C(NCc1ccnc(-c2c[nH]c3ncccc23)c1)c1cccn(Cc2ccc(F)c(F)c2)c1=O] | +++ | | aa | |

TABLE 2-continued
| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 286 | 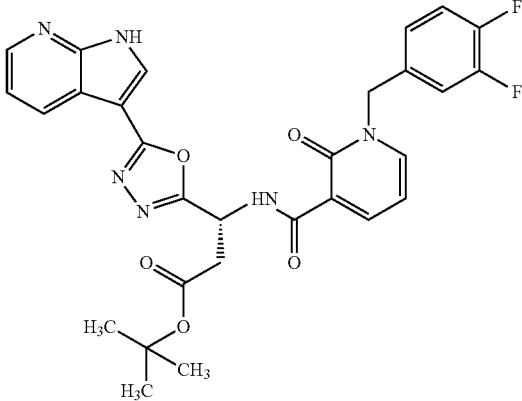 [SMILES: CC(C)(C)OC(=O)C[C@@H](NC(=O)c1cccn(Cc2ccc(F)c(F)c2)c1=O)c1nnc(-c2c[nH]c3ncccc23)o1] | +++ | +++ | aaa | bbb |
| 287 | 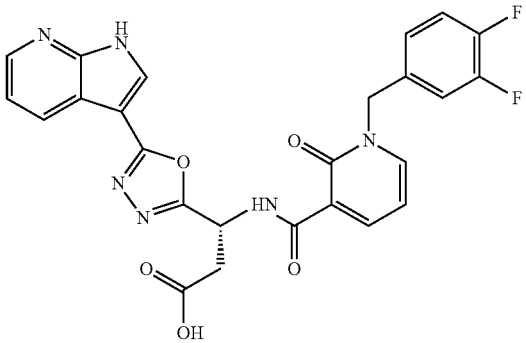 [SMILES: O=C(O)C[C@@H](NC(=O)c1cccn(Cc2ccc(F)c(F)c2)c1=O)c1nnc(-c2c[nH]c3ncccc23)o1] | +++ | +++ | | bb |
| 288 | 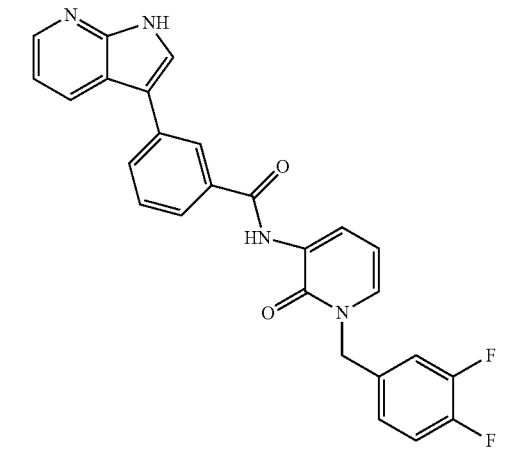 [SMILES: O=C(Nc1cccn(Cc2ccc(F)c(F)c2)c1=O)c1cccc(-c2c[nH]c3ncccc23)c1] | | +++ | | |
| 289 | 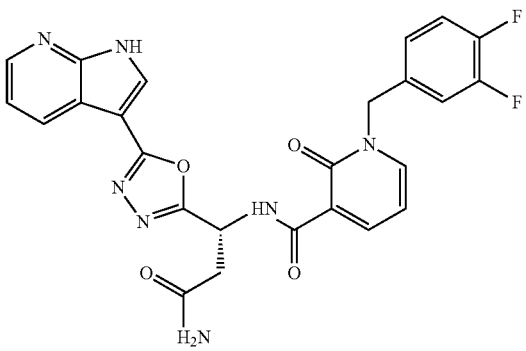 [SMILES: NC(=O)C[C@@H](NC(=O)c1cccn(Cc2ccc(F)c(F)c2)c1=O)c1nnc(-c2c[nH]c3ncccc23)o1] | | +++ | | b |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 290 | 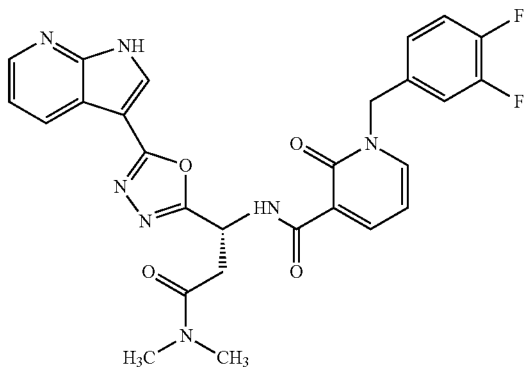 [SMILES: CN(C)C(=O)C[C@@H](NC(=O)c1cccn(Cc2ccc(F)c(F)c2)c1=O)c1nnc(-c2c[nH]c3ncccc23)o1] | ++ | +++ | | bb |
| 291 | 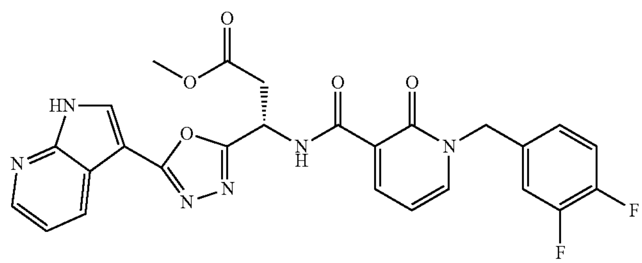 [SMILES: COC(=O)C[C@H](NC(=O)c1cccn(Cc2ccc(F)c(F)c2)c1=O)c1nnc(-c2c[nH]c3ncccc23)o1] | | +++ | aaa | bbb |
| 292 | Chiral | +++ | +++ | aa | |
| 293 | Chiral | +++ | +++ | | bb |
| 294 | 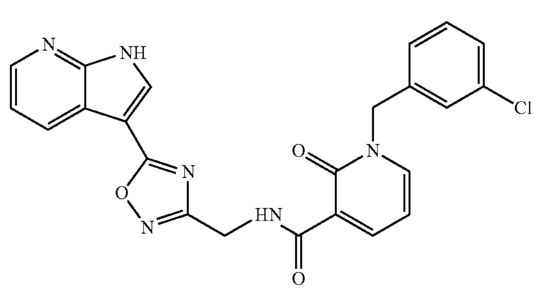 [SMILES: O=C(NCc1noc(-c2c[nH]c3ncccc23)n1)c1cccn(Cc2cccc(Cl)c2)c1=O] | +++ | +++ | | bb |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 295 | 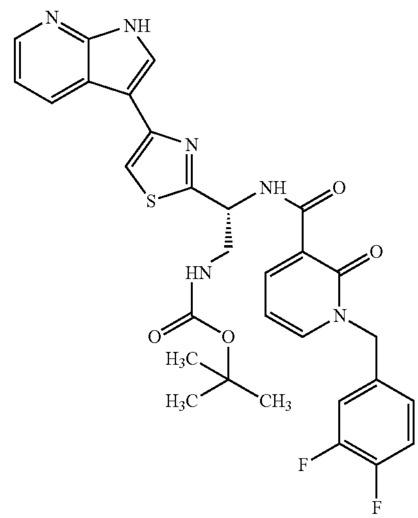 [SMILES: CC(C)(C)OC(=O)NC[C@@H](NC(=O)c1cccn(Cc2ccc(F)c(F)c2)c1=O)c1nc(-c2c[nH]c3ncccc23)cs1] | +++ | +++ | aa | bb |
| 296 | 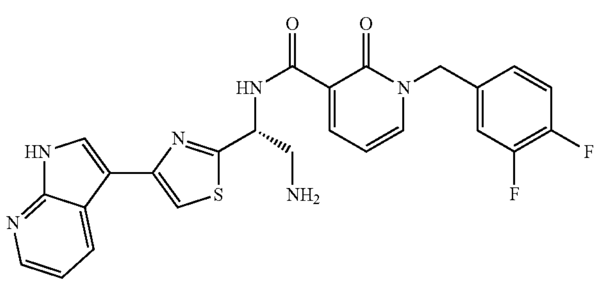 [SMILES: NC[C@@H](NC(=O)c1cccn(Cc2ccc(F)c(F)c2)c1=O)c1nc(-c2c[nH]c3ncccc23)cs1] | +++ | +++ | aa | bb |
| 297 | 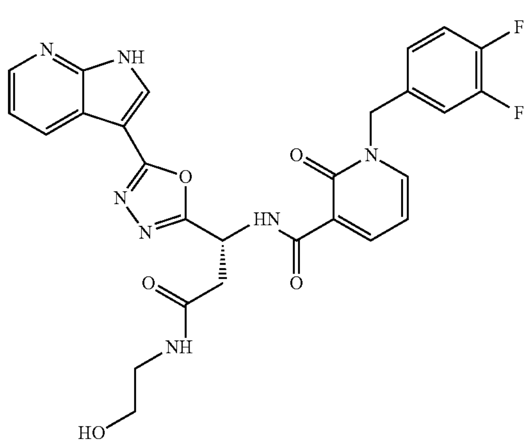 [SMILES: O=C(C[C@@H](NC(=O)c1cccn(Cc2ccc(F)c(F)c2)c1=O)c1nnc(-c2c[nH]c3ncccc23)o1)NCCO] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 298 | 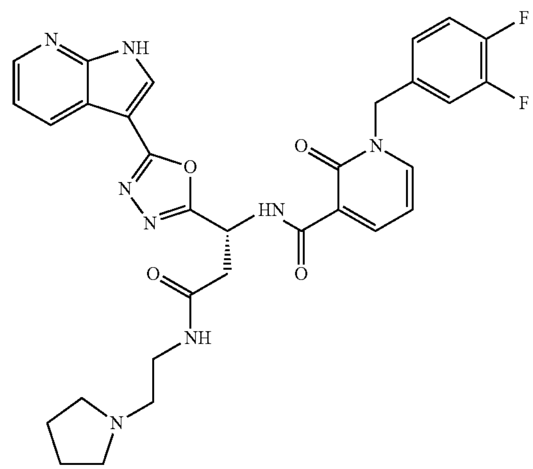 [SMILES: O=C(C[C@@H](NC(=O)c1cccn(Cc2ccc(F)c(F)c2)c1=O)c1nnc(-c2c[nH]c3ncccc23)o1)NCCN1CCCC1] | +++ | +++ | | b |
| 299 | 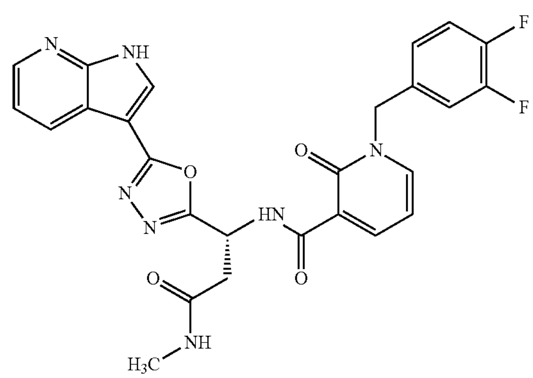 [SMILES: CNC(=O)C[C@@H](NC(=O)c1cccn(Cc2ccc(F)c(F)c2)c1=O)c1nnc(-c2c[nH]c3ncccc23)o1] | +++ | | | bb |
| 300 | 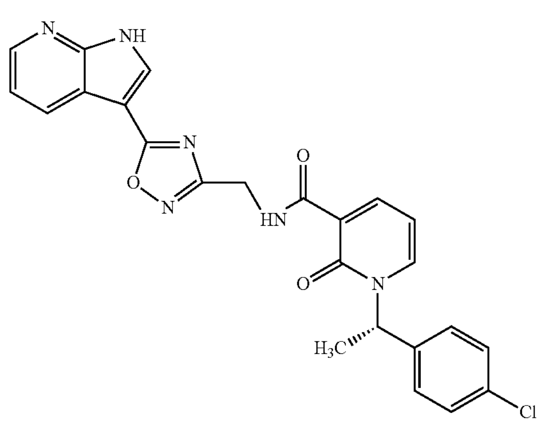 [SMILES: C[C@@H](c1ccc(Cl)cc1)n1cccc(C(=O)NCc2noc(-c3c[nH]c4ncccc34)n2)c1=O] | +++ | +++ | aa | bbb |

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 301 | 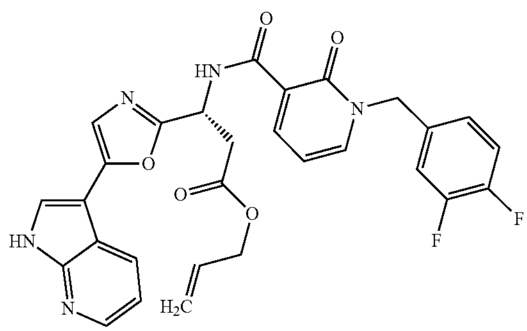 [SMILES: C=CCOC(=O)C[C@@H](NC(=O)c1cccn(Cc2ccc(F)c(F)c2)c1=O)c1ncc(-c2c[nH]c3ncccc23)o1] | +++ | +++ | aa | bbb |
| 302 | 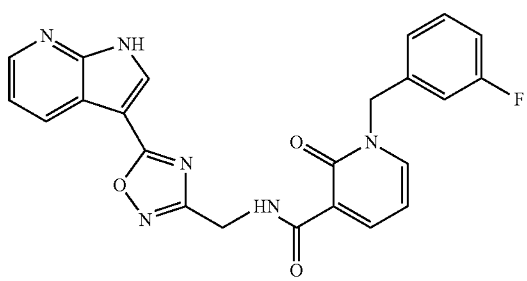 [SMILES: O=C(NCc1noc(-c2c[nH]c3ncccc23)n1)c1cccn(Cc2cccc(F)c2)c1=O] | +++ | +++ | | bbb |
| 303 | 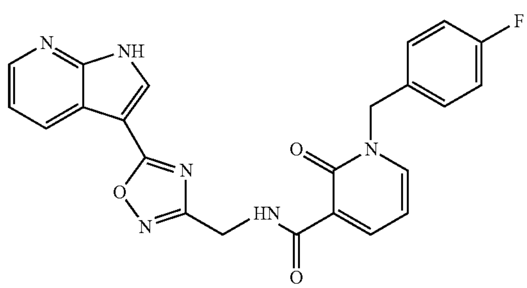 [SMILES: O=C(NCc1noc(-c2c[nH]c3ncccc23)n1)c1cccn(Cc2ccc(F)cc2)c1=O] | +++ | +++ | | bbb |
| 304 | 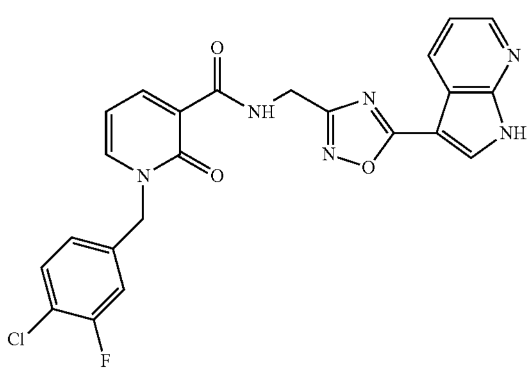 [SMILES: O=C(NCc1noc(-c2c[nH]c3ncccc23)n1)c1cccn(Cc2ccc(Cl)c(F)c2)c1=O] | +++ | +++ | aa | bbb |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 305 | 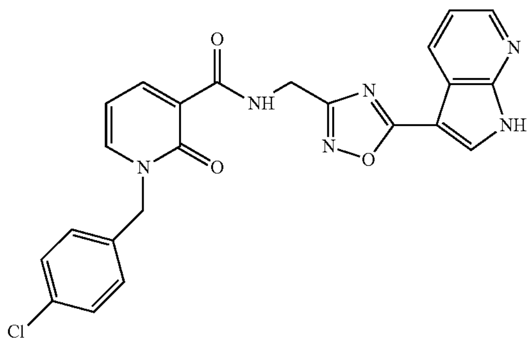 [SMILES: O=C(NCc1noc(-c2c[nH]c3ncccc23)n1)c1cccn(Cc2ccc(Cl)cc2)c1=O] | +++ | +++ | aa | bbb |
| 306 | 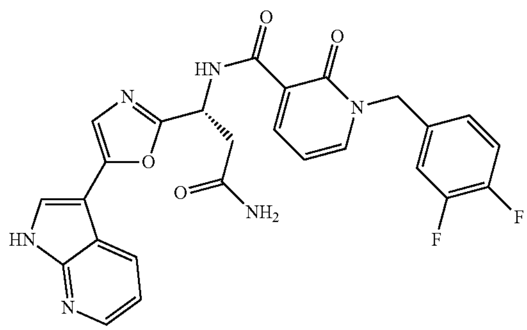 [SMILES: NC(=O)C[C@@H](NC(=O)c1cccn(Cc2ccc(F)c(F)c2)c1=O)c1ncc(-c2c[nH]c3ncccc23)o1] | +++ | +++ | | bbb |
| 307 | 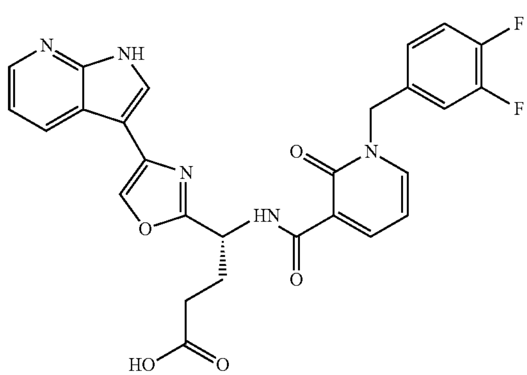 [SMILES: O=C(O)CC[C@@H](NC(=O)c1cccn(Cc2ccc(F)c(F)c2)c1=O)c1nc(-c2c[nH]c3ncccc23)co1] | +++ | +++ | | b |
| 308 | 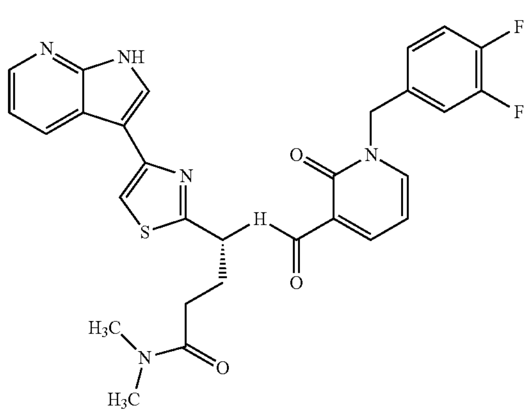 | +++ | +++ | | bb |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 309 | 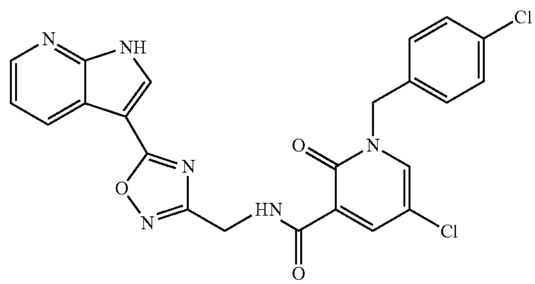 [SMILES: O=C(NCc1noc(-c2c[nH]c3ncccc23)n1)c1cc(Cl)cn(Cc2ccc(Cl)cc2)c1=O] | +++ | +++ | aa | bb |
| 310 | 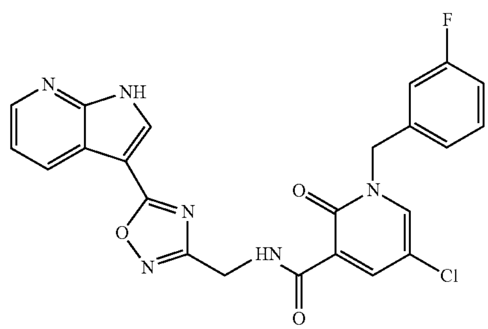 [SMILES: O=C(NCc1noc(-c2c[nH]c3ncccc23)n1)c1cc(Cl)cn(Cc2cccc(F)c2)c1=O] | +++ | +++ | aa | bb |
| 311 | 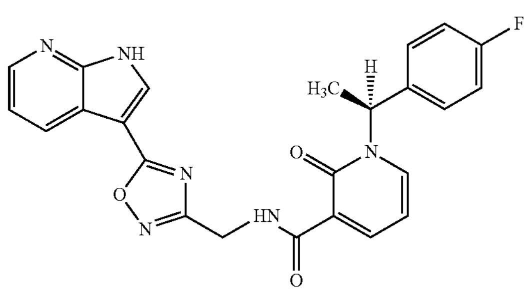 [SMILES: C[C@@H](c1ccc(F)cc1)n1cccc(C(=O)NCc2noc(-c3c[nH]c4ncccc34)n2)c1=O] | +++ | +++ | | |
| 312 | 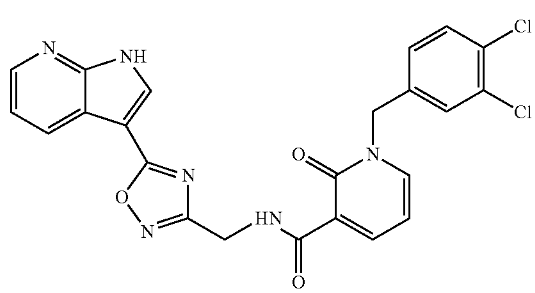 [SMILES: O=C(NCc1noc(-c2c[nH]c3ncccc23)n1)c1cccn(Cc2ccc(Cl)c(Cl)c2)c1=O] | +++ | | aa | |
| 313 | 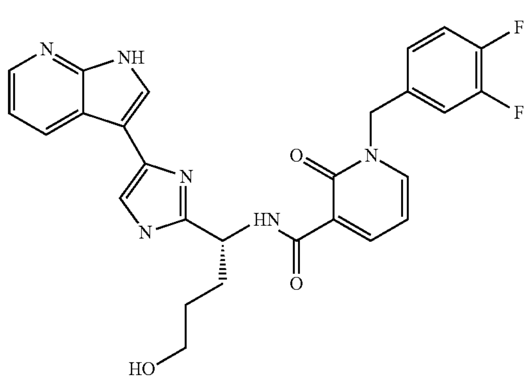 [SMILES: O=C(N[C@H](CCCO)c1nc(-c2c[nH]c3ncccc23)c[nH]1)c1cccn(Cc2ccc(F)c(F)c2)c1=O] | +++ | +++ | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 314 | 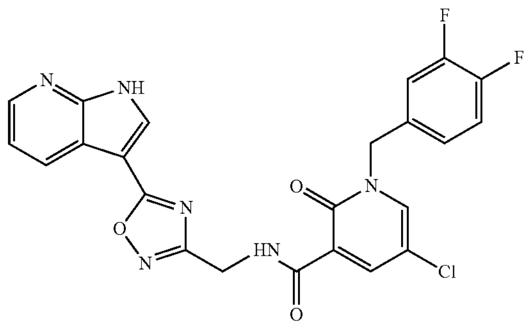 [SMILES: O=C(NCc1noc(-c2c[nH]c3ncccc23)n1)c1cc(Cl)cn(Cc2ccc(F)c(F)c2)c1=O] | +++ | +++ | a | |
| 315 | 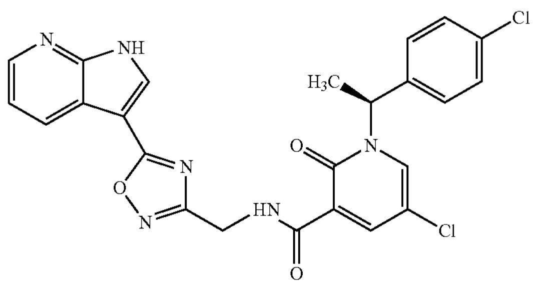 [SMILES: C[C@@H](c1ccc(Cl)cc1)n1cc(Cl)cc(C(=O)NCc2noc(-c3c[nH]c4ncccc34)n2)c1=O] | +++ | | aaa | |
| 316 | 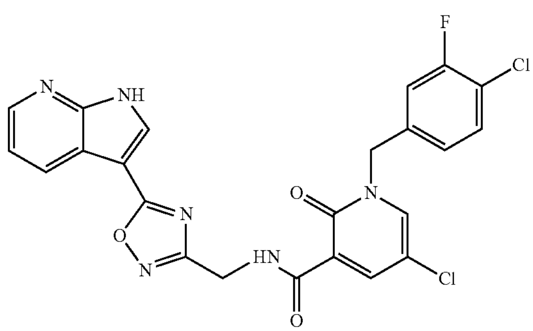 [SMILES: O=C(NCc1noc(-c2c[nH]c3ncccc23)n1)c1cc(Cl)cn(Cc2ccc(Cl)c(F)c2)c1=O] | +++ | +++ | | |
| 317 | 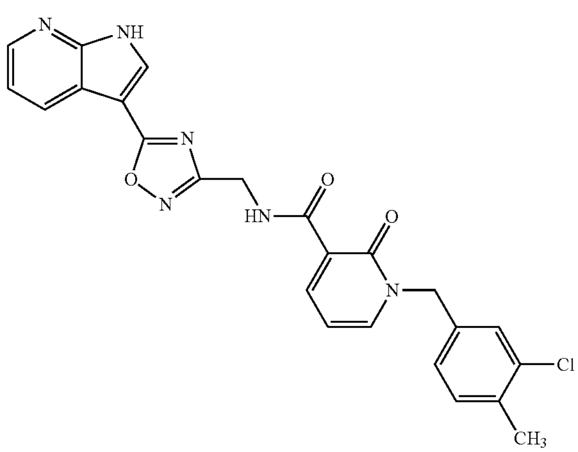 [SMILES: Cc1ccc(Cn2cccc(C(=O)NCc3noc(-c4c[nH]c5ncccc45)n3)c2=O)cc1Cl] | +++ | +++ | a | |

TABLE 2-continued

| Cpd No. | Structure | Inhibition of phospo- PDK1 in vitro | Inhibition of dephospo- PDK1 in vitro | Inhibition of P308 Akt in cells using MSD | Reduction of Cellular Levels of Akt p308 By Western |
|---|---|---|---|---|---|
| 318 | 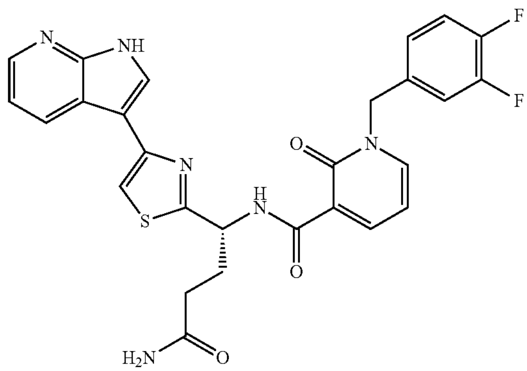 [SMILES: NC(=O)CC[C@@H](NC(=O)c1cccn(Cc2ccc(F)c(F)c2)c1=O)c1nc(-c2c[nH]c3ncccc23)cs1] | +++ | +++ | | |
| 319 | 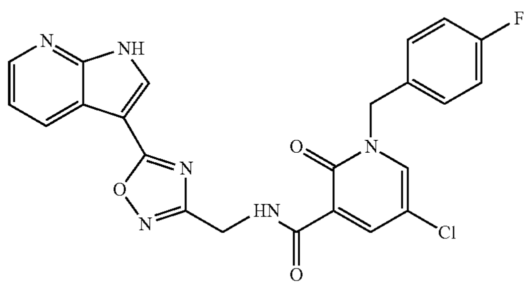 [SMILES: O=C(NCc1noc(-c2c[nH]c3ncccc23)n1)c1cc(Cl)cn(Cc2ccc(F)cc2)c1=O] | +++ | +++ | a | |
| 320 | 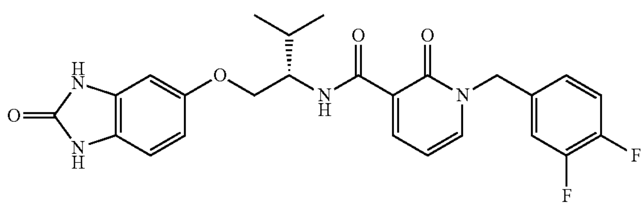 [SMILES: CC(C)[C@@H](COc1ccc2[nH]c(=O)[nH]c2c1)NC(=O)c1cccn(Cc2ccc(F)c(F)c2)c1=O] | ++ | +++ | | |
| 321 | 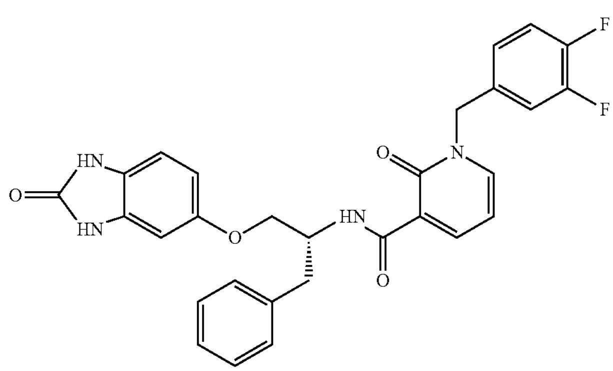 [SMILES: O=C(N[C@@H](COc1ccc2[nH]c(=O)[nH]c2c1)Cc1ccccc1)c1cccn(Cc2ccc(F)c(F)c2)c1=O] | +++ | +++ | a | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 322 | 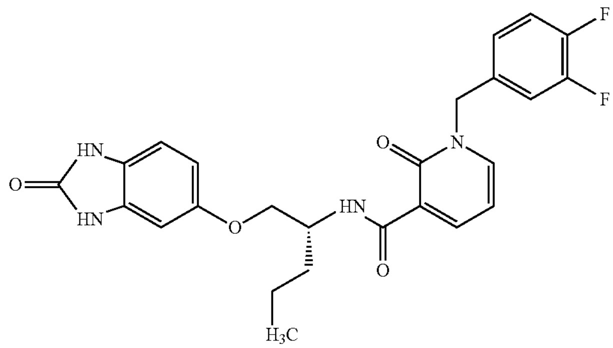 [SMILES: CCC[C@H](COc1ccc2[nH]c(=O)[nH]c2c1)NC(=O)c1cccn(Cc2ccc(F)c(F)c2)c1=O] | +++ | +++ | aa | |
| 323 | 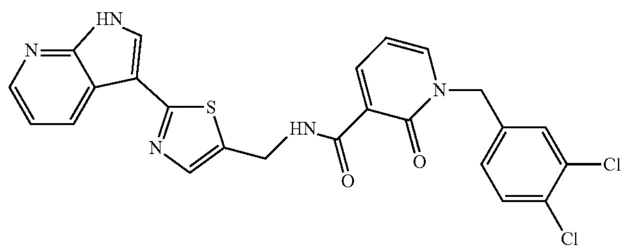 [SMILES: O=C(NCc1cnc(-c2c[nH]c3ncccc23)s1)c1cccn(Cc2ccc(Cl)c(Cl)c2)c1=O] | +++ | +++ | aa | |
| 324 | 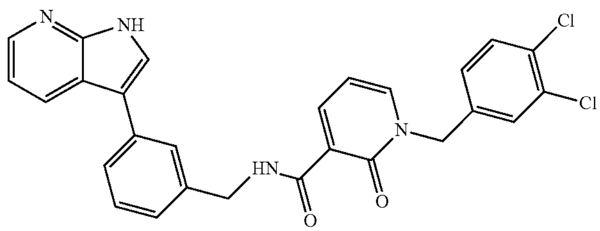 [SMILES: O=C(NCc1cccc(-c2c[nH]c3ncccc23)c1)c1cccn(Cc2ccc(Cl)c(Cl)c2)c1=O] | +++ | | a | |
| 325 | 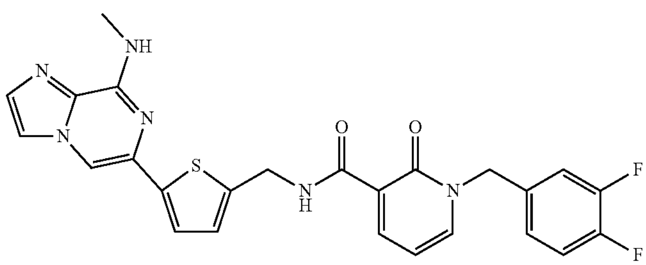 [SMILES: CNc1nc(-c2ccc(CNC(=O)c3cccn(Cc4ccc(F)c(F)c4)c3=O)s2)cn2ccnc12] | ++ | +++ | a | |
| 326 | 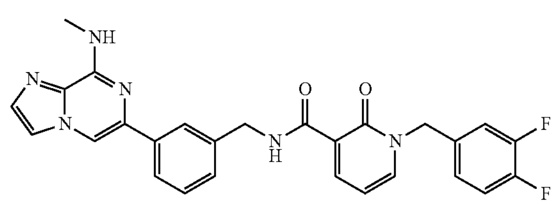 [SMILES: CNc1nc(-c2cccc(CNC(=O)c3cccn(Cc4ccc(F)c(F)c4)c3=O)c2)cn2ccnc12] | ++ | ++ | a | |
| 327 | 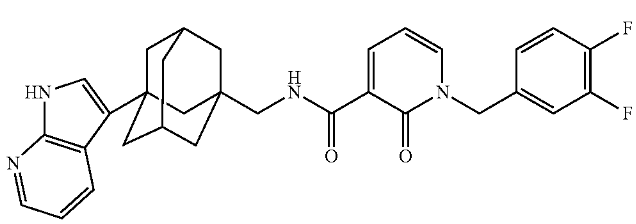 [SMILES: O=C(NCC12CC3CC(C1)CC(c1c[nH]c4ncccc14)(C3)C2)c1cccn(Cc2ccc(F)c(F)c2)c1=O] | ++ | | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 328 | 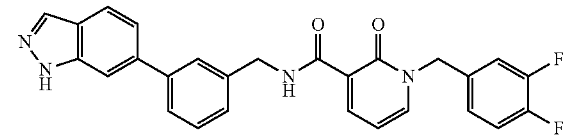 [SMILES: O=C(NCc1cccc(-c2ccc3cn[nH]c3c2)c1)c1cccn(Cc2ccc(F)c(F)c2)c1=O] | +++ | +++ | a | |
| 329 | 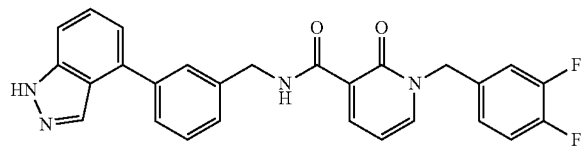 [SMILES: O=C(NCc1cccc(-c2cccc3[nH]ncc23)c1)c1cccn(Cc2ccc(F)c(F)c2)c1=O] | | ++ | a | |
| 330 | 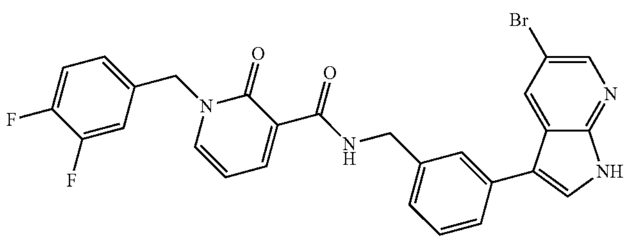 [SMILES: O=C(NCc1cccc(-c2c[nH]c3ncc(Br)cc23)c1)c1cccn(Cc2ccc(F)c(F)c2)c1=O] | +++ | | aa | |
| 331 | 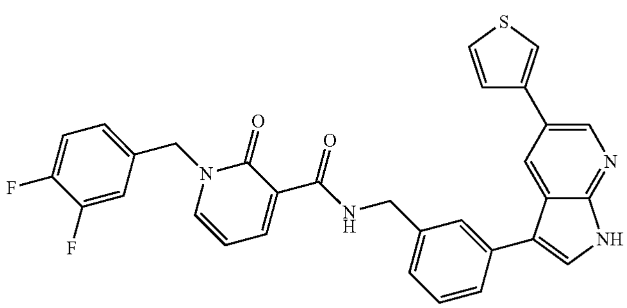 [SMILES: O=C(NCc1cccc(-c2c[nH]c3ncc(-c4ccsc4)cc23)c1)c1cccn(Cc2ccc(F)c(F)c2)c1=O] | +++ | | aa | |
| 332 | 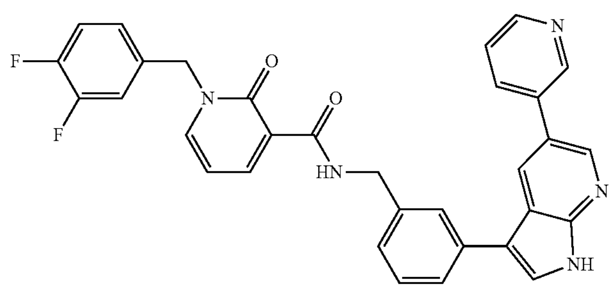 [SMILES: O=C(NCc1cccc(-c2c[nH]c3ncc(-c4cccnc4)cc23)c1)c1cccn(Cc2ccc(F)c(F)c2)c1=O] | +++ | | aaa | |
| 333 | 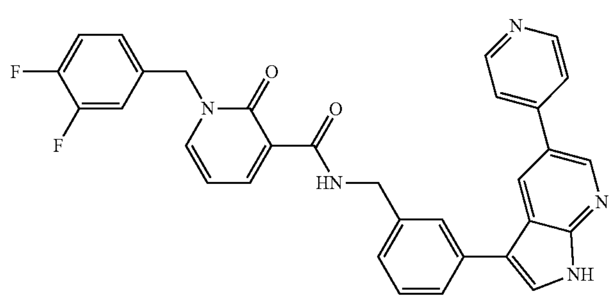 [SMILES: O=C(NCc1cccc(-c2c[nH]c3ncc(-c4ccncc4)cc23)c1)c1cccn(Cc2ccc(F)c(F)c2)c1=O] | +++ | | aaa | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 334 | 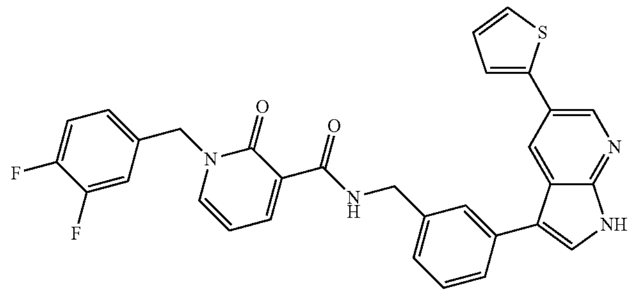 [SMILES: O=C(NCc1cccc(-c2c[nH]c3ncc(-c4cccs4)cc23)c1)c1cccn(Cc2ccc(F)c(F)c2)c1=O] | +++ | | aa | |
| 335 | 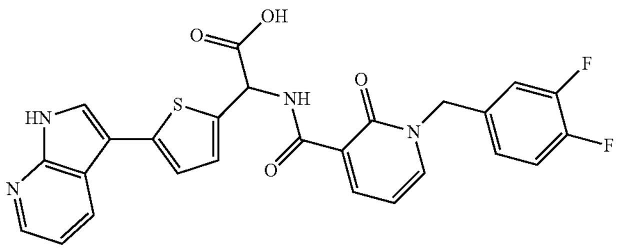 [SMILES: O=C(NC(C(=O)O)c1ccc(-c2c[nH]c3ncccc23)s1)c1cccn(Cc2ccc(F)c(F)c2)c1=O] | ++ | | | |
| 336 | 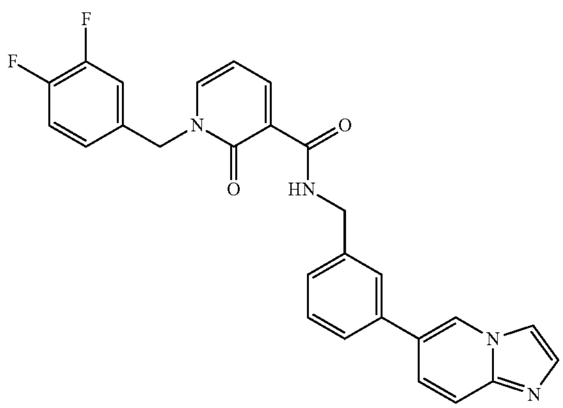 [SMILES: O=C(NCc1cccc(-c2ccc3nccn3c2)c1)c1cccn(Cc2ccc(F)c(F)c2)c1=O] | +++ | | | |
| 337 | 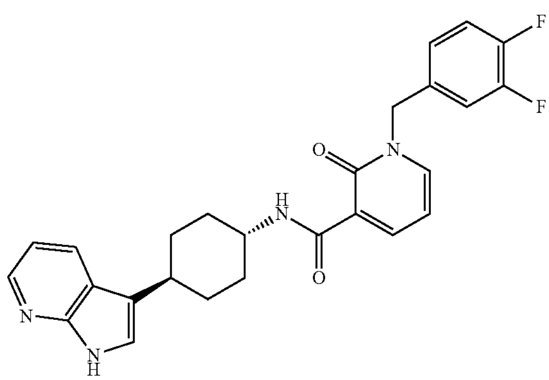 [SMILES: O=C(N[C@H]1CC[C@H](c2c[nH]c3ncccc32)CC1)c1cccn(Cc2ccc(F)c(F)c2)c1=O] | + | | | |
| 338 | 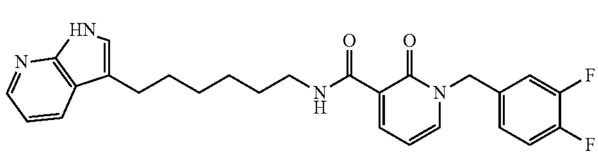 [SMILES: O=C(NCCCCCCc1c[nH]c2ncccc12)c1cccn(Cc2ccc(F)c(F)c2)c1=O] | +++ | | | |

TABLE 2-continued

| Cpd No. | Structure | Inhibition of phospo-PDK1 in vitro | Inhibition of dephospo-PDK1 in vitro | Inhibition of P308 Akt in cells using MSD | Reduction of Cellular Levels of Akt p308 By Western |
|---|---|---|---|---|---|
| 339 | (7-azaindole linked via butyl chain to NH-C(=O)- pyridinone N-substituted with 3,4-difluorobenzyl) | | | +++ | |

In Table 2, "+++" indicates an IC50 of less than 0.5 μM; a "++" indicates an IC50 of from 0.5 μM to 10 μM; and a "+" indicates an IC50 of more than 10 μM. An "aaa" indicates an EC50 of less than 1.0 μM; an "aa" represents an EC50 of from 1.0 μM to 5.0 μM, and an "a" represents an EC50 of more than 5.0 μM. A "b" indicates inhibition of less 25%; a "bb" indicates inhibition of from 25% to 75%; and a "bbb" indicates inhibition of more than 75%.

TABLE 3

| Cpd No | Reduction of Cellular Levels of Akt p308 By MSD ELISA (EC50 μM) | Percent Inhibition of phospho-Akt (308) By Western At 2 μM or 5 μM | Percent Inhibition of phospho-Akt (308) By MSD ELISA At 1 μM or 10 μM |
|---|---|---|---|
| 1 | c | | |
| 2 | cc | | |
| 3 | cc | | 1 μM = d; 10 μM = ddd |
| 4 | | | 1 μM = dd; 10 μM = ddd |
| 213 | cc | | |
| 216 | | 5 μM = dd | |
| 217 | | | |
| 6 | | | 1 μM = dd; 10 μM = dd |
| 220 | | | 1 μM = dd; 10 μM = dd |
| 7 | ccc | | 1 μM = dd; 10 μM = ddd |
| 222 | c | 5 μM = dd | |
| 225 | ccc | 5 μM = ddd | |
| 9 | | 5 μM = ddd | 1 μM = dd; 10 μM = ddd |
| 230 | | 5 μM = d | 1 μM = dd; 10 μM = ddd |
| 10 | | 5 μM = ddd | 1 μM = dd; 10 μM = ddd |
| 11 | ccc | 5 μM = ddd | |
| 12 | | 2 μM = dd | 1 μM = dd; 10 μM = ddd |
| 13 | | | 1 μM = dd; 10 μM = ddd |
| 14 | | 2 μM = dd | 1 μM = dd; 10 μM = dd |
| 15 | c | | |
| 16 | c | 2 μM = d | |
| 17 | | 2 μM = ddd | 1 μM = dd; 10 μM = ddd |
| 235 | c | | |
| 335 | c | | |
| 236 | c | | |
| 237 | | | 1 μM = d; 10 μM = dd |
| 18 | cc | 2 μM = dd | |
| 19 | cc | 2 μM = ddd | |
| 20 | c | | |
| 21 | c | 2 μM = d | |
| 22 | cc | | |
| 23 | c | | |
| 24 | cc | | |
| 25 | ccc | | |
| 26 | ccc | | |
| 239 | ccc | | |
| 27 | ccc | | |
| 28 | ccc | | |
| 29 | ccc | | |
| 30 | ccc | | |
| 31 | cc | | |
| 32 | cc | | |
| 33 | cc | | |
| 34 | cc | | |
| 35 | ccc | | |
| 36 | c | | |
| 240 | cc | | 1 μM = d; 10 μM = d |
| 241 | | | 1 μM = d; 10 μM = dd |
| 242 | | | 1 μM = d; 10 μM = ddd |
| 243 | cc | | |
| 244 | ccc | | |
| 39 | ccc | | |
| 40 | cc | | |
| 41 | ccc | | |
| 42 | cc | | |
| 43 | c | | |
| 132 | | 5 μM = ddd | 1 μM = dd; 10 μM = ddd |
| 133 | | 5 μM = ddd | 1 μM = d; 10 μM = dd |
| 135 | cc | 5 μM = ddd | |
| 136 | | 5 μM = dd | |
| 137 | | 5 μM = ddd | 1 μM = dd; 10 μM = ddd |
| 138 | cc | | |
| 140 | cc | | |
| 141 | cc | | |
| 143 | c | | |
| 144 | ccc | 2 μM = ddd | |
| 145 | cc | | |
| 146 | cc | | |
| 147 | ccc | | |
| 148 | cc | | |
| 112 | d | | |
| 123 | | | 1 μM = dd; 10 μM = ddd |
| 125 | cc | | 1 μM = dd; 10 μM = ddd |
| 126 | ccc | | |
| 278 | cc | | 1 μM = dd; 10 μM = dd |
| 129 | | | 1 μM = dd; 10 μM = d |
| 131 | cc | | |
| 279 | c | | |
| 280 | | | 1 μM = dd; 10 μM = dd |
| 282 | | | 1 μM = d; 10 μM = dd |
| 5 | | | |
| 283 | cc | 5 μM = dd | |
| 284 | cc | | |
| 285 | cc | | |
| 286 | | 5 μM = ddd | 1 μM = dd; 10 μM = ddd |
| 287 | | 5 μM = dd | 1 μM = d; 10 μM = d |
| 289 | | 5 μM = d | 1 μM = d; 10 μM = d |
| 290 | | 5 μM = dd | 1 μM = dd; 10 μM = dd |

TABLE 3-continued

| Cpd No | Reduction of Cellular Levels of Akt p308 By MSD ELISA (EC50 µM) | Percent Inhibition of phospho-Akt (308) By Western At 2 µM or 5 µM | Percent Inhibition of phospho-Akt (308) By MSD ELISA At 1 µM or 10 µM |
|---|---|---|---|
| 291 |  | 5 µM = ddd | 1 µM = dd; 10 µM = ddd |
| 134 |  | 5 µM = ddd | 1 µM = d; 10 µM = ddd |
| 293 |  | 5 µM = dd | 1 µM = dd; 10 µM = ddd |
| 294 |  | 5 µM = dd |  |
| 295 |  | 5 µM = dd | 1 µM = d; 10 µM = ddd |
| 296 |  | 5 µM = dd | 1 µM = d; 10 µM = ddd |
| 297 |  |  | 1 µM = d; 10 µM = d |
| 298 |  | 5 µM = d | 1 µM = d; 10 µM = d |
| 299 |  | 5 µM = dd | 1 µM = d; 10 µM = d |
| 300 |  | 5 µM = ddd | 1 µM = dd; 10 µM = ddd |
| 301 | cc | 5 µM = ddd | 1 µM = dd; 10 µM = dd |
| 302 |  | 5 µM = ddd | 1 µM = d; 10 µM = dd |
| 303 |  | 5 µM = ddd | 1 µM = d; 10 µM = d |
| 304 |  | 5 µM = ddd | 1 µM = d; 10 µM = ddd |
| 305 |  | 5 µM = ddd | 1 µM = d; 10 µM = dd |
| 306 |  | 5 µM = ddd | 1 µM = d; 10 µM = dd |
| 307 |  | 5 µM = d | 1 µM = d; 10 µM = d |
| 308 |  | 5 µM = dd | 1 µM = d; 10 µM = dd |
| 309 |  | 5 µM = dd | 1 µM = dd; 10 µM = ddd |
| 310 |  | 5 µM = dd | 1 µM = d; 10 µM = ddd |
| 311 |  |  | 1 µM = d; 10 µM = ddd |
| 312 |  |  | 1 µM = dd; 10 µM = ddd |
| 313 |  |  | 1 µM = d; 10 µM = dd |
| 314 |  |  | 1 µM = dd; 10 µM = ddd |
| 315 |  |  | 1 µM = d; 10 µM = ddd |
| 316 |  |  | 1 µM = dd; 10 µM = dd |
| 317 |  |  | 1 µM = dd; 10 µM = dd |
| 318 |  |  | 1 µM = d; 10 µM = dd |
| 319 |  |  | 1 µM = d; 10 µM = dd |
| 320 |  |  | 1 µM = d; 10 µM = dd |
| 321 |  |  | 1 µM = d; 10 µM = ddd |
| 322 | cc |  |  |
| 323 | cc |  |  |
| 324 | c |  |  |
| 336 |  | 5 µM = ddd | 1 µM = dd; 10 µM = ddd |

The compound numbers in Table 3 correspond to the structures set forth in Table 2. In Table 3, "ccc" indicates an EC50 of less than 1.0 µM; "cc" indicates an EC50 of from 1.0 µM to 5.0 µM; and "c" indicates an EC50 of more than 5.0 µM. A "d" indicates inhibition of less than 25%; a "dd" indicates inhibition of from 25% to 75%; and a "ddd" indicates inhibition of more than 75%.

What is claimed is:

1. A method of selectively reducing PDK1 mediated phosphorylation of Akt relative to PDK1 mediated phosphorylation of PKC in a cell, the method comprising the step of contacting said cell with an effective amount of a compound of the formula:

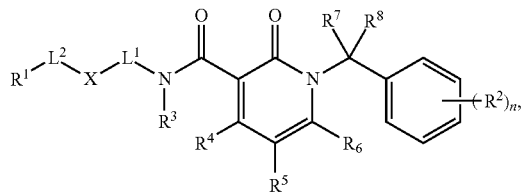

or a pharmaceutically acceptable salt thereof, wherein n is an integer from 2 to 3;

$L^1$ and $L^2$ are independently absent, —O—, —NH—, —S—, —S(O)—, S(O)$_2$—, substituted or unsubstituted alkylene, or substituted or unsubstituted heteroalkylene;

X is absent, substituted or unsubstituted cycloalkylene, substituted or unsubstituted heterocycloalkylene, substituted or unsubstituted arylene, or substituted or unsubstituted heteroarylene, wherein if X is substituted or unsubstituted phenylene and $L^1$ is absent, then $R^1$ is not substituted or unsubstituted pyridinyl, substituted or unsubstituted benzo-oxazolyl, substituted or unsubstituted phenyl, or substituted or unsubstituted quinazolinyl, and wherein if X is substituted or unsubstituted phenylene, then $R^1$ is not substituted or unsubstituted cyclohexyl;

$R^1$ is substituted or unsubstituted cycloalkyl, substituted or unsubstituted heterocycloalkyl, substituted or unsubstituted aryl, or substituted or unsubstituted heteroaryl, wherein if $R^1$ is substituted or unsubstituted phenyl and X absent, then $L^1$ is not absent, and wherein if $R^1$ is substituted or unsubstituted phenyl, then X is not substituted or unsubstituted pyridinonyl, or substituted or unsubstituted imidazolyl;

each $R^2$ is halogen;

$R^4$, $R^5$, and $R^6$ are hydrogen;

$R^7$, and $R^8$ are independently hydrogen, halogen, —OH, —CF$_3$, —NO$_2$, —OR$^{10}$, —C(O)R$^{12}$, —NR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, —OH, —CF$_3$, —OR$^{10}$, —C(O)R$^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ is optionally attached to X thereby forming a substituted or unsubstituted cycloalkyl, substituted or unsubstituted heterocycloalkyl, substituted or unsubstituted aryl, or substituted or unsubstituted heteroaryl;

each instance of $R^{10}$ is independently —C(O)R$^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{12}$ and $R^{15}$ is independently hydrogen, —NR$^{19}$R$^{20}$, —OR$^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{13}$ is independently hydrogen, —C(O)R$^{15}$, —S(O)$_2$R$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{14}$, $R^{19}$, $R^{20}$ and $R^{21}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each instance of $R^{16}$ is independently hydrogen, —NR$^{19}$R$^{20}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The method of claim 1, wherein $R^1$ is substituted or unsubstituted imidazopyridinyl, substituted or unsubstituted triazolopyridinyl, substituted or unsubstituted pyrrolopyridinyl, substituted or unsubstituted pyrrolopyrimidinyl, substituted or unsubstituted pyrrolopyrazinyl, substituted or unsubstituted pyrazolopyridyl, substituted or unsubstituted pyrazolopyrimidinyl, substituted or unsubstituted pyrazolopyrazinyl, substituted or unsubstituted amino-benzimidazolyl, substituted or unsubstituted 2-indolinonyl, substituted or unsubstituted 2-benzimidazolinonyl, substituted or unsubstituted 2-pyrrolidinonyl, substituted or unsubstituted benzimidazolyl, substituted or unsubstituted tetrazolyl, substituted or unsubstituted pyridinonyl, substituted or unsubstituted pyrazolyl, substituted or unsubstituted 5,8-dihydro-6H-pyrido-pyrimidin-7-one-yl, substituted or unsubstituted indazolyl, substituted or unsubstituted dihydro-imidazopyridinon-2-yl, substituted or unsubstituted indolyl, substituted or unsubstituted benzothiadiazolyl, substituted or unsubstituted benzo-oxodiazolyl, substituted or unsubstituted imidazopyridinyl, substituted or unsubstituted triazolopyridinonyl, substituted or unsubstituted dihydro-pyrazolone, substituted or unsubstituted triazolopyridinyl, or substituted or unsubstituted pyrimidinyl.

3. The method of claim 1, wherein $R^1$ is substituted or unsubstituted pyrimidinyl and $L^1$ is —NH-$L^{1A}$- thereby forming a substituent with the formula $R^1$—NH-$L^{1A}$, wherein $L^{1A}$ is absent, substituted or unsubstituted alkylene, or substituted or unsubstituted heteroalkylene.

4. The method of claim 1, wherein
$R^7$, and $R^8$ are independently hydrogen, halogen, —OH, —$CF_3$, —$NO_2$, —$OR^{10}$, —$C(O)R^{12}$, —$NR^{13}R^{14}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl;
$R^3$ is hydrogen, —OH, —$CF_3$, —$OR^{10}$, —$C(O)R^{12}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl;
each instance of $R^{10}$ is independently —$C(O)R^{15}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl;
each instance of $R^{12}$ and $R^{15}$ is independently hydrogen, —$NR^{19}R^{20}$, —$OR^{21}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl;
each instance of $R^{13}$ is independently hydrogen, —$C(O)R^{15}$, —$S(O)_2R^{16}$, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl;

each instance of $R^{14}$, $R^{19}$, $R^{20}$ and $R^{21}$ is independently hydrogen, substituted or unsubstituted $C_1$-$C_{10}$ alkyl, substituted or unsubstituted 2 to 10 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl.

5. The method of claim 1, wherein X is absent, substituted or unsubstituted $C_3$-$C_6$ cycloalkylene, substituted or unsubstituted 3 to 6 membered heterocycloalkylene, or substituted or unsubstituted heteroarylene.

6. The method of claim 5, wherein $L^2$ is unsubstituted $C_1$-$C_5$ alkylene.

7. The method of claim 5, wherein $L^1$ is unsubstituted $C_1$-$C_5$ alkylene.

8. The method of claim 1 wherein the compound is of the formula:

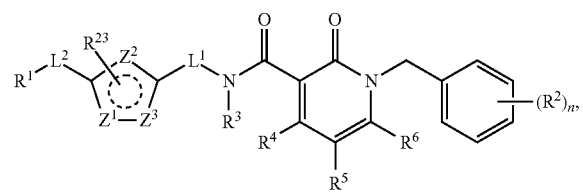

or a pharmaceutically acceptable salt thereof, wherein
$Z^1$, $Z^2$, and $Z^3$ are independently —N=, —NH—, —O—, —S—, or 13 CH=; and
$R^{23}$ is hydrogen, halogen, —OH, —$CF_3$, —$NO_2$, —$OR^{10}$, —$C(O)R^{12}$, —$NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

9. The method of claim 1, wherein $L^1$ is —$C(R^{24})(R^{25})$—, wherein $R^{24}$ and $R^{25}$ are independently hydrogen, halogen, —OH, —$CF_3$, —$NO_2$, —$OR^{10}$, —$C(O)R^{12}$, —$N^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

10. The method of claim 1 wherein the compound is of the formula:

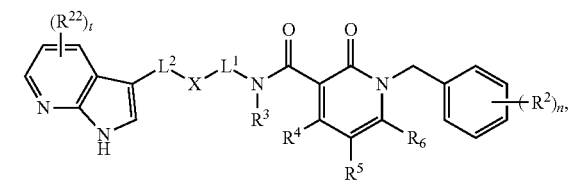

or a pharmaceutically acceptable salt thereof, wherein
t is an integer from 1 to 4;
each instance of $R^{22}$ is hydrogen, halogen, —OH, —$CF_3$, —$NO_2$, —$OR^{10}$, —$C(O)R^{12}$, —$NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
each instance of $R^{10}$ is independently —$C(O)R^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{12}$ and $R^{15}$ is independently hydrogen, $-NR^{19}R^{20}$, $-OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{13}$ is independently hydrogen, $-C(O)R^{15}$, $-S(O)_2R^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each instance of $R^{14}$, $R^{19}$, $R^{20}$ and $R^{21}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

11. The method of claim 10 wherein X is of the formula:

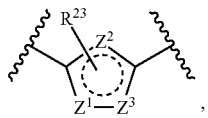

wherein
$Z^1$, $Z^2$, and $Z^3$ are independently $-N=$, $-NH-$, $-O-$, $-S-$, or $-CH=$; and
$R^{23}$ is hydrogen, halogen, $-OH$, $-CF_3$, $-NO_2$, $-OR^{10}$, $-C(O)R^{12}$, $-NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

12. The compound of claim 11, wherein $L^1$ is $-C(R^{24})(R^{25})-$, wherein $R^{24}$ and $R^{25}$ are independently hydrogen, halogen, $-OH$, $-CF_3$, $-NO_2$, $-OR^{10}$, $-C(O)R^{12}$, $-N^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

13. The method of claim 1, wherein the compound is of the formula:

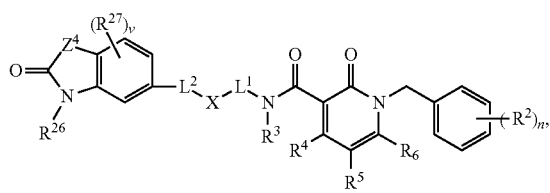

or a pharmaceutically acceptable salt thereof, wherein
v is an integer from 1 to 3;
$Z^4$ is $-N(R^{28})-$, $-C(R^{29})(R^{30})-$, or

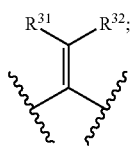

each instance of $R^{26}$, $R^{27}$, $R^{28}$, $R^{29}$, $R^{30}$, $R^{31}$, and $R^{32}$ is independently selected from hydrogen, halogen, $-OH$, $-CF_3$, $-NO_2$, $-OR^{10}$, $-C(O)R^{12}$, $-NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently $-C(O)R^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{12}$ and $R^{15}$ is independently hydrogen, $-NR^{19}R^{20}$, $-OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{13}$ is independently hydrogen, $-C(O)R^{15}$, $-S(O)_2R^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{14}$, $R^{19}$, $R^{20}$ and $R^{21}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each instance of $R^{16}$ is independently hydrogen, $-NR^{19}R^{20}$, or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

14. The method of claim 1, wherein the compound is of the formula:

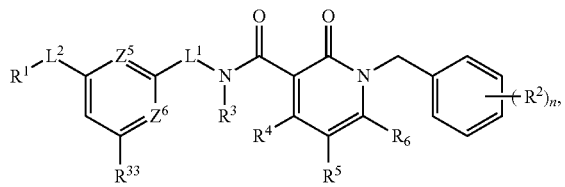

or a pharmaceutically acceptable salt thereof, wherein
$Z^5$ and $Z^6$ are independently $=N-$ and $=C(R^{23})-$; and
each instance of $R^{23}$ and $R^{33}$ is independently hydrogen, halogen, $-OH$, $-CF_3$, $-NO_2$, $-OR^{10}$, $-C(O)R^{12}$, $-NR^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{10}$ is independently $-C(O)R^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of $R^{12}$ and $R^{15}$ is independently hydrogen, $-NR^{19}R^{20}$, $-OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of R¹³ is independently hydrogen, —C(O)R¹⁵, —S(O)₂R¹⁶, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each instance of R¹⁴, R¹⁹, R²⁰ and R²¹ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each instance of R¹⁶ is independently hydrogen, —NR¹⁹R²⁰, or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

15. The method of claim 1, wherein the compound is of the formula:

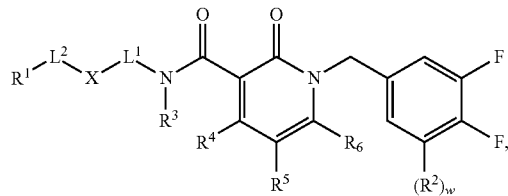

or a pharmaceutically acceptable salt thereof, wherein
w is 0 or 1; and
R² is halogen.

* * * * *

UNITED STATES PATENT AND TRADEMARK OFFICE
CERTIFICATE OF CORRECTION

| | |
|---|---|
| PATENT NO. | : 9,873,693 B2 |
| APPLICATION NO. | : 14/328256 |
| DATED | : January 23, 2018 |
| INVENTOR(S) | : Kenneth Egnard Lind et al. |

It is certified that error appears in the above-identified patent and that said Letters Patent is hereby corrected as shown below:

At Column 468, Claim number 8, Line number 31, replace:
"-O-, -S-, or 13 CH=; and"
With:
-- -O-, -S-, or -CH=; and --

At Column 468, Claim number 9, Line number 40, replace:
"-OH, -CF$_3$, -NO$_2$, -OR$^{10}$, -C(O)R$^{12}$, -N$^{14}$, substi-"
With:
-- -OH, -CF$_3$, -NO$_2$, -OR$^{10}$, -C(O)R$^{12}$, -NR$^{13}$R$^{14}$, substi- --

At Column 469, Claim number 12, Line number 41, replace:
"-N$^{14}$, substituted or unsubstituted alkyl, substituted or"
With:
-- -NR$^{13}$R$^{14}$, substituted or unsubstituted alkyl, substituted or --

Signed and Sealed this
Twenty-seventh Day of March, 2018

Andrei Iancu
*Director of the United States Patent and Trademark Office*